(12) United States Patent
Ohkawa et al.

(10) Patent No.: US 7,507,841 B2
(45) Date of Patent: Mar. 24, 2009

(54) CANNABINOID RECEPTOR MODULATOR

(75) Inventors: Shigenori Ohkawa, Osaka (JP); Tetsuya Tsukamoto, Osaka (JP); Yoshihiro Kiyota, Osaka (JP); Mika Goto, Osaka (JP); Shouzou Yamamoto, Osaka (JP); Masato Shimojou, Osaka (JP); Masaki Setou, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 11/822,941

(22) Filed: Jul. 11, 2007

(65) Prior Publication Data
US 2008/0021087 A1  Jan. 24, 2008

Related U.S. Application Data

(62) Division of application No. 10/561,483, filed on Dec. 20, 2005.

(30) Foreign Application Priority Data
Jun. 26, 2003  (JP) .............................. 2003-182039

(51) Int. Cl.
C07D 307/76  (2006.01)
(52) U.S. Cl. .................................... 549/496
(58) Field of Classification Search ................ 549/496
See application file for complete search history.

(56) References Cited

U.S. PATENT DOCUMENTS

| 5,266,707 | A  | 11/1993 | Matsumoto et al. |
| 5,376,681 | A  | 12/1994 | Aono et al. |
| 5,496,853 | A  | 3/1996  | Shiota et al. |
| 6,172,085 | B1 | 1/2001  | Ohkawa et al. |
| 6,479,536 | B1 | 11/2002 | Ohkawa et al. |
| 6,509,352 | B1 | 1/2003  | Inaba et al. |
| 6,525,087 | B2 | 2/2003  | Mittendorf et al. |
| 6,930,118 | B2 | 8/2005  | Moloney et al. |
| 7,030,139 | B2 | 4/2006  | Cheng et al. |

FOREIGN PATENT DOCUMENTS

| EP | 1 136 477 A1 | 9/2001 |
| EP | 1 323 716 A1 | 7/2003 |
| JP | 5-140142 A   | 6/1993 |
| JP | 10-503185 A  | 3/1998 |
| JP | 10-505089 A  | 5/1998 |
| JP | 10-330380 A  | 12/1998 |
| JP | 11-500411 A  | 1/1999 |
| JP | 11-503467 A  | 3/1999 |
| JP | 2000-256323 A | 9/2000 |
| JP | 2002-348239 A | 12/2002 |
| WO | WO 96/02248 A1 | 2/1996 |
| WO | WO 96/07651 A1 | 3/1996 |
| WO | WO 96/18391 A2 | 6/1996 |
| WO | WO 97/28143 A1 | 8/1997 |
| WO | WO 00/34242 A1 | 6/2000 |
| WO | WO 00/34262    | * 6/2000 |
| WO | WO 02/036590 A1 | 5/2002 |
| WO | WO 02/085866 A1 | 10/2002 |

OTHER PUBLICATIONS

European Search Report dated Aug. 4, 2008 issued in European Application No. 04 74 6824.
Smith et al., The Chemistry of Vitamin E. XXIII. A New Synthesis of 2, 4, 6, 7-Tetramethyl-5-hydroxycoumaran and of 2-Methyl-5-hydroxycoumaran. Oxidation Products of the Tetramethylcoumaran, Journal of the American Chemical Society, vol. 62, Jul. 1940, pp. 1863-1869.
Ohkawa et al., "5-Aminocoumarans: Dual Inhibitors of Lipid Peroxidation and Dopamine Release with Protective Effects against Central Nervous System Trauma and schemia", J. Med. Chem. 1997, 40, pp. 559-573.
Janusz et al., "New Cyclooxygenase-2/5-Lipoxygenase Inhibitors. 3. 7-tert-Butyl-2,3-dimethylbenzofuran Derivatives as Gastrointestinal Safe Anttinflammatory and Analgesic Agents: Variations at the 5 Position", J. Med. Chem. 1998, 41, pp. 3515-3529.

* cited by examiner

*Primary Examiner*—Kamal A Saeed
*Assistant Examiner*—Robert Havlin
(74) *Attorney, Agent, or Firm*—Sughrue Mion, PLLC

(57) ABSTRACT

A cannabinoid receptor modulator containing a compound represented by Formula ($I_0$)

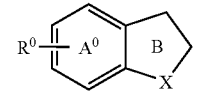

wherein, X is an oxygen atom, etc., $R^0$ is an optionally substituted acylamino group, ring $A^0$ is a benzene ring which may further have a substituent in addition to $R^0$, and ring B is an optionally substituted 5-membered heterocycle, or a salt thereof or a prodrug thereof.

2 Claims, No Drawings

CANNABINOID RECEPTOR MODULATOR

This is a divisional of application Ser. No. 10/561,483 filed Dec. 20, 2005, which is the National Stage of International Application No. PCT/JP2004/009355. The entire disclosure of the prior application, application Ser. No. 10/561,483, is hereby incorporated by reference.

TECHNICAL FIELD

The present invention relates to a benzene ring-fused 5-membered heterocyclic compound, especially a benzofuran derivative as a cannabinoid receptor modulator, and a pharmaceutical composition containing the same.

BACKGROUND ART

Cannabinoid receptors belong to G-protein conjugated receptor having the seven transmembraneous domain. Among these, CB1 receptor is predominately distributed in the central nervous system, of which existence is known by Devane W A et al. (Molecular Pharmacology, 34, 605-613 (1988)). CB2 receptor, which has a predominant cell distribution in the immune system and in the peripheral tissues, has been discovered by Munro S et al. (Nature, 365, 61-65 (1993)). CB1 receptor and CB2 receptor show 48% of homology. 97-99% amino acid sequence of CB1 receptor is maintained in rat, mouse and human.

In the brain, CB1 receptor exists predominately in hippocampus, striatum, substanta nigra, basal forebrain area, olfactory bulb and cerebellum, and little in the brain stem, medulla and thalamus. CB1 receptor is localized in the presynapse, and is considered to control inhibitively the release of neurotransmitters (Trends Pharmacological Sciences, 22, 565-572 (2001)). For CB1 receptor, four kinds of agonist are well known, i.e., classic cannabinoids of tetrahydrocannabinol (THC) derivatives which are dibenzopyran rings, non-classic cannabinoids which are bicyclic and tricyclic derivatives prepared by cleavage of the pyran rings of the THC structure, aminoalkyl indols, and arachidonic acid derivatives such as anandamide which is known as an endogenous agonist (Science, 258, 1946-1949 (1992)).

WIN55,212-2, a cannabinoid receptor agonist, has been reported to inhibit neural cell death based on cerebral ischemia (Journal of Neuroscience, 19, 2987-2995 (1999)). The action is believed to be caused by inhibiting the release of glutamic acid through the activation of the CB1 receptor in the presynapse of glutamic acid neuron. Further, anandamide which is an endogenous ligand has been reported to show inhibitory action on neural cell death after brain injury (Nature, 413, 527-531 (2001)). Further, Baker et al. have reported that WIN55,212-2, JWH-133, THC and methanandamide, which are cannabinoid receptor agonists, improved tremor or spasticity in the animal model of multiple sclerosis (Nature, 404, 84 (2000)).

Cerebrovascular disorders are the $2^{nd}$ or $3^{rd}$ leading cause of death in Japan, USA and Europe, and the $1^{st}$ leading cause of serious aftereffect of diseases, incurring a big medical loss. At present, active treatment to resolve the etiology (tPA, etc.) is performed for some of the patients suffering from cerebro-embolism and cerebro-thrombus, but it can be applied only to several percentages of the patients due to limited time-window for treatment. In most cases, only maintenance therapy of inhibiting cerebral edema and suppressing recurrence or enlargement (thrombolytics) has been performed, but effective drugs for treating the etiology or protecting the brain have not been developed. So far, many drugs having various mechanisms (e.g., glutamate antagonist, calcium antagonist, antioxidant, etc.) have been tried, but most of them have failed in the clinical trials.

Clinical efficacy of the brain-hypothermia therapy as a brain protecting therapy, has been studied, with building up intensive care system for cerebral stroke. Brain-hypothermia therapy is a therapy that maintains the brain temperature (cerebral temperature) low as 32 to 33° C., which has prominent brain-protecting effects. Therefore, this therapy has been drawing attention. However, this therapy requires 24-hour intensive care by intensive treatment facility and many staffs, which makes it difficult to be accepted as a general therapy.

On the other hand, the following compounds have been reported as a compound which has an aminoacyl group on the benzene ring of a bicyclic heterocycle in which the benzene is fused with a 5-membered heterocycle.

1) A compound represented by the following Formula

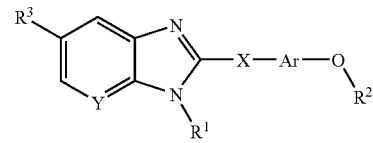

[wherein, $R^3$ is an acylamino group, etc.] (Pamphlet of WO02/085866) which has analgesic action.

2) A compound represented by the following Formula

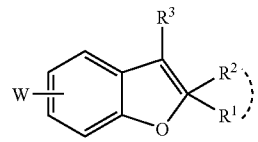

[wherein, W is an acylamino group, etc.] which has proliferating and differentiating action on stem cells or precursor cells of neuron (JP-A-2002-348239).

3) A compound represented by the following Formula

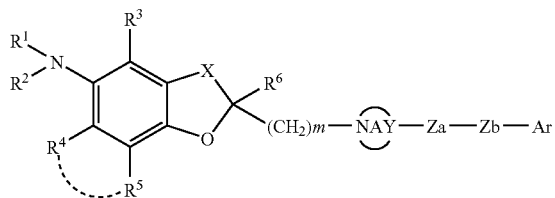

[wherein, the group $NR^1R^2$ is an amincacyl group, etc.] which has sodium channel regulating action (Pamphlet of WO98/08842).

DISCLOSURE OF INVENTION

Cerebrovascular disorders are broadly classified into cerebral infarction, cerebral hemorrhage and subarachnoid hemorrhage. For the treatment, a confirmation waiting time for a proper diagnosis by X-ray, CT or MRI image diagnosis is required, which limits time-window for treatment.

However, a cannabinoid receptor agonist can resolve the problem of time-window for treatment since it is not selective for a certain type of disease. Further, a cannabinoid receptor agonist is expected to be a useful agent of preventing, treating or diagnosing cerebrovascular disorders such as cerebral infarction, cerebral hemorrhage, subarachnoid hemorrhage, etc., or head injury, or various inflammatory diseases. In addition, it eliminates the need for heavy intensive care system by the intensive treatment facilities and staffs which are normally required in the hypothermia therapy, but is expected to exert equivalent brain protecting effects to the hypothermia therapy.

Therefore, the object of the present invention is to provide a benzene ring-fused 5-membered heterocyclic compound, having excellent modulating action on cannabinoid receptor function.

The present inventors have made extensive studies to solve above problems, and as results, have found unexpectedly that the compounds represented by Formula ($I_0$), (I), (I') and (I") which have an aminoacyl group on the benzene-fused 5-membered heterocyclic group, have excellent modulating action on cannabinoid receptor function, to complete the present invention.

That is, the present invention provides the followings:

(1) a cannabinoid receptor modulator containing a compound represented by Formula ($I_0$)

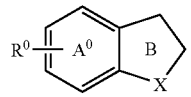

wherein, X is an oxygen atom, an optionally substituted sulfur atom or an optionally substituted imino group, $R^0$ is an optionally substituted acylamino group, ring $A_0$ is a benzene ring which may further have a substituent in addition to $R^0$, and ring B is an optionally substituted 5-membered heterocycle, or a salt thereof or a prodrug thereof, (2) the modulator as described in (1) wherein the compound represented by Formula)($I_0$) or a salt thereof or a prodrug thereof is a compound represented by Formula (I)

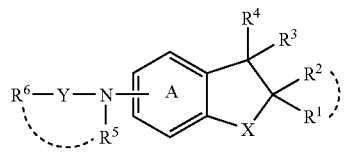

wherein, X is an oxygen atom, an optionally substituted sulfur atom or an optionally substituted imino group, $R^1$, $R^2$, $R^3$ and $R^4$ are independently a hydrogen atom, an optionally substituted hydrocarbon group, an optionally substituted heterocyclic group, an optionally substituted hydroxyl group, an optionally substituted mercapto group or an optionally substituted amino group, or $R^2$ and $R^3$ may be taken together to form a bond, or $R^1$ and $R^2$ may be taken with the adjacent carbon atom to form an optionally substituted ring, Y is —CO—, —SO—, or —$SO_2$—, $R^5$ is a hydrogen atom or an optionally substituted hydrocarbon group, $R^6$ is a hydrogen atom, an optionally substituted hydrocarbon group, an optionally substituted hydroxyl group or an optionally substituted amino group, or $R^5$ and $R^6$ may be taken with the adjacent carbon atom or sulfur atom and nitrogen atom to form an optionally substituted ring, and ring A is a benzene ring which may further have a substituent in addition to a group represented by the following formula

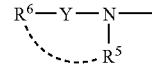

wherein, each symbol has the same meaning as described above, or a salt thereof or a prodrug thereof, (3) the modulator as described in (2) wherein $R^1$ and $R^2$ are a hydrogen atom, (4) the modulator as described in (2) wherein $R^1$ and $R^2$ are respectively a hydrogen atom or a $C_{1-4}$ alkyl group, provided that $R^1$ and $R^2$ are not a hydrogen atom at the same time, (5) the modulator as described in (1) wherein the compound represented by Formula ($I_0$) or the salt thereof is a cannabinoid receptor agonist, (6) the modulator as described in (5) wherein cannabinoid receptor is type 1 cannabinoid receptor, (7) the modulator as described in (1) wherein the compound represented by Formula ($I_0$) or the salt thereof is a cannabinoid receptor antagonist, (8) the modulator as described in (7) wherein the cannabinoid receptor is type 1 cannabinoid receptor, (9) the modulator as described in (1) wherein the compound represented by Formula ($I_0$) or a salt thereof is type 2 cannabinoid receptor agonist,

(10) the modulator as described in (1) which is an agent of preventing, treating or pain-relieving acute cerebrovascular disorders, spinal damage, head injury, multiple sclerosis, glaucoma, depression, vomit, arthritis or asthma,

(11) the modulator as described in (1) which is an agent of preventing or treating memory disorders, psychiatric diseases, obesity, mental diseases, anxiety, depression, drug-dependency, Alzheimer's dementia or Parkinson's disease, or an aid for smoking cessation,

(12) the modulator as described in (1) which is an agent of preventing or treating multiple sclerosis, neurodegenerative diseases, irritable bowel syndrome, Crohn's Disease, reflux oesophagitis, COPD, psoriasis, autoimmune diseases, graft rejection, allergic diseases, neuropathic pain, hepatitis virus or hypertension, or an agent of regulating immunity,

(13) a compound represented by Formula (I')

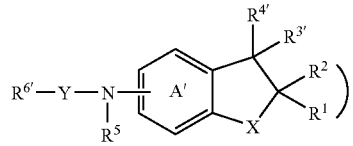

wherein, X is an oxygen atom, an optionally substituted sulfur atom or an optionally substituted imino group, $R^1$ and $R^2$ are independently a hydrogen atom, an optionally substituted hydrocarbon group, an optionally substituted heterocyclic group, an optionally substituted hydroxyl group, an optionally substituted mercapto group or an optionally substituted amino group, or $R^1$ and $R^2$ may be taken with the adjacent carbon atom to form an optionally substituted ring, $R^3$ is a hydrogen atom, an optionally substituted hydrocarbon group, an optionally substituted hydroxyl group, an optionally substituted mercapto group or an optionally substituted amino group, $R^{4'}$ is a hydrogen atom, an optionally substituted alkyl group, an optionally substituted aryl group, or an optionally substituted heterocyclic group, Y is —CO—, —SO—, or —SO₂—, R⁵ is a hydrogen atom or an optionally substituted hydrocarbon group, R⁶' is an optionally substituted hydrocarbon group (provided that both of R¹ and R² are not a hydrogen atom, R⁶' has no benzene ring), an optionally substituted hydroxyl group or an optionally substituted amino group, and ring A' is a benzene ring which may have further substituent in addition to a group represented by the following formula

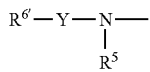

wherein, each symbol has the same meaning as described above, or a salt thereof,

(14) the compound as described in (13) wherein R¹ and R² are independently a hydrogen atom, an optionally substituted hydrocarbon group, an optionally substituted heterocyclic group, an optionally substituted hydroxyl group, an optionally substituted mercapto group or an optionally substituted amino group,

(15) the compound as described in (13) wherein R¹ and R² are a hydrogen atom,

(16) the compound as described in (13) wherein R¹ and R² are respectively a hydrogen atom or a C₁₋₄ alkyl group, provided that R¹ and R² are not a hydrogen atom at the same time,

(17) the compound as described in (13) wherein R³' is a hydrogen atom,

(18) the compound as described in (13) wherein R⁴' is an optionally substituted C₆₋₁₄ aryl group or an optionally substituted 5 to 14-membered heterocyclic group,

(19) the compound as described in (13) wherein R⁴ is an optionally substituted phenyl group,

(20) the compound as described in (19) wherein R⁴ is a phenyl group which may be substituted with an optionally substituted C₁₋₄ alkyl group or an optionally substituted C₁₋₄ alkoxy group,

(21) the compound as described in (13) wherein Y is —CO—,

(22) the compound as described in (13) wherein R⁵ is a hydrogen atom,

(23) the compound as described in (13) wherein X is an oxygen atom,

(24) the compound as described in (13) wherein 5-position of the fused-heterocycle in Formula (I') is substituted by a group represented by the following formula

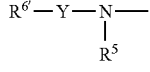

wherein, each symbol has the same meaning as described above,

(25) the compound as described in (24) wherein 7-position of the fused-heterocycle in Formula (I') is further substituted by an optionally substituted C₆₋₁₄ aryl-C₁₋₄ alkyl group,

(26) the compound as described in (25) wherein the optionally substituted C₆₋₁₄ aryl-C₁₋₄ alkyl group is an optionally substituted benzyl group,

(27) the compound as described in (13) wherein ring A' is a benzene ring which may further have 1 to 3 substituents selected from an optionally substituted C₁₋₆ alkyl group, an optionally substituted C₆₋₁₂ aryl group, an optionally substituted 5- or 6-membered heterocyclic group and an acyl group in addition to a group represented by the following formula

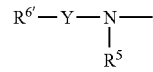

wherein, each symbol has the same meaning as described above,

(28) the compound as described in (27) wherein 7-position of the fused-heterocycle in Formula (I₀) is substituted by an optionally substituted C₁₋₄ alkyl group, an optionally substituted C₆₋₁₂ aryl group, an optionally substituted 5- or 6-membered heterocyclic group, or an acyl group,

(29) the compound as described in (27) wherein 7-position of the fused-heterocycle in Formula (I₀) is substituted by an phenyl group, a furanyl group, a thienyl group, a pyridyl group, an acetyl group, a propionyl group, a butyryl group, or a benzoyl group, which may be substituted, respectively,

(30) N-(3-(4-isopropylphenyl)-4,6,7-trimethyl-2,3-dihydro-1-benzofuran-5-yl)-3,3-dimethylbutanamide, (+)-N-((3R)-3-(4-isopropylphenyl)-4,6,7-trimethyl-2,3-dihydro-1-benzofuran-5-yl)-3,3-dimethylbutanamide, N-(7-acetyl-3-(4-isopropylphenyl)-4,6-dimethyl-2,3-dihydro-1-benzofuran-5-yl)-3,3-dimethylbutanamide, N-(3-(4-isopropylphenyl)-7-methoxy-4,6-dimethyl-2,3-dihydro-1-benzofuran-5-yl)-3,3-dimethylbutanamide, (+)-N-((3R)-7-acetyl-3-(4-isopropylphenyl)-4,6-dimethyl-2,3-dihydro-1-benzofuran-5-yl)-3,3-dimethylbutanamide, (+)-N-(tert-butyl)-N'-((3R)-3-(4-isopropylphenyl)-4,6,7-trimethyl-2,3-dihydro-1-benzofuran-5-yl)urea, N-(3-(4-isopropylphenyl)-4,6-dimethyl-7-phenyl-2,3-dihydro-1-benzofuran-5-yl)-3,3-dimethylbutanamide, N-(7-(3-dimethylaminophenyl)-3-(4-isopropylphenyl)-4,6-dimethyl-2,3-dihydro-1-benzofuran-5-yl)-3,3-dimethylbutanamide, N-(3-hydroxypropyl)-N'-(3-(4-isopropylphenyl)-4,6,7-trimethyl-2,3-dihydro-1-benzofuran-5-yl)urea, N-((4-isopropyl-3-(2-methoxyethoxy)-4-isopropylphenyl)-4,6,7-trimethyl-2,3-dihydro-1-benzofuran-5-yl)-3,3-dimethylbutanamide, N-(7-(4-isopropylbenzyl)-3,4,6-trimethyl-2,3-dihydro-1-benzofuran-5-yl)-3,3-dimethylbutanamide, N-(3-(4-tert-butylphenyl)-2,2,4,6,7-pentamethyl-2,3-dihydro-1-benzofuran-5-yl)-3,3-dimethylbutanamide, or N-(3-(4-isopropylphenyl)-4,6,7-trimethyl-3H-spiro(1-benzofuran-2,1'-cyclopentan)-5-yl)-3,3-dimethylbutanamide,

(31) a prodrug of the compound as described in (13),

(32) a drug comprising the compound as described in (13) or a prodrug thereof,

(33) a method of preventing treating or pain-relieving acute cerebrovascular disorders, spinal damage, head injury, multiple sclerosis, glaucoma, depression, vomit, arthritis or asthma, which is characterized by administering an effective amount of a compound represented by Formula (I₀)

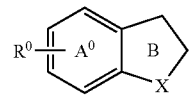

wherein, X is an oxygen atom, an optionally substituted sulfur atom or an optionally substituted imino group, R⁰ is an acylamino group, ring $A_0$ is a benzene ring which may further have a substituent in addition to $R^0$, and ring B is an optionally substituted 5-membered heterocycle, or a salt thereof or a prodrug thereof to a subject in need of such treatment,

(34) a method of preventing or treating memory disorders, psychiatric diseases, obesity, mental diseases, anxiety, depression, drug-dependency, Alzheimer's dementia or Parkinson's disease, or a method of aiding smoking cessation, which is characterized by administering an effective amount of a compound represented by Formula ($I_0$)

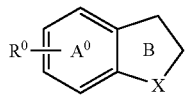

wherein, X is an oxygen atom, an optionally substituted sulfur atom or an optionally substituted imino-group, $R^0$ is an acylamino group, ring $A_0$ is a benzene ring which may further have a substituent in addition to $R^0$, and ring B is an optionally substituted 5-membered heterocycle, or a salt thereof or a prodrug thereof to a subject in need of such treatment,

(35) a method of preventing or treating multiple sclerosis, neurodegenerative diseases, irritable bowel syndrome, Crohn's Disease, reflux oesophagitis, COPD, psoriasis, autoimmune diseases, graft rejection, allergic diseases, psychogenic pain, hepatitis virus or hypertension, or a method of regulating immunity, which is characterized by administering an effective amount of a compound represented by Formula ($I_0$)

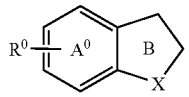

wherein, X is an oxygen atom, an optionally substituted sulfur atom or an optionally substituted imino group, $R^0$ is an acylamino group, ring $A_0$ is a benzene ring which may further have a substituent in addition to $R^0$, and ring B is an optionally substituted 5-membered heterocycle, or a salt thereof or a prodrug thereof to a subject in need of such treatment,

(36) use of a compound represented by Formula ($I_0$)

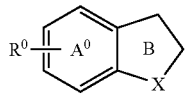

wherein, X is an oxygen atom, an optionally substituted sulfur atom or an optionally substituted imino group, $R^0$ is an acylamino group, ring $A_0$ is a benzene ring which may further have a substituent in addition to $R^0$, and ring B is an optionally substituted 5-membered heterocycle, or a salt thereof or a prodrug thereof, for manufacturing an agent of preventing or treating acute cerebrovascular disorders, spinal damage, head injury, multiple sclerosis, glaucoma, depression, vomit, arthritis or asthma; or for manufacturing an analgesic agent,

(37) use of a compound represented by Formula ($I_0$)

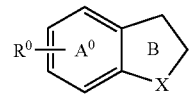

wherein, X is an oxygen atom, an optionally substituted sulfur atom or an optionally substituted imino group, $R^0$ is an acylamino group, ring AD is a benzene ring which may further have a substituent in addition to $R^0$, and ring B is an optionally substituted 5-membered heterocycle, or a salt thereof or a prodrug thereof, for manufacturing an agent of preventing or treating memory disorders, psychiatric diseases, obesity, mental diseases, anxiety, depression, drug-dependency, Alzheimer's dementia or Parkinson's disease, or an aid for smoking cessation,

(38) use of a compound represented by Formula ($I_0$)

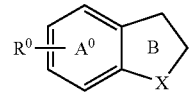

wherein, X is an oxygen atom, an optionally substituted sulfur atom or an optionally substituted imino group, $R^0$ is an acylamino group, ring $A_0$ is a benzene ring which may further have a substituent in addition to $R^0$, and ring B is an optionally substituted 5-membered heterocycle, or a salt thereof or a prodrug thereof, for manufacturing an agent of preventing or treating multiple sclerosis, neurodegenerative diseases, irritable bowel syndrome, Crohn's Disease, reflux oesophagitis, COPD, psoriasis, autoimmune diseases, graft rejection, allergic diseases, neuropathic pain, hepatitis virus or hypertension, or an agent of regulating immunity, and

(39) a method of preparing a compound represented by the following formula

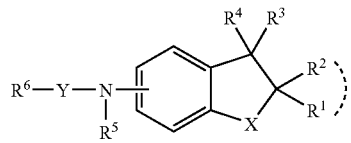

wherein, each symbol has the same meaning as described below, or a salt thereof, comprising reacting a compound represented by the following formula

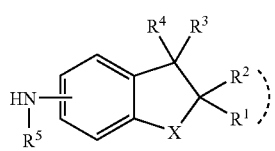

wherein, X is an oxygen atom, an optionally substituted sulfur atom or an optionally substituted imino group, $R^1$, $R^2$, $R^3$ and $R^4$ are independently a hydrogen atom, an optionally substituted hydrocarbon group, an optionally substituted heterocyclic group, an optionally substituted hydroxyl group, an optionally substituted mercapto group or an optionally substituted amino group, or $R^2$ and $R^3$ may be taken together to form a bond, or $R^1$ and $R^2$ may be taken with the adjacent carbon atom to form an optionally substituted ring, $R^5$ is a hydrogen atom or an optionally substituted hydrocarbon group, $R^6$ is a hydrogen atom, an optionally substituted hydrocarbon group, an optionally substituted hydroxyl group or an optionally substituted amino group, or $R^5$ and $R^6$ may be taken with the adjacent carbon atom or sulfur atom and nitrogen atom to form an optionally substituted ring, and ring A is a benzene ring which may have further substituent in addition to a group represented by Formula —$NHR^5$ (wherein, each symbol has the same meaning as described above), or a salt thereof with, $R^6YL$, $(R^6Y)_2O$ or $R^6N$=Y, wherein, L is a leaving group, and Y is —CO—, —SO—, or —$SO_2$—.

In addition, as alternative embodiments, the present invention provides the followings:

(1') a cannabinoid receptor modulator containing the compound represented by Formula ($I_0$) or a salt thereof or a prodrug thereof, (2') the modulator as described in (1') wherein the compound represented by Formula ($I_0$) or a salt thereof or a prodrug thereof is a compound represented by Formula (I) or a salt thereof or a prodrug thereof, (3') the modulator as described in (2') wherein $R^1$ and $R^2$ are respectively a hydrogen atom, (4') the modulator as described in (2') wherein $R^1$ and $R^2$ are respectively a $C_{1-4}$ alkyl group, (5') the modulator as described in (2') wherein $R^3$ is a hydrogen atom, (6') the modulator as described in (2') wherein $R^4$ is an optionally substituted $C_{6-14}$ aryl group or an optionally substituted 5 to 14-membered heterocycle, (7') the modulator as described in (2') wherein $R^5$ is a hydrogen atom, (8') the modulator as described in (2') wherein $R^6$ is an optionally substituted alkyl group or an optionally substituted amino group, and Y is —CO—, (9') the modulator as described in (2') wherein $R^1$, $R^2$, $R^3$ and $R^4$ are independently a hydrogen atom, an optionally substituted hydrocarbon group, an optionally substituted heterocyclic group, an optionally substituted hydroxyl group, an optionally substituted mercapto group or an optionally substituted amino group, (10') the modulator as described in (1') wherein X is an oxygen atom, (11') the modulator as described in (1') wherein $R^0$ is substituted at 5-position of the fused-heterocycle in Formula ($I_0$), (12') the modulator as described in (11') wherein the optionally substituted $C_{6-14}$ aryl-$C_{1-4}$ alkyl group is further substituted at 7-position of the fused-heterocycle in Formula ($I_0$), (13') the modulator as described in (1') wherein ring $A_0$ is a benzene ring further having 1 to 3 $C_{1-6}$ alkyl groups in addition to $R^0$, (14') the modulator as described in (1') wherein the compound represented by Formula ($I_0$) or a salt thereof is a cannabinoid receptor agonist, (15') the modulator as described in (14') wherein the cannabinoid receptor is type 1 cannabinoid receptor, (16') the modulator as described in (1') wherein the compound represented by Formula ($I_0$) or a salt thereof is a cannabinoid receptor antagonist, (17') the modulator as described in (16') wherein the cannabinoid receptor is type 1 cannabinoid receptor, (18') the modulator as described in (1') which is an agent of preventing or treating acute cerebrovascular disorders, spinal damage, head injury, multiple sclerosis, glaucoma, or asthma, (19') the modulator as described in (1') which is an agent of preventing or treating memory disorders, psychiatric diseases, or obesity, (20') a compound represented by Formula (I")

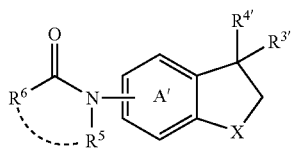

wherein, $R^{3'}$ is a hydrogen atom, an optionally substituted hydrocarbon group, an optionally substituted hydroxyl group, an optionally substituted mercapto group or an optionally substituted amino group, $R^{4'}$ is an optionally substituted aryl group, or an optionally substituted heterocyclic group, ring A' is a benzene ring which may have further substituent in addition to a group represented by the following formula

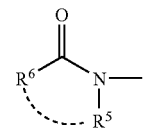

wherein, each symbol has the same meaning as described above, and other symbols have same meanings as defined in (2'), or a salt thereof, (21') the compound as described in (20') wherein $R^{3'}$ is a hydrogen atom, (22') the compound as described in (20') wherein $R^{4'}$ is an optionally substituted $C_{6-14}$ aryl group or an optionally substituted 5 to 14-membered heterocyclic group, (23') the compound as described in (20') wherein $R^{4'}$ is an optionally substituted phenyl group, (24') the compound as described in (20') wherein X is an oxygen atom, (25') the compound as described in (20') wherein 5-position of the fused-heterocycle in Formula (I") is substituted by a group represented by the following formula

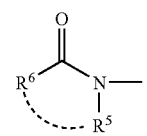

wherein, each symbol has the same meaning as described above, (26') the compound as described in (20') wherein ring A is a benzene ring further having 1 to 3 $C_{1-6}$ alkyl groups in addition to a group represented by the following formula

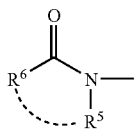

wherein, each symbol has the same meaning as described above, (27') a prodrug of the compound as described in (20'), (28') a drug comprising the compound as described in (20') or the prodrug as described in (27'), (29') a pharmaceutical composition comprising the compound as described in (20') or the prodrug as described in (27') and a pharmaceutically acceptable carrier.

According to the present invention, an excellent cannabinoid receptor modulator is provided. In addition, a novel compound represented by the above-mentioned Formula (I') and (I") or a salt thereof is provided.

DETAILED DESCRIPTION OF THE INVENTION

The compound represented by Formula ($I_0$) or a salt thereof [hereinafter, it may be abbreviated as Compound ($I_0$).] is preferably the compound represented by Formula (I) [hereinafter, it may be abbreviated as Compound (I).] or a salt thereof. As mentioned above, the compounds represented by Formula (I') and (I") or a salt thereof which are contained in Compound ($I_0$) and Compound (I), are novel compounds [hereinafter, the compound represented by Formula (I') will be explained, but explanations for the compound represented by Formula (I') are also applied to the compound represented by Formula (I"). Further, the compound represented by Formula (I') or a salt thereof may be abbreviated as Compound (I').].

The acylamino group represented by $R^0$ in the above-mentioned formulas is, for example, an acylamino group represented by the following formula

wherein, Y is —CO—, —SO—, or —$SO_2$—, $R^5$ is a hydrogen atom or an optionally substituted hydrocarbon group, $R^6$ is a hydrogen atom, an optionally substituted hydrocarbon group, an optionally substituted hydroxyl group or an optionally substituted amino group, or $R^5$ and $R^6$ may be taken with an adjacent carbon atom or a sulfur atom and a nitrogen atom to form an optionally substituted ring, etc.

As used herein, Y is preferably —CO—, $R^5$ is preferably a hydrogen atom, etc., and $R^6$ is preferably an optionally substituted hydrocarbon group or an optionally substituted amino group, etc.

The hydrocarbon group of the "optionally substituted hydrocarbon group" represented by $R^5$, $R^6$ and $R^{6'}$ is, for example, a chain or cyclic hydrocarbon group (e.g., alkyl, alkenyl, alkynyl, cycloalkyl, cycloalkenyl, cycloalkandienyl, aryl, etc.) or a combined group thereof (e.g., $C_{7-14}$ aralkyl such as benzyl; $C_{2-6}$alkyl-$C_{6-14}$ aryl such as ethylphenyl, propylphenyl, etc.; $C_{2-6}$alkenyl-$C_{6-14}$ aryl such as vinylphenyl, isopropenylphenyl, etc.), or the like. Among these, a $Cl_{16}$ chain or cyclic hydrocarbon group, etc. are preferred. Among these, alkyl is preferred for $R^6$.

The "alkyl" is preferably, for example, $C_{1-10}$ alkyl (e.g., methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methylheptyl, nonyl, etc.), or the like. Among these, $C_{1-6}$ alkyl is further preferred, and $C_{1-4}$ alkyl is especially preferred for $R^5$. On the other hand, $C_{2-10}$ alkyl is further preferred, and $C_{2-6}$alkyl is especially preferred for $R^6$.

The "alkenyl" is preferably, for example, $C_{2-6}$ alkenyl (e.g., vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc.), or the like.

The "alkynyl" is preferably, for example, $C_{2-6}$ alkynyl (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc.), or the like.

The "cycloalkyl" is preferably, for example, $C_{3-6}$ cycloalkyl (e.g., cyclopropyl, cyclobutyl, cyclopentyl, cyclohexyl, etc.), or the like.

The "cycloalkenyl" is preferably, for example, $C_{3-6}$ cycloalkenyl (e.g., 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, etc.), or the like.

The "cycloalkandienyl" is preferably, for example, $C_{5-6}$ cycloalkandienyl (e.g., 2,4-cyclopentandien-1-yl, 2,4-cyclohexandien-1-yl, 2,5-cyclohexandien-1-yl, etc.), or the like.

The "aryl" is preferably, for example, $C_{6-14}$ aryl (e.g., phenyl, 1-naphthyl, 2-naphthyl, biphenylyl, anthryl, etc.), or the like.

The "aralkyl" is preferably, for example, $C_{6-14}$ aryl-$C_{1-6}$ alkyl group (e.g., benzyl, α-methylbenzyl, etc.), or the like.

The "substituent" of the "optionally substituted hydrocarbon group" is preferably, for example, (1) a halogen atom (e.g., fluorine, chlorine, bromine, iodine, etc.), (2) $C_{1-3}$ alkylenedioxy (e.g., methylenedioxy, ethylenedioxy, etc.), (3) nitro, (4) cyano, (5) an optionally halogenated or hydroxylated $C_{1-6}$ alkyl, (6) an optionally halogenated $C_{2-6}$ alkenyl, (7) an optionally halogenated $C_{2-6}$ alkynyl, (8) an optionally halogenated $C_{3-6}$ cycloalkyl, (9) $C_{6-14}$ aryl (e.g., phenyl, 1-naphthyl, 2-naphthyl, biphenylyl, anthryl, etc.), (10) an optionally halogenated or acylated $C_{1-6}$ alkoxy, (11) an optionally halogenated $C_{1-6}$ alkylthio or mercapto, (12) hydroxy, (13) amino, (14) mono-$C_{1-6}$ alkylamino (e.g., methylamino, ethylamino, etc.), (15) mono-$C_{6-14}$ arylamino (e.g., phenylamino, 1-naphthylamino, 2-naphthylamino, etc.), (16) di-$C_{1-6}$ alkylamino (e.g., dimethylamino, diethylamino, etc.), (17) di-$C_{6-14}$ arylamino (e.g., diphenylamino, etc.), (18) acyl, (19) acylamino, (20) acyloxy, (21) an optionally substituted 5- to 7-membered saturated cyclic amino, (22) a 5- to 10-membered heterocyclic group (e.g., 5- to 10-membered aromatic heterocyclic group such as 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, etc.; a 5- to 10-membered non-aromatic heterocyclic group such as 1,3-dioxolan-2-yl, etc.), (23) sulfo, (24) $C_{6-14}$ aryloxy (e.g., phenyloxy, naphthyloxy, etc.) or (25) oxo, etc.

The "hydrocarbon group" may have, for example, the 1 to 5, preferably 1 to 3 above-mentioned substituents at any substitutable position, and if the number of substituent is two or more, each substituent is the same or different.

The above-mentioned "optionally halogenated or hydroxylated $C_{1-6}$ alkyl" is, for example, $C_{1-6}$ alkyl (e.g., methyl, ethyl, propyl, isopropyl, butyl, isobutyl, sec-butyl, tert-butyl, pentyl, hexyl, etc.) which may be substituted with 1 to 5, preferably 1 to 3 halogen atoms (e.g., fluorine, chlorine, bromine, iodine, etc.) or hydroxyl group, etc. Specific examples are methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

The above-mentioned "optionally halogenated $C_{2-6}$ alkenyl" is, for example, $C_{2-6}$ alkenyl (e.g., vinyl, allyl, isopropenyl, butenyl, isobutenyl, sec-butenyl, etc.) which may be substituted with 1 to 5, preferably 1 to 3 halogen atoms (e.g., fluorine, chlorine, bromine, iodine, etc.), or the like. Specific examples are vinyl, allyl, isopropenyl, butenyl, isobutenyl, sec-butenyl, 3,3,3-trifluoro-1-propenyl, 4,4,4-trifluoro-1-butenyl, etc.

The above-mentioned "optionally halogenated $C_{2-6}$ alkynyl" is, for example, $C_{2-6}$ alkynyl (e.g., ethynyl, propargyl, butynyl, 1-hexynyl, etc.) which may be substituted with 1 to 5, preferably 1 to 3 halogen atoms (e.g., fluorine, chlorine, bromine, iodine, etc.), or the like. Specific examples are ethynyl, propargyl, butynyl, 1-hexynyl, 3,3,3-trifluoro-1-propynyl, 4,4,4-trifluoro-1-butynyl, etc.

The above-mentioned "optionally halogenated $C_{3-6}$ cycloalkyl" is, for example, $C_{3-6}$ cycloalkyl (e.g., cyclopropyl, cyclobutyl, cyclopentyl, cyclohexyl, etc.) which may be substituted with 1 to 5, preferably 1 to 3 halogen atoms (e.g., fluorine, chlorine, bromine, iodine, etc.), or the like. Specific examples are cyclopropyl, cyclobutyl, cyclopentyl, cyclohexyl, 4,4-dichlorocyclohexyl, 2,2,3,3-tetrafluorocyclopentyl, 4-chlorocyclohexyl, etc.

The above-mentioned "optionally halogenated, hydroxylated, alkoxylated or acylated $C_{1-6}$ alkoxy" is, for example, $C_{1-6}$ alkoxy (e.g., methoxy, ethoxy, propoxy, isopropoxy, butoxy, isobutoxy, sec-butoxy, pentyloxy, hexyloxy, etc.) which may be substituted with 1 to 5, preferably 1 to 3 substituents selected from a halogen atom (e.g., fluorine, chlorine, bromine, iodine, etc.), a hydroxyl group, a $C_{1-6}$ alkoxy group (e.g., methoxy, ethoxy, etc.), or an acyl group (e.g., $C_{1-6}$ alkyl-carbonyl such as acetyl and propionyl; $C_{1-6}$ alkoxy-carbonyl such as methoxycarbonyl and ethoxycarbonyl), etc. Specific examples are methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.

The above-mentioned "optionally halogenated $C_{1-6}$ alkylthio." is, for example, $C_{1-6}$ alkylthio (e.g., methylthio, ethylthio, propylthio, isopropylthio, butylthio, sec-butylthio, tert-butylthio, etc.) which may be substituted with 1 to 5, preferably 1 to 3 halogen atoms (e.g., fluorine, chlorine, bromine, iodine, etc.), or the like. Specific examples are methylthio, difluoromethylthio, trifluoromethylthio, ethylthio, propylthio, isopropylthio, butylthio, 4,4,4-trifluorobutylthio, pentylthio, hexylthio, etc.

The above-mentioned "acyl" is, for example, formyl, carboxyl, carbamoyl, $C_{1-6}$ alkyl-carbonyl (e.g., acetyl, propionyl, etc.), $C_{3-6}$ cycloalkyl-carbonyl (e.g., cyclopropylcarbonyl, cyclopentylcarbonyl, cyclohexylcarbonyl, etc.), $C_{1-6}$ alkoxy-carbonyl (e.g., methoxycarbonyl, ethoxycarbonyl, propoxycarbonyl, tert-butoxycarbonyl, etc.), $C_{6-14}$ aryl-carbonyl (e.g., benzoyl, 1-naphthoyl, 2-naphthoyl, etc.), $C_{7-16}$ aralkyl-carbonyl (e.g., phenylacetyl, phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, phenethyloxycarbonyl, etc.), 5- or 6-membered heterocyclic carbonyl (e.g., nicotinoyl, isonicotinoyl, 2-tenoyl, 3-tenoyl, 2-furoyl, 3-furoyl, morpholinocarbonyl, thiomorpholinocarbonyl, piperidinocarbonyl, 1-pyrrolidinylcarbonyl, etc.), mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-14}$ arylcarbamoyl (e.g., phenylcarbamoyl, 1-naphthylcarbamoyl, 2-naphthylcarbamoyl, etc.), thiocarbamoyl, 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), $C_{1-6}$ alkylsulfonyl (e.g., methylsulfonyl, ethylsulfonyl, etc.), $C_{6-14}$ arylsulfonyl (e.g., phenylsulfonyl, 1-naphthylsulfonyl, 2-naphthylsulfonyl, etc.), $C_{1-6}$ alkylsulfinyl (e.g., methylsulfinyl, ethylsulfinyl, etc.), $C_{6-14}$ arylsulfinyl (e.g., phenylsulfinyl, 1-naphthylsulfinyl, 2-naphthylsulfinyl, etc.), or the like.

The above-mentioned "acylamino" is, for example, formylamino, $C_{1-6}$ alkyl-carbonylamino (e.g., acetylamino, etc.), $C_{6-14}$ aryl-carbonylamino (e.g., phenylcarbonylamino, naphthylcarbonylamino, etc.), $C_{1-6}$ alkoxy-carbonylamino (e.g., methoxycarbonylamino, ethoxycarbonylamino, propoxycarbonylamino, butoxycarbonylamino, etc.), $C_{1-6}$ alkylsulfonylamino (e.g., methylsulfonylamino, ethylsulfonylamino, etc.), $C_{6-14}$ arylsulfonylamino (e.g., phenylsulfonylamino, 2-naphthylsulfonylamino, 1-naphthylsulfonylamino, etc.), or the like.

The above-mentioned "acyloxy" is, for example, $C_{1-6}$ alkyl-carbonyloxy (e.g., acetoxy, propionyloxy, etc.), $C_{6-14}$ aryl-carbonyloxy (e.g., benzoyloxy, naphthylcarbonyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-14}$ aryl-carbamoyloxy (e.g., phenylcarbamoyloxy, naphthylcarbamoyloxy, etc.), nicotinoyloxy, etc.

The above-mentioned "optionally substituted 5- to 7-membered saturated cyclic amino" of the "5- to 7-membered saturated cyclic amino" is, for example, morpholino, thiomorpholino, piperazin-1-yl, piperidino, pyrrolidin-1-yl, etc. The "substituent" of the "optionally substituted 5- to 7-membered saturated cyclic amino" is, for example, $C_{1-6}$ alkyl (e.g., methyl, ethyl, propyl, isopropyl, butyl, isobutyl, sec-butyl, tert-butyl, pentyl, hexyl, etc.), $C_{6-14}$ aryl (e.g., phenyl, 1-naphthyl, 2-naphthyl, biphenylyl, 2-anthryl, etc.), 5- to 10-membered aromatic heterocyclic group (e.g., 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo [b]thienyl, benzo[b]furanyl, etc.), or the like. The "5- to 7-membered saturated cyclic amino" may have 1 to 3 substituents.

The substituent in the "optionally substituted hydroxyl group" and the "optionally substituted amino group" represented by $R^6$ and $R^{6'}$ are, for example, one as defined in the "optionally substituted hydrocarbon group" represented by $R^5$ and $R^6$ and the substituent thereof. The "amino group" may have 1 to 2 substituents.

The "ring" that $R^5$ and $R^6$ may be taken with the adjacent carbon atom and the nitrogen atom to form is, for example, a 5- to 7-membered saturated or non-saturated nitrogen-containing heterocycle which may contain 1 to 2 heteroatoms selected from an oxygen atom, a sulfur atom and a nitrogen atom, etc. as a ring-constituting atom in addition to nitrogen atom (e.g., pyrrolidin-2-one, thiazolidin-2-one, thiazolidin-4-one, oxazolidin-2-one, oxazolidin-4-one, imidazolidin-2-one, imidazolidin-4-one, piperidin-2-one, thiazinan-4-one, thiomorpholin-3-one, azepan-2-one, dihydropyrrol-2-one, dihydropyridine-2-one, pyridine-2-one, tetrahydroazepin-2-one, dihydroazepin-2-one, etc.), or the like. The heteroatom in the "nitrogen-containing heterocycle" is preferably 1 to 2 kinds. This "ring" may have further substituent in addition to oxo group. The "substituent" is, for example, one as defined in the substituent of the "optionally substituted hydrocarbon group" represented by $R^5$ and $R^6$. The number of the "substituent" is, for example, 1 to 5 (preferably 1 to 3, further preferably is 1 to 2).

The substituent that ring $A_0$ in the above-mentioned formulas may further have in addition to $R^0$, the substituent that ring A in the above-mentioned formulas may further have in addition to a group represented by the following formula

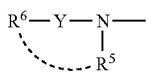

wherein, each symbol has the same meaning as described above, and the substituent that ring A' in the above-mentioned formulas may further have in addition to a group represented by the following formula

wherein, each symbol has the same meaning as described above (hereinafter, these may be referred to simply as the substituent that ring A, etc. may further have) are, for example, an optionally substituted hydrocarbon group, an optionally substituted heterocyclic group, an acyl group, an optionally substituted hydroxyl group, an optionally substituted amino group, a halogen atom (e.g., fluorine, chlorine, bromine, iodine), or dihydroxyboryl, etc. The "optionally substituted hydrocarbon group", the "optionally substituted hydroxyl group" and the "optionally substituted amino group" are, for example, one as defined in the "optionally substituted hydrocarbon group", the "optionally substituted hydroxyl group" and the "optionally substituted amino group", respectively represented by $R^6$. The "optionally substituted heterocyclic group" is, for example, one as defined in the "optionally substituted heterocyclic group" as the "substituent of optionally substituted 5-membered heterocycle represented by ring B" in the below. The "acyl group" is exemplified by those for the acyl group in the acylamino represented by $R^0$:$R^6$—Y—.

Among these, the substituent that ring A, etc. may further have, is preferably an optionally substituted $C_{1-6}$ alkyl group, an optionally substituted $C_{6-12}$ aryl group, an optionally substituted 5- or 6-membered heterocyclic group, or an acyl group. Especially, when 7-position (in the following formula, represented by number 7.) of the fused-heterocycle in Formula ($I_0$), Formula (I) and Formula (I') is substituted by the substituent that ring A, etc. may further have, an optionally substituted $C_{6-14}$ aryl-$C_{1-6}$ alkyl group is also preferred. The "$C_{6-14}$ aryl-$C_{1-6}$ alkyl group" of the "optionally substituted $C_{6-14}$ aryl-$C_{1-6}$ alkyl group" is, for example, benzyl, α-meth-ylbenzyl, etc., and the substituent thereof is, for example, one as defined in the substituent of the "optionally substituted hydrocarbon group" represented by $R^6$.

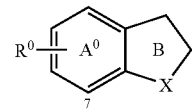

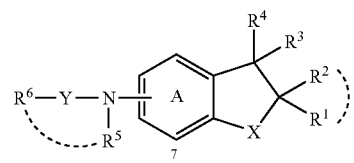

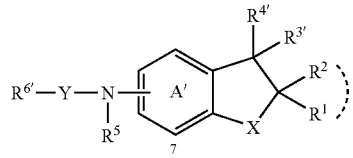

The number of the "substituent" that ring A, etc. may further have is, for example, 1 to 3 (preferably 2 to 3). When the number of the "substituent" that ring A, etc. may further have is 2 or more, 2 substituents among them may form an optionally substituted 5 to 6-membered ring with the carbon atom to which they are bonded. The "5 to 6-membered ring" is preferably a saturated or non-saturated $C_{5-6}$ carbonic ring. The substituent of the "5 to 6-membered ring" is, for example, a $C_{1-6}$ alkyl group, a $C_{1-6}$ alkoxy group, a nitro group, a hydroxyl group, an amino group or a halogen atom, etc.

The "optionally substituted 5-membered heterocycle" represented by ring B in the above-mentioned formulas is preferably a ring represented by the following formula

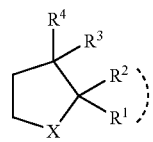

wherein, each symbol is as defined in Formula (I). As used herein, when $R^2$ and $R^3$ are taken together to represent a bond, this ring is, 5-membered ring represented by the following formula

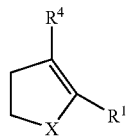

wherein, each symbol is as defined in Formula (I).

The "optionally substituted sulfur atom" represented by X in the above-mentioned formulas is preferably a non-substituted sulfur atom or an oxidized sulfur atom (e.g., SO, $SO_2$). Further, the substituent of the "optionally substituted imino group" represented by X in the above-mentioned formulas is, for example, a $C_{1-6}$ alkyl group or a $C_{2-6}$ alkenyl group which may be substituted with a halogen atom, a cyano group, a nitro group or a hydroxyl group, respectively.

In other words, a 5-membered heterocycle of the "optionally substituted 5-membered heterocycle" represented by ring B is, for example, dihydropyrrole, ethene, pyrrole, dihydrothiophene, dihydrothiophene-1-oxide, dihydrothiophene-1,1-dioxide, thiophene, dihydrofuran or furan.

The substituent of the "optionally substituted 5-membered heterocycle" in the above-mentioned formulas represented by ring B is, for example, an optionally substituted hydrocarbon group, an optionally substituted hydroxyl group, an optionally substituted amino group, an optionally substituted heterocyclic group, or an optionally substituted mercapto group, etc. Ring B may have 1 to 5 (preferably 2 to 4) substituents. When ring B is non-substituted, ring A, ring $A_0$, and ring A' are preferably substituted with the above-mentioned "optionally substituted $C_{6-14}$ aryl-$C_{1-6}$ alkyl group" at 7-position of the fused-heterocycle in Formula ($I_0$), Formula (I) and Formula (I'), respectively.

The "optionally substituted hydrocarbon group", the "optionally substituted hydroxyl group", and the "optionally substituted amino group" are, for example, ones as defined in the "optionally substituted hydrocarbon group", the "optionally substituted hydroxyl group", and the "optionally substituted amino group" represented by $R^6$, respectively.

The "heterocyclic group" of the "optionally substituted heterocyclic group" is preferably a 5- to 14-membered heterocyclic group. The 5- to 14-membered heterocyclic group is, for example, a 5- to 14-membered heterocyclic group (aromatic heterocyclic group, saturated or non-saturated non-aromatic heterocyclic group) containing at least 1 (preferably 1 to 4) of one to three kinds of heteroatoms selected from nitrogen atom, sulfur atom and oxygen atom in addition to carbon atom, etc.

The "aromatic heterocyclic group" is, for example, a 5- to 14-membered (preferably 5- to 10-membered) aromatic heterocyclic group containing at least 1 heteroatoms selected from a nitrogen atom, a sulfur atom and an oxygen atom (for example, 1 to 4) in addition to a carbon atom, etc. Specific examples are aromatic heterocycle such as thiophene, benzothiophene, benzofuran, benzimidazole, benzoxazole, benzothiazole, benzisothiazole, naphtho[2,3-b]thiophene, furan, isoindolidine, xanthrene, phenoxathine, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthiridine, quinoxaline, quinazoline, cinnoline, carbazole, β-carboline, phenanthridine, acrydine, phenazine, thiazole, isothiazole, phenothiazine, oxazole, isoxazole, furazane, phenoxazine, etc., or a group obtained by subtracting any one hydrogen atom from a ring which is formed by fusion of such ring (s) (preferably, single ring) with one or more (preferably 1 or 2) aromatic ring (e.g., benzene ring, etc.), or the like. The examples include 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, 2- or 3-thienyl, etc.

The "non-aromatic heterocyclic group" is, for example, a 3 to 8-membered (preferably 5- or 6-membered) saturated or non-saturated non-aromatic heterocyclic group such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc.

The substituent of the "optionally substituted heterocyclic group" is, for example, one as defined in the "optionally substituted hydrocarbon group" represented by $R^5$ and $R^6$.

The substituent of the "optionally substituted mercapto group" is, for example, one as defined in the substituent of the "optionally substituted hydrocarbon group" represented by $R^5$ and $R^6$.

The optional substituent of these groups may be substituted in the number of 1 to 5 (preferably 1 to 4, further preferably 1 to 2) at any substitutable position.

The "optionally substituted hydrocarbon group", the "optionally substituted heterocyclic group", the "optionally substituted hydroxyl group", the "optionally substituted mercapto group" and the "optionally substituted amino group" represented by $R^1$, $R^2$, $R^3$, $R^3$ and $R^4$ in the above-mentioned formulas are, for example, ones as defined in the substituent of the "optionally substituted 5-membered heterocycle" represented by ring B.

Among these, a hydrogen atom, a $C_{1-4}$ alkyl group (e.g., methyl, ethyl, propyl, isopropyl, butyl, isobutyl, sec-butyl, tert-butyl, etc.), or the like, are preferred respectively for $R^1$, $R^2$, $R^3$, and $R^{3'}$. A hydrogen atom, etc. are further preferred for $R^3$ and $R^{3a}$.

In addition, among these, an optionally substituted alkyl group, an optionally substituted aryl group, and an optionally substituted heterocyclic group, etc. are preferred for $R^4$.

The "alkyl group" of the "optionally substituted alkyl group" is, for example, one as defined in the "alkyl group" exemplified for $R^5$, $R^6$ and $R^{6'}$. The substituent of the "optionally substituted alkyl group" is, for example, one as defined in the "substituent" of the "optionally substituted hydrocarbon group" which is a substituent of the "optionally substituted 5-membered heterocycle" represented by ring B.

The "aryl group" of the "optionally substituted aryl group" (and the "optionally substituted aryl group" represented by $R^{4'}$) is, for example, $C_{6-14}$ aryl (e.g., phenyl, 1-naphthyl, 2-naphthyl, biphenylyl, anthryl, etc.), or the like. The substituent of the "optionally substituted aryl group" is, for example, one as defined in the "substituent" of the "optionally substituted hydrocarbon group" which is a substituent of the "optionally substituted 5-membered heterocycle" represented by ring B.

The heterocyclic group of the "optionally substituted heterocyclic group" (and the "optionally substituted heterocyclic group" represented by $R^{4'}$) is, for example, one as defined in the "optionally substituted heterocyclic group" as substituent of the "optionally substituted 5-membered heterocycle" represented by ring B.

$R^4$ (and $R^{4'}$) is especially preferably an optionally substituted phenyl group, and most preferably, a phenyl group which may be substituted with an optionally substituted $C_{1-4}$ alkyl group (e.g., methyl, ethyl, n-propyl, isopropyl, n-butyl, isobutyl, sec-butyl, tert-butyl) or an optionally substituted $C_{1-4}$ alkoxy group (e.g., methoxy, ethoxy, propoxy, isopropoxy, butoxy, isobutoxy, sec-butoxy). The "$C_{1-4}$ alkyl group" and the "$C_{1-4}$ alkoxy group" are preferably substituted at 4-position of the phenyl group. The "substituent" of the "optionally substituted $C_{1-4}$ alkyl group" and the "optionally substituted $C_{1-4}$ alkyl group" as substituent is, for example, a nitro group, a hydroxyl group, an amino group or a halogen atom, etc.

The ring of the "optionally substituted ring" that $R^1$ and $R^2$ may be taken with the adjacent carbon atom to form is, for example, a 3- to 8-membered homo- or heterocycle.

The "3- to 8-membered homocycle" is, for example, $C_{3-8}$cycloalkane, etc.

The "3- to 8-membered heterocycle" is, for example, a 3- to 8-membered heterocycle containing 1 to 4 heteroatoms selected from nitrogen atom, sulfur atom and oxygen atom in addition to carbon atom (e.g., aziridine, azetidine, morpholine, thiomorpholine, piperazine, piperidine, pyrrolidine, hexamethyleneimine, heptamethyleneimine, hexahydropyrimidine, etc.).

The "substituent" of the "optionally substituted ring" that $R^1$ and $R^2$ may form with the adjacent carbon atom is, for example, one as defined in the "substituent" of the "optionally substituted hydrocarbon group" represented by the abovementioned $R^5$ and $R^6$, of the same number.

The 5-positions of the fused-heterocycle in Formula ($I_0$), Formula (I) and Formula (I'), are preferably substituted by a group represented by $R_0$,

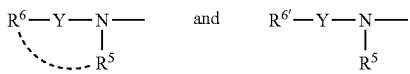

wherein, each symbol has the same meaning as described above, respectively. In other words, the compounds represented by Formula ($I_0$), Formula (I) and Formula (I'), respectively are preferably,

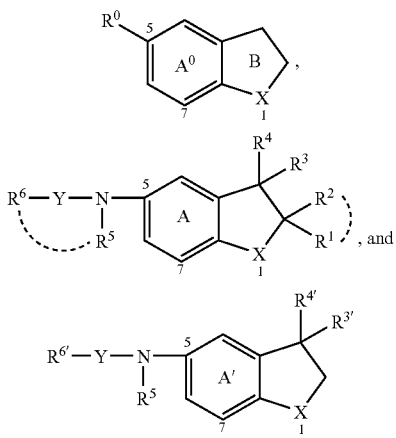

wherein, numbers around the rings indicate position number, respectively.

Salts of the compounds represented by Formula ($I_0$), Formula (I), and Formula (I') (hereinafter, they may be abbreviated as Compound (I), etc.) include salts with an inorganic base (e.g., alkali metals such as sodium and potassium and alkaline earth metals such as calcium and magnesium, transitional metals such as zinc, iron and copper, etc.) or with an organic base (e.g., organic amines such as trimethylamine, triethylamine, pyridine, picoline, ethanolamine, diethanolamine, triethanolamine, dicyclohexylamine and N,N'-dibenzylethylenediamine or with basic amino acids such as arginine, lysine, ornithine, etc.), or the like when Compound (I) has an acidic group such as a carboxyl group.

On the other hand, when Compound (I), etc. have a basic group such as an amino group, etc., such salts include salts with inorganic acids and organic acids (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.), acidic amino acids such as asparaginic acid, glutamic acid, etc.

The prodrug of Compound (I), etc. means a compound which is converted to Compound (I), etc. under the physiological condition by a reaction by an enzyme, an gastric acid, etc. in the living body, that is, by enzymatic oxidation, reduction, hydrolysis, etc.; by hydrolysis with gastric acid, etc. Examples of the prodrug of Compound (I), etc. include a compound wherein the amino group of Compound (I), etc. is acylated, alkylated or phosphorylated (e.g., a compound wherein the amino group of Compound (I), etc. is eicosanylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated); a compound wherein the hydroxyl group of Compound (I), etc. is acylated, alkylated, phosphorylated or converted into borate (e.g., a compound wherein the hydroxyl group of Compound (I), etc. is acetylated, palmitoylated, propanoylated, pivaloylated, succinylated, fumarylated, alanylated or dimethylaminomethylcarbonylated); a compound wherein a carboxyl group of Compound (I), etc. is esterified or amidated (e.g., a compound wherein a carboxyl group of Compound (I), etc. is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, methylamidated, etc.); etc. These prodrugs can be produced by per se known methods from Compound (I), etc.

In addition, the prodrug of Compound (I), etc. may be a compound which is converted into Compound (I), etc. under the physiological conditions as described in "Pharmaceutical Research and Development", Vol. 7 (Drug Design), pp. 163-198 published in 1990 by Hirokawa Publishing Co.

Hereinafter, the methods of producing Compound (I), etc. of the present invention will be explained.

Compound (I), etc. of the present invention can be produced by the methods below or analogous methods thereto.

In the following Reaction Schemes, each symbol of the compounds has the same meaning unless otherwise stated. The compounds in Reaction Scheme include salts thereof, and the salts are, for example, ones as defined in Compound (I), etc.

Compound (I) can be produced by a method described in the following Reaction Scheme 1.

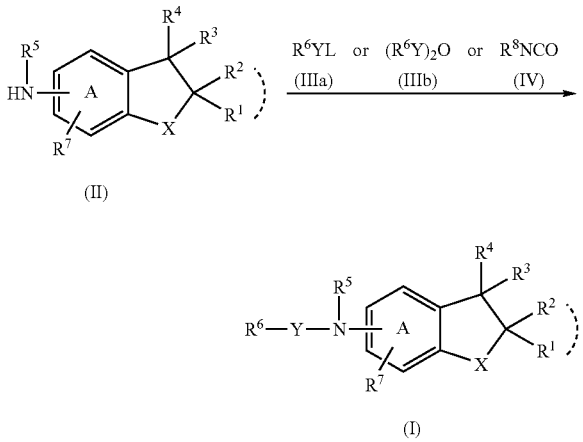

In Reaction Scheme 1, L is a leaving group, R$^7$ is a substituent that ring A may further have in addition to a group represented by the following formula

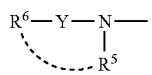

wherein, each symbol has the same meaning as described above, or a corresponding group thereto, R$^8$ is a group formed by subtracting a NH group from an optionally substituted amino group represented by R$^6$, and other symbols have the same meanings as defined above.

Compound (I) can be produced by reacting Compound (II) with Compound (IIIa), Compound (IIIb) or Compound (IV), if desired, under the presence of base or acid.

Compound (IIIa), Compound (IIIb) or Compound (IV) is commercially available, and further can be produced by per se known methods or analogous methods thereto.

The "leaving group" represented by L is, for example, hydroxy, a halogen atom (for example, fluorine, chlorine, bromine, iodine, etc.), optionally halogenated $C_{1-5}$ alkylsulfonyloxy (e.g., methanesulfonyloxy, ethanesulfonyloxy, trichloromethanesulfonyloxy, etc.), optionally substituted $C_{6-10}$ arylsulfonyloxy, optionally substituted phenyloxy group, optionally substituted 2-thiobenzothiazole, etc. The "optionally substituted $C_{6-10}$ arylsulfonyloxy" is, for example, $C_{6-10}$ arylsulfonyloxy (e.g., phenylsulfonyloxy, naphthylsulfonyloxy, etc.) which may have 1 to 3 substituents selected from $C_{1-6}$ alkyl (e.g., methyl, ethyl, propyl, isopropyl, butyl, isobutyl, sec-butyl, tert-butyl, pentyl, hexyl, etc.), $C_{1-6}$ alkoxy (e.g., methoxy, ethoxy, propoxy, isopropoxy, butoxy, isobutoxy, sec-butoxy, pentyloxy, hexyloxy, etc.) or nitro, etc., specifically, benzenesulfonyloxy, m-nitrobenzenesulfonyloxy, p-toluenesulfonyloxy, etc.

Compound (IIIa), Compound (IIIb) or Compound (IV) is used in an amount of about 1.0 to 10 moles, preferably about 1.0 to 2.0 moles, relative to 1 mole of Compound (II).

The "base" is, for example, basic salts such as sodium carbonate, potassium carbonate, cecium carbonate, sodium hydrogen carbonate, etc., aromatic amines such as pyridine, lutidine, etc., tertiary amines such as triethylamine, tripropylamine, tributylamine, cyclohexyldimethylamine, 4-dimethylaminopyridine, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., metal alkoxides such as sodium methoxide, sodium ethoxide, potassium tert-butoxide, etc., or the like.

The "acid" is, for example, methanesulfonic acid, p-toluenesulfonic acid, camphor-sulfonic acid, etc.

The "base" is used in an amount of about 0.1 to 10 equivalents, preferably 0.8 to 2 equivalents, relative to Compound (II).

The "acid" is used in an amount of about 0.1 to 10 equivalents, preferably 0.8 to 3 equivalents, relative to Compound (II).

The present reaction is advantageously carried out without a solvent or with a solvent inert to the reaction. Such solvents are not particularly limited if the reaction proceeds, and include, for example, water, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., nitrogen-containing aromatic hydrocarbons such as pyridine, lutidine, quinoline, etc. or mixed solvent thereof. The reaction temperature is about −40 to 150° C., preferably 0 to 100° C. The reaction time is usually 5 minutes to 24 hours, preferably 10 minutes to 5 hours.

Thus obtained product (I) may be isolated from the reaction mixture by a conventional method, and easily purified by conventional means of separation such as recrystallization, distillation, chromatography, etc.

Alternatively, Compound (II) and Compound (IIIa) may be reacted under the presence of a suitable condensing agent reaction.

Compound (IIIa) is used in an amount of about 0.8 to about 10.0 moles, preferably about 0.8 to about 2.0 moles, relative to 1 mole of Compound (II).

The "condensing agent" is, for example, N,N'-dicarbodiimides such as N,N'-dicyclohexylcarbodiimide, 1-ethyl-3-(3-dimethylaminopropyl)carbodiimide (WSC) hydrochloride, etc., azolides such as N,N'-carbonylimidazole, etc., a dehydrating agent such as N-ethoxycarbonyl-2-ethoxy-1,2-dihydroquinoline, diethyl cyanophosphate, phosphorus oxychloride, anhydrous acetic acid, etc., a 2-halogenopyridinium salt such as 2-chloromethylpyridinium iodide, 2-fluoro-1-chloromethylpyridinium iodide, etc.

The condensing agent is used in an amount of about 0.8 to about 5.0 moles, preferably about 1.0 to about 3.0 moles, relative to 1 mole of Compound (II).

In addition, if desired, the reaction may be conducted under the coexistence of base with the condensing agent.

The "base" is, for example, basic salts such as potassium acetate, sodium acetate, etc., tertiary amines such as triethylamine, tripropylamine, tributylamine, cyclohexyldimethylamine, 4-dimethylaminopyridine, N-methylpiperidine, N-methylpyrrolidine, N-methylmorpholine, etc., or 1-hydroxy-1H-benzotriazole (HOBt) monohydrates, etc. The base is used in an amount of about 0.5 to about 5.0 moles, preferably about 2.0 to about 3.0 moles, relative to 1 mole of Compound (II).

The present reaction is advantageously carried out using an inert solvent. Such solvents are, for example, alcohols such as methanol, ethanol, propanol, etc., hydrocarbons such as hexane, cyclohexane, benzene, toluene, xylene, etc., ethers such as diethyl ether, diisopropyl ether, tetrahydrofuran, dioxane, 1,2-dimethoxyethane, etc., amides such as N,N-dimethylformamide, N,N-dimethylacetamide, hexamethylphosphoric triamide, etc., sulfoxides such as dimethylsulfoxide, etc., halogenated carbons such as dichloromethane, chloroform, tetrachlorocarbon, 1,2-dichloroethane, etc., nitriles such as acetonitrile, propionitrile, etc., acid anhydrides such as acetic anhydride, etc., or a mixed solvent thereof, or the like.

The reaction time is usually about 10 minutes to about 48 hours, preferably about 30 minutes to about 24 hours. The reaction temperature is usually about −20 to about 150° C., preferably about 0 to about 100° C.

The product can be used in the next reaction as a reaction solution as is or a crude product, or can be isolated from the reaction mixture according to a conventional method, and easily purified by conventional means of separation (e.g., recrystallization, distillation, chromatography, etc.).

When R$^5$ is an optionally substituted alkyl group, Compound (I) can be produced according to a method described in the following Reaction Scheme 2.

Reaction Scheme 2

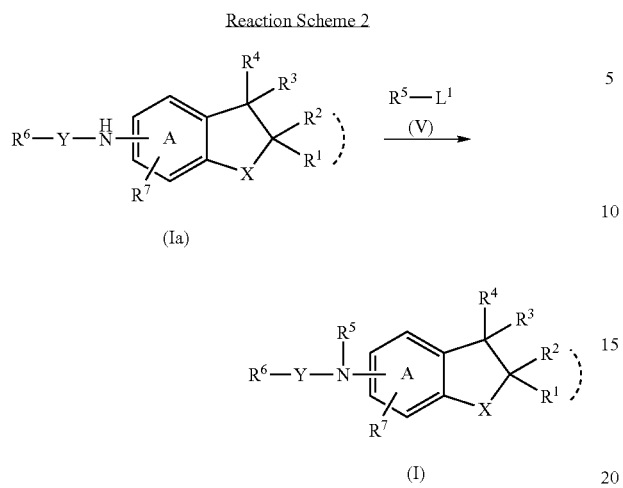

In Reaction Scheme 2, $L^1$ is a leaving group, and other symbols have the same meanings as defined above.

The "leaving group" represented by $L^1$ is, for example, hydroxy, a halogen atom (e.g., fluorine, chlorine, bromine, iodine, etc.), optionally halogenated $C_{1-5}$ alkylsulfonyloxy (e.g., methanesulfonyloxy, ethanesulfonyloxy, trichloromethanesulfonyloxy, etc.), optionally substituted $C_{6-10}$arylsulfonyloxy, etc.

Compound (Ia) is reacted with an alkylating agent (V) corresponding to Compound (I), if desired, under the presence of base.

The alkylating agent (V) is used in an amount of about 1.0 to about 10.0 moles, preferably about 1.0 to about 2.0 moles, relative to 1 mole of Compound (Ia).

The "base" is, for example, basic salts such as sodium carbonate, potassium carbonate, cecium carbonate, sodium hydrogen carbonate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., metal alkoxides such as sodium methoxide, sodium ethoxide, potassium tert-butoxide, etc., or the like.

The base is used in an amount of about 1.0 to about 10.0 moles, preferably about 1.0 to about 2.0 moles, relative to 1 mole of Compound (Ia).

The present reaction is advantageously carried out using a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The reaction time is usually about 30 minutes to about 48 hours, preferably about 1 hour to about 24 hours. The reaction temperature is usually about −20 to about 200° C., preferably about 0 to about 150° C.

In addition, Compound (Ib) which is contained in Compound (I), can be also produced by a method described in the following Reaction Scheme 3.

Reaction Scheme 3

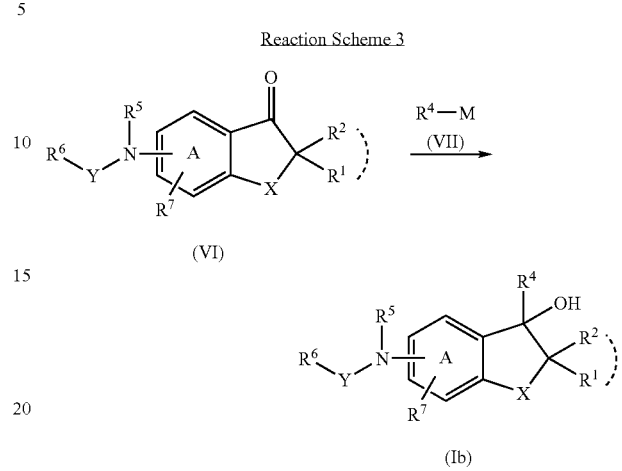

In Reaction Scheme 3, M is a metal and other symbols have the same meanings as defined above.

In the formula, an organic metallic Compound (VII) represented by $R^4$-M is commercially available, and further can be also produced by per se known methods, for example, the method described in Experimental Chemistry Lecture, 4$^{th}$ Ed., 25 (Japanese Society of Chemistry), Maruzen, Co., Ltd.

As shown in Reaction Scheme 3, Compound (Ib) is obtained by reacting Compound (VI) with the organic metallic Compound (VII).

The organic metallic Compound (VII) is preferably a Grignard reagent or an organic lithium reagent.

Compound (VII) is used in an amount of about 0.8 to about 30 moles, preferably about 1.0 to about 10 moles, relative to 1 mole of Compound (VI).

The present reaction is advantageously carried out without a solvent or with a solvent inert to the reaction. Such solvents are not particularly limited if the reaction proceeds, and include, for example, hydrocarbons such as hexane, cyclohexane, benzene, toluene, xylene, etc., ethers such as diethyl ether, diisopropyl ether, tetrahydrofuran, dioxane, 1,2-dimethoxyethane, etc., halogenated carbons such as dichloromethane, chloroform, tetrachlorocarbon, 1,2-dichloroethane, etc., or a mixed solvent thereof, or the like.

The reaction time is usually about 10 minutes to about 24 hours, preferably about 30 minutes to about 5 hours. The reaction temperature is usually about −100 to about 120° C., preferably about −80 to about 60° C.

The product can be used in the next reaction as a crude product, or can be isolated from the reaction mixture according to a conventional method, and easily purified by conventional means of separation (e.g., recrystallization, distillation, chromatography, etc.).

Compound (Ic) and Compound (Id), which are contained in Compound (I), can be produced by each method described in the following Reaction Scheme 4, respectively, from Compound (Ib) produced by the method described in Reaction Scheme 3, etc.

Reaction Scheme 4

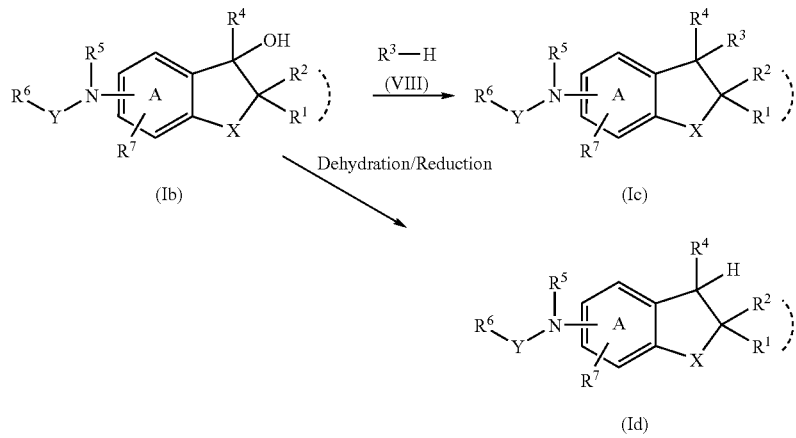

In Reaction Scheme 4, each symbol has the same meaning as defined above.

Compound (Ib) is subjected to known acylation, etherification, amination, halogenation, alkylation, or a combination of two or more of these reactions, to produce Compound (Ic).

For example, when $R^3$ is alkoxy (e.g., methoxy, ethoxy, phenoxy, etc.), Compound (Ib) is reacted with alcohol (e.g., methanol, ethanol, phenol, etc.) under the presence of acid catalyst to give Compound (Ic).

The "acid catalyst" is, for example, organic acids such as formic acid, acetic acid, trifluoroacetic acid, p-toluenesulfonic acid, etc., mineral acids such as sulfuric acid, hydrochloric acid, hydrobromic acid, etc., Lewis acids such as zinc chloride, etc.

The alcohol is used in an amount of about 0.8 moles to excessive amount, relative to 1 mole of Compound (Ib). The acid catalyst is used respectively in an amount of about 0.1 to about 100 moles, preferably about 0.1 to about 50 moles, relative to 1 mole of Compound (Ib).

The present reaction is advantageously carried out without a solvent or with a solvent inert to the reaction.

Such solvents are not particularly limited if the reaction proceeds, and include, for example, hydrocarbons such as hexane, cyclohexane, benzene, toluene, xylene, etc., ethers such as diethyl ether, diisopropyl ether, tetrahydrofuran, dioxane, 1,2-dimethoxyethane, etc., amides such as N,N-dimethylformamide, N,N-dimethylacetamide, hexamethylphosphoric triamide, etc., sulfoxides such as dimethylsulfoxide, etc., halogenated carbons such as dichloromethane, chloroform, tetrachlorocarbon, 1,2-dichloroethane, etc., nitriles such as acetonitrile, propionitrile, etc., or a mixed solvent thereof, or the like.

The reaction time is usually about 10 minutes to about 48 hours, preferably about 30 minutes to about 12 hours. The reaction temperature is usually about 0 to about 200° C., preferably about 25 to about 100° C.

The product can be used in the next reaction as the reaction solution itself or the crude product, or can be isolated from the reaction mixture according to a conventional method, and easily purified by conventional means of separation (e.g., recrystallization, distillation, chromatography, etc.).

In addition, Compound (Id) can be produced by subjecting Compound (Ib) to reductive dehydration.

The reductive dehydration is, for example, per se known catalytic reduction, a method in which an organosilyl reagent (an alkylsilane reagent, etc.) is used, etc.

In the catalytic reduction, Compound (Ib) is reacted with a metal catalyst under hydrogen atmosphere to produce Compound (Id). A suitable acid catalyst may be added, if desired.

The "metal catalyst" is, for example, Raney nickel, platinum oxide, metal palladium, palladium on activated carbon, etc. The "metal catalyst" is used respectively in an amount of usually about 0.1 to about 1000% by weight, preferably about 1 to about 20% by weight, relative to Compound (Ib).

The "acid catalyst" is, for example, organic acids such as formic acid, acetic acid, trifluoroacetic acid, p-toluenesulfonic acid, etc., mineral acids such as sulfuric acid, hydrochloric acid, hydrobromic acid, etc. The "acid catalyst" is used respectively in an amount of about 0.1 to excessive amount, relative to 1 mole of Compound (Ib).

The present reaction is advantageously carried out using a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., organic acids such as acetic acid, etc., water, etc., or a mixed solvent thereof, or the like. The hydrogen pressure is usually about 1 to about 100 atm., preferably about 1 to about 5 atm. The reaction time is usually about 30 minutes to about 48 hours, preferably about 1 to 24 hours. The reaction temperature is usually about 0 to about 120° C., preferably about 20 to about 80° C.

After the catalyst is removed, the product may be isolated from the reaction mixture according to a conventional method, and easily purified by conventional means of separation (e.g., recrystallization, distillation, chromatography, etc.).

In the method wherein the organosilyl reagent (alkylsilane reagent) is used, Compound (Id) can be produced by reacting Compound (Ib) with the alkylsilane reagent and an acid.

The alkylsilane reagent is, for example, triethylsilane, phenyldimethylsilane, etc. The "alkylsilane reagent" is used respectively in an amount of about 0.8 to about 20 moles, preferably about 1 to about 5 moles, relative to 1 mole of Compound (Ib).

The acid is, for example, organic acids such as trifluoroacetic acid, etc. The acid is used respectively in an amount of about 0.1 to excessive amount, relative to 1 mole of Compound (Ib).

The present reaction is advantageously carried out without a solvent or with a solvent inert to the reaction.

Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., halogenated carbons such as dichloromethane, chloroform, tetrachlorocarbon, 1,2-dichloroethane, etc., organic acids such as acetic acid, trifluoroacetic acid, etc., or a mixed solvent thereof, or the like.

The product may be isolated from the reaction mixture according to a conventional method, and easily purified by conventional means of separation (e.g., recrystallization, distillation, chromatography, etc.).

When Compound (X) represented by $R^4$—H is amine, alcohol, thiol, phenol or thiophenol, Compound (I) corresponding to Compound (X) can be also produced by a method described in the following Reaction Scheme 5.

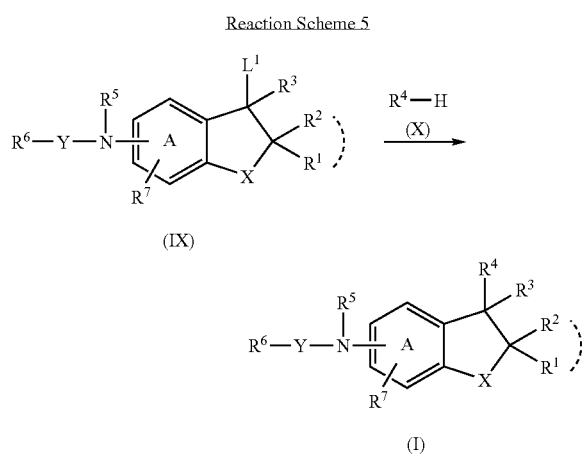

Reaction Scheme 5

In Reaction Scheme 5, each symbol has the same meaning as defined above.

Compound (X) represented by $R^4$—H is commercially available, and further can also be produced by per se known methods.

According to Reaction Scheme 5, Compound (I) is obtained by reacting Compound (IX) and Compound (X) under the presence of acid catalyst or base.

Compound (X) is used in an amount of about 1 mole to about 50 moles, preferably about 1 to about 5 moles, relative to 1 mole of Compound (IX).

The "acid catalyst" is, for example, organic acids such as formic acid, acetic acid, trifluoroacetic acid, p-toluenesulfonic acid, etc., mineral acids such as sulfuric acid, hydrochloric acid, hydrobromic acid, etc., Lewis acids such as zinc chloride, etc.

The "base" is, for example, basic salts such as sodium carbonate, potassium carbonate, cecium carbonate, sodium hydrogen carbonate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., metal alkoxides such as sodium methoxide, sodium ethoxide, potassium tert-butoxide, etc., or the like.

The acid catalyst is used in an amount of about 0.1 moles to excessive amount, preferably about 0.1 to about 50 moles, relative to 1 mole of Compound (IX).

The base is used in an amount of about 1.0 to 5.0 moles, preferably about 1.0 to 2.0 moles, relative to 1 mole of Compound (IX).

The present reaction is advantageously carried out without a solvent or with a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The reaction time is usually about 10 minutes to about 48 hours, preferably about 30 minutes to about 24 hours. The reaction temperature is usually −20 to 200° C., preferably 0 to 150° C.

Mitsunobu reaction (Synthesis, 1981, pp. 1~27) can be also used in stead of the above-mentioned reaction.

This reaction is carried out by reacting Compound (X) and Compound (IX) wherein $L^1$ is OH, under the presence of azodicarboxylates (e.g., diethylazodicarboxylate, etc.) and phosphines (e.g., triphenylphosphine, tributylphosphine, etc.).

Compound (X) is used in an amount of about 1.0 to 5.0 moles, preferably about 1.0 to 2.0 moles, relative to 1 mole of Compound (IX).

The "azodicarboxylates" and the "phosphines" are used in an amount of about 1.0 to 5.0 moles, preferably about 1.0 to 2.0 moles, respectively, relative to 1 mole of Compound (IX).

The present reaction is advantageously carried out using a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The reaction time is usually 5 minutes to 48 hours, preferably 30 minutes to 24 hours. The reaction temperature is usually −20 to 200° C., preferably 0 to 100° C. The product can be used in the next reaction as a reaction solution as is or a crude product, or can be isolated from the reaction mixture according to a conventional method, and easily purified by conventional means of separation (e.g., recrystallization, distillation, chromatography, etc.).

When $R^4$ is an optionally substituted amino group, Compound (Id) which is contained in Compound (I), can also be produced by reductive amination described in the following Reaction Scheme 6.

Reaction Scheme 6

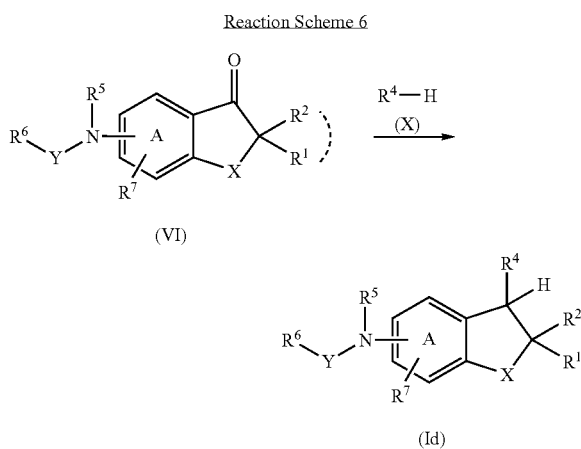

In Reaction Scheme 6, $R^4$ is an optionally substituted amino group, and other symbols have the same meanings as defined above.

Compound (Id) is produced by condensing Compound (VI) and Compound (X) which is amine and reducing it by a reducing agent.

Compound (X) is used in an amount of about 1.0 to about 5.0 moles, preferably about 1.0 to about 2.0 moles, relative to 1 mole of Compound (VI).

The "reducing agent" is, for example, metal hydrides such as sodium borohydride, sodium cyanoborohydride, lithium aluminum hydride, etc., boranes such as borane tetrahydrofuran complex, etc., hydrosilanes such as triethylsilane, or formic acid, etc. Further acid catalyst may be added with the reducing agent, if desired. The acid catalyst is, for example, mineral acids such as hydrochloric acid, hydrobromic acid, sulfuric acid, etc., sulfonic acids such as methanesulfonic acid, p-toluenesulfonic acid, etc., organic acids such as acetic acid, propionic acid, trifluoroacetic acid, etc., Lewis acids such as zinc chloride, aluminum chloride, etc.

The "reducing agent" is used in an amount of about 0.25 to about 5.0 moles, preferably about 0.5 to about 2.0 moles respectively, relative to 1 mole of Compound (VI).

The amount of the acid catalyst used is, for example, usually about 1 to about 100 moles, preferably about 1 to about 20 moles, relative to 1 mole of Compound (VI) when mineral acids are used.

The present reaction is advantageously carried out using a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., or a mixed solvent thereof, or the like.

The reaction time is usually about 5 minutes to about 48 hours, preferably about 30 minutes to about 24 hours. The reaction temperature is usually about −20 to about 200° C., preferably about 0 to about 100° C.

This reaction is also carried out by condensation of Compound (VI) and Compound (X), followed by catalytic hydrogenation under hydrogen atmosphere under the coexistence of various catalysts, instead of reduction by reducing agent. The catalyst to be used is, for example, platinum oxide, platinum on activated carbon, palladium on activated carbon, nickel, copper-chrome oxide, rhodium, cobalt, ruthenium, etc. The catalyst is used in an amount of about 0.1 to about 1000% by weight, preferably about 1 to about 1000% by weight, relative to Compound (VI).

The present reaction is advantageously carried out using a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, water, etc., or a mixed solvent thereof, or the like.

The reaction time is usually about 30 minutes to about 48 hours, preferably about 30 minutes to about 24 hours. The reaction temperature is usually about 0 to about 120° C., preferably about 20 to about 80° C.

The product may be isolated from the reaction mixture according to a conventional method, and easily purified by conventional means of separation (e.g., recrystallization, distillation, chromatography, etc.).

The following compounds which are contained in Compound (I) (Ie to Ik) are produced by a method described in the following Reaction Scheme 7 from Compound (I).

Reaction Scheme 7

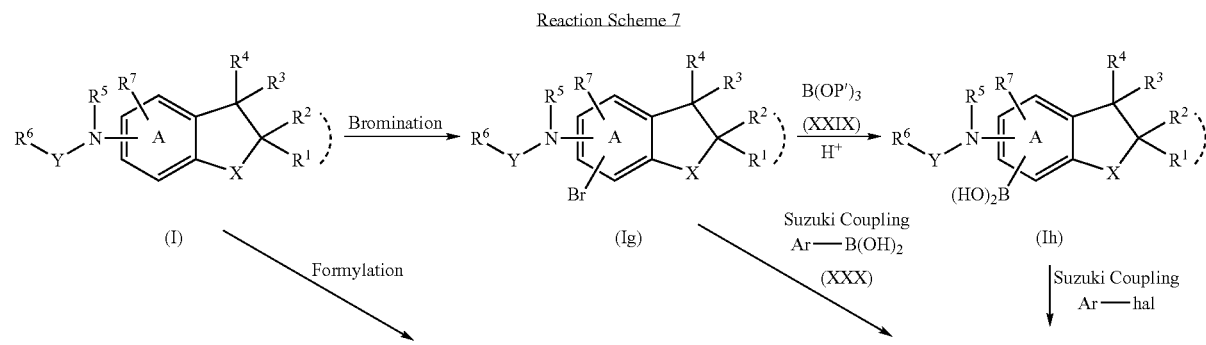

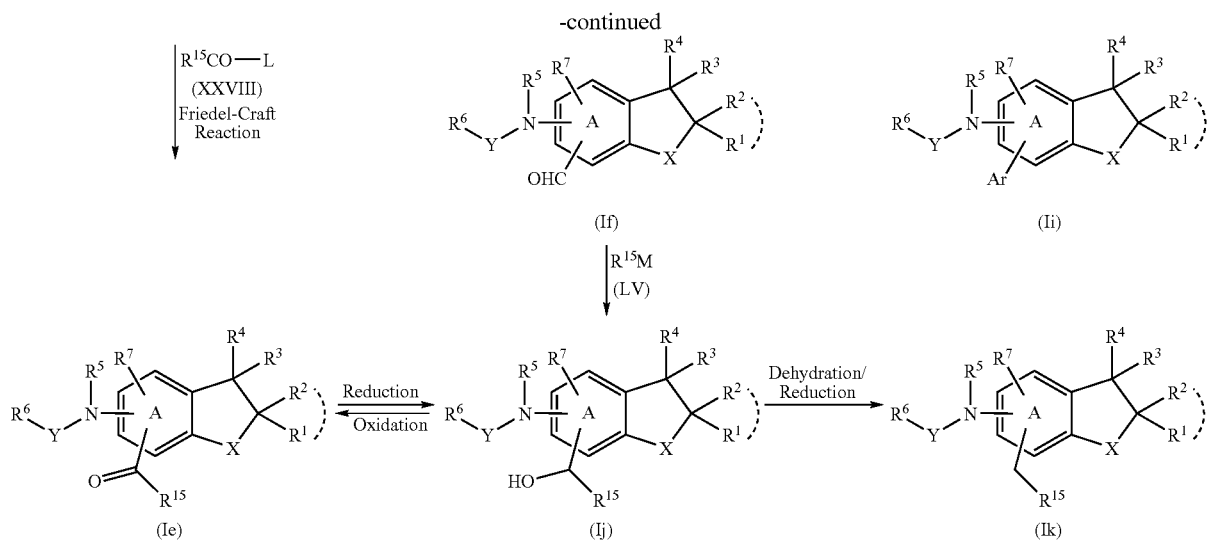

In Reaction Scheme 7, P' is a protective group of hydroxyl group, $R^{15}$ is an optionally substituted alkyl group (methyl, ethyl, phenyl group, etc.), Ar is an optionally substituted aromatic ring (a benzene ring, a naphthalene ring, a pyridine ring, a furan ring, a thiophene ring, an imidazole ring, etc.), Ar-hal is aromatic halide, and other symbols have the same meanings as defined above.

Compound (Ie) having an acyl group as a substituent of $R^7$ can be produced by acylation such as Friedel-Craft reaction, etc. of Compound (I).

This reaction is carried out by reacting Compound (I) and Compound (XXVIII) under the presence of acid catalyst.

Compound (XXVIII) is used in an amount of about 1 mole to about 20 moles, preferably about 1 to about 5 moles, relative to 1 mole of Compound (I).

The "acid catalyst" is, for example, aluminum chloride, iron chloride, stannous chloride, tetrachloro titanium, boron trifluoride diethyl ether, Lewis acids such as zinc chloride, etc. and polyphosphoric acid, etc. The acid catalyst is used in an amount of about 0.5 moles to about 20 moles, preferably about 0.8 to about 5 moles, relative to 1 mole of Compound (I) when Lewis acid is used. When polyphosphoric acid is used, the acid catalyst is used in an amount of about 5 moles to excessive amount, relative to 1 mole of Compound (I).

The present reaction is advantageously carried out without a solvent or with a solvent inert to the reaction.

Such solvents are not particularly limited if the reaction proceeds, and include, for example, hydrocarbons such as hexane, cyclohexane, benzene, toluene, xylene, etc., halogenated carbons such as dichloromethane, chloroform, tetrachlorocarbon, 1,2-dichloroethane, etc., carbon disulfide or mixed solvent thereof, or the like.

The reaction time is usually 10 minutes to 48 hours, preferably 30 minutes to 12 hours. The reaction temperature is usually −70 to 150° C., preferably −20 to 100° C.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (Ig) having a bromo group as a substituent of $R^7$ can be produced by reacting Compound (I) and brominating reagent.

The "brominating reagent" is, for example, bromine adducts such as bromine, N-bromosuccinimide, copper bromide, benzyltrimethylammonium tribromide like, etc. The brominating reagent is used in an amount of about 0.5 moles to about 10 moles, preferably about 1 to about 3 moles, relative to 1 mole of Compound (I).

The present reaction is carried out under the presence of base or Lewis acid or iron, if desired.

The "base" is, for example, basic salts such as sodium carbonate, calcium carbonate, cecium carbonate, sodium hydrogen carbonate, sodium acetate, potassium acetate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.

The base is used in an amount of about 0.8 to about 10 moles, relative to 1 mole of Compound (I).

The "Lewis acid" is, for example, aluminum chloride, iron chloride, stannous chloride, tetrachloro titanium, boron trifluoride diethyl ether, etc. Lewis acid is used in an amount of about 0.01 to about 2 moles, relative to 1 mole of Compound (I).

The "iron" is used, for example, in an amount of about 0.01 to about 2 moles, relative to 1 mole of Compound (I).

The present reaction is advantageously carried out using a solvent inert to the reaction. Such solvents are not particularly limited if the reaction proceeds, and include, for example, ethers such as diethyl ether, diisopropyl ether, tetrahydrofuran, dioxane, 1,2-dimethoxyethane, etc., alcohols such as methanol, ethanol, propanol, etc., hydrocarbons such as benzene, toluene, carbon disulfide, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., organic acids such as acetic acid, propionic acid, etc., nitroalkanes such as nitromethane, etc., or a mixed solvent thereof, or the like.

The reaction temperature is usually −20 to 200° C., preferably 0 to 100° C. The reaction time is usually about 5 minutes to about 24 hours, preferably about 10 minutes to about 5 hours.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (If) having formyl group as a substituent of $R^7$ can be produced by per se known methods, for example, the method described in Journal of Organic Chemistry, Vol. 49, 409 (1984), Journal of the Indian Chemical Society, Vol. 36, pp. 76 (1959), etc., or analogous methods thereto.

Compound (Ih) having boric acid as a substituent of $R^7$ is produced by treating Compound (Ig) with lithium reagent or Grignard reagent, followed by reacting with boric acid ester (XXIX).

The "lithium reagent" is, for example, alkyl lithiums such as n-butyl lithium, etc. The lithium reagent is used in an amount of about 0.8 to about 5.0 moles, preferably about 1.0 to about 3.0 moles, relative to 1 mole of Compound (Ig).

The "Grignard reagent" is, for example, magnesium, etc. Magnesium, etc. are used in an amount of about 0.8 to about 5.0 moles, preferably about 1.0 to about 2.0 moles, relative to 1 mole of Compound (Ig).

The "boric acid ester" is, for example, trimethylboric acid ester, triisopropylboric acid ester, etc. The boric acid ester is used in an amount of about 0.9 to about 30 moles, preferably about 0.9 to about 15 moles, relative to 1 mole of Compound (Ig).

The present reaction is advantageously carried out using a solvent inert to the reaction. Such solvents are not particularly limited if the reaction proceeds, and include, for example, ethers such as diethyl ether, diisopropyl ether, tetrahydrofuran, dioxane, 1,2-dimethoxyethane, etc., hydrocarbons such as benzene, toluene, carbon disulfide, cyclohexane, hexane, etc., or a mixed solvent thereof, or the like.

The reaction temperature is usually −100 to 120° C., preferably −80 to 70° C. The reaction time is usually about 5 minutes to about 24 hours, preferably about 10 minutes to about 5 hours.

In the present reactions, Compound (Ih) can be obtained by treating with acid (for example, hydrogen chloride, hydrochloric acid, sulfuric acid, acetic acid, etc.), if necessary.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (Ii) having an aromatic ring (a benzene ring, a naphthalene ring, a pyridine ring, a furan ring, a thiophene ring, an imidazole ring, etc.) as a substituent of $R^7$, can be produced by reacting Compound (Ig) and aromatic boronic acid (XXX), in a solvent under basic condition under the presence of a transitional metal catalyst.

The "aromatic boronic acid (XXX)" is used in an amount of about 0.5 to about 10 moles, preferably about 0.9 to about 3 moles, relative to 1 mole of Compound (Ig).

The "base" is for example, carbonate of alkali metal or alkali earth metal (for example, sodium carbonate, potassium carbonate, etc.), hydrogen carbonate of alkali metal or alkali earth metal (for example, sodium hydrogen carbonate, potassium hydrogen carbonate, etc.), hydroxide of alkali metal or alkali earth metal (for example, sodium hydroxide, potassium hydroxide, etc.), triethylamine, 4-dimethylaminopyridine, N,N-diisopropylethylamine, triethylenediamine, 4-methylmorpholine, etc.

The "transitional metal catalyst" is, for example, a palladium catalyst [for example, tetrakis(triphenylphosphine)palladium, 1,1-bis(diphenylphosphino)ferrocene dichloropalladium, dichlorobis(triphenylphosphine)palladium, etc.], etc. The transitional metal catalyst is used in an amount of about 0.001 to about 3 moles, preferably about 0.02 to about 0.2 moles, relative to 1 mole of Compound (Ig).

The solvent is, for example, ethers such as diethyl ether, diisopropyl ether, tetrahydrofuran, dioxane, 1,2-dimethoxyethane, etc., alcohols such as methanol, ethanol, propanol, etc., hydrocarbons such as benzene, toluene, carbon disulfide, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., water or mixed solvent thereof, or the like.

The reaction temperature is usually 0 to 250° C., preferably 50 to 150° C. The reaction time is usually about 5 minutes to about 48 hours, preferably about 30 minutes to about 24 hours.

In the present reaction, the reaction time can be shortened using microwave reactor, etc.

The product can be used in the next reaction as a reaction solution as is or a crude product, or can be isolated from the reaction mixture according to a conventional method, and easily purified by conventional means of separation (e.g., recrystallization, distillation, chromatography, etc.).

In addition, Compound (Ii) can be also produced by reacting Compound (Ih) and aromatic halide in a solvent under basic condition under the presence of a transitional metal catalyst.

The "aromatic halide" is used in an amount of about 0.5 to about 10 moles, preferably about 0.9 to about 3 moles, relative to 1 mole of Compound (Ih).

The "base" is for example, carbonate of alkali metal or alkali earth metal (for example, sodium carbonate, potassium carbonate, etc.), hydrogen carbonate of alkali metal or alkali earth metal (for example, sodium hydrogen carbonate, potassium hydrogen carbonate, etc.), hydroxide of alkali metal or alkali earth metal (for example, sodium hydroxide, potassium hydroxide, etc.), triethylamine, 4-dimethylaminopyridine, N,N-diisopropylethylamine, triethylenediamine, 4-methylmorpholine, etc.

The "transitional metal catalyst" is, for example, a palladium catalyst [for example, tetrakis(triphenylphosphine)palladium, 1,1-bis(diphenylphosphino)ferrocene dichloropalladium, dichlorobis(triphenylphosphine)palladium, etc.], etc. The transitional metal catalyst is used in an amount of about 0.001 to about 3 moles, preferably about 0.02 to about 0.2 moles, relative to 1 mole of Compound (Ih).

The solvent is, for example, ethers such as diethyl ether, diisopropyl ether, tetrahydrofuran, dioxane, 1,2-dimethoxyethane, etc., alcohols such as methanol, ethanol, propanol, etc., hydrocarbons such as benzene, toluene, carbon disulfide, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., water or mixed solvent thereof, or the like.

The reaction temperature is usually 0 to 250° C., preferably 50 to 150° C. The reaction time is usually about 5 minutes to about 48 hours, preferably about 30 minutes to about 24 hours.

In the present reaction, the reaction time can be shortened using microwave reactor, etc.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (Ij) having hydroxylated hydrocarbon group as a substituent of $R^7$ is produced by reacting Compound (If) and organic metallic Compound (LV) represented by $R^{15}$-M.

The organic metallic Compound (LV) represented by $R^{15}$-M is commercially available, and further can be also produced by per se known methods, for example, the method described in Experimental Chemistry Lecture, $4^{th}$ Ed., 25 (Japanese Society of Chemistry), Maruzen, Co., Ltd.

The organic metallic Compound (LV) is preferably a Grignard reagent or an organic lithium reagent.

The organic metallic Compound (LV) is used in an amount of about 0.8 to about 30 moles, preferably about 1.0 to about 10 moles, relative to 1 mole of Compound (If).

The present reaction is advantageously carried out without a solvent or with a solvent inert to the reaction. Such solvents are not particularly limited if the reaction proceeds, and include, for example, hydrocarbons such as hexane, cyclohexane, benzene, toluene, xylene, etc., ethers such as diethyl ether, diisopropyl ether, tetrahydrofuran, dioxane, 1,2-dimethoxyethane, etc., halogenated carbons such as dichloromethane, chloroform, tetrachlorocarbon, 1,2-dichloroethane, etc., or a mixed solvent thereof, or the like.

The reaction time is usually about 10 minutes to about 24 hours, preferably about 30 minutes to about 5 hours. The reaction temperature is usually about −100 to about 120° C., preferably about −80 to about 60° C.

The product can be used in the next reaction as a crude product, or can be isolated from the reaction mixture according to a conventional method, and easily purified by conventional means of separation (e.g., recrystallization, distillation, chromatography, etc.).

In addition, Compound (Ij) can be also produced by reducing Compound (Ie).

The "reducing agent" is, for example, metal hydrides such as aluminum hydride, isobutylaluminum hydride, etc., complex metal hydrides such as lithium aluminum hydride, sodium borohydride, sodium cyanoborohydride, etc. The reducing agent is used in an amount of about 0.3 to about 5.0 moles, preferably about 0.5 to about 2.0 moles, relative to 1 mole of Compound (Ie).

The present reaction is advantageously carried out using a solvent inert to the reaction. Such solvents are not particularly limited if the reaction proceeds, and include, for example, ethers such as diethyl ether, diisopropyl ether, tetrahydrofuran, dioxane, 1,2-dimethoxyethane, etc., alcohols such as methanol, ethanol, propanol, etc., hydrocarbons such as benzene, toluene, carbon disulfide, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The reaction temperature is usually −40 to 120° C., preferably −20 to 80° C. The reaction time is usually about 5 minutes to about 24 hours, preferably about 10 minutes to about 5 hours.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (Ie) can be also produced by reacting oxidizing Compound (Ij).

The "oxidizing agent" is, for example, anhydrous chromic acid, chromates such as pyridinium chlorochromate, pyridinium dichromate, sodium bichromate, potassium bichromate, etc., periodates such as para-periodic acid, meta-periodic acid, sodium meta-periodate, etc., metal oxides such as manganese dioxide, silver oxide, lead oxide, etc. Combination with sulfoxides such as dimethylsulfoxide, etc. and a dehydrating agent such as oxalyl chloride, N,N-dicyclohexylcarbodiimide, etc. may be used. The oxidizing agent is used in an amount of about 1 to about 30 moles, preferably about 1 to about 5 moles, relative to 1 mole of Compound (Ij).

The present reaction is advantageously carried out using a solvent inert to the reaction. Such solvents are not particularly limited if the reaction proceeds, and include, for example, ethers such as diethyl ether, diisopropyl ether, tetrahydrofuran, dioxane, 1,2-dimethoxyethane, etc., alcohols such as methanol, ethanol, propanol, etc., hydrocarbons such as benzene, toluene, carbon disulfide, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., water or mixed solvent thereof, or the like.

The reaction temperature is usually −90 to 200° C., preferably −80 to 120° C. The reaction time is usually about 5 minutes to about 48 hours, preferably about 10 minutes to about 16 hours.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (Ik) having a hydroxylated aralkyl group ($R^{15}CH_2$) as a substituent of $R^7$ can be produced by subjecting Compound (Ij) to reductive dehydration.

The reductive dehydration is, for example, per se known catalytic reduction, a method in which an organosilyl reagent (an alkylsilane reagent, etc.) is used, etc.

In the catalytic reduction, Compound (Ij) is reacted with a metal catalyst under hydrogen atmosphere to produce Compound (Ik). A suitable acid catalyst may be added, if desired.

The "metal catalyst" is, for example, Raney nickel, platinum oxide, metal palladium, palladium on activated carbon, etc. The "metal catalyst" is respectively used in an amount of usually about 0.1 to about 1000% by weight, preferably about 1 to about 20% by weight, relative to Compound (Ij).

The "acid catalyst" is, for example, organic acids such as formic acid, acetic acid, trifluoroacetic acid, p-toluenesulfonic acid, etc., mineral acids such as sulfuric acid, hydrochloric acid, hydrobromic acid, etc. The "acid catalyst" is used respectively in an amount of about 0.1 to excessive amount, relative to 1 mole of Compound (Ij).

The present reaction is advantageously carried out using a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., organic acids such as acetic acid, water, etc., or a mixed solvent thereof, or the like. The hydrogen pressure is usually about 1 to about 100 atm., preferably about 1 to about 5 atm. The reaction time is usually about 30 minutes to about 48 hours, preferably about 1 to 24 hours. The reaction temperature is usually about 0 to about 120° C., preferably about 20 to about 80° C.

After the catalyst is removed, the product may be isolated from the reaction mixture according to a conventional method, and easily purified by conventional means of separation (e.g., recrystallization, distillation, chromatography, etc.).

In the method wherein organosilyl reagent (alkylsilane reagent) is used, Compound (Ik) can be produced by reacting Compound (Ij) with an alkylsilane reagent and an acid.

The alkylsilane reagent is, for example, triethylsilane, phenyldimethylsilane, etc. The "alkylsilane reagent" is used respectively in an amount of about 0.8 to about 20 moles, preferably about 1 to about 5 moles, relative to 1 mole of Compound (Ij).

The acid is, for example, organic acids such as trifluoroacetic acid, etc. The acid is used respectively in an amount of about 0.1 to excessive amount, relative to 1 mole of Compound (Ij).

The present reaction is advantageously carried out without a solvent or with a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., halogenated carbons such as dichloromethane, chloroform, tetrachlorocarbon, 1,2-dichloroethane, etc., organic acids such as acetic acid, trifluoroacetic acid, etc., or a mixed solvent thereof, or the like.

The product may be isolated from the reaction mixture according to a conventional method, and easily purified by conventional means of separation (e.g., recrystallization, distillation, chromatography, etc.).

The above-mentioned Compound (II) is produced by, per se known methods, for example, the method described in JP-A-1993-140142, or analogous methods thereto, etc.

In addition, Compound (IIa), a dihydrobenzofuran derivative which is contained in Compound (II), can be produced by per se known methods, for example, the method described in Reaction Scheme 8 or Reaction Scheme 9 below which is described in WO2003-004485, etc. Further, other compounds which are contained in Compound (II), can be also produced by known method from Compound (IIa), if necessary.

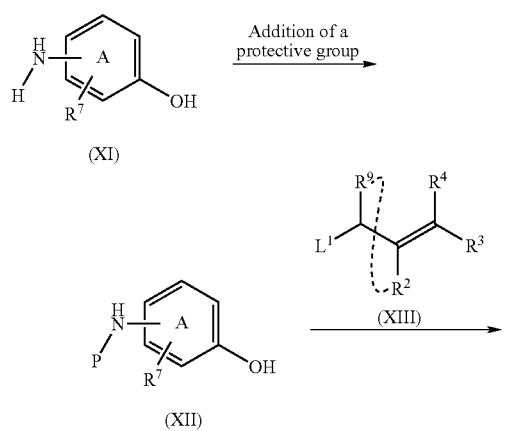

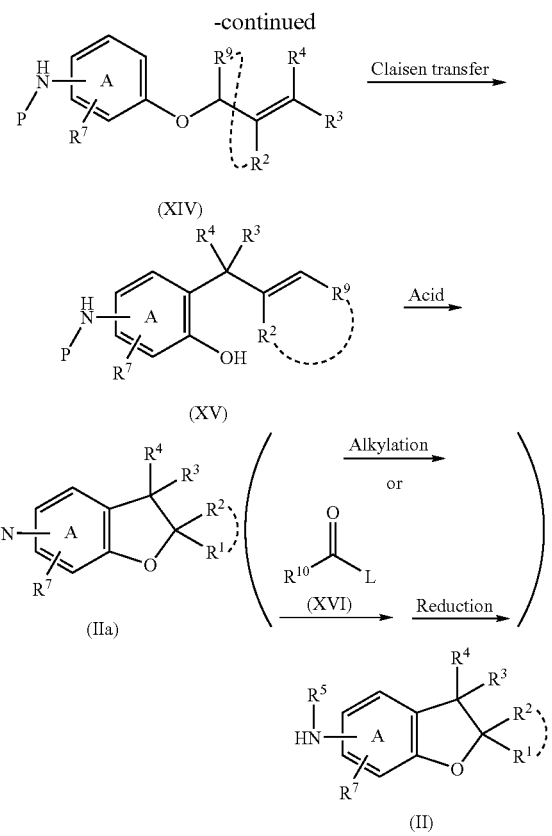

In Reaction Scheme 8, $R^9$ is a hydrogen atom or a group formed by deducting one methylene from $R^1$. $R^{10}$ is a group formed by deducting one methylene from $R^5$. Other symbols have the same meanings as defined above.

Obtained Compound (IIa) can be subjected to alkylation, if necessary. The alkylation can be carried out by reacting Compound (IIa) with an alkylating agent corresponding to the objective, compound (II), if desired, under the presence of base.

The alkylating agent is used in an amount of about 1.0 to about 5.0 moles, preferably about 1.0 to about 2.0 moles, relative to 1 mole of Compound (IIa).

The "base" is, for example, basic salts such as sodium carbonate, potassium carbonate, cecium carbonate, sodium hydrogen carbonate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., metal alkoxides such as sodium methoxide, sodium ethoxide, potassium tert-butoxide, etc., or the like.

The base is used in an amount of about 1.0 to about 5.0 moles, preferably about 1.0 to about 2.0 moles, relative to 1 mole of Compound (IIa).

The present reaction is advantageously carried out using a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The reaction time is usually about 30 minutes to about 48 hours, preferably about 1 hour to about 24 hours. The reaction temperature is usually about −20 to about 200° C., preferably about 0 to about 150° C.

Alternatively, a method can be used wherein Compound (IIa) and Compound (XVI) are reacted, if desired, under the presence of base or acid to produce acylamide, which is reduced by a reducing agent.

Compound (XVI) is used in an amount of about 1.0 to 5.0 moles, preferably about 1.0 to 2.0 moles, relative to 1 mole of Compound (IIa).

The "base" is, for example, organic bases such as triethylamine, pyridine, etc.

The "acid" is, for example, methanesulfonic acid, p-toluenesulfonic acid, camphor-sulfonic acid, etc.

The "base" is used in an amount of about 0.1 to 10 equivalents, preferably 0.8 to 2 equivalents, relative to Compound (IIa).

The "acid" is used in an amount of about 0.1 to 10 equivalents, preferably 0.8 to 3 equivalents, relative to Compound (IIa).

The present reaction is advantageously carried out without a solvent or with a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., nitrogen-containing aromatic hydrocarbons such as pyridine, lutidine, quinoline, etc., or a mixed solvent thereof, or the like. The reaction temperature is about −20 to 150° C., preferably 0 to 100° C. The reaction time is usually 5 minutes to 24 hours, preferably 10 minutes to 5 hours.

Thus obtained acylamide can be used in the next reaction as a reaction solution as is or a crude product, or can be isolated from the reaction mixture according to a conventional method, and easily purified by conventional means of separation (e.g., recrystallization, distillation, chromatography, etc.).

The reducing agent is, for example, metal hydrides such as sodium borohydride, lithium aluminum hydride, etc., boranes such as borane tetrahydrofuran complex, etc.

In addition, an acid catalyst may be added with the reducing agent, if desired. The acid catalyst is, for example, Lewis acids such as trifluoroborane diethyl ether complex, aluminum chloride, etc.

The reducing agent is used respectively in an amount of about 0.25 to about 10 moles, preferably about 0.5 to about 5 moles, relative to 1 mole of acylamide.

The Lewis acids are used respectively in an amount of about 0.25 to about 10 moles, preferably about 0.5 to about 5 moles, relative to 1 mole of acylamide.

The present reaction is advantageously carried out using a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, water, etc., or a mixed solvent thereof, or the like.

The reaction time is usually about 30 minutes to about 24 hours, preferably about 1 hour to about 16 hours. The reaction temperature is usually about 0 to about 150° C., preferably about 20 to about 100° C.

Thus obtained product (II) can be used in the method described in Reaction Scheme (I) as a reaction solution as is or a crude product, can be isolated from the reaction mixture according to a conventional method, and easily purified by conventional means of separation (e.g., recrystallization, distillation, chromatography, etc.).

Reaction Scheme 9

In Reaction Scheme 9, P' is a protective group of hydroxyl group, and other symbols have the same meanings as defined above.

Compound (XVII) is produced by subjecting Compound (XII) to addition of a protective group which is generally used in the peptide chemistry, etc.

Compound (IIa) is provided to the next reaction, if necessary, as in the method described in Reaction Scheme 8.

In addition, Compounds (IIb), (IIc), and (IId) which are contained in Compound (II), are also produced by a method described in the following Reaction Scheme 10.

moles, relative to 1 mole of Compound (XXI) when mineral acids are used, and usually about 0.1 to about 20 moles, preferably about 0.1 to about 5 moles, relative to 1 mole of Compound (XXI) when sulfonic acids are used.

The present reaction is advantageously carried out without a solvent or with a solvent inert to the reaction. Such solvents are not particularly limited if the reaction proceeds. For example, when mineral acids are used, the solvent is, prefer-

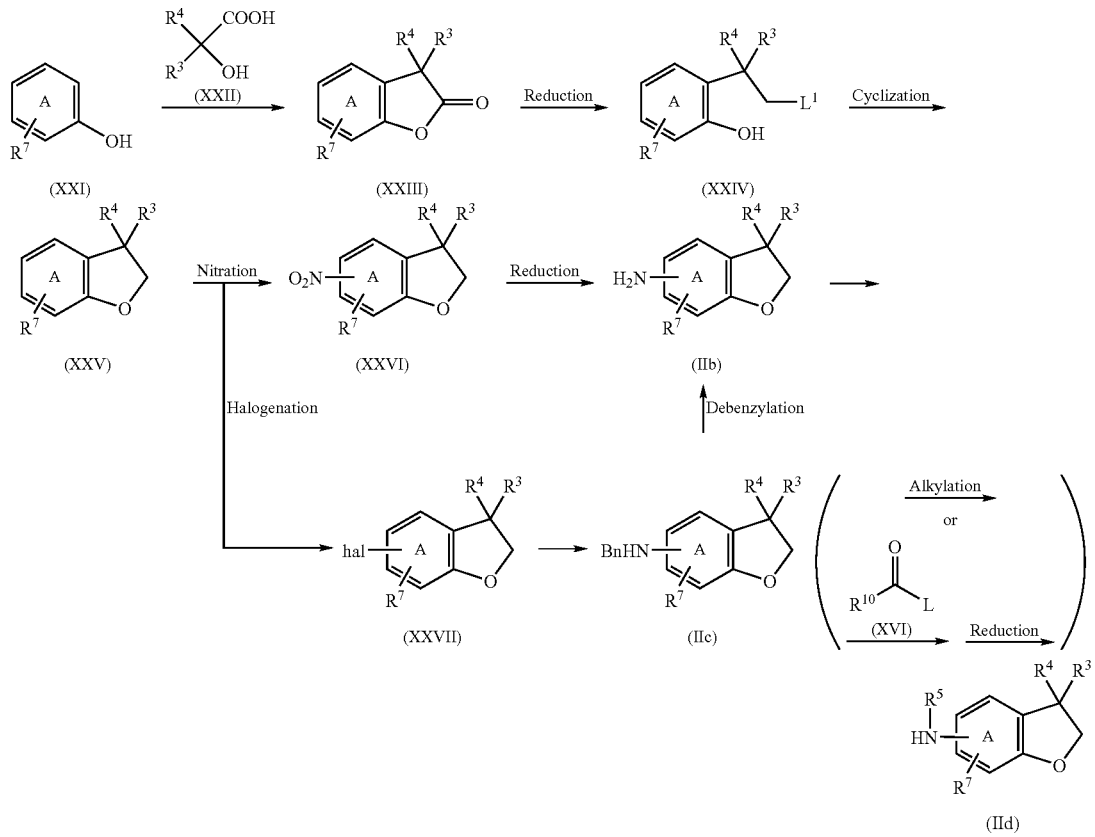

Reaction Scheme 10

In Reaction Scheme 10, hal is a halogen atom (e.g., fluorine, chlorine, bromine, iodine, etc.), and other symbols have the same meanings as defined above.

Compound (XXIII) can be produced by reacting Compound (XXI) with Compound (XXII) under acidic condition.

Compound (XXI) is commercially available, and further can be also produced by per se known methods, for example, the method described in Experimental Chemistry Lecture 20, $4^{th}$ Ed., (Japanese Society of Chemistry), 111 to 185, Maruzen, Co., Ltd. and analogous methods thereto.

Compound (XXII) is commercially available, and further can be also produced by per se known methods and analogous methods thereto.

The "acid" is, for example, Lewis acids such as aluminum chloride, iron chloride, stannous chloride, tetrachloro titanium, boron trifluoride diethyl ether, etc., mineral acids such as polyphosphoric acid, sulfuric acid, etc., organic acids such as trifluoroacetic acid, methanesulfonic acid, p-toluenesulfonic acid, trifluoromethanesulfonic acid, etc.

The acid is used in an amount of, for example, usually about 0.5 to about 100 moles, preferably about 10 to about 50 ably a mixed solvent of water and organic solvents such as saturated hydrocarbons such as cyclohexane, hexane, etc., aromatic hydrocarbons such as benzene, toluene, xylene, etc., ethers such as tetrahydrofuran, dioxane, 1,2-dimethoxyethane, diethyl ether, diisopropyl ether, etc., halogenated hydrocarbons such as dichloromethane, chloroform, tetrachlorocarbon, 1,2-dichloroethane, etc., or water.

The reaction time is usually about 30 minutes to about 24 hours, preferably about 30 minutes to about 6 hours. The reaction temperature is usually about −78 to about 200° C., preferably about −20 to about 150° C.

The product can be used in the next reaction as a crude product, or can be isolated from the reaction mixture according to a conventional method, and easily purified by conventional means of separation (e.g., recrystallization, distillation, chromatography, etc.).

Compound (XXIV) is produced by reducing Compound (XXIII).

The reducing agent is, for example, metal hydrides such as aluminum hydride, diisobutylaluminum hydride, etc., complex metal hydrides such as sodium borohydride, lithium borohydride, lithium aluminum hydride, sodium aluminum bis(2-methoxyethoxy) hydride, etc., borane complexes such as borane tetrahydrofuran complex, borane dimethylsulfide, etc., alkylboranes such as thexylborane, diamylborane, etc., diborane, etc.

In addition, an acid catalyst may be added with the reducing agent, if desired. The acid catalyst is, for example, Lewis acids such as trifluoroborane diethyl ether complex, aluminum chloride, etc.

The reducing agent is used respectively in an amount of about 0.25 to about 10 moles, preferably about 0.5 to about 5 moles, relative to 1 mole of Compound (XXIII).

The Lewis acids are used respectively in an amount of about 0.25 to about 10 moles, preferably about 0.5 to about 5 moles, relative to 1 mole of Compound (XXIII).

The present reaction is advantageously carried out using a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, water, etc., or a mixed solvent thereof, or the like.

The reaction time is usually about 30 minutes to about 24 hours, preferably about 1 hour to about 16 hours. The reaction temperature is usually about 0 to about 150° C., preferably about 20 to about 100° C.

Thus obtained product (XXIV) can be isolated from the reaction mixture according to a conventional method, and easily purified by conventional means of separation, such as recrystallization, distillation, chromatography, etc.

Compound (XXV) is produced by converting Compound (XXIV) (e.g., the compound in which $L^1$ is hydroxy) to sulfonate or halide, and subjecting it to cyclization. The sulfonate compound is synthesized by reacting Compound (XXIV) and corresponding sulfonyl chloride compound (for example, benzenesulfonyl chloride, toluenesulfonyl chloride, $C_{1-4}$ alkylsulfonyl chloride, for example, methanesulfonyl chloride, etc.) under the presence of base.

The sulfonyl chloride compound is used respectively in an amount of about 1.0 to about 10 moles, preferably about 1.0 to about 5 moles, relative to 1 mole of Compound (XXIV). The base is, for example, organic bases such as triethylamine, pyridine, etc.

The base is used respectively in an amount of about 1.0 to about 50 moles, preferably about 1.0 to about 20 moles, relative to 1 mole of Compound (XXIV).

The present reaction is advantageously carried out without a solvent or with a solvent inert to the reaction.

Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., nitrogen-containing aromatic hydrocarbons such as pyridine, lutidine, quinoline, etc., or a mixed solvent thereof, or the like. The reaction temperature is about −78 to 150° C., preferably −30 to 100° C. The reaction time is usually 5 minutes to 24 hours, preferably 10 minutes to 5 hours.

The product can be used in the next reaction as a reaction solution as is or a crude product, or can be isolated from the reaction mixture according to a conventional method, and easily purified by conventional means of separation (e.g., recrystallization, distillation, chromatography, etc.).

The halide is synthesized by reacting Compound (XXIV) and a halogenating agent (for example, phosphorus halide such as phosphorus trichloride, phosphorus oxychloride, phosphorus pentachloride, phosphorus tribromide, etc., halogen, thionyl chloride, etc.).

The halogenating agent is used in an amount of about 1.0 to about 100 moles, preferably about 1.0 to about 10 moles, relative to 1 mole of Compound (XXIV). The present reaction is advantageously carried out without a solvent or with a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like. The reaction temperature is about 0 to 200° C., preferably 10 to 100° C. The reaction time is usually 10 minutes to 24 hours, preferably 10 minutes to 5 hours.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (XXV) is also synthesized by subjecting thus obtained sulfonate compound or halide to cyclization under the presence of base. The base is, for example, organic bases such as triethylamine, pyridine, etc.

The base is used respectively in an amount of about 1.0 to about 50 moles, preferably about 1.0 to about 20 moles, relative to 1 mole of the sulfonate compound or halide. The present reaction is advantageously carried out without a solvent or with a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., esters such as ethyl acetate, etc., water or mixed solvent thereof, or the like. The reaction temperature is about −10 to 250° C., preferably 0 to 120° C. The reaction time is usually 10 minutes to 6 hours, preferably 10 minutes to 2 hours.

The product can be used in the next reaction as a reaction solution as is or a crude product, or can be isolated from the reaction mixture according to a conventional method, and easily purified by conventional means of separation (e.g., recrystallization, distillation, chromatography, etc.).

Alternatively, Mitsunobu reaction (Synthesis, 1981, pp. 1-27) can be also used.

In this reaction, Compound (XXIV) in which $L^1$ is OH, is subjected to intra-molecular cyclization under the presence of azodicarboxylates (e.g., diethyl azodicarboxylate, etc.) and phosphines (e.g., triphenylphosphine, tributylphosphine, etc.) to give Compound (XXV).

The "azodicarboxylates" and the "phosphines" are used respectively in an amount of about 1.0 to 5.0 moles, preferably about 1.0 to 2.0 moles, relative to 1 mole of Compound (XXIV).

The present reaction is advantageously carried out using a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The reaction time is usually 5 minutes to 48 hours, preferably 30 minutes to 24 hours. The reaction temperature is usually −20 to 200° C., preferably 0 to 100° C.

In addition, Compound (XXVI) can be synthesized by nitrating Compound (XXV). The nitrating agent is, for example, mixed acid, acetyl nitrate, fuming nitric acid, potassium nitrate, ammonium nitrate, nitronium tetrafluoroborate, nitronium trifluoromethanesulfonate, etc. The nitrating agent is used in an amount of about 1.0 to about 50 moles, preferably about 1.0 to about 10 moles, relative to 1 mole of Compound (XXV). The present reaction is advantageously carried out without a solvent or with a solvent inert to the reaction. Such solvents are not particularly limited if the reaction proceeds, and include, for example, organic acids such as acetic acid, trifluoroacetic acid, etc., acid anhydride such as acetic anhydride, trifluoroacetic anhydride, etc., mineral acids such as sulfuric acid, nitric acid, etc., saturated hydrocarbons such as hexane, cyclohexane, etc., halogenated carbons such as dichloromethane, chloroform, tetrachlorocarbon, 1,2-dichloroethane, etc., or a mixed solvent thereof, or the like.

The reaction time is usually about 10 minutes to about 24 hours, preferably about 10 minutes to about 16 hours. The reaction temperature is usually about −10 to about 200° C., preferably about −10 to about 120° C.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (IIb) is produced by reducing Compound (XXVI).

The reducing agent which is used in the reduction is, for example, metal hydrides such as aluminum hydride, diisobutylaluminum hydride, etc., complex metal hydrides such as sodium borohydride, lithium aluminum hydride, etc., borane complexes such as borane tetrahydrofuran complex, borane dimethylsulfide, etc., alkylboranes such as thexylborane, diamylborane, etc., diborane, or metals such as zinc, aluminum, tin, iron, etc., alkali metals (sodium, lithium, etc.)/liquid ammonia (batch reduction), etc.

Further, the hydrogenating catalyst is, for example, palladium carbon, platinum oxide, Raney nickel, Raney cobalt, etc. The hydrogen source is, for example, formic acid, ammonium formate, hydrazine, etc. in addition to gas-phase hydrogen.

The "reducing agent" is used in an amount of, for example, about 1.0 to about 10 moles, preferably about 1.0 to about 3.0 moles, relative to 1 mole of Compound (XXVI) when metal hydrides or complex metal hydride is used, about 1.0 to about 10 moles, preferably about 1.0 to about 5.0 moles when borane complexes, alkylboranes or diborane is used, and about 1.0 to about 20 equivalents, preferably about 1.0 to about 5.0 equivalents when metals or alkali metals are used to 1 mole of Compound (XXVI). In case of hydrogenation, the catalyst such as palladium carbon, platinum oxide, Raney nickel, Raney cobalt, etc. is used in an amount of about 5 to 1000% by weight, preferably about 10 to 300% by weight, relative to Compound (XXVI). When the hydrogen source other than gas-phase hydrogen is used, it is used in an amount of about 1.0 to about 20 moles, preferably about 2.0 to about 10 moles, relative to 1 mole of Compound (XXVI).

The present reaction is advantageously carried out using a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., formic acid, organic acids such as acetic acid, water, etc., or a mixed solvent thereof, or the like. When the catalyst of Raney nickel or Raney cobalt is used, amines such as ammonia, etc. may be further added to inhibit reverse reaction.

The reaction time is varied depending on kinds or amount of reducing agent, or activity or amount of catalyst, but usually about 1 hour to about 100 hours, preferably about 1 hour to about 50 hours. The reaction temperature is usually about 0 to about 150° C., preferably about 20 to about 100° C. When a hydrogenation catalyst is used, hydrogen pressure is usually 1 to 100 atm.

Thus obtained product (IIb) can be isolated from the reaction mixture according to a conventional method, and easily purified by conventional means of separation (e.g., recrystallization, distillation, chromatography, etc.).

Compound (XXVII) is produced by reacting Compound (XXV) and a halogenating reagent.

The "halogenating reagent" is, for example, chlorine, bromine, iodine, imides such as N-chlorosuccinimide or N-bromosuccinimide, etc., halogen adducts such as benzyltrimethylammonium tribromide, etc. The "halogenating reagent" is used in an amount of about 0.8 to about 5.0 moles, preferably about 1.0 to about 2.0 moles, relative to 1 mole of Compound (XXV).

The present reaction is advantageously carried out using a solvent inert to the reaction. Such solvents are not particularly limited if the reaction proceeds, and include, for example, ethers such as diethyl ether, diisopropyl ether, tetrahydrofuran, dioxane, 1,2-dimethoxyethane, etc., alcohols such as methanol, ethanol, propanol, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., organic acids such as acetic acid, propionic acid, etc., nitroalkanes such as nitromethane, etc., aromatic amines such as pyridine, lutidine, quinoline, etc., or a mixed solvent thereof, or the like.

The present reaction is carried out under the presence of base or Lewis acid or iron, if desired.

The "base" is, for example, basic salts such as sodium carbonate, calcium carbonate, cecium carbonate, sodium hydrogen carbonate, sodium acetate, potassium acetate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The base is used in an amount of about 0.8 to about 10 moles, relative to 1 mole of Compound (XXV).

The "Lewis acid" is, for example, iron chloride, aluminum chloride, boron trifluoride, etc. The Lewis acid is used in an amount of about 0.01 to about 5 moles, relative to 1 mole of Compound (XXV).

The "iron" is used in an amount of about 0.01 to about 5 moles, relative to 1 mole of Compound (XXV).

The reaction temperature is usually about −50 to about 150° C., preferably about −20 to about 100° C. The reaction time is usually about 5 minutes to about 24 hours, preferably about 10 minutes to about 12 hours.

In addition, when a halogen atom is substituted on ring A of Compound (XXI), Compound (XXVII) can be produced without halogenation.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (IIc) is produced by reacting Compound (XXVII) and benzylamine, if desired, under the presence of base. If necessary, a catalyst such as copper, copper salt, etc. may be used, or a catalyst such as palladium or nickel, etc. and a ligand (for example, phosphine or pyridines, etc.) may be also used according to the method described in Chemistry Letters, 1983, pp. 927-928.

The benzylamine is used in an amount of about 0.8 to about 10.0 moles, preferably about 1.0 to about 5.0 moles, relative to 1 mole of Compound (XXVII).

The "base" is, for example, basic salts such as sodium carbonate, potassium carbonate, cecium carbonate, sodium hydrogen carbonate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., metal alkoxides such as sodium methoxide, sodium ethoxide, sodium tert-butoxide, potassium tert-butoxide, etc., or the like.

The "base" is used in an amount of about 0.8 to about 10.0 moles, preferably about 1.0 to about 5.0 moles, relative to 1 mole of Compound (XXVII).

The present reaction is advantageously carried out using a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The "copper catalyst" is, for example, copper, halogenated copper (CuI, CuBr, CuCl, etc.), copper oxide (CuO), etc. The copper catalyst is used in an amount of about 0.1 to about 10.0 moles, preferably about 0.5 to about 2.0 moles, relative to 1 mole of Compound (XXVII).

The "ligand" is preferably phosphines such as trialkylphosphine, triarylphosphine, trialkoxyphosphine, etc. The palladium catalyst is, for example, palladium acetate, palladium chloride, tetrakis(triphenylphosphine)palladium, bis(dibenzylideneacetone)palladium, etc.

The "phosphine" is used in an amount of about 0.001 to about 10.0 moles, preferably about 0.01 to about 1.0 mole, relative to 1 mole of Compound (XXVII). The palladium catalyst is used in an amount of about 0.001 to about 5.0 moles, preferably about 0.01 to about 0.5 moles, relative to 1 mole of Compound (XXVII).

The reaction time is usually about 30 minutes to about 72 hours, preferably about 1 hour to about 48 hours. The reaction temperature is usually about −20 to about 200° C., preferably about 0 to about 150° C.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (IIb) is produced by debenzylation of Compound (IIc). The debenzylation is carried out by per se known reaction, for example, the method described in T. W. Green, Protective Groups in Organic Synthesis, 3$^{rd}$ Ed., 1999, Chapter of "Protection for the Amino Group", etc.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (IId) is produced from Compound (IIb) by the same method as shown in Reaction Scheme 9 in which Compound (II) is produced from Compound (IIa), if necessary.

When $R^3$ is a hydrogen atom, Compound (IIf) and Compound (IIg) which are contained in Compound (II), are also produced by a method described in the following Reaction Scheme 11.

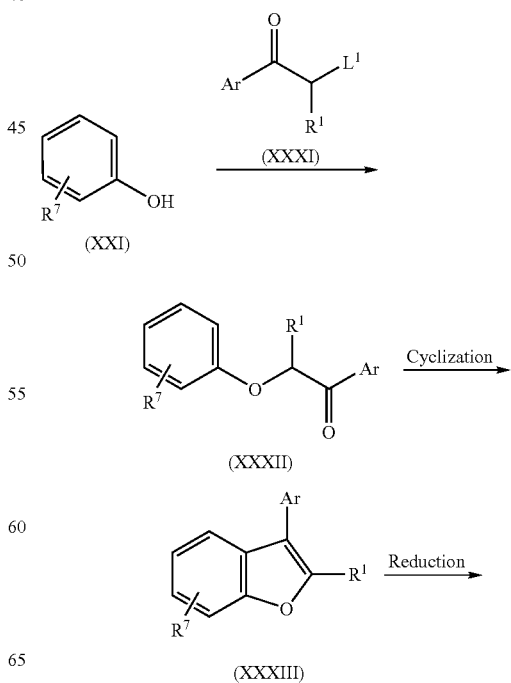

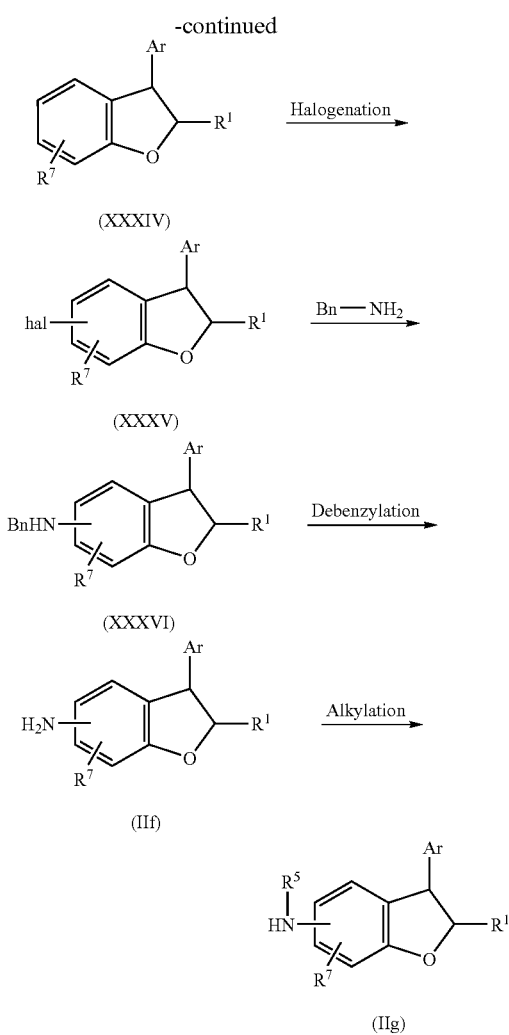

In Reaction Scheme 11, each symbol has the same meaning as defined above.

Compound (XXXII) is produced by reacting Compound (XXI) and Compound (XXXI), if desired, under the presence of base.

Compound (XXXI) is commercially available, and further can be also produced by per se known methods.

The "base" is, for example, basic salts such as sodium carbonate, potassium carbonate, cecium carbonate, sodium hydrogen carbonate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., metal alkoxides such as sodium methoxide, sodium ethoxide, potassium tert-butoxide, etc., or the like.

Compound (XXXI) is used in an amount of about 0.7 to about 5.0 moles, preferably about 1.0 to about 3.0 moles, relative to 1 mole of Compound (XXI).

The base is used in an amount of about 0.8 to about 5.0 moles, preferably about 1.0 to about 3.0 moles, relative to 1 mole of Compound (XXI). Further, if desired, quaternary ammonium salt may be combined and reacted with the base in producing Compound (XXXII). The "quaternary ammonium salt" is, for example, tetrabutylammonium iodide, etc.

The quaternary ammonium salt is used in an amount of about 0.1 to about 2.0 moles, preferably about 0.5 to about 1.0 mole, relative to 1 mole of Compound (XXI).

The present reaction is advantageously carried out using a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The reaction time is usually about 30 minutes to about 96 hours, preferably about 1 hour to about 72 hours. The reaction temperature is usually about 0 to about 120° C., preferably about 0 to about 60° C.

Mitsunobu reaction (Synthesis, 1981, pp. 1-27) can be also used in stead of the above-mentioned reaction.

This reaction is carried out by reacting Compound (XXI) and Compound (XXXI) in which $L^1$ is OH under the presence of azodicarboxylates (e.g., diethyl azodicarboxylate, etc.) and phosphines (e.g., triphenylphosphine, tributylphosphine, etc.). Compound (XXXI) is used in an amount of about 0.8 to about 5.0 moles, preferably about 1.0 to about 3.0 moles, relative to 1 mole of Compound (XXI).

The "azodicarboxylates" and the "phosphines" are used respectively in an amount of about 0.8 to about 5.0 moles, preferably about 1.0 to about 3.0 moles, relative to 1 mole of Compound (XXI).

The present reaction is advantageously carried out using a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The reaction time is usually about 5 minutes to about 48 hours, preferably about 30 minutes to about 24 hours. The reaction temperature is usually about −20 to about 200° C., preferably about 0 to about 100° C.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (XXXIII) is produced by subjecting Compound (XXXII) to per se known cyclization.

For this cyclization, an acid is used.

The "acid" is, for example, Lewis acids such as aluminum chloride, iron chloride, stannous chloride, tetrachloro titanium, boron trifluoride diethyl ether, etc., mineral acids such as polyphosphoric acid, sulfuric acid, etc., organic acids such as trifluoroacetic acid, methanesulfonic acid, p-toluenesulfonic acid, trifluoromethanesulfonic acid, etc., acidic resin or clay such as zeolite, Amberlite, Montmorillonite, etc., or the like.

The "acid" is used respectively in an amount of catalytic amount to excessive amount to Compound (XXXII), preferably about 0.8 to about 5 moles, relative to 1 mole of Compound (XXXII). The acidic resin or clay is used in an amount of about 0.1 to 50 grams, preferably 1 to 5 grams, relative to 1 gram of Compound (XXXII).

The present reaction is advantageously carried out without a solvent or with a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., carbon disulfide, nitroalkanes such as nitromethane, etc., nitroaryls such as nitrobenzene, etc., halogenated carbons such as dichloromethane, chloroform, tetrachlorocarbon, 1,2-dichloroethane, 1,2-dichlorobenzene, etc., organic acids such as acetic acid, trifluoroacetic acid, etc., or a mixed solvent thereof, or the like.

The reaction time is usually about 10 minutes to about 96 hours, preferably about 30 minutes to about 16 hours. The reaction temperature is usually about −70 to about 200° C., preferably about −20 to about 150° C.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (XXXIV) is produced by reducing Compound (XXXIII).

The reduction is carried out by catalytic reduction, a method in which an organosilyl reagent (an alkylsilane reagent, etc.) is used, etc.

The catalytic reduction is carried out by per se known reaction, for example, using catalyst such as palladium carbon, etc. under hydrogen atmosphere. After the catalyst is removed, the product can be used in the next reaction as a reaction solution as is or a crude product, or can be isolated from the reaction mixture according to a conventional method, and easily purified by conventional means of separation (e.g., recrystallization, distillation, chromatography, etc.).

In the method wherein organosilyl reagent (alkylsilane reagent) is used, Compound (XXXIV) can be produced by reacting Compound (XXXIII) with an alkylsilane reagent and an acid.

The alkylsilane reagent is, for example, triethylsilane, phenyldimethylsilane, etc. The "alkylsilane reagent" is used respectively in an amount of about 0.8 to about 20 moles, preferably about 1 to about 5 moles, relative to 1 mole of Compound (XXXIII).

The acid is, for example, organic acids such as trifluoroacetic acid, etc. The acid is used respectively in an amount of about 0.1 to excessive amount, relative to 1 mole of Compound (XXXIII).

The present reaction is advantageously carried out without a solvent or with a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., halogenated carbons such as dichloromethane, chloroform, tetrachlorocarbon, 1,2-dichloroethane, etc., organic acids such as acetic acid, trifluoroacetic acid, etc., or a mixed solvent thereof, or the like.

The product may be isolated from the reaction mixture according to a conventional method, and easily purified by conventional means of separation (e.g., recrystallization, distillation, chromatography, etc.).

Compound (XXXV) is produced by reacting Compound (XXXIV) and halogenating reagent.

The "halogenating reagent" is, for example, chlorine, bromine, iodine, imides such as N-chlorosuccinimide or N-bromosuccinimide, etc., halogen adducts such as benzyltrimethylammonium tribromide, etc., or the like. The halogenating reagent is used in an amount of about 0.8 to about 5.0 moles, preferably about 1.0 to about 2.0 moles, relative to 1 mole of Compound (XXXIV).

The present reaction is advantageously carried out using a solvent inert to the reaction. Such solvents are not particularly limited if the reaction proceeds, and include, for example, ethers such as diethyl ether, diisopropyl ether, tetrahydrofuran, dioxane, 1,2-dimethoxyethane, etc., alcohols such as methanol, ethanol, propanol, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., organic acids such as acetic acid, propionic acid, etc., nitroalkanes such as nitromethane, etc., aromatic amines such as pyridine, lutidine, quinoline, etc., or a mixed solvent thereof, or the like.

The present reaction is carried out under the presence of base or Lewis acid or iron, if desired.

The "base" is, for example, basic salts such as sodium carbonate, calcium carbonate, cecium carbonate, sodium hydrogen carbonate, sodium acetate, potassium acetate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The base is used in an amount of about 0.8 to about 10 moles, relative to 1 mole of Compound (XXXIV).

The "Lewis acid" is, for example, iron chloride, aluminum chloride, boron trifluoride, etc. The Lewis acid is used in an amount of about 0.01 to about 5 moles, relative to 1 mole of Compound (XXXIV).

The "iron" is used in an amount of about 0.01 to about 5 moles, relative to 1 mole of Compound (XXXIV).

The reaction temperature is usually about −50 to about 150° C., preferably about −20 to about 100° C. The reaction time is usually about 5 minutes to about 24 hours, preferably about 10 minutes to about 12 hours. The product can be used in the next reaction as a reaction solution as is or a crude product, or can be isolated from the reaction mixture according to a conventional method, and easily purified by conventional means of separation (e.g., recrystallization, distillation, chromatography, etc.).

In addition, when a halogen atom is substituted on a benzene ring of Compound (XXI), Compound (XXXV) can be produced without halogenation.

Compound (XXXVI) is produced by reacting Compound (XXXV) and benzylamine, if desired, under the presence of base. If necessary, a catalyst such as copper, copper salt, etc. may be used, or a catalyst such as palladium or nickel, etc. and a ligand (for example, phosphine or pyridines, etc.) may be also used according to the method described in Chemistry Letters, 1983, pp. 927-928 catalyst.

The benzylamine is used in an amount of about 0.8 to about 10.0 moles, preferably about 1.0 to about 5.0 moles, relative to 1 mole of Compound (XXXV).

The "base" is, for example, basic salts such as sodium carbonate, potassium carbonate, cecium carbonate, sodium hydrogen carbonate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., metal alkoxides such as sodium methoxide, sodium ethoxide, sodium tert-butoxide, potassium tert-butoxide, etc., or the like.

The base is used in an amount of about 0.8 to about 10.0 moles, preferably about 1.0 to about 5.0 moles, relative to 1 mole of Compound (XXXV).

The present reaction is advantageously carried out using a solvent inert to the reaction. Such solvents are not particularly limited if the reaction proceeds, and include, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The copper catalyst is, for example, copper, halogenated copper (CuI, CuBr, CuCl, etc.), copper oxide (CuO), etc.

The copper catalyst is used in an amount of about 0.1 to about 10.0 moles, preferably about 0.5 to about 2.0 moles, relative to 1 mole of Compound (XXXV).

The "ligand" is preferably phosphines such as trialkylphosphine, triarylphosphine, trialkoxyphosphine, etc. The palladium catalyst is, for example, palladium acetate, palladium chloride, tetrakis(triphenylphosphine)palladium, bis(dibenzylideneacetone)palladium, etc. The phosphine is used in an amount of about 0.001 to about 10.0 moles, preferably about 0.01 to about 1.0 mole, relative to 1 mole of Compound (XXXV). Palladium catalyst is used in an amount of about 0.001 to about 5.0 moles, preferably about 0.01 to about 0.5 moles, relative to 1 mole of Compound (XXXV).

The reaction time is usually about 30 minutes to about 72 hours, preferably about 1 hour to about 48 hours. The reaction temperature is usually about −20 to about 200° C., preferably about 0 to about 150° C. The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (IIf) is produced by debenzylation of Compound (XXXVI). The debenzylation is carried out by per se known reaction, for example, the method described in T. W. Green, Protective Groups in Organic Synthesis, 3$^{rd}$ Ed., 1999, Chapter of "Protection for the Amino Group", etc. The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (IIg) is produced from Compound (IIf) by the same method as shown in Reaction Scheme 9 in which Compound (II) is produced from Compound (IIa), if necessary.

In addition, Compound (VI) is also produced by a method described in the following Reaction Scheme 12.

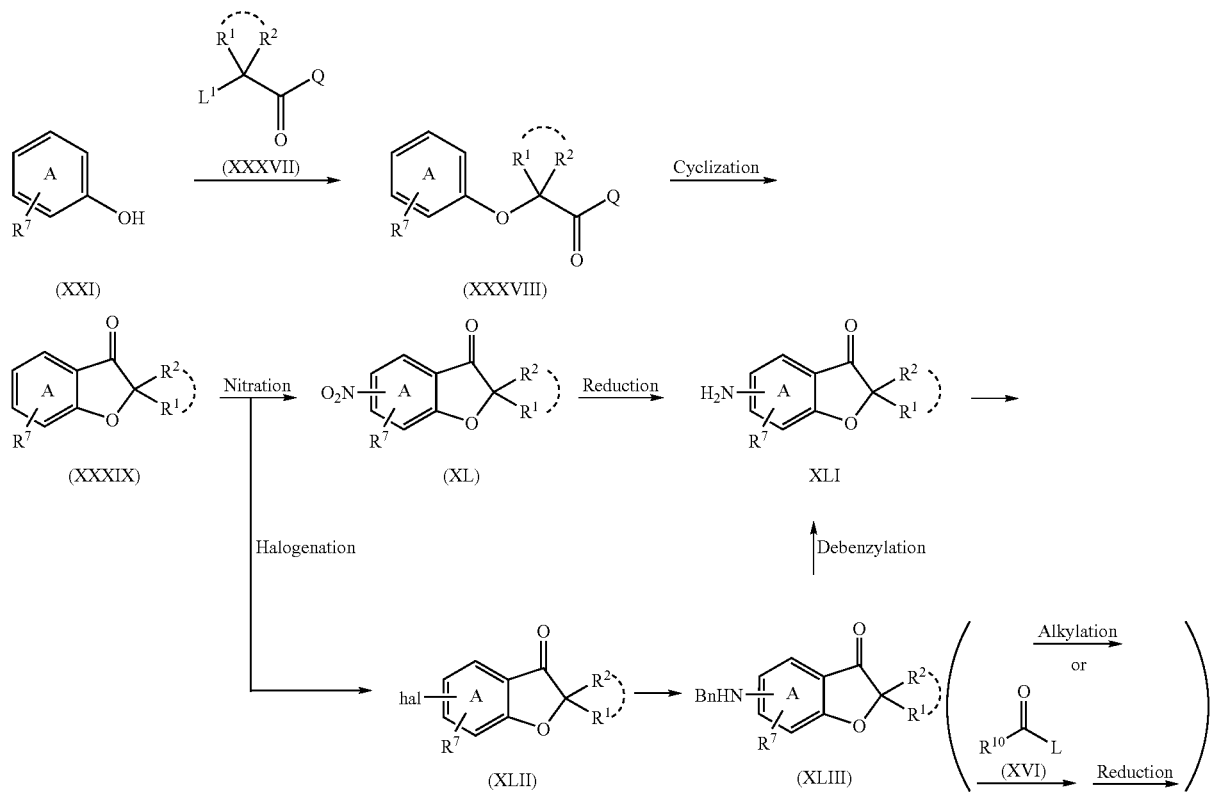

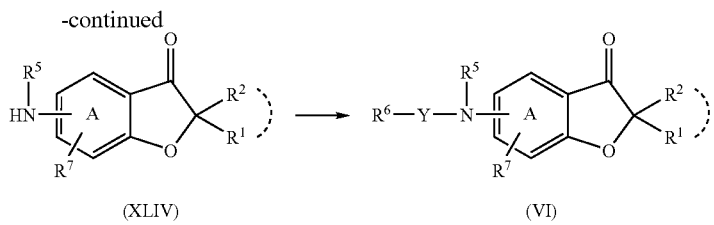

(XLIV) → (VI)

In Reaction Scheme 12, the group represented by —CO-Q is carbonic acid or a reactive derivative thereof, and other symbols have the same meanings as defined above.

Compound (XXXVIII) is produced by reacting Compound (XXI) and Compound (XXXVII), if desired, under the presence of base.

The "base" is, for example, basic salts such as sodium carbonate, potassium carbonate, cecium carbonate, sodium hydrogen carbonate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., metal alkoxides such as sodium methoxide, sodium ethoxide, potassium tert-butoxide, etc., or the like.

Compound (XXXVII) is used in an amount of about 0.8 to about 5.0 moles, preferably about 1.0 to about 3.0 moles, relative to 1 mole of Compound (XXI).

The base is used in an amount of about 0.8 to about 5.0 moles, preferably about 1.0 to about 3.0 moles, relative to 1 mole of Compound (XXI). Further, if desired, quaternary ammonium salt may be added with the base in producing Compound (XXXVIII). The "quaternary ammonium salt" is, for example, tetrabutylammonium iodide, etc.

The quaternary ammonium salt is used in an amount of about 0.1 to about 2.0 moles, preferably about 0.5 to about 1.0 mole, relative to 1 mole of Compound (XXI).

The present reaction is advantageously carried out using a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The reaction time is usually about 30 minutes to about 96 hours, preferably about 1 hour to about 72 hours. The reaction temperature is usually about 0 to about 120° C., preferably about 0 to about 60° C.

Mitsunobu reaction (Synthesis, 1981, pp. 1-27) can be also used in stead of the above-mentioned reaction.

This reaction is carried out by reacting Compound (XXI) and Compound (XXXVII) in which $L^1$ is OH under the presence of azodicarboxylates (e.g., diethyl azodicarboxylate, etc.) and phosphines (e.g., triphenylphosphine, tributylphosphine, etc.).

Compound (XXXVII) is used in an amount of about 0.8 to about 5.0 moles, preferably about 1.0 to about 3.0 moles, relative to 1 mole of Compound (XXI).

The "azodicarboxylates" and the "phosphines" are used respectively in an amount of about 0.8 to about 5.0 moles, preferably about 1.0 to about 3.0 moles, relative to 1 mole of Compound (XXI).

The present reaction is advantageously carried out using a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The reaction time is usually about 5 minutes to about 48 hours, preferably about 30 minutes to about 24 hours. The reaction temperature is usually about −20 to about 200° C., preferably about 0 to about 100° C.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (XXXIX) is produced by subjecting Compound (XXXVIII) to per se known cyclization.

Q in the formula is preferably, a hydroxyl group, a halogen atom, etc. In this reaction, Compound (XXXVIII) is reacted with acid to give Compound (XXXIX), if desired.

The "acid" is, for example, Lewis acids such as aluminum chloride, iron chloride, stannous chloride, tetrachloro titanium, boron trifluoride diethyl ether, etc., mineral acids such as polyphosphoric acid, sulfuric acid, etc., organic acids such as trifluoroacetic acid, methanesulfonic acid, p-toluenesulfonic acid, trifluoromethane sulfonic acid, etc.

The "acid" is used respectively in an amount of catalytic amount to excessive amount relative to Compound (XXXVIII), preferably about 0.8 to about 5 moles, relative to 1 mole of Compound (XXXVIII).

The present reaction is advantageously carried out without a solvent or with a solvent inert to the reaction.

Such solvents are not particularly limited if the reaction proceeds, and include, for example, carbon disulfide, nitroalkanes such as nitromethane, etc., nitroaryls such as nitrobenzene, etc., halogenated carbons such as dichloromethane, 1,2-dichloroethane, 1,2-dichlorobenzene, etc., organic acids such as acetic acid, trifluoroacetic acid, etc., acid anhydride such as acetic anhydride, trifluoroacetic anhydride, etc., or a mixed solvent thereof, or the like.

The reaction time is usually about 10 minutes to about 96 hours, preferably about 10 minutes to about 12 hours. The reaction temperature is usually about −70 to about 200° C., preferably about −40 to about 150° C.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (XLIV) is produced from Compound (XXXIX) by the same method as the method of producing Compound (IId) from Compound (XXV).

Compound (VI) is produced from Compound (XLIV) by the same method as the method of producing Compound (I) from Compound (II).

Compound (IIf) and Compound (IIg) which are contained in Compound (II) are also produced by a method described in the following Reaction Scheme 13 when $R^2$ of Compound (IIf) and Compound (IIg) is H.

Reaction Scheme 13

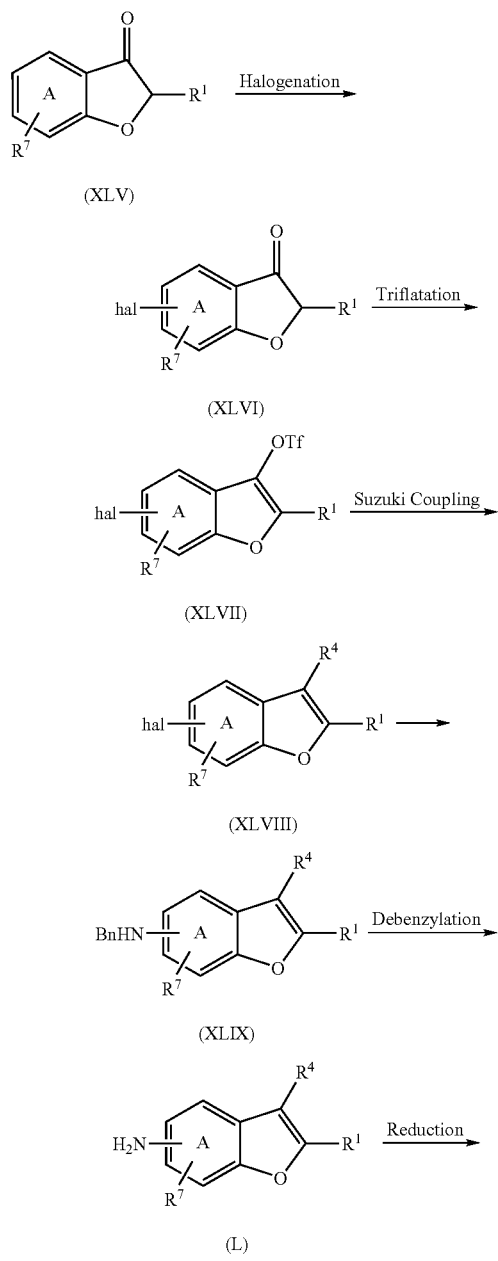

(XLV)

(XLVI)

(XLVII)

(XLVIII)

(XLIX)

(L)

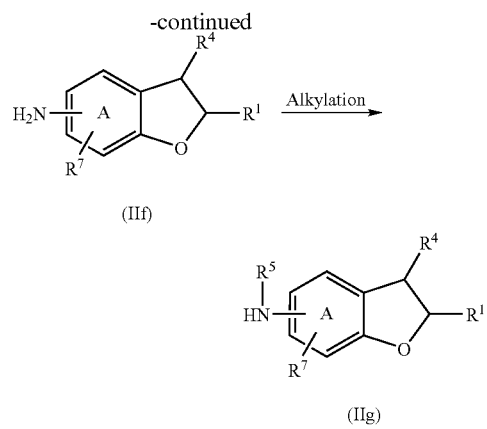

(IIf)

(IIg)

In Reaction Scheme 13, Ar is an optionally substituted aromatic ring (a benzene ring, a naphthalene ring, a pyridine ring, a furan ring, a thiophene ring, an imidazole ring, etc.), and other symbols have the same meanings as defined above.

Compound (XLVI) is produced by reacting Compound (XLV) and a halogenating reagent.

The "halogenating reagent" is, for example, chlorine, bromine, iodine, imides such as N-chlorosuccinimide or N-bromosuccinimide, etc., halogen adducts such as benzyltrimethylammonium tribromide, etc., or the like. The halogenating reagent is used in an amount of about 0.8 to about 5.0 moles, preferably about 1.0 to about 2.0 moles, relative to 1 mole of Compound (XLV).

The present reaction is advantageously carried out using a solvent inert to the reaction. Such solvents are not particularly limited if the reaction proceeds, and include, for example, ethers such as diethyl ether, diisopropyl ether, tetrahydrofuran, dioxane, 1,2-dimethoxyethane, etc., alcohols such as methanol, ethanol, propanol, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., organic acids such as acetic acid, propionic acid, etc., nitroalkanes such as nitromethane, etc., aromatic amines such as pyridine, lutidine, quinoline, etc., or a mixed solvent thereof, or the like.

The present reaction is carried out under the presence of base or Lewis acid or iron, if desired.

The "base" is, for example, basic salts such as sodium carbonate, calcium carbonate, cecium carbonate, sodium hydrogen carbonate, sodium acetate, potassium acetate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The base is used in an amount of about 0.8 to about 10 moles, relative to 1 mole of Compound (XLV).

The "Lewis acid" is, for example, iron chloride, aluminum chloride, boron trifluoride, etc. The Lewis acid is used in an amount of about 0.01 to about 5 moles, relative to 1 mole of Compound (XLV).

The "iron" is used in an amount of about 0.01 to about 5 moles, relative to 1 mole of Compound (XLV).

The reaction temperature is usually about −50 to about 150° C., preferably about −20 to about 100° C. The reaction time is usually about 5 minutes to about 24 hours, preferably about 10 minutes to about 12 hours. The product can be used in the next reaction as a reaction solution as is or a crude product, or can be isolated from the reaction mixture according to a conventional method, and easily purified by conventional means of separation (e.g., recrystallization, distillation, chromatography, etc.).

In addition, when a halogen atom is substituted on ring A of Compound (XLV), Compound (XLVI) can be produced without halogenation.

Compound (XLVII) can be produced by reacting Compound (XLVI) and a triflating agent under the presence of base.

The "triflating agent" is, for example, trifluoromethanesulfonic acid, trifluoromethanesulfonic anhydride, trifluoromethanesulfonyl chloride, N-phenylbis(trifluoromethanesulfonimide), etc.

The triflating agent is used in an amount of about 0.8 to about 5.0 moles, preferably about 1.0 to about 3.0 moles, relative to 1 mole of Compound (XLVI).

The "base" is, for example, aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., metal alkoxides such as sodium methoxide, sodium ethoxide, potassium tert-butoxide, etc., or the like.

The base is used in an amount of about 0.8 to about 5.0 moles, preferably about 1.0 to about 3.0 moles, relative to 1 mole of Compound (XLVI).

The present reaction is advantageously carried out using a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The reaction time is usually about 30 minutes to about 96 hours, preferably about 1 hour to about 72 hours. The reaction temperature is usually about 0 to about 120° C., preferably about 0 to about 60° C.

Compound (XLVIII) produced by subjecting Compound (XLVII) to Suzuki coupling.

This reaction is carried out by reacting Compound (XLVII) with boronic acids such as substituted boronic acid and substituted boronic acid ester, etc. in a solvent under basic condition under the presence of a transitional metal catalyst.

The "boronic acids" are used in an amount of about 0.5 to about 10 moles, preferably about 0.9 to about 3 moles, relative to 1 mole of Compound (XLVII).

The "base" is, for example, basic salts such as sodium carbonate, potassium carbonate, cecium carbonate, sodium hydrogen carbonate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., metal alkoxides such as sodium methoxide, sodium ethoxide, sodium tert-butoxide, potassium tert-butoxide, etc., or the like.

The "transitional metal catalyst" is, for example, a palladium catalyst such as palladium acetate, palladium chloride, tetrakis(triphenylphosphine)palladium, 1,1-bis(diphenylphosphino)ferrocene dichloropalladium, dichlorobis (triphenylphosphine)palladium, etc. The transitional metal catalyst is used in an amount of about 0.001 to about 3 moles, preferably about 0.02 to about 0.2 moles, relative to 1 mole of Compound (XLVII).

The solvent is, for example, ethers such as diethyl ether, diisopropyl ether, tetrahydrofuran, dioxane, 1,2-dimethoxyethane, etc., alcohols such as methanol, ethanol, propanol, etc., hydrocarbons such as benzene, toluene, carbon disulfide, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., water or mixed solvent thereof, or the like.

The reaction temperature is usually 0 to 250° C., preferably 50 to 150° C. The reaction time is usually about 5 minutes to about 48 hours, preferably about 30 minutes to about 24 hours.

In the present reaction, the reaction time can be shortened using microwave reactor, etc.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (XLIX) is produced from Compound (XLVIII) by the same method as the method of producing Compound (XXXVI) from Compound (XXXV) as shown in Reaction Scheme 11.

Compound (L) is produced from Compound (XLIX) by the same method as the method of producing Compound (IIf) from Compound (XXXVI) as shown in Reaction Scheme 11.

Compound (IIf) is produced from Compound (L) by the same method as the method of producing Compound (XXXIV) from Compound (XXXIII).

Compound (IIg) is produced from Compound (IIf) by the same method as the method of producing Compound (IId) from Compound (XXV).

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (LIV) can be also produced by a method described in the following Reaction Scheme 14.

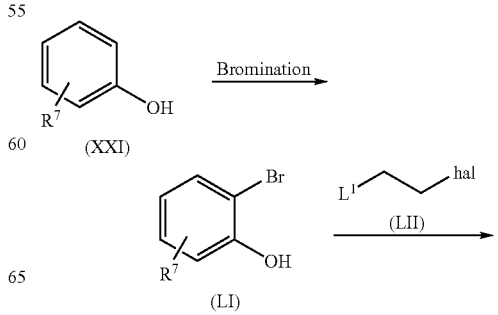

Reaction Scheme 14

-continued

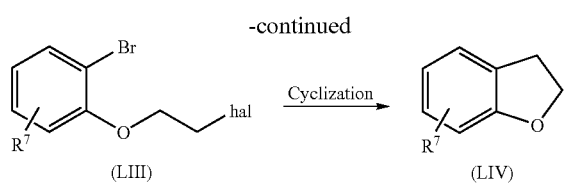

In Reaction Scheme 13, each symbol has the same meaning as defined above.

Compound (LI) is produced by reacting Compound (XXI) and brominating reagent.

The "brominating reagent" is, for example, bromine, N-bromosuccinimide, benzyltrimethylammonium tribromide, etc. bromine adducts, etc.

The present reaction is advantageously carried out using a solvent inert to the reaction. Such solvents are not particularly limited if the reaction proceeds, and include, for example, ethers such as diethyl ether, diisopropyl ether, tetrahydrofuran, dioxane, 1,2-dimethoxyethane, etc., alcohols such as methanol, ethanol, propanol, etc., hydrocarbons such as benzene, toluene, carbon disulfide, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., organic acids such as acetic acid, propionic acid, etc., nitroalkanes such as nitromethane, etc., aromatic amines such as pyridine, lutidine, quinoline, etc., or a mixed solvent thereof, or the like.

The reaction temperature is usually about 0 to about 150° C., preferably about 20 to about 100° C. The reaction time is usually about 5 minutes to about 24 hours, preferably about 10 minutes to about 12 hours.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (LIII) is produced by reacting Compound (LI) and Compound (LII) under the presence of base.

The "base" is, for example, basic salts such as sodium carbonate, potassium carbonate, cecium carbonate, sodium hydrogen carbonate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., metal alkoxides such as sodium methoxide, sodium ethoxide, potassium tert-butoxide, etc., or the like.

Compound (LII) is used in an amount of about 0.7 moles to excessive amount, relative to 1 mole of Compound (LI).

The base is used in an amount of about 0.8 to about 10 moles, preferably about 1.0 to about 5 moles, relative to 1 mole of Compound (LI). Further, if desired, quaternary ammonium salt may be added with the base.

The "quaternary ammonium salt" is, for example, benzyltributylammonium iodide, etc.

The quaternary ammonium salt is used in an amount of about 0.1 to about 2.0 moles, preferably about 0.5 to about 1.0 mole, relative to 1 mole of Compound (LI).

The present reaction is advantageously carried out using a solvent inert to the reaction. Such solvents are not particularly limited if the reaction proceeds, and include, for example, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, tetrachlorocarbon, 1,2-dichloroethane, etc., nitriles such as acetonitrile, propionitrile, etc., sulfoxides such as dimethylsulfoxide, etc., or a mixed solvent thereof, or the like.

The reaction time is usually about 30 minutes to about 96 hours, preferably about 1 hour to about 72 hours. The reaction temperature is usually about 0 to about 120° C., preferably about 0 to about 60° C.

The product can be used in the next reaction as a reaction solution as is or a crude product, or can be isolated from the reaction mixture according to a conventional method, and easily purified by conventional means of separation (e.g., recrystallization, distillation, chromatography, etc.).

Compound (LIV) is produced by cyclization of Compound (LIII) under the presence of a metallic compound (e.g., Grignard reagents, organic lithium reagents, magnesium, etc.).

The metallic compound is used in an amount of about 0.8 to about 30 moles, preferably about 1.0 to about 10 moles, relative to 1 mole of Compound (VIII).

The present reaction is advantageously carried out using a solvent inert to the reaction. Such solvents are not particularly limited if the reaction proceeds, and include, for example, hydrocarbons such as hexane, cyclohexane, benzene, toluene, xylene, etc., ethers such as diethyl ether, diisopropyl ether, tetrahydrofuran, dioxane, 1,2-dimethoxyethane, etc., halogenated carbons such as dichloromethane, chloroform, tetrachlorocarbon, 1,2-dichloroethane, etc., or a mixed solvent thereof, or the like.

The reaction time is usually about 10 minutes to about 24 hours, preferably about 30 minutes to about 5 hours. The reaction temperature is usually about −100 to about 120° C., preferably about −80 to about 60° C.

The product can be used in the next reaction as a crude product, or can be isolated from the reaction mixture according to a conventional method, and easily purified by conventional means of separation (e.g., recrystallization, distillation, chromatography, etc.).

The compounds which are raw materials for the above-mentioned Compound (I), etc. may form a salt. Kinds of the salt are not particularly limited if the reactions are achieved, and include, for example, the salts that the above-mentioned Compound (I), etc. may form.

Configurational isomers ((E)- and (Z)-forms) of Compound (I), etc. and Compounds (Ia), (Ib), (Ic) and (Id) which are contained in Compound (I), and Compound (I'), can be isolated and purified by conventional means of separation (e.g., extraction, recrystallization, distillation, chromatography, etc.) to produce pure compounds at the point when the isomers are generated. Further, the corresponding pure isomers can be also obtained by progressing isomerization of a double bond with an acid catalyst, a transitional metal complex, a metal catalyst, a radical species catalyst, an illumination or a strong base catalyst, or by heating, etc., according to the method described in New Experimental Chemistry Lecture 14 (Japanese Society of Chemistry), pp. 251-253, Experimental Chemistry Lecture 19 (Japanese Society of Chemistry), $4^{th}$ Ed., pp. 273-274 and analogous methods thereto.

In addition, stereoisomers of Compound (I), etc. are generated depending on kinds of substituents, and these isomers which are isolated or mixed, are contained in the present invention.

Compound (I), etc. may be a hydrate or a non-hydrate.

In any case, Compound (I), etc. can be synthesized by deprotection, acylation, alkylation, hydrogenation, oxidation, reduction, carbon chain extension reaction, substituent exchange reaction, or a combination of two or more, if further desired.

When the objective compound is obtained in free form, it can be converted to a salt by a conventional method. When the objective compound is obtained in salt form, it can be converted to free form or another salt by a conventional method. Thus obtained Compound (I), etc. can be isolated and purified from the reaction solution by known means such as solvent conversion, concentration, solvent extraction, fractional distillation, crystallization, recrystallization, chromatography, etc.

When compound (I) exists as configurational isomers, diastreomers, conformers, etc., the respective isomers can be isolated by the above-mentioned means of isolation and purification. Further, when compound (I), etc. are racemic compounds, they can be separated into (d) and (l) forms by any conventional optical resolution means.

In the above reactions, when the starting compounds have an amino group, a carboxyl group, a hydroxyl group, etc. as substituents, these groups may be protected by conventional protective groups such as those generally employed in peptide chemistry, and the like. After the reaction, the protective groups may be removed to obtain the objective compound, if necessary.

The protective group is, for example, formyl or, $C_{1-6}$ alkyl-carbonyl (e.g., acetyl, propionyl, etc.), phenylcarbonyl, $C_{1-6}$ alkoxy-carbonyl (e.g., methoxycarbonyl, ethoxycarbonyl, etc.), phenyloxycarbonyl, $C_{7-10}$ aralkyloxy-carbonyl (e.g., benzyloxycarbonyl, etc.), trityl, phthaloyl, etc, which are optionally substituted, respectively. The substituent is, for example, a halogen atom (e.g., fluorine, chlorine, bromine, iodine, etc.), $C_{1-6}$ alkyl-carbonyl (e.g., acetyl, propionyl, valeryl, etc.), nitro, etc. The number of the substituent is, for example, 1 to 3.

In addition, the protective group may be removed by per se known methods or analogous methods thereto, for example, a method of treating the protective group with an acid, a base, ultraviolet ray, hydrazine, phenylhydrazine, sodium N-methyldithiocarbamate, tetrabutylammonium fluoride, palladium acetate, etc., or reduction.

Compound ($I_0$) and a prodrug thereof have modulating action on cannabinoid receptors of CB1 agonist, CB1 antagonist, or CB2 agonist, etc.

The primary compounds among the compounds represented by Formula ($I_0$) wherein the 2-position of the fused-heterocycle in Formula ($I_0$) is not substituted (e.g., the compound of Formula (I) wherein both of $R^1$ and $R^2$ are a hydrogen atom), have CB1 agonistic action, and useful for treating and preventing various diseases as described in Clin. Pharmacokinet., 2003 42(4) 327-360. Specific examples include, but are not limited to, cerebrovascular disorders such as cerebral infarction, cerebral hemorrhage, etc.; head injury; spinal damage; atmospheric hypoxia and ischemia by nerve gas damage; nausea, vomit by anticancer agent; low appetite such as anorexia, cachexia, etc. in cancer and AIDS; nausea by emetics; seizure by multiple sclerosis; psychogenic pain; chronic pain; Tourette's syndrome, imbalance; motor function disorders such as levodopa-induced motor disorders, etc.; asthma; glaucoma; allergy; inflammation; epilepsy; refractory hiccup; depression; bipolar depression; anxiety; dependency and withdrawal syndrome on opiate and alcohol; renal diseases such as renal failure, etc.; various syndromes of Alzheimer's dementia; autoimmune diseases such as multiple sclerosis, arthritis, rheumatism, Crohn's Disease, etc.; hypertension; cancer; diarrhea; respiratory tract obstruction; sleep apnea, etc.

The primary compounds among the compounds represented by Formula ($I_0$) wherein the 2-position of the fused-heterocycle in Formula ($I_0$) is substituted (e.g., the compound of Formula (I) wherein both of $R^1$ and $R^2$ are not a hydrogen atom), have CB1 agonistic action, and are considered to be useful for, but are not limited to, treating and preventing anxiety, mood disorders, delirium, general mental diseases, schizophrenia, depression, drug use-related diseases such as alcohol dependency, nicotine dependency, etc., neuropathy, migraine, mental stress, epilepsy, motor disorders such as dyskinesia of Parkinson's disease, memory disorders, cognitive disorders, panic disorders, Parkinson's disease, Huntington chorea, Raynaud's Disease, tremor, obsessive-compulsive syndrome, geriatric or Alzheimer's disease, hyperkinesia, wake disorders, neuro-protection in neurodegenerative diseases, appetite suppression in intake disorders, excessive appetite, overeating and obesity, type II diabetes mellitus, digestive tract disorders, diarrhea, ulcer, vomit, urinary tract or bladder function disorders, circulation disorders, infertility, inflammative pneumonia, infection, anticancer, smoking cessation, endotoxin shock, bleeding shock, hypotension and insomnia, and further, pain-relieving, potentiating opiate or non-opiate analgesics, and improving digestive tract movement. Pharmacological tools in human or animal can be used as itself or as labeled with radioisotope for detecting and labeling CB1 receptor.

Further, the compounds represented by Formula ($I_0$) has broad CB2 agonistic action, and are considered to be useful for, but are not limited to, preventing or treating multiple sclerosis, neurodegenerative diseases, irritable bowel syndrome, Crohn's Disease, reflux oesophagitis, COPD, psoriasis, autoimmune diseases, graft rejection, allergic diseases, psychogenic pain, hepatitis virus or hypertension, or regulating immunity, etc.

The compound of the present invention has low toxicity (for example, acute toxicity, chronic toxicity, genotoxicity, reproduction toxicity, cardiotoxicity, drug interaction, carcinogenecity, etc.) and can be administered safely alone or in the form of a pharmaceutical composition prepared by formulating it with a pharmacologically acceptable carrier according to per se known means in such dosage forms as tablets (including sugar-coated tablets, film-coated tablets and orally disintegrating tablets), powders, granules, capsules (including soft capsules), solutions, injections, suppositories, controlled release dosage forms and patches, whether orally or by other routes (e.g. topically, rectally, intravenously, etc.).

The content of the compound of the present invention in the preparation of the present invention is about 0.001 to about 100% by weight based on the total weight of the preparation.

The dosage is varied depending on the characteristics of the patient or the recipient, the route of administration, the disease to be treated, and other factors. For example, when an injectable dosage form is administered to an adult patient for the treatment of a brain trauma, the recommended dosage in terms of active ingredient of the present compound is about 0.001 to about 20 mg/kg body weight, preferably about 0.005 to about 5 mg/kg body weight, and more preferably about 0.05 to about 1 mg/kg body weight per day in a single dose or in divided doses.

The present compound can be used in combination with other active ingredients [(e.g., a thrombolytic agent (e.g., tissue plasminogen activator, urokinase, etc.), an anticoagulant (e.g., argatroban, heparin, etc.), Factor X-inhibitor, thromboxane-synthetase inhibitor, (e.g., ozagrel, etc.), an antioxidant (e.g., edaravon, etc.), an anti-edema agent (e.g., glycerol, mannitol, etc.), neuron-creating or regenerating promoter (e.g., Akt/PKB activator, GSK-3β-inhibitor, etc.), acetylcholinesterase inhibitor (e.g., donepezil, rivastigmine, galantamine, zanapezil, etc.), a suppressor for production, secretion, accumulation, aggregation and/or deposition of β-amyloid protein [β-secretase inhibitor (e.g. the compound described in WO 98/38156, the compound described in WO 02/2505, WO 02/2506 or WO 02/2512, OM99-2 (WO 01/00663)), γ-secretase inhibitor, inhibitor of β-amyloid protein aggregation (e.g., PTI-00703, ALZHEMED (NC-531), PPI-368 (JP-A-1999-514333), PPI-558 (JP-2001-500852), SKF-74652 (Biochem. J. (1999), 340(1), 283-289)), β-amyloid vaccine, β-amyloid decomposing enzyme, etc.], brain function enhancing agent (e.g., aniracetam, nicergoline, etc.), other treating agent for Parkinson's disease [(e.g., dopamine receptor agonist (L-dopa, bromocriptine, pergolide, talipexol, pramipexol, cabergoline, adamantadine, etc.), monoamine oxidase (MAO) inhibitor (Deprenyl, selegiline, remacemide, riluzole, etc.), anticolinergics (e.g., trihexyphenidyl, biperiden, etc.), COMT inhibitor (e.g., entacapone, etc.)], an agent of treating amyotrophic lateral sclerosis (e.g., riluzole, etc., neuro-nutrition factor, etc.), an agent of treating hyperlipidemia such as a cholesterol-lowering agent, etc. [statins (e.g., flavastatin sodium, atrovastatin, simvastatin, rosuvastatin, etc.), fibrate (e.g., clofibrate, etc.), squalene-synthetase inhibitor], an agent of treating abnormal behavior, loitering, etc. which are involved in dementia (e.g., sedatives, anxiolytics, etc.), apotosis inhibitor (e.g., CPI-1189, IDN-6556, CEP-1347, etc.), an agent of promoting differentiating and regenerating nerves (Leteprinim, Xaliproden (SR-57746-A), SB-216763, etc.], anti-hypertensives, an agent of treating diabetes mellitus, anti-depressive, anxiolytics, non-steroid anti-inflammative agent (e.g., meloxicam, tenoxicam, indometacin, ibuprofen, celecoxib, rofecoxib, aspirin, etc.), disease-modifying anti-rheumatic drugs (DMARDs), anti-cytokine drugs (TNF inhibitor, MAP kinase inhibitor, etc.), steroids (e.g., dexamethasone, hexesterol, colchicines acetate, etc.), sexual hormones or derivatives thereof (e.g., progesterone, estradiol, estradiol benzoate, etc.), para-thyroid hormone (PTH), calcium receptor antagonist, interferon (e.g., interferon α, interferon β), etc.]. These other active ingredients can be formulated in combination with the present compound or salt thereof according to per se known methods to provide a pharmaceutical composition (e.g., tablets, powders, granules, capsules (including soft capsules), solutions, injections, suppositories, controlled release dosage forms, etc.), or can be formulated separately to be administered to the same subject at the same time or at time interval.

The pharmacologically acceptable carrier that can be used in the manufacture of a pharmaceutical composition of the present invention includes various kinds of organic or inorganic carriers which are conventionally used in pharmaceutical practice, such as excipient, lubricant, binder, and disintegrator for solid preparations; or the solvent, solubilizer, suspending agent, isotonizing agent, buffer, and local anesthetic or soothing agent for liquid preparations. Further, common additives such as antiseptics, antioxidant, colorant, sweetener, adsorbent, wetting agent, etc. can also be incorporated, if necessary.

The excipient includes lactose, sucrose, D-mannitol, starch, corn starch, crystalline cellulose, light silicic anhydride, etc.

The lubricant includes magnesium stearate, calcium stearate, talc, colloidal silica, etc.

The binder includes, for example, crystalline cellulose, sucrose, D-mannitol, dextrin, hydroxypropylcellulose, hydroxypropylmethylcellulose, polyvinylpyrrolidone, starch, cane sugar, gelatin, methylcellulose, carboxymethylcellulose sodium, etc.

The disintegrator includes starch, carboxymethylcellulose, carboxymethylcellulose calcium, croscarmellose sodium, carboxymethyl starch sodium, L-hydroxypropylcellulose, etc. The solvent includes water for injection, alcohol, propylene glycol, macrogols, sesame oil, corn oil, olive oil, etc.

The solubilizer includes polyethylene glycol, propylene glycol, D-mannitol, benzyl benzoate, ethanol, trisaminomethane, hydrophilic surfactant such as Tween 80(trademark), cholesterol, cyclodextrin (for example, α-, β- or γ-cyclodextrin or 2-hydroxypropyl-β-cyclodextrin or methyl-β-cyclodextrin, etc.) triethanolamine, sodium carbonate, sodium citrate, etc.

The suspending agent includes surfactants such as stearyl-triethanolamine, sodium lauryl sulfate, laurylaminopropionic acid, lecithin, benzalkonium chloride, benzethonium chloride, glyceryl monostearate, etc.; and hydrophilic macromolecular substances such as polyvinyl alcohol, polyvinylpyrrolidone, carboxymethylcellulose sodium, methylcellulose, hydroxymethylcellulose, hydroxyethylcellulose, hydroxypropylcellulose, etc.

The isotonizing agent includes glucose, D-sorbitol, sodium chloride, glycerin, D-mannitol, etc.

The buffer includes phosphate, acetate, carbonate, citrate, etc.

The local anesthetic includes benzyl alcohol, etc.

The antiseptic includes paraoxybenzoic acid esters, chlorobutanol, benzyl alcohol, phenethyl alcohol, dehydroacetic acid, sorbic acid, etc.

The antioxidant includes sulfites, ascorbic acid, α-tocopherol, etc.

The following Reference Examples, Examples, Formulation Examples and Experimental examples are intended to describe the present invention in further detail and should by no means be construed as defining the scope of the invention.

As used in the following reference and working examples, the term "room temperature" generally means about 10 to 35° C. The symbol % stands for percentage by weight unless otherwise indicated.

The other abbreviations used in the text have the following meanings.

s: singlet
d: doublet
dd: doublet of doublets
dt: doublet of triplets
t: triplet
q: quartet
septet: septet
m: multiplet
br: broad
J: coupling constant
Hz: Hertz
$CDCl_3$: deuterated chloroform
DMSO-$d_6$: deuterated dimethylsulfoxide
$^1$H-NMR: proton nuclear magnetic resonance
THF: tetrahydrofuran
DMF: dimethylformamide
BINAP: 2,2'-bis(diphenylphosphino)-1,1'-binaphthyl For ¹H-NMR, proton on a hydroxyl group or an amino group has very gentle peak, is not indicated. Further, data for a free form was described as a free base for a compound forming a salt.

Kieselgel 60 made by Merk was used for silica gel chromatography, and Chromatorex NH made by Fuji Silica Chemistry, Co., Ltd for basic silica gel chromatography.

REFERENCE EXAMPLE 1

Hydroxy(4-isopropylphenyl)acetic acid

To a mixture of lithium chloride (17.0 g, 418 mmol), potassium hydroxide (44.9 g, 800 mmol) and ice (150 g) was added a solution of bromoform (17.5 mL, 200 mmol) and 4-isopropyl benzaldehyde (30.3 mL, 200 mmol) in 1,4-dioxane (150 mL) at 0° C., and the mixture was stirred at 5-10° C. for 24 hours and then stirred at 35° C. for 24 hours. The aqueous layer was acidified with hydrochloric acid and was extracted with ethyl acetate. The extract was washed with water and then was dried over anhydrous sodium sulfate. The solvent was distilled off under reduced pressure to obtain a residue, which was crystallized from hexane-ethyl acetate to obtain 28.5 g (yield 73%) of the title compound. Melting point: 156-157° C.

¹H-NMR (CDCl₃) δ: 1.24 (6H, d, J=7.0 Hz), 2.91 (1H, septet, J=7.0 Hz), 5.21 (1H, s), 7.24 (2H, d, J=8.8 Hz), 7.36 (2H, d, J=8.8 Hz), 2H unidentified.

REFERENCE EXAMPLE 2

3-(4-Isopropylphenyl)-4,6,7-trimethyl-1-benzofuran-2(3H)-one

To a mixture of hydroxy(4-isopropylphenyl)acetic acid synthesized in Reference Example 1 (11.8 g, 60.8 mmol) and 2,3,5-trimethylphenol (12.4 g, 91.2 mmol) was added 70% sulfuric acid (10 mL) at room temperature, and the mixture was stirred at 115° C. for 12 hours. The mixture was added to water and was extracted with diisopropyl ether. The extract was washed with water and a saturated sodium hydrogen carbonate solution, and then was dried over anhydrous sodium sulfate. The solvent was distilled off under reduced pressure to obtain a residue, which was purified by silica gel column chromatography (hexane ethyl acetate=8:1) to obtain 10.9 g (yield 65%) of the title compound. Melting point: 107-108° C. (hexane-ethyl acetate).

¹H-NMR (CDCl₃) δ: 1.22 (6H, d, J=6.6 Hz), 1.93 (3H, s), 2.24 (3H, s), 2.29 (3H, s), 2.88 (1H, septet, J=6.6 Hz), 4.76 (1H, s), 6.76 (1H, s), 7.07 (2H, d, J=8.1 Hz), 7.17 (2H, d, J=8.1 Hz).

REFERENCE EXAMPLE 3

3-(4-Isopropylphenyl)-6,7-dimethyl-1-benzofuran-2(3H)-one

Using hydroxy(4-isopropylphenyl)acetic acid synthesized in Reference Example 1 and 2,3-dimethylphenol, the title compound was synthesized in the same manner as in Reference Example 2. Yield 44%. Melting point: 58-60° C. (methanol).

¹H-NMR (CDCl₃) δ: 1.22 (6H, d, J=6.9 Hz), 2.27 (3H, s), 2.32 (3H, s), 2.88 (1H, septet, J=6.6 Hz), 4.85 (1H, s), 6.91 (1H, d, J=7.8 Hz), 6.95 (1H, d, J=7.8 Hz), 7.13 (2H, d, J=8.1 Hz), 7.19 (2H, d, J=8.1 Hz).

REFERENCE EXAMPLE 4

3-(4-Isopropylphenyl)-4,6-dimethyl-1-benzofuran-2(3H)-one

Using hydroxy(4-isopropylphenyl)acetic acid synthesized in Reference Example 1 and 3,5-dimethylphenol, the title compound was synthesized in the same manner as in Reference Example 2. Yield 45%. Melting point: 76-77° C. (ethyl acetate-hexane).

¹H-NMR (CDCl₃) δ: 1.23 (6H, d, J=7.0 Hz), 1.97 (3H, s), 2.38 (3H, s), 2.88 (1H, septet, J=7.0 Hz), 4.73 (1H, s), 6.78 (1H, s), 6.84 (1H, s), 7.07 (2H, d, J=8.2 Hz), 7.18 (2H, d, J=8.2 Hz).

REFERENCE EXAMPLE 5

5-Bromo-3-(4-isopropylphenyl)-1-benzofuran-2(3H)-one

Using hydroxy(4-isopropylphenyl)acetic acid synthesized in Reference Example 1 and 4-bromophenol, the title compound was synthesized in the same manner as in Reference Example 2. Yield 30%. Melting point: 157-158° C. (methanol).

¹H-NMR (CDCl₃) δ: 1.24 (6H, d, J=6.9 Hz), 2.90 (1H, septet, J=6.9 Hz), 4.86 (1H, s), 7.06 (1H, d, J=8.7 Hz), 7.11 (2H, d, J=8.4 Hz), 7.23 (2H, d, J=8.4 Hz), 7.33 (1H, s), 7.47 (1H, d, J=8.7 Hz).

REFERENCE EXAMPLE 6

3-(4-Isopropylphenyl)-3,4,6,7-tetramethyl-1-benzofuran-2(3H)-one

To a solution of 3-(4-isopropylphenyl)-4,6,7-trimethyl-1-benzofuran-2(3H)-one synthesized in Reference Example 2 (2.10 g, 7.13 mmol) in DMF (30 mL) was added sodium hydride (a 60% fluidized paraffin dispersion, 314 mg, 7.84 mmol) at 0° C., and the mixture was stirred at room temperature for 30 minutes. To the reaction solution was added methyl iodide (1.11 g, 7.84 mmol) and the mixture was stirred for at room temperature 30 minutes. Water was added to the reaction solution and the product was extracted with ethyl acetate. The combined extract was washed with water, dried over magnesium sulfate and then concentrated under reduced pressure to obtain the residue, which was purified by silica gel column chromatography (hexane:ethyl acetate=4:1) to obtain 2.07 g (yield 94%) of the title compound as an oily matter.

¹H-NMR (CDCl₃) δ: 1.21 (6H, d, J=6.9 Hz), 1.94 (3H, s), 1.98 (3H, s), 2.25 (3H, s), 2.29 (3H, s), 2.87 (1H, septet, J=6.9 Hz), 6.77 (1H, s), 7.09-7.22 (4H, m).

REFERENCE EXAMPLE 7

3-(4-Isopropylphenyl)-3,6,7-trimethyl-1-benzofuran-2(3H)-one

Using 3-(4-isopropylphenyl)-6,7-dimethyl-1-benzofuran-2(3H)-one synthesized in Reference Example 3, the title compound was synthesized in the same manner as in Reference Example 6. Yield 59%. Oily matter.

¹H-NMR (CDCl₃) δ: 1.21 (6H, d, J=6.8 Hz), 1.87 (3H, s), 2.28 (3H, s), 2.33 (3H, s), 2.87 (1H, septet, J=6.9 Hz), 6.94 (1H, d, J=7.8 Hz), 6.94 (1H, d, J=7.8 Hz), 7.17 (2H, d, J=8.4 Hz), 7.25 (2H, d, J=8.4 Hz).

REFERENCE EXAMPLE 8

2-(2-Hydroxy-1-(4-isopropylphenyl)ethyl)-3,5,6-trimethylphenol

To a solution of 3-(4-isopropylphenyl)-4,6,7-trimethyl-1-benzofuran-2(3H)-one (8.42 g, 28.6 mmol) obtained in Reference Example 2 in THF (80 mL) was added lithium aluminum hydride (1.63 g, 42.9 mmol) at 0° C., and the mixture was heated under reflux for 1 hour. Water was added to the reaction solution and the product was extracted with ethyl acetate. The combined extract was washed with water, dried over magnesium sulfate and then concentrated under reduced pressure. The obtained residue was crystallized from hexane-ethyl acetate to obtain 8.00 g (yield 94%) of the title compound. Melting point: 101-102° C.

$^1$H-NMR (CDCl$_3$) δ: 1.22 (6H, d, J=6.9 Hz), 2.13-2.35 (10H, m), 2.86 (1H, septet, J=6.9 Hz), 4.24 (1H, dd, J=10.8 Hz), 4.42 (1H, dd, J=10.8, 5.1 Hz), 4.50 (1H, dd, J=5.1, 2.7 Hz), 6.58 (1H, s), 7.15 (4H, s), 8.01 (1H, br s).

REFERENCE EXAMPLE 9

6-(2-Hydroxy-1-(4-isopropylphenyl)ethyl)-2,3-dimethylphenol

Using 3-(4-isopropylphenyl)-6,7-dimethyl-1-benzofuran-2(3H)-one synthesized in Reference Example 3, the title compound was synthesized in the same manner as in Reference Example 8.

Yield 36%. Melting point: 83-84° C. (ethyl acetate-hexane).

$^1$H-NMR (CDCl$_3$) δ: 1.24 (6H, d, J=7.2 Hz), 2.03 (1H, br s), 2.18 (3H, s), 2.25 (3H, s), 2.87 (1H, septet, J=7.2 Hz), 4.18-4.39 (3H, m), 6.68 (1H, d, J=7.8 Hz), 6.77 (1H, d, J=7.8 Hz), 6.84 (1H, s), 7.14 (2H, d, J=9.0 Hz), 7.18 (2H, d, J=9.0 Hz).

REFERENCE EXAMPLE 10

2-(2-Hydroxy-1-(4-isopropylphenyl)ethyl)-3,5-dimethylphenol

Using 3-(4-isopropylphenyl)-4,6-dimethyl-1-benzofuran-2(3H)-one synthesized in Reference Example 4, the title compound was synthesized in the same manner as in Reference Example 8. Yield 93%. Melting point: 101-102° C. (ethyl acetate-hexane).

$^1$H-NMR (CDCl$_3$) δ: 1.21 (6H, d, J=6.9 Hz), 2.19 (3H, s), 2.25 (3H, s), 2.27 (1H, br s), 2.86 (1H, septet, J=6.9 Hz), 4.21 (1H, dd, J=11.1, 2.7 Hz), 4.39 (1H, dd, J=11.1, 5.1 Hz), 4.48 (1H, dd, J=5.1, 2.7 Hz), 6.57 (1H, s), 6.62 (1H, s), 7.15 (4H, s), 8.14 (1H, br s).

REFERENCE EXAMPLE 11

4-Bromo-2-(2-hydroxy-1-(4-isopropylphenyl)ethyl) phenol

Using 5-bromo-3-(4-isopropylphenyl)-1-benzofuran-2(3H)-one synthesized in Reference Example 5, the title compound was synthesized in the same manner as in Reference Example 8. Yield 44%. Oily matter.

$^1$H-NMR (CDCl$_3$) δ: 1.24 (6H, d, J=6.9 Hz), 1.38 (1H, br s), 2.88 (1H, septet, J=7.2 Hz), 4.18-4.37 (3H, m), 6.76 (1H, d, J=8.1 Hz), 7.08-7.25 (6H, m), 7.47 (1H, br s).

REFERENCE EXAMPLE 12

2-(2-Hydroxy-1-(4-isopropylphenyl)-1-methylethyl)-3,5,6-trimethylphenol

Using 3-(4-isopropylphenyl)-3,4,6,7-tetramethyl-1-benzofuran-2(3H)-one synthesized in Reference Example 6, the title compound was synthesized in the same manner as in Reference Example 8. Yield 83%. Melting point: 116-117° C. (ethyl acetate-hexane).

$^1$H-NMR (CDCl$_3$) δ: 1.23 (6H, d, J=6.9 Hz), 1.73 (6H, s), 2.20 (3H, s), 2.21 (3H, s), 2.56-2.64 (1H, m), 2.88 (1H, septet, J=6.9 Hz), 3.77 (1H, dd, J=11.1, 3.6 Hz), 4.13-4.22 (1H, m), 6.49 (1H, s), 7.11 (2H, d, J=8.4 Hz), 7.15 (2H, d, J=8.4 Hz), 8.70 (1H, s).

REFERENCE EXAMPLE 13

3-(4-Isopropylphenyl)-4,6,7-trimethyl-2,3-dihydro-1-benzofuran

To a solution of 2-(2-hydroxy-1-(4-isopropylphenyl) ethyl)-3,5,6-trimethylphenol obtained in Reference Example 8 (7.85 g, 26.3 mmol) and triphenylphosphine (7.58 g, 28.9 mmol) in THF (60 mL) was added diethyl azodicarboxylate (a 40% toluene solution, 12.6 g, 28.9 mmol) with ice-cooling, and the mixture was stirred at room temperature for 1 hour. The solvent was concentrated under reduced pressure to obtain the residue, which was purified by silica gel column chromatography (hexane:ethyl acetate=10:1) to obtain 5.70 g (yield 84%) of the title compound. Melting point: 48-49° C. (methanol).

$^1$H-NMR (CDCl$_3$) δ: 1.22 (6H, d, J=6.9 Hz), 1.89 (3H, s), 2.15 (3H, s), 2.23 (3H, s), 2.86 (1H, septet, J=6.9 Hz), 4.37-4.56 (2H, m), 4.79-4.88 (1H, m), 6.48 (1H, s), 7.06 (2H, d, J=8.1 Hz), 7.13 (2H, d, J=8.1 Hz).

REFERENCE EXAMPLE 14

3-(4-Isopropylphenyl)-6,7-dimethyl-2,3-dihydro-1-benzofuran

Using 6-(2-hydroxy-1-(4-isopropylphenyl)ethyl)-2,3-dimethylphenol synthesized in Reference Example 9, the title compound was synthesized in the same manner as in Reference Example 13. Yield 80%. Melting point: 50-51° C. (methanol).

$^1$H-NMR (CDCl$_3$) δ: 1.23 (6H, d, J=6.9 Hz), 2.18 (3H, s), 2.25 (3H, s), 2.88 (1H, septet, J=6.9 Hz), 4.35-4.42 (1H, m), 4.62 (1H, t, J=8.7 Hz), 4.82-4.90 (1H, m), 6.67 (1H, d, J=7.8 Hz), 6.75 (1H, d, J=7.8 Hz), 7.13 (2H, d, J=9.0 Hz), 7.17 (2H, d, J=9.0 Hz).

REFERENCE EXAMPLE 15

3-(4-Isopropylphenyl)-4,6-dimethyl-2,3-dihydro-1-benzofuran

Using 2-(2-hydroxy-1-(4-isopropylphenyl)ethyl)-3,5-dimethylphenol synthesized in Reference Example 10, the title compound was synthesized in the same manner as in Reference Example 13. Yield 85%. Melting point: 46-47° C. (methanol).

$^1$H-NMR (CDCl$_3$) δ: 1.22 (6H, d, J=7.0 Hz), 1.92 (3H, s), 2.29 (3H, s), 2.86 (1H, septet, J=7.0 Hz), 4.35-4.53 (2H, m), 4.75-4.90 (1H, m), 6.47 (1H, s), 6.55 (1H, s), 7.05 (2H, d, J=8.0 Hz), 7.13 (2H, d, J=8.0 Hz).

REFERENCE EXAMPLE 16

5-Bromo-3-(4-isopropylphenyl)-2,3-dihydro-1-benzofuran

Using 4-bromo-2-(2-hydroxy-1-(4-isopropylphenyl) ethyl)phenol synthesized in Reference Example 11, the title compound was synthesized in the same manner as in Reference Example 13. Yield 62%. Melting point: 90-91° C. (methanol).

$^1$H-NMR (CDCl$_3$) δ: 1.24 (6H, d, J=6.8 Hz), 2.90 (1H, septet, J=6.8 Hz), 4.37-4.47 (1H, m), 4.56-4.67 (1H, m), 4.89 (1H, dd, J=9.6, 8.8 Hz), 6.74 (1H, d, J=8.4 Hz), 7.07-7.29 (6H, m).

REFERENCE EXAMPLE 17

3-(4-Isopropylphenyl)-3,4,6,7-tetramethyl-2,3-dihydro-1-benzofuran

Using 2-(2-hydroxy-1-(4-isopropylphenyl)-1-methylethyl)-3,5,6-trimethylphenol synthesized in Reference Example 12, the title compound was synthesized in the same manner as in Reference Example 13. Yield 95%. Oily matter.

$^1$H-NMR (CDCl$_3$) δ: 1.23 (6H, d, J=6.9 Hz), 1.74 (3H, s), 1.80 (3H, s), 2.15 (3H, s), 2.22 (3H, s), 2.87 (1H, septet, J=6.9 Hz), 4.38 (1H, d, J=8.4 Hz), 4.46 (1H, d, J=8.4 Hz), 6.45 (1H, s), 7.13 (2H, d, J=8.4 Hz), 7.20 (2H, d, J=8.4 Hz).

REFERENCE EXAMPLE 18

5-Bromo-3-(4-isopropylphenyl)-4,6,7-trimethyl-2,3-dihydro-1-benzofuran

To a mixture of 3-(4-isopropylphenyl)-4,6,7-trimethyl-2,3-dihydro-1-benzofuran synthesized in Reference Example 13 (6.10 g, 21.8 mmol) and sodium acetate (1.97 g, 24.0 mmol) in acetonitrile (30 mL) was added bromine (1.17 mL, 22.9 mmol), and the mixture was stirred at the same temperature for 1 hour. Water was poured into the reaction mixture, which was extracted with ethyl acetate. The extract was washed with a saturated sodium hydrogen carbonate solution and water, dried over magnesium sulfate, filtered and then concentrated under reduced pressure. The obtained residue was crystallized from methanol to obtain 7.90 g (yield 99%) of the title compound. Melting point: 86-87° C. (methanol).

$^1$H-NMR (CDCl$_3$) δ: 1.22 (6H, d, J=6.9 Hz), 2.04 (3H, s), 2.23 (3H, s), 2.38 (3H, s), 2.86 (1H, septet, J=6.9 Hz), 4.41 (1H, dd, J=8.4, 4.8 Hz), 4.54 (1H, dd, J=9.0, 4.8 Hz), 4.81 (1H, t, J=9.0 Hz), 7.01 (2H, d, J=8.1 Hz), 7.12 (2H, d, J=8.1 Hz).

REFERENCE EXAMPLE 19

5-Bromo-3-(4-isopropylphenyl)-6,7-dimethyl-2,3-dihydro-1-benzofuran

Using 3-(4-isopropylphenyl)-6,7-dimethyl-2,3-dihydro-1-benzofuran synthesized in Reference Example 14, the title compound was synthesized in the same manner as in Reference Example 18. Yield 68%. Melting point: 114-115° C. (methanol).

$^1$H-NMR (CDCl$_3$) δ: 1.24 (6H, d, J=7.0 Hz), 2.23 (3H, s), 2.33 (3H, s), 2.89 (1H, septet, J=7.0 Hz), 4.39 (1H, dd, J=8.4, 7.8 Hz), 4.54-4.66 (1H, m), 4.86 (1H, dd, J=9.2, 8.4 Hz), 7.03 (1H, s), 7.11 (2H, d, J=8.4 Hz), 7.18 (2H, d, J=8.4 Hz).

REFERENCE EXAMPLE 20

5-Bromo-3-(4-isopropylphenyl)-3,4,6,7-tetramethyl-2,3-dihydro-1-benzofuran

Using 3-(4-isopropylphenyl)-3,4,6,7-tetramethyl-2,3-dihydro-1-benzofuran synthesized in Reference Example 17, the title compound was synthesized in the same manner as in Reference Example 18. Yield 98%. Oily matter.

$^1$H-NMR (CDCl$_3$) δ: 1.23 (6H, d, J=6.9 Hz), 1.74 (3H, s), 1.90 (3H, s), 2.23 (3H, s), 2.38 (3H, s), 2.88 (1H, septet, J=6.9 Hz), 4.37 (1H, d, J=8.7 Hz), 4.42 (1H, d, J=8.7 Hz), 7.14 (2H, d, J=8.4 Hz), 7.19 (2H, d, J=8.4 Hz).

REFERENCE EXAMPLE 21

5-Bromo-3-(4-isopropylphenyl)-3,6,7-trimethyl-1-benzofuran-2(3H)-one

Using 3-(4-isopropylphenyl)-3,6,7-trimethyl-1-benzofuran-2(3H)-one synthesized in Reference Example 7, the title compound was synthesized in the same manner as in Reference Example 18. Yield 73%. Melting point: 116-117° C. (methanol).

$^1$H-NMR (CDCl$_3$) δ: 1.22 (6H, d, J=6.9 Hz), 1.86 (3H, s), 2.34 (3H, s), 2.41 (3H, s), 2.88 (1H, septet, J=6.9 Hz), 7.15-7.25 (5H, m).

REFERENCE EXAMPLE 22

4-Bromo-6-(2-hydroxy-1-(4-isopropylphenyl)-1-methylethyl)-2,3-dimethylphenol

Using 5-bromo-3-(4-isopropylphenyl)-3,6,7-trimethyl-1-benzofuran-2(3H)-one synthesized in Reference Example 21, the title compound was synthesized in the same manner as in Reference Example 8. Yield 83%. Melting point: 110-111° C. (ethyl acetate-hexane).

$^1$H-NMR (CDCl$_3$) δ: 1.24 (6H, d, J=6.9 Hz), 1.58 (3H, s), 2.15 (3H, s), 2.37 (3H, s), 2.89 (1H, septet, J=6.9 Hz), 3.99 (1H, d, J=11.7 Hz), 4.23 (1H, d, J=11.7 Hz), 6.27 (1H, br s), 7.19 (4H, s), 7.40 (1H, s), 1H unidentified.

REFERENCE EXAMPLE 23

5-Bromo-3-(4-isopropylphenyl)-4,6-dimethyl-2,3-dihydro-1-benzofuran

To a solution of 3-(4-isopropylphenyl)-4,6-dimethyl-2,3-dihydro-1-benzofuran synthesized in Reference Example 15 (5.62 g, 21.1 mmol) in acetonitrile (60 mL) was added N-bromosuccinimide (3.76 g, 21.1 mmol) at 0° C., and the mixture was stirred at the same temperature for 1 hour.

The solvent was distilled off under reduced pressure to obtain a residue, which was purified by silica gel column chromatography (hexane:ethyl acetate=10:1) to obtain 5.95 g (yield 82%) of the title compound. Melting point: 90-91° C. (methanol).

$^1$H-NMR (CDCl$_3$) δ: 1.22 (6H, d, J=6.9 Hz), 2.05 (3H, s), 2.39 (3H, s), 2.86 (1H, septet, J=6.9 Hz), 4.41 (1H, dd, J=8.4, 4.5 Hz), 4.52 (1H, dd, J=9.0, 4.5 Hz), 4.78-4.86 (1H, m), 6.66 (1H, s), 7.01 (2H, d, J=8.1 Hz), 7.13 (2H, d, J=8.1 Hz).

REFERENCE EXAMPLE 24

N-Benzyl-3-(4-isopropylphenyl)-4,6,7-trimethyl-2,3-dihydro-1-benzofuran-5-amine

To a solution of 5-bromo-3-(4-isopropylphenyl)-4,6,7-trimethyl-2,3-dihydro-1-benzofuran obtained in Reference Example 18 (920 mg, 2.56 mmol) and benzylamine (0.34 mL, 3.07 mmol) in toluene (10 mL), were added palladium acetate (6 mg, 0.03 mmol) and BINAP (48 mg, 0.09 mmol) at room temperature, and the mixture was stirred under argon stream for 15 minutes. Sodium tert-butoxide (344 mg, 3.58 mmol) was added to the reaction solution at room temperature, and then the mixture was heated under reflux for 18 hours. Water was added to the reaction solution, which was extracted with ethyl acetate, the organic layer was washed with water and a saturated brine and then was dried over anhydrous sodium sulfate, and the solvent was distilled off under reduced pressure. The obtained residue was purified by silica gel column chromatography (hexane:ethyl acetate=50:1) to obtain 900 mg (yield 91%) of the title compound as an oily matter. Oily matter.

$^1$H-NMR (CDCl$_3$) δ: 1.23 (6H, d, J=6.9 Hz), 1.87 (3H, s), 2.20 (3H, s), 2.27 (3H, s), 2.67-3.02 (2H, m), 3.91 (2H, s), 4.38 (1H, dd, J=8.4, 4.8 Hz), 4.52 (1H, dd, J=9.0, 4.8 Hz), 4.80 (1H, t, J=9.0 Hz), 7.03 (2H, d, J=8.1 Hz), 7.12 (2H, d, J=8.1 Hz), 7.20-7.42 (5H, m).

REFERENCE EXAMPLE 25

N-Benzyl-3-(4-isopropylphenyl)-6,7-dimethyl-2,3-dihydro-1-benzofuran-5-amine

Using 5-bromo-3-(4-isopropylphenyl)-6,7-dimethyl-2,3-dihydro-1-benzofuran synthesized in Reference Example 19, the title compound was synthesized in the same manner as in Reference Example 24. Yield 85%. Melting point: 108-109° C. (methanol).

$^1$H-NMR (CDCl$_3$) δ: 1.24 (6H, d, J=6.9 Hz), 2.08 (3H, s), 2.22 (3H, s), 2.88 (1H, septet, J=7.0 Hz), 3.42 (1H, br s), 4.18 (2H, s), 4.28 (1H, t, J=7.5 Hz), 4.55-4.64 (1H, m), 4.79 (1H, t, J=9.0 Hz), 6.30 (1H, s), 7.11 (2H, d, J=8.4 Hz), 7.15 (2H, d, J=8.4 Hz), 7.21-7.37 (5H, m).

REFERENCE EXAMPLE 26

N-Benzyl-3-(4-isopropylphenyl)-4,6-dimethyl-2,3-dihydro-1-benzofuran-5-amine

Using 5-bromo-3-(4-isopropylphenyl)-4,6-dimethyl-2,3-dihydro-1-benzofuran synthesized in Reference Example 23, the title compound was synthesized in the same manner as in Reference Example 24. Yield 99%. Melting point: 82-83° C. (methanol).

$^1$H-NMR (CDCl$_3$) δ: 1.22 (6H, d, J=6.9 Hz), 1.90 (3H, s), 2.27 (3H, s), 2.67-3.02 (2H, m), 3.93 (2H, s), 4.38 (1H, dd, J=8.4, 4.5 Hz), 4.49 (1H, dd, J=9.0, 4.5 Hz), 4.75-4.83 (1H, m), 6.59 (1H, s), 7.02 (2H, d, J=8.1 Hz), 7.12 (2H, d, J=8.1 Hz), 7.19-7.39 (5H, m).

REFERENCE EXAMPLE 27

N-Benzyl-3-(4-isopropylphenyl)-2,3-dihydro-1-benzofuran-5-amine

Using 5-bromo-3-(4-isopropylphenyl)-2,3-dihydro-1-benzofuran synthesized in Reference Example 16, the title compound was synthesized in the same manner as in Reference Example 24. Yield 89%. Oily matter.

$^1$H-NMR (CDCl$_3$) δ: 1.24 (6H, d, J=6.9 Hz), 2.88 (1H, septet, J=6.9 Hz), 3.42 (1H, br s), 4.20 (2H, s), 4.31 (1H, dd, J=8.7, 7.8 Hz), 4.51-4.59 (1H, m), 4.80 (1H, dd, J=9.0, 8.7 Hz), 6.38 (1H, d, J=2.4 Hz), 6.46 (1H, dd, J=8.1, 2.4 Hz), 6.71 (1H, d, J=8.1 Hz), 7.08-7.37 (9H, m).

REFERENCE EXAMPLE 28

N-Benzyl-3-(4-isopropylphenyl)-3,4,6,7-tetramethyl-2,3-dihydro-1-benzofuran-5-amine Using 5-bromo-3-(4-isopropylphenyl)-3,4,6,7-tetramethyl-2,3-dihydro-1-benzofuran synthesized in Reference Example 20, the title compound was synthesized in the same manner as in Reference Example 24. Yield 25%. Oily matter.

$^1$H-NMR (CDCl$_3$) δ: 1.23 (6H, d, J=6.9 Hz), 1.73 (3H, s), 1.74 (3H, s), 2.20 (3H, s), 2.27 (3H, s), 2.78-3.10 (2H, m), 3.88 (1H, d, J=13.2 Hz), 3.93 (1H, d, J=13.2 Hz), 4.35 (1H, d, J=8.4 Hz), 4.39 (1H, d, J=8.4 Hz), 7.10-7.38 (9H, m).

REFERENCE EXAMPLE 29

N-Benzyl-3-(4-isopropylphenyl)-3,6,7-trimethyl-2,3-dihydro-1-benzofuran-5-amine

To a solution of 4-bromo-6-(2-hydroxy-1-(4-isopropylphenyl)-1-methylethyl)-2,3-dimethylphenol obtained in Reference Example 22 (830 mg, 2.21 mmol) and triphenylphosphine (638 mg, 2.43 mmol) in THF (60 mL) was added diethyl azodicarboxylate (a 40% toluene solution, 1.06 g, 2.43 mmol) with ice-cooling, and the mixture was stirred at room temperature for 1 hour. The solvent was concentrated under reduced pressure to obtain a residue, which was purified by silica gel column chromatography (hexane:ethyl acetate=10:1) to obtain oily 5-bromo-3-(4-isopropylphenyl)-3,6,7-trimethyl-2,3-dihydro-1-benzofuran 660 mg. To a solution of said compound (660 mg, 1.84 mmol) and benzylamine (0.24 mL, 2.21 mmol) in toluene (10 mL) were added palladium acetate (4 mg, 0.02 mmol) and BINAP (34 mg, 0.6 mmol) at room temperature, and the mixture was stirred under argon stream for 15 minutes.

Sodium tert-butoxide (248 mg, 2.58 mmol) was added to the reaction solution at room temperature, and the mixture was heated under argon stream for 18 hours. Water was added to the reaction solution, which was extracted with ethyl acetate, the organic layer was washed with water and a saturated brine and then was dried over anhydrous sodium sulfate, and the solvent was distilled off under reduced pressure. The obtained residue was purified by silica gel column chromatography (hexane:ethyl acetate=50:1), to obtain 660 mg (yield 77%) of the title compound as an oily matter.

$^1$H-NMR (CDCl$_3$) δ: 1.23 (6H, d, J=7.0 Hz), 1.69 (3H, s), 2.09 (3H, s), 2.22 (3H, s), 2.87 (1H, septet, J=7.0 Hz), 3.47 (1H, br s), 4.23 (2H, s), 4.35 (1H, d, J=8.4 Hz), 4.48 (1H, d, J=8.4 Hz), 6.32 (1H, s), 7.07-7.42 (9H, m).

REFERENCE EXAMPLE 30

3-(4-Isopropylphenyl)-4,6,7-trimethyl-2,3-dihydro-1-benzofuran-5-amine

A mixture of N-benzyl-3-(4-isopropylphenyl)-4,6,7-trimethyl-2,3-dihydro-1-benzofuran-5-amine obtained in Reference Example 24 (900 mg, 2.33 mmol), 10%-palladium carbon (50% hydrous, 90 mg) and ammonium formate (294 mg, 4.66 mmol) in ethanol (10 mL) was heated under reflux for 2 hours. The solid material was removed and the filtrate was concentrated under reduced pressure. Water and ethyl acetate were added to the residue to separate the organic layer, and the aqueous layer was extracted with ethyl acetate. The combined organic layer was washed with water, and dried over anhydrous sodium sulfate. The solvent was distilled off under reduced pressure to obtain a residue, which was crystallized from ethyl acetate-hexane to obtain 510 mg (yield 74%) of the title compound. Melting point: 171-173° C.

$^1$H-NMR (CDCl$_3$) δ: 1.22 (6H, d, J=6.9 Hz), 1.84 (3H, s), 2.11 (3H, s), 2.20 (3H, s), 2.86 (1H, septet, J=6.9 Hz), 3.26 (2H, br s), 4.30-4.41 (1H, m), 4.47-4.60 (1H, m), 4.70-4.82 (1H, m), 7.05 (2H, d, J=8.1 Hz), 7.12 (2H, d, J=8.1 Hz).

REFERENCE EXAMPLE 31

3-(4-Isopropylphenyl)-6,7-dimethyl-2,3-dihydro-1-benzofuran-5-amine

Using N-benzyl-3-(4-isopropylphenyl)-6,7-dimethyl-2,3-dihydro-1-benzofuran-5-amine synthesized in Reference Example 25, the title compound was synthesized in the same manner as in Reference Example 30. Yield 88%. Oily matter.

$^1$H-NMR (CDCl$_3$) δ: 1.23 (6H, d, J=6.9 Hz), 2.00 (2H, br s), 2.08 (3H, s), 2.20 (3H, s), 2.88 (1H, septet, J=6.9 Hz), 4.31 (1H, t, J=7.8 Hz), 4.56 (1H, t, J=7.8 Hz), 4.75-4.83 (1H, m), 6.29 (1H, s), 7.14 (2H, d, J=9.0 Hz), 7.17 (2H, d, J=9.0 Hz).

REFERENCE EXAMPLE 32

3-(4-Isopropylphenyl)-4,6-dimethyl-2,3-dihydro-1-benzofuran-5-amine

Using N-benzyl-3-(4-isopropylphenyl)-4,6-dimethyl-2,3-dihydro-1-benzofuran-5-amine synthesized in Reference Example 26, the title compound was synthesized in the same manner as in Reference Example 30. Yield 72%. Melting point: 81-82° C.

$^1$H-NMR (CDCl$_3$) δ: 1.22 (6H, d, J=6.9 Hz), 1.85 (3H, s), 2.18 (3H, s), 2.86 (1H, septet, J=6.9 Hz), 3.07 (2H, br s), 4.35 (1H, dd, J=8.4, 4.5 Hz), 4.49 (1H, dd, J=9.0, 4.5 Hz), 4.71-4.80 (1H, m), 6.54 (1H, s), 7.03 (2H, d, J=8.1 Hz), 7.11 (2H, d, J=8.1 Hz).

REFERENCE EXAMPLE 33

3-(4-Isopropylphenyl)-2,3-dihydro-1-benzofuran-5-amine

Using N-benzyl-3-(4-isopropylphenyl)-2,3-dihydro-1-benzofuran-5-amine synthesized in Reference Example 27, the title compound was synthesized in the same manner as in Reference Example 30. Yield 77%. Oily matter.

$^1$H-NMR (CDCl$_3$) δ: 1.23 (6H, d, J=6.9 Hz), 2.88 (1H, septet, J=6.9 Hz), 3.32 (2H, br s), 4.32 (1H, dd, J=8.7, 7.5 Hz), 4.49-4.57 (1H, m), 4.80 (1H, dd, J=9.0, 8.7 Hz), 6.38 (1H, d, J=2.4 Hz), 6.49 (1H, dd, J=8.1, 2.4 Hz), 6.67 (1H, d, J=8.1 Hz), 7.12 (2H, d, J=8.4 Hz), 7.16 (2H, d, J=8.4 Hz).

REFERENCE EXAMPLE 34

3-(4-Isopropylphenyl)-3,4,6,7-tetramethyl-2,3-dihydro-1-benzofuran-5-amine

Using N-benzyl-3-(4-isopropylphenyl)-3,4,6,7-tetramethyl-2,3-dihydro-1-benzofuran-5-amine synthesized in Reference Example 28, the title compound was synthesized in the same manner as in Reference Example 30. Yield 79%. Oily matter.

$^1$H-NMR (CDCl$_3$) δ: 1.23 (6H, d, J=6.9 Hz), 1.69 (3H, s), 1.77 (3H, s), 2.15 (3H, s), 2.20 (3H, s), 2.85 (1H, septet, J=6.9 Hz), 3.10 (2H, br s), 4.30 (1H, d, J=8.4 Hz), 4.34 (1H, d, J=8.4 Hz), 7.12 (2H, d, J=8.4 Hz), 7.22 (2H, d, J=8.4 Hz).

REFERENCE EXAMPLE 35

3-(4-Isopropylphenyl)-3,6,7-trimethyl-2,3-dihydro-1-benzofuran-5-amine

Using N-benzyl-3-(4-isopropylphenyl)-3,6,7-trimethyl-2,3-dihydro-1-benzofuran-5-amine synthesized in Reference Example 29, the title compound was synthesized in the same manner as in Reference Example 30. Yield 71%. Oily matter.

$^1$H-NMR (CDCl$_3$) δ: 1.23 (6H, d, J=6.9 Hz), 1.69 (3H, s), 2.09 (3H, s), 2.20 (3H, s), 2.87 (1H, septet, J=6.9 Hz), 3.30 (2H, br s), 4.35 (1H, d, J=8.7 Hz), 4.50 (1H, d, J=8.7 Hz), 6.29 (1H, s), 7.14 (2H, d, J=8.1 Hz), 7.23 (2H, d, J=8.1 Hz).

REFERENCE EXAMPLE 36

2-(2,3-Dimethylphenoxy)-2-methylpropionic acid

To a solution of 2,3-dimethylphenol (25.0 g, 205 mmol) in dimethylsulfoxide (200 mL) were added ethyl 2-bromo-isobutyrate (60 mL, 409 mmol) and potassium carbonate (56.5 g, 409 mmol) at room temperature, and the mixture was stirred for 36 hours. Water was added to the reaction solution and the mixture was extracted with ethyl acetate. The organic layer was washed with water and a saturated brine, dried over anhydrous sodium sulfate, and then concentrated under reduced pressure to obtain crude oily ethyl 2-(2,3-dimethylphenoxy)-2-methylpropionate. 12 N Aqueous sodium hydroxide solution (20 mL, 240 mmol) was added to the mixed solution of this compound in THF (160 mL) and methanol (40 mL) at room temperature, stirred for 12 hours, and then concentrated under reduced pressure. Water and hydrochloric acid were added to the reaction solution to acidity the aqueous layer, which was extracted with ethyl acetate. The organic layer was washed with water and a saturated brine and then was dried over anhydrous sodium sulfate. The solvent was distilled off under reduced pressure to obtain a residue, which was crystallized from ethyl acetate-hexane to obtain 21.3 g (yield 50%) of the title compound. Melting point: 71-73° C.

$^1$H-NMR (CDCl$_3$) δ: 1.60 (6H, s), 2.16 (3H, s), 2.27 (3H, s), 6.72 (1H, d, J=7.8 Hz), 6.88 (1H, d, J=7.5 Hz), 7.00 (1H, 7, J=7.8 Hz), 1H unidentified.

REFERENCE EXAMPLE 37

2-(3,5-Dimethylphenoxy)-2-methylpropionic acid

Using 3,5-dimethylphenol, the title compound was synthesized in the same manner as in Reference Example 36. Yield 96%. Oily matter.

$^1$H-NMR (CDCl$_3$) δ: 1.59 (6H, s), 2.27 (6H, s), 6.56 (1H, s), 6.72 (1H, s).

REFERENCE EXAMPLE 38

2-(2,5-Dimethylphenoxy)-2-methylpropionic acid

Using 2,5-dimethylphenol, the title compound was synthesized in the same manner as in Reference Example 36.

Yield 57%. Melting point: 107-109° C. (ethyl acetate-hexane).

$^1$H-NMR (CDCl$_3$) δ: 1.62 (6H, s), 2.20 (3H, s), 2.27 (3H, s), 6.64 (1H, s), 6.77 (1H, d, J=7.5 Hz), 7.05 (1H, d, J=7.5 Hz), 9.50 (1H, br s).

REFERENCE EXAMPLE 39

2-(2,3,5-Trimethyl phenoxy)-2-methylpropionic acid

Using 2,3,5-trimethylphenol, the title compound was synthesized in the same manner as in Reference Example 36.

Yield 65%. Melting point: 91-94° C. (ethyl acetate-hexane).

$^1$H-NMR (CDCl$_3$) δ: 1.59 (6H, s), 2.12 (3H, s), 2.22 (3H, s), 2.23 (3H, s), 6.53 (1H, s), 6.71 (1H, s), 1H unidentified.

REFERENCE EXAMPLE 40

2-(3,4,5-Trimethyl phenoxy)-2-methylpropionic acid

Using 3,4,5-trimethylphenol, the title compound was synthesized in the same manner as in Reference Example 36.

Yield 57%. Melting point: 77-78° C. (hexane).

$^1$H-NMR (CDCl$_3$) δ: 1.56 (6H, s), 2.11 (3H, s), 2.24 (6H, s), 6.61 (2H, s), 1H unidentified.

REFERENCE EXAMPLE 41

2,2,6,7-Tetramethyl-1-benzofuran-3(2H)-one

To a solution of 2-(2,3-dimethylphenoxy)-2-methylpropionic acid obtained in Reference Example 36 (21.0 g, 101 mmol) in THF (200 mL) was added DMF (0.1 mL), and then to the mixture was added dropwise oxalyl chloride (10.6 mL, 121 mmol). The reaction solution was warmed to room temperature, stirred for 1 hour, and then concentrated under reduced pressure. The residue was dissolved in dichloromethane (200 mL), to which was added aluminum chloride (32.3 g, 242 mmol) at −70° C. or lower, and then warmed to room temperature over 12 hours. The reaction solution was added to water with ice-cooling and dichloromethane was distilled off under reduced pressure, which was extracted with ethyl acetate. The organic layer was washed with water, a saturated sodium hydrogen carbonate solution, water and a saturated brine, and then was dried over anhydrous sodium sulfate. The residue after distilling off the solvent under reduced pressure was crystallized from hexane to obtain 17.5 g (yield 71%) of the title compound. Melting point: 79-81° C. (methanol).

$^1$H-NMR (CDCl$_3$) δ: 1.46 (6H, s), 2.21 (3H, s), 2.35 (3H, s), 6.88 (1H, d, J=8.0 Hz), 7.40 (1H, d, J=8.0 Hz).

REFERENCE EXAMPLE 42

2,2,4,6-Tetramethyl-1-benzofuran-3(2H)-one

Using 2-(3,5-dimethylphenoxy)-2-methylpropionic acid obtained in Reference Example 37, the title compound was synthesized in the same manner as in Reference Example 41.

Yield 92%. Oily matter.

$^1$H-NMR (CDCl$_3$) δ: 1.43 (6H, s), 2.37 (3H, s), 2.54 (3H, s), 6.62 (1H, s), 6.66 (1H, s).

REFERENCE EXAMPLE 43

2,2,4,7-Tetramethyl-1-benzofuran-3(2H)-one

Using 2-(2,5-dimethylphenoxy)-2-methylpropionic acid obtained in Reference Example 38, the title compound was synthesized in the same manner as in Reference Example 41.

Yield 97%. Oily matter.

$^1$H-NMR (CDCl$_3$) δ: 1.45 (6H, s), 2.25 (3H, s), 2.55 (3H, s), 6.70 (1H, d, J=7.5 Hz), 7.26 (1H, d, J=7.5 Hz).

REFERENCE EXAMPLE 44

2,2,4,6,7-Pentamethyl-2,3-dihydro-1-benzofuran-3(2H)-one

Using 2-(2,3,5-trimethyl phenoxy)-2-methylpropionic acid obtained in Reference Example 39, the title compound was synthesized in the same manner as in Reference Example 41. Yield 33%. Melting point: 99-101° C. (hexane).

$^1$H-NMR (CDCl$_3$) δ: 1.44 (6H, s), 2.16 (3H, s), 2.30 (3H, s), 2.52 (3H, s), 6.63 (1H, s).

REFERENCE EXAMPLE 45

2,2,4,5,6-Pentamethyl-1-benzofuran-3(2H)-one

Using 2-(3,4,5-trimethyl phenoxy)-2-methylpropionic acid obtained in Reference Example 40, the title compound was synthesized in the same manner as in Reference Example 41. Yield 90%. Melting point: 77-78° C. (hexane).

$^1$H-NMR (CDCl$_3$) δ: 1.42 (6H, s), 2.14 (3H, s), 2.34 (3H, s), 2.57 (3H, s), 6.73 (1H, s).

REFERENCE EXAMPLE 46

2,2,6,7-Tetramethyl-5-nitro-1-benzofuran-3(2H)-one

To a solution of 2,2,6,7-tetramethyl-1-benzofuran-3(2H)-one obtained in Reference Example 41 (5.20 g, 27.3 mmol) in anhydrous trifluoroacetic acid (50 mL) and chloroform (5 mL) was added ammonium nitrate (2.10 g, 32.8 mmol) at 0° C., and the mixture was stirred at the same temperature for 2 hours, and then concentrated under reduced pressure. Water was added to the residue, which was extracted with ethyl acetate. The extract was washed with water and a saturated sodium hydrogen carbonate solution, and then was dried over anhydrous sodium sulfate.

The solvent was distilled off under reduced pressure to obtain a residue, which was purified by silica gel column chromatography (hexane:ethyl acetate=50:1) to obtain 5.40 g (yield 84%) of the title compound. Melting point: 131-132° C. (ethyl acetate-hexane).

$^1$H-NMR (CDCl$_3$) δ: 1.50 (6H, s), 2.32 (3H, s), 2.52 (3H, s), 8.08 (1H, s).

REFERENCE EXAMPLE 47

2,2,4,7-Tetramethyl-5-nitro-1-benzofuran-3(2H)-one

Using 2,2,4,7-tetramethyl-1-benzofuran-3(2H)-one obtained in Reference Example 43, the title compound was synthesized in the same manner as in Reference Example 46.

Yield 46%. Melting point: 124-126° C. (ethyl acetate-hexane).

$^1$H-NMR (CDCl$_3$) δ: 1.50 (6H, s), 2.32 (3H, s), 2.87 (3H, s), 8.11 (1H, s).

REFERENCE EXAMPLE 48

5-Bromo-2,2,4,6-tetramethyl-1-benzofuran-3(2H)-one

Using 2,2,4,6-tetramethyl-1-benzofuran-3(2H)-one obtained in Reference Example 42, the title compound was synthesized in the same manner as in Reference Example 18.

Yield 73%. Melting point: 63-64° C. (methanol).

$^1$H-NMR (CDCl$_3$) δ: 1.44 (6H, s), 2.48 (3H, s), 2.68 (3H, s), 6.83 (1H, s).

REFERENCE EXAMPLE 49

5-Bromo-2,2,4,6,7-pentamethyl-1-benzofuran-3(2H)-one

Using 2,2,4,6,7-pentamethyl-2,3-dihydro-1-benzofuran-3(2H)-one obtained in Reference Example 44, the title compound was synthesized in the same manner as in Reference Example 18. Yield 73%. Melting point: 92-93° C. (methanol).

$^1$H-NMR (CDCl$_3$) δ: 1.44 (6H, s), 2.26 (3H, s), 2.47 (3H, s), 2.66 (3H, s).

REFERENCE EXAMPLE 50

7-Bromo-2,2,4,5,6-pentamethyl-1-benzofuran-3(2H)-one

Using 2,2,4,5,6-pentamethyl-1-benzofuran-3(2H)-one obtained in Reference Example 45, the title compound was synthesized in the same manner as in Reference Example 18.

Yield 79%. Melting point: 145-146° C. (methanol).

$^1$H-NMR (CDCl$_3$) δ: 1.49 (6H, s), 2.23 (3H, s), 2.49 (3H, s), 2.55 (3H, s).

REFERENCE EXAMPLE 51

5-(Benzylamino)-2,2,4,6-tetramethyl-1-benzofuran-3(2H)-one

Using 5-bromo-2,2,4,6-tetramethyl-2,3-dihydro-1-benzofuran-3(2H)-one obtained in Reference Example 48, the title compound was synthesized in the same manner as in Reference Example 24. Yield 75%. Oily matter.

$^1$H-NMR (CDCl$_3$) δ: 1.43 (6H, s), 2.35 (3H, s), 2.54 (3H, s), 3.02 (1H, br s), 3.99 (2H, s), 6.73 (1H, s), 7.24-7.42 (5H, m).

REFERENCE EXAMPLE 52

5-(Benzylamino)-2,2,4,6,7-pentamethyl-1-benzofuran-3(2H)-one

Using 5-bromo-2,2,4,6,7-pentamethyl-1-benzofuran-3(2H)-one obtained in Reference Example 49, the title compound was synthesized in the same manner as in Reference Example 24. Yield 88%. Melting point: 98-99° C. (ethyl acetate-hexane).

$^1$H-NMR (CDCl$_3$) δ: 1.43 (6H, s), 2.21 (3H, s), 2.35 (3H, s), 2.50 (3H, s), 3.04 (1H, br s), 3.94 (2H, s), 7.26-7.41 (5H, m).

REFERENCE EXAMPLE 53

7-(Benzylamino)-2,2,4,5,6-pentamethyl-1-benzofuran-3(2H)-one

Using 7-bromo-2,2,4,5,6-pentamethyl-1-benzofuran-3(2H)-one obtained in Reference Example 50, the title compound was synthesized in the same manner as in Reference Example 24. Yield 72%. Melting point: 108-109° C. (ethyl acetate-hexane).

$^1$H-NMR (CDCl$_3$) δ: 1.38 (6H, s), 2.14 (3H, s), 2.28 (3H, s), 2.51 (3H, s), 3.61 (1H, br s), 4.27 (2H, s), 7.19-7.37 (5H, m).

REFERENCE EXAMPLE 54

5-Amino-2,2,6,7-tetramethyl-1-benzofuran-3(2H)-one

A mixture of 2,2,6,7-tetramethyl-5-nitro-1-benzofuran-3(2H)-one obtained in Reference Example 46 (5.0 g, 21.3 mmol), 10%-palladium carbon (50% hydrous, 500 mg) and ammonium formate (7.06 g, 85.0 mmol) in methanol (100 mL) was heated under reflux for two hours. The solid material was removed and the filtrate was concentrated under reduced pressure. Water and ethyl acetate were added to the residue to separate the organic layer, and the aqueous layer was extracted with ethyl acetate. The combined organic layer was washed with water, dried over anhydrous sodium sulfate and then concentrated under reduced pressure. The solvent was distilled off under reduced pressure to obtain a residue, which was crystallized with ethyl acetate-hexane to obtain 4.0 g (yield 92%) of the title compound. Melting point: 149-150° C.

$^1$H-NMR (CDCl$_3$) δ: 1.43 (6H, s), 2.19 (3H, s), 2.24 (3H, s), 3.50 (2H, br s), 6.78 (1H, s).

REFERENCE EXAMPLE 55

5-Amino-2,2,4,6-tetramethyl-1-benzofuran-3(2H)-one

Using 5-(benzylamino)-2,2,4,6-tetramethyl-1-benzofuran-3(2H)-one obtained in Reference Example 51, the title compound was synthesized in the same manner as in Reference Example 30. Yield 95%. Oily matter.

$^1$H-NMR (CDCl$_3$) δ: 1.43 (6H, s), 2.19 (3H, s), 2.24 (3H, s), 3.50 (2H, br s), 6.78 (1H, s).

REFERENCE EXAMPLE 56

5-Amino-2,2,4,7-tetramethyl-1-benzofuran-3(2H)-one

Using 2,2,4,7-tetramethyl-5-nitro-1-benzofuran-3(2H)-one obtained in Reference Example 47, the title compound was synthesized in the same manner as in Reference Example 54. Yield 97%. Melting point: 124-126° C. (ethyl acetate-hexane).

$^1$H-NMR (CDCl$_3$) δ: 1.42 (6H, s), 2.21 (3H, s), 2.40 (3H, s), 3.40 (2H, br s), 6.82 (1H, s).

REFERENCE EXAMPLE 57

5-Amino-2,2,4,6,7-pentamethyl-1-benzofuran-3(2H)-one

Using 5-(benzylamino)-2,2,4,6,7-pentamethyl-1-benzofuran-3(2H)-one obtained in Reference Example 52, the title compound was synthesized in the same manner as in Reference Example 30. Yield 88%. Melting point: 92-93° C. (ethyl acetate-hexane).

$^1$H-NMR (CDCl$_3$) δ: 1.41 (6H, s), 2.19 (3H, s), 2.21 (3H, s), 2.45 (3H, s), 3.44 (2H, br s).

REFERENCE EXAMPLE 58

7-Amino-2,2,4,5,6-pentamethyl-1-benzofuran-3 (2H)-one

Using 7-(benzylamino)-2,2,4,5,6-pentamethyl-1-benzofuran-3(2H)-one obtained in Reference Example 53, the title compound was synthesized in the same manner as in Reference Example 30. Yield: quantitative. Melting point: 141-142° C. (ethyl acetate-hexane).

$^1$H-NMR (CDCl$_3$) δ: 1.44 (6H, s), 2.16 (3H, s), 2.19 (3H, s), 2.50 (3H, s), 3.59 (2H, br s).

REFERENCE EXAMPLE 59 tert-Butyl (2,2,6,7-tetramethyl-3-oxo-2,3-dihydro-1-benzofuran-5-yl)carbamate

A solution of 5-amino-2,2,6,7-tetramethyl-1-benzofuran-3(2H)-one obtained in Reference Example 54 (3.89 g, 19.5 mmol) and dicarbonic acid ditert-butyl (6.73 mL, 29.3 mmol) in THF (50 mL) was heated under reflux for 16 hours. Water was added to the residue to separate the organic layer, and the aqueous layer was extracted with ethyl acetate. The combined organic layer was washed with water, dried over anhydrous sodium sulfate and then concentrated under reduced pressure. The obtained residue was crystallized with hexane-ethyl acetate to obtain 4.80 g (yield 81%) of the title compound. Melting point: 154-155° C.

$^1$H-NMR (CDCl$_3$) δ: 1.44 (6H, s), 1.50 (9H, s), 2.24 (3H, s), 2.25 (3H, s), 6.12 (1H, br s), 7.58 (1H, s).

REFERENCE EXAMPLE 60 tert-Butyl (2,2,4,6-tetramethyl-3-oxo-2,3-dihydro-1-benzofuran-5-yl)carbamate

Using 5-amino-2,2,4,6-tetramethyl-1-benzofuran-3(2H)-one obtained in Reference Example 55, the title compound was synthesized in the same manner as in Reference Example 59. Yield 71%. Melting point: 156-157° C. (ethyl acetate-hexane).

$^1$H-NMR (CDCl$_3$) δ: 1.44 (6H, s), 1.50 (9H, s), 2.24 (3H, s), 2.25 (3H, s), 6.12 (1H, br s), 7.58 (1H, s).

REFERENCE EXAMPLE 61 tert-Butyl (2,2,4,7-tetramethyl-3-oxo-2,3-dihydro-1-benzofuran-5-yl)carbamate

Using 5-amino-2,2,4,7-tetramethyl-1-benzofuran-3(2H)-one obtained in Reference Example 56, the title compound was synthesized in the same manner as in Reference Example 59. Yield 96%. Melting point: 144-145° C. (ethyl acetate-hexane).

$^1$H-NMR (CDCl$_3$) δ: 1.43 (6H, s), 1.51 (9H, s), 2.25 (3H, s), 2.47 (3H, s), 6.11 (1H, br s), 7.66 (1H, s).

REFERENCE EXAMPLE 62 tert-Butyl (2,2,4,6,7-pentamethyl-3-oxo-2,3-dihydro-1-benzofuran-5-yl)carbamate

Using 5-amino-2,2,4,6,7-pentamethyl-1-benzofuran-3(2H)-one obtained in Reference Example 57, the title compound was synthesized in the same manner as in Reference Example 59. Yield 90%. Melting point: 105-106° C. (ethyl acetate-hexane).

$^1$H-NMR (CDCl$_3$) δ: 1.42 (6H, s), 1.51 (9H, s), 2.19 (3H, s), 2.25 (3H, s), 2.49 (3H, s), 5.81 (1H, br s).

REFERENCE EXAMPLE 63

3,3-Dimethyl-N-(2,2,4,6,7-pentamethyl-3-oxo-2,3-dihydro-1-benzofuran-5-yl)butanamide To a solution of 5-amino-2,2,4,6,7-pentamethyl-1-benzofuran-3(2H)-one obtained in Reference Example 57 (3.00 g, 13.7 mmol) and tert-butylacetyl chloride (2.03 g, 15.1 mmol) in dichloromethane (30 mL) was added triethylamine (2.3 mL, 16.4 mmol) at room temperature, and the mixture was stirred at room temperature for 30 minutes. Water was added to the residue to separate the organic layer, and the aqueous layer was extracted with dichloromethane. The combined organic layer was washed with 1 N hydrochloric acid and a saturated sodium hydrogen carbonate solution, dried over magnesium sulfate, filtered, and then concentrated under reduced pressure. The residue was crystallized from ethyl acetate-hexane to obtain the targeted product 2.34 g (yield 54%). Melting point: 155-156° C.

$^1$H-NMR (CDCl$_3$) δ: 1.15 (9H, s), 1.43 (6H, s), 2.19 (3H, s), 2.22 (3H, s), 2.32 (2H, s), 2.47 (3H, s), 6.62 (1H, br s).

REFERENCE EXAMPLE 64

3,3-Dimethyl-N-(2,2,4,5,6-pentamethyl-3-oxo-2,3-dihydro-1-benzofuran-7-yl)butanamide Using 7-amino-2,2,4,5,6-pentamethyl-1-benzofuran-3(2H)-one obtained in Reference Example 58, the title compound was synthesized in the same manner as in Reference Example 63. Yield 76%. Melting point: 158-159° C. (ethyl acetate-hexane).

$^1$H-NMR (CDCl$_3$) δ: 1.15 (9H, s), 1.40 (6H, s), 2.16 (3H, s), 2.24 (3H, s), 2.32 (2H, s), 2.54 (3H, s), 6.78 (1H, br s).

REFERENCE EXAMPLE 65

3,3-Dimethyl-N-(2,2,6,7-tetramethyl-3-oxo-2,3-dihydro-1-benzofuran-5-yl)butanamide Using 5-amino-2,2,6,7-tetramethyl-1-benzofuran-3(2H)-one obtained in Reference Example 54, the title compound was synthesized in the same manner as in Reference Example 63. Yield 88%. Melting point: 175-176° C. (ethyl acetate-hexane).

¹H-NMR (CDCl₃) δ: 1.13 (9H, s), 1.44 (6H, s), 2.24-2.26 (8H, m), 6.84 (1H, br s), 7.50 (1H, s).

REFERENCE EXAMPLE 66 tert-Butyl (7-bromo-2,2,4,6-tetramethyl-3-oxo-2,3-dihydro-1-1-benzofura-5-yl)carbamate To a solution of tert-butyl(2,2,4,6-tetramethyl-3-oxo-2,3-dihydro-1-benzofuran-5-yl)carbamate obtained in Reference Example 60 (4.86 g, 15.9 mmol) in acetonitrile (70 mL) was added N-bromosuccinimide (5.67 g, 31.8 mmol) was heated under reflux for 1.5 hours. The reaction solution was cooled to room temperature, followed by addition of water, which was extracted with ethyl acetate, and the organic layer was washed with water and a saturation brine, dried over anhydrous sodium sulfate, and then was concentrated under reduced pressure. The residue was purified by silica gel column chromatography (ethyl acetate:hexane=3:7), and then was recrystallized with ethyl acetate-hexane to obtain 4.40 g (yield 72%) of the title compound. Melting point: 131-132° C.

¹H-NMR (CDCl₃) δ: 1.33-1.55 (15H, m), 2.46 (3H, s), 2.49 (3H, s), 5.87 (1H, br s).

REFERENCE EXAMPLE 67

3-Bromo-2,4,5-trimethylbenzaldehyde

To a solution of 2,4,5-trimethylbenzaldehyde (21.3 g, 144 mmol) in dichloromethane (200 mL) was added aluminum chloride (48.0 g, 360 mmol) with ice-cooling, and the mixture was warmed to room temperature. Bromine (7.80 mL, 151 mmol) was added dropwised to the reaction solution at room temperature, the mixture was stirred for 4 hours, water was added to the reaction solution, and dichloromethane was distilled off under reduced pressure.

The residue was extracted with ethyl acetate and the organic layer was washed with water, a saturated sodium hydrogen carbonate solution, 5% sodium sulfite aqueous solution, water and a saturated brine. The organic layer was dried over anhydrous sodium sulfate and then was concentrated under reduced pressure to obtain 32.5 g (yield 100%) of the title compound. Melting point: 108-110° C.

¹H-NMR (CDCl₃) δ: 2.38 (3H, s), 2.46 (3H, s), 2.73 (3H, s), 7.54 (1H, s), 10.21 (1H, s).

REFERENCE EXAMPLE 68

3-Bromo-2,4,5-trimethylphenol

To a solution of 3-bromo-2,4,5-trimethylbenzaldehyde obtained in Reference Example 67 (32.0 g, 141 mmol) in THF (100 mL) was added methanol (200 mL) with ice-cooling, followed by addition of p-toluenesulfonic acid monohydrate (5.40 g, 28.4 mmol) with ice-cooling. Hydrogen peroxide (30%, 24.0 g, 212 mmol) was added dropwise to the reaction solution at 10° C. or lower, and the mixture was warmed to room temperature and stirred for 12 hours. Then the reaction solution was stirred at 50° C. for 36 hours, followed by addition of an aqueous sodium sulfite solution, and methanol and THF were distilled off under reduced pressure. The residue was extracted with ethyl acetate, the organic layer was washed with water and a saturated brine, and then was dried over anhydrous sodium sulfate.

The solvent was distilled off under reduced pressure to obtain a residue, which was purified by silica gel column chromatography (hexane:ethyl acetate=10:1) to obtain 9.1 g (yield 30%) of the title compound. Melting point: 86-88° C.

¹H-NMR (CDCl₃) δ: 2.25 (3H, s), 2.30 (3H, s), 2.32 (3H, s), 4.63 (1H, s), 6.56 (1H, s).

REFERENCE EXAMPLE 69

2-(3-Bromo-2,4,5-trimethylphenoxy)-2-methylpropionic acid

Using 3-bromo-2,4,5-trimethylphenol obtained in Reference Example 68, the title compound was synthesized in the same manner as in Reference Example 36. Yield 40%. Melting point: 151-153° C. (hexane).

¹H-NMR (CDCl₃) δ: 1.59 (6H, s), 2.26 (3H, s), 2.33 (6H, s), 6.67 (1H, s), 9.60 (1H, br s).

REFERENCE EXAMPLE 70

6-Bromo-2,2,4,5,7-pentamethyl-1-benzofuran-3(2H)-one

Using 2-(3-bromo-2,4,5-trimethylphenoxy)-2-methylpropionic acid obtained in Reference Example 69, the title compound was synthesized in the same manner as in Reference Example 41. Yield 97%. Melting point: 125-127° C.

¹H-NMR (CDCl₃) δ: 1.44 (6H, s), 2.34 (3H, s), 2.37 (3H, s), 2.60 (3H, s).

REFERENCE EXAMPLE 71

6-(Benzylamino)-2,2,4,5,7-pentamethyl-1-benzofuran-3(2H)-one

Using 6-bromo-2,2,4,5,7-pentamethyl-1-benzofuran-3(2H)-one obtained in Reference Example 70, the title compound was synthesized in the same manner as in Reference Example 24. Yield 95%. Melting point: 79-83° C.

¹H-NMR (CDCl₃) δ: 1.43 (6H, s), 2.11 (3H, s), 2.16 (3H, s), 2.55 (3H, s), 3.86 (1H, br s), 4.34 (2H, s), 7.26-7.42 (5H, m).

REFERENCE EXAMPLE 72

6-Amino-2,2,4,5,7-pentamethyl-1-benzofuran-3(2H)-one

Using 6-(benzylamino)-2,2,4,5,7-pentamethyl-1-benzofuran-3(2H)-one obtained in Reference Example 71, the title compound was synthesized in the same manner as in Reference Example 30. Yield 87%. Melting point: 150-151° C.

¹H-NMR (CDCl₃) δ: 1.41 (6H, s), 2.04 (3H, s), 2.06 (3H, s), 2.55 (3H, s), 4.27 (2H, br s).

REFERENCE EXAMPLE 73

(2,2,4,5,7-Pentamethyl-3-oxo-2,3-dihydro-1-benzofuran-6-yl)formamide

A mixture of formic acid (5 mL) with 6-amino-2,2,4,5,7-pentamethyl-1-benzofuran-3(2H)-one (700 mg, 3.19 mmol) obtained in Reference Example 72, was heated under reflux for 5 hours. The solvent was distilled off under reduced pressure, water and ethyl acetate were added to the residue, and the aqueous layer was extracted with ethyl acetate. The combined organic layer was washed with water and a saturated sodium hydrogen carbonate solution, dried over anhydrous sodium sulfate, and then concentrated under reduced pressure. The obtained residue was crystallized from hexane-ethyl acetate to obtain 640 mg (yield 81%) of the title compound. Melting point: 191-192° C.

$^1$H-NMR (CDCl$_3$) δ: 1.40-1.52 (6H, m), 2.00-2.28 (3H, m), 2.56, 2.57 (1.5H x2, s), 2.60 (3H, s), 7.07 (0.5H, br s), 7.20-7.35 (0.5H, m), 8.18 (0.5H, d, J=11.6 Hz), 8.46 (0.5H, d, J=1.4 Hz).

REFERENCE EXAMPLE 74

3-(4-Isopropylphenyl)-2,2,6,7-tetramethyl-2,3-dihydro-1-benzofuran-5-amine hydrochloride To a solution of 4-bromocumene (6.25 g, 31.4 mmol) in THF (50 mL) was added dropwise a solution of n-butyl-lithium in hexane (1.60 M, 19.6 mL, 31.4 mmol) under arogon atmosphere at −78° C., and the mixture was stirred at the same temperature for 30 minutes. Then, to the reaction solution was added dropwise a solution of tert-butyl (2,2,6,7-tetramethyl-3-oxo-2,3-dihydro-1-benzofuran-5-yl)carbamate obtained in Reference Example 59 (500 mg, 2.02 mmol) in THF (5 mL) at the same temperature, and the reaction solution was stirred at room temperature for 1 hour, followed by addition of water, which was extracted with ethyl acetate. The organic layer was washed with water and saturated brine, dried over anhydrous sodium sulfate and then concentrated under reduced pressure. The residue was purified by silica gel column chromatography (hexane:ethyl acetate=10:1) to obtain oily tert-butyl (3-hydroxy-3-(4-isopropylphenyl)-2,2,6,7-tetramethyl-2,3-dihydro-1-benzofuran-5-yl)carbamate. A mixture of said compound with trifluoroacetic acid (10 mL) was added triethylsilane (1.0 mL, 6.4 mmol) with ice-cooling, and the mixture was stirred at room temperature for 1 hour. The reaction solution was concentrated under reduced pressure, and to the residue was added a saturated sodium hydrogen carbonate solution to alkalify the aqueous layer, which was extracted with ethyl acetate. The organic layer was washed with water and saturated brine, dried over anhydrous sodium sulfate and then concentrated under reduced pressure. The residue was purified by silica gel column chromatography (hexane:ethyl acetate=10:1) to obtain the free salt of the title compound. Then, it was made hydrochloride in a 4 N hydrochloric acid/methanol solution to obtain 2.03 g (yield 37%) of the title compound. Melting point: 166-168° C. (decomp.) (methanol).

$^1$H-NMR (DMSO-d$_6$) δ: 0.90 (3H, s), 1.19 (6H, d, J=6.8 Hz), 1.51 (3H, s), 2.14 (3H, s), 2.21 (3H, s), 2.87 (1H, septet, J=6.8 Hz), 4.39 (1H, s), 6.96 (1H, s), 6.97 (2H, d, J=8.0 Hz), 7.20 (2H, d, J=8.0 Hz), 10.1 (2H, br s), 1H unidentified.

REFERENCE EXAMPLE 75

3-(4-Isopropylphenyl)-2,2,4,7-tetramethyl-2,3-dihydro-1-benzofuran-5-amine hydrochloride Using tert-butyl (2,2,4,7-tetramethyl-3-oxo-2,3-dihydro-1-benzofuran-5-yl)carbamate obtained in Reference Example 61 and 4-bromocumene, the title compound was synthesized in the same manner as in Reference Example 74.

Yield 78%. Melting point: 239-240° C. (decomp.) (methanol).

$^1$H-NMR (DMSO-d$_6$) δ: 0.97 (3H, s), 1.17 (6H, d, J=6.9 Hz), 1.44 (3H, s), 1.85 (3H, s), 2.15 (3H, s), 2.84 (1H, septet, J=6.9 Hz), 4.29 (1H, s), 6.58-7.27 (5H, m), 9.98 (2H, br s), 1H unidentified.

REFERENCE EXAMPLE 76

3-(4-Tert-butylphenyl)-2,2,4,6,7-pentamethyl-2,3-dihydro-1-benzofuran-5-amine hydrochloride Using tert-butyl (2,2,4,6,7-pentamethyl-3-oxo-2,3-dihydro-1-benzofuran-5-yl)carbamate obtained in Reference Example 62 and 4-bromo-tert-butylbenzene, the title compound was synthesized in the same manner as in Reference Example 74. Yield 23%. Melting point: 265-267° C. (decomp.) (methanol).

$^1$H-NMR (DMSO-d$_6$) δ: 0.96 (3H, s), 1.25 (9H, s), 1.43 (3H, s), 1.90 (3H, s), 2.12 (3H, s), 2.24 (3H, s), 4.26 (1H, s), 6.60-7.40 (4H, m), 9.46 (2H, br s), 1H unidentified.

REFERENCE EXAMPLE 77

3-(4-Isopropylphenyl)-2,2,4,5,7-pentamethyl-2,3-dihydro-1-benzofuran-6-amine

To a solution of 4-bromocumene (2.01 g, 10.1 mmol) in THF (20 mL) was added dropwise a solution of n-butyl-lithium in hexane (1.60 M, 6.25 mL, 10.0 mmol) under arogon atmosphere at −78° C., and the mixture was stirred at the same temperature for 30 minutes. Then, to the reaction solution was added dropwise a solution of (2,2,4,5,7-pentamethyl-3-oxo-2,3-dihydro-1-benzofuran-6-yl)formamide obtained in Reference Example 73 (500 mg, 2.02 mmol) in THF (5 mL) at the same temperature, and the reaction solution was stirred at room temperature for 1 hour, followed by addition of water, which was extracted with ethyl acetate. The organic layer was washed with water and saturated brine, dried over anhydrous sodium sulfate and then concentrated under reduced pressure. The residue was purified by silica gel column chromatography (hexane:ethyl acetate=4:1) to obtain 3-hydroxy-3-(4-isopropylphenyl)-2,2,4,5,7-pentamethyl-2,3-dihydro-1-benzofuran-6-yl)formamide. To a mixture of said compound with trifluoroacetic acid (5 mL) was added triethylsilane (0.5 mL, 3.2 mmol) with ice-cooling, and the mixture was stirred at room temperature for 1 hour. The reaction solution was concentrated under reduced pressure, and to the residue was added a saturated sodium hydrogen carbonate solution to alkalify the aqueous layer, which was extracted with ethyl acetate. The organic layer was washed with water and saturated brine, dried over anhydrous sodium sulfate and then concentrated under reduced pressure.

To a solution of the obtained residue in methanol (20 mL) was added concentrated hydrochloric acid, and the mixture was heated under reflux for 2 hours. The solvent was distilled off under reduced pressure and the residue was neutralized with a 12 N aqueous sodium hydroxide solution. After extracting with ethyl acetate, the organic layer was washed with water and saturated brine, dried over anhydrous sodium sulfate and then concentrated under reduced pressure. The obtained residue was purified by silica gel column chromatography (hexane:ethyl acetate=4:1) to obtain 440 mg (yield 67%) of the title compound. Melting point: 120-121° C. (ethyl acetate-hexane).

$^1$H-NMR (CDCl$_3$) δ: 0.99 (3H, s), 1.21 (6H, d, J=7.0 Hz), 1.48 (3H, s), 1.84 (3H, s), 2.01 (3H, s), 2.10 (3H, s), 2.85 (1H, septet, J=6.9 Hz), 3.58 (2H, br s), 4.07 (1H, s), 6.60-7.12 (4H, m).

REFERENCE EXAMPLE 78

3-(4-Isopropylphenyl)-2,2,4,6-tetramethyl-2,3-dihydro-1-benzofuran-5-amine

Using tert-butyl (2,2,4,6-tetramethyl-3-oxo-2,3-dihydro-1-benzofuran-5-yl)carbamate obtained in Reference Example 60 and 4-bromocumene, the title compound was synthesized in the same manner as in Reference Example 74.

Yield 89%. Melting point: 98-100° C. (methanol).

$^1$H-NMR (CDCl$_3$) δ: 0.99 (3H, s), 1.21 (6H, d, J=7.2 Hz), 1.48 (3H, s), 1.79 (3H, s), 2.18 (3H, s), 2.85 (1H, septet, J=7.2 Hz), 4.06 (1H, s), 4.60 (2H, br s), 6.49 (1H, s), 6.60-7.10 (4H, m).

REFERENCE EXAMPLE 79

3-Benzyl-2,2,4,5,7-pentamethyl-2,3-dihydro-1-benzofuran-6-amine

A solution of (2,2,4,5,7-pentamethyl-3-oxo-2,3-dihydro-1-benzofuran-6-yl)formamide obtained in Reference Example 73 (600 mg, 2.43 mmol) in THF (5 mL) was added dropwise to a solution of benzylmagnesium chloride (a 2.0 M THF solution, 10.0 mL, 20.0 mmol) in THF (20 mL) under argon atmosphere, and the mixture was stirred at room temperature for 2 hours. Water was added thereto, which was extracted with ethyl acetate. The organic layer was washed with 1 N hydrochloric acid, dried over anhydrous sodium sulfate, and then concentrated under reduced pressure. The residue was purified by silica gel column chromatography (hexane:ethyl acetate=4:1) to obtain (3-benzyl-3-hydroxy-2,2,4,5,7-pentamethyl-2,3-dihydro-1-benzofuran-6-yl)formamide. To a mixture of said compound with trifluoroacetic acid (5 mL) was added triethylsilane (0.5 mL, 3.2 mmol) with ice-cooling, and the mixture was stirred at room temperature for 30 minutes. The reaction solution was concentrated under reduced pressure, and to the residue was added a saturated sodium hydrogen carbonate solution to alkalify the aqueous layer, which was extracted with ethyl acetate. The organic layer was washed with water and saturated brine, dried over anhydrous sodium sulfate and then concentrated under reduced pressure. To a solution of the obtained residue in methanol (20 mL) was added concentrated hydrochloric acid (10 ml), and the mixture was heated under reflux for 2 hours. The solvent was distilled off under reduced pressure and the residue was neutralized with a 12 N aqueous sodium hydroxide solution. After extracting with ethyl acetate, the organic layer was washed with water and saturated brine, dried over anhydrous sodium sulfate and then concentrated under reduced pressure. The obtained residue was purified by silica gel column chromatography (hexane:ethyl acetate 4:1) to obtain 440 mg (yield 62%) of the title compound. Melting point: 75-76° C. (ethyl acetate-hexane).

$^1$H-NMR (CDCl$_3$) δ: 1.26 (3H, s), 1.40 (3H, s), 1.79 (3H, s), 1.98 (3H, s), 2.05 (3H, s), 2.74 (1H, dd, J=14.4, 5.7 Hz), 2.88 (1H, dd, J=14.4, 8.4 Hz), 3.25 (1H, dd, J=14.4, 8.4 Hz), 3.53 (2H, br s), 7.10-7.28 (5H, m).

REFERENCE EXAMPLE 80

5-Amino-2,2,4,6,7-pentamethyl-3-(4-methylphenyl)-2,3-dihydro-1-benzofuran-3-ol To a solution of 4-bromotoluene (2.73 g, 16.0 mmol) in THF (30 mL) was added dropwise a solution of n-butyllithium in hexane (1.60 M, 10.0 mL, 16.0 mmol) under argon atmosphere at −78° C., and the mixture was stirred at the same temperature for 30 minutes. Then, to the reaction solution was added dropwise a solution of 5-amino-2,2,4,6,7-pentamethyl-1-benzofuran-3(2H)-one obtained in Reference Example 57 (1.0 g, 4.56 mmol) in THF (10 mL) at the same temperature, and the reaction solution was stirred at room temperature for 1 hour, followed by addition of water, which was extracted with ethyl acetate. The organic layer was washed with water and saturated brine, dried over anhydrous sodium sulfate and then concentrated under reduced pressure. The obtained residue was purified by silica gel column chromatography (hexane:ethyl acetate=10:1), to obtain 921 mg (yield 65%) of the title compound. Melting point: 165-166° C. (ethyl acetate-hexane).

$^1$H-NMR (CDCl$_3$) δ: 0.85 (3H, s), 1.50 (3H, s), 1.83 (3H, s), 2.11 (1H, s), 2.14 (3H, s), 2.18 (3H, s), 2.34 (3H, s), 3.31 (2H, br s), 6.80-7.70 (4H, m).

REFERENCE EXAMPLE 81

5-Amino-2,2,4,6,7-pentamethyl-3-(2-naphthyl)-2,3-dihydro-1-benzofuran-3-ol

Using 5-amino-2,2,4,6,7-pentamethyl-1-benzofuran-3(2H)-one obtained in Reference Example 57 and 2-bromonaphthalene, the title compound was synthesized in the same manner as in Reference Example 80. Yield 66%. Melting point: 121-122° C. (ethyl acetate-hexane).

$^1$H-NMR (CDCl$_3$) δ: 0.88 (3H, s), 1.56 (3H, s), 1.79 (3H, s), 2.16 (3H, s), 2.22 (3H, s), 2.42 (1H, s), 3.32 (2H, br s), 7.07-7.21 (1H, m), 7.37-8.00 (5H, m), 8.16-8.31 (1H, m).

REFERENCE EXAMPLE 82

1-(4-Isopropylphenyl)-1-(2-methoxyphenyl)-2-methylpropan-1-ol

To a solution of 2-bromoanisole (5.0 g, 26.7 mmol) in THF (50 mL) was added n-butyllithium (1.6 M, 18 mL, 29 mmol) at −78° C., and the mixture was stirred at the same temperature for 30 minutes. To the reaction solution was added 1-(4-isopropylphenyl)-2-methylpropan-1-one (5.70 g, 30.0 mmol), and the mixture was stirred at room temperature for 1 hour. Water was poured into the reaction mixture which was extracted with ethyl acetate, and the combined organic layer was washed with water, dried over magnesium sulfate, filtered and then concentrated under reduced pressure. The obtained residue was purified by silica gel column chromatography (hexane:ethyl acetate=20:1) to obtain 3.4 g (yield 43%) of the title compound. Melting point: 85-86° C. (methanol).

$^1$H-NMR (CDCl$_3$) δ: 0.76 (3H, d, J=6.9 Hz), 0.94 (3H, d, J=6.9 Hz), 1.20 (6H, d, J=6.9 Hz), 2.68 (1H, septet, J=6.9 Hz), 2.83 (1H, septet, J=6.9 Hz), 3.59 (3H, s), 4.91 (1H, s), 6.82 (1H, d, J=8.1 Hz), 6.99 (1H, dt, J=7.5, 1.5 Hz), 7.06 (2H, d, J=7.5 Hz), 7.13-7.25 (3H, m), 7.52 (1H, dd, J=7.5, 1.5 Hz).

REFERENCE EXAMPLE 83

3-(4-Isopropylphenyl)-2,2-dimethyl-2,3-dihydro-1-benzofuran

A mixture of 1-(4-isopropylphenyl)-1-(2-methoxyphenyl)-2-methylpropan-1-ol obtained in Reference Example 82 (3.4 g, 11.4 mmol), 48% hydrobromic acid (50 mL) and acetic acid (10 mL) was heated under reflux under argon atmosphere for 16 hours. After cooling, water was added to the reaction solution, which was extracted with ethyl acetate, and the combined organic layer was washed with water, dried over magnesium sulfate, filtered and then concentrated under reduced pressure. The obtained residue was purified by silica gel column chromatography (hexane:ethyl acetate=20:1) to obtain 2.71 g (yield 89%) of the title compound. Oily matter.

$^1$H-NMR (CDCl$_3$) δ: 0.96 (3H, s), 1.24 (6H, d, J=7.2 Hz), 1.59 (3H, s), 2.89 (1H, septet, J=7.2 Hz), 4.33 (1H, s), 6.77-6.89 (2H, m), 6.98-7.06 (3H, m), 7.12-7.19 (3H, m)

REFERENCE EXAMPLE 84

5-Bromo-3-(4-isopropylphenyl)-2,2-dimethyl-2,3-dihydro-1-benzofuran

Using 3-(4-isopropylphenyl)-2,2-dimethyl-2,3-dihydro-1-benzofuran obtained in Reference Example 83, the title compound was synthesized in the same manner as in Reference Example 23. Yield: quantitative. Oily matter.

$^1$H-NMR (CDCl$_3$) δ: 0.97 (3H, s), 1.25 (6H, d, J=6.9 Hz), 1.57 (3H, s), 2.89 (1H, septet, J=6.9 Hz), 4.30 (1H, s), 6.69 (1H, d, J=8.2 Hz), 6.99 (2H, d, J=8.1 Hz), 7.12-7.28 (4H, m).

REFERENCE EXAMPLE 85

N-Benzyl-3-(4-isopropylphenyl)-2,2-dimethyl-2,3-dihydro-1-benzofuran-5-amine

Using 5-bromo-3-(4-isopropylphenyl)-2,2-dimethyl-2,3-dihydro-1-benzofuran obtained in Reference Example 84, the title compound was synthesized in the same manner as in Reference Example 24. Yield 46%. Melting point: 85-86° C. (methanol).

$^1$H-NMR (CDCl$_3$) δ: 0.93 (3H, s), 1.25 (6H, d, J=7.0 Hz), 1.57 (3H, s), 2.89 (1H, septet, J=7.0 Hz), 3.62 (1H, br s), 4.22 (2H, s), 4.26 (1H, s), 6.40-6.55 (2H, m), 6.68 (1H, d, J=8.2 Hz), 7.02 (2H, d, J=8.0 Hz), 7.15 (2H, d, J=8.0 Hz), 7.20-7.40 (5H, m).

REFERENCE EXAMPLE 86

3-(4-Isopropylphenyl)-2,2-dimethyl-2,3-dihydro-1-benzofuran-5-amine

Using N-benzyl-3-(4-isopropylphenyl)-2,2-dimethyl-2,3-dihydro-1-benzofuran-5-amine obtained in Reference Example 85, the title compound was synthesized in the same manner as in Reference Example 30. Yield 98%. Melting point: 109-110° C. (hexane).

$^1$H-NMR (CDCl$_3$) δ: 0.94 (3H, s), 1.24 (6H, d, J=6.9 Hz), 1.55 (3H, s), 2.89 (1H, septet, J=6.9 Hz), 3.33 (2H, br s), 4.23 (1H, s), 6.44 (1H, d, J=2.1 Hz), 6.52 (1H, d, J=8.1, 2.1 Hz), 6.63 (1H, d, J=8.2 Hz), 7.02 (2H, d, J=8.1 Hz), 7.14 (2H, d, J=8.1 Hz).

REFERENCE EXAMPLE 87

1-Isopropyl-4-(2-methyl-3-(4-methylphenoxy)propene-1-yl)benzene

To a solution of p-cresol (3.50 g, 32.3 mmol) in DMF (70 mL) was added sodium hydride (a 60% liquid paraffin dispersion, 1.42 g, 35.5 mmol) under nitrogen atmosphere at 0° C., and the mixture was stirred at the same temperature for 30 minutes. To the reaction solution was added 1-(3-bromo-2-methyl-1-propenyl)-4-isopropyl benzene (9.0 g, 35.5 mmol), and the mixture was stirred at room temperature for 3 hours. Water was added to the reaction solution, and the product was extracted with diisopropyl ether. The extract was washed with water, dried over magnesium sulfate, and then concentrated under reduced pressure. The obtained residue was purified by silica gel column chromatography (hexane:ethyl acetate=20:1) to obtain 8.20 g (yield 91%) of the title compound. Oily matter.

$^1$H-NMR (CDCl$_3$) δ: 1.25 (6H, d, J=6.6 Hz), 1.98 (3H, s), 2.21 (3H, s), 2.90 (1H, septet, J=7.0 Hz), 4.53 (2H, s), 6.58 (1H, s), 6.86 (2H, d, J=8.8 Hz), 7.08 (2H, d, J=8.8 Hz), 7.14-7.25 (4H, m).

REFERENCE EXAMPLE 88

4-((3-(4-Isopropylphenyl)-2-methyl-2-propenyl)oxy)-2,6-dimethylphenyl acetate

Using 4-hydroxy-2,6-dimethylphenyl acetate, the title compound was synthesized in the same manner as in Reference Example 87. Yield 83%. Oily matter.

$^1$H-NMR (CDCl$_3$) δ: 1.26 (6H, d, J=7.2 Hz), 1.97 (3H, s), 2.12 (6H, s), 2.32 (3H, s), 2.90 (1H, septet, J=7.2 Hz), 4.49 (2H, s), 6.57 (1H, s), 6.66 (2H, s), 7.18-7.25 (4H, m).

REFERENCE EXAMPLE 89

2-(1-(4-Isopropylphenyl)-2-methyl-2-propenyl)-4-methylphenol

A solution of 1-isopropyl-4-(2-methyl-3-(4-methylphenoxy)propene-1-yl)benzene obtained in Reference Example 87 (8.2 g, 29.2 mmol) in N,N-dimethylaniline (50 mL) was stirred under argon atmosphere at 215° C. for 16 hours. After cooling, the reaction mixture was diluted with diisopropyl ether, washed with 5 N hydrochloric acid and water, dried over magnesium sulfate, and then concentrated under reduced pressure. The obtained residue was purified by silica gel column chromatography (hexane:ethyl acetate=4:1) to obtain 7.80 g (yield 95%) of the title compound. Oily matter.

$^1$H-NMR (CDCl$_3$) δ: 1.23 (6H, d, J=7.2 Hz), 1.83 (3H, s), 2.22 (3H, s), 2.89 (1H, septet, J=7.2 Hz), 4.61 (1H, s), 4.75 (1H, s), 5.04 (1H, s), 5.12 (1H, s), 6.70-6.78 (2H, m), 6.94 (1H, d, J=8.0 Hz), 7.09 (2H, d, J=8.6 Hz), 7.17 (2H, d, J=8.6 Hz).

REFERENCE EXAMPLE 90

3-(4-Isopropylphenyl)-2,2,5-trimethyl-2,3-dihydro-1-benzofuran

Using 2-(1-(4-isopropylphenyl)-2-methyl-2-propenyl)-4-methylphenol obtained in Reference Example 89, the title compound was synthesized in the same manner as in Reference Example 83. Yield 37%. Melting point: 65-66° C.

$^1$H-NMR (CDCl$_3$) δ: 0.95 (3H, s), 1.25 (6H, d, J=6.9 Hz), 1.57 (3H, s), 2.25 (3H, s), 2.89 (1H, septet, J=6.9 Hz), 4.28 (1H, s), 6.71 (1H, d, J=8.1 Hz), 6.86 (1H, s), 6.93-7.03 (3H, m), 7.15 (2H, d, J=7.8 Hz).

REFERENCE EXAMPLE 91

3-(4-Isopropylphenyl)-5-methoxy-2,2,4,6-tetramethyl-2,3-dihydro-1-benzofuran

A solution of 4-((3-(4-isopropylphenyl)-2-methylpropene-2-yl)oxy)-2,6-dimethylphenyl acetate obtained in Reference Example 88 (6.3 g, 17.9 mmol) in N,N-dimethylaniline (30 mL) was stirred under argon atmosphere at 215° C. for 16 hours. After cooling, the reaction mixture was diluted with diisopropyl ether, washed with 5 N hydrochloric acid and water, dried over magnesium sulfate, and then concentrated under reduced pressure. A mixture of the obtained residue and 48% hydrobromic acid (30 mL)-acetic acid (5 mL) was heated under reflux under argon atmosphere for 16 hours. After cooling, water was added to the reaction solution, which was extracted with ethyl acetate, and the combined organic layer was washed with water, dried over magnesium sulfate, filtered and then concentrated under reduced pressure. To a solution of the obtained residue in DMF (30 mL) was added sodium hydride (a 60% liquid paraffin dispersion, 556 mg, 13.9 mmol) under nitrogen atmosphere at 0° C., and the mixture was stirred at the same temperature for 30 minutes. To the reaction solution was added methyl iodide (1.97 g, 13.9 mmol), and the mixture was stirred at room temperature for 3 hours. To the reaction solution, is added water, and the product was extracted with ethyl acetate. The combined extract was washed with water, dried over magnesium sulfate, and concentrated under reduced pressure, and the obtained residue was purified by silica gel column chromatography (hexane:ethyl acetate=4:1) to obtain 2.10 g (yield 36%) of the title compound as an oily matter. Melting point: 121-123° C. (methanol).

$^1$H-NMR (CDCl$_3$) δ: 0.99 (3H, s), 1.22 (6H, d, J=7.2 Hz), 1.49 (3H, s), 1.85 (3H, s), 2.27 (3H, s), 2.86 (1H, septet, J=6.9 Hz), 3.63 (3H, s), 4.06 (1H, s), 6.49 (1H, s), 6.51-7.11 (4H, m).

REFERENCE EXAMPLE 92

7-Bromo-3-(4-isopropylphenyl)-2,2,5-trimethyl-2,3-dihydro-1-benzofuran

Using 3-(4-isopropylphenyl)-2,2,5-trimethyl-2,3-dihydro-1-benzofuran obtained in Reference Example 90, the title compound was synthesized in the same manner as in Reference Example 18. Yield 86%. Oily matter.

$^1$H-NMR (CDCl$_3$) δ: 1.00 (3H, s), 1.25 (6H, d, J=6.9 Hz), 1.61 (3H, s), 2.23 (3H, s), 2.89 (1H, septet, J=6.9 Hz), 4.35 (1H, s), 6.77 (1H, s), 6.99 (2H, d, J=8.1 Hz), 7.10-7.21 (3H, m).

REFERENCE EXAMPLE 93

7-Bromo-3-(4-isopropylphenyl)-5-methoxy-2,2,4,6-tetramethyl-2,3-dihydro-1-benzofuran Using 3-(4-isopropylphenyl)-5-methoxy-2,2,4,6-tetramethyl-2,3-dihydro-1-benzofuran obtained in Reference Example 91, the title compound was synthesized in the same manner as in Reference Example 18. Yield: quantitative. Oily matter.

$^1$H-NMR (CDCl$_3$) δ: 1.05 (3H, s), 1.23 (6H, d, J=7.0 Hz), 1.53 (3H, s), 1.82 (3H, s), 2.36 (3H, s), 2.86 (1H, septet, J=7.0 Hz), 3.62 (3H, s), 4.08 (1H, s), 6.60-7.20 (4H, m).

REFERENCE EXAMPLE 94

N-Benzyl-3-(4-isopropylphenyl)-2,2,5-trimethyl-2,3-dihydro-1-benzofuran-7-amine

Using 7-bromo-3-(4-isopropylphenyl)-2,2,5-trimethyl-2,3-dihydro-1-benzofuran obtained in Reference Example 92, the title compound was synthesized in the same manner as in Reference Example 24. Yield 79%. Melting point: 80-81° C. (ethyl acetate-hexane).

$^1$H-NMR (CDCl$_3$) δ: 0.94 (3H, s), 1.24 (6H, d, J=6.9 Hz), 1.56 (3H, s), 2.20 (3H, s), 2.89 (1H, septet, J=6.9 Hz), 4.01 (1H, br s), 4.28 (2H, s), 4.37 (1H, s), 6.27 (1H, s), 6.37 (1H, s), 7.02 (2H, d, J=8.1 Hz), 7.14 (2H, d, J=8.1 Hz), 7.21-7.44 (5H, m).

REFERENCE EXAMPLE 95

N-Benzyl-3-(4-isopropylphenyl)-5-methoxy-2,2,4,6-tetramethyl-2,3-dihydro-1-benzofuran-7-amine Using 7-bromo-3-(4-isopropylphenyl)-5-methoxy-2,2,4,6-tetramethyl-2,3-dihydro-1-benzofuran obtained in Reference Example 93, the title compound was synthesized in the same manner as in Reference Example 24. Yield 79%. Oily matter.

$^1$H-NMR (CDCl$_3$) δ: 0.98 (3H, s), 1.22 (6H, d, J=6.9 Hz), 1.44 (3H, s), 1.78 (3H, s), 2.14 (3H, s), 2.85 (1H, septet, J=6.9 Hz), 3.42-3.67 (4H, m), 4.01 (1H, s), 4.35 (1H, d, J=14.4 Hz), 4.42 (1H, d, J=14.4 Hz), 6.50-7.18 (4H, m), 7.20-7.38 (5H, m).

REFERENCE EXAMPLE 96

3-(4-Isopropylphenyl)-2,2,5-trimethyl-2,3-dihydro-1-benzofuran-7-amine

Using N-benzyl-3-(4-isopropylphenyl)-2,2,5-trimethyl-2,3-dihydro-1-benzofuran-7-amine obtained in Reference Example 94, the title compound was synthesized in the same manner as in Reference Example 30. Yield 65%. Oily matter.

$^1$H-NMR (CDCl$_3$) δ: 0.95 (3H, s), 1.24 (6H, d, J=7.2 Hz), 1.56 (3H, s), 2.18 (3H, s), 2.88 (1H, septet, J=7.2 Hz), 3.50 (2H, br s), 4.26 (1H, s), 6.31 (1H, s), 6.43 (1H, s), 7.02 (2H, d, J=8.1 Hz), 7.14 (2H, d, J=8.1 Hz).

REFERENCE EXAMPLE 97

3-(4-Isopropylphenyl)-5-methoxy-2,2,4,6-tetramethyl-2,3-dihydro-1-benzofuran-7-amine Using N-benzyl-3-(4-isopropylphenyl)-5-methoxy-2,2,4,6-tetramethyl-2,3-dihydro-1-benzofuran-7-amine obtained in Reference Example 95, the title compound was synthesized in the same manner as in Reference Example 30.

Yield 83%. Melting point: 111-112° C. (ethyl acetate-hexane).

$^1$H-NMR (CDCl$_3$) δ: 1.00 (3H, s), 1.22 (6H, d, J=6.9 Hz), 1.50 (3H, s), 1.78 (3H, s), 2.14 (3H, s), 2.86 (1H, septet, J=6.9 Hz), 3.44 (2H, br s), 3.60 (3H, s), 4.08 (1H, s), 6.62-7.11 (4H, m).

REFERENCE EXAMPLE 98

N-Benzyl-2,2,4,6-tetramethyl-2,3-dihydro-1-benzofuran-5-amine

To a solution of 5-(benzylamino)-2,2,4,6-tetramethyl-1-benzofuran-3(2H)-one obtained in Reference Example 51 (8.5 g, 28.8 mmol) in methanol (20 mL) was added sodium borohydride (2.18 g, 57.6 mmol) at room temperature, and the mixture was stirred for 2 hours. The reaction solution was concentrated under reduced pressure, and the residue was extracted with ethyl acetate. The organic layer was washed with water, dried over anhydrous sodium sulfate, and concentrated under reduced pressure to obtain the crude product, 5-(benzylamino)-2,2,4,6-tetramethyl-2,3-dihydro-1-benzofuran-3-ol. To a mixture of said compound with trifluoroacetic acid (30 mL) was added triethylsilane (10 mL, 64 mmol) with ice-cooling, and the mixture was stirred at room temperature for 1 hour. The reaction solution was concentrated under reduced pressure, and to the residue was added a saturated sodium hydrogen carbonate solution to alkalify the aqueous layer, which was extracted with ethyl acetate. The organic layer was washed with water and saturated brine, dried over anhydrous sodium sulfate and then concentrated under reduced pressure. The obtained residue was crystallized with ethyl acetate-hexane to obtain 4.1 g (yield 51%) of the title compound. Melting point: 80-81° C. (ethyl acetate-hexane).

$^1$H-NMR (CDCl$_3$) δ: 1.47 (6H, s), 2.18 (3H, s), 2.23 (3H, s), 2.83 (1H, br s), 2.91 (2H, s), 3.96 (2H, s), 6.43 (1H, s), 7.25-7.42 (5H, m).

REFERENCE EXAMPLE 99

Ethyl 3-(4-isopropylphenyl)-2-methylacrylate

To a suspension of sodium hydride (a 60% liquid paraffin dispersion, 5.92 g, 148 mmol) in DMF (150 mL) was added triethyl 2-phosphonopropionate (35.0 g, 148 mmol) at 0° C., and the mixture was stirred at the same temperature for 10 minutes. To the reaction solution was added 4-isopropylbenzaldehyde (20.0 g, 135 mmol), and the mixture was stirred at room temperature 30 minutes. Water was added to the reaction solution, and the product was extracted twice with ethyl acetate. The combined extract was washed with water, dried over magnesium sulfate, and then concentrated under reduced pressure to obtain 30.1 g (yield 96%) of the oily title compound.

$^1$H-NMR (CDCl$_3$) δ: 1.26 (6H, d, J=7.0 Hz), 1.35 (3H, t, J=7.0 Hz), 2.13 (3H, s), 2.92 (1H, septet, J=7.0 Hz), 4.27 (2H, q, J=7.0 Hz), 7.21-7.38 (4H, m), 7.67 (1H, s).

REFERENCE EXAMPLE 100

Ethyl 2-methyl-3-(4-methylphenyl)acrylate

Using 4-methylbenzaldehyde, the title compound was synthesized in the same manner as in Reference Example 99.
Yield 91%. Oily matter.

$^1$H-NMR (CDCl$_3$) δ: 1.34 (3H, t, J=7.0 Hz), 2.12 (3H, d, J=1.4 Hz), 2.37 (3H, s), 4.26 (2H, q, J=7.0 Hz), 7.19 (2H, d, J=8.4 Hz), 7.31 (2H, d, J=8.4 Hz), 7.66 (1H, s).

REFERENCE EXAMPLE 101

Ethyl 3-(4-fluorophenyl)-2-methylacrylate

Using 4-fluorobenzaldehyde, the title compound was synthesized in the same manner as in Reference Example 99.
Yield 97%. Oily matter.

$^1$H-NMR (CDCl$_3$) δ: 1.35 (3H, t, J=7.0 Hz), 2.10 (3H, d, J=1.2 Hz), 4.28 (2H, q, J=7.0 Hz), 7.08 (2H, t, J=8.8 Hz), 7.32-7.43 (2H, m), 7.65 (1H, s).

REFERENCE EXAMPLE 102

Ethyl(E)-3-(4-isopropylphenyl)-2-acrylate

To a suspension of sodium hydride (a 60% liquid paraffin dispersion, 10.4 g, 260 mmol) in DMF (200 mL) was added triethyl phosphonoacetate (58.2 g, 236 mmol) at 0° C., and the mixture was stirred at the same temperature for 10 minutes. To the reaction solution was added 4-isopropylbenzaldehyde (35.0 g, 260 mmol) and the mixture was stirred at room temperature for 30 minutes. Water was added to the reaction solution, and the product was twice extracted with ethyl acetate. The combined extract was washed with water, dried over magnesium sulfate and then concentrated under reduced pressure to obtain the oily title compound 47.5 g (yield 92%).

$^1$H-NMR (CDCl$_3$) δ: 1.25 (6H, d, J=7.0 Hz), 1.33 (3H, t, J=7.0 Hz), 2.92 (1H, septet, J=7.0 Hz), 4.26 (2H, q, J=7.0 Hz), 6.40 (1H, d, J=15.8 Hz), 7.24 (2H, d, J=8.2 Hz), 7.46 (2H, d, J=8.2 Hz), 7.67 (1H, d, J=15.8 Hz).

REFERENCE EXAMPLE 103

3-(4-Isopropylphenyl)-2-methyl-2-propen-1-ol

To a suspension of ethyl 3-(4-isopropylphenyl)-2-methyl-2-acrylate (9.00 g, 38.7 mmol) obtained in Reference Example 99 and cerous chloride (1.00 g, 4.06 mmol) in THF (50 mL) was added lithium aluminum hydride (1.47 g, 38.7 mmol) in four batches for 30 minutes, and the mixture was stirred at the same temperature for 30 minutes. Water was added to the reaction solution, and the product was twice extracted with ethyl acetate. The combined extract was washed with water, dried over magnesium sulfate, and then concentrated under reduced pressure. The residue was purified by silica gel column chromatography (hexane:ethyl acetate=8:1) to obtain the oily title compound 6.30 g (yield 86%).

$^1$H-NMR (CDCl$_3$) δ: 1.25 (6H, d, J=7.0 Hz), 1.91 (3H, d, J=1.4 Hz), 2.90 (1H, septet, J=7.0 Hz), 4.17 (2H, d, J=0.8 Hz), 6.49 (1H, dd, J=2.6, 1.4 Hz), 7.15-7.25 (4H, m), 1H unidentified

REFERENCE EXAMPLE 104

2-Methyl-3-(4-methylphenyl)-2-propen-1-ol

Using ethyl 2-methyl-3-(4-methylphenyl)-2-acrylate synthesized in Reference Example 100, the title compound was synthesized in the same manner as in Reference Example 103. Yield 42%. Oily matter.

$^1$H-NMR (CDCl$_3$) δ: 1.87 (3H, s), 2.32 (3H, s), 4.13 (2H, s), 6.46 (1H, s), 7.08-7.22 (4H, m), 1H unidentified

REFERENCE EXAMPLE 105

3-(4-Fluorophenyl)-2-methyl-2-propen-1-ol

Using ethyl 3-(4-fluorophenyl)-2-methyl-2-acrylate synthesized in Reference Example 101, the title compound was synthesized in the same manner as in Reference Example 103. Yield 95%. Oily matter.

$^1$H-NMR (CDCl$_3$) δ: 1.98 (3H, d, J=1.6 Hz), 4.11 (2H, s), 6.58 (1H, s), 7.01 (2H, t, J=8.8 Hz), 7.18-7.28 (2H, m), 1H unidentified

REFERENCE EXAMPLE 106

3-(4-Bromophenyl)-2-methyl-2-propen-1-ol

To a solution of sodium tert-butoxide (10.6 g, 110 mmol) in DMF (60 mL) was added triethyl phosphonoacetate (26.2 g, 110 mmol) under argon atmosphere at −10° C. and the mixture was stirred at the same temperature for 1 hour. 4-bromobenzaldehyde (18.5 g, 100 mmol) was added to the solution at 10° C. or lower, and the mixture was warmed to room temperature, and then stirred for 2 hours. Water was added to the reaction solution after ice-cooling, which was extracted with toluene. The extract was washed with a saturated brine, dried over sodium sulfate, and then concentrated under reduced pressure. The obtained oily matter was dissolved in toluene (200 mL), dihydrobis(2-methoxyethoxy) sodium aluminate (a 70% toluene solution, 41.5 g, 144 mmol) was added dropwise at −10° C., and then the mixture was stirred at the same temperature for 1 hour. A 10% aqueous potassium sodium tartrate solution was added to separate the organic layer. The organic layer was washed with a 10% aqueous potassium sodium tartrate solution and a saturated brine, dried over sodium sulfate, and then concentrated under reduced pressure. The obtained residue was purified by silica gel column chromatography (hexane:ethyl acetate=2:1) to obtain 20.1 g (yield 88%) of the title compound as an oily matter.

$^1$H-NMR (CDCl$_3$) δ: 1.54 (1H, t, J=6.0 Hz), 1.87 (3H, d, J=1.2 Hz), 4.19 (2H, d, J=6.0 Hz), 6.46 (1H, s), 7.14 (2H, d, J=8.4 Hz), 7.45 (2H, d, J=8.4 Hz).

REFERENCE EXAMPLE 107

(E)-3-(4-Isopropylphenyl)-2-propen-1-ol

Using ethyl(E)-3-(4-isopropylphenyl)-2-acrylate synthesized in Reference Example 102, the title compound was synthesized in the same manner as in Reference Example 103. Yield 65%. Oily matter.

$^1$H-NMR (CDCl$_3$) δ: 1.24 (6H, d, J=7.0 Hz), 2.79-3.00 (2H, m), 4.30 (2H, d, J=5.6 Hz), 6.35 (1H, dt, J=15.8, 5.6 Hz), 6.59 (1H, d, J=15.8 Hz), 7.10-7.39 (4H, m).

REFERENCE EXAMPLE 108

1-(3-Bromo-2-methyl-1-propenyl)-4-isopropylbenzene

To a solution of 3-(4-isopropylphenyl)-2-methyl-2-propen-1-ol synthesized in Reference Example 103 (6.30 g, 33.1 mmol) in isopropyl ether (50 mL) was added phosphorus tribromide (5.98 g, 22.1 mmol) with ice-cooling and the mixture was stirred at room temperature for 30 minutes. Water was added to the reaction solution and the mixture was extracted with isopropyl ether. The organic layer was washed with water and a saturated sodium hydrogen carbonate solution, dried over magnesium sulfate, filtered, and then concentrated under reduced pressure to obtain the oily title compound 7.63 g (yield 91%)

$^1$H-NMR (CDCl$_3$) δ: 1.25 (6H, d, J=7.0 Hz), 2.03 (3H, d, J=1.4 Hz), 2.90 (1H, septet, J=7.0 Hz), 4.15 (2H, d, J=0.8 Hz), 6.62 (1H, s), 7.14-7.26 (4H, m).

REFERENCE EXAMPLE 109

1-(3-Bromo-2-methyl-1-propenyl)benzene

Using 2-methyl-3-phenyl-2-propen-1-ol, the title compound was synthesized in the same manner as in Reference Example 108. Yield 89%. Oily matter.

$^1$H-NMR (CDCl$_3$) δ: 2.01 (3H, d, J=1.4 Hz), 4.13 (2H, d, J=0.8 Hz), 6.64 (1H, s), 7.19-7.44 (5H, m).

REFERENCE EXAMPLE 110

1-(3-Bromo-2-methyl-1-propenyl)-4-methylbenzene

Using 2-methyl-3-(4-methylphenyl)-2-propen-1-ol synthesized in Reference Example 104, the title compound was synthesized in the same manner as in Reference Example 108. Yield 80%. Oily matter.

$^1$H-NMR (CDCl$_3$) δ: 2.01 (3H, s), 2.34 (3H, s), 4.13 (2H, s), 6.60 (1H, s), 7.09-7.22 (4H, m).

REFERENCE EXAMPLE 111

1-(3-Bromo-2-methyl-1-propenyl)-4-fluorobenzene

Using 3-(4-fluorophenyl)-2-methyl-2-propen-1-ol synthesized in Reference Example 105, the title compound was synthesized in the same manner as in Reference Example 108. Yield 79%. Oily matter.

$^1$H-NMR (CDCl$_3$) δ: 1.87 (3H, s), 4.17 (2H, s), 6.48 (1H, s), 7.01 (2H, t, J=8.8 Hz), 7.18-7.27 (2H, m).

REFERENCE EXAMPLE 112

1-Bromo-4-(3-bromo-2-methyl-1-propenyl)benzene

To an acetonitrile solution (180 mL) of triphenylphosphine (24.3 g, 92.7 mmol) was added dropwise bromine (4.78 mL, 185 mmol) at 0° C. and the mixture was stirred at the same temperature for 30 minutes. To the solution was added the acetonitrile solution (60 mL) of 3-(4-bromophenyl)-2-methyl-2-propen-1-ol obtained in Reference Example 106 (20.1 g, 88.3 mmol) and the mixture was stirred at 0° C. for 1 hour. The reaction solution was concentrated under reduced pressure, diethyl ether (200 mL) was added to the residue, and the insolubles were filtered off. The solution was washed with a saturated brine, dried over sodium sulfate, and then concentrated under reduced pressure to obtain 25.0 g (yield 98%) of the title compound as an oily matter.

$^1$H-NMR (CDCl$_3$) δ: 1.99 (3H, d, J=1.4 Hz), 4.12 (2H, s), 6.57 (1H, s), 7.15 (2H, d, J=8.4 Hz), 7.45 (2H, d, J=8.4 Hz).

REFERENCE EXAMPLE 113

1-((E)-3-Bromo-1-propenyl)-4-isopropylbenzene

Using (E)-3-(4-isopropylphenyl)-2-propen-1-ol synthesized in Reference Example 107, the title compound was synthesized in the same manner as in Reference Example 108. Yield 72%. Oily matter.

$^1$H-NMR (CDCl$_3$) δ: 1.24 (6H, d, J=7.0 Hz), 2.89 (1H, septet, J=7.0 Hz), 4.16 (2H, dd, J=7.8, 0.8 Hz), 6.35 (1H, dt, J=15.4, 7.8 Hz), 6.63 (1H, d, J=15.4 Hz), 7.14-7.35 (4H, m).

REFERENCE EXAMPLE 114

N-(4-((3-(4-Isopropylphenyl)-2-methyl-2-propenyl) oxy)-2,3,6-trimethylphenyl)formamide To a solution of N-(4-hydroxy-2,3,6-trimethylphenyl)formamide (3.00 g, 16.7 mmol) in DMF (30 mL) was added sodium hydride (a 60% liquid paraffin dispersion, 0.74 g, 18.4 mmol) under nitrogen atmosphere at 0° C., and the mixture was stirred at the same temperature for 10 minutes. To the reaction solution was added 1-(3-bromo-2-methyl-1-propenyl)-4-isopropylbenzene synthesized in Reference Example 108 (4.66 g, 18.4 mmol) and the mixture was stirred at room temperature for 30 minutes. Water was added to the reaction solution and the product was twice extracted with ethyl acetate. The combined extract was washed with water, dried over magnesium sulfate, and then concentrated under reduced pressure. The obtained residue was crystallized from ethyl acetate-hexane to obtain 3.70 g (yield 63%) of the title compound. Melting point: 153-155° C.

$^1$H-NMR (CDCl$_3$) δ: 1.26 (6H, d, J=7.0 Hz), 2.00 (3H, s), 2.07-2.34 (9H, m), 2.91 (1H, septet, J=7.0 Hz), 4.54 (2H, d, J=5.4 Hz), 6.59-6.84 (3H, m), 7.17-7.36 (4H, m), 7.98 (0.5H, d, J=12.0 Hz), 8.41 (0.5H, s).

REFERENCE EXAMPLE 115

N-(2,3,6-Trimethyl-4-((2-methyl-3-phenyl-2-propenyl)oxy)phenyl)formamide

Using 1-(3-bromo-2-methyl-1-propenyl)benzene synthesized in Reference Example 109, the title compound was synthesized in the same manner as in Reference Example 114. Yield 41%. Melting point: 152-154° C. (ethyl acetate-hexane)

$^1$H-NMR (CDCl$_3$) δ: 1.98 (3H, d, J=1.6 Hz), 2.10-2.32 (9H, m), 4.54 (2H, d, J=5.2 Hz), 6.65 (1H, s), 6.67 (1H, s), 6.69-6.90 (1H, m), 7.11-7.41 (5H, m), 7.98 (0.5H, d, J=12.0 Hz), 8.41 (0.5H, d, J=1.4 Hz).

REFERENCE EXAMPLE 116

N-(2,3,6-Trimethyl-4-((2-methyl-3-(4-methylphenyl)-2-propenyl)oxy)phenyl)formamide Using 1-(3-bromo-2-methyl-1-propenyl)-4-methylbenzene synthesized in Reference Example 110, the title compound was synthesized in the same manner as in Reference Example 114. Yield 44%. Melting point: 167-169° C.

$^1$H-NMR (CDCl$_3$) δ: 1.98 (3H, s), 2.07-2.38 (9H, m), 2.35 (3H, s), 4.53 (2H, d, J=6.6 Hz), 6.61 (1H, s), 6.66 (1H, d, J=2.4 Hz), 6.82-7.09 (1H, m), 7.11-7.31 (4H, m), 7.98 (0.5H, d, J=12.2 Hz), 8.3.8 (0.5H, s).

REFERENCE EXAMPLE 117

N-(4-((3-(4-Fluorophenyl)-2-methyl-2-propenyl)oxy)-2,3,6-trimethylphenyl)formamide Using 1-(3-bromo-2-methyl-1-propenyl)-4-fluorobenzene synthesized in Reference Example 111, the title compound was synthesized in the same manner as in Reference Example 114. Yield 52%. Melting point: 164-165° C. (ethyl acetate-hexane).

$^1$H-NMR (CDCl$_3$) δ: 1.96 (3H, s), 2.12-2.32 (9H, m), 4.53 (2H, d, J=5.2 Hz), 6.60 (1H, s), 6.66 (1H, s), 6.71-6.95 (1H, m), 7.04 (2H, t, J=8.8 Hz), 7.22-7.33 (2H, m), 8.04 (0.5H, d, J=12.0 Hz), 8.40 (0.5H, d, J=1.4 Hz).

REFERENCE EXAMPLE 118

N-(4-((3-(4-Bromophenyl)-2-methyl-2-propenyl)oxy)-2,3,6-trimethylphenyl)formamide Using 1-bromo-4-(3-bromo-2-methyl-1-propenyl)benzene synthesized in Reference Example 112, the title compound was synthesized in the same manner as in Reference Example 114. Yield 79%.

$^1$H-NMR (CDCl$_3$) δ: 1.95-1.97 (3H, m), 2.18-2.27 (9H, m), 4.52 (2H, br d, J=4.4 Hz), 6.58 (1H, br s), 6.65 (1H, br s), 6.78 (1H, br d, J=15.0 Hz), 7.17 (2H, d, J=8.2 Hz), 7.47 (2H, d J=8.2 Hz), 7.99 (0.5H, d, J=8.1 Hz), 8.42 (0.5H, d, J=1.5 Hz).

REFERENCE EXAMPLE 119

N-(4-(((E)-3-(4-Isopropylphenyl)-2-propenyl)oxy)-2,3,6-trimethylphenyl)formamide Using 1-((E)-3-bromo-1-propenyl)-4-isopropylbenzene synthesized in Reference Example 113, the title compound was synthesized. Yield 59%. Melting point: 165-167° C. (ethyl acetate-hexane)

$^1$H-NMR (CDCl$_3$) δ: 1.25 (6H, d, J=6.8 Hz), 2.13-2.27 (9H, m), 2.90 (1H, septet, J=6.8 Hz), 4.66 (2H, t, J=5.8 Hz), 6.37 (1H, dt, J=15.8, 5.8 Hz), 6.65-6.88 (3H, m), 7.16-7.26 (2H, m), 7.35 (2H, d, J=8.0 Hz), 7.98 (0.5H, d, J=12.0 Hz), 8.40 (0.5H, d, J=1.4 Hz).

REFERENCE EXAMPLE 120

3-(4-Isopropylphenyl)-2,2,4,6,7-pentamethyl-2,3-dihydro-1-benzofuran-5-amine

A solution of N-(4-((3-(4-isopropylphenyl)-2-methyl-2-propenyl)oxy)-2,3,6-trimethylphenyl)formamide synthesized in Reference Example 114 (3.70 g, 10.5 mmol) in N,N-dimethylaniline (20 mL) was stirred under argon atmosphere at 215° C. for 6 hours. After cooling, the reaction mixture was extracted with ethyl acetate, washed with 2 N hydrochloric acid and water, dried over magnesium sulfate, and then concentrated under reduced pressure to obtain the crude product of N-(4-hydroxy-3-(1-(4-isopropylphenyl)-2-methyl-2-propenyl)-2,5,6-trimethylphenyl)formamide. A mixture of this compound (2.98 g, 8.47 mmol) and concentrated hydrochloric acid (20 mL)-methanol (60 mL) was heated under reflux under nitrogen atmosphere for 2 hours. The solvent was concentrated under reduced pressure, and the obtained residue was neutralized with a 8 N aqueous sodium hydroxide solution. The product was twice extracted with ethyl acetate. The combined extract was washed with water, dried over magnesium sulfate, and then concentrated under reduced pressure. The obtained residue was crystallized from isopropyl ether-hexane to obtain 2.23 g (yield 66%) of the title compound. Melting point: 130-132° C.

$^1$H-NMR (CDCl$_3$) δ: 1.00 (3H, s), 1.21 (6H, d, J=6.6 Hz), 1.47 (3H, s), 1.78 (3H, s), 2.12 (3H, s), 2.19 (3H, s), 2.40-2.60 (3H, m), 4.08 (1H, s), 6.72-7.00 (2H, m), 7.07 (2H, d, J=8.0 Hz).

REFERENCE EXAMPLE 121

2,2,4,6,7-Pentamethyl-3-phenyl-2,3-dihydro-1-benzofuran-5-amine

Using N-(2,3,6-trimethyl-4-((2-methyl-3-phenyl-2-propenyl)oxy)phenyl)formamide synthesized in Reference Example 115, the title compound was synthesized in the same manner as in Reference Example 120. Yield 67%. Melting point: 129-131° C.

¹H-NMR (CDCl₃) δ: 1.00 (3H, s), 1.48 (3H, s), 1.77 (3H, s), 2.13 (3H, s), 2.19 (3H, s), 3.20 (2H, br s), 4.12 (1H, s), 6.70-7.30 (5H, m).

REFERENCE EXAMPLE 122

2,2,4,6,7-Pentamethyl-3-(4-methylphenyl)-2,3-dihydro-1-benzofuran-5-amine

Using N-(2,3,6-trimethyl-4-((2-methyl-3-(4-methylphenyl)-2-propenyl)oxy)phenyl)formamide synthesized in Reference Example 116, the title compound was synthesized in the same manner as in Reference Example 120.

Yield 57%. Melting point: 114-115° C. (petroleum ether).
¹H-NMR (CDCl₃) δ: 0.99 (3H, s), 1.47 (3H, s), 1.77 (3H, s), 2.12 (3H, s), 2.19 (3H, s), 2.30 (3H, s), 3.23 (2H, br s), 4.08 (1H, s), 6.60-7.23 (4H, m).

REFERENCE EXAMPLE 123

3-(4-Fluorophenyl)-2,2,4,6,7-pentamethyl-2,3-dihydro-1-benzofuran-5-amine

Using N-(4-((3-(4-fluorophenyl)-2-methyl-2-propenyl)oxy)-2,3,6-trimethylphenyl)formamide synthesized in Reference Example 117, the title compound was synthesized in the same manner as in Reference Example 120.

Yield 78%. Melting point: 125-127° C. (petroleum ether).
¹H-NMR (CDCl₃) δ: 0.99 (3H, s), 1.47 (3H, s), 1.77 (3H, s), 2.12 (3H, s), 2.19 (3H, s), 3.10 (2H, br s), 4.09 (1H, s), 6.62-7.20 (4H, m).

REFERENCE EXAMPLE 124

3-(4-Bromophenyl)-2,2,4,6,7-pentamethyl-2,3-dihydro-1-benzofuran-5-amine

Using N-(4-((3-(4-bromophenyl)-2-methyl-2-propenyl)oxy)-2,3,6-trimethylphenyl)formamide synthesized in Reference Example 118, the title compound was synthesized in the same manner as in Reference Example 120.

Yield 56%.
¹H-NMR (CDCl₃) δ: 1.00 (3H, s), 1.47 (3H, s), 1.77 (3H, s), 2.12 (3H, s), 2.18 (3H, s), 3.23 (2H, br), 4.07 (1H, s), 6.83 (2H, br), 7.36 (2H, brd, J=8.0 Hz).

REFERENCE EXAMPLE 125

N-(4-Hydroxy-3-(1-(4-isopropylphenyl)-2-propenyl)-2,5,6-trimethylphenyl)formamide A solution of N-(4-(((E)-3-(4-isopropylphenyl)-2-propenyl)oxy)-2,3,6-trimethylphenyl)formamide synthesized in Reference Example 119 (5.80 g, 17.2 mmol) in N,N-dimethylaniline (50 mL) was stirred under argon atmosphere at 215° C. for 6 hours. After cooling, the reaction mixture was diluted with ethyl acetate, was washed with 2 N hydrochloric acid and water, dried over magnesium sulfate, and then concentrated under reduced pressure. The residue was crystallized from ethyl acetate to obtain 3.50 g (yield 60%) of the title compound. Melting point: 170-171° C.

¹H-NMR (CDCl₃) δ: 1.18-1.40 (6H, m), 2.11-2.27 (9H, m), 2.77-3.00 (1H, m), 5.00-5.22 (2H, m), 5.30-5.42 (1H, m), 6.30-6.85 (2H, m), 7.10-7.37 (5H, m), 7.97 (0.5H, d, J=12.2 Hz), 8.43 (0.5H, d, J=1.4 Hz).

REFERENCE EXAMPLE 126

3-(4-Isopropylphenyl)-2,4,6,7-tetramethyl-1-benzofuran-5-amine hydrochloride

To a suspension of N-(4-hydroxy-3-(1-(4-isopropylphenyl)-2-propenyl)-2,5,6-trimethylphenyl)formamide synthesized in Reference Example 125 (3.50 g, 10.4 mmol) and calcium carbonate (1.35 g, 13.5 mmol) in THF (15 mL)-methanol (15 mL) was added slowly benzyltrimethylammonium iodidodichloride (3.90 g, 11.4 mmol). The reaction solution was stirred at room temperature for 30 minutes. After separating the insolubles, the solvent was concentrated under reduced pressure, and ethyl acetate and water were added to the residue. The organic layer was separated and an aqueous layer was twice extracted with ethyl acetate. The combined organic layer was washed with a 10% sodium hydrosulfite aqueous solution, water, a saturated sodium hydrogen carbonate solution and a saturated brine, dried over magnesium sulfate, and then concentrated under reduced pressure to obtain 4.08 g of N-(2-iodomethyl-3-(4-isopropylphenyl)-4,6,7-trimethyl-2,3-dihydro-1-benzofuran-5-yl)formamide. A solution of this compound (4.08 g, 8.81 mmol) and 1,8-diazabicyclo(5,4,0)-7-undecene (6.58 mL, 44.0 mmol) in toluene (30 mL) was stirred at 100° C. under argon atmosphere for 3 hours. Water was added to the reaction solution, which was twice extracted with ethyl acetate. The extract was washed with 2 N hydrochloric acid and water, dried over magnesium sulfate, and then concentrated under reduced pressure. The residue was purified by silica gel column chromatography (hexane:ethyl acetate=20:1) to obtain N-(3-(4-isopropylphenyl)-2,4,6,7-tetramethyl-1-benzofuran-5-yl)formamide 2.40 g. A mixture of this compound (2.40 g, 7.18 mmol) in hydrochloric acid (20 ml)-methanol (60 mL) was heated under reflux under nitrogen atmosphere for two hours. The solvent was concentrated under reduced pressure, and the obtained residue was neutralized with 8 N aqueous sodium hydroxide solution. The product was twice extracted with ethyl acetate. The combined extract was washed with water, dried over magnesium sulfate, and then concentrated under reduced pressure to obtain the oily free base 1.80 g. The oily free base (0.50 g, 1.63 mmol) was dissolved in hydrochloric acid-methanol solution, the solvent was concentrated under reduced pressure, and the obtained residue was crystallized by methanol to obtain the object compound 0.41 g (yield 41%). Melting point: 194-197° C.

¹H-NMR (CDCl₃) δ: 1.29 (6H, d, J=7.0 Hz), 2.30 (6H, s), 2.41 (3H, s), 2.60 (3H, s), 2.94 (1H, septet, J=7.0 Hz), 7.13-7.26 (4H, m), 10.1 (2H, br s), 1H unidentified

REFERENCE EXAMPLE 127

4-Methoxy-2,3,6-trimethylaniline

N-(4-Hydroxy-2,3,6-trimethylphenyl)formamide (30.0 g, 167 mmol) was dissolved in a mixed solvent of 4 N potassium hydroxide aqueous solution (100 mL) and methanol (300 mL), and dimethyl sulfate (42.0 g, 334 mmol) was added to the solution at room temperature and the mixture was heated under reflux for 14 hours. After ice-cooling, the precipitated crystals were collected by filtration to obtain the crude product of N-(4-methoxy-2,3,6-trimethylphenyl)formamide. To a suspension of the compound in methanol (200 mL) was added concentrated hydrochloric acid (50 mL) and the mixture was heated under reflux for 3 hours. The reaction mixture was cooled to room temperature, and then was neutralized with a 8 N aqueous sodium hydroxide solution. The product was twice extracted with ethyl acetate, and the combined extract was washed with 10% sodium hydrosulfite aqueous solution and water, dried over magnesium sulfate, and then concentrated under reduced pressure. The residue was crystallized from isopropyl ether to obtain the object compound 21.0 g (yield 76%). Melting point: 70-72° C.

$^1$H-NMR (CDCl$_3$) δ: 2.11 (3H, s), 2.16 (3H, s), 2.18 (3H, s), 3.16 (1H, br s), 3.74 (3H, s), 6.54 (1H, s)

REFERENCE EXAMPLE 128 tert-Butyl 4-methoxy-2,3,6-trimethylphenylcarbamate

To a solution of 4-methoxy-2,3,6-trimethylaniline synthesized in Reference Example 127 (21.0 g, 127 mmol) and triethylamine (21.0 mL, 152 mmol) in THF (150 mL) was added di-tert-butyl dicarbonate (32 mL, 140 mmol) at room temperature, and the mixture was heated under reflux for 14 hours. The solvent was concentrated under reduced pressure. Water was poured into the residue, which was twice extracted with ethyl acetate. The combined organic layer was washed with 1 N hydrochloric acid and a saturated sodium hydrogen carbonate solution, dried over magnesium sulfate, filtered and then concentrated under reduced pressure. The residue was crystallized from ethyl acetate-hexane to obtain 25.2 g (yield 75%) of the title compound. Melting point: 104-106° C.

$^1$H-NMR (CDCl$_3$) δ: 1.50 (9H, s), 2.12 (3H, s), 2.17 (3H, s), 2.24 (3H, s), 3.78 (3H, s), 5.81 (1H, br s), 6.58 (1H, s).

REFERENCE EXAMPLE 129 tert-Butyl 3-bromo-4-methoxy-2,5,6-trimethylphenylcarbamate

To a solution of tert-butyl 4-methoxy-2,3,6-trimethylphenylcarbamate synthesized in Reference Example 128 (12.7 g, 47.9 mmol) and sodium acetate (4.72 g, 57.5 mmol) in acetic acid (50 mL) was added bromine (8.42 g, 52.7 mmol) at room temperature and the mixture was stirred at the same temperature for 1 hour. Water (80 mL) was poured into the reaction mixture, and the precipitated crystals were collected by filtration and then dissolved in ethyl acetate. The solution was washed with a saturated sodium hydrogen carbonate solution and water, dried over magnesium sulfate, filtered, and then concentrated under reduced pressure. The residue was crystallized from methanol to obtain 15.0 g (yield 91%) of the title compound. Melting point: 159-161° C.

$^1$H-NMR (CDCl$_3$) δ: 1.50 (9H, s), 2.15 (3H, s), 2.24 (3H, s), 2.35 (3H, s), 3.74 (3H, s), 5.92 (1H, br s).

REFERENCE EXAMPLE 130

2,2,4,6,7-Pentamethyl-3-(4-methylphenyl)-2,3-dihydro-1-benzofuran-5-amine

To a solution of tert-butyl 3-bromo-4-methoxy-2,5,6-trimethylphenylcarbamate synthesized in Reference Example 129 (27.8 g, 80.8 mmol) in THF (150 mL) was added n-butyllithium (1.6 M, 110 mL, 176 mmol) hexane solution at −78° C. and the mixture was stirred at the same temperature for 20 minutes. 2-Methyl-1-(4-methylphenyl)propane-1-one (13.1 g, 80.7 mmol) was added to the reaction solution, and the mixture was stirred at room temperature for 1 hour. Water (150 mL) was poured into the reaction mixture, which was three times extracted with ethyl acetate, the combined organic layer was washed with water, dried over magnesium sulfate, and then concentrated under reduced pressure to obtain the crude product 26.0 g of tert-butyl 3-(1-hydroxy-2-methyl-1-(4-methylphenyl)propyl)-4-methoxy-2,5,6-trimethylphenylcarbamate. A mixture of this compound and 47% hydrobromic acid (100 mL) was heated under reflux under argon atmosphere for 4 hours. The reaction mixture was cooled to room temperature, and then was neutralized with a 8 N aqueous sodium hydroxide solution. The product was twice extracted with ethyl acetate, and the combined extract was washed with a saturated sodium hydrogen carbonate solution, dried over magnesium sulfate, and then concentrated under reduced pressure. The residue was crystallized from isopropyl ether-hexane to obtain 14.8 g (yield 62%) of the title compound. Melting point: 114-115° C.

$^1$H-NMR (CDCl$_3$) δ: 0.99 (3H, s), 1.47 (3H, s), 1.78 (3H, s), 2.12 (3H, s), 2.17 (3H, s), 2.30 (3H, s), 2.80 (2H, br s), 4.08 (1H, s), 6.60-7.10 (4H, m).

REFERENCE EXAMPLE 131

(+)-2,2,4,6,7-Pentamethyl-3-(4-methylphenyl)-2,3-dihydro-1-benzofuran-5-amine 2,2,4,6,7-Pentamethyl-3-(4-methylphenyl)-2,3-dihydro-1-benzofuran-5-amine synthesized in Reference Example 130 was subjected to high performance liquid chromatography (apparatus: Waters Semi-Preparative System, Column: CHIRALCEL OD (20 (i, d)×250 mm) manufactured by Daicel Chemical Industries, Ltd., Mobile phase: hexane:isopropanol=95:5, Flow rate: 5 mL/min, Column temperature: 30° C., Injection amount: 40 mg), to preparatively separate a fraction with a longer retention time. Melting point: 87-89° C. $[\alpha]_D^{20}$=+4.7° (c=0.495, methanol).

REFERENCE EXAMPLE 132

(−)-2,2,4,6,7-Pentamethyl-3-(4-methylphenyl)-2,3-dihydro-1-benzofuran-5-amine 2,2,4,6,7-Pentamethyl-3-(4-methylphenyl)-2,3-dihydro-1-benzofuran-5-amine synthesized in Reference Example 130 was subjected to high performance liquid chromatography (apparatus: Waters Semi-Preparative System, Column: CHIRALCEL OD (20 (i, d)×250 mm) manufactured by Daicel Chemical Industries, Ltd., Moving phase: hexane isopropanol=95:5, Flow rate: 5 mL/min, Column temperature: 30° C., Injection amount: 40 mg), to preparatively separate a fraction with a shorter retention time. Melting point: 88-90° C. $[\alpha]_D^{20}$=−4.3 (c=0.499, methanol).

REFERENCE EXAMPLE 133

(+)-3-(4-Bromophenyl)-2,2,4,6,7-pentamethyl-2,3-dihydro-1-benzofuran-5-amine

Di-p-toluoyl-D-tartaric acid (3.86 g, 10 mmol) was dissolved in isopropanol (14.2 mL) at 70° C., and a solution of 3-(4-bromophenyl)-2,2,4,6,7-pentamethyl-2,3-dihydro-1-benzofuran-5-amine synthesized in Reference Example 124 (3.60 g, 10 mmol) in acetonitrile (47.5 mL) was added dropwise thereto with maintaining the inside temperature of 60° C. The solution was cooled to 30° C. for 3 hours, and then was stirred at the same temperature for 2 hours. The precipitated crystals were taken, and then were washed with a small amount of cold acetonitrile. The obtained, crude diastereomeric salt was suspended in acetonitrile (29.6 mL) and was stirred over night. The crystals were collected by filtration, washed with a small amount of cold acetonitrile, and then dried under reduced pressure. The crystals were suspended in ethyl acetate (100 mL), a saturated sodium hydrogen carbonate solution (100 mL) was added thereto, and the mixture was stirred thoroughly to separate the organic layer. The organic layer was washed with water (100 mL) and a saturated brine, and then was dried over anhydrous sodium sulfate. The solvent was dried under reduced pressure, and was crystallized with cold hexane to obtain 1.13 g (yield 31%) of the title compound. Melting point: 143-144° C. (hexane). $[\alpha]_D^{20}$=+11.6° (c=0.5, methanol).

$^1$H-NMR (CDCl$_3$) δ: 1.00 (3H, s), 1.47 (3H, s), 1.77 (3H, s), 2.12 (3H, s), 2.18 (3H, s), 3.25 (2H, br s), 4.07 (1H, s), 6.85 (2H, br), 7.36 (2H, br d, J=6.9 Hz).

REFERENCE EXAMPLE 134

(3R)-(+)-2,2,4,6,7-Pentamethyl-3-(4-methylphenyl)-2,3-dihydro-1-benzofuran-5-amine Using 2,2,4,6,7-pentamethyl-3-(4-methylphenyl)-2,3-dihydro-1-benzofuran-5-amine synthesized in Reference Example 122, the title compound was obtained in the same manner as in Reference Example 133. Yield 39%. Melting point: 87-89° C. (hexane). $[\alpha]_D^{20}$=+4.7° (c=0.5, methanol).

$^1$H-NMR (CDCl$_3$) δ: 1.00 (3H, s), 1.47 (3H, s), 1.78 (3H, s), 2.12 (3H, s), 2.18 (3H, s), 2.30 (3H, s), 2.78 (2H, br), 4.09 (1H, s), 6.83 (2H, br), 7.04 (2H, br d, J=7.4 Hz).

REFERENCE EXAMPLE 135

2-(2,3-Dimethylphenoxy)-2-methyl-1-(4-methylphenyl)propane-1-ol

To a mixture of 2,3-dimethylphenol (12.2 g, 100 mmol) and potassium carbonate (27.4 g, 200 mmol) in dimethylsulfoxide (138 mL) was added 2-bromo-1-(4-bromophenyl)-2-methylpropane-1-one (42.2 g, 175 mmol) at room temperature, and the mixture was warmed to 35° C. The mixture was stirred at the same temperature for 24 hours, poured into cold water (300 mL), and then extracted with diethyl ether. The organic layer was washed with a 4 N aqueous sodium hydroxide solution and a saturated brine, and then was dried over sodium sulfate. The solvent was concentrated under reduced pressure, and then was purified by silica gel column chromatography (ethyl acetate:hexane=1:9) to obtain 2-(2,3-dimethylphenoxy)-2-methyl-1-(4-methylphenyl)propane-1-one of oily matter. The obtained oily matter was dissolved in methanol (200 mL), sodium borohydride (3.8 g, 100 mmol) was added thereto at 0° C., and the mixture was warmed to room temperature. The oily matter was stirred at the same temperature for 1 hour, cooled to 0° C., and neutralized with 1 N hydrochloric acid, and then the solvent was distilled off under reduced pressure. The residue was extracted with ethyl acetate, and the extract solution was washed with a saturated brine, and then was dried over sodium sulfate. The solvent was distilled off under reduced pressure to obtain 17.1 g (yield 60%) of the title compound as an oily matter.

$^1$H-NMR (CDCl$_3$) δ: 1.12 (3H, s), 1.23 (3H, s), 2.19 (3H, s), 2.27 (3H, s), 2.35 (3H, s), 3.38 (1H, d, J=2.0 Hz), 4.88 (1H, d, J=2.0 Hz), 6.83-7.07 (3H, m), 7.14 (2H, d, J=8.0 Hz), 7.37 (2H, d, J=8.0 Hz).

REFERENCE EXAMPLE 136

2,2,6,7-Tetramethyl-3-(4-methylphenyl)-2,3-dihydro-1-benzofuran

To a solution of 2-(2,3-dimethylphenoxy)-2-methyl-1-(4-methylphenyl)propane-1-ol synthesized in Reference Example 135 (17.0 g, 60 mmol) in toluene (200 mL) was added trifluoromethanesulfonate (0.53 mL, 6 mmol) at 0° C., and the mixture was warmed to 50° C. The mixture was stirred at the same temperature for 30 minutes and was reacted under reflux condition for 2 hours. The reaction solution was cooled to 0° C., and then was poured into a saturated sodium hydrogen carbonate solution. The organic layer was separated, washed with a saturated brine, and dried over sodium sulfate, and the solvent then was distilled off under reduced pressure. The residue was purified by silica gel column chromatography (ethyl acetate:hexane=1:9) to obtain 9.3 g (yield 58%) of the title compound as an oily matter.

$^1$H-NMR (CDCl$_3$) δ: 0.95 (3H, s), 1.57 (3H, s), 2.16 (3H, s), 2.26 (3H, s), 2.33 (3H, s), 4.29 (1H, s), 6.66 (1H, d, J=7.6 Hz), 6.74 (1H, d, J=7.6, Hz), 6.98 (2H, d, J=8.0 Hz), 7.19 (2H, d, J=8.0 Hz).

REFERENCE EXAMPLE 137

5-Bromo-2,2,6,7-tetramethyl-3-(4-methylphenyl)-2,3-dihydro-1-benzofuran

Using 2,2,6,7-tetramethyl-3-(4-methylphenyl)-2,3-dihydro-1-benzofuran obtained in Reference Example 136, the title compound was synthesized in the same manner as in Reference Example 18. Yield 92%. Oily matter.

$^1$H-NMR (CDCl$_3$) δ: 0.95 (3H, s), 1.55 (3H, s), 2.22 (3H, s), 2.33 (3H, s), 2.34 (3H, s), 4.27 (1H, s), 6.96 (2H, d, J=8.0 Hz), 7.04 (1H, s), 7.11 (2H, d, J=8.0 Hz).

REFERENCE EXAMPLE 138

N-Benzyl-2,2,6,7-tetramethyl-3-(4-methylphenyl)-2,3-dihydro-1-benzofuran-5-amine Using 5-bromo-2,2,6,7-tetramethyl-3-(4-methylphenyl)-2,3-dihydro-1-benzofuran obtained in Reference Example 137, the title compound was synthesized in the same manner as in Reference Example 24. Yield 99%. Oily matter.

$^1$H-NMR (CDCl$_3$) δ: 0.92 (3H, s), 1.55 (3H, s), 2.09 (3H, s), 2.21 (3H, s), 2.33 (3H, s), 3.47 (2H, s), 4.17 (1H, s), 4.27 (1H, s), 6.31 (1H, s), 6.97 (2H, d, J=7.8 Hz), 7.09 (2H, d, J=7.8 Hz), 7.20-7.36 (5H, m).

REFERENCE EXAMPLE 139

2,2,6,7-Tetramethyl-3-(4-methylphenyl)-2,3-dihydro-1-benzofuran-5-amine

To a solution of N-benzyl-2,2,6,7-tetramethyl-3-(4-methylphenyl)-2,3-dihydro-1-benzofuran-5-amine obtained in Reference Example 138 (6.60 g, 17.8 mmol) in ethanol (70 mL) was added 12 N hydrochloric acid (0.1 mL) and 10%-palladium carbon (hydrous 50%, 0.33 g), and the mixture was stirred under hydrogen condition of 5 atmosphere pressure at room temperature for 2 hours. The catalyst is filtered off, and the solution was concentrated under reduced pressure. The residue was diluted with ethyl acetate, was washed with a saturated brine, and then was dried over sodium sulfate. The solvent was distilled off under reduced pressure, and the residue was purified by silica gel column chromatography (ethyl acetate:hexane=1:4) to obtain 4.42 g (yield 88%) of the title compound as an oily matter.

$^1$H-NMR (CDCl$_3$) δ: 0.94 (3H, s), 1.54 (3H, s), 2.09 (3H, s), 2.18 (3H, s), 2.33 (3H, s), 3.25 (2H, br), 4.23 (1H, s), 6.30 (1H, s), 7.00 (2H, d, J=8.1 Hz), 7.10 (2H, d, J=8.1 Hz).

REFERENCE EXAMPLE 140

N-(3-(4-Isopropylphenyl)-2,4,6,7-tetramethyl-1-benzofuran-5-yl)-3,3-dimethylbutanamide Using 3-(4-isopropylphenyl)-2,4,6,7-tetramethyl-1-benzofuran-5-amine hydrochloride obtained in Reference Example 126, the title compound was synthesized in the same manner as in Reference Example 63. Yield 24%. Melting point: 253-254° C. (ethyl acetate-hexane).

$^1$H-NMR (CDCl$_3$) δ: 1.14 (9H, s), 1.30 (6H, d, J=6.9 Hz), 1.97 (3H, s), 2.25 (3H, s), 2.30 (5H, s), 2.43 (3H, s), 2.96 (1H, septet, J=6.9 Hz), 6.62 (1H, br s), 7.23 (4H, s).

REFERENCE EXAMPLE 141

(+)-(3R)-3-(4-Isopropylphenyl)-4,6-dimethyl-2,3-dihydro-1-benzofuran-5-amine

A suspension of 3-(4-isopropylphenyl)-4,6-dimethyl-2,3-dihydro-1-benzofuran-5-amine obtained in Reference Example 32 (22.5 g, 80 mmol) and (2S, 3S)-(4'-methyl)-tartranilic acid (19.14 g, 80 mmol) in ethanol (480 mL) was heated at 85° C. for dissolution. The solution was cooled to 0° C. for 2 hours, and the precipitated crystals were taken. The crystals were washed with cold ethanol, and then were dried under reduced pressure. The obtained crystals were suspended in a 2 N aqueous sodium hydroxide solution (400 mL), which was extracted with diethyl ether. The extract was washed with a saturated sodium hydrogen carbonate solution and a saturated brine, and then was dried over sodium sulfate. The solvent was distilled off under reduced pressure to obtain 9.44 g (yield 34%) of the title compound as an oily matter. The obtained oily matter was, if necessary, crystallized with cold hexane. Melting point: 53-55° C. [α]$_D$$^{20}$=+64.0° (c=0.44, chloroform).

$^1$H-NMR (CDCl$_3$) δ: 1.21 (6H, d, J=6.9 Hz), 1.85 (3H, s), 2.18 (3H, s), 2.86 (1H, septet, J=6.9 Hz), 3.52 (2H, br), 4.34 (1H, dd, J=4.7, 8.8 Hz), 4.50 (1H, dd, J=4.7, 8.8 Hz), 4.76 (1H, t, J=8.8 Hz), 6.56 (1H, s), 7.04 (2H, d, J=8.0 Hz), 7.12 (2H, d, J=8.0 Hz).

REFERENCE EXAMPLE 142

1-(4-Isopropylphenyl)-2-(3,5-dimethylphenoxy)ethanone

To a solution of cumene (27.8 mL, 200 mmol) and aluminum chloride (32.0 g, 240 mmol) in dichloromethane (300 mL) was added bromoacetylbromide (19.1 mL, 220 mmol) at −10° C., and the mixture was stirred at the same temperature for 2 hours. The reaction solution was poured into ice-cold water, and an organic layer was separated. The organic layer was washed with a saturated sodium hydrogen carbonate solution and a saturated brine, and then was dried over sodium sulfate. The solvent was distilled off under reduced pressure, and the residue was purified by silica gel column chromatography (ethyl acetate:hexane=1:9) to obtain 2-bromo-1-(4-isopropylphenyl)ethanone of oily matter. The obtained oily matter was added to a solution of 3,5-dimethylphenol (29.3 g, 240 mmol) and potassium carbonate (33.2 g, 240 mmol) in acetone (500 mL), and the mixture then was stirred under heat and reflux for 12 hours. The reaction solution was ice-cooled and poured into cold water, which was extracted with diethyl ether.

The extract was washed with a saturated brine, and then was dried over sodium sulfate. Then, the solvent was distilled off under the reduced pressure, and the residue was purified by silica gel column chromatography (ethyl acetate:hexane=1:4). The obtained oily matter was crystallized with hexane to obtain 39.4 g (yield 75%) of the title compound. Melting point: 68-69° C.

$^1$H-NMR (CDCl$_3$) δ: 1.28 (6H, d, J=6.9 Hz), 2.27 (3H, s), 2.28 (3H, s), 2.98 (1H, septet, J=6.9 Hz), 5.22 (2H, s), 6.57 (2H, s), 6.63 (1H, s), 7.35 (2H, d, J=8.4 Hz), 7.95 (2H, d, J=8.4 Hz).

REFERENCE EXAMPLE 143

3-(4-Isopropylphenyl)-4,6-dimethylbenzofuran

A solution of 1-(4-isopropylphenyl)-2-(3,5-dimethylphenoxy)ethanone obtained in Reference Example 142 (38.1 g, 135 mmol) and Montmorillonite KSF (57.2 g) in toluene (400 mL) was heated at 95° C., and was reacted for 16 hours. The reaction solution was cooled to room temperature, and then Montmorillonite KSF was filtered off.

The solution was purified by silica gel column chromatography (ethyl acetate:hexane=1:9), and the solvent was distilled off under reduced pressure to obtain 35.6 g (yield 100%) of the title compound as an oily matter. The oily matter was, if necessary, crystallized with methanol. Melting point: 44-45° C.

$^1$H-NMR (CDCl$_3$) δ: 1.30 (6H, d, J=6.9 Hz), 2.30 (3H, s), 2.43 (3H, s), 2.96 (1H, septet, J=6.9 Hz), 6.83 (1H, s), 7.18 (1H, s), 7.25 (2H, d, J=8.6 Hz), 7.45 (2H, d, J=8.6 Hz).

REFERENCE EXAMPLE 144

3-(4-Isopropylphenyl)-4,6-dimethyl-2,3-dihydro-1-benzofuran 3-(4-Isopropylphenyl)-4,6-dimethyl-1-benzofuran (36.5 g, 135 mmol) obtained in Reference Example 143 and 10%-palladium carbon (50% hydrous, 3.7 g) were suspended in ethanol (400 mL), and reductive reaction was performed under hydrogen atmosphere of 5 atmospheric pressure at 60° C. for 6 hours. The reaction solution was cooled to room temperature, the catalyst was filtered off, and the solution was concentrated under reduced pressure. The obtained oily matter was crystallized with methanol to obtain 27.5 g (yield 77%) of the title compound. Melting point: 48-50° C.

$^1$H-NMR (CDCl$_3$) δ: 1.22 (6H, d, J=6.9 Hz), 1.92 (3H, s), 2.29 (3H, s), 2.86 (1H, septet, J=6.9 Hz), 4.35-4.53 (2H, m), 4.83 (1H, t, J=8.1 Hz), 6.47 (1H, s), 6.56 (1H, s), 7.04 (2H, d, J=8.2 Hz), 7.13 (2H, d, J=8.2 Hz).

REFERENCE EXAMPLE 145

3-(4-Methoxyphenyl)-N-(2,2,6,7-tetramethyl-3-(4-methylphenyl)-2,3-dihydro-1-benzofuran-5-yl)-propionamide Using 2,2,6,7-tetramethyl-3-(4-methylphenyl)-2,3-dihydro-1-benzofuran-5-amine obtained Reference Example 139 and 3-(4-methoxyphenyl)propionic acid, the title compound was obtained in the same manner as in Reference Example 359.

Yield 64%. Melting point: 149-150° C. (ethyl acetate-hexane).

$^1$H-NMR (CDCl$_3$) δ: 0.94 (3H, s), 1.55 (3H, s), 1.98 (3H, s), 2.15 (3H, s), 2.32 (3H, s), 2.58 (2H, d, J=7.5 Hz), 2.94 (2H, d, J=7.5 Hz), 3.73 (3H, s), 4.28 (1H, s), 6.63-6.98 (6H, m), 7.03-7.18 (4H, m).

REFERENCE EXAMPLE 146

2-Hydroxy-4,6-dimethylbenzaldehyde

A mixed solution of 3,5-dimethylphenol (20.0 g, 164 mmol), paraformaldehyde (14.8 g, 492 mmol), magnesium chloride (23.4 g, 246 mmol) and triethylamine (80 mL, 573 mmol) in acetonitrile (500 mL) was heated under reflux for 4 hours. The reaction solution was acidified with hydrochloric acid, which was extracted with diethyl ether.

The organic layer was washed with a saturated sodium hydrogen carbonate solution and a saturated brine, dried over anhydrous sodium sulfate, filtered, and then concentrated under reduced pressure. The obtained residue was purified by silica gel column chromatography (ethyl acetate:hexane=1:9) to obtain 20.8 g (yield 84%) of the title compound. Melting point: 48-49° C. (hexane).

$^1$H-NMR (CDCl$_3$) δ: 2.31 (3H, s), 2.55 (3H, s), 6.53 (1H, s), 6.62 (1H, s), 10.23 (1H, s), 11.95 (1H, s).

REFERENCE EXAMPLE 147

2-(Hydroxy(4-isopropylphenyl)methyl)-3,5-dimethylphenol

To a solution of 1-bromo-4-isopropylbenzene (3.32 g, 16.7 mmol) in THF (30 mL) was added dropwise n-butyllithium (a 1.59 M hexane solution, 9.2 mL, 14.7 mmol) under argon atmosphere at −78° C. The reaction solution was stirred for 30 minutes, a solution of 2-hydroxy-4,6-dimethylbenzaldehyde obtained in Reference Example 146 (1.0 g, 6.7 mmol) in THF (10 mL) was added dropwise thereto at −78° C., and the mixture then was stirred for 30 minutes. The reaction solution was warmed to room temperature, water was added thereto to separate the organic layer, and the aqueous layer was extracted with ethyl acetate. The combined organic layer was washed with a saturated brine, dried over anhydrous sodium sulfate, filtered, and then concentrated under reduced pressure, and the obtained residue was purified by silica gel column chromatography (ethyl acetate:hexane=1:2) to obtain 1.64 g (yield 91%) of the title compound. Melting point: 103-104° C. (ethyl acetate-hexane).

$^1$H-NMR (CDCl$_3$) δ: 1.22 (6H, d, J=6.9 Hz), 2.13 (3H, s), 2.26 (3H, s), 2.77 (1H, d, J=2.4 Hz), 2.88 (1H, septet, J=6.9 Hz), 6.14 (1H, d, J=2.4 Hz), 6.50 (1H, s), 6.62 (1H, s), 7.17 (2H, d, J=8.1 Hz), 7.28 (2H, d, J=8.1 Hz), 8.56 (1H, s).

REFERENCE EXAMPLE 148

2-(4-Isopropylbenzyl)-3,5-dimethylphenol

A mixture of 2-(hydroxy(4-isopropylphenyl)methyl)-3,5-dimethylphenol obtained in Reference Example 147 (12.3 g, 45.5 mmol) and 10%-palladium carbon (50% hydrous, 1.23 g) in acetic acid (90 mL) was heated under hydrogen atmosphere at 90° C. for 16 hours. The catalyst was removed, and the reaction solution was concentrated under reduced pressure.

The obtained residue was dissolved in ethyl acetate, washed with 1 N aqueous sodium hydroxide solution and a saturated sodium hydrogen carbonate solution, dried over anhydrous sodium sulfate, filtered, and then concentrated under reduced pressure. The obtained residue was purified by silica gel column chromatography (ethyl acetate:hexane=1:3) to obtain 10.5 g (yield 90%) of the title compound. Oily matter.

$^1$H-NMR (CDCl$_3$) δ: 1.20 (6H, d, J=6.9 Hz), 2.24 (3H, s), 2.25 (3H, s), 2.84 (1H, septet, J=6.9 Hz), 3.97 (2H, s), 4.58 (1H, s), 6.50 (1H, s), 6.62 (1H, s), 7.05-7.12 (4H, m).

REFERENCE EXAMPLE 149

2-Bromo-3,5-dimethylphenol

To a solution of 3,5-dimethylphenol (15.0 g, 123 mmol) in carbon disulfide (330 mL) was slowly added N-bromosuccinimide (21.9 g, 123 mmol) in several batches with ice-cooling, and the mixture was stirred at room temperature for 1 hour. The solvent was distilled off under reduced pressure, and the precipitated crystals were filtered and then were washed with ethyl acetate-hexane (10:1). The solution was concentrated, and the residue was purified by silica gel chromatography (ethyl-acetate:hexane=1:9) to obtain 16.3 g (yield 66%) of the title compound. Oily matter.

$^1$H-NMR (CDCl$_3$) δ: 2.24 (3H, s), 2.34 (3H, s), 5.52 (1H, s), 6.62 (1H, s), 6.68 (1H, s).

REFERENCE EXAMPLE 150

2-Bromo-6-(4-isopropylbenzyl)-3,5-dimethylphenol

Using 2-(4-isopropylbenzyl)-3,5-dimethylphenol obtained in Reference Example 148, the title compound was synthesized in the same manner as in Reference Example 149.

Yield 75%. Oily matter.

$^1$H-NMR (CDCl$_3$) δ: 1.21 (6H, d, J=6.9 Hz), 2.20 (3H, s), 2.34 (3H, s), 2.85 (1H, septet, J=6.9 Hz), 4.04 (2H, s), 5.66 (1H, s), 6.68 (1H, s), 7.09 (4H, s).

REFERENCE EXAMPLE 151

2-Bromo-5-isopropylphenol

2-Bromo-3-isopropylphenol

To a solution of 3-isopropylphenol (10.0 g, 73.4 mmol) in carbon disulfide (200 mL) was slowly added N-bromosuccinimide (13.1 g, 73.4 mmol) with ice-cooling, and the mixture was stirred for 1 hour. The reaction solution was stirred at room temperature for 1 hour, and then water was added thereto, which was extracted with ethyl acetate.

The combined organic layer was washed with water and a saturated brine, dried over anhydrous sodium sulfate, and then concentrated under reduced pressure. The obtained residue was purified by silica gel column chromatography (ethyl acetate:hexane=15:85) to obtain a mixture of 2-bromo-5-isopropylphenol and 2-bromo-3-isopropylphenol (3:1) 11.0 g (yield 70%).

REFERENCE EXAMPLE 152

1-Bromo-4-isopropyl-2-methoxybenzene

2-Bromo-1-isopropyl-3-methoxybenzene

A mixed solution of the mixture of 2-bromo-5-isopropylphenol obtained in Reference Example 151 and 2-bromo-3- isopropylphenol (10.0 g, 51.3 mmol), methyl iodide (7.28 g, 51.3 mmol) and potassium carbonate (7.08 g, 51.3 mmol) in acetone (200 mL) was heated under reflux under argon atmosphere for 8 hours. Water was added to the reaction solution, which was extracted with ethyl acetate.

The combined organic layer was washed with a saturated brine, dried over anhydrous sodium sulfate, and then concentrated under reduced pressure to obtain a mixture of 1-bromo-4-isopropyl-2-methoxybenzene and 2-bromo-1-isopropyl-3-methoxybenzene 9.81 g (yield 83%).

REFERENCE EXAMPLE 153

Ethyl 2-(2-(4-isopropylbenzyl)-3,5-dimethylphenoxy)-2-methylpropanoate

A solution of 2-(4-isopropylbenzyl)-3,5-dimethylphenol obtained in Reference Example 148 (5.0 g, 19.7 mmol), 2-bromo isobutyric acid ethyl (11.5 g, 59.0 mmol) and potassium carbonate (8.13 g, 59.0 mmol) in dimethylsulfoxide (20 mL) was stirred at 50° C. for 40 hours under argon atmosphere. Water was added to the reaction solution, which was extracted with ethyl acetate. The combined organic layer was washed with a saturated brine, dried over anhydrous sodium sulfate, and then concentrated under reduced pressure. The obtained residue was purified by silica gel column chromatography (ethyl acetate:hexane=1:4) to obtain 6.64 g (yield 92%) of the title compound. Oily matter.

$^1$H-NMR (CDCl$_3$) δ: 1.18-1.28 (9H, m), 1.47 (6H, s), 2.19 (3H, s), 2.22 (3H, s), 2.83 (1H, septet, J=6.9 Hz), 3.97 (2H, s), 4.23 (2H, q, J=6.9 Hz), 6.33 (1H, s), 6.61 (1H, s), 7.07 (4H, s).

REFERENCE EXAMPLE 154

Ethyl (2-(4-isopropylbenzyl)-3,5-dimethylphenoxy)acetate

Using 2-(4-isopropylbenzyl)-3,5-dimethylphenol obtained in Reference Example 148 and ethyl bromoacetate, the title compound was synthesized in the same manner as in Reference Example 153. Yield 95%. Oily matter.

$^1$H-NMR (CDCl$_3$) δ: 1.20 (6H, d, J=6.9 Hz), 1.27 (3H, t, J=7.5 Hz), 2.22 (3H, s), 2.27 (3H, s), 2.83 (1H, septet, J=6.9 Hz), 4.04 (2H, s), 4.24 (2H, q, J=7.5 Hz), 4.58 (2H, s), 6.46 (1H, s), 6.66 (1H, s), 7.03-7.13 (4H, m).

REFERENCE EXAMPLE 155

Ethyl (2,3,5-trimethylphenoxy)acetate

Using 2,3,5-trimethylphenol and ethyl bromoacetate, the title compound was synthesized in the same manner as in Reference Example 153. Yield: quantitative. Oily matter.

$^1$H-NMR (CDCl$_3$) δ: 1.30 (3H, t, J=7.5 Hz), 2.17 (3H, s), 2.23 (3H, s), 2.36 (3H, s), 4.26 (2H, q, J=7.5 Hz), 4.60 (2H, s), 6.42 (1H, s), 6.65 (1H, s).

REFERENCE EXAMPLE 156

2-(2-(4-Isopropylbenzyl)-3,5-dimethylphenoxy)-2-methylpropanoic acid

A mixed solution of ethyl 2-(2-(4-isopropylbenzyl)-3,5-dimethylphenoxy)-2-methylpropanoate obtained in Reference Example 153 (6.65 g, 18.1 mmol) and a 8 N aqueous sodium hydroxide solution (4.5 mL) in methanol (40 mL)-THF (20 mL) was stirred at room temperature for 16 hours. The reaction solution was acidified with hydrochloric acid, and the aqueous layer was extracted with ethyl acetate. The organic layer was dried over anhydrous sodium sulfate, filtered, and then concentrated under reduced pressure to obtain 5.59 g (yield 91%) of the title compound. Oily matter.

$^1$H-NMR (CDCl$_3$) δ: 1.20 (6H, d, J=6.9 Hz), 1.49 (6H, s), 2.22 (3H, s), 2.26 (3H, s), 2.84 (1H, septet, J=6.9 Hz), 3.97 (2H, s), 6.50 (1H, s), 6.71 (1H, s), 7.01 (2H, d, J=8.4 Hz), 7.09 (2H, d, J=8.4 Hz), 1H unidentified.

REFERENCE EXAMPLE 157

(2-(4-Isopropylbenzyl)-3,5-dimethylphenoxy)acetic acid

Using ethyl (2-(4-isopropylbenzyl)-3,5-dimethylphenoxy)acetate obtained in Reference Example 154, the title compound was synthesized in the same manner as in Reference Example 156. Yield 75%. Melting point: 104-105° C. (ethyl acetate-hexane).

$^1$H-NMR (CDCl$_3$) δ: 1.20 (6H, d, J=6.9 Hz), 2.26 (3H, s), 2.30 (3H, s), 2.84 (1H, septet, J=6.9 Hz), 4.02 (2H, s), 4.57 (2H, s), 6.48 (1H, s), 6.73 (1H, s), 7.04 (2H, d, J=8.1 Hz), 7.10 (2H, d, J=8.1 Hz), 1H unidentified.

REFERENCE EXAMPLE 158

(2,3,5-Trimethylphenoxy)acetic acid

Using ethyl (2,3,5-dimethylphenoxy)acetate obtained in Reference Example 155, the title compound was synthesized in the same manner as in Reference Example 156. Yield 92%. Melting point: 129-130° C. (ethyl acetate-hexane).

$^1$H-NMR (CDCl$_3$) δ: 2.16 (3H, s), 2.24 (3H, s), 2.27 (3H, s), 4.67 (2H, s), 6.44 (1H, s), 6.68 (1H, s), 1H unidentified

REFERENCE EXAMPLE 159

1-(2-(4-Isopropylbenzyl)-3,5-dimethylphenoxy)acetone

A mixed solution of 2-(4-isopropylbenzyl)-3,5-dimethylphenol obtained in Reference Example 148 (1.0 g, 3.93 mmol), potassium carbonate (1.30 g, 9.44 mmol), chloroacetone (436 mg, 4.72 mmol) and potassium iodide (100 mg) in acetone (15 mL) was heated under reflux for 16 hours. Water was added to the reaction solution, which was extracted with ethyl acetate. The combined organic layer was washed with a saturated brine, dried over anhydrous sodium sulfate, filtered, and then concentrated under reduced pressure, and the obtained residue was purified by silica gel column chromatography (ethyl acetate:hexane=1:4) to obtain 888 mg (yield 73%) of the title compound. Oily matter.

$^1$H-NMR (CDCl$_3$) δ: 1.20 (6H, d, J=6.9 Hz), 2.10 (3H, s), 2.24 (3H, s), 2.28 (3H, s), 2.80-2.90 (1H, septet, J=6.9 Hz), 4.04 (2H, s), 4.42 (2H, s), 6.40 (1H, s), 6.68 (1H, s), 7.02 (2H, d, J=8.1 Hz), 7.07 (2H, d, J=8.1 Hz).

REFERENCE EXAMPLE 160)

1-(2-(4-Isopropylbenzyl)-3,5-dimethylphenoxy)butan-2-one

Using 2-(4-isopropylbenzyl)-3,5-dimethylphenol obtained in Reference Example 148 and 1-bromobutan-2-one, the title compound was synthesized in the same manner as in Reference Example 159. Yield 88%. Oily matter.

¹H-NMR (CDCl₃) δ: 0.97 (3H, t, J=7.2 Hz), 1.20 (6H, d, J=6.9 Hz), 2.45 (3H, s), 2.88 (3H, s), 2.42 (2H, q, J=7.2 Hz), 2.84 (1H, septet, J=6.9 Hz), 4.05 (2H, s), 4.45 (2H, s), 6.42 (1H, s), 6.69 (1H, s), 7.04 (2H, d, J=8.1 Hz), 7.08 (2H, d, J=8.1 Hz).

REFERENCE EXAMPLE 161

1-(3-Bromophenyl)-2-(2,3,5-trimethylphenoxy)ethanone

Using 2,3,5-trimethylphenol and 2-bromo-1-(3-bromophenyl)ethanone, the title compound was synthesized in the same manner as in Reference Example 159. Yield 52%. Oily matter.

¹H-NMR (CDCl₃) δ: 2.16 (3H, s), 2.24 (3H, s), 2.26 (3H, s), 5.16 (2H, s), 6.46 (1H, s), 6.66 (1H, s), 7.37 (1H, t, J=8.0 Hz), 7.70-7.76 (1H, m), 7.91-7.96 (1H, m), 8.15-8.17 (1H, m).

REFERENCE EXAMPLE 162

1-(3-Methoxyphenyl)-2-(2,3,5-trimethylphenoxy)ethanone

Using 2,3,5-trimethylphenol and 2-bromo-1-(3-methoxyphenyl)ethanone, the title compound was synthesized in the same manner as in Reference Example 159. Yield 88%. Oily matter.

¹H-NMR (CDCl₃) δ: 2.18 (3H, s), 2.23 (3H, s), 2.25 (3H, s), 3.86 (3H, s), 5.22 (2H, s), 6.46 (1H, s), 6.65 (1H, s), 7.13-7.20 (1H, m), 7.40 (1H, t, J=7.5 Hz), 7.53-7.61 (2H, m).

REFERENCE EXAMPLE 163

1-(4-Methylphenyl)-2-(2,3,5-trimethylphenoxy)ethanone

Using 2,3,5-trimethylphenol and 2-bromo-1-(4-methylphenyl)ethanone, the title compound was synthesized in the same manner as in Reference Example 159. Yield 75%. Melting point: 94-95° C. (methanol).

¹H-NMR (CDCl₃) δ: 2.17 (3H, s), 2.23 (3H, s), 2.25 (3H, s), 2.42 (3H, s), 5.18 (2H, s), 6.45 (1H, s), 6.63 (1H, s), 7.27 (2H, d, J=8.1 Hz), 7.91 (2H, d, J=8.1 Hz).

REFERENCE EXAMPLE 164

2-Bromo-1-(4-isopropylphenyl)ethanone

To a solution of cumene (42 g, 350 mmol) and aluminum chloride (56.0 g, 420 mmol) in dichloromethane (500 mL) was added bromoacetylbromide (33.5 mL, 385 mmol) at −40° C. for 40 minutes, and the mixture was stirred until it was warmed to −10° C. for 2 hours. The reaction solution was poured into ice-cold water to separate the organic layer. The organic layer was washed with a saturated sodium hydrogen carbonate solution and a saturated brine, and then was dried over sodium sulfate. The solvent was distilled off under reduced pressure to obtain 84 g (yield 99%) of the title compound. Oily matter.

¹H-NMR (CDCl₃) δ: 1.28 (6H, d, J=6.9 Hz), 2.98 (1H, septet, J=6.9 Hz), 4.44 (2H, s), 7.34 (2H, d, J=8.4 Hz), 7.92 (2H, d, J=8.4 Hz).

REFERENCE EXAMPLE 165

4-Bromo-1-(4-isopropylphenyl)-2-(2,3,5-trimethylphenoxy)ethanone

Using 2,3,5-trimethylphenol, 4-bromo-2,3,5-trimethylphenol was synthesized in the same manner as in Reference Example 23. Using this compound and 2-bromo-1-(4-isopropylphenyl)ethanone obtained in Reference Example 164, the title compound was synthesized in the same manner as in Reference Example 159. Yield 51%. Melting point: 71-72° C. (ethyl acetate-hexane).

¹H-NMR (CDCl₃) δ: 1.28 (6H, d, J=6.6 Hz), 2.28 (3H, s), 2.35 (3H, s), 2.40 (3H, s), 2.98 (1H, septet, J=6.6 Hz), 5.23 (2H, s), 6.55 (1H, s), 7.35 (2H, d, J=8.1 Hz), 7.94 (2H, d, J=8.1 Hz).

REFERENCE EXAMPLE 166

1-((2-(4-Isopropylbenzyl)-3,5-dimethylphenoxy)acetyl)-2-methylaziridine

To a solution of (2-(4-isopropylbenzyl)-3,5-dimethylphenoxy)acetic acid obtained in Reference Example 157 (9.00 g, 28.8 mmol) in THF (90 mL) was added dropwise oxalylchloride (3.77 mL, 43.2 mmol) with ice-cooling, and was then added DMF (four drops), and then the mixture was stirred for 30 minutes. The reaction solution was stirred at room temperature for 30 minutes, and the solvent was distilled off under reduced pressure. To a solution of propyleneimine (1.97 g, 34.6 mmol) and triethylamine (4.82 mL, 34.6 mmol) in THF (80 mL) was added dropwise the obtained solution of acid chloride in THF (100 mL) with ice-cooling. The mixture was stirred for 30 minutes, and then was warmed to room temperature, and water was added to the reaction solution, which was extracted with ethyl acetate. The combined organic layer was washed with a saturated brine, dried over sodium sulfate, and then concentrated under reduced pressure. The obtained residue was purified by silica gel column chromatography (ethyl acetate:hexane=2:3) to obtain 10.0 g (yield 99%) of the title compound. Oily matter.

¹H-NMR (CDCl₃) δ: 1.15 (3H, d, J=5.7 Hz), 1.20 (6H, d, J=6.9 Hz), 1.86 (1H, d, J=3.6 Hz), 2.23 (3H, s), 2.26-2.30 (4H, m), 2.40-2.50 (1H, m), 2.84 (1H, septet, J=6.9 Hz), 4.05 (2H, s), 4.56 (1H, d, J=15.6 Hz), 4.63 (1H, d, J=15.6 Hz), 6.53 (1H, s), 6.69 (1H, s), 7.05-7.10 (4H, m).

REFERENCE EXAMPLE 167

(2,3,5-Trimethylphenoxy)acetyl)-2-methylaziridine

Using (2,3,5-trimethylphenoxy)acetic acid obtained in Reference Example 158, the title compound was obtained in the same manner as in Reference Example 166. Yield 77%. Oily matter.

¹H-NMR (CDCl₃) δ: 1.32 (3H, d, J=5.4 Hz), 2.03-2.05 (1H, m), 2.18 (3H, s), 2.24 (3H, s), 2.26 (3H, s), 2.45 (1H, d, J=5.4 Hz), 2.60-2.69 (1H, m), 4.63 (2H, s), 6.46 (1H, s), 6.65 (1H, s).

REFERENCE EXAMPLE 168

1-(5-Methylpyridine-2-yl)-2-(2,3,5-trimethylphenoxy)ethanone

To a solution of 2-bromo-5-methylpyridine (958 mg, 5.57 mmol) in THF (3 mL)-ether (10 ml) was added dropwise n-butyllithium (a 1.56 M hexane solution, 3.9 mL, 6.13 mmol) at −78° C. under argon atmosphere. The reaction solution was stirred for 30 minutes, to which a solution of (2,3,5-trimethylphenoxy)acetyl)-2-methylaziridine obtained in Reference Example 167 (1.43 g, 6.13 mmol) in THF (5 ml) was added dropwise at the same temperature. The reaction solution was warmed to room temperature, ice was added thereto, which was extracted with ethyl acetate. The combined organic layer was washed with a saturated brine, dried over sodium sulfate, and then concentrated under reduced pressure. The obtained residue was purified by silica gel column chromatography (ethyl acetate:hexane 1:4) to obtain 795 mg (yield 53%) of the title compound. Melting point: 94-95° C. (methanol).

$^1$H-NMR (CDCl$_3$) δ: 2.25 (9H, s), 2.45 (3H, s), 5.60 (2H, s), 6.52 (1H, s), 6.64 (1H, s), 7.65-7.70 (1H, m), 8.00 (1H, d, J=7.8 Hz), 8.49-8.51 (1H, m).

REFERENCE EXAMPLE 169

1-(2-(4-Isopropylbenzyl)-3,5-dimethylphenoxy)pentan-2-one

To a solution of 1-((2-(4-isopropylbenzyl)-3,5-dimethylphenoxy)acetyl)-2-methylaziridine obtained in Reference Example 166 (1.0 g, 2.85 mmol) in THF (20 mL) was added dropwise n-propylmagnesium bromide (a 2.0 M THF solution, 1.43 mL, 2.85 mmol) under argon atmosphere with ice-cooling, and the mixture was stirred for 30 minutes. The reaction solution was warmed to room temperature, water was added thereto, which was extracted with ethyl acetate.

The organic layer was dried over anhydrous sodium sulfate, and then was concentrated under reduced pressure. The obtained residue was purified by silica gel column chromatography (ethyl acetate:hexane=1:4) to obtain 920 mg (yield 95%) of the title compound. Oily matter.

$^1$H-NMR (CDCl$_3$) δ: 0.83 (3H, t, J=7.5 Hz), 1.20 (6H, d, J=6.9 Hz), 1.40-1.59 (2H, m), 2.25 (3H, s), 2.29 (3H, s), 2.39 (2H, t, J=7.5 Hz), 2.84 (1H, septet, J=6.9 Hz), 4.05 (2H, s), 4.43 (2H, s), 6.41 (1H, s), 6.69 (1H, s), 7.03 (2H, d, J=8.4 Hz), 7.08 (2H, d, J=8.4 Hz).

REFERENCE EXAMPLE 170

1-(2-(4-Isopropylbenzyl)-3,5-dimethylphenoxy-3-methylbutan-2-one

Using 1-((2-(4-isopropylbenzyl)-3,5-dimethylphenoxy)acetyl)-2-methylaziridine obtained in Reference Example 166 and isopropylmagnesium bromide, the title compound was synthesized in the same manner as in Reference Example 169. Yield 24%. Oily matter.

$^1$H-NMR (CDCl$_3$) δ: 0.98 (6H, d, J=7.8 Hz), 1.20 (6H, d, J=6.9 Hz), 2.25 (3H, s), 2.29 (3H, s), 2.75-2.89 (2H, m), 4.05 (2H, s), 4.51 (2H, s), 6.42 (1H, s), 6.69 (1H, s), 7.03 (2H, d, J=8.1 Hz), 7.08 (2H, d, J=8.1 Hz).

REFERENCE EXAMPLE 171

1-(2-Isopropyl-6-methoxyphenyl)-2-(2,3,5-trimethylphenoxy)ethanone 1-(4-Isopropyl-2-methoxyphenyl)-2-(2,3,5-trimethylphenoxy)ethanone To a solution of the mixture of 1-bromo-4-isopropyl-2-methoxybenzene and 2-bromo-1-isopropyl-3-methoxybenzene obtained in Reference Example 152 (5.73 g, 25.0 mmol) in THF (100 mL) was added dropwise n-butyllithium (a 1.60 M hexane solution, 17.2 mL, 27.5 mmol) under argon atmosphere at −70° C. The reaction solution was stirred for 30 minutes, and then to which a solution of the 2-methyl-1-((2,3,5-(trimethylphenoxy)acetyl)aziridine obtained in Reference Example 167 (5.84 g, 25.0 mmol) in THF (20 mL) was added dropwise, and the mixture was stirred at −70° C. for 30 minutes, and then was warmed to room temperature. Water was added to the reaction solution, which was extracted with ethyl acetate, and the organic layer was dried over anhydrous sodium sulfate, and then concentrated under reduced pressure. The obtained residue was purified by silica gel column chromatography (ethyl acetate:hexane=1:4) to obtain 6.27 g (yield 77%) of a mixture of the title compounds.

REFERENCE EXAMPLE 172

4-Hydroxy-2-methyl-1-naphthyl acetate

To a solution of 4-(acetyloxy)-2-methyl-1-naphthyl acetate (25 g, 96.8 mmol) in methanol (300 mL) was added potassium carbonate (58.1 g, 420 mmol), and the mixture was stirred under argon atmosphere at room temperature for 15 minutes. Water was poured into the mixture, which was neutralized with hydrochloric acid and then extracted with ethyl acetate. The extract was washed with a saturated brine and dried over sodium sulfate, and the solvent was distilled off under reduced pressure to obtain 21 g (yield: quantitative) of the title compound. Oily matter.

$^1$H-NMR (CDCl$_3$) δ: 2.19 (3H, s), 2.48 (3H, s), 5.90 (1H, br s), 6.43 (1H, s), 7.34-7.51 (2H, m), 7.63 (1H, d, J=8.4 Hz), 8.00 (1H, d, J=9.6 Hz).

REFERENCE EXAMPLE 173

3-Methyl-5,6,7,8-tetrahydro-1-naphthalenyl acetate

To a suspension of sodium hydride (a 60% liquid paraffin dispersion, 1.8 g, 40 mmol) in DMF (60 mL) was added triethyl 3-methyl-4-phosphonocrotonate (11 g, 41.6 mmol) at 0° C., and the mixture was stirred at room temperature for 1 hour. To the reaction solution was added cyclohexanone (3.93 g, 40 mmol), and the mixture was stirred for 3 hours. Water was added to the reaction solution and the product was extracted with diisopropyl ether. The combined extract was washed with water, dried over magnesium sulfate, and then concentrated under reduced pressure to obtain oily crude resultant product of ethyl 4-cyclohexylidene-3-methyl-2-butenoate. To a mixed solution of this compound in THF (160 mL) and methanol (40 mL) was added a 12 N aqueous sodium hydroxide solution (4.0 mL) at room temperature, and the mixture was stirred for 16 hours, and then was concentrated under reduced pressure. To the residue was added water and hydrochloric acid, and the mixture was acidified, which was extracted with ethyl acetate. The organic layer was washed with water, and then was dried over anhydrous sodium sulfate. The solvent was distilled off under reduced pressure to obtain the crude resultant product of 4-cyclohexylidene-3-methyl-2-butenoic acid. To a mixture of this compound (6.1 g, 33.8 mmol) in acetic acid (150 mL) was added sodium acetate (12 g, 33.8 mmol) at room temperature, and the mixture was heated under reflux under argon atmosphere for 24 hours. The solvent was concentrated under reduced pressure, water was added to the residue, which was extracted with ethyl acetate, and the organic layer was washed with a saturated sodium hydrogen carbonate solution and water, dried over anhydrous sodium sulfate, and then concentrated under reduced pressure. The obtained residue was purified by silica gel column chromatography (ethyl acetate:hexane=1:10) to obtain 5.1 g (yield 63%) of the title compound. Oily matter.

$^1$H-NMR (CDCl$_3$) δ: 1.68-1.87 (4H, m), 2.27 (3H, s), 2.29 (3H, s), 2.44-2.58 (2H, m), 2.68-2.79 (2H, m), 6.64 (1H, s), 6.78 (1H, s).

REFERENCE EXAMPLE 174

6-Methyl-2,3-dihydro-1H-inden-4-yl acetate

Using cyclopentanone, the title compound was synthesized in the same manner as in Reference Example 173.

Yield 21%. Oily matter.

$^1$H-NMR (CDCl$_3$) δ: 2.00-2.14 (2H, m), 2.28 (3H, s), 2.31 (3H, s), 2.73 (2H, t, J=7.5 Hz), 2.90 (2H, t, J=7.5 Hz), 6.65 (1H, s), 6.91 (1H, s).

REFERENCE EXAMPLE 175

3-Methyl-5,6,7,8-tetrahydro-1-naphtalenol

To a mixed solution of 3-methyl-5,6,7,8-tetrahydro-1-naphthalenyl acetate synthesized in Reference Example 173 (5.1 g, 25.1 mmol) in THF (120 mL) and methanol (30 mL) was added 12 N aqueous sodium hydroxide solution (2.5 mL) at room temperature, and the mixture was stirred for 30 minutes, and then concentrated under reduced pressure. Water and hydrochloric acid were added to the residue, and the mixture was acidified, which was extracted with ethyl acetate. The organic layer was washed with water and a saturated brine, and then was dried over anhydrous sodium sulfate. The solvent was distilled off under reduced pressure, and the obtained residue was crystallized with ethyl acetate-hexane to obtain 4.1 g (yield 99%) of the title compound. Melting point: 95-96° C. (hexane-ethyl acetate).

$^1$H-NMR (CDCl$_3$) δ: 1.68-1.87 (4H, m), 2.23 (3H, s), 2.58 (2H, t, J=6.0 Hz), 2.70 (2H, t, J=6.0 Hz), 4.67 (1H, br s), 6.42 (1H, s), 6.50 (1H, s).

REFERENCE EXAMPLE 176

6-Methyl-4-indanol

Using 6-methyl-2,3-dihydro-1H-inden-4-yl acetate synthesized in Reference Example 174, the title compound was synthesized in the same manner as in Reference Example 175. Yield 81%. Melting point: 82-83° C. (hexane-ethyl acetate).

$^1$H-NMR (CDCl$_3$) δ: 2.02-2.14 (2H, m), 2.27 (3H, s), 2.80 (2H, t, J=7.5 Hz), 2.87 (2H, t, J=7.5 Hz), 4.62 (1H, br s), 6.43 (1H, s), 6.65 (1H, s).

REFERENCE EXAMPLE 177

2-(3,4,5-Trimethylphenoxy)-1-(4-isopropylphenyl) ethanone

2-Bromo-1-(4-isopropylphenyl)ethanone obtained in Reference Example 164 (20 g, 82.9 mmol) and 3,4,5-trimethylphenol (10.3 g, 75.4 mmol) were added to a solution of potassium carbonate (12.5 g, 90.5 mmol) in acetonitrile solution (200 mL), and mixture was stirred with heating under reflux for 6 hours. The reaction solution was ice-cooled, was poured into cold water, which was extracted with ethyl acetate. The extract was washed with a saturated brine, and then was dried over sodium sulfate. Then, the solvent was distilled off under reduced pressure, and the residue was purified by silica gel column chromatography (ethyl acetate: hexane=1:10). The obtained oily matter was crystallized from hexane-ethyl acetate to obtain 21.5 g (yield 96%) of the title compound. Melting point: 96-98° C.

$^1$H-NMR (CDCl$_3$) δ: 1.28 (6H, d, J=6.9 Hz), 2.09 (3H, s), 2.23 (6H, s), 2.97 (1H, septet, J=6.9 Hz), 5.19 (2H, s), 6.61 (2H, s), 7.33 (2H, d, J=8.4 Hz), 7.93 (2H, d, J=8.4 Hz).

REFERENCE EXAMPLE 178

4-(2-(4-Isopropylphenyl)-2-oxoethoxy)-2-methyl-1-naphthyl acetate

Using 4-hydroxy-2-methyl-1-naphthyl acetate synthesized in Reference Example 172, the title compound was synthesized in the same manner as in Reference Example 177. Yield 65%. Melting point: 105-106° C. (methanol).

$^1$H-NMR (CDCl$_3$) δ: 1.28 (6H, d, J=6.9 Hz), 2.27 (3H, s), 2.45 (3H, s), 2.98 (1H, septet, J=6.9 Hz), 5.36 (2H, s), 6.60 (1H, s), 7.35 (2H, d, J=8.1 Hz), 7.40-7.56 (2H, m), 7.66 (1H, d, J=8.7 Hz), 7.99 (2H, d, J=8.1 Hz), 8.30 (1H, d, J=8.7 Hz).

REFERENCE EXAMPLE 179

1-(4-Isopropylphenyl)-2-((3-methyl-5,6,7,8-tetrahydro-1-naphthalenyl)oxy)ethanone Using 3-methyl-5,6,7,8-tetrahydro-1-naphtalenol synthesized in Reference Example 175, the title compound was synthesized in the same manner as in Reference Example 177. Yield 65%. Oily matter.

$^1$H-NMR (CDCl$_3$) δ: 1.28 (6H, d, J=6.9 Hz), 1.65-1.82 (4H, m), 2.25 (3H, s), 2.62-2.75 (4H, m), 2.98 (1H, septet, J=6.9 Hz), 5.20 (2H, s), 6.39 (1H, s), 6.55 (1H, s), 7.33 (2H, d, J=8.1 Hz), 7.95 (2H, d, J=8.1 Hz).

REFERENCE EXAMPLE 180

1-(4-Isopropylphenyl)-2-((6-methyl-2,3-dihydro-1H-inden-4-yl) oxy)ethanone

Using 6-methyl-4-indanol synthesized in Reference Example 176, the title compound was synthesized in the same manner as in Reference Example 177. Yield 91%. Melting point: 68-69° C. (hexane-ethyl acetate).

$^1$H-NMR (CDCl$_3$) δ: 1.28 (6H, d, J=6.9 Hz), 1.65-1.82 (2H, quintet, J=7.5 Hz), 2.27 (3H, s), 2.82-3.05 (5H, m), 5.22 (2H, s), 6.38 (1H, s), 6.70 (1H, s), 7.34 (2H, d, J=8.4 Hz), 7.96 (2H, d, J=8.4 Hz).

REFERENCE EXAMPLE 181

2-((3,5-Dimethylphenyl)thio)-1-(4-isopropylphenyl) ethanone

Using 3,5-dimethylthiophenol, the title compound was synthesized in the same manner as in Reference Example 177.

Yield 81%. Melting point: 46-47° C. (methanol).
$^1$H-NMR (CDCl$_3$) δ: 1.27 (6H, d, J=6.9 Hz), 2.26 (6H, s), 2.97 (1H, septet, J=6.9 Hz), 4.24 (2H, s), 6.85 (1H, s), 7.01 (2H, s), 7.31 (2H, d, J=8.1 Hz), 7.88 (2H, d, J=8.1 Hz).

REFERENCE EXAMPLE 182

7-(4-Isopropylbenzyl)-3,4,6-trimethyl-1-benzofuran

Using 1-(2-(4-isopropylbenzyl)-3,5-dimethylphenoxy)acetone obtained in Reference Example 159, the title compound was obtained in the same manner as in Reference 143. Yield 76%. Melting point: 106-107° C. (ethyl acetate-hexane).
$^1$H-NMR (CDCl$_3$) δ: 1.19 (6H, d, J=6.9 Hz), 2.30 (3H, s), 2.36 (3H, s), 2.58 (3H, s), 2.80-2.90 (1H, septet, J=6.9 Hz), 4.19 (2H, s), 6.79 (1H, s), 7.07 (4H, s), 7.29 (1H, s).

REFERENCE EXAMPLE 183

3-Ethyl-7-(4-isopropylbenzyl)-4,6-dimethyl-1-benzofuran

Using 1-(2-(4-isopropylbenzyl)-3,5-dimethylphenoxy)butan-2-one obtained in Reference Example 160, the title compound was obtained in the same manner as in Reference Example 143. Yield 98%. Melting point: 62-64° C. (diisopropyl ether-methanol).
$^1$H-NMR (CDCl$_3$) δ: 1.19 (6H, d, J=6.6 Hz), 1.31 (3H, t, J=7.6 Hz), 2.31 (3H, s), 2.76 (3H, s), 2.77-2.89 (3H, m), 4.19 (2H, s), 6.79 (1H, s), 7.07 (4H, s), 7.29 (1H, s).

REFERENCE EXAMPLE 184

7-(4-Isopropylbenzyl)-4,6-dimethyl-3-propyl-1-benzofuran

Using 1-(2-(4-isopropylbenzyl)-3,5-dimethylphenoxy)pentan-2-one obtained in Reference Example 169, the title compound was obtained in the same manner as in Reference Example 143. Yield 92%. Melting point: 89-90° C. (methanol).
$^1$H-NMR (CDCl$_3$) δ: 1.03 (3H, t, J=7.5 Hz), 1.19 (6H, d, J=6.9 Hz), 1.70 (2H, m), 2.31 (3H, s), 2.57 (3H, s), 2.74 (2H, t, J=7.5 Hz), 2.83 (1H, septet, J=6.9 Hz), 4.20 (2H, s), 6.80 (1H, s), 7.08 (4H, s), 7.30 (1H, s).

REFERENCE EXAMPLE 185

3-Isopropyl-7-(4-isopropylbenzyl)-4,6-dimethyl-1-benzofuran

Using 1-(2-(4-isopropylbenzyl)-3,5-dimethylphenoxy-3-methylbutan-2-one obtained in Reference Example 170, the title compound was synthesized in the same manner as in Reference Example 143. Yield 87%. Oily matter.
$^1$H-NMR (CDCl$_3$) δ: 1.19 (6H, d, J=6.9 Hz), 1.33 (6H, d, J=6.9 Hz), 2.32 (3H, s), 2.59 (3H, s), 2.83 (1H, septet, J=6.9 Hz), 3.28 (1H, septet, J=6.9 Hz), 4.20 (2H, s), 6.81 (1H, s), 7.08 (4H, s), 7.30 (1H, s).

REFERENCE EXAMPLE 186

3-(3-Bromophenyl)-4,6,7-trimethyl-1-benzofuran

Using 1-(3-bromophenyl)-2-(2,3,5-trimethylphenoxy)ethanone obtained in Reference Example 161, the title compound was synthesized in the same manner as in Reference Example 143. Yield 82%. Oily matter.
$^1$H-NMR (CDCl$_3$) δ: 2.19 (3H, s), 2.36 (3H, s), 2.43 (3H, s), 6.84 (1H, s), 7.28 (1H, t, J=8.1 Hz), 7.35-7.39 (1H, m), 7.48-7.53 (2H, m), 7.59-7.60 (1H, m).

REFERENCE EXAMPLE 187

3-(3-Methoxyphenyl)-4,6,7-trimethyl-1-benzofuran

Using 1-(3-methoxyphenyl)-2-(2,3,5-trimethylphenoxy)ethanone obtained in Reference Example 162, the title compound was synthesized in the same manner as in Reference Example 143. Yield 82%. Oily matter.
$^1$H-NMR (CDCl$_3$) δ: 2.21 (3H, s), 2.36 (3H, s), 2.43 (3H, s), 3.83 (3H, s), 6.84 (1H, s), 6.90-7.04 (3H, m), 7.32 (1H, t, J=7.5 Hz), 7.51 (1H, s).

REFERENCE EXAMPLE 188

3-(4-Isopropyl-2-methoxyphenyl)-4,6,7-trimethyl-1-benzofuran

A mixed solution of the mixture of 1-(2-isopropyl-6-methoxyphenyl)-2-(2,3,5-trimethylphenoxy)ethanone and 1-(4-isopropyl-2-methoxyphenyl)-2-(2,3,5-trimethylphenoxy)ethanone obtained in Reference Example 171 (6.27 g, 19.2 mmol) and Montmorillonite KSF (9.40 g) in toluene (100 mL) was stirred under argon atmosphere at 90° C. for 5 hours. The reaction solution was filtered through celite, and the filtrate was concentrated under reduced pressure. The residue was purified by silica gel chromatography (ethyl acetate hexane=15:85) to obtain 2.34 g (yield 40%) of the title compound. Oily matter.
$^1$H-NMR (CDCl$_3$) δ: 1.31 (6H, d, J=6.9 Hz), 2.10 (3H, s), 2.34 (3H, s), 2.41 (3H, s), 3.00 (1H, septet, J=6.9 Hz), 3.76 (3H, s), 6.77-6.80 (2H, m), 6.83-6.86 (1H, m), 7.17 (1H, d, J=7.8 Hz), 7.44 (1H, s).

REFERENCE EXAMPLE 189

1-(4-Bromo-2-(4-isopropylbenzyl)-3,5-dimethylphenoxy)acetone

Using 1-(2-(4-isopropylbenzyl)-3,5-dimethylphenoxy)acetone obtained in Reference Example 159, the title compound was synthesized in the same manner as in Reference Example 23. Yield 73%. Melting point: 93-94° C. (methanol-THF).
$^1$H-NMR (CDCl$_3$) δ: 1.20 (6H, d, J=6.9 Hz), 2.12 (3H, s), 2.39 (6H, s), 2.84 (1H, septet, J=6.9 Hz), 4.13 (2H, s), 4.44 (2H, s), 6.51 (1H, s), 7.00 (2H, d, J=8.4 Hz), 7.08 (2H, d, J=8.4 Hz).

REFERENCE EXAMPLE 190

5-Bromo-7-(4-isopropylbenzyl)-3,4,6-trimethyl-1-benzofuran

Using 1-(4-bromo-1-(2-(4-isopropylbenzyl)-3,5-dimethylphenoxy)acetone obtained in Reference Example 189, the title compound was synthesized in the same manner as in Reference Example 143. Yield 84%. Melting point: 76-77° C. (methanol-THF).

$^1$H-NMR (CDCl$_3$) δ: 1.20 (6H, d, J=6.9 Hz), 2.37 (3H, s), 2.44 (3H, s), 2.71 (3H, s), 2.83 (1H, septet, J=6.9 Hz), 4.28 (2H, s), 7.04 (2H, d, J=8.7 Hz), 7.08 (2H, d, J=8.7 Hz), 7.32 (1H, s).

REFERENCE EXAMPLE 191

4,6,7-Trimethyl-3-(4-methylphenyl)-1-benzofuran

A mixture of 1-(4-methylphenyl)-2-(2,3,5-trimethylphenoxy)ethanone obtained in Reference Example 163 (1.0 g, 3.73 mmol) and polyphosphoric acid (6.0 g) was stirred at 80° C. for one and half hours. Water was added to the reaction solution, which was extracted with ethyl acetate. The organic layer was washed with a saturated sodium hydrogen carbonate solution, dried over anhydrous sodium sulfate, and then concentrated under reduced pressure to obtain 770 mg (yield 83%) of the title compound. Melting point: 112-113° C. (ethyl acetate-methanol).

$^1$H-NMR (CDCl$_3$) δ: 2.19 (3H, s), 2.35 (3H, s), 2.41 (3H, s), 2.42 (3H, s), 6.81 (1H, s), 7.20 (2H, d, J=7.8 Hz), 7.31 (2H, d, J=7.8 Hz), 7.46 (1H, s).

REFERENCE EXAMPLE 192

5-Methyl-2-(4,6,7-trimethyl-1-benzofuran-3-yl)pyridine

Using 1-(5-methylpyridin-2-yl)-2-(2,3,5-trimethylphenoxy)ethanone obtained in Reference Example 168, the title compound was synthesized in the same manner as in Reference Example 191. Yield 87%. Melting point: 134-135° C. (ethyl acetate-hexane).

$^1$H-NMR (CDCl$_3$) δ: 2.30 (3H, s), 2.36 (3H, s), 2.39 (3H, s), 2.42 (3H, s), 6.85 (1H, s), 7.37 (1H, d, J=8.1 Hz), 7.53 (1H, dd, J=2.1, 8.1 Hz), 7.67 (1H, s), 8.54 (1H, d, J=2.1 Hz).

REFERENCE EXAMPLE 193

5-Bromo-3-(4-isopropyl)-4,6,7-trimethyl-1-benzofuran

Using 4-bromo-1-(4-isopropylphenyl)-2-(2,3,5-trimethylphenoxy)ethanone obtained in Reference Example 165, the title compound was synthesized in the same manner as in Reference Example 143. Yield 86%. Oily matter.

$^1$H-NMR (CDCl$_3$) δ: 1.31 (6H, d, J=7.0 Hz), 2.30 (3H, s), 2.51 (6H, s), 2.97 (1H, septet, J=7.0 Hz), 7.24-7.35 (4H, m), 7.48 (1H, s).

REFERENCE EXAMPLE 194)

3-(4-Isopropylphenyl)-4,5,6-trimethyl-1-benzofuran

Using 2-(3,4,5-trimethylphenoxy)-1-(4-isopropylphenyl)ethanone obtained in Reference Example 177, the title compound was synthesized in the same manner as in Reference Example 143. Yield 96%. Oily matter.

$^1$H-NMR (CDCl$_3$) δ: 1.30 (6H, d, J=6.9 Hz), 2.18 (3H, s), 2.21 (3H, s), 2.39 (3H, s), 2.96 (1H, septet, J=6.9 Hz), 7.19 (1H, s), 7.25 (2H, d, J=8.1 Hz), 7.33 (2H, d, J=8.1 Hz), 7.39 (1H, s).

REFERENCE EXAMPLE 195

3-(4-Isopropylphenyl)-4-methylnaphtho[1,2-b]furan-5-yl acetate

Using 4-(2-(4-isopropylphenyl)-2-oxoethoxy)-2-methyl-1-naphthyl acetate obtained in Reference Example 178, the title compound was synthesized in the same manner as in Reference Example 143. Yield 88%. Melting point: 118-119° C. (methanol).

$^1$H-NMR (CDCl$_3$) δ: 1.31 (6H, d, J=6.9 Hz), 2.15 (3H, s), 2.47 (3H, s), 2.98 (1H, septet, J=6.9 Hz), 7.28 (2H, d, J=8.4 Hz), 7.39 (2H, d, J=8.4 Hz), 7.47-7.59 (2H, m), 7.67 (1H, s), 7.77 (1H, d, J=8.7 Hz), 8.31 (1H, d, J=8.7 Hz).

REFERENCE EXAMPLE 196

3-(4-Isopropylphenyl)-4-methyl-6,7,8,9-tetrahydronaphtho[1,2-b]furan

Using 1-(4-isopropylphenyl)-2-((3-methyl-5,6,7,8-tetrahydro-1-naphthalenyl)oxy)ethanone obtained in Reference Example 179, the title compound was synthesized in the same manner as in Reference Example 143. Yield 56%. Melting point: 97-98° C.

$^1$H-NMR (CDCl$_3$) δ: 1.30 (6H, d, J=6.9 Hz), 1.75-1.98 (4H, m), 2.20 (3H, s), 2.75-3.02 (5H, m), 6.74 (1H, s), 7.26 (2H, d, J=8.1 Hz), 7.35 (2H, d, J=8.1 Hz), 7.48 (1H, s).

REFERENCE EXAMPLE 197

3-(4-Isopropylphenyl)-4-methyl-7,8-dihydro-6H-indeno[4,5-b]furan

Using 1-(4-isopropylphenyl)-2-((6-methyl-2,3-dihydro-1H-inden-4-yl)oxy)ethanone obtained in Reference Example 180, the title compound was synthesized in the same manner as in Reference Example 143. Yield 77%. Melting point: 70-72° C. (methanol).

$^1$H-NMR (CDCl$_3$) δ: 1.30 (6H, d, J=6.9 Hz), 2.11-2.24 (5H, m), 2.90-3.06 (3H, m), 3.13 (2H, t, J=7.5 Hz), 6.91 (1H, s), 7.24 (2H, d, J=8.1 Hz), 7.34 (2H, d, J=8.1 Hz), 7.46 (1H, s).

REFERENCE EXAMPLE 198

3-(4-Isopropylphenyl)-4,6-dimethyl-1-benzothiophene

Using 2-((3,5-(dimethylphenyl)thio)-1-(4-isopropylphenyl)ethanone obtained in Reference Example 181, the title compound was synthesized in the same manner as in Reference Example 143. Yield 86%. Melting point: 83-84° C. (methanol).

$^1$H-NMR (CDCl$_3$) δ: 1.30 (6H, d, J=6.9 Hz), 2.06 (3H, s), 2.43 (3H, s), 2.97 (1H, septet, J=6.9 Hz), 6.91 (1H, s), 7.10 (1H, s), 7.22 (2H, d, J=8.4 Hz), 7.28 (2H, d, J=8.4 Hz), 7.53 (1H, s).

REFERENCE EXAMPLE 199

3-Ethyl-7-(4-isopropylbenzyl)-4,6-dimethyl-2,3-dihydro-1-benzofuran

To a mixed solution of 3-ethyl-7-(4-isopropylbenzyl)-4,6-dimethyl-3-propyl-1-benzofuran obtained in Reference Example 183 (941 mg, 2.94 mmol) in trifluoroacetic acid (5 mL) was added dropwise triethylsilane (0.94 mL, 5.87 mmol), and the mixture was stirred at room temperature for 1 hour. Water was added to the reaction solution, which was extracted with ethyl acetate, and then the organic layer was washed with a saturated sodium hydrogen carbonate solution, dried over anhydrous sodium sulfate, and then concentrated under reduced pressure. The obtained residue was purified by silica gel column chromatography (ethyl acetate:hexane=1:4) to obtain 940 mg (yield 99%) of the title compound. Oily matter.

$^1$H-NMR (CDCl$_3$) δ: 0.95 (3H, t, J=7.6 Hz), 1.19 (6H, d, J=6.9 Hz), 1.48-1.64 (2H, m), 2.16 (3H, s), 2.24 (3H, s), 2.83 (1H, septet, J=6.9 Hz), 3.30-3.36 (1H, m), 3.90 (2H, s), 4.36 (1H, dd, J=3.6, 8.7 Hz), 4.50 (1H, t, J=8.7 Hz), 4.52 (1H, s), 7.08 (4H, s).

REFERENCE EXAMPLE 200

7-(4-Isopropylbenzyl)-3,4,6-trimethyl-2,3-dihydro-1-benzofuran

Using 7-(4-isopropylbenzyl)-3,4,6-trimethyl-1-benzofuran obtained in Reference Example 182, the title compound was synthesized in the same manner as in Reference Example 199. Yield: quantitative. Oily matter.

$^1$H-NMR (CDCl$_3$) δ: 1.20 (6H, d, J=6.9 Hz), 1.28 (3H, d, J=6.9 Hz), 2.16 (3H, s), 2.24 (3H, s), 2.80-2.90 (1H, septet, J=6.9 Hz), 3.40-3.55 (1H, m), 3.90 (2H, s), 3.17 (1H, dd, J=4.2, 8.4 Hz), 4.56 (1H, t, J=4.2, 8.4 Hz), 6.48 (1H, s), 7.07 (4H, s).

REFERENCE EXAMPLE 201

7-(4-Isopropylbenzyl)-4,6-dimethyl-3-propyl-2,3-dihydro-1-benzofuran

Using 7-(4-isopropylbenzyl)-4,6-dimethyl-3-propyl-1-benzofuran obtained in Reference Example 184, the title compound was synthesized in the same manner as in Reference Example 199. Yield 99%. Oily matter.

$^1$H-NMR (CDCl$_3$) δ: 0.94 (3H, t, J=7.5 Hz), 1.15 (6H, d, J=6.9 Hz), 1.37 (2H, m), 1.47-1.69 (2H, m), 2.16 (3H, s), 2.24 (3H, s), 2.83 (1H, septet, J=6.9 Hz), 3.30-3.90 (1H, m), 3.89 (2H, s), 4.34 (1H, dd, J=3.3, 8.7 Hz), 4.48 (1H, t, J=8.7 Hz), 6.48 (1H, s), 7.06 (4H, s).

REFERENCE EXAMPLE 202

3-Isopropyl-7-(4-isopropylbenzyl)-4,6-dimethyl-2,3-dihydro-1-benzofuran

Using 3-isopropyl-7-(4-isopropylbenzyl)-4,6-dimethyl-1-benzofuran obtained in Reference Example 185, the title compound was synthesized in the same manner as in Reference Example 199. Yield: quantitative. Oily matter.

$^1$H-NMR (CDCl$_3$) δ: 0.73 (3H, d, J=6.9 Hz), 0.99 (3H, d, J=6.9 Hz), 1.19 (6H, d, J=6.9 Hz), 2.05-2.17 (1H, m), 2.15 (3H, s), 2.24 (3H, s), 2.83 (1H, septet, J=6.9 Hz), 3.33-3.38 (1H, m), 3.84 (1H, d, J=15.6 Hz), 3.95 (1H, d, J=15.6 Hz), 4.36 (1H, t, J=9.0 Hz), 4.50 (1H, dd, J=2.7, 9.0 Hz), 6.49 (1H, s), 7.06 (4H, s)

REFERENCE EXAMPLE 203

3-(3-Bromophenyl)-4,6,7-trimethyl-2,3-dihydro-1-benzofuran

Using 3-(3-bromophenyl)-4,6,7-trimethyl-1-benzofuran obtained in Reference Example 186, the title compound was synthesized in the same manner as in Reference Example 199.

Yield 82%. Melting point: 73-74° C. (ethyl acetate-hexane).

$^1$H-NMR (CDCl$_3$) δ: 1.90 (3H, s), 2.15 (3H, s), 2.23 (3H, s), 4.39 (1H, dd, J=4.8, 9.0 Hz), 4.50 (1H, dd, J=4.8, 9.0 Hz), 4.83 (1H, t, J=9.0 Hz), 6.50 (1H, s), 7.06 (1H, d, J=7.5 Hz), 7.15 (1H, t, J=7.7 Hz), 7.30 (1H, s), 7.35 (1H, d, J=7.7 Hz).

REFERENCE EXAMPLE 204

3-(3-Methoxyphenyl)-4,6,7-trimethyl-2,3-dihydro-1-benzofuran

Using 3-(3-methoxyphenyl)-4,6,7-trimethyl-1-benzofuran obtained in Reference Example 187, the title compound was synthesized in the same manner as in Reference Example 199.

Yield 82%. Oily matter.

$^1$H-NMR (CDCl$_3$) δ: 1.91 (3H, s), 2.15 (3H, s), 2.23 (3H, s), 3.76 (3H, s), 4.42 (1H, dd, J=4.8, 8.7 Hz), 4.52 (1H, dd, J=4.8, 8.7 Hz), 4.84 (1H, t, J=8.7 Hz), 6.48 (1H, s), 6.68-6.77 (3H, m), 7.20 (1H, t, J=7.8 Hz).

REFERENCE EXAMPLE 205

3-(4-Isopropyl-2-methoxyphenyl)-4,6,7-trimethyl-2,3-dihydro-1-benzofuran

Using 3-(4-isopropyl-2-methoxyphenyl)-4,6,7-trimethyl-1-benzofuran obtained in Reference Example 188, the title compound was synthesized in the same manner as in Reference Example 199. Yield 79%. Melting point: 102-103° C. (methanol).

$^1$H-NMR (CDCl$_3$) δ: 1.22 (6H, d, J=6.9 Hz), 1.95 (3H, s), 2.14 (3H, s), 2.24 (3H, s), 2.86 (1H, septet, J=6.9 Hz), 3.87 (3H, s), 4.34 (1H, dd, J=3.3, 7.5 Hz), 4.78-4.88 (2H, m), 6.52 (1H, s), 6.66 (2H, s), 6.73 (1H, s).

REFERENCE EXAMPLE 206

4,6,7-Trimethyl-3-(4-methylphenyl)-2,3-dihydro-1-benzofuran

Using 4,6,7-trimethyl-3-(4-methylphenyl)-1-benzofuran obtained in Reference Example 191, the title compound was synthesized in the same manner as in Reference Example 144.

Yield 81%. Melting point: 65-66° C. (THF-methanol).

$^1$H-NMR (CDCl$_3$) δ: 1.88 (3H, s), 2.15 (3H, s), 2.23 (3H, s), 2.31 (3H, s), 4.39 (1H, dd, J=5.2, 8.8 Hz), 4.51 (1H, dd,

J=5.2, 8.8 Hz), 4.84 (1H, t, J=8.8 Hz), 6.48 (1H, s), 7.02 (2H, d, J=8.4 Hz), 7.09 (2H, d, J=8.4 Hz).

REFERENCE EXAMPLE 207

5-Methyl-2-(4,6,7-trimethyl-2,3-dihydro-1-benzofuran-3-yl)pyridine

Using 5-methyl-2-(4,6,7-trimethyl-1-benzofuran-3-yl)pyridine obtained in Reference Example 192, the title compound was synthesized in the same manner as in Reference Example 144. Yield 89%. Melting point: 69-70° C. (methanol).

$^1$H-NMR (CDCl$_3$) δ: 1.92 (3H, s), 2.14 (3H, s), 2.22 (3H, s), 2.29 (3H, s), 4.55 (1H, dd, J=4.5, 9.0 Hz), 4.72 (1H, dd, J=4.5, 9.0 Hz), 4.88 (1H, t, J=9.0 Hz), 6.49 (1H, s), 6.89 (1H, d, J=7.8 Hz), 7.37 (1H, dd, J=2.1, 7.8 Hz), 8.37 (1H, d, J=2.1 Hz)

REFERENCE EXAMPLE 208

3-(4-Isopropylphenyl)-4,5,6-trimethyl-2,3-dihydro-1-benzofuran

Using 3-(4-isopropylphenyl)-4,5,6-trimethyl-1-benzofuran obtained in Reference Example 194, the title compound was synthesized in the same manner as in Reference Example 199. Yield 74%. Melting point: 70-71° C. (methanol).

$^1$H-NMR (CDCl$_3$) δ: 1.22 (6H, d, J=6.9 Hz), 1.93 (3H, s), 2.06 (3H, s), 2.26 (3H, s), 2.86 (1H, septet, J=6.9 Hz), 4.38 (1H, dd, J=8.7, 4.5 Hz), 4.49 (1H, dd, J=9.0, 4.2 Hz), 4.78 (1H, t, J=8.7 Hz), 6.59 (1H, s), 7.03 (2H, d, J=8.1 Hz), 7.11 (2H, d, J=8.0 Hz).

REFERENCE EXAMPLE 209

3-(4-Isopropylphenyl)-4-methyl-2,3-dihydronaphtho[1,2-b]furan-5-yl acetate

Using 3-(4-isopropylphenyl)-4-methylnaphtho[1,2-b]furan-5-yl acetate obtained in Reference Example 195, the title compound was synthesized in the same manner as in Reference Example 199. Yield 74%. Melting point: 109-110° C. (hexane-ethyl acetate).

$^1$H-NMR (CDCl$_3$) δ: 1.22 (6H, d, J=6.9 Hz), 1.93 (3H, s), 2.42 (3H, s), 2.86 (1H, septet, J=6.9 Hz), 4.63 (1H, dd, J=8.7, 5.1 Hz), 4.74 (1H, dd, J=9.3, 5.1 Hz), 5.06 (1H, t, J=9.0 Hz), 7.05 (2H, d, J=8.4 Hz), 7.12 (2H, d, J=8.4 Hz), 7.38-7.50 (2H, m), 7.66 (1H, d, J=8.7 Hz), 7.97 (1H, d, J=8.7 Hz).

REFERENCE EXAMPLE 210

3-(4-Isopropylphenyl)-4-methyl-2,3,6,7,8,9-hexahydronaphtho[1,2-b]furan

Using 3-(4-isopropylphenyl)-4-methyl-6,7,8,9-tetrahydronaphtho[1,2-b]furan obtained in Reference Example 196, the title compound was synthesized in the same manner as in Reference Example 199. Yield 80%. Melting point: 54-55° C. (methanol).

$^1$H-NMR (CDCl$_3$) δ: 1.22 (6H, d, J=6.9 Hz), 1.70-1.98 (7H, m), 2.57-2.76 (4H, m), 2.87 (1H, septet, J=6.9 Hz), 4.43 (1H, dd, J=8.4, 5.4 Hz), 4.50 (1H, dd, J=9.0, 5.7 Hz), 4.85 (1H, t, J=8.7 Hz), 6.40 (1H, s), 7.07 (2H, d, J=8.1 Hz), 7.13 (2H, d, J=8.1 Hz).

REFERENCE EXAMPLE 211

3-(4-Isopropylphenyl)-4-methyl-3,6,7,8-tetrahydro-2H-indeno[4,5-b]furan

Using 3-(4-isopropylphenyl)-4-methyl-7,8-dihydro-6H-indeno[4,5-b]furan obtained in Reference Example 197, the title compound was synthesized in the same manner as in Reference Example 199. Yield 59%. Melting point: 77-78° C. (methanol).

$^1$H-NMR (CDCl$_3$) δ: 1.22 (6H, d, J=6.9 Hz), 1.93 (3H, s), 2.10 (2H, quintet, J=7.5 Hz), 2.75-2.95 (5H, m), 4.40-4.54 (2H, m), 4.86 (1H, t, J=8.1 Hz), 6.57 (1H, s), 7.06 (2H, d, J=8.1 Hz), 7.13 (2H, d, J=8.1 Hz).

REFERENCE EXAMPLE 212

3-(4-Isopropylphenyl)-4,6-dimethyl-2,3-dihydro-1-benzothiophene

Using 3-(4-isopropylphenyl)-4,6-dimethyl-1-benzothiophene obtained in Reference Example 198, the title compound was synthesized in the same manner as in Reference Example 199. Yield 85%. Melting point: 74-75° C. (methanol).

$^1$H-NMR (CDCl$_3$) δ: 1.21 (6H, d, J=6.9 Hz), 1.96 (3H, s), 2.28 (3H, s), 2.85 (1H, septet, J=6.9 Hz), 3.15 (1H, dd, J=11.1, 2.4 Hz), 3.90 (1H, dd, J=11.1, 8.4 Hz), 4.64 (1H, dd, J=8.4, 2.4 Hz), 6.63 (1H, s), 6.95 (1H, s), 7.02 (2H, d, J=8.1 Hz), 7.10 (2H, d, J=8.1 Hz)

REFERENCE EXAMPLE 213

2-(4-Isopropylbenzyl)-1-methoxy-3,5-dimethylbenzene

To a mixed solution of sodium hydride (a 60% liquid paraffin dispersion, 757 mg, 18.9 mmol) in DMF (50 mL) was added dropwise 2-(4-isopropylbenzyl)-3,5-dimethylphenol obtained in Reference Example 148 (4.01 g, 15.8 mmol) in DMF (15 mL) under argon atmosphere at 0° C., and the mixture was stirred for 30 minutes. To the reaction solution was added dropwise a solution of methyl iodide (2.69 mL, 18.9 mmol) in DMF (8 mL) at the same temperature, and the mixture was stirred for 30 minutes. The reaction solution was warmed to room temperature, water was added thereto, which was extracted with ethyl acetate. The organic layer was washed with water, dried over anhydrous sodium sulfate, filtered, and then concentrated under reduced pressure.

The obtained residue was purified by silica gel column chromatography (hexane:ethyl acetate=8:1) to obtain 3.49 g (yield 82%) of the title compound. Oily matter.

$^1$H-NMR (CDCl$_3$) δ: 1.20 (6H, d, J=6.9 Hz), 2.19 (3H, s), 2.31 (3H, s), 2.83 (1H, septet, J=6.9 Hz), 3.78 (3H, s), 3.97 (2H, s), 6.59 (1H, s), 6.61 (1H, s), 7.03 (2H, d, J=8.1 Hz), 7.06 (2H, d, J=8.1 Hz).

REFERENCE EXAMPLE 214

1-(Allyloxy)-3,5-dimethylbenzene

Using 3,5-dimethylphenol and allyl bromide, the title compound was synthesized in the same manner as in Reference Example 213. Yield 78%. Oily matter.

$^1$H-NMR (CDCl$_3$) δ: 2.28 (6H, s), 4.48-4.52 (2H, m), 5.24-5.29 (1H, m), 5.36-5.43 (1H, m), 5.99-6.10 (1H, m), 6.55 (2H, s), 6.60 (1H, s).

REFERENCE EXAMPLE 215

2-Allyl-3,5-dimethylphenol

A solution of 1-(allyloxy)-3,5-dimethylbenzene obtained in Reference Example 214 (1.0 g, 6.2 mmol) in N,N-diethylaniline (4 mL) was stirred under argon atmosphere at 210° C. for 5 hours. To the reaction solution was added ethyl acetate, and the mixture was washed with hydrochloric acid and a saturated brine, dried over anhydrous sodium sulfate, filtered, and then concentrated under reduced pressure. The obtained residue was purified by silica gel column chromatography (hexane-ethyl acetate 7:3) to obtain 938 mg (yield 94%) of the title compound. Oily matter.

$^1$H-NMR (CDCl$_3$) δ: 2.24 (6H, s), 3.37-3.40 (2H, m), 4.79 (1H, s), 4.98-5.08 (2H, m), 5.88-6.01 (1H, m), 6.50 (1H, s), 6.50 (1H, s).

REFERENCE EXAMPLE 216

2,4,6-Trimethyl-2,3-dihydro-1-benzofuran

To a solution of 2-allyl-3,5-dimethylphenol obtained in Reference Example 215 (935 mg, 5.77 mmol) in methanol (5 mL) was added concentrated hydrochloric acid (5 mL), and the mixture was heated under reflux under argon atmosphere for 20 hours. The reaction solution was neutralized by aqueous sodium hydroxide solution, which was extracted with ethyl acetate. The organic layer was washed with a saturated sodium hydrogen carbonate solution, dried over anhydrous sodium sulfate, filtered, and then concentrated under reduced pressure to obtain the residue, which was purified by silica gel column chromatography (ethyl acetate:hexane=1:4) to obtain 472 mg (yield 50%) of the title compound. Oily matter.

$^1$H-NMR (CDCl$_3$) δ: 1.45 (3H, d, J=6.3 Hz), 2.18 (3H, s), 2.26 (3H, s), 2.67 (1H, dd, J=7.5, 15.0 Hz), 3.19 (1H, dd, J=8.7, 15.0 Hz), 4.86-4.96 (1H, m), 6.41 (1H, s), 6.47 (1H, s).

REFERENCE EXAMPLE 217

1-Bromo-2-(2-chloroethoxy)-2,4-dimethylbenzene

A mixed solution of 2-bromo-3,5-dimethylphenol obtained in Reference Example 149 (16.3 g, 74.6 mmol) and benzyl-tri-n-butylammonium chloride (23.3 g, 7.46 mmol) in 1,2-dichloroethane (150 mL)—a 8 N aqueous sodium hydroxide solution (26 mL)—water (110 mL), was heated under reflux for 5 hours. Water was added to the reaction solution, which was extracted with ethyl acetate. The combined organic layer was washed with water, a saturated sodium hydrogen carbonate solution, and a saturated brine, dried over anhydrous sodium sulfate, filtered, and then concentrated under reduced pressure. The residue was purified by silica gel column chromatography (ethyl acetate:hexane=1:4) to obtain 16.6 g (yield 90%) of the title compound. Oily matter.

$^1$H-NMR (CDCl$_3$) δ: 2.28 (3H, s), 2.37 (3H, s), 3.85 (2H, t, J=6.3 Hz), 4.25 (2H, t, J=6.3 Hz), 6.57 (1H, s), 6.73 (1H, s).

REFERENCE EXAMPLE 218

2-Bromo-3-(2-chloroethoxy)-4-(4-isopropylphenyl)-1,5-dimethylbenzene

Using 2-bromo-6-(4-isopropylbenzyl)-3,5-dimethylphenol obtained in Reference Example 150, the title compound was synthesized in the same manner as in Reference Example 217.

Yield: quantitative. Oily matter.

$^1$H-NMR (CDCl$_3$) δ: 1.21 (6H, d, J=6.9 Hz), 2.15 (3H, s), 2.37 (3H, s), 2.85 (1H, septet, J=6.9 Hz), 3.75 (2H, t, J=6.0 Hz), 3.98-4.07 (4H, m), 6.89 (1H, s), 7.00 (2H, d, J=8.4 Hz), 7.09 (2H, d, J=8.4 Hz).

REFERENCE EXAMPLE 219

4,6-Dimethyl-2,3-dihydro-1-benzofuran

To a solution of 1-bromo-2-(2-chloroethoxy)-2,4-dimethylbenzene obtained in Reference Example 217 (8.70 g, 33.0 mmol) in THF (210 mL) was quickly added n-butyllithium (1.6 M hexane solution, 31 mL, 49.5 mmol) under argon atmosphere at 0° C., and the mixture was stirred for 30 minutes. The reaction solution was warmed to room temperature, to which ice was added, which was extracted with ethyl acetate. The organic layer was dried over anhydrous sodium sulfate, was filtered, and then was concentrated under reduced pressure to obtain 4.70 g (yield 96%) of the title compound. Oily matter.

$^1$H-NMR (CDCl$_3$) δ: 2.20 (3H, s), 2.26 (3H, s), 3.06 (2H, t, J=8.7 Hz), 4.54 (2H, t, J=8.7 Hz), 6.45 (1H, s), 6.48 (1H, s).

REFERENCE EXAMPLE 220

7-(4-Isopropylbenzyl)-4,6-dimethyl-2,3-dihydro-1-benzofuran

Using 2-bromo-3-(2-chloroethoxy)-4-(4-isopropylphenyl)-1,5-dimethylbenzene obtained in Reference Example 218, the title compound was synthesized in the same manner as in Reference Example 219. Yield 81%. Oily matter.

$^1$H-NMR (CDCl$_3$) δ: 1.20 (6H, d, J=6.9 Hz), 2.17 (3H, s), 2.19 (3H, s), 2.83 (1H, septet, J=6.9 Hz), 3.11 (2H, t, J=8.7 Hz), 3.90 (2H, s), 4.56 (2H, t, J=8.7 Hz), 6.49 (1H, s), 7.07 (4H, s).

REFERENCE EXAMPLE 221

5-Bromo-7-(4-isopropylbenzyl)-3,4,6-trimethyl-2,3-dihydro-1-benzofuran

Using 7-(4-isopropylbenzyl)-3,4,6-trimethyl-2,3-dihydro-1-benzofuran obtained in Reference Example 200, the title compound was synthesized in the same manner as in Reference Example 23. Yield 87%. Oily matter.

$^1$H-NMR (CDCl$_3$) δ: 1.20 (6H, d, J=6.9 Hz), 1.28 (3H, d, J=6.9 Hz), 2.30 (3H, s), 2.35 (3H, s), 2.80-2.90 (1H, septet, J=6.9 Hz), 3.40-3.55 (1H, m), 3.98 (2H, s), 4.21 (1H, dd, J=3.0, 8.7 Hz), 4.54 (1H, t, J=8.7 Hz), 7.03 (2H, d, J=8.4 Hz), 7.08 (2H, d, J=8.4 Hz).

REFERENCE EXAMPLE 222

5-Bromo-3-ethyl-7-(4-isopropylbenzyl)-4,6-dimethyl-2,3-dihydro-1-benzofuran

Using 3-ethyl-7-(4-isopropylbenzyl)-4,6-dimethyl-2,3-dihydro-1-benzofuran obtained in Reference Example 199, the title compound was synthesized in the same manner as in Reference Example 23. Yield 99%. Oily matter.

$^1$H-NMR (CDCl$_3$) δ: 0.93 (3H, t, J=7.6 Hz), 1.20 (6H, d, J=6.9 Hz), 1.49-1.64 (2H, m), 2.30 (3H, s), 2.34 (3H, s), 2.84 (1H, septet, J=6.9 Hz), 3.31-3.37 (1H, m), 3.97 (2H, s), 4.38

(1H, dd, J=3.0, 8.7 Hz), 4.48 (1H, t, J=8.7 Hz), 7.04 (2H, d, J=8.1 Hz), 7.09 (2H, d, J=8.1 Hz).

REFERENCE EXAMPLE 223

5-Bromo-7-(4-isopropylbenzyl)-4,6-dimethyl-3-propyl-2,3-dihydro-1-benzofuran

Using 7-(4-isopropylbenzyl)-4,6-dimethyl-3-propyl-2,3-dihydro-1-benzofuran obtained in Reference Example 201, the title compound was synthesized in the same manner as in Reference Example 23. Yield: quantitative. Oily matter.
$^1$H-NMR (CDCl$_3$) δ: 0.94 (3H, t, J=7.5 Hz), 1.20 (6H, d, J=6.9 Hz), 1.22-1.42 (2H, m), 1.47-1.62 (2H, m), 2.29 (3H, s), 2.34 (3H, s), 2.84 (1H, septet, J=6.9 Hz), 3.30-3.40 (1H, m), 3.98 (2H, s), 4.38 (1H, dd, J=3.3, 9.0 Hz), 4.47 (1H, t, J=9.0 Hz), 7.04 (2H, d, J=8.4 Hz), 7.09 (2H, d, J=8.4 Hz).

REFERENCE EXAMPLE 224

5-Bromo-3-isopropyl-7-(4-isopropylbenzyl)-4,6-dimethyl-2,3-dihydro-1-benzofuran

Using 3-isopropyl-7-(4-isopropylbenzyl)-4,6-dimethyl-2,3-dihydro-1-benzofuran obtained in Reference Example 202, the title compound was synthesized in the same manner as in Reference Example 23. Yield: quantitative. Oily matter.
$^1$H-NMR (CDCl$_3$) δ: 0.73 (3H, d, J=6.9 Hz), 0.98 (3H, d, J=6.9 Hz), 1.20 (6H, d, J=6.9 Hz), 2.01-2.10 (1H, m), 2.29 (3H, s), 2.34 (3H, s), 2.84 (1H, septet, J=6.9 Hz), 3.34-3.39 (1H, m), 3.92 (1H, d, J=15.3 Hz), 4.02 (1H, d, J=15.3 Hz), 4.36 (1H, t, J=9.0 Hz), 4.50 (1H, dd, J=2.7, 9.0 Hz), 7.03 (2H, d, J=8.7 Hz), 7.08 (2H, d, J=8.7 Hz).

REFERENCE EXAMPLE 225

5-Bromo-2,4,6-trimethyl-2,3-dihydro-1-benzofuran

Using 2,4,6-trimethyl-2,3-dihydro-1-benzofuran obtained in Reference Example 216, the title compound was synthesized in the same manner as in Reference Example 23.
Yield 89%. Oily matter.
$^1$H-NMR (CDCl$_3$) δ: 1.44 (3H, d, J=6.3 Hz), 2.28 (3H, s), 2.35 (3H, s), 2.74 (1H, dd, J=7.5, 15.0 Hz), 3.26 (1H, dd, J=8.7, 15.0 Hz), 4.85-4.97 (1H, m), 6.52 (1H, s).

REFERENCE EXAMPLE 226

5-Bromo-4,6-dimethyl-2,3-dihydro-1-benzofuran

Using 4,6-dimethyl-2,3-dihydro-1-benzofuran obtained in Reference Example 219, the title compound was synthesized in the same manner as in Reference Example 23.
Yield 92%. Oily matter.
$^1$H-NMR (CDCl$_3$) δ: 2.31 (3H, s), 2.35 (3H, s), 3.15 (2H, t, J=8.7 Hz), 4.56 (2H, t, J=8.7 Hz), 6.56 (1H, s).

REFERENCE EXAMPLE 227

5-Bromo-7-(4-isopropylbenzyl)-4,6-dimethyl-2,3-dihydro-1-benzofuran

Using 7-(4-isopropylbenzyl)-4,6-dimethyl-2,3-dihydro-1-benzofuran obtained in Reference Example 220, the title compound was synthesized in the same manner as in Reference Example 23. Yield 92%. Melting point: 95-96° C. (methanol).
$^1$H-NMR (CDCl$_3$) δ: 1.20 (6H, d, J=6.9 Hz), 2.31 (6H, s), 2.84 (1H, septet, J=6.9 Hz), 3.19 (2H, t, J=8.4 Hz), 3.97 (2H, s), 4.56 (2H, t, J=8.7 Hz), 7.04 (2H, d, J=8.4 Hz), 7.08 (2H, d, J=8.4 Hz).

REFERENCE EXAMPLE 228

3-Phenyl-4,6,7-trimethyl-1-benzofuran-2(3H)-one

Using 2,3,5-trimethylphenol and hydroxy(phenyl)acetic acid, the title compound was synthesized in the same manner as in Reference Example 2. Yield 37%. Melting point: 129-130° C. (ethyl acetate-hexane).
$^1$H-NMR (CDCl$_3$) δ: 1.92 (3H, s), 2.25 (3H, s), 2.30 (3H, s), 4.80 (1H, s), 6.78 (1H, s), 7.16-7.20 (2H, m), 7.27-7.40 (3H, m).

REFERENCE EXAMPLE 229

3-(4-Bromophenyl)-4,6,7-trimethyl-1-benzofuran-2(3H)-one

Using 2,3,5-trimethylphenol and hydroxy(4-bromophenyl)acetic acid, the title compound was synthesized in the same manner as in Reference Example 2. Yield 43%. Melting point: 168-169° C. (ethyl acetate-hexane).
$^1$H-NMR (CDCl$_3$) δ: 1.93 (3H, s), 2.24 (3H, s), 2.30 (3H, s), 4.76 (1H, s), 6.79 (1H, s), 7.06 (2H, d, J=8.1 Hz), 7.47 (2H, d, J=8.1 Hz).

REFERENCE EXAMPLE 230

3-(4-Isopropylphenyl)-4,7-dimethyl-1-benzofuran-2(3H)-one

Using hydroxy(4-isopropylphenyl)acetic acid and 2,5-dimethylphenol synthesized in Reference Example 1, the title compound was synthesized in the same manner as in Reference Example 2. Yield 20%. Melting point: 107-109° C. (hexane-ethyl acetate).
$^1$H-NMR (CDCl$_3$) δ: 1.22 (6H, d, J=7.0 Hz), 1.97 (3H, s), 2.33 (3H, s), 2.89 (1H, septet, J=7.0 Hz), 4.77 (1H, s), 6.86 (1H, d, J=7.6 Hz), 7.05-7.13 (3H, m), 7.19 (2H, d, J=8.0 Hz).

REFERENCE EXAMPLE 231

2-(2-Hydroxy-1-(phenyl)ethyl)-3,5,6-trimethylphenol

Using 3-phenyl-4,6,7-trimethyl-1-benzofuran-2(3H)-one obtained in Reference Example 228, the title compound was synthesized in the same manner as in Reference Example 8.
Yield 82%. Melting point: 103-104° C. (ethyl acetate-hexane).
$^1$H-NMR (CDCl$_3$) δ: 2.15 (3H, s), 2.19 (3H, s), 2.24 (3H, s), 4.26 (1H, d, J=10.8 Hz), 4.47 (1H, dd, J=5.1, 10.8 Hz), 4.53 (1H, br), 6.60 (1H, s), 7.20-7.35 (5H, m), 8.00 (1H, br), 1H unidentified.

REFERENCE EXAMPLE 232

2-(2-Hydroxy-1-(4-bromophenyl)ethyl)-3,5,6-trimethylphenol

Using 3-(4-bromophenyl)-4,6,7-trimethyl-1-benzofuran-2(3H)-one obtained in Reference Example 229, the title compound was synthesized in the same manner as in Reference Example 8. Yield 93%. Melting point: 114-115° C. (ethyl acetate-hexane).

$^1$H-NMR (CDCl$_3$) δ: 2.13 (3H, s), 2.19 (3H, s), 2.23 (3H, s), 4.20-4.30 (1H, m), 4.40-4.52 (2H, m), 6.60 (1H, s), 7.13 (2H, d, J=8.4H), 7.41 (2H, d, J=8.4H), 7.72 (1H, s), 1H unidentified.

REFERENCE EXAMPLE 233

2-(2-Hydroxy-1-(4-isopropylphenyl)ethyl)-3,6-dimethylphenol

Using 3-(4-isopropylphenyl)-4,7-dimethyl-1-benzofuran-2(3H)-one synthesized in Reference Example 230, the title compound was synthesized in the same manner as in Reference Example 8. Yield 88%. Melting point: 88-89° C. (hexane-ethyl acetate).

$^1$H-NMR (CDCl$_3$) δ: 1.22 (6H, d, J=6.9 Hz), 2.21 (3H, s), 2.23 (3H, s), 2.25 (1H, br s), 2.87 (1H, septet, J=6.9 Hz), 4.20-4.30 (1H, m), 4.32-4.52 (2H, m), 6.65 (1H, d, J=7.2 Hz), 6.96 (1H, d, J=7.2 Hz), 7.17 (4H, s), 8.18 (1H, br s).

REFERENCE EXAMPLE 234

3-Bromo-6-(2-hydroxy-1-(4-isopropylphenyl)ethyl)-2,4,5-trimethylphenol

To a mixture of hydroxy(4-isopropylphenyl)acetic acid (10.0 g, 46.5 mmol) synthesized in Reference Example 1 and 3-bromo-2,4,5-trimethylphenol synthesized in Reference Example 68 (8.2 g, 42.2 mmol) was added 70% sulfuric acid (10 mL) at room temperature, and the mixture was stirred at 115° C. for 4 hours. The mixture was added to water, which was extracted with diisopropyl ether. The extract was washed with water and a saturated sodium hydrogen carbonate solution, and then was dried over anhydrous sodium sulfate.

The solvent was distilled off under reduced pressure to obtain the residue, which was purified by silica gel column chromatography (ethyl acetate:hexane=1:8) to obtain 6-bromo-3-(4-isopropylphenyl)-4,5,7-trimethyl-1-benzofuran-2(3H)-one. To a solution of the compound in THF (80 mL) was added lithium aluminum hydride (2.40 g, 63.3 mmol) at 0° C., and the mixture was heated under reflux for 1 hour. Water was added to the reaction solution, and the product was extracted with ethyl acetate. The combined extract was washed with water, dried over magnesium sulfate, and then concentrated under reduced pressure. The obtained residue was crystallized from hexane-ethyl acetate to obtain 15.5 g (yield 97%) of the title compound. Melting point: 96-97° C.

$^1$H-NMR (CDCl$_3$) δ: 1.22 (6H, d, J=6.9 Hz), 2.19 (3H, s), 2.38 (3H, s), 2.39 (3H, s), 2.87 (1H, septet, J=6.9 Hz), 4.24 (1H, dt, J=11.4, 2.7 Hz), 4.42 (1H, ddd, J=11.4, 5.4, 2.7 Hz), 4.60 (1H, dd, J=5.4, 2.7 Hz), 4.93 (1H, d, J=6.3 Hz), 7.13 (2H, d, J=8.7 Hz), 7.17 (2H, d, J=8.7 Hz), 8.27 (1H, br s).

REFERENCE EXAMPLE 235

4,6,7-Trimethyl-3-phenyl-2,3-dihydro-1-benzofuran

Using 2-(2-hydroxy-1-(phenyl)ethyl)-3,5,6-trimethylphenol obtained in Reference Example 231, the title compound was synthesized in the same manner as in Reference Example 13. Yield 95%. Melting point: 72-73° C. (methanol).

$^1$H-NMR (CDCl$_3$) δ: 1.88 (3H, s), 2.16 (3H, s), 2.23 (3H, s), 4.43 (1H, dd, J=5.1, 9.0 Hz), 4.55 (1H, dd, J=5.1, 9.0 Hz), 4.86 (1H, t, J=9.0 Hz), 6.49 (1H, s), 7.13-7.31 (5H, m).

REFERENCE EXAMPLE 236

3-(4-Bromophenyl)-4,6,7-trimethyl-2,3-dihydro-1-benzofuran

Using 2-(2-hydroxy-1-(4-bromophenyl)ethyl)-3,5,6-trimethylphenol obtained in Reference Example 232, the title compound was synthesized in the same manner as in Reference Example 13. Yield 95%. Melting point: 72-73° C. (methanol).

$^1$H-NMR (CDCl$_3$) δ: 1.88 (3H, s), 2.15 (3H, s), 2.23 (3H, s), 4.36 (1H, dd, J=5.1, 9.0 Hz), 4.50 (1H, dd, J=5.1, 9.0 Hz), 4.83 (1H, t, J=9.0 Hz), 6.49 (1H, s), 7.01 (2H, d, J=8.7 Hz), 7.40 (2H, d, J=8.7 Hz).

REFERENCE EXAMPLE 237

3-(4-Isopropylphenyl)-4,7-dimethyl-2,3-dihydro-1-benzofuran

Using 2-(2-hydroxy-1-(4-isopropylphenyl)ethyl)-3,6-dimethylphenol synthesized in Reference Example 233, the title compound was synthesized in the same manner as in Reference Example 13. Yield 85%. Oily matter.

$^1$H-NMR (CDCl$_3$) δ: 1.22 (6H, d, J=7.0 Hz), 1.92 (3H, s), 2.29 (3H, s), 2.86 (1H, septet, J=7.0 Hz), 4.35-4.53 (2H, m), 4.75-4.90 (1H, m), 6.47 (1H, s), 6.55 (1H, s), 7.05 (2H, d, J=8.0 Hz), 7.13 (2H, d, J=8.0 Hz).

REFERENCE EXAMPLE 238

6-Bromo-3-(4-isopropylphenyl)-4,5,7-trimethyl-2,3-dihydro-1-benzofuran

Using 3-bromo-6-(2-hydroxy-1-(4-isopropylphenyl)ethyl)-2,4,5-trimethylphenol synthesized in Reference Example 234, the title compound was synthesized in the same manner as in Reference Example 13. Yield 57%. Melting point: 56-57° C. (hexane-ethyl acetate).

$^1$H-NMR (CDCl$_3$) δ: 1.22 (6H, d, J=6.9 Hz), 1.95 (3H, s), 2.28 (3H, s), 2.32 (3H, s), 2.86 (1H, septet, J=6.9 Hz), 4.42 (1H, dd, J=8.7, 4.8 Hz), 4.50 (1H, dd, J=9.0, 4.2 Hz), 4.81 (1H, t, J=8.7 Hz), 7.01 (2H, d, J=8.1 Hz), 7.12 (2H, d, J=8.1 Hz).

REFERENCE EXAMPLE 239

5-Bromo-4,6,7-trimethyl-3-phenyl-2,3-dihydro-1-benzofuran

Using 4,6,7-trimethyl-3-phenyl-2,3-dihydro-1-benzofuran obtained in Reference Example 235, the title compound was synthesized in the same manner as in Reference Example 23. Yield 79%. Melting point: 107-108° C. (methanol).

$^1$H-NMR (CDCl$_3$) δ: 2.03 (3H, s), 2.24 (3H, s), 2.39 (3H, s), 4.41 (1H, dd, J=4.5, 9.0 Hz), 4.59 (1H, dd, J=4.5, 9.0 Hz), 4.84 (1H, t, J=9.0 Hz), 7.08-7.13 (2H, m), 7.18-7.34 (3H, m).

REFERENCE EXAMPLE 240

5-Bromo-4,6,7-trimethyl-3-(4-methylphenyl)-2,3-dihydro-1-benzofuran

Using 4,6,7-trimethyl-3-(4-methylphenyl)-2,3-dihydro-1-benzofuran obtained in Reference Example 206, the title compound was synthesized in the same manner as in Reference Example 23. Yield 96%. Melting point: 108-109° C. (methanol).

$^1$H-NMR (CDCl$_3$) δ: 2.03 (3H, s), 2.23 (3H, s), 2.31 (3H, s), 2.38 (3H, s), 4.38 (1H, dd, J=4.8, 8.4 Hz), 4.55 (1H, dd, J=4.8, 8.4 Hz), 4.82 (1H, t, J=8.4 Hz), 6.99 (2H, d, J=8.0 Hz), 7.09 (2H, d, J=8.0 Hz).

REFERENCE EXAMPLE 241

5-Bromo-3-(4-isopropylphenyl)-4,7-dimethyl-2,3-dihydro-1-benzofuran

Using 3-(4-isopropylphenyl)-4,7-dimethyl-2,3-dihydro-1-benzofuran obtained in Reference Example 237, the title compound was synthesized in the same manner as in Reference Example 23. Yield 77%. Oily matter.

$^1$H-NMR (CDCl$_3$) δ: 1.22 (6H, d, J=7.0 Hz), 1.99 (3H, s), 2.21 (3H, s), 2.87 (1H, septet, J=7.0 Hz), 4.43 (1H, dd, J=8.2, 4.8 Hz), 4.53 (1H, dd, J=9.0, 4.4 Hz), 4.85 (1H, t, J=8.3 Hz), 7.02 (2H, d, J=8.2 Hz), 7.14 (2H, d, J=8.2 Hz), 7.19 (1H, s).

REFERENCE EXAMPLE 242

5-Methyl-2-(5-bromo-4,6,7-trimethyl-2,3-dihydro-1-benzofuran-3-yl)pyridine

Using 5-methyl-2-(4,6,7-trimethyl-2,3-dihydro-1-benzofuran-3-yl)pyridine obtained in Reference Example 207, the title compound was synthesized in the same manner as in Reference Example 23. Yield 84%. Melting point: 105-106° C. (methanol).

$^1$H-NMR (CDCl$_3$) δ: 2.06 (3H, s), 2.22 (3H, s), 2.29 (3H, s), 2.37 (3H, s), 4.63 (1H, dd, J=4.5, 9.0 Hz), 4.76 (1H, dd, J=4.5, 9.0 Hz), 4.87 (1H, t, J=9.0 Hz), 6.86 (1H, d, J=8.1 Hz), 7.37 (1H, d, J=8.1 Hz), 8.37 (1H, s).

REFERENCE EXAMPLE 243

3-(Biphenyl-4-yl)-5-bromo-4,6,7-trimethyl-2,3-dihydro-1-benzofuran

A mixed solution of 3-(4-bromophenyl)-4,6,7-trimethyl-2,3-dihydro-1-benzofuran obtained in Reference Example 236 (1.0 g, 3.15 mmol), phenylboronic acid (500 mg, 4.10 mmol), tetrakis(triphenylphosphine)palladium(O) (73 mg, 0.063 mmol) in 2 N sodium carbonate aqueous solution (4 mL)-ethanol (4 mL)-toluene (15 mL) was reacted under argon atmosphere at 80° C. for 5 hours. Water was added to the reaction solution, which was extracted with ethyl acetate.

The combined organic layer was washed with a saturated brine, was dried over anhydrous sodium sulfate, and then was concentrated under reduced pressure to obtain the residue, which was purified by silica gel column chromatography (ethyl acetate:hexane=1:4) to obtain (3-biphenyl-4-yl)-4,6,7-trimethyl-2,3-dihydro-1-benzofuran 750 mg (yield 76%). Using this compound, 873 mg of the title compound was synthesized in the same manner as in Reference Example 23. Yield 93%. Melting point: 153-154° C. (methanol).

$^1$H-NMR (CDCl$_3$) δ: 2.08 (3H, s), 2.26 (3H, s), 2.40 (3H, s), 4.46 (1H, dd, J=5.0, 9.0 Hz), 4.62 (1H, dd, J=5.0, 9.0 Hz), 4.88 (1H, t, J=9.0 Hz), 7.15-7.60 (9H, m).

REFERENCE EXAMPLE 244

2-Bromo-4-(4-isopropylbenzyl)-5-methoxy-1,3-dimethylbenzene

To a solution of 2-(4-isopropylbenzyl)-1-methoxy-3,5-dimethylbenzene obtained in Reference Example 213 (3.45 g, 12.9 mmol) in acetonitrile (40 mL) was added N-bromosuccinimide (2.29 g, 12.9 mmol) with ice-cooling, and the mixture was stirred for 30 minutes. Water was added to the reaction solution, which was extracted with ethyl acetate, and then the organic layer was dried over anhydrous sodium sulfate, was filtered, and then was concentrated under reduced pressure.

Ethyl acetate-hexane (1:9) was added to the residue, and the precipitated crystals were filtered, and the filtrate was concentrated to obtain 4.50 g (yield is quantitative) of the title compound. Oily matter.

$^1$H-NMR (CDCl$_3$) δ: 1.20 (6H, d, J=6.9 Hz), 2.34 (3H, s), 2.42 (3H, s), 2.84 (1H, septet, J=6.9 Hz), 3.78 (3H, s), 4.06 (2H, s), 6.70 (1H, s), 7.00 (2H, d, J=8.1 Hz), 7.04 (2H, d, J=8.1 Hz).

REFERENCE EXAMPLE 245

3-(3-Formylphenyl)-4,6,7-trimethyl-1-benzofuran

To a solution of 3-(3-bromophenyl)-4,6,7-trimethyl-2,3-dihydro-1-benzofuran obtained in Reference Example 203 (1.77 g, 5.57 mmol) in THF (20 mL) was added dropwise n-butyllithium (1.6 M hexane solution, 4.18 mL, 6.68 mmol) under argon atmosphere at −78° C., and the mixture was stirred for 30 minutes. To the reaction solution was added dropwise DMF (0.86 mL, 11.14 mmol) at the same temperature, and the mixture was stirred for 30 minutes, and then was warmed to room temperature. Water was added to the reaction solution, which was extracted with ethyl acetate, and then the organic layer was dried over anhydrous sodium sulfate, was filtered, and then was concentrated under reduced pressure to give 1.48 g (yield is quantitative) of the title compound. Oily matter.

$^1$H-NMR (CDCl$_3$) δ: 1.88 (3H, s), 2.17 (3H, s), 2.24 (3H, s), 4.42 (1H, dd, J=4.5, 9.0 Hz), 4.63 (1H, dd, J=4.5, 9.0 Hz), 4.88 (1H, t, J=9.0 Hz), 6.50 (1H, s), 7.39-7.49 (2H, m), 7.67-7.69 (1H, m), 7.73-7.76 (1H, m), 9.98 (1H, s).

REFERENCE EXAMPLE 246

3-(4-Formylphenyl)-4,6,7-trimethyl-2,3-dihydro-1-benzofuran

Using 3-(4-bromophenyl)-4,6,7-trimethyl-2,3-dihydro-1-benzofuran obtained in Reference Example 236, the title compound was synthesized in the same manner as in Reference Example 245. Yield 73%. Melting point: 87-88° C. (methanol).

$^1$H-NMR (CDCl$_3$) δ: 1.88 (3H, s), 2.17 (3H, s), 2.24 (3H, s), 4.43 (1H, dd, J=4.5, 9.0 Hz), 4.62 (1H, dd, J=4.5, 9.0 Hz), 4.88 (1H, t, J=9.0 Hz), 6.51 (1H, s), 7.32 (2H, d, J=8.1 Hz), 7.81 (2H, d, J=8.1 Hz), 9.98 (1H, s).

REFERENCE EXAMPLE 247

3-(3-(1,3-(Dioxolan-2-yl)phenyl)-4,6,7-trimethyl-2,3-dihydro-1-benzofuran

A solution of 3-(3-formylphenyl)-4,6,7-trimethyl-1-benzofuran obtained in Reference Example 245 (1.48 g, 5.57 mmol), ethylene glycol (0.62 mL, 11.14 mmol) and p-toluenesulfonic acid monohydrate (50 mg) in toluene (20 mL) was heated under reflux using Dean-Starks apparatus for 16 hours. The reaction solution was diluted with ethyl acetate, was washed with water and a saturated brine, dried over anhydrous sodium sulfate, filtered, and then concentrated under reduced pressure to obtain 1.52 g (yield 88%) of the title compound. Oily matter.

$^1$H-NMR (CDCl$_3$) δ: 1.87 (3H, s), 2.15 (3H, s), 2.23 (3H, s), 3.98-4.13 (4H, m), 4.39 (1H, dd, J=5.4, 9.0 Hz), 4.57 (1H, dd, J=5.4, 9.0 Hz), 4.85 (1H, t, J=9.0 Hz), 5.75 (1H, s), 6.47 (1H, s), 7.08-7.12 (1H, m), 7.25-7.35 (3H, m).

REFERENCE EXAMPLE 248

3-(4-(1,3-Dioxolan-2-yl)phenyl)-4,6,7-trimethyl-2,3-dihydro-1-benzofuran

Using 3-(4-formylphenyl)-4,6,7-trimethyl-2,3-dihydro-1-benzofuran obtained in Reference Example 246, the title compound was synthesized in the same manner as in Reference Example 247. Yield 73%. Melting point: 107-108° C. (methanol).

$^1$H-NMR (CDCl$_3$) δ: 1.87 (3H, s), 2.15 (3H, s), 2.23 (3H, s), 3.97-4.16 (4H, m), 4.39 (1H, dd, J=4.5, 8.4 Hz), 4.56 (1H, dd, J=4.5, 8.4 Hz), 4.85 (1H, t, J=8.4 Hz), 5.77 (1H, s), 6.48 (1H, s), 7.17 (2H, d, J=8.4 Hz), 7.40 (2H, d, J=8.4 Hz).

REFERENCE EXAMPLE 249

5-Bromo-3-(3-(1,3-(dioxolan-2-yl)phenyl)-4,6,7-trimethyl-2,3-dihydro-1-benzofuran Using 3-(3-(1,3-(dioxolan-2-yl)phenyl)-4,6,7-trimethyl-2,3-dihydro-1-benzofuran obtained in Reference Example 247, the title compound was synthesized in the same manner as in Reference Example 23. Yield 73%. Oily matter.

$^1$H-NMR (CDCl$_3$) δ: 2.02 (3H, s), 2.24 (3H, s), 2.39 (3H, s), 4.00-4.16 (4H, m), 4.39 (1H, dd, J=4.5, 9.0 Hz), 4.62 (1H, dd, J=4.5, 9.0 Hz), 4.84 (1H, t, J=9.0 Hz), 5.76 (1H, s), 7.05-7.09 (1H, m), 7.26-7.38 (3H, m).

REFERENCE EXAMPLE 250

5-Bromo-3-(4-(1,3-(dioxolan-2-yl)phenyl)-4,6,7-trimethyl-2,3-dihydro-1-benzofuran Using 3-(4-(1,3-(dioxolan-2-yl)phenyl)-4,6,7-trimethyl-2,3-dihydro-1-benzofuran obtained in Reference Example 248, the title compound was synthesized in the same manner as in Reference Example 23. Yield: quantitative. Melting point: 146-147° C. (methanol).

$^1$H-NMR (CDCl$_3$) δ: 2.01 (3H, s), 2.24 (3H, s), 2.39 (3H, s), 4.00-4.15 (4H, m), 4.38 (1H, dd, J=4.5, 9.0 Hz), 4.60 (1H, dd, J=4.5, 9.0 Hz), 4.83 (1H, t, J=9.0 Hz), 5.77 (1H, s), 7.13 (2H, d, J=8.4 Hz), 7.40 (2H, d, J=8.4 Hz).

REFERENCE EXAMPLE 251

5-Bromo-3-(4-isopropyl-2-methoxyphenyl)-4,6,7-trimethyl-2,3-dihydro-1-benzofuran Using 3-(4-isopropyl-2-methoxyphenyl)-4,6,7-trimethyl-2,3-dihydro-1-benzofuran obtained in Reference Example 205, the title compound was synthesized in the same manner as in Reference Example 23. Yield 96%. Melting point: 102-103° C. (methanol).

$^1$H-NMR (CDCl$_3$) δ: 1.23 (6H, d, J=6.9 Hz), 2.07 (3H, s), 2.22 (3H, s), 2.39 (3H, s), 2.86 (1H, septet, J=6.9 Hz), 3.87 (3H, s), 4.33 (1H, dd, J=3.3, 9.0 Hz), 4.82 (1H, t, J=9.0 Hz), 4.90 (1H, dd, J=3.3, 9.0 Hz), 6.60 (1H, d, J=7.5 Hz), 6.67 (1H, d, J=7.5 Hz), 6.74 (1H, s).

REFERENCE EXAMPLE 252

3-(4-Isopropylphenyl)-4-methyl-2,3-dihydronaphtho[1,2-b]furan-5-ol

Using 3-(4-isopropylphenyl)-4-methyl-2,3-dihydronaphtho[1,2-b]furan-5-yl acetate synthesized in Reference Example 209, the title compound was synthesized in the same manner as in Reference Example 175. Yield 91%. Melting point: 94-96° C.

$^1$H-NMR (CDCl$_3$) δ: 1.22 (6H, d, J=6.9 Hz), 2.04 (3H, s), 2.86 (1H, septet, J=6.9 Hz), 4.52-4.74 (3H, m), 4.92-5.08 (1H, m), 7.04 (2H, d, J=8.1 Hz), 7.12 (2H, d, J=8.1 Hz), 7.35-7.53 (2H, m), 7.91-8.12 (2H, m).

REFERENCE EXAMPLE 253

3-(4-Isopropylphenyl)-4-methyl-2,3-dihydronaphtho[1,2-b]furan-5-yl trifluoromethanesulfonate To a solution of 3-(4-isopropylphenyl)-4-methyl-2,3-dihydronaphtho[1,2-b]furan-5-ol obtained in Reference Example 252 (2.60 g, 8.17 mmol) and 4-dimethylaminopyridine (2.0 g, 16.3 mmol) in pyridine (30 mL) was added anhydrous trifluoromethanesulfonate (1.51 mL, 9.00 mmol) at room temperature at 0° C., and the mixture was stirred at 50° C. for 8 hours. Water was added to the reaction solution to separate the organic layer, and the aqueous layer was extracted with ethyl acetate. The combined organic layer was washed with 1 N hydrochloric acid and a saturated sodium hydrogen carbonate solution, dried over magnesium sulfate, filtered, and then concentrated under reduced pressure to obtain 2.8 g (yield 76%) of the title compound. Oily matter.

$^1$H-NMR (CDCl$_3$) δ: 1.23 (6H, d, J=7.0 Hz), 2.16 (3H, s), 2.87 (1H, septet, J=7.0 Hz), 4.62-4.80 (2H, m), 5.10 (1H, t, J=9.0 Hz), 7.04 (2H, d, J=8.1 Hz), 7.15 (2H, d, J=8.1 Hz), 7.46-7.64 (2H, m), 7.96-8.05 (2H, m).

REFERENCE EXAMPLE 254

3-(4-Isopropylphenyl)-4-methyl-2,3-dihydronaphtho[1,2-b]furan

To a solution of 3-(4-isopropylphenyl)-4-methyl-2,3-dihydronaphtho[1,2-b]furan-5-yl trifluoromethanesulfonate obtained in Reference Example 253 (2.23 g, 4.96 mmol), dichlorobis(triphenylphosphine)palladium (210 mg, 0.30 mmol), 1,3-bis(diphenylphosphino)propane (310 mg, 0.750 mmol) and tributylamine (5 mL, 21 mmol) in toluene (15 mL) was added formic acid (0.5 mL) at room temperature, and the mixture was stirred under argon atmosphere at 90° C. for 16 hours. Water was added to the reaction solution, which was extracted with ethyl acetate, the organic layer was washed with water and a saturated brine and then was dried over anhydrous sodium sulfate, and the solvent was distilled off under reduced pressure. The obtained residue was purified by silica gel column chromatography (ethyl acetate:hexane=1:20) to obtain 270 mg (yield 18%) of the title compound. Oily matter.

$^1$H-NMR (CDCl$_3$) δ: 1.22 (6H, d, J=6.9 Hz), 2.11 (3H, s), 2.86 (1H, septet, J=6.9 Hz), 4.64 (1H, dd, J=8.7, 4.8 Hz), 4.72 (1H, dd, J=9.3, 5.1 Hz), 5.06 (1H, t, J=8.7 Hz), 7.07 (2H, d, J=8.1 Hz), 7.13 (2H, d, J=8.1 Hz), 7.14 (1H, s), 7.39-7.48 (2H, m), 7.70-7.76 (1H, m), 7.94-8.02 (1H, m).

REFERENCE EXAMPLE 255

5-Bromo-3-(4-isopropylphenyl)-4-methyl-2,3-dihydronaphtho[1,2-b]furan

Using 3-(4-isopropylphenyl)-4-methyl-2,3-dihydronaphtho[1,2-b]furan obtained in Reference Example 254, the title compound was synthesized in the same manner as in Reference Example 23. Yield 88%. Oily matter.

$^1$H-NMR (CDCl$_3$) δ: 1.22 (6H, d, J=6.9 Hz), 2.26 (3H, s), 2.87 (1H, septet, J=6.9 Hz), 4.64 (1H, dd, J=8.7, 4.5 Hz), 4.75 (1H, dd, J=9.6, 4.5 Hz), 5.05 (1H, t, J=8.7 Hz), 7.03 (2H, d, J=8.1 Hz), 7.13 (2H, d, J=8.1 Hz), 7.40-7.62 (2H, m), 7.98 (1H, d, J=8.1 Hz), 8.24 (1H, d, J=8.4 Hz).

REFERENCE EXAMPLE 256

7-Bromo-3-(4-isopropylphenyl)-4,5,6-trimethyl-2,3-dihydro-1-benzofuran

Using 3-(4-isopropylphenyl)-4,5,6-trimethyl-2,3-dihydro-1-benzofuran obtained in Reference Example 208, the title compound was synthesized in the same manner as in Reference Example 23. Yield 95%. Oily matter.

$^1$H-NMR (CDCl$_3$) δ: 1.22 (6H, d, J=6.9 Hz), 1.90 (3H, s), 2.14 (3H, s), 2.40 (3H, s), 2.87 (1H, septet, J=6.9 Hz), 4.48 (1H, dd, J=8.4, 4.5 Hz), 4.63 (1H, dd, J=9.0, 4.5 Hz), 4.90 (1H, t, J=9.0 Hz), 7.04 (2H, d, J=8.1 Hz), 7.13 (2H, d, J=8.1 Hz).

REFERENCE EXAMPLE 257

5-Bromo-3-(4-isopropylphenyl)-4-methyl-2,3,6,7,8,9-hexahydronaphtho[1,2-b]furan

Using 3-(4-isopropylphenyl)-4-methyl-2,3,6,7,8,9-hexahydronaphtho[1,2-b]furan obtained in Reference Example 210, the title compound was synthesized in the same manner as in Reference Example 23. Yield 85%. Melting point: 108-109° C.

$^1$H-NMR (CDCl$_3$) δ: 1.22 (6H, d, J=6.9 Hz), 1.68-1.90 (4H, m), 2.03 (3H, s), 2.60-2.89 (4H, m), 2.86 (1H, septet, J=6.9 Hz), 4.42 (1H, dd, J=8.7, 4.8 Hz), 4.54 (1H, dd, J=9.0, 4.5 Hz), 4.83 (1H, t, J=9.0 Hz), 7.01 (2H, d, J=8.1 Hz), 7.12 (2H, d, J=8.1 Hz).

REFERENCE EXAMPLE 258

5-Bromo-3-(4-isopropylphenyl)-4-methyl-3,6,7,8-tetrahydro-2H-indeno[4,5-b]furan

Using 3-(4-isopropylphenyl)-4-methyl-3,6,7,8-tetrahydro-2H-indeno[4,5-b]furan obtained in Reference Example 211, the title compound was synthesized in the same manner as in Reference Example 23. Yield 84%. Melting point: 127-128° C. (hexane-ethyl acetate).

$^1$H-NMR (CDCl$_3$) δ: 1.22 (6H, d, J=6.9 Hz), 2.01 (3H, s), 2.13 (2H, quintet, J=7.5 Hz), 2.80-3.03 (5H, m), 4.45 (1H, dd, J=8.7, 4.8 Hz), 4.53 (1H, dd, J=9.0, 4.8 Hz), 4.86 (1H, t, J=8.7 Hz), 7.03 (2H, d, J=8.1 Hz), 7.14 (2H, d, J=8.1 Hz).

REFERENCE EXAMPLE 259

5-Bromo-3-(4-isopropylphenyl)-4,6-dimethyl-2,3-dihydro-1-benzothiophene

To a mixture of 3-(4-isopropylphenyl)-4,6-dimethyl-2,3-dihydro-1-benzothiophene synthesized in Reference Example 212 (4.45 g, 15.8 mmol) and iron powder (59 mg, 1.05 mmol) in dichloromethane (20 mL) was added bromine (0.81 mL, 15.8 mmol) at 0° C., and the mixture was stirred at the same temperature for 1 hour. Water was poured into the reaction mixture, which was extracted with ethyl acetate.

The extract was washed with a saturated sodium hydrogen carbonate solution and water, was dried over magnesium sulfate, was filtered and then was concentrated under reduced pressure. The obtained residue was purified by silica gel column chromatography (ethyl acetate:hexane=1:10) to obtain 4.6 g (yield 80%) of the title compound. Melting point: 98-100° C. (hexane-ethyl acetate).

$^1$H-NMR (CDCl$_3$) δ: 1.22 (6H, d, J=6.9 Hz), 2.12 (3H, s), 2.39 (3H, s), 2.86 (1H, septet, J=6.9 Hz), 3.15 (1H, dd, J=11.1, 1.8 Hz), 3.93 (1H, dd, J=11.1, 8.7 Hz), 4.64 (1H, d, J=8.7 Hz), 7.01 (2H, d, J=8.1 Hz), 7.05 (1H, s), 7.12 (2H, d, J=8.1 Hz).

REFERENCE EXAMPLE 260

4,6,7-Trimethyl-1-benzofuran-3(2H)-one

Using (2,3,5-trimethylphenoxy)acetic acid obtained in Reference Example 158, the title compound was synthesized in the same manner as in Reference Example 41. Yield 75%. Melting point: 92-93° C. (hexane).

$^1$H-NMR (CDCl$_3$) δ: 2.17 (3H, s), 2.30 (3H, s), 2.53 (3H, s), 4.58 (2H, s), 6.64 (1H, s).

REFERENCE EXAMPLE 261

5-Bromo-4,6,7-trimethyl-1-benzofuran-3-yl trifluoromethanesulfonate

Using 4,6,7-trimethyl-1-benzofuran-3(2H)-one obtained in Reference Example 260, 5-bromo-4,6,7-trimethyl-1-benzofuran-3(2H)-one was synthesized in the same manner as in Reference Example 23. Yield 86%. To a solution of this compound (1.0 g, 5.7 mmol) in dichloromethane (10 mL) was added dropwise diisopropylethylamine (1.14 mL, 6.53 mmol) under argon atmosphere at −30° C. To the reaction solution was added dropwise trifluoromethanesulfonic anhydride (0.96 mL, 5.70 mmol), and the mixture was warmed to room temperature, and then was stirred for 16 hours. Water was added to the reaction solution, which was extracted with ethyl acetate. The combined organic layer was washed with a saturated brine, was dried over anhydrous sodium sulfate, and then was concentrated under reduced pressure, the residue was purified by silica gel column chromatography (ethyl acetate:hexane=1:4) to synthesize 1.38 g (yield 63%) of the title compound. Melting point: 54-55° C. (hexane), $^1$H-NMR (CDCl$_3$) δ: 2.46 (3H, s), 2.50 (3H; s), 2.64 (3H, s), 7.77 (1H, s).

REFERENCE EXAMPLE 262

5-Bromo-3-(4-ethylphenyl)-4,6,7-trimethyl-1-benzofuran

A mixed solution of 5-bromo-4,6,7-trimethyl-1-benzofuran-3-yl trifluoromethanesulfonate obtained in Reference Example 261 (1.35 g, 3.49 mmol), 4-ethylphenyl boronic acid (523 mg, 3.49 mmol), tetrakis(triphenylphosphine)palladium(0) (81 mg, 0.07 mmol) in a 2 N aqueous sodium carbonate solution (4 mL)-ethanol (4 mL)-toluene (15 mL) was reacted under argon atmosphere at 80° C. for 5 hours. Water was added to the reaction solution, which was extracted with ethyl acetate. The combined organic layer was washed with a saturated brine, dried over anhydrous sodium sulfate, and then concentrated under reduced pressure, the residue was purified by silica gel column chromatography (hexane) to obtain 1.10 g (yield 92%) of the title compound. Oily matter.

$^1$H-NMR (CDCl$_3$) δ: 1.30 (3H, t, J=7.5 Hz), 2.30 (3H, s), 2.52 (6H, s), 2.72 (2H, q, J=7.5 Hz), 7.25 (2H, d, J=8.1 Hz), 7.32 (2H, d, J=8.1 Hz), 7.48 (1H, s).

REFERENCE EXAMPLE 263

N-Benzyl-7-(4-isopropylbenzyl)-3,4,6-trimethyl-2,3-dihydro-1-benzofuran-5-amine

Using 5-bromo-7-(4-isopropylbenzyl)-3,4,6-trimethyl-2,3-dihydro-1-benzofuran obtained in Reference Example 221, the title compound was synthesized in the same manner as in Reference Example 24. Yield 84%. Oily matter.

$^1$H-NMR (CDCl$_3$) δ: 1.20 (6H, d, J=6.9 Hz), 1.28 (3H, d, J=6.9 Hz), 2.16 (3H, s), 2.24 (3H, s), 2.80-2.90 (1H, septet, J=6.9 Hz), 3.40-3.55 (1H, m), 3.85-3.95 (4H, m), 4.17 (1H, dd, J=3.3, 8.7 Hz), 4.53 (1H, t, J=8.7 Hz), 7.07 (4H, s), 7.25-7.38 (5H, m) 1H unidentified.

REFERENCE EXAMPLE 264

N-Benzyl-3-ethyl-7-(4-isopropylbenzyl)-4,6-dimethyl-2,3-dihydro-1-benzofuran-5-amine Using 5-bromo-3-ethyl-7-(4-isopropylbenzyl)-4,6-dimethyl-2,3-dihydro-1-benzofuran obtained in Reference Example 222, the title compound was synthesized in the same manner as in Reference Example 24. Yield 76%. Oily matter.

$^1$H-NMR (CDCl$_3$) δ: 0.92 (3H, t, J=7.5 Hz), 1.20 (6H, d, J=6.9 Hz), 1.50-1.66 (2H, m), 2.15 (3H, s), 2.21 (3H, s), 2.84 (1H, septet, J=6.9 Hz), 2.88 (1H, br), 3.26-3.37 (1H, m), 3.87-4.00 (4H, m), 4.34 (1H, dd, J=3.0, 9.0 Hz), 4.46 (1H, t, J=9.0 Hz), 7.06 (4H, s), 7.25-7.38 (5H, s).

REFERENCE EXAMPLE 265

N-Benzyl-7-(4-isopropylbenzyl)-4,6-dimethyl-3-propyl-2,3-dihydro-1-benzofuran-5-amine Using 5-bromo-7-(4-isopropylbenzyl)-4,6-dimethyl-3-propyl-2,3-dihydro-1-benzofuran obtained in Reference Example 223, the title compound was synthesized in the same manner as in Reference Example 24. Yield 85%. Oily matter.

$^1$H-NMR (CDCl$_3$) δ: 0.94 (3H, t, J=7.2 Hz), 1.21 (6H, d, J=6.9 Hz), 1.27-1.42 (2H, m), 1.50-1.63 (2H, m), 2.15 (3H, s), 2.22 (3H, s), 2.84 (1H, septet, J=6.9 Hz), 2.89 (1H, br), 3.30-3.39 (1H, m), 3.93 (2H, s), 4.34 (1H, dd, J=3.3, 9.0 Hz), 4.45 (1H, t, J=9.0 Hz), 7.08 (4H, s), 7.09 (2H, d, J=8.4 Hz), 7.16-7.40 (5H, m).

REFERENCE EXAMPLE 266

N-Benzyl-3-isopropyl-7-(4-isopropylbenzyl)-4,6-dimethyl-2,3-dihydro-1-benzofuran-5-amine Using 5-bromo-3-isopropyl-7-(4-isopropylbenzyl)-4,6-dimethyl-2,3-dihydro-1-benzofuran obtained in Reference Example 224, the title compound was synthesized in the same manner as in Reference Example 24. Yield 73%. Oily matter.

$^1$H-NMR (CDCl$_3$) δ: 0.73 (3H, d, J=6.9 Hz), 0.99 (3H, d, J=6.9 Hz), 1.21 (6H, d, J=6.9 Hz), 2.01-2.10 (1H, m), 2.14 (3H, s), 2.19 (3H, s), 2.84 (1H, septet, J=6.9 Hz), 2.90 (1H, br), 3.30-3.35 (1H, m), 3.81-4.01 (4H, m), 4.34 (1H, t, J=9.0 Hz), 4.47 (1H, dd, J=2.7, 9.0 Hz), 7.06 (4H, s), 7.24-7.36 (5H, m).

REFERENCE EXAMPLE 267

N-Benzyl-3-(4-isopropylbenzyl)-4-methoxy-2,6-dimethylaniline

Using 5-bromo-2,4,6-trimethyl-2,3-dihydro-1-benzofuran obtained in Reference Example 244, the title compound was synthesized in the same manner as in Reference Example 24.

Yield: quantitative. Oily matter.

$^1$H-NMR (CDCl$_3$) δ: 1.20 (6H, d, J=6.9 Hz), 2.19 (3H, s), 2.28 (3H, s), 2.84 (1H, septet, J=6.9 Hz), 3.76 (3H, s), 3.95 (2H, s), 4.02 (2H, s), 6.63 (1H, s), 7.01 (2H, d, J=8.1 Hz), 7.07 (2H, d, J=8.1 Hz), 7.24-7.37 (5H, m), 1H unidentified.

REFERENCE EXAMPLE 268

N-Benzyl-2,4,6-trimethyl-2,3-dihydro-1-benzofuran-5-amine

Using 4-bromo-2-(4-isopropylbenzyl)-1-methoxy-3,5-dimethylbenzene obtained in Reference Example 225, the title compound was synthesized in the same manner as in Reference Example 24. Yield 70%. Oily matter.

$^1$H-NMR (CDCl$_3$) δ: 1.45 (3H, d, J=6.3 Hz), 2.19 (3H, s), 2.23 (3H, s), 2.70 (1H, dd, J=7.5, 15.0 Hz), 3.21 (1H, dd, J=8.7, 15.0 Hz), 3.95 (2H, s), 4.85-4.97 (1H, m), 6.45 (1H, s), 7.25-7.41 (5H, m), 1H unidentified.

REFERENCE EXAMPLE 269

N-Benzyl-7-(4-isopropylbenzyl)-3,4,6-trimethyl-1-benzofuran-5-amine

Using 5-bromo-7-(4-isopropylbenzyl)-3,4,6-trimethyl-1-benzofuran obtained in Reference Example 190, the title compound was obtained in the same manner as in Reference Example 24. Yield 93%. Oily matter.

$^1$H-NMR (CDCl$_3$) δ: 1.20 (6H, d, J=6.9 Hz), 2.26 (3H, s), 2.38 (3H, s), 2.60 (3H, s), 2.83 (1H, septet, J=6.9 Hz), 3.11 (1H, br s), 3.98 (2H, s), 4.23 (2H, s), 7.05 (4H, s), 7.24-7.41 (6H, m).

REFERENCE EXAMPLE 270

N-Benzyl-4,6-dimethyl-2,3-dihydro-1-benzofuran-5-amine

Using 5-bromo-4,6-dimethyl-2,3-dihydro-1-benzofuran obtained in Reference Example 226, the title compound was obtained in the same manner as in Reference Example 24. Yield 89%. Oily matter.

$^1$H-NMR (CDCl$_3$) δ: 2.21 (3H, s), 2.22 (3H, s), 3.10 (2H, t, J=8.7 Hz), 3.96 (2H, s), 4.53 (2H, t, J=8.7 Hz), 6.49 (1H, s), 7.24-7.40 (5H, m), 1H unidentified.

REFERENCE EXAMPLE 271

N-Benzyl-7-(4-isopropylbenzyl)-4,6-dimethyl-2,3-dihydro-1-benzofuran-5-amine

Using 5-bromo-7-(4-isopropylbenzyl)-4,6-dimethyl-2,3-dihydro-1-benzofuran obtained in Reference Example 227, the title compound was obtained in the same manner as in Reference Example 24. Yield 84%. Melting point: 115-116° C. (methanol).

$^1$H-NMR (CDCl$_3$) δ: 1.20 (6H, d, J=6.9 Hz), 2.15 (3H, s), 2.20 (3H, s), 2.84 (1H, septet, J=6.9 Hz), 3.14 (2H, t, J=8.7 Hz), 3.92 (2H, s), 3.94 (2H, s), 4.53 (2H, t, J=8.7 Hz), 7.07 (4H, s), 7.24-7.40 (5H, m), 1H unidentified.

REFERENCE EXAMPLE 272

5-(Benzylamino)-7-(4-isopropylbenzyl)-2,2,4,6-tetramethyl-1-benzofuran-3(2H)-one To a solution of 2-(2-(4-isopropylbenzyl)-3,5-dimethylphenoxy)-2-methylpropanoic acid obtained in Reference Example 156 (5.55 g, 16.3 mmol) in THF (50 mL) was added dropwise oxalyl chloride (2.13 mL, 24.5 mmol) with ice-cooling. The mixture was stirred for 20 minutes, and DMF (3 drops) was added thereto, and the mixture was stirred with ice-cooling for 30 minutes, and then, was warmed to room temperature. The solvent was removed by concentration under reduced pressure, and to a solution of the residue in dichloromethane (50 mL) was added aluminum chloride (3.26 g, 24.5 mmol) at −78° C., and the mixture was slowly warmed to room temperature. Ice was added to the reaction solution to separate the organic layer, and the aqueous layer was extracted with ethyl acetate. The combined organic layer was washed with a saturated sodium hydrogen carbonate solution, dried over anhydrous sodium sulfate, filtered, and then concentrated under reduced pressure. The obtained residue was purified by silica gel column chromatography (ethyl acetate:hexane=1:4) to obtain 3.35 g (yield 64%) of 7-(4-isopropylbenzyl)-2,2,4,6-tetramethyl-1-benzofuran-3(2H)-one as crude product. To a solution of this compound (3.35 g, 10.4 mmol) in acetonitrile (40 mL) was added N-bromosuccinimide (1.85 g, 10.4 mmol) with ice-cooling, and the mixture was stirred for 30 minutes. The reaction solution was warmed to room temperature, to which water was added, which was extracted with ethyl acetate. The combined organic layer was washed with a saturated brine, dried over anhydrous sodium sulfate, filtered, and then concentrated under reduced pressure. The obtained residue was purified by silica gel column chromatography (ethyl acetate:hexane=1:19) to obtain 2.76 g (yield 66%) of 5-bromo-7-(4-isopropylbenzyl)-2,2,4,6-tetramethyl-1-benzofuran-3(2H)-one as crude product. The compound (2.76 g, 6.89 mmol), palladium acetate (31 mg, 0.14 mmol) and BINAP (257 mg, 0.41 mmol) were mixed at room temperature, and the mixture was stirred under argon stream for 15 minutes. To the reaction solution was added sodium tert-butoxide (926 mg, 9.63 mmol) at room temperature, and the mixture was heated under argon stream at 110° C. for 16 hours. Water was added to the reaction solution, which was extracted with ethyl acetate. The combined organic layer was washed with water and a saturated brine, dried over anhydrous sodium sulfate, filtered, and then concentrated under reduced pressure. The obtained residue was purified by silica gel column chromatography (ethyl acetate:hexane=1:9) to obtain 675 mg (yield 23%) of the title compound. Oily matter.

$^1$H-NMR (CDCl$_3$) δ: 1.21 (6H, d, J=6.9 Hz), 1.57 (6H, s), 2.28 (3H, s), 2.54 (3H, s), 2.86 (1H, septet, J=6.9 Hz), 3.03 (1H, br s), 3.93 (2H, s), 4.04 (2H, s), 7.10 (4H, s), 7.26-7.47 (5H, m).

REFERENCE EXAMPLE 273

N-Benzyl-3-(4-isopropyl-2-methoxyphenyl)-4,6,7-trimethyl-2,3-dihydro-1-benzofuran-5-amine Using 5-bromo-3-(4-isopropyl-2-methoxyphenyl)-4,6,7-trimethyl-2,3-dihydro-1-benzofuran obtained in Reference Example 251, the title compound was synthesized in the same manner as in Example 24. Yield 98%. Oily matter.

$^1$H-NMR (CDCl$_3$) δ: 1.23 (6H, d, J=6.9 Hz), 1.90 (3H, s), 2.18 (3H, s), 2.28 (3H, s), 2.86 (1H, septet, J=6.9 Hz), 3.00 (1H, br s), 3.87 (3H, s), 3.95 (2H, s), 4.30 (1H, dd, J=3.3, 8.4 Hz), 4.78 (1H, t, J=8.4 Hz), 4.85 (1H, dd, J=3.3, 8.4 Hz), 6.60 (1H, d, J=7.5 Hz), 6.66 (1H, d, J=7.5 Hz), 6.73 (1H, s), 7.26-7.40 (5H, m).

REFERENCE EXAMPLE 274

N-Benzyl-3-(3-(1,3-dioxolan-2-yl)phenyl)-4,6,7-trimethyl-2,3-dihydro-1-benzofuran-5-amine Using 5-bromo-3-(3-(1,3-dioxolan-2-yl)phenyl)-4,6,7-trimethyl-2,3-dihydro-1-benzofuran obtained in Reference Example 249, the title compound was synthesized in the same manner as in Reference Example 24. Yield 90%. Melting point: 97-99° C. (methanol).

$^1$H-NMR (CDCl$_3$) δ: 1.85 (3H, s), 2.17 (3H, s), 2.26 (3H, s), 2.83 (1H, br s), 3.90 (2H, s), 4.00-4.16 (4H, m), 4.37 (1H, dd, J=4.8, 9.0 Hz), 4.59 (1H, dd, J=4.8, 9.0 Hz), 4.82 (1H, t, J=9.0 Hz), 5.76 (1H, s), 7.06-7.10 (1H, m), 7.23-7.36 (8H, m).

REFERENCE EXAMPLE 275

N-Benzyl-3-(3-methoxyphenyl)-4,6,7-trimethyl-2,3-dihydro-1-benzofuran-5-amine

Using 3-(3-methoxyphenyl)-4,6,7-trimethyl-2,3-dihydro-1-benzofuran obtained in Reference Example 204, 5-bromo-3-(3-methoxyphenyl)-4,6,7-trimethyl-2,3-dihydro-1-benzofuran was obtained in the same manner as in Reference Example 23. Using this compound, the title compound was synthesized in the same manner as in Reference Example 24. Yield 76%. Oily matter.

$^1$H-NMR (CDCl$_3$) δ: 1.88 (3H, s), 2.19 (3H, s), 2.26 (3H, s), 3.90 (1H, br), 3.77 (3H, s), 3.91 (2H, s), 4.38 (1H, dd,

J=4.8, 8.7 Hz), 4.53 (1H, dd, J=4.8, 8.7 Hz), 4.81 (1H, t, J=8.7 Hz), 6.70-6.77 (3H, m), 7.17-7.38 (6H, m).

REFERENCE EXAMPLE 276

N-Benzyl-4,6,7-trimethyl-3-phenyl-2,3-dihydro-1-benzofuran-5-amine

Using 5-bromo-4,6,7-trimethyl-3-phenyl-2,3-dihydro-1-benzofuran obtained in Reference Example 239, the title compound was synthesized in the same manner as in Reference Example 24. Yield 91%. Melting point: 107-108° C. (methanol).
$^1$H-NMR (CDCl$_3$) δ: 1.86 (3H, s), 2.20 (3H, s), 2.27 (3H, s), 2.93 (1H, br s), 3.91 (2H, s), 4.38 (1H, dd, J=4.5, 9.0 Hz), 4.55 (1H, dd, J=4.5, 9.0 Hz), 4.83 (1H, t, J=9.0 Hz), 7.09-7.34 (10H, m).

REFERENCE EXAMPLE 277

5-Benzyl-4,6,7-trimethyl-3-(4-methylphenyl)-2,3-dihydro-1-benzofuran-5-amine

Using 5-bromo-4,6,7-trimethyl-3-(4-methylphenyl)-2,3-dihydro-1-benzofuran obtained in Reference Example 240, the title compound was synthesized in the same manner as in Reference Example 24. Yield 88%. Melting point: 99-100° C. (hexane).
$^1$H-NMR (CDCl$_3$) δ: 1.87 (3H, s), 2.20 (3H, s), 2.27 (3H, s), 2.31 (3H, s), 2.91 (1H, br s), 3.90 (2H, s), 4.35 (1H, dd, J=4.5, 9.0 Hz), 4.52 (1H, dd, J=4.5, 9.0 Hz), 4.81 (1H, t, J=9.0 Hz), 7.01 (2H, d, J=8.4 Hz), 7.08 (2H, d, J=8.4 Hz), 7.23-7.40 (5H, m).

REFERENCE EXAMPLE 278

N-Benzyl-4,6,7-trimethyl-3-(5-methylpyridin-2-yl)-2,3-dihydro-1-benzofuran-5-amine Using 5-methyl-2-(5-bromo-4,6,7-trimethyl-2,3-dihydro-1-benzofuran-3-yl)pyridine obtained in Reference Example 242, the title compound was synthesized in the same manner as in Reference Example 24. Yield 79%. Melting point: 104-105° C. (methanol).
$^1$H-NMR (CDCl$_3$) δ: 1.90 (3H, s), 2.19 (3H, s), 2.26 (3H, s), 2.30 (3H, s), 2.92 (1H, br s), 3.91 (2H, s), 4.52 (1H, dd, J=4.5, 8.4 Hz), 4.73 (1H, dd, J=4.5, 8.4 Hz), 4.85 (1H, t, J=8.4 Hz), 6.84 (1H, d, J=7.8 Hz), 7.25-7.37 (6H, m), 8.36 (1H, s).

REFERENCE EXAMPLE 279

N-Benzyl-3-(biphenyl-4-yl)-4,6,7-trimethyl-2,3-dihydro-1-benzofuran-5-amine

Using 5-bromo-3-(biphenyl-4-yl)-4,6,7-trimethyl-2,3-dihydro-1-benzofuran obtained in Reference Example 243, the title compound was synthesized in the same manner as in Reference Example 24. Yield 85%. Melting point: 77-78° C. (hexane).
$^1$H-NMR (CDCl$_3$) δ: 1.90 (3H, s), 2.22 (3H, s), 2.28 (3H, s), 2.94 (1H, br s), 3.92 (2H, s), 4.42 (1H, dd, J=4.4, 8.8 Hz), 4.59 (1H, dd, J=4.4, 8.8 Hz), 4.85 (1H, t, J=8.8 Hz), 7.19 (2H, d, J=8.0 Hz), 7.25-7.64 (12H, m).

REFERENCE EXAMPLE 280

N-Benzyl-3-(4-isopropylphenyl)-4,6,7-trimethyl-1-benzofuran-5-amine

Using 5-bromo-3-(4-isopropylphenyl)-4,6,7-trimethyl-1-benzofuran obtained in Reference Example 193, the title compound was synthesized in the same manner as in Reference Example 24. Yield: quantitative. Oily matter.
$^1$H-NMR (CDCl$_3$) δ: 1.30 (6H, d, J=6.9 Hz), 2.18 (3H, s), 2.39 (3H, s), 2.47 (3H, s), 2.97 (1H, septet, J=6.9 Hz), 3.13 (1H, br s), 3.99 (2H, s), 7.25-7.44 (10H, m).

REFERENCE EXAMPLE 281

N-Benzyl-3-(4-ethylphenyl)-4,6,7-trimethyl-1-benzofuran-5-amine

Using 5-bromo-3-(4-ethylphenyl)-4,6,7-trimethyl-1-benzofuran obtained in Reference Example 262, the title compound was synthesized in the same manner as in Reference Example 24. Yield 93%. Oily matter.
$^1$H-NMR (CDCl$_3$) δ: 1.29 (3H, t, J=7.5 Hz), 2.17 (3H, s), 2.38 (3H, s), 2.47 (3H, s), 2.71 (2H, q, J=7.5 Hz), 3.13 (1H, br s), 3.99 (2H, s), 7.20-7.47 (10H, m).

REFERENCE EXAMPLE 282

N-Benzyl-3-(4-isobutylphenyl)-4,6,7-trimethyl-1-benzofuran-5-amine

Using 5-bromo-4,6,7-trimethyl-1-benzofuran-3-yl trifluoromethanesulfonate obtained in Reference Example 261 and (4-isobutylphenyl)boronic acid, 5-bromo-3-(4-isobutylphenyl)-4,6,7-trimethyl-1-benzofuran was synthesized in the same manner as in Reference Example 262. Using this compound, the title compound was synthesized in the same manner as in Reference Example 24. Yield 74%. Oily matter.
$^1$H-NMR (CDCl$_3$) δ: 0.94 (6H, d, J=7.0 Hz), 1.91 (1H, septet, J=6.9 Hz), 2.16 (3H, s), 2.38 (3H, s), 2.47 (3H, s), 2.53 (2H, d, J=7.0 Hz), 3.12 (1H, br), 3.99 (2H, s), 7.15-7.47 (10H, m).

REFERENCE EXAMPLE 283

N-Benzyl-3-(4-cyclohexylphenyl)-4,6,7-trimethyl-1-benzofuran-5-amine

Using 5-bromo-4,6,7-trimethyl-1-benzofuran-3-yl trifluoromethanesulfonate obtained in Reference Example 261 and (4-cyclohexylphenyl)boronic acid, 5-bromo-3-(4-cyclohexylphenyl)-4,6,7-trimethyl-1-benzofuran was synthesized in the same manner as in Reference Example 262. Using this compound, the title compound was synthesized in the same manner as in Reference Example 24. Yield 61%. Oily matter.
$^1$H-NMR (CDCl$_3$) δ: 1.26-1.52 (4H, m), 1.73-2.00 (6H, m), 2.17 (3H, s), 2.38 (3H, s), 2.47 (3H, s), 2.50-2.60 (1H, m), 3.15 (1H, br), 3.99 (2H, s), 7.20-7.48 (10H, m).

REFERENCE EXAMPLE 284

N-Benzyl-3-(4-(1,3-dioxolan-2-yl)phenyl)-4,6,7-trimethyl-2,3-dihydro-1-benzofuran-5-amine Using 5-bromo-3-(4-(1,3-(dioxolan-2-yl)phenyl)-4,6,7-trimethyl-2,3-dihydro-1-benzofuran obtained in Reference Example 250, the title compound was synthesized in the same manner as in Reference Example 24. Yield 88%. Oily matter.

$^1$H-NMR (CDCl$_3$) δ: 1.85 (3H, s), 1.20 (3H, s), 2.26 (3H, s), 3.89 (2H, s), 3.98-4.17 (4H, m), 4.35 (1H, dd, J=4.4, 9.0 Hz), 4.56 (1H, dd, J=4.4, 9.0 Hz), 4.82 (1H, t, J=9.0 Hz), 5.77 (1H, s), 7.14 (2H, d, J=8.0 Hz), 7.25-7.41 (7H, m). 1H unidentified.

REFERENCE EXAMPLE 285

N-Benzyl-3-(4-isopropylphenyl)-4,7-dimethyl-2,3-dihydro-1-benzofuran-5-amine

Using 5-bromo-3-(4-isopropylphenyl)-4,7-dimethyl-2,3-dihydro-1-benzofuran synthesized in Reference Example 241, the title compound was synthesized in the same manner as in Reference Example 24. Yield 96%. Melting point: 82-83° C. (methanol).

$^1$H-NMR (CDCl$_3$) δ: 1.22 (6H, d, J=6.9 Hz), 1.90 (3H, s), 2.27 (3H, s), 2.67-3.02 (2H, m), 3.93 (2H, s), 4.38 (1H, dd, J=8.4, 4.5 Hz), 4.49 (1H, dd, J=9.0, 4.5 Hz), 4.75-4.83 (1H, m), 6.59 (1H, s), 7.02 (2H, d, J=8.1 Hz), 7.12 (2H, d, J=8.1 Hz), 7.19-7.39 (5H, m).

REFERENCE EXAMPLE 286

N-Benzyl-3-(4-isopropylphenyl)-4,5,7-trimethyl-2,3-dihydro-1-benzofuran-6-amine

Using 6-bromo-3-(4-isopropylphenyl)-4,5,7-trimethyl-2,3-dihydro-1-benzofuran synthesized in Reference Example 238, the title compound was synthesized in the same manner as in Reference Example 24. Yield 76%. Oily matter.

$^1$H-NMR (CDCl$_3$) δ: 1.23 (6H, d, J=6.9 Hz), 1.91 (3H, s), 2.13 (3H, s), 2.17 (3H, s), 2.87 (1H, septet, J=6.9 Hz), 4.05 (2H, s), 4.38 (1H, dd, J=8.7, 4.5 Hz), 4.52 (1H, dd, J=9.0, 4.5 Hz), 4.79 (1H, t, J=9.0 Hz), 7.03 (2H, d, J=8.1 Hz), 7.12 (2H, d, J=8.1 Hz), 7.21-7.42 (5H, m), 1H unidentified.

REFERENCE EXAMPLE 287

N-Benzyl-3-(4-isopropylphenyl)-4,5,6-trimethyl-2,3-dihydro-1-benzofuran-7-amine

Using 7-bromo-3-(4-isopropylphenyl)-4,5,6-trimethyl-2,3-dihydro-1-benzofuran synthesized in Reference Example 256, the title compound was synthesized in the same manner as in Reference Example 24. Yield 81%. Oily matter.

$^1$H-NMR (CDCl$_3$) δ: 1.22 (6H, d, J=6.9 Hz), 1.89 (3H, s), 2.07 (3H, s), 2.19 (3H, s), 2.86 (1H, septet, J=6.9 Hz), 4.23-4.52 (4H, m), 4.75 (1H, t, J=8.7 Hz), 6.99 (2H, d, J=7.8 Hz), 7.12 (2H, d, J=7.8 Hz), 7.19-7.39 (5H, m), 1H unidentified.

REFERENCE EXAMPLE 288

N-Benzyl-3-(4-isopropylphenyl)-4-methyl-2,3-dihydronaphtho[1,2-b]furan-5-amine

Using 5-bromo-3-(4-isopropylphenyl)-4-methyl-2,3-dihydronaphtho[1,2-b]furan synthesized in Reference Example 255, the title compound was synthesized in the same manner as in Reference Example 24. Yield 53%. Oily matter.

$^1$H-NMR (CDCl$_3$) δ: 1.22 (6H, d, J=6.9 Hz), 1.95 (3H, s), 2.86 (1H, septet, J=6.9 Hz), 3.25 (1H, br s), 4.14 (2H, s), 4.60 (1H, dd, J=8.7, 4.8 Hz), 4.70 (1H, dd, J=9.3, 4.8 Hz), 5.02 (1H, t, J=9.0 Hz), 7.03 (2H, d, J=8.1 Hz), 7.12 (2H, d, J=8.1 Hz), 7.20-7.57 (7H, m), 7.98-8.04 (1H, m), 8.13-8.18 (1H, m).

REFERENCE EXAMPLE 289

N-Benzyl-3-(4-isopropylphenyl)-4-methyl-2,3,6,7,8,9-hexahydronaphtho[1,2-b]furan-5-amine Using 5-bromo-3-(4-isopropylphenyl)-4-methyl-2,3,6,7,8,9-hexahydronaphtho[1,2-b]furan synthesized in Reference Example 257, the title compound was synthesized in the same manner as in Reference Example 24. Yield 84%. Melting point: 98-99° C. (hexane-ethyl acetate).

$^1$H-NMR (CDCl$_3$) δ: 1.23 (6H, d, J=6.9 Hz), 1.72-1.87 (4H, m), 1.91 (3H, s), 2.60-2.78 (4H, m), 2.87 (1H, septet, J=6.9 Hz), 3.92 (2H, s), 4.41 (1H, dd, J=8.7, 5.1 Hz), 4.52 (1H, dd, J=9.3, 5.1 Hz), 4.82 (1H, t, J=9.0 Hz), 7.06 (2H, d, J=8.1 Hz), 7.13 (2H, d, J=8.1 Hz), 7.20-7.40 (5H, m), 1H unidentified.

REFERENCE EXAMPLE 290

N-Benzyl-3-(4-isopropylphenyl)-4-methyl-3,6,7,8-tetrahydro-2H-indeno[4,5-b]furan-5-amine Using 5-bromo-3-(4-isopropylphenyl)-4-methyl-3,6,7,8-tetrahydro-2H-indeno[4,5-b]furan synthesized in Reference Example 258, the title compound was synthesized in the same manner as in Reference Example 24. Yield 76%. Melting point: 95-96° C. (hexane-ethyl acetate).

$^1$H-NMR (CDCl$_3$) δ: 1.23 (6H, d, J=6.9 Hz), 1.87 (3H, s), 2.10 (2H, quintet, J=7.5 Hz), 2.76-2.93 (6H, m), 4.05 (2H, s), 4.41 (1H, dd, J=8.7, 4.8 Hz), 4.50 (1H, dd, J=9.0, 4.8 Hz), 4.83 (1H, t, J=8.7 Hz), 7.04 (2H, d, J=8.1 Hz), 7.13 (2H, d, J=8.1 Hz), 7.20-7.37 (5H, m)

REFERENCE EXAMPLE 291

3-(4-isopropylphenyl)-4,6-dimethyl-2,3-dihydro-1-benzothiophene-5-amine

To a solution of 5-bromo-3-(4-isopropylphenyl)-4,6-dimethyl-2,3-dihydro-1-benzothiophene obtained in Reference Example 259 (870 mg, 2.41 mmol) and benzophenone imine (0.76 mL, 2.89 mmol) in toluene (15 mL) were added tris(dibenzylideneacetone)dipalladium (22 mg, 0.024 mmol) and BINAP (45 mg, 0.072 mmol) at room temperature, and the mixture was stirred under argon atmosphere for 15 minutes. To the reaction solution was added sodium tert-butoxide (324 mg, 3.37 mmol) at room temperature, and the mixture was heated under reflux under argon stream for 16 hours. Water was added to the reaction solution, which was extracted with ethyl acetate, and the organic layer was washed with water and a saturated brine, was dried over anhydrous sodium sulfate, and then the solvent was distilled off under reduced pressure to obtain the crude product of N-(diphenylmethylene)-3-(4-isopropylphenyl)-4,6-dimethyl-2,3-dihydro-1-benzothien-5-amine. This compound was dissolved in THF (10 mL), to which 1 N hydrochloric acid (2 mL) was added, and the mixture then was heated under reflux for 30 minutes. The solvent was concentrated under reduced pressure to obtain the residue, which was neutralized with 1 N aqueous sodium hydroxide solution. The product was extracted with ethyl acetate. The combined extract was washed with water, dried over magnesium sulfate, and then concentrated under reduced pressure. The obtained residue was purified by silica gel column chromatography (ethyl acetate:hexane=1:10) to obtain 521 mg (yield 73%) of the title compound. Melting point: 121-122° C. (hexane-ethyl acetate).

$^1$H-NMR (CDCl$_3$) δ: 1.21 (6H, d, J=6.9 Hz), 1.88 (3H, s), 2.17 (3H, s), 2.85 (1H, septet, J=6.9 Hz), 3.11 (1H, dd, J=11.1, 1.8 Hz), 3.42 (2H, br s), 3.89 (1H, dd, J=11.1, 8.7 Hz), 4.64 (1H, d, J=8.7 Hz), 6.90 (1H, s), 7.02 (2H, d, J=8.1 Hz), 7.09 (2H, d, J=8.1 Hz).

REFERENCE EXAMPLE 292

7-(4-Isopropylbenzyl)-3,4,6-trimethyl-2,3-dihydro-1-benzofuran-5-amine

Using N-benzyl-7-(4-isopropylbenzyl)-3,4,6-trimethyl-2,3-dihydro-1-benzofuran-5-amine obtained in Reference Example 263, the title compound was synthesized in the same manner as in Reference Example 30. Yield 84%. Oily matter.

$^1$H-NMR (CDCl$_3$) δ: 1.19 (6H, d, J=6.9 Hz), 1.27 (3H, d, J=7.2 Hz), 2.02 (3H, br s), 2.15 (3H, br s), 2.80-2.90 (1H, septet, J=6.9 Hz), 3.29 (2H, br s), 3.44 (1H, br s), 3.95 (2H, m), 4.15 (1H, br s), 4.74 (1H, br s), 7.06 (4H, s).

REFERENCE EXAMPLE 293

3-Ethyl-7-(4-isopropylbenzyl)-4,6-dimethyl-2,3-dihydro-1-benzofuran-5-amine

Using N-benzyl-3-ethyl-7-(4-isopropylbenzyl)-4,6-dimethyl-2,3-dihydro-1-benzofuran-5-amine obtained in Reference Example 264, the title compound was synthesized in the same manner as in Reference Example 30. Yield 93%. Oily matter.

$^1$H-NMR (CDCl$_3$) δ: 0.93 (3H, t, J=7.5 Hz), 1.20 (6H, d, J=6.9 Hz), 1.50-1.61 (2H, m), 2.02 (3H, s), 2.14 (3H, s), 2.83 (1H, septet, J=6.9 Hz), 3.23-3.31 (3H, m), 3.94 (2H, s), 4.32 (1H, dd, J=2.7, 8.7 Hz), 4.40 (1H, t, J=9.0 Hz), 7.05 (4H, s).

REFERENCE EXAMPLE 294

7-(4-Isopropylbenzyl)-4,6-dimethyl-3-propyl-2,3-dihydro-1-benzofuran-5-amine

Using N-benzyl-7-(4-isopropylbenzyl)-4,6-dimethyl-3-propyl-2,3-dihydro-1-benzofuran-5-amine obtained in Reference Example 265, the title compound was synthesized in the same manner as in Reference Example 30. Yield 85%. Oily matter.

$^1$H-NMR (CDCl$_3$) δ: 0.93 (3H, t, J=7.2 Hz), 1.21 (6H, d, J=6.9 Hz), 1.30-1.43 (2H, m), 1.50-1.63 (2H, m), 2.02 (3H, s), 2.14 (3H, s), 2.83 (1H, septet, J=6.9 Hz), 3.30-3.39 (3H, m), 3.94 (2H, s), 4.31 (1H, dd, J=3.3, 8.7 Hz), 4.39 (1H, t, J=8.7 Hz), 7.06 (4H, s).

REFERENCE EXAMPLE 295

3-Isopropyl-7-(4-isopropylbenzyl)-4,6-dimethyl-2,3-dihydro-1-benzofuran-5-amine

Using N-benzyl-3-isopropyl-7-(4-isopropylbenzyl)-4,6-dimethyl-2,3-dihydro-1-benzofuran-5-amine obtained in Reference Example 266, the title compound was synthesized in the same manner as in Reference Example 30. Yield 74%. Oily matter.

$^1$H-NMR (CDCl$_3$) δ: 0.72 (3H, d, J=6.9 Hz), 0.99 (3H, d, J=6.9 Hz), 1.19 (6H, d, J=6.9 Hz), 2.01 (3H, s), 2.01-2.08 (1H, m), 2.14 (3H, s), 2.82 (1H, septet, J=6.9 Hz), 3.23-3.35 (3H, m), 3.88 (1H, d, J=15.6 Hz), 3.99 (1H, d, J=15.6 Hz), 4.29 (1H, t, J=9.0 Hz), 4.44 (1H, dd, J=2.4, 9.0 Hz), 7.04 (4H, s).

REFERENCE EXAMPLE 296

7-(4-Isopropylbenzyl)-3,4,6-trimethyl-1-benzofuran-5-amine

Using N-benzyl-7-(4-isopropylbenzyl)-3,4,6-trimethyl-1-benzofuran-5-amine obtained in Reference Example 269, the title compound was synthesized in the same manner as in Reference Example 30. Yield 87%. Oily matter.

$^1$H-NMR (CDCl$_3$) δ: 1.19 (6H, d, J=6.9 Hz), 2.16 (3H, s), 2.38 (3H, s), 2.44 (3H, s), 2.82 (1H, septet, J=6.9 Hz), 3.46 (2H, br s), 4.24 (2H, s), 7.06 (4H, s), 7.24 (1H, s).

REFERENCE EXAMPLE 297

4,6-Dimethyl-2,3-dihydro-1-benzofuran-5-amine

Using N-benzyl-4,6-dimethyl-2,3-dihydro-1-benzofuran-5-amine obtained in Reference Example 270, the title compound was synthesized in the same manner as in Reference Example 30. Yield 86%. Melting point: 85-86° C. (ethyl acetate-hexane).

$^1$H-NMR (CDCl$_3$) δ: 2.11 (3H, s), 2.15 (3H, s), 3.10 (2H, t, J=8.7 Hz), 3.27 (2H, br s), 4.48 (2H, t, J=8.7 Hz), 6.44 (1H, s).

REFERENCE EXAMPLE 298

7-(4-Isopropylbenzyl)-4,6-dimethyl-2,3-dihydro-1-benzofuran-5-amine

Using N-benzyl-7-(4-isopropylbenzyl)-4,6-dimethyl-2,3-dihydro-1-benzofuran-5-amine obtained in Reference Example 271, the title compound was synthesized in the same manner as in Reference Example 30. Yield 92%. Melting point: 114-115° C. (ethyl acetate-hexane).

$^1$H-NMR (CDCl$_3$) δ: 1.19 (6H, d, J=6.9 Hz), 2.03 (3H, s), 2.11 (3H, s), 2.83 (1H, septet, J=6.9 Hz), 3.14 (2H, t, J=8.7 Hz), 3.20 (2H, br), 3.95 (2H, s), 4.48 (2H, t, J=8.7 Hz), 7.06 (4H, s).

REFERENCE EXAMPLE 299

5-Amino-(4-isopropylbenzyl)-2,2,4,6-tetramethyl-1-benzofuran-3(2H)-one

Using 5-(benzylamino)-7-(4-isopropylbenzyl)-2,2,4,6-tetramethyl-1-benzofuran-3(2H)-one obtained in Reference Example 272, the title compound was synthesized in the same manner as in Reference Example 30. Yield 99%. Oily matter.

$^1$H-NMR (CDCl$_3$) δ: 1.22 (6H, d, J=6.9 Hz), 1.43 (6H, s), 2.14 (3H, s), 2.47 (3H, s), 2.84 (1H, septet, J=6.9 Hz), 3.42 (2H, br s), 4.04 (2H, s), 7.08 (4H, s).

REFERENCE EXAMPLE 300

(3-(4-Isopropylbenzyl)-4-methoxy-2,6-dimethylphenyl)amine

Using N-benzyl-3-(4-isopropylbenzyl)-4-methoxy-2,6-dimethylaniline obtained in Reference Example 267, the title compound was synthesized in the same manner as in Reference Example 30. Yield 86%. Melting point: 91-92° C. (ethyl acetate-hexane).

¹H-NMR (CDCl₃) δ: 1.20 (6H, d, J=6.9 Hz), 2.06 (3H, s), 2.21 (3H, s), 2.83 (1H, septet, J=6.9 Hz), 3.26 (2H, br s), 3.73 (3H, s), 4.04 (2H, s), 6.61 (1H, s), 7.02 (2H, d, J=8.1 Hz), 7.07 (2H, d, J=8.1 Hz).

REFERENCE EXAMPLE 301

3-(3-(1,3-(Dioxolan-2-yl)phenyl)-4,6,7-trimethyl-2,3-dihydro-1-benzofuran-5-amine Using N-benzyl-3-(3-(1,3-dioxolan-2-yl)phenyl)-4,6,7-trimethyl-2,3-dihydro-1-benzofuran-5-amine obtained in Reference Example 274, the title compound was synthesized in the same manner as in Reference Example 30. Yield 81%. Melting point: 138-139° C. (ethyl acetate-hexane).

¹H-NMR (CDCl₃) δ: 1.81 (3H, s), 2.12 (3H, s), 2.20 (3H, s), 3.26 (2H, br s), 4.00-4.16 (4H, m), 4.32 (1H, dd, J=4.8, 9.0 Hz), 4.59 (1H, dd, J=4.8, 9.0 Hz), 4.77 (1H, t, J=9.0 Hz), 5.75 (1H, s), 7.08-7.12 (1H, m), 7.26-7.36 (3H, m).

REFERENCE EXAMPLE 302

3-(3-Methoxyphenyl)-4,6,7-trimethyl-2,3-dihydro-1-benzofuran-5-amine

Using N-benzyl-3-(3-methoxyphenyl)-4,6,7-trimethyl-2,3-dihydro-1-benzofuran-5-amine obtained in Reference Example 275, the title compound was synthesized in the same manner as in Reference Example 30. Yield: quantitative. Oily matter.

¹H-NMR (CDCl₃) δ: 1.84 (3H, s), 2.11 (3H, s), 2.20 (3H, s), 3.26 (2H, br s), 3.75 (3H, s), 4.33 (1H, dd, J=4.8, 8.7 Hz), 4.53 (1H, dd, J=4.8, 8.7 Hz), 4.76 (1H, t, J=8.7 Hz), 6.67-6.75 (3H, m), 7.18 (1H, t, J=7.8 Hz).

REFERENCE EXAMPLE 303

3-(4-Isopropyl-2-methoxyphenyl)-4,6,7-trimethyl-2,3-dihydro-1-benzofuran-5-amine Using N-benzyl-3-(4-isopropyl-2-methoxyphenyl)-4,6,7-trimethyl-2,3-dihydro-1-benzofuran-5-amine obtained in Reference Example 273, the title compound was synthesized in the same manner as in Reference Example 30. Yield 87%. Melting point: 120-121° C. (ethyl acetate-hexane).

¹H-NMR (CDCl₃) δ: 1.22 (6H, d, J=6.9 Hz), 1.88 (3H, s), 2.13 (3H, s), 2.19 (3H, s), 2.85 (1H, septet, J=6.9 Hz), 3.29 (2H, br s), 3.88 (3H, s), 4.27 (1H, dd, J=3.3, 8.7 Hz), 4.73 (1H, t, J=8.7 Hz), 4.86 (1H, dd, J=3.3, 8.7 Hz), 6.65 (2H, s), 6.73 (1H, s).

REFERENCE EXAMPLE 304

2,4,6-Trimethyl-2,3-dihydro-1-benzofuran-5-amine

Using N-benzyl-2,4,6-trimethyl-2,3-dihydro-1-benzofuran-5-amine obtained in Reference Example 268, the title compound was synthesized in the same manner as in Reference Example 30. Yield 71%. Oily matter.

¹H-NMR (CDCl₃) δ: 1.43 (3H, d, J=6.3 Hz), 2.09 (3H, s), 2.15 (3H, s), 2.71 (1H, dd, J=7.5, 15.0 Hz), 3.18-3.27 (3H, m), 4.80-4.91 (1H, m), 6.42 (1H, s).

REFERENCE EXAMPLE 305

3-(4-Isopropylphenyl)-4,6,7-trimethyl-1-benzofuran-5-amine

Using N-benzyl-3-(4-isopropylphenyl)-4,6,7-trimethyl-1-benzofuran-5-amine obtained in Reference Example 280, the title compound was synthesized in the same manner as in Reference Example 30. Yield 80%. Oily matter.

¹H-NMR (CDCl₃) δ: 1.30 (6H, d, J=6.9 Hz), 2.08 (3H, s), 2.24 (3H, s), 2.47 (3H, s), 2.97 (1H, septet, J=6.9 Hz), 3.49 (2H, br s), 7.27 (2H, d, J=7.8 Hz), 7.36 (2H, d, J=7.8 Hz), 7.42 (1H, s).

REFERENCE EXAMPLE 306

4,6,7-Trimethyl-3-phenyl-2,3-dihydro-1-benzofuran-5-amine

Using N-benzyl-4,6,7-trimethyl-3-phenyl-2,3-dihydro-1-benzofuran-5-amine obtained in Reference Example 276, the title compound was synthesized in the same manner as in Reference Example 30. Yield 72%. Melting point: 94-95° C. (ethyl acetate-hexane).

¹H-NMR (CDCl₃) δ: 1.82 (3H, s), 2.11 (3H, s), 2.21 (3H, s), 3.26 (2H, br s), 4.33 (1H, dd, J=4.5, 9.0 Hz), 4.56 (1H, dd, J=4.5, 9.0 Hz), 4.77 (1H, t, J=9.0 Hz), 7.11-7.29 (5H, m)

REFERENCE EXAMPLE 307

4,6,7-Trimethyl-3-(4-methylphenyl)-2,3-dihydro-1-benzofuran-5-amine

Using N-benzyl-4,6,7-trimethyl-3-(4-methylphenyl)-2,3-dihydro-1-benzofuran-5-amine obtained in Reference Example 277, the title compound was synthesized in the same manner as in Reference Example 30. Yield 91%. Melting point: 121-122° C. (hexane).

¹H-NMR (CDCl₃) δ: 1.83 (3H, s), 2.12 (3H, s), 2.24 (3H, s), 2.31 (3H, s), 3.26 (2H, s), 4.31 (1H, dd, J=4.5, 9.0 Hz), 4.53 (1H, dd, J=4.5, 9.0 Hz), 4.76 (1H, t, J=9.0 Hz), 7.13 (2H, d, J=8.1 Hz), 7.08 (2H, d, J=8.1 Hz).

REFERENCE EXAMPLE 308

4,6,7-Trimethyl-3-(5-methylpyridin-2-yl)-2,3-dihydro-1-benzofuran-5-amine

Using N-benzyl-4,6,7-trimethyl-3-(5-methylpyridin-2-yl)-2,3-dihydro-1-benzofuran-5-amine obtained in Reference Example 278, the title compound was synthesized in the same manner as in Reference Example 30. Yield 85%. Melting point: 125-127° C. (ethyl acetate-hexane).

¹H-NMR (CDCl₃) δ: 1.87 (3H, s), 2.11 (3H, s), 2.19 (3H, s), 2.29 (3H, s), 3.27 (2H, br s), 4.48 (1H, dd, J=3.9, 9.0 Hz), 4.73 (1H, dd, J=3.9, 9.0 Hz), 4.81 (1H, t, J=9.0 Hz), 6.87 (1H, d, J=7.8 Hz), 7.35 (1H, dd, J=1.8, 7.8 Hz), 8.36 (1H, d, J=1.8 Hz).

REFERENCE EXAMPLE 309

3-(Biphenyl-4-yl)-4,6,7-trimethyl-2,3-dihydro-1-benzofuran-5-amine

Using N-benzyl-3-(biphenyl-4-yl)-4,6,7-trimethyl-2,3-dihydro-1-benzofuran-5-amine obtained in Reference Example 279, the title compound was synthesized in the same manner as in Reference Example 30. Yield 89%. Melting point: 149-150° C. (hexane).

$^1$H-NMR (CDCl$_3$) δ: 1.88 (3H, s), 2.13 (3H, s), 2.22 (3H, s), 3.29 (2H, br s), 4.38 (1H, dd, J=4.4, 8.8 Hz), 4.60 (1H, dd, J=4.4, 8.8 Hz), 4.81 (1H, t, J=8.8 Hz), 7.20 (2H, d, J=8.2 Hz), 7.28-7.59 (7H, m).

REFERENCE EXAMPLE 310

3-(4-(1,3-Dioxolan-2-yl)phenyl)-4,6,7-trimethyl-2,3-dihydro-1-benzofuran-5-amine Using N-benzyl-3-(4-(1,3-dioxolan-2-yl)phenyl)-4,6,7-trimethyl-2,3-dihydro-1-benzofuran-5-amine obtained in Reference Example 284, the title compound was synthesized in the same manner as in Reference Example 30. Yield 87%. Melting point: 125-136° C. (hexane).

$^1$H-NMR (CDCl$_3$) δ: 1.81 (3H, s), 2.11 (3H, s), 2.20 (3H, s), 3.26 (2H, br s), 3.97-4.17 (4H, m), 4.30 (1H, dd, J=4.8, 9.0 Hz), 4.57 (1H, dd, J=4.8, 9.0 Hz), 4.77 (1H, t, J=9.0 Hz), 5.77 (1H, s), 7.15 (2H, d, J=8.0 Hz), 7.42 (2H, d, J=8.0 Hz).

REFERENCE EXAMPLE 311

3-(4-Ethylphenyl)-4,6,7-trimethyl-1-benzofuran-5-amine

Using N-benzyl-3-(4-ethylphenyl)-4,6,7-trimethyl-1-benzofuran-5-amine obtained in Reference Example 281, the title compound was synthesized in the same manner as in Reference Example 30. Yield 85%. Melting point: 68-69° C. (ethyl acetate-hexane).

$^1$H-NMR (CDCl$_3$) δ: 1.30 (3H, t, J=7.5 Hz), 2.07 (3H, s), 2.24 (3H, s), 2.47 (3H, s), 2.72 (2H, q, J=7.5 Hz), 3.48 (2H, br s), 7.24 (2H, d, J=8.1 Hz), 7.35 (2H, d, J=8.1 Hz), 7.42 (1H, s).

REFERENCE EXAMPLE 312

3-(4-Isobutylphenyl)-4,6,7-trimethyl-1-benzofuran-5-amine

Using N-benzyl-3-(4-isobutylphenyl)-4,6,7-trimethyl-1-benzofuran-5-amine obtained in Reference Example 282, the title compound was synthesized in the same manner as in Reference Example 30. Yield 88%. Oily matter.

$^1$H-NMR (CDCl$_3$) δ: 0.95 (6H, d, J=6.9 Hz), 1.94 (1H, septet, J=6.9 Hz), 2.05 (3H, s), 2.24 (3H, s), 2.47 (3H, s), 2.53 (2H, d, 6.9 Hz), 3.48 (2H, br s), 7.18 (2H, d, J=8.4 Hz), 7.33 (2H, d, J=8.4 Hz), 7.43 (1H, s)

REFERENCE EXAMPLE 313

3-(4-Cyclohexylphenyl)-4,6,7-trimethyl-1-benzofuran-5-amine

Using N-benzyl-3-(4-cyclohexylphenyl)-4,6,7-trimethyl-1-benzofuran-5-amine obtained in Reference Example 283, the title compound was synthesized in the same manner as in Reference Example 30. Yield 79%. Melting point: 139-140° C. (hexane).

$^1$H-NMR (CDCl$_3$) δ: 1.26-1.50 (4H, m), 1.74-1.92 (6H, m), 1.95 (3H, s), 2.23 (3H, s), 2.47 (3H, s), 2.50-2.60 (1H, m), 3.48 (2H, br s), 7.24 (2H, d, J=8.4 Hz), 7.34 (2H, d, J=8.4 Hz), 7.41 (1H, s).

REFERENCE EXAMPLE 314

3-(4-Ethylphenyl)-4,6,7-trimethyl-2,3-dihydro-1-benzofuran-5-amine

Using 3-(4-ethylphenyl)-4,6,7-trimethyl-1-benzofuran-5-amine obtained in Reference Example 311, the title compound was synthesized in the same manner as in Reference Example 144. Yield 80%. Melting point: 88-89° C. (hexane).

$^1$H-NMR (CDCl$_3$) δ: 1.21 (3H, t, J=7.5 Hz), 1.84 (3H, s), 2.12 (3H, s), 2.21 (3H, s), 2.61 (2H, q, J=7.5 Hz), 3.27 (2H, br s), 4.53 (1H, dd, J=4.8, 8.4 Hz), 4.53 (1H, dd, J=4.8, 8.4 Hz), 4.76 (1H, t, J=8.4 Hz), 7.05 (2H, d, J=8.1 Hz), 7.10 (2H, d, J=8.1 Hz).

REFERENCE EXAMPLE 315

3-(4-Isopropylphenyl)-4,7-dimethyl-2,3-dihydro-1-benzofuran-5-amine

Using N-benzyl-3-(4-isopropylphenyl)-4,7-dimethyl-2,3-dihydro-1-benzofuran-5-amine synthesized in Reference Example 285, the title compound was synthesized in the same manner as in Reference Example 30. Yield 92%. Oily matter.

$^1$H-NMR (CDCl$_3$) δ: 1.22 (6H, d, J=6.9 Hz), 1.79 (3H, s), 2.18 (3H, s), 2.73 (2H, br s), 2.86 (1H, septet, J=6.9 Hz), 4.36 (1H, dd, J=8.7, 4.5 Hz), 4.49 (1H, dd, J=9.0, 4.5 Hz), 4.77 (1H, t, J=8.7 Hz), 6.40 (1H, s), 7.03 (2H, d, J=8.1 Hz), 7.11 (2H, d, J=8.1 Hz).

REFERENCE EXAMPLE 316

3-(4-Isopropylphenyl)-4-5,7-trimethyl-2,3-dihydro-1-benzofuran-6-amine

Using N-benzyl-3-(4-isopropylphenyl)-4-5,7-trimethyl-2,3-dihydro-1-benzofuran-6-amine synthesized in Reference Example 286, the title compound was synthesized in the same manner as in Reference Example 30. Yield 83%. Melting point: 88-89° C. (hexane-ethyl acetate).

$^1$H-NMR (CDCl$_3$) δ: 1.22 (6H, d, J=6.9 Hz), 1.91 (3H, s), 2.00 (3H, s), 2.11 (3H, s), 2.86 (1H, septet, J=6.9 Hz), 3.59 (2H, br s), 4.36 (1H, dd, J=8.7, 4.5 Hz), 4.50 (1H, dd, J=9.0, 4.2 Hz), 4.77 (1H, t, J=8.7 Hz), 7.03 (2H, d, J=8.1 Hz), 7.11 (2H, d, J=8.1 Hz).

REFERENCE EXAMPLE 317

3-(4-Isopropylphenyl)-4,5,6-trimethyl-2,3-dihydro-1-benzofuran-7-amine

Using N-benzyl-3-(4-isopropylphenyl)-4,5,6-trimethyl-2,3-dihydro-1-benzofuran-7-amine synthesized in Reference Example 287, the title compound was synthesized in the same manner as in Reference Example 30. Yield 80%. Melting point: 122-123° C. (hexane-ethyl acetate).

$^1$H-NMR (CDCl$_3$) δ: 1.22 (6H, d, J=6.9 Hz), 1.88 (3H, s), 2.09 (3H, s), 2.13 (3H, s), 2.86 (1H, septet, J=6.9 Hz), 3.40 (2H, br s), 4.42 (1H, dd, J=8.7, 4.5 Hz), 4.53 (H, dd, J=9.3, 4.5 Hz), 4.81 (1H, t, J=9.3 Hz), 7.04 (2H, d, J=8.1 Hz), 7.12 (2H, d, J=8.1 Hz).

REFERENCE EXAMPLE 318

3-(4-Isopropylphenyl)-4-methyl-2,3-dihydronaphtho[1,2-b]furan-5-amine

Using N-benzyl-3-(4-isopropylphenyl)-4-methyl-2,3-dihydronaphtho[1,2-b]furan-5-amine synthesized in Reference Example 288, the title compound was synthesized in the same manner as in Reference Example 30. Yield 83%. Oily matter.

$^1$H-NMR (CDCl$_3$) δ: 1.21 (6H, d, J=6.9 Hz), 2.01 (3H, s), 2.86 (1H, septet, J=6.9 Hz), 3.54 (2H, br s), 4.47-4.58 (2H, m), 4.90-5.03 (1H, m), 7.04 (2H, d, J=8.1 Hz), 7.10 (2H, d, J=8.1 Hz), 7.30-7.50 (2H, m), 7.74-7.85 (1H, m), 7.89-8.05 (1H, m).

REFERENCE EXAMPLE 319

3-(4-Isopropylphenyl)-4-methyl-2,3,6,7,8,9-hexahydro naphtho[1,2-b]furan-5-amine Using N-benzyl-3-(4-isopropylphenyl)-4-methyl-2,3,6,7,8,9-hexahydronaphtho[1,2-b]furan-5-amine synthesized in Reference Example 289, the title compound was synthesized in the same manner as in Reference Example 30. Yield 76%. Melting point: 106-107° C. (hexane-ethyl acetate).

$^1$H-NMR (CDCl$_3$) δ: 1.22 (6H, d, J=6.9 Hz), 1.59-1.92 (7H, m), 2.49 (2H, t, J=7.5 Hz), 2.67 (2H, t, J=7.5 Hz), 2.86 (1H, septet, J=6.9 Hz), 3.20 (2H, br s), 4.36 (1H, dd, J=8.7, 5.1 Hz), 4.52 (1H, dd, J=9.0, 4.5 Hz), 4.77 (1H, t, J=8.7 Hz), 7.06 (2H, d, J=8.1 Hz), 7.12 (2H, d, J=8.1 Hz).

REFERENCE EXAMPLE 320

3-(4-Isopropylphenyl)-4-methyl-3,6,7,8-tetrahydro-2H-indeno[4,5-b]furan-5-amine Using N-benzyl-3-(4-isopropylphenyl)-4-methyl-3,6,7,8-tetrahydro-2H-indeno[4,5-b]furan-5-amine synthesized in Reference Example 290, the title compound was synthesized in the same manner as in Reference Example 30. Yield 91%. Melting point: 112-113° C. (hexane-ethyl acetate).

$^1$H-NMR (CDCl$_3$) δ: 1.22 (6H, d, J=6.9 Hz), 1.83 (3H, s), 2.10-2.25 (2H, m), 2.68-2.98 (5H, m), 3.22 (2H, br s), 4.38 (1H, dd, J=8.4, 4.5 Hz), 4.49 (1H, dd, J=8.7, 4.5 Hz), 4.79 (1H, t, J=8.7 Hz), 7.05 (2H, d, J=8.1 Hz), 7.11 (2H, d, J=8.1 Hz).

REFERENCE EXAMPLE 321

Ethyl 3-(5-amino-3-(4-isopropylphenyl)-4,6-dimethyl-2,3-dihydro-1-benzofuran-7-yl)propanoate To a suspension of sodium hydride (a 60% liquid paraffin dispersion, 430 mg, 10.8 mmol) in DMF (50 mL) was added triethyl phosphonoacetate (2.19 g, 9.78 mmol) at 0° C., and the mixture was stirred at the same temperature for 30 minutes.

To the reaction solution was added (7-formyl-3-(4-isopropylphenyl)-4,6-dimethyl-2,3-dihydro-1-benzofuran-5-yl)formamide obtained in Example 60 (3.0 g, 8.89 mmol), and the mixture was stirred at room temperature for 30 minutes. Water was added to the reaction solution, and the product was extracted with diisopropyl ether. The combined extract was washed with water, dried over magnesium sulfate, and then concentrated under reduced pressure to obtain the crude product of oily ethyl (2E)-3-(5-(formylamino)-3-(4-isopropylphenyl)-4,6-dimethyl-2,3-dihydro-1-benzofuran-7-yl)-2-propenoate. A mixture of said compound with 10%—palladium carbon (50% hydrous, 300 mg) and ammonium formate (1.26 g, 20 mmol) in ethanol (50 mL), was heated under reflux for 2 hours. The solid material was removed and the filtrate was concentrated under reduced pressure. Water and ethyl acetate were added to the residue to separate the organic layer, and the aqueous layer was extracted with ethyl acetate. The combined organic layer was washed with water and was dried over magnesium sulfate and then concentrated under reduced pressure. The solvent was distilled off under reduced pressure to obtain the crude product of ethyl 3-(5-(formylamino)-3-(4-isopropylphenyl)-4,6-dimethyl-2,3-dihydro-1-benzofuran-7-yl)propanoate. A mixture of said compound with concentrated hydrochloric acid (10 mL)-ethanol (30 mL), was heated under reflux for 1.5 hours. The solvent was distilled off under reduced pressure and the obtained residue was neutralized with a 12 N aqueous sodium hydroxide solution. The product was extracted with ethyl acetate.

The combined extract was washed with water, dried over anhydrous sodium sulfate and then concentrated under reduced pressure. The obtained residue was purified by silica gel column chromatography (ethyl acetate:hexane=1:4) to obtain 1.55 g (yield 46%) of the title compound. Oily matter.

$^1$H-NMR (CDCl$_3$) δ: 1.22 (6H, d, J=6.9 Hz), 1.26 (3H, t, J=7.2 Hz), 1.84 (3H, s), 2.14 (3H, s), 2.53 (2H, dd, J=9.6, 6.0 Hz), 2.86 (1H, septet, J=6.9 Hz), 2.99 (2H, dd, J=9.3, 7.2 Hz), 3.26 (2H, br s), 4.14 (2H, q, J=7.2 Hz), 4.33 (1H, dd, J=8.7, 4.8 Hz), 4.50 (1H, dd, J=9.3, 4.8 Hz), 4.74 (1H, t, J=9.0 Hz), 7.02 (2H, d, J=8.1 Hz), 7.11 (2H, d, J=8.1 Hz).

REFERENCE EXAMPLE 322

3-(5-Amino-3-(4-isopropylphenyl)-4,6-dimethyl-2,3-dihydro-1-benzofuran-7-yl)propan-1-ol To a suspension of ethyl 3-(5-amino-3-(4-isopropylphenyl)-4,6-dimethyl-2,3-dihydro-1-benzofuran-7-yl)propanoate synthesized in Reference Example 321 (1.28 g, 3.36 mmol) in THF, was added Lithium aluminum hydride (255 mg, 6.72 mmol) at 0° C., and the mixture was stirred at the same temperature for 30 minutes and heated under reflux for 30 minutes. To the reaction solution was added water, and the product was extracted with ethyl acetate. The combined extract was washed with water, dried over magnesium sulfate and then concentrated under reduced pressure. The obtained residue was crystallized from hexane-ethyl acetate to obtain 750 mg (yield 66%) of the title compound. Melting point: 110-111° C. (hexane-ethyl acetate).

$^1$H-NMR (CDCl$_3$) δ: 1.22 (6H, d, J=7.0 Hz), 1.70-1.90 (5H, m), 2.13 (3H, s), 2.70-2.91 (3H, m), 3.24 (2H, br s), 3.56 (2H, t, J=5.4 Hz), 4.36 (1H, dd, J=8.4, 4.0 Hz), 4.53 (1H, dd, J=8.8, 4.4 Hz), 4.75 (1H, t, J=8.6 Hz), 7.0.2 (2H, d, J=8.0 Hz), 7.12 (2H, d, J=8.0 Hz), 1H unidentified.

REFERENCE EXAMPLE 323

(4-Bromo-3-(4-isopropylphenyl)-6,7-dimethyl-2,3-dihydro-1-benzofuran-5-yl)amine To a solution of 3-(4-isopropylphenyl)-6,7-dimethyl-2,3-dihydro-1-benzofuran-5-amine synthesized in Reference Example 31 (5.62 g, 21.1 mmol) in acetonitrile (60 mL), was added N-bromosuccinimide (3.76 g, 21.1 mmol) at −20° C., and the mixture was stirred at the same temperature for 10 minutes. The solvent was distilled off under reduced pressure, and the residue was purified by silica gel column chromatography (ethyl acetate:hexane=1:4) to obtain 0.90 g (yield 34%) of the title compound. Melting point: 191-193° C. (hexane-ethyl acetate).

$^1$H-NMR (CDCl$_3$) δ: 1.21 (6H, d, J=6.9 Hz), 2.13 (3H, s), 2.17 (3H, s), 2.86 (1H, septet, J=6.9 Hz), 3.68 (2H, br s), 4.42 (1H, dd, J=8.4, 3.9 Hz), 4.50 (1H, dd, J=8.7, 3.9 Hz), 4.76 (1H, t, J=8.7 Hz), 7.07 (2H, d, J=8.4 Hz), 7.12 (2H, d, J=8.4 Hz).

REFERENCE EXAMPLE 324

Cyclopentyl(4-isopropylphenyl)methanone

To a solution of cumene (16.4 g, 137 mmol) and aluminum chloride (21.9 g, 164 mmol) in dichloromethane (200 mL) was added cyclopentanecarbonyl chloride (20 g, 151 mmol) at −50° C. (the inside temperature), and the mixture was stirred for two hours until the temperature reached −10° C. (the inside temperature).

The reaction solution was poured into ice-cold water to separate the organic layer.

The organic layer was washed with a 12 N sodium hydroxide solution and a saturated brine, and then dried over sodium sulfate.

The solvent was distilled off under reduced pressure to obtain 22.5 g (yield 80%) of the title compound as oily matter.

Oily matter.

$^1$H-NMR (CDCl$_3$) δ: 1.27 (6H, d, J=6.9 Hz), 1.57-1.92 (8H, m), 2.96 (1H, septet, J=6.9 Hz), 3.69 (1H, quartet, J=7.8 Hz), 7.29 (2H, d, J=8.4 Hz), 7.90 (2H, d, J=8.4 Hz).

REFERENCE EXAMPLE 325

3-(4-Isopropylphenyl)-4,6,7-trimethyl-3H-spiro(1-benzofuran-2,1'-cyclopentane)-5-amine To a solution of tert-butyl 3-bromo-4-methoxy-2,5,6-trimethylphenylcarbamate (2.0 g, 5.81 mmol) synthesized in Reference Example 129 in THF (20 mL) was added n-butyl lithium (a 1.6 M hexane solution, 8 mL, 12.8 mmol) at −78° C., and the mixture was stirred at the same temperature for 20 minutes. To the reaction solution was added a solution of cyclopentyl(4-isopropylphenyl)methanone synthesized in Reference Example 324 (1.38 g, 6.39 mmol) in THF (5 mL), and the mixture was stirred at room temperature for 1 hours. To the reaction solution was added a solution of cyclopentyl (4-isopropylphenyl)methanone synthesized in Reference Example 324 (1.38 g, 6.39 mmol) in THF (5 mL), and the mixture was stirred for 1 hours. Water was poured into the reaction mixture which was extracted with ethyl acetate, and the organic layer was washed with water, dried over magnesium sulfate, filtered and then concentrated under reduced pressure.

The obtained residue was purified by silica gel column chromatography (hexane:ethyl acetate=4:1) to obtain tert-butyl 3-(cyclopentyl(hydroxy)(4-isopropylphenyl)methyl)-4-methoxy-2,5,6-trimethylphenylcarbamate. A mixture of said compound and 47% hydrobromic acid (50 mL) was heated under reflux under argon atmosphere for 3 hours. The reaction mixture was cooled to room temperature, and then neutralized with 12 N aqueous sodium hydroxide solution. The product was extracted with ethyl acetate, and the combined extract was washed with water, dried over magnesium sulfate and then concentrated under reduced pressure. The obtained residue was purified by silica gel column chromatography (hexane:ethyl acetate=4:1) to obtain 400 mg (yield 22%) of the title compound. Melting point: 132-133° C. (hexane-ethyl acetate).

$^1$H-NMR (CDCl$_3$) δ: 1.11-1.35 (7H, m), 1.45-1.92 (9H, m), 1.96-2.22 (7H, m), 2.84 (1H, septet, J=6.9 Hz), 3.21 (2H, br s), 4.13 (1H, s), 6.88 (2H, d, J=8.1 Hz), 7.05 (2H, d, J=8.1 Hz).

REFERENCE EXAMPLE 326

(S)-3-(4-Isopropylphenyl)-4,6-dimethyl-2,3-dihydro-1-benzofuran-5-amine

Using 3-(4-isopropylphenyl)-3,5-dimethyl-2,3-dihydro-1-benzofuran-5-amine and -(2R,3R)-(4'-methyl)-tartranilic acid obtained in Reference Example 32, the title compound was synthesized in the same manner as in Reference Example 141. Yield 40%. Oily matter.

$^1$H-NMR (CDCl$_3$) δ: 1.22 (6H, d, J=6.9 Hz), 1.85 (3H, s), 2.18 (3H, s), 2.86 (1H, septet, J=6.9 Hz), 3.07 (2H, br s), 4.35 (1H, dd, J=8.4, 4.5 Hz), 4.49 (1H, dd, J=9.0, 4.5 Hz), 4.71-4.80 (1H, m), 6.54 (1H, s), 7.03 (2H, d, J=8.1 Hz), 7.11 (2H, d, J=8.1 Hz).

REFERENCE EXAMPLE 327

3-(4-Isopropylphenyl)-7-methoxy-4,6-dimethyl-2,3-dihydro-1-benzofuran-5-amine

A mixture of (7-bromo-3-(4-isopropylphenyl)-4,6-dimethyl-2,3-dihydro-1-benzofuran-5-yl)formamide (800 mg, 2.06 mmol) synthesized in Example 59, copper(I) bromide (296 mg, 2.06 mmol), ethyl acetate (0.402 mL, 4.12 mmol) and a 28% sodium methoxide-methanol solution (20 mL), was heated under reflux for 6 hours.

1 N hydrochloric acid was added to the reaction solution, and the product was extracted with ethyl acetate to obtain the crude product of (3-(4-isopropylphenyl)-7-methoxy-4,6-dimethyl-2,3-dihydro-1-benzofuran-5-yl)formamide. This compound was dissolved in methanol (6 mL), concentrated hydrochloric acid (2 mL) was added thereto, and the mixture was heated under reflux for 24 hours. The solvent was distilled off under reduced pressure and the obtained residue was neutralized with a 12 N aqueous sodium hydroxide solution. The product was extracted with ethyl acetate, and the extract was washed with water, dried over magnesium sulfate and then concentrated under reduced pressure. The obtained residue was purified by silica gel column chromatography (ethyl acetate:hexane=1:4) to obtain 310 mg (yield 48%) of the title compound. Oily matter.

$^1$H-NMR (CDCl$_3$) δ: 1.22 (6H, d, J=6.9 Hz), 1.81 (3H, s), 2.12 (3H, s), 2.86 (1H, septet, J=6.9 Hz), 3.28 (2H, br s), 3.88 (3H, s), 4.39 (1H, dd, J=4.5, 8.7 Hz), 4.50 (1H, dd, J=4.2, 9.0 Hz), 4.79 (1H, t, J=8.7 Hz), 7.03 (2H, d, J=8.1 Hz), 7.11 (2H, d, J=8.1 Hz).

REFERENCE EXAMPLE 328

7-Ethyl-3-(4-isopropylphenyl)-4,6-dimethyl-2,3-dihydro-1-benzofuran-5-amine

To a solution of methylmagnesium bromide (a 1.0 M THF solution, 10 mL, 10 mmol) in THF was added (7-formyl-3-(4-isopropylphenyl)-4,6-dimethyl-2,3-dihydro-1-benzofuran-5-yl)formamide obtained in Example 60 (600 mg, 1.78 mmol) at 0° C., and the mixture was stirred at room temperature for 1 hour. The reaction solution was added to water, which was extracted with ethyl acetate. The organic layer was washed with 1 N hydrochloric acid and saturated brine, dried over anhydrous sodium sulfate and then concentrated under reduced pressure. To a mixture of the obtained residue and trifluoroacetic acid (5 mL) was added triethylsilane (0.27 mL, 2.46 mmol), and the mixture was stirred at room temperature for 1 hour. The reaction solution was concentrated under reduced pressure, and the residue was added to a saturated sodium hydrogen carbonate solution to alkalify the aqueous layer, which was extracted with ethyl acetate. The organic layer was washed with water and saturated brine, dried over anhydrous sodium sulfate and then concentrated under reduced pressure. The obtained residue was dissolved in methanol (6 mL), to which concentrated hydrochloric acid (2 mL) was added, and the mixture was heated under reflux for 24 hours. The solvent was distilled off under reduced pressure and the obtained residue was neutralized with a 12 N aqueous sodium hydroxide solution.

The product was extracted with ethyl acetate, and the extract was washed with water, dried over magnesium sulfate and then concentrated under reduced pressure. The obtained residue was purified by silica gel column chromatography (ethyl acetate:hexane=1:4) to obtain 250 mg (yield 45%) of the title compound. Oily matter.

$^1$H-NMR (CDCl$_3$) δ: 1.15 (3H, t, J=7.5 Hz), 1.22 (6H, d, J=6.9 Hz), 1.84 (3H, s), 2.14 (3H, s), 2.67 (2H, q, J=7.5 Hz), 2.86 (1H, septet, J=6.9 Hz), 4.20-4.60 (2H, m), 4.61-4.82 (1H, m), 7.04 (2H, d, J=8.1 Hz), 7.11 (2H, d, J=8.1 Hz), 2H unidentified.

REFERENCE EXAMPLE 329

3-(4-Isopropylphenyl)-4,6-dimethyl-7-phenyl-2,3-dihydro-1-benzofuran-5-amine

A mixture of (7-bromo-3-(4-isopropylphenyl)-4,6-dimethyl-2,3-dihydro-1-benzofuran-5-yl)formamide obtained in Example 59 (1.0 g, 2.58 mmol), phenylboronic acid (345 mg, 2.83 mmol) and tetrakis(triphenylphosphine)palladium (99 mg, 0.086 mmol) in 2 N sodium carbonate aqueous solution (30 mL)-1,2-dimethoxyethane (15 mL) was heated under reflux under nitrogen atmosphere for 16 hours. The reaction solution was diluted with ethyl acetate, the insolubles were taken by filtration, and the filtrate was washed with a saturated brine and then dried over anhydrous sodium sulfate, and the solvent was distilled off under reduced pressure to give the crude product of (3-(4-isopropylphenyl)-4,6-dimethyl-7-phenyl-2,3-dihydro-1-benzofuran-5-yl)formamide. This compound was dissolved in methanol (18 mL), to which concentrated hydrochloric acid (6 mL) was added, and the mixture was heated under reflux for 2 hours. The solvent was distilled off under reduced pressure and the obtained residue was neutralized with a 12 N aqueous sodium hydroxide solution. The product was extracted with ethyl acetate. The extract was washed with water, dried over magnesium sulfate, and then concentrated under reduced pressure. The obtained residue was purified by silica gel column chromatography (ethyl acetate:hexane=1:4) to obtain 642 mg (yield 70%) of the title compound. Melting point: 101-102° C. (hexane-ethyl acetate).

$^1$H-NMR (CDCl$_3$) δ: 1.22 (6H, d, J=6.9 Hz), 1.91 (3H, s), 2.03 (3H, s), 2.86 (1H, septet, J=6.9 Hz), 3.34 (2H, br s), 4.31 (1H, dd, J=4.2, 9.0 Hz), 4.55 (1H, dd, J=4.8, 9.3 Hz), 4.72 (1H, t, J=8.7 Hz), 7.09 (2H, d, J=8.1 Hz), 7.13 (2H, d, J=8.1 Hz), 7.28-7.45 (5H, m).

REFERENCE EXAMPLE 330

N-(7-(4-Isopropylbenzyl)-2,2,4,6-tetramethyl-3-oxo-2,3-dihydro-1-benzofuran-5-yl)-3,3-dimethylbutanamide Using 5-amino-7-(4-isopropylbenzyl)-2,2,4,6-tetramethyl-1-benzofuran-3-(2H)-one obtained in Reference Example 299, the title compound was synthesized in the same manner as in Reference Example 63. Yield 86%. Melting point: 193-194° C. (ethyl acetate-hexane).

$^1$H-NMR (CDCl$_3$) δ: 1.14 (9H, s), 1.20 (6H, d, J=6.9 Hz), 1.44 (6H, s), 2.20 (3H, s), 2.29 (2H, s), 2.49 (3H, s), 2.84 (1H, septet, J=6.9 Hz), 4.02 (2H, s), 6.56 (1H, br s), 7.09 (4H, s).

REFERENCE EXAMPLE 331

N-(7-(4-Isopropylbenzyl)-3,4,6-trimethyl-1-benzofuran-5-yl)-3,3-dimethylbutanamide Using 7-(4-isopropylbenzyl)-3,4,6-trimethyl-1-benzofuran-5-amine obtained in Reference Example 296, the title compound was synthesized in the same manner as in Reference Example 63. Yield 90%. Melting point: 171-172° C. (ethyl acetate-hexane).

$^1$H-NMR (CDCl$_3$) δ: 1.16 (9H, s), 1.19 (6H, d, J=6.9 Hz), 2.21 (3H, s), 2.32 (2H, s), 2.36 (3H, s), 2.56 (3H, s), 2.82 (1H, septet, J=6.9 Hz), 4.22 (2H, br s), 6.64 (1H, s), 7.04 (4H, s), 7.29 (1H, s).

REFERENCE EXAMPLE 332

N-Benzyl-N-(3-(4-isopropylbenzyl)-4-methoxy-2,6-dimethylphenyl)-3,3-dimethylbutanamide Using N-benzyl-3-(4-isopropylbenzyl)-4-methoxy-2,6-dimethylaniline obtained in Reference Example 267, the title compound was obtained in the same manner as in Example 63. Yield 94%. Oily matter.

$^1$H-NMR (CDCl$_3$) δ: 0.98 (9H, s), 1.23 (6H, d, J=6.9 Hz), 1.61 (3H, s), 1.73 (2H, s), 1.91 (3H, s), 2.84 (1H, septet, J=6.9 Hz), 3.79 (3H, s), 3.89 (1H, d, J=15.6 Hz), 4.00 (1H, d, J=15.6 Hz), 4.55 (1H, d, J=13.5 Hz), 4.83 (1H, d, J=13.5 Hz), 6.63 (1H, s), 6.89 (2H, d, J=7.8 Hz), 7.07 (2H, d, J=7.8 Hz), 7.11-7.20 (5H, m).

REFERENCE EXAMPLE 333

N-(3-(4-Isopropylbenzyl)-4-methoxy-2,6-dimethylphenyl)-3,3-dimethylbutanamide

Using (3-(4-isopropylbenzyl)-4-methoxy-2,6-dimethylphenyl)amine obtained in Reference Example 300, the title compound was synthesized in the same manner as in Example 63. Yield 94%. Melting point: 181-182° C. (ethyl acetate-hexane).

$^1$H-NMR (CDCl$_3$) δ: 1.13 (9H, s), 1.20 (6H, d, J=6.9 Hz), 2.10 (3H, s), 2.25 (3H, s), 2.27 (2H, s), 2.83 (1H, septet, J=6.9

Hz), 3.78 (3H, s), 4.00 (2H, s), 6.55 (1H, br s), 6.67 (1H, s), 7.01 (2H, d, J=8.1 Hz), 7.06 (2H, d, J=8.1 Hz).

REFERENCE EXAMPLE 334

(7-(1-(4-Isopropylphenyl)vinyl)-4,6-dimethyl-2,3-dihydro-1-benzofuran-5-yl)amine To a solution of tert-butyl (7-(1-hydroxy-1-(4-isopropylphenyl)ethyl)-4,6-dimethyl-2,3-dihydro-1-benzofuran-5-yl)carbamate obtained in Example 223 (306 mg, 0.72 mmol) in ethyl acetate (5 mL) was added dropwise a solution of 4 N hydrochloric acid-ethyl acetate (5 mL) under ice-cooling, and the reaction solution was stirred for 30 minutes. The reaction solution was added to a saturated sodium hydrogen carbonate solution, which was extracted with ethyl acetate. The combined organic layer was washed with a saturated sodium hydrogen carbonate solution and a saturated brine, dried over anhydrous sodium sulfate, filtered and then concentrated under reduced pressure to obtain 221 mg (yield: quantitative) of the title compound. Oily matter.
$^1$H-NMR (CDCl$_3$) δ: 1.22 (6H, d, J=6.9 Hz), 1.97 (3H, s), 2.16 (3H, s), 2.86 (1H, septet, J=6.9 Hz), 3.14 (2H, t, J=8.4 Hz), 3.34 (2H, br s), 4.44 (2H, t, J=8.4 Hz), 5.14 (1H, s), 5.94 (1H, s), 7.10 (2H, d, J=8.1 Hz), 7.25 (2H, d, J=8.1 Hz).

REFERENCE EXAMPLE 335

N-(3-(4-Isopropylbenzyl)-4-hydroxy-2,6-dimethylphenyl)-3,3-dimethylbutanamide

To a solution of N-(3-(4-isopropylbenzyl)-4-methoxy-2,6-dimethylphenyl)-3,3-dimethylbutanamide obtained in Reference Example 333 (1.99 g, 5.21 mmol) in dichloromethane (25 mL) was added dropwise boron tribromide
(a 1.0 M dichloromethane solution, 10.4 mL, 10.4 mmol) under argon atmosphere at −78° C., and the mixture was stirred for 30 minutes. The reaction solution was warmed to room temperature and was stirred for 14 hours. The reaction solution was added to a saturated sodium hydrogen carbonate solution to separate the organic layer, and then the aqueous layer was extracted with ethyl acetate. The entire organic layer was washed with a saturated brine, dried over anhydrous sodium sulfate, filtered and then concentrated under reduced pressure to obtain 1.83 g (yield 97%) of the oily title compound. Melting point: 202-203° C. (ethyl acetate).
$^1$H-NMR (CDCl$_3$) δ: 1.15 (9H, s), 1.19 (6H, d, J=6.9 Hz), 2.11 (3H, s), 2.12 (3H, s), 2.29 (2H, s), 2.82 (1H, septet, J=6.9 Hz), 3.93 (2H, s), 6.34 (1H, s), 6.37 (1H, br), 6.62 (1H, s), 7.06 (4H, s).

REFERENCE EXAMPLE 336

N-Benzyl-N-(3-(4-isopropylbenzyl)-4-hydroxy-2,6-dimethylphenyl)-3,3-dimethylbutanamide Using N-benzyl-N-(3-(4-isopropylbenzyl)-4-methoxy-2,6-dimethylphenyl)-3,3-dimethylbutanamide obtained in Reference Example 332, the title compound was synthesized in the same manner as in Reference Example 335. Yield 83%. Melting point: 167-168° C. (ethyl acetate-hexane).
$^1$H-NMR (CDCl$_3$) δ: 0.99 (9H, s), 1.23 (6H, d, J=6.9 Hz), 1.66 (3H, s), 1.80 (2H, s), 1.87 (3H, s), 2.85 (1H, septet, J=6.9 Hz), 3.90 (1H, d, J=16.2 Hz), 3.97 (1H, d, J=16.2 Hz), 4.54 (1H, d, J=13.5 Hz), 4.57 (1H, d, J=13.5 Hz), 4.98 (1H, br), 6.59 (1H, s), 6.94 (2H, d, J=7.8 Hz), 7.11 (2H, d, J=7.8 Hz), 7.10-7.16 (5H, m).

REFERENCE EXAMPLE 337

N-Benzyl-N-(3-bromo-5-(4-isopropylbenzyl)-4-hydroxy-2,6-dimethylphenyl)-3,3-dimethylbutanamide Using N-benzyl-N-(3-(4-isopropylbenzyl)-4-hydroxy-2,6-dimethylphenyl)-3,3-dimethylbutanamide obtained in Reference Example 336, the title compound was synthesized in the same manner as in Reference Example 66. Yield 98%. Melting point: 107-108° C. (ethyl acetate-hexane).
$^1$H-NMR (CDCl$_3$) δ: 0.99 (9H, s), 1.23 (6H, d, J=6.9 Hz), 1.66 (3H, s), 1.76 (2H, s), 2.00 (3H, s), 2.87 (1H, septet, J=6.9 Hz), 3.96 (1H, d, J=15.6 Hz), 4.08 (1H, d, J=15.6 Hz), 4.49 (1H, d, J=13.5 Hz), 4.87 (1H, d, J=13.5 Hz), 5.76 (1H, s), 6.93 (2H, d, J=8.4 Hz), 7.09-7.21 (7H, m).

REFERENCE EXAMPLE 338

N-Benzyl-N-(3-bromo-4-(2-chloroethoxy)-5-(4-isopropylbenzyl)-2,6-dimethylphenyl)-3,3-dimethylbutanamide Using N-benzyl-N-(3-bromo-5-(4-isopropylbenzyl)-4-hydroxy-2,6-dimethylphenyl)-3,3-dimethylbutanamide obtained in Reference Example 337, the title compound was synthesized in the same manner as in Reference Example 217. Yield 87%. Oily matter.
$^1$H-NMR (CDCl$_3$) δ: 0.98 (9H, s), 1.22 (6H, d, J=6.9 Hz), 1.54 (3H, s), 1.73 (2H, s), 2.07 (3H, s), 2.86 (1H, septet, J=6.9 Hz), 3.75 (2H, t, J=6.0 Hz), 3.99-4.13 (4H, m), 4.42 (1H, d, J=13.5 Hz), 4.96 (1H, d, J=13.5 Hz), 6.84 (2H, d, J=8.1 Hz), 7.00-7.20 (7H, m).

REFERENCE EXAMPLE 339

N-(3-(4-Isopropylbenzyl)-2,6-dimethyl-4-((2-methylprop-2-en-1-yl)oxy)phenyl)-3,3-dimethylbutanamide To a mixed solution of N-(3-(4-isopropylbenzyl)-4-methoxy-2,6-dimethyl)-amino-2-(4-isopropylbenzyl)-1-hydroxy-3,5-dimethylphenyl)-3,3-dimethylbutanamide obtained in Reference Example 335 (300 mg, 0.82 mmol), methallyl chloride (89 mg, 0.98 mmol) and potassium carbonate (135 mg, 0.98 mmol) in DMF (5 mL) was stirred at 80° C. for 18 hours under argon atmosphere. Water was added to the reaction solution, which was extracted with ethyl acetate. The combined organic layer was washed with water and saturated brine, dried over anhydrous sodium sulfate, filtered and then concentrated under reduced pressure. The obtained residue was purified by silica gel column chromatography (ethyl acetate:hexane=2:3) to obtain 280 mg (yield 81%) of the title compound. Melting point: 129-130° C. (ethyl acetate-hexane).
$^1$H-NMR (CDCl$_3$) δ: 1.13 (9H, s), 1.19 (6H, d, J=6.9 Hz), 1.72 (3H, s), 2.12 (3H, s), 2.22 (3H, s), 2.26 (2H, s), 2.82 (1H, septet, J=6.9 Hz), 4.03 (2H, s), 4.38 (2H, s), 4.90 (1H, s), 5.02 (1H, s), 6.53 (1H, s), 6.63 (1H, br), 7.04 (4H, s).

REFERENCE EXAMPLE 340

N-(4-(Allyloxy)-3-bromo-5-(4-isopropylbenzyl)-2,6-dimethylphenyl)-3,3-dimethylbutanamide Using N-(3-(4-isopropylbenzyl)-4-hydroxy-2,6-dimethylphenyl)-3,3-dimethylbutanamide obtained in Reference Example 335, N-(3-bromo-5-(4-isopropylbenzyl)-4-hydroxy-2,6-dimethylphenyl)-3,3-dimethylbutanamide was synthesized in the same manner as in Reference Example 66. Using this compound, the title compound was synthesized in the same manner as in Reference Example 213. Yield 33%. Oily matter.

$^1$H-NMR (CDCl$_3$) δ: 1.14 (9H, s), 1.20 (6H, d, J=6.9 Hz), 2.06 (3H, s), 2.28 (2H, s), 2.37 (3H, s), 2.84 (1H, septet, J=6.9 Hz), 4.08 (2H, br s), 4.29 (2H, br s), 5.20 (1H, d, J=10.5 Hz), 5.28-5.36 (1H, m), 5.98-6.20 (1H, m), 6.65 (1H, s), 7.00 (2H, d, J=8.1 Hz), 7.08 (2H, d, J=8.1 Hz).

REFERENCE EXAMPLE 341

N-(4-Hydroxy-3-(4-isopropylbenzyl)-2,6-dimethyl-5-(2-methylprop-2-en-1-yl)phenyl)-3,3-dimethylbutanamide Using N-(3-(4-isopropylbenzyl)-2,6-dimethyl-4-((2-methylprop-2-en-1-yl)oxy)phenyl)-3,3-dimethylbutanamide obtained in Reference Example 339, the title compound was synthesized in the same manner as in Reference Example 215.

Yield 93%. Melting point: 124-125° C. (ethyl acetate-hexane).

$^1$H-NMR (CDCl$_3$) δ: 1.14 (9H, s), 1.20 (6H, d, J=6.9 Hz), 1.78 (3H, s), 2.15 (3H, s), 2.16 (3H, s), 2.29 (2H, s), 2.84 (1H, septet, J=6.9 Hz), 3.38 (2H, s), 4.03 (2H, br s), 4.65 (1H, s), 4.84 (1H, s), 5.05 (1H, s), 6.60 (1H, s), 7.04 (2H, d, J=8.1 Hz), 7.09 (2H, d, J=8.1 Hz).

REFERENCE EXAMPLE 342

3,3-Dimethyl-N-(2,2,4,6-tetramethyl-3-oxo-2,3-dihydro-1-benzofuran-5-yl)butanamide Using 5-amino-2,2,4,6-tetramethyl-2,3-dihydro-1-benzofuran-3-(2H)-one obtained in Reference Example 55, the title compound was synthesized in the same manner as in Example 1. Yield 91%. Melting point: 181-182° C. (THF-hexane).

$^1$H-NMR (CDCl$_3$) δ: 1.15 (9H, s), 1.42 (6H, s), 2.30-2.32 (5H, m), 2.49 (3H, s), 6.55 (1H, br s), 6.79 (1H, s).

REFERENCE EXAMPLE 343

3,3-Dimethyl-N-(3-(4-isopropylphenyl)-4,6,7-trimethyl-1-benzofuran-5-yl)butanamide Using 3-(4-isopropylphenyl)-4,6,7-trimethyl-1-benzofuran-5-amine obtained in Reference Example 305, the title compound was synthesized in the same manner as in Example 63. Yield 50%. Melting point: 229-230° C. (THF-hexane).

$^1$H-NMR (CDCl$_3$) δ: 1.15 (9H, s), 1.30 (6H, d, J=6.9 Hz), 2.11 (3H, s), 2.27 (3H, s), 2.31 (2H, s), 2.45 (3H, s), 2.96 (1H, septet, J=6.9 Hz), 6.67 (1H, br s), 7.24 (2H, d, J=8.4 Hz), 7.33 (2H, d, J=8.4 Hz), 7.48 (1H, s).

REFERENCE EXAMPLE 344

7-Acetyl-3-(4-isopropylphenyl)-4,6-dimethyl-2,3-dihydro-1-benzofuran-5-amine

N-(7-Acetyl-3-(4-isopropylphenyl)-4,6-dimethyl-2,3-dihydro-1-benzofuran-5-yl)formamide obtained in Example 203 (808 mg, 2.3 mmol) was added to a solution of methanol (10 mL) and concentrated hydrochloric acid (5 mL), and the mixture was heated under reflux for 2 hours. The reaction solution was cooled to room temperature and was poured into a cold sodium bicarbonate solution, which was extracted with ethyl acetate. The extract was washed with a saturated brine, dried over sodium sulfate and then concentrated under reduced pressure. The residue was purified by silica gel column chromatography (hexane ethyl acetate=1:1) to obtain the title compound as an oily matter.

$^1$H-NMR (CDCl$_3$) δ: 1.22 (6H, d, J=6.9 Hz), 1.87 (3H, s), 2.18 (3H, s), 2.60 (3H, s), 2.87 (1H, septet, J=6.9 Hz), 3.34 (2H, br), 4.36-4.43 (1H, m), 4.48-4.56 (1H, m), 4.76-4.85 (1H, m), 7.03 (2H, d, J=8.1 Hz), 7.12 (2H, d, J=8.1 Hz).

REFERENCE EXAMPLE 345

2-Bromo-1-(4-isopropylphenyl)propan-1-one

Using 2-bromopropanoyl chloride, the title compound was synthesized in the same manner as in Reference Example 164. Yield 97%. Oily matter.

$^1$H-NMR (200 MHz, CDCl$_3$) δ: 1.28 (6H, d, J=7.0 Hz), 1.90 (3H, d, J=7.0 Hz), 2.98 (1H, septet, J=7.0 Hz), 5.28 (1H, q, J=7.0 Hz), 7.34 (2H, d, J=8.0 Hz), 7.97 (2H, d, J=8.0 Hz).

REFERENCE EXAMPLE 346

1-(4-Isopropylphenyl)-2-(2,3,5-trimethylphenoxy)propan-1-one

Using 2-bromo-1-(4-isopropylphenyl)propan-1-one obtained in Reference Example 345 and 2,3,5-trimethylphenol, the title compound was synthesized in the same manner as in Reference Example 159. Yield: quantitative. Oily matter.

$^1$H-NMR (CDCl$_3$) δ: 1.26 (6H, d, J=7.0 Hz), 1.69 (3H, d, J=7.0 Hz), 2.16 (3H, s), 2.19 (3H, s), 2.21 (3H, s), 2.95 (1H, septet, J=7.0 Hz), 5.37 (1H, q, J=7.0 Hz), 6.40 (1H, s), 6.59 (1H, s), 7.29-7.32 (2H, m), 8.00-8.04 (2H, m).

REFERENCE EXAMPLE 347

3-(4-Isopropylphenyl)-2,4,6,7-tetramethyl-1-benzofuran

A mixed solution of 1-(4-isopropylphenyl)-2-(2,3,5-trimethylphenoxy)propan-1-one obtained in Reference Example 346 (61.3 g, 194 mmol), Amberlyst 15 (61.0 g) and a molecular sieve MS 4A (30 g) in toluene (200 mL) was heated under reflux at 80° C. for 2 hours. The reaction solution was filtered through celite, and the filtrate was concentrated under reduced pressure. The obtained residue was purified by silica gel column chromatography (ethyl acetate:hexane 1:100) to obtain 54.4 g (yield 96%) of the title compound. Oily matter.

$^1$H-NMR (CDCl$_3$) δ: 1.30 (6H, d, J=7.0 Hz), 2.06 (3H, s), 2.32 (3H, s), 2.34 (3H, s), 2.41 (3H, s), 2.96 (1H, septet, J=7.0 Hz), 6.75 (1H, s), 7.25 (4H, s).

REFERENCE EXAMPLE 348

3-(4-Isopropylphenyl)-2,6,7-trimethyl-1-benzofuran

Using 2-bromo-1-(4-isopropylphenyl)propan-1-one obtained in Reference Example 345 and 2,3-dimethylphenol, 1-(4-isopropylphenyl)-2-(2,3-dimethylphenoxy)propan-1-one was obtained in the same manner as in Reference Example 159. Using this compound, the title compound was obtained in the same manner as in Reference Example 143. Yield 81%. Oily matter.

¹H-NMR (CDCl₃) δ: 1.31 (6H, d, J=7.0 Hz), 2.38 (3H, s), 2.44 (3H, s), 2.53 (3H, s), 2.97 (1H, septet, J=7.0 Hz), 7.02 (1H, d, J=8.0 Hz), 7.29-7.45 (5H, m).

REFERENCE EXAMPLE 349

(cis)-3-(4-Isopropylphenyl)-2,4,6,7-tetramethyl-2,3-dihydro-1-benzofuran

Using 3-(4-isopropylphenyl)-2,4,6,7-tetramethyl-1-benzofuran obtained in Reference Example 347, the title compound was synthesized in the same manner as in Reference Example 144. Yield 63%. Melting point: 79-80° C. (methanol).

¹H-NMR (CDCl₃) δ: 1.09 (3H, d, J=7.0 Hz), 1.21 (6H, d, J=7.0 Hz), 1.90 (3H, s), 2.16 (3H, s), 2.24 (3H, s), 2.85 (1H, septet, J=7.0 Hz), 4.30 (1H, d, J=7.0 Hz), 4.91-5.05 (1H, m), 6.49 (1H, s), 6.83 (2H, d, J=8.0 Hz), 7.08 (2H, d, J=8.0 Hz).

REFERENCE EXAMPLE 350

(cis)-N-Benzyl-3-(4-isopropylphenyl)-2,6,7-trimethyl-2,3-dihydro-1-benzofuran-5-amine Using 3-(4-isopropylphenyl)-2,6,7-trimethyl-1-benzofuran obtained in Reference Example 348, 3-(4-isopropylphenyl)-2,6,7-trimethyl-2,3-dihydro-1-benzofuran was synthesized in the same manner as in Reference Example 144. Using this compound, 5-bromo-3-(4-isopropylphenyl)-2,6,7-trimethyl-2,3-dihydro-1-benzofuran was obtained in the same manner as in Reference Example 23. Using this compound, the title compound was synthesized in the same manner as in Reference Example 24.

Yield 22%. Oily matter.

¹H-NMR (CDCl₃) δ: 1.00 (3H, d, J=7.0 Hz), 1.23 (6H, d, J=7.0 Hz), 2.10 (3H, s), 2.24 (3H, s), 2.87 (1H, septet, J=7.0 Hz), 3.44 (1H, br s), 4.19 (2H, s), 4.44 (1H, d, J=8.0 Hz), 4.90-4.99 (1H, m), 6.37 (1H, s), 6.90 (2H, d, J=8.0 Hz), 7.10 (2H, d, J=8.0 Hz), 7.23-7.36 (5H, m).

REFERENCE EXAMPLE 351

(cis)-3-(4-Isopropylphenyl)-2,6,7-trimethyl-2,3-dihydro-1-benzofuran-5-amine hydrochloride Using (cis)-N-benzyl-3-(4-isopropylphenyl)-2,6,7-trimethyl-2,3-dihydro-1-benzofuran-5-amine obtained in Reference Example 350, the title compound was synthesized in the same manner as in Reference Example 30. Yield 96%. Melting point: 189-190° C. (diisopropyl ether-hexane).

¹H-NMR (CDCl₃) δ: 1.02 (3H, d, J=6.0 Hz), 1.22 (6H, d, J=7.0 Hz), 2.09 (3H, s), 2.21 (3H, s), 2.86 (1H, septet, J=7.0 Hz), 3.23 (3H, br), 4.39 (1H, d, J=8.0 Hz), 4.89-4.99 (1H, m), 6.36 (1H, s), 6.90 (2H, d, J=8.0 Hz), 7.11 (2H, d, J=8.0 Hz).

REFERENCE EXAMPLE 352

(cis)-3-(4-Isopropylphenyl)-2,4,6,7-tetramethyl-2,3-dihydro-1-benzofuran-5-amine Using (cis)-3-(4-isopropylphenyl)-2,4,6,7-tetramethyl-2,3-dihydro-1-benzofuran obtained in Reference Example 349, (cis)-5-bromo-3-(4-isopropylphenyl)-2,4,6,7-tetramethyl-2,3-dihydro-1-benzofuran was synthesized in the same manner as in Reference Example 23. Using this compound, (cis)-N-benzyl-3-(4-isopropylphenyl)-2,4,6,7-tetramethyl-2,3-dihydro-1-benzofuran-5-amine were synthesized in the same manner as in Reference Example 24. Using this compound, the title compound was synthesized in the same manner as in Reference Example 30. Yield 83%. Melting point: 91-92° C. (hexane).

¹H-NMR (CDCl₃) δ: 1.06 (3H, d, J=7.0 Hz), 1.21 (6H, d, J=7.0 Hz), 1.84 (3H, s), 2.12 (3H, s), 2.21 (3H, s), 2.85 (1H, septet, J=7.0 Hz), 3.25 (2H, br s), 4.29 (1H, d, J=8.0 Hz), 4.83-4.96 (1H, m), 6.83 (2H, d, J=8.0 Hz), 7.07 (2H, d, J=8.0 Hz).

REFERENCE EXAMPLE 353

2-(3,5-Dimethylphenoxy)-1-phenylethanone

Using 3,5-dimethylphenol and phenacyl bromide, the title compound was synthesized in the same manner as in Reference Example 177. Yield 86%. Melting point: 104-105° C. (methanol).

¹H-NMR (CDCl₃) δ: 2.28 (6H, s), 5.23 (2H, s), 6.58 (2H, s), 6.63 (1H, s), 7.46-7.54 (2H, m), 7.58-7.65 (1H, m), 7.98-8.04 (2H, m).

REFERENCE EXAMPLE 354

4,6-Dimethyl-3-phenyl-1-benzofuran

Using 2-(3,5-dimethylphenoxy)-1-phenylethanone obtained in Reference Example 353, the title compound was synthesized in the same manner as in Reference Example 143. Yield: quantitative. Oily matter.

¹H-NMR (CDCl₃) δ: 2.21 (3H, s), 2.43 (3H, s), 6.83 (1H, s), 7.17 (1H, s), 7.38-7.50 (6H, m).

REFERENCE EXAMPLE 355

4,6-Dimethyl-3-phenyl-2,3-dihydro-1-benzofuran

Using 4,6-dimethyl-3-phenyl-1-benzofuran obtained in Reference Example 354, the title compound was synthesized in the same manner as in Reference Example 199. Yield 91%. Oily matter.

¹H-NMR (CDCl₃) δ: 1.91 (3H, s), 2.29 (3H, s), 4.41 (1H, dd, J=8.4, 4.8 Hz), 4.51 (1H, dd, J=9.0, 5.1 Hz), 4.85 (1H, d, J=9.0 Hz), 6.48 (1H, s), 6.57 (1H, s), 7.11-7.31 (5H, m).

REFERENCE EXAMPLE 356

5-Bromo-4,6-dimethyl-3-phenyl-2,3-dihydro-1-benzofuran

Using 4,6-dimethyl-3-phenyl-2,3-dihydro-1-benzofuran obtained in Reference Example 355, the title compound was synthesized in the same manner as in Reference Example 23. Yield 78%. Melting point: 135-136° C. (ethyl acetate-hexane).

¹H-NMR (CDCl₃) δ: 2.04 (3H, s), 2.39 (3H, s), 4.41 (1H, dd, J=9.0, 4.5 Hz), 4.56 (1H, dd, J=9.3, 4.2 Hz), 4.85 (1H, d, J=9.0 Hz), 6.67 (1H, s), 7.07-7.25 (2H, m), 7.19-7.32 (3H, m).

REFERENCE EXAMPLE 357

N-Benzyl-4,6-dimethyl-3-phenyl-2,3-dihydro-1-benzofuran-5-amine

Using 5-bromo-4,6-dimethyl-3-phenyl-2,3-dihydro-1-benzofuran obtained in Reference Example 356, the title compound was synthesized in the same manner as in Reference Example 24. Yield 72%. Oily matter.

$^1$H-NMR (CDCl$_3$) δ: 1.89 (3H, s), 2.26 (3H, s), 2.87 (1H, br s), 3.92 (2H, s), 4.37 (1H, dd, J=8.4, 4.8 Hz), 4.52 (1H, dd, J=9.0, 4.2 Hz), 4.82 (1H, d, J=9.0 Hz), 6.60 (1H, s), 7.05-7.40 (10H, m).

REFERENCE EXAMPLE 358

4,6-Dimethyl-3-phenyl-2,3-dihydro-1-benzofuran-5-amine

Using N-benzyl-4,6-dimethyl-3-phenyl-2,3-dihydro-1-benzofuran-5-amine obtained in Reference Example 357, the title compound was synthesized in the same manner as in Reference Example 30. Yield 84%. Melting point: 127-128° C. (ethyl acetate-hexane).

$^1$H-NMR (CDCl$_3$) δ: 1.84 (3H, s), 2.19 (3H, s), 3.26 (2H, br s), 4.33 (1H, dd, J=8.7, 4.5 Hz), 4.53 (1H, dd, J=9.0, 4.5 Hz), 4.78 (1H, dd, J=9.0, 8.7 Hz), 6.56 (1H, s), 7.09-7.29 (5H, m).

REFERENCE EXAMPLE 359

(+)-N-((3R)-2,2,4,6,7-Pentamethyl-3-(4-methylphenyl)-2,3-dihydro-1-benzofuran-5-yl)-2-(4-(trifluoromethyl)phenyl)acetamide To a DMF solution of (3R)-(+)-2,2,4,6,7-pentamethyl-3-(4-methylphenyl)-2,3-dihydro-1-benzofuran-5-amine obtained in Reference Example 134 (0.89 g, 3 mmol), were added triethylamine (0.84 mL, 6 mmol), (4-trifluoromethyl) phenylacetic acid (0.67 g, 3.3 mmol) and diethyl phosphorocyanidate (0.46 mL, 3.3 mmol) at 0° C., and the mixture was warmed to room temperature. After stirring at the same temperature for 1 hour, the reaction solution was poured into cold water (50 mL). The precipitated crystals were taken, and the crystals were dissolved in ethyl acetate again. The organic layer was washed with a saturated sodium hydrogen carbonate solution and a saturated brine, and then dried over anhydrous sodium sulfate. The solvent was dried under reduced pressure, and the residue was purified by silica gel column chromatography (hexane:ethyl acetate=1:1) to obtain 1.19 g (yield 83%) of the title compound. Melting point: 187-189° C. (diethyl ether-hexane).

$^1$H-NMR (CDCl$_3$) δ: 0.99 (3H, s), 1.47 (3H, s), 1.65 (3H, s), 2.04 (3H, s), 2.13 (3H, s), 2.29 (3H, s), 3.79 (2H, s), 4.06 (1H, s), 6.44 (1H, br), 7.02 (4H, br), 7.49 (2H, d, J=8.2 Hz), 7.62 (2H, d, J=8.2 Hz).

REFERENCE EXAMPLE 360

(+)-2-(4-Methoxyphenyl)-N-((3R)-2,2,4,6,7-pentamethyl-3-(4-methylphenyl)-2,3-dihydro-1-benzofuran-5-yl)acetamide Using (+)-(3R)-2,2,4,6,7-pentamethyl-3-(4-methylphenyl)-2,3-dihydro-1-benzofuran-5-amine obtained in Reference Example 134 and -4-methoxyphenylacetic acid, the title compound was synthesized in the same manner as in Reference Example 359. Yield 74%. Melting point: 186-188° C. (ethyl acetate-hexane).

$^1$H-NMR (CDCl$_3$) δ: 0.99 (3H, s), 1.46 (3H, s), 1.64 (3H, s), 2.04 (3H, s), 2.13 (3H, s), 2.28 (3H, s), 3.68 (2H, s), 3.80 (3H, s), 4.06 (1H, s), 6.44 (1H, br), 6.89 (2H, d, J=8.6 Hz), 7.02 (4H, br), 7.25 (2H, d, J=8.6 Hz).

REFERENCE EXAMPLE 361

(+)-3-(4-Methoxyphenyl)-N-((3R)-2,2,4,6,7-pentamethyl-3-(4-methylphenyl)-2,3-dihydro-1-benzofuran-5-yl)propionamide Using (+)-(3R)-2,2,4,6,7-pentamethyl-3-(4-methylphenyl)-2,3-dihydro-1-benzofuran-5-amine obtained in Reference Example 134 and -4-methoxyphenylpropionic acid, the title compound was synthesized in the same manner as in Reference Example 359. Yield 21%. Melting point: 170-172° C. (ethyl acetate-hexane).

$^1$H-NMR (CDCl$_3$) δ: 0.99 (3H, s), 1.48 (3H, s), 1.63 (3H, s), 1.99 (3H, s), 2.13 (3H, s), 2.29 (3H, s), 2.64 (2H, d, J=7.4 Hz), 2.99 (2H, d, J=7.4 Hz), 3.76 (3H, s), 4.08 (1H, s), 6.44 (1H, br), 6.81 (2H, d, J=8.5 Hz), 7.02 (4H, br), 7.16 (2H, d, J=8.5 Hz).

REFERENCE EXAMPLE 362

3-(4-Methoxyphenyl)-N-(2,2,4,6,7-pentamethyl-3-(4-methylphenyl)-2,3-dihydro-1-benzofuran-5-yl)propionamide Using 2,2,4,6,7-pentamethyl-3-(4-methylphenyl)-2,3-dihydro-1-benzofuran-5-amine obtained in Reference Example 130 and 4-methoxyphenylpropionic acid, the title compound was synthesized in the same manner as in Reference Example 359. Yield 29%. Melting point: 180-183° C. (ethyl acetate-hexane).

$^1$H-NMR (CDCl$_3$) δ: 0.99 (3H, s), 1.48 (3H, s), 1.63 (3H, s), 1.99 (3H, s), 2.13 (3H, s), 2.29 (3H, s), 2.64 (2H, d, J=7.3 Hz), 2.99 (2H, d, J=7.3 Hz), 3.76 (3H, s), 4.08 (1H, s), 6.45 (1H, br), 6.81 (2H, d, J=8.5 Hz), 7.02 (4H, br), 7.16 (2H, d, J=8.5 Hz).

REFERENCE EXAMPLE 363

2-(4-Methoxyphenyl)-N-(2,2,4,6,7-pentamethyl-3-(4-methylphenyl)-2,3-dihydro-1-benzofuran-5-yl) acetamide Using 2,2,4,6,7-pentamethyl-3-(4-methylphenyl)-2,3-dihydro-1-benzofuran-5-amine obtained in Reference Example 130 and 4-methoxyphenylacetic acid, the title compound was synthesized in the same manner as in Reference Example 359. Yield 62%. Melting point: 166-167° C. (ethyl acetate-hexane).

$^1$H-NMR (CDCl$_3$) δ: 0.99 (3H, s), 1.46 (3H, s), 1.63 (3H, s), 2.03 (3H, s), 2.12 (3H, s), 2.28 (3H, s), 3.68 (2H, s), 3.79 (3H, s), 4.05 (1H, s), 6.43 (1H, br), 6.87 (2H, d, J=8.6 Hz), 7.00 (4H, br), 7.25 (2H, d, J=8.6 Hz).

REFERENCE EXAMPLE 364

4-(4-Methoxyphenyl)-N-(2,2,4,6,7-pentamethyl-3-(4-methylphenyl)-2,3-dihydro-1-benzofuran-5-yl) butanamide Using 2,2,4,6,7-pentamethyl-3-(4-methylphenyl)-2,3-dihydro-1-benzofuran-5-amine obtained in Reference Example 130 and 4-(4-methoxyphenyl)butanoic acid, the title compound was synthesized in the same manner as in Reference Example 359. Yield 11%. Melting point: 166-167° C. (ethyl acetate-hexane).

¹H-NMR (CDCl₃) δ: 0.99 (3H, s), 1.46 (3H, s), 1.63 (3H, s), 2.03 (3H, s), 2.12 (3H, s), 2.28 (3H, s), 3.68 (2H, s), 3.79 (3H, s), 4.05 (1H, s), 6.43 (1H, br), 6.87 (2H, d, J=8.6 Hz), 7.00 (4H, br), 7.25 (2H, d, J=8.6 Hz).

REFERENCE EXAMPLE 365

N-(3-(4-Isopropylphenyl)-2,2,4,6,7-pentamethyl-2,3-dihydro-1-benzofuran-5-yl)-4-methoxyphenylacetamide Using 3-(4-isopropylphenyl)-2,2,4,6,7-pentamethyl-2,3-dihydro-1-benzofuran-5-amine obtained in Reference Example 120 and 4-methoxyphenylacetyl chloride, the title compound was synthesized in the same manner as in Reference Example 63. Yield 74%. Melting point: 171-173° C. (methanol).
¹H-NMR (CDCl₃) δ: 0.98 (3H, s), 1.20 (6H, d, J=6.6 Hz), 1.46 (3H, s), 1.64 (3H, s), 2.03 (3H, s), 2.12 (3H, s), 2.84 (1H, septet, J=6.6 Hz), 3.68 (2H, s), 3.80 (3H, s), 4.06 (1H, s), 6.45 (1H, br), 6.6-6.9 (2H, m), 6.89 (2H, d, J=8.6 Hz), 7.05 (2H, d, J=8.0 Hz), 7.26 (d, 2H, J=8.6 Hz).

REFERENCE EXAMPLE 366

N-(3-(4-Isopropylphenyl)-2,2,4,6,7-pentamethyl-2,3-dihydro-1-benzofuran-5-yl)-3-(4-methoxyphenyl)propionamide Using 3-(4-isopropylphenyl)-2,2,4,6,7-pentamethyl-2,3-dihydro-1-benzofuran-5-amine obtained in Reference Example 120 and 4-methoxyphenylpropionyl chloride, the title compound was synthesized in the same manner as in Reference Example 63. Yield 72%. Melting point: 188-191° C. (ethyl acetate-hexane).
¹H-NMR (CDCl₃) δ: 0.99-1.01 (3H, m), 1.19-1.26 (6H, m), 1.48 (3H, s), 1.64-1.68 (3H, m), 1.99 (3H, s), 2.05-2.13 (5H, m), 2.65-3.04 (3H, m), 3.72-3.77 (3H, m), 4.08 (1H, s), 6.47-7.19 (9H, m).

REFERENCE EXAMPLE 367

N-(3-(4-Isopropylphenyl)-2,2,4,6,7-pentamethyl-2,3-dihydro-1-benzofuran-5-yl)-N-(2-(4-methoxyphenyl)ethyl)acetamide To a suspension of aluminum chloride (1.23 g, 9.25 mmol) in THF (40 mL) was slowly added lithium aluminium hydride (354 mg, 9.31 mmol) with ice-cooling, and the mixture was stirred at the same temperature for 10 minutes. To this mixture was added N-(3-(4-isopropylphenyl)-2,2,4,6,7-pentamethyl-2,3-dihydro-1-benzofuran-5-yl)-4-methoxyphenylacetamide obtained in Reference Example 365 (536 mg, 1.14 mmol), and the mixture was heated under reflux for 3 hours. The reaction mixture was added to ice-water, and the mixture was neutralized with a 8 N aqueous sodium hydroxide solution. Thereafter, the product was twice extracted with ethyl acetate, and the combined organic layer was washed with water, dried over magnesium sulfate, filtered and then concentrated under reduced pressure. The residue was purified by silica gel column chromatography (hexane:ethyl acetate=3:1) to obtain 3-(4-isopropylphenyl)-N-(2-(4-methoxyphenyl)ethyl)-2,2,4,6,7-pentamethyl-2,3-dihydro-1-benzofuran-5-amine. This compound (537.9 mg, 1.18 mmol) was added to a suspension of sodium hydride (a 60% paraffin dispersion, 232.1 mg, 5.80 mmol) in DMF (25 mL) at 60° C., and the mixture was stirred for 20 minutes. Acetyl chloride (0.5 mL, 7.03 mmol) was added thereto, and the mixture was stirred at the same temperature for 1 hour. The reaction mixture was cooled to room temperature, and a saturated sodium hydrogen carbonate solution was added to the mixture, which was twice extracted with ethyl acetate. The extract was washed with water, dried over magnesium sulfate, filtered and then concentrated under reduced pressure. The residue was purified by silica gel column chromatography (hexane:ethyl acetate=3:1) to obtain the rotational isomer of the object compound (Rf=0.38; hexane:ethyl acetate=3:1) (yield 43%). Melting point: 134-136° C. (ethyl acetate-hexane).
¹H-NMR (CDCl₃) δ: 1.03 (3H, s), 1.22 (6H, d, J=7.0 Hz), 1.54 (3H, s), 1.66 (3H, s), 1.72 (3H, s), 2.12 (3H, s), 2.18 (3H, s), 2.77-2.89 (3H, m), 3.59-3.70 (2H, m), 3.77 (3H, s), 4.11 (1H, s), 6.77-7.13 (8H, m).

REFERENCE EXAMPLE 368

N-(3-(4-Isopropylphenyl)-2,2,4,6,7-pentamethyl-2,3-dihydro-1-benzofuran-5-yl)-N-(2-(4-methoxyphenyl)ethyl)acetamide The residue, as operated in the same manner as in Reference Example 367, was purified by silica gel column chromatography (hexane:ethyl acetate=3:1) to obtain the rotational isomer of the object compound (Rf=0.25; hexane:ethyl acetate=3:1) (yield 34%). Amorphous matter.
¹H-NMR (CDCl₃) δ: 1.03 (3H, s), 1.23 (6H, d, J=6.8 Hz), 1.53 (3H, s), 1.73 (3H, s), 1.75 (3H, s), 2.12 (3H, s), 2.18 (3H, s), 2.67-2.75 (2H, m), 2.80-2.94 (1H, septet, J=6.8 Hz), 3.57-3.74 (2H, m), 3.77 (3H, s), 4.14 (1H, s), 6.77-7.13 (8H, m).

EXAMPLE 1

N-(3-(4-Isopropylphenyl)-4,6,7-trimethyl-2,3-dihydro-1-benzofuran-5-yl)-3,3-dimethylbutanamide To a solution of 3-(4-isopropylphenyl)-4,6,7-trimethyl-2,3-dihydro-1-benzofuran-5-amine (430 mg, 1.46 mmol) obtained in Reference Example 30 and tert-butylacetyl chloride (0.22 mL, 1.53 mmol) in dichloromethane (10 mL) was added triethylamine (0.22 mL, 1.61 mmol) at room temperature, and the reaction mixture was stirred at room temperature for 1 hour. Water was added to the reaction solution, the organic layer was separated, and the aqueous layer was extracted with dichloromethane. The combined organic layers were washed with 1 N hydrochloric acid and an aqueous saturated sodium hydrogen carbonate solution, dried over magnesium sulfate, filtered, and then concentrated under reduced pressure. The obtained residue was purified by silica gel column chromatography (hexane:ethyl acetate=8:1) to obtain 400 mg (yield: 70%) of the title compound. Melting point: 171-173° C. (ethyl acetate-hexane).
¹H-NMR (CDCl₃) δ: 1.12 (9H, s), 1.21 (6H, d, J=6.9 Hz), 1.81 (3H, s), 2.15 (3H, s), 2.17 (3H, s), 2.25 (2H, s), 2.86 (1H, septet, J=6.9 Hz), 4.41 (1H, dd, J=8.7, 4.8 Hz), 4.52 (1H, dd, J=8.7, 4.8 Hz), 4.82 (1H, t, J=8.7 Hz), 6.49 (1H, br s), 7.04 (2H, d, J=8.1 Hz), 7.12 (2H, d, J=8.4 Hz).

EXAMPLE 2

N-(3-(4-Isopropylphenyl)-6,7-dimethyl-2,3-dihydro-1-benzofuran-5-yl)-3,3-dimethylbutanamide Using 3-(4-isopropylphenyl)-6,7-dimethyl-2,3-dihydro-1-benzofuran-5-amine obtained in Reference Example 31, the title compound was synthesized in the same manner as in Example 1. Yield: 54%. Melting point: 177-178° C. (ethyl acetate-hexane).

$^1$H-NMR (CDCl$_3$) δ: 1.09 (9H, s), 1.24 (6H, d, J=7.2 Hz), 2.13 (3H, s), 2.18 (2H, s), 2.20 (3H, s), 2.87 (1H, septet, J=7.2 Hz), 4.28 (1H, dd, J=9.0, 7.5 Hz), 4.56-4.63 (1H, m), 4.84 (1H, t, J=9.0 Hz), 6.69 (1H, br s), 6.94 (1H, s), 7.11 (2H, d, J=8.4 Hz), 7.15 (2H, d, J=8.4 Hz).

EXAMPLE 3

N-(3-(4-Isopropylphenyl)-4,6-dimethyl-2,3-dihydro-1-benzofuran-5-yl)-3,3-dimethylbutanamide Using 3-(4-isopropylphenyl)-4,6-dimethyl-2,3-dihydro-1-benzofuran-5-amine obtained in Reference Example 32, the title compound was synthesized in the same manner as in Example 1. Yield: 67%. Melting point: 130-131° C. (ethyl acetate-hexane).

$^1$H-NMR (CDCl$_3$) δ: 1.11 (9H, s), 1.21 (6H, d, J=6.9 Hz), 1.85 (3H, s), 2.21 (3H, s), 2.23 (2H, s), 2.85 (1H, septet, J=6.9 Hz), 4.40 (1H, dd, J=8.4, 4.8 Hz), 4.49 (1H, dd, J=9.0, 4.8 Hz), 4.77-4.85 (1H, m), 6.48 (1H, br s), 6.62 (1H, s), 7.03 (2H, d, J=8.1 Hz), 7.11 (2H, d, J=8.1 Hz).

EXAMPLE 4

N-(3-(4-Isopropylphenyl)-2,3-dihydro-1-benzofuran-5-yl)-3,3-dimethylbutanamide

Using 3-(4-isopropylphenyl)-2,3-dihydro-1-benzofuran-5-amine obtained in Reference Example 33, the title compound was synthesized in the same manner as in Example 1. Yield: 71%. Melting point: 119-120° C. (ethyl acetate-hexane).

$^1$H-NMR (CDCl$_3$) δ: 1.06 (9H, s), 1.23 (6H, d, J=6.9 Hz), 2.13 (2H, s), 2.88 (1H, septet, J=6.9 Hz), 4.40 (1H, dd, J=9.0, 7.5 Hz), 4.56-4.64 (1H, m), 4.87 (1H, t, J=9.0 Hz), 6.79 (1H, d, J=8.7 Hz), 6.89 (1H, br s), 7.08-7.23 (6H, m)

EXAMPLE 5

N-(3-(4-Isopropylphenyl)-3,4,6,7-tetramethyl-2,3-dihydro-1-benzofuran-5-yl)-3,3-dimethylbutanamide Using 3-(4-isopropylphenyl)-3,4,6,7-tetramethyl-2,3-dihydro-1-benzofuran-5-amine obtained in Reference Example 34, the title compound was synthesized in the same manner as in Example 1. Yield: 37%. Melting point: 194-195° C. (ethyl acetate-hexane).

$^1$H-NMR (CDCl$_3$) δ: 1.12 (9H, s), 1.23 (6H, d, J=6.9 Hz), 1.72 (3H, s), 1.74 (3H, s), 2.15 (3H, s), 2.17 (3H, s), 2.24 (2H, s), 2.87 (1H, septet, J=6.9 Hz), 4.37 (1H, d, J=8.4 Hz), 4.42 (1H, d, J=8.4 Hz), 6.48 (1H, br s), 7.13 (2H, d, J=8.4 Hz), 7.21 (2H, d, J=8.4 Hz).

EXAMPLE 6

N-(3-(4-Isopropylphenyl)-3,6,7-trimethyl-2,3-dihydro-1-benzofuran-5-yl)-3,3-dimethylbutanamide Using 3-(4-isopropylphenyl)-3,6,7-trimethyl-2,3-dihydro-1-benzofuran-5-amine obtained in Reference Example 35, the title compound was synthesized in the same manner as in Example 1. Yield: 59%. Melting point: 132-133° C. (ethyl acetate-hexane).

$^1$H-NMR (CDCl$_3$) δ: 1.11 (9H, s), 1.22 (6H, d, J=6.9 Hz), 1.71 (3H, s), 2.14 (3H, s), 2.19 (3H, s), 2.20 (2H, s), 2.86 (1H, septet, J=6.9 Hz), 4.40 (1H, d, J=8.7 Hz), 4.57 (1H, d, J=8.7 Hz), 6.72 (1H, br s), 6.97 (1H, s), 7.13 (2H, d, J=8.4 Hz), 7.20 (2H, d, J=8.4 Hz).

EXAMPLE 7

(+)-N-((3R)-3-(4-Isopropylphenyl)-4,6,7-trimethyl-2,3-dihydro-1-benzofuran-5-yl)-3,3-dimethylbutanamide N-(3-(4-Isopropylphenyl)-4,6,7-trimethyl-2,3-dihydro-1-benzofuran-5-yl)-3,3-dimethylbutanamide obtained in Example 1 was separated using high performance liquid chromatography (apparatus: GIGAPREP SK-1 manufactured by Shiseido Co., Ltd., Column: CHIRALCEL OD (50 (i, d)×500 mm) manufactured by Daicel Chemical Industries, Ltd.), Mobile phase: hexane:ethanol=95:5, Flow rate: 60 mL/min, Column temperature: 35° C., Sample injection amount: 30 mg/times, Detect: UV 220 nm), and a shorter retention time was obtained as the title compound. Recovery: 44%. Melting point: 186-187° C. (ethyl acetate-hexane). [α]$_D^{20}$=+64.0° (c=0.44, chloroform).

$^1$H-NMR (CDCl$_3$) δ: 1.12 (9H, s), 1.21 (6H, d, J=6.9 Hz), 1.84 (3H, s), 2.14 (3H, s), 2.17 (3H, s), 2.25 (2H, s), 2.85 (1H, septet, J=6.9 Hz), 4.40 (1H, dd, J=8.7, 4.8 Hz), 4.51 (1H, dd, J=9.3, 4.8 Hz), 4.81 (1H, t, J=9.0 Hz), 6.47 (1H, br s), 7.03 (2H, d, J=8.4 Hz), 7.11 (2H, d, J=8.4 Hz).

EXAMPLE 8

(−)-N-((3S)-3-(4-Isopropylphenyl)-4,6,7-trimethyl-2,3-dihydro-1-benzofuran-5-yl)-3,3-dimethylbutanamide N-(3-(4-Isopropylphenyl)-4,6,7-trimethyl-2,3-dihydro-1-benzofuran-5-yl)-3,3-dimethylbutanamide obtained in Example 1 was separated using high performance liquid chromatography (apparatus: GIGAPREP SK-1 manufactured by Shiseido Co., Ltd., Column: CHIRALCEL OD (50 (i, d)×500 mm) manufactured by Daicel Chemical Industries, Ltd.), Mobile phase: hexane:ethanol=95:5, Flow rate: 60 mL/min, Column temperature: 35° C., Sample injection amount: 30 mg/times, Detect: UV 220 nm), and a longer retention time was obtained as the title compound. Recovery: 42%. Melting point: 185-186° C. (ethyl acetate-hexane). [α]$_D^{20}$=−61.2° (c=0.42, chloroform).

$^1$H-NMR (CDCl$_3$) δ: 1.12 (9H, s), 1.21 (6H, d, J=6.9 Hz), 1.84 (3H, s), 2.14 (3H, s), 2.17 (3H, s), 2.24 (2H, s), 2.85 (1H, septet, J=6.9 Hz), 4.40 (1H, dd, J=8.7, 4.8 Hz), 4.51 (1H, dd, J=9.0, 4.8 Hz), 4.81 (1H, t, J=8.7 Hz), 6.49 (1H, br s), 7.03 (2H, d, J=8.1 Hz), 7.10 (2H, d, J=8.1 Hz).

EXAMPLE 9

N-(3-(4-Isopropylphenyl)-4,6,7-trimethyl-2,3-dihydro-1-benzofuran-5-yl)propionamide Using 3-(4-isopropylphenyl)-4,6,7-trimethyl-2,3-dihydro-1-benzofuran-5-amine obtained in Reference Example 30 and propionyl chloride, the title compound was synthesized in the same manner as in Example 1. Yield: 74%. Melting point: 164-165° C. (ethyl acetate-hexane).

$^1$H-NMR (CDCl$_3$) δ: 1.00-1.37 (9H, m), 1.82 (3H, s), 2.09-2.45 (8H, m), 2.85 (1H, septet, J=6.9 Hz), 4.37-4.60 (2H, m), 4.77-4.89 (1H, m), 6.54 (1H, br s), 6.99-7.19 (4H, m)

EXAMPLE 10

N-(3-(4-Isopropylphenyl)-4,6,7-trimethyl-2,3-dihydro-1-benzofuran-5-yl)butanamide Using 3-(4-isopropylphenyl)-4,6,7-trimethyl-2,3-dihydro-1-benzofuran-5-amine obtained in Reference Example 30 and butyryl chloride, the title compound was synthesized in the same manner as in Example 1. Yield: 80%. Melting point: 177-178° C. (THF-diisopropyl ether).

$^1$H-NMR (CDCl$_3$) δ: 1.02 (3H, t, J=7.5 Hz), 1.22 (6H, d, J=6.9 Hz), 1.71-1.87 (5H, m), 2.13 (3H, s), 2.18 (3H, s), 2.35 (2H, t, J=7.5 Hz), 2.86 (1H, septet, J=6.9 Hz), 4.42 (1H, dd, J=9.0, 4.5 Hz), 4.53 (1H, dd, J=9.0, 4.5 Hz), 4.83 (1H, t, J=9.0 Hz), 6.54 (1H, br s), 6.99-7.06 (2H, m), 7.11-7.15 (2H, m).

EXAMPLE 11

N-(3-(4-Isopropylphenyl)-4,6,7-trimethyl-2,3-dihydro-1-benzofuran-5-yl)pentanamide Using 3-(4-isopropylphenyl)-4,6,7-trimethyl-2,3-dihydro-1-benzofuran-5-amine obtained in Reference Example 30 and pentanoyl chloride, the title compound was synthesized in the same manner as in Example 1. Yield: 72%. Melting point: 128-129° C. (ethyl acetate-hexane).

$^1$H-NMR (CDCl$_3$) δ: 0.72-1.00 (3H, m), 1.21 (6H, d, J=6.9 Hz), 1.36-1.90 (7H, m), 2.11-2.42 (8H, m), 2.85 (1H, septet, J=6.9 Hz), 4.37-4.59 (2H, m), 4.77-4.89 (1H, m), 6.53 (1H, br s), 6.99-7.17 (4H, m).

EXAMPLE 12

N-(3-(4-Isopropylphenyl)-4,6,7-trimethyl-2,3-dihydro-1-benzofuran-5-yl)-2-(4-methoxyphenyl)acetamide Using 3-(4-isopropylphenyl)-4,6,7-trimethyl-2,3-dihydro-1-benzofuran-5-amine obtained in Reference Example 30 and (4-methoxyphenyl)acetyl chloride, the title compound was synthesized in the same manner as in Example 1. Yield: 62%. Melting point: 166-167° C. (Methanol).

$^1$H-NMR (CDCl$_3$) δ: 1.20 (6H, d, J=6.9 Hz), 1.72 (3H, s), 2.02 (3H, s), 2.14 (3H, s), 2.83 (1H, septet, J=6.9 Hz), 3.69 (2H, s), 3.80 (3H, s), 4.39 (1H, dd, J=9.0, 4.5 Hz), 4.48 (1H, dd, J=9.0, 4.5 Hz), 4.80 (1H, t, J=9.0 Hz), 6.46 (1H, br s), 6.90 (2H, d, J=8.4 Hz), 7.01 (2H, d, J=8.4 Hz), 7.13 (2H, d, J=8.4 Hz), 7.26 (2H, d, J=8.4 Hz).

EXAMPLE 13

N-(3-(4-Isopropylphenyl)-4,6,7-trimethyl-2,3-dihydro-1-benzofuran-5-yl)-3-(4-methoxyphenyl)propionamide Using 3-(4-isopropylphenyl)-4,6,7-trimethyl-2,3-dihydro-1-benzofuran-5-amine obtained in Reference Example 30 and 3-(4-methoxyphenyl)propionyl chloride, the title compound was synthesized in the same manner as in Example 1.

Yield: 83%. Melting point: 119-120° C. (ethyl acetate-hexane).

1H-NMR (CDCl$_3$) δ: 1.21 (6H, d, J=7.2 Hz), 1.66-1.75 (3H, m), 1.97-2.20 (6H, m), 2.61-3.02 (5H, m), 3.71-3.78 (3H, m), 4.35-4.56 (2H, m), 4.77-4.85 (1H, m), 6.45 (1H, br s), 6.62-7.20 (8H, m).

EXAMPLE 14

N-(tert-Butyl)-N'-(3-(4-isopropylphenyl)-4,6,7-trimethyl-2,3-dihydro-1-benzofuran-5-yl)urea To a solution of 3-(4-isopropylphenyl)-4,6,7-trimethyl-2,3-dihydro-1-benzofuran-5-amine (300 mg, 1.02 mmol) obtained in Reference Example 30 in dichloromethane (5 mL) was added tert-butyl isocyanate (0.14 mL, 1.22 mmol) and the resulting mixture was refluxed for 20 hours. The reaction solution was added to water and the product was extracted with ethyl acetate. The organic layer was washed with water and saturated brine, dried over anhydrous sodium sulfate, and concentrated under reduced pressure. The residue was purified by silica gel column chromatography (hexane:ethyl acetate=2:1) and recrystallized from THF-hexane to obtain 283 mg (yield: 70%) of the title compound. Melting point: 201-202° C.

$^1$H-NMR (CDCl$_3$) δ: 1.10-1.40 (15H, m), 1.87 (3H, s), 2.19 (6H, s), 2.86 (1H, septet, J=6.9 Hz), 4.00 (1H, br s), 4.45 (1H, dd, J=8.7, 4.5 Hz), 4.55 (1H, dd, J=8.7, 4.5 Hz), 4.86 (1H, t, J=8.7 Hz), 5.31 (1H, br s), 7.00 (2H, d, J=8.0 Hz), 7.12 (2H, d, J=8.0 Hz).

EXAMPLE 15

Ethyl (3-(4-isopropylphenyl)-4,6,7-trimethyl-2,3-dihydro-1-benzofuran-5-yl)oxamate Using 3-(4-isopropylphenyl)-4,6,7-trimethyl-2,3-dihydro-1-benzofuran-5-amine obtained in Reference Example 30 and ethyloxalyl chloride, the title compound was synthesized in the same manner as in Example 1. Yield: 76%. Melting point: 83-84° C. (ethyl acetate-hexane).

$^1$H-NMR (CDCl$_3$) δ: 1.22 (6H, d, J=6.9 Hz), 1.42 (3H, t, J=7.2 Hz), 1.83 (3H, s), 2.13 (3H, s), 2.19 (3H, s), 2.86 (1H, septet, J=6.9 Hz), 4.37-4.46 (3H, m), 4.54 (1H, dd, J=9.0, 4.5 Hz), 4.85 (1H, t, J=9.0 Hz), 7.04 (2H, d, J=8.1 Hz), 7.13 (2H, d, J=8.1 Hz), 8.27 (1H, br s).

EXAMPLE 16

N-(3-(4-Isopropylphenyl)-4,6,7-trimethyl-2,3-dihydro-1-benzofuran-5-yl)-3,3-dimethyl-2-oxobutanamide To a solution of ethyl (3-(4-isopropylphenyl)-4,6,7-trimethyl-2,3-dihydro-1-benzofuran-5-yl)oxamate (100 mg, 0.25 mmol) obtained in Example 15 in THF (3 ml) was added dropwise at 0° C. under an argon atmosphere tert-butylmagnesium chloride (2.0 M THF solution, 0.26 mL, 0.5 mmol) and the mixture was stirred for 30 minutes. After the reaction solution was stirred at room temperature for 1 hour, the reaction solution was added to ice and the product was extracted with ethyl acetate. The organic layer was washed with water and saturated brine, dried over anhydrous sodium sulfate, and concentrated under reduced pressure. The residue was purified by silica gel column chromatography (hexane:ethyl acetate=4:1) and recrystallized from ethyl acetate-hexane to obtain 29 mg (yield: 28%) of the title compound. Melting point: 142-143° C.

$^1$H-NMR (CDCl$_3$) δ: 1.22 (6H, d, J=6.9 Hz), 1.37 (9H, s), 1.81 (3H, s), 2.10 (3H, s), 2.18 (3H, s), 2.86 (1H, septet, J=6.9 Hz), 4.42 (1H, dd, J=9.0, 4.5 Hz), 4.52 (1H, dd, J=9.0, 4.5 Hz), 4.82 (1H, t, J=9.0 Hz), 7.03 (2H, d, J=7.8 Hz), 7.12 (2H, d, J=7.8 Hz), 8.00 (1H, br s).

EXAMPLE 17

N-(3-(4-Isopropylphenyl)-4,6,7-trimethyl-2,3-dihydro-1-benzofuran-5-yl)-2-oxobutanamide To a solution of 2-oxobutanoic acid (259 mg, 2.54 mmol) in THF (5 mL) was added dropwise with ice-cooling oxalyl chloride (0.33 mL, 3.80 mmol) and added DMF (three drops), and the mixture was stirred for 30 minutes. The reaction solution was warmed to room temperature and stirred at the same temperature for 1 hour, and then the solvent was distilled off under reduced pressure. The residue was dissolved in dichloromethane (5 mL) and the product was added dropwise with ice-cooling to a solution of 3-(4-isopropylphenyl)-4,6,7-trimethyl-2,3-dihydro-1-benzofuran-5-amine (500 mg, 1.69 mmol) obtained in Reference Example 30 and triethylamine (0.24 mL, 1.69 mmol) in THF (5 mL), and the resulting mixture was stirred for 30 minutes. After the reaction solution was warmed to room temperature, water was added to the reaction solution and the product was extracted with ethyl acetate. The organic layer was washed with water and saturated brine, dried over anhydrous sodium sulfate, filtered, and then concentrated under reduced pressure. The obtained residue was purified by silica gel column chromatography (hexane:ethyl acetate=2:1) to obtain 363 mg (yield: 57%) of the title compound. Yield: 57%. Melting point: 97-98° C. (ethyl acetate-hexane).

$^1$H-NMR (CDCl$_3$) δ: 1.15 (3H, t, J=7.2 Hz), 1.22 (6H, d, J=6.9 Hz), 1.79 (3H, s), 2.09 (3H, s), 2.18 (3H, s), 2.86 (1H, septet, J=6.9 Hz), 3.01 (2H, q, J=7.2 Hz), 4.42 (1H, dd, J=9.0, 4.5 Hz), 4.53 (1H, dd, J=9.0, 4.5 Hz), 4.83 (1H, t, J=9.0 Hz), 7.03 (2H, d, J=7.8 Hz), 7.12 (2H, d, J=7.8 Hz), 8.13 (1H, s).

EXAMPLE 18

2-Hydroxy-N-(3-(4-isopropylphenyl)-4,6,7-trimethyl-2,3-dihydro-1-benzofuran-5-yl)butanamide To a solution of N-(3-(4-isopropylphenyl)-4,6,7-trimethyl-2,3-dihydro-1-benzofuran-5-yl)-2-oxobutanamide obtained in Example 17 (237 mg, 0.62 mmol) in methanol (5 mL) was added sodium borohydride (24 mg, 0.62 mmol) at 0° C. and the resulting mixture was stirred at room temperature for 30 minutes. Water was added to the reaction solution and the product was extracted with ethyl acetate. The organic layer was washed with water and saturated brine, dried over anhydrous sodium sulfate, and concentrated under reduced pressure. The residue was recrystallized from ethyl acetate-hexane to obtain 170 mg (yield: 72%) of the title compound. Melting point: 146-147° C.

$^1$H-NMR (CDCl$_3$) δ: 1.06 (3H, t, J=7.5 Hz), 1.22 (6H, d, J=6.9 Hz), 1.70-1.88 (4H, m), 1.88-2.05 (1H, m), 2.12 (3H, s), 2.18 (3H, s), 2.50-2.60 (2H x 0.5, m), 2.86 (1H, septet, J=6.9 Hz), 4.22-4.28 (2H x 0.5, m), 4.41 (1H, dd, J=9.0, 4.5 Hz), 4.52 (1H, dd, J=9.0, 4.5 Hz), 4.82 (1H, t, J=9.0 Hz), 7.03 (2H, d, J=7.5 Hz), 7.11 (2H, d, J=7.5 Hz), 7.58 (1H x 0.5, br s), 7.60 (1H x 0.5, br s).

EXAMPLE 19

2-Hydroxy-N-(3-(4-isopropylphenyl)-4,6,7-trimethyl-2,3-dihydro-1-benzofuran-5-yl)-3,3-dimethylbutanamide To a solution of ethyl (3-(4-isopropylphenyl)-4,6,7-trimethyl-2,3-dihydro-1-benzofuran-5-yl)oxamate (500 mg, 1.26 mmol) obtained in Example 15 in THF (10 mL) was added dropwise at 0° C. under an argon atmosphere tert-butylmagnesium chloride (2.0 M THF solution, 1.9 mL, 3.78 mmol) and the mixture was stirred for 30 minutes. After the reaction solution was warmed to room temperature and was stirred at the same temperature for 1 hour, the reaction solution was added to ice and the product was extracted with ethyl acetate. The organic layer was washed with water and saturated brine, dried over anhydrous sodium sulfate, and concentrated under reduced pressure. The residue was purified by silica gel column chromatography (hexane:ethyl acetate=4:1) and recrystallized from ethyl acetate-hexane to obtain 194 mg (yield: 38%) of the title compound as a diastereomer mixture. Melting point: 165-166° C.

$^1$H-NMR (CDCl$_3$) δ: 1.09 (9H, s), 1.20-1.26 (6H, m), 1.84 (3H, s), 2.14 (3H, s), 2.18 (3H, s), 2.64 (1H x 0.5, d, J=5.1 Hz), 2.70 (1H x 0.5, d, J=5.1 Hz), 2.80-2.92 (1H, m), 3.91 (1H x 0.5, d, J=5.1 Hz), 3.92 (1H x 0.5, d, J=5.1 Hz), 4.41 (1H, dd, J=9.0, 4.5 Hz), 4.52 (1H, dd, J=9.0, 4.5 Hz), 4.82 (1H, t, J=9.0 Hz), 7.03 (2H, d, J=7.8 Hz), 7.12 (2H, d, J=7.8 Hz), 7.36 (1H x 0.5, br s), 7.47 (1H x 0.5, br s).

EXAMPLE 20

N-(7-Formyl-3-(4-isopropylphenyl)-4,6-dimethyl-2,3-dihydro-1-benzofuran-5-yl)-3,3-dimethylbutanamide To a solution of N-(3-(4-isopropylphenyl)-4,6-dimethyl-2,3-dihydro-1-benzofuran-5-yl)-3,3-dimethylbutanamide (650 mg, 1.71 mmol) obtained in Example 3 and 1,1-dichloromethyl methyl ether (237 mg, 2.06 mmol) in dichloromethane (5 mL) was added dropwise at 0° C. under an argon atmosphere and ice-cooling titanium tetrachloride (0.34 mL, 3.07 mmol), and the mixture was stirred at the same temperature for 20 minutes. Water was added to the reaction solution and the product was extracted with dichloromethane. The organic layer was washed with an aqueous saturated sodium hydrogen carbonate solution, dried over anhydrous sodium sulfate, and concentrated under reduced pressure. The obtained residue was purified by silica gel column chromatography (hexane:ethyl acetate=4:1) to obtain 520 mg (yield: 75%) of the title compound. Melting point: 177-178° C (ethyl acetate-hexane).

$^1$H-NMR (CDCl$_3$) δ: 1.11 (9H, s), 1.22 (6H, d, J=6.9 Hz), 1.91 (3H, s), 2.26 (2H, s), 2.51 (3H, s), 2.86 (1H, septet, J=6.9 Hz), 4.49-4.61 (2H, m), 4.92-5.05 (1H, m), 6.55 (hi, br s), 7.03 (2H, d, J=8.1 Hz), 7.13 (2H, d, J=8.1 Hz), 10.4 (1H, s).

EXAMPLE 21

N-(7-(Hydroxymethyl)-3-(4-isopropylphenyl)-4,6-dimethyl-2,3-dihydro-1-benzofuran-5-yl)-3,3-dimethylbutanamide To a solution of N-(7-formyl-3-(4-isopropylphenyl)-4,6-dimethyl-2,3-dihydro-1-benzofuran-5-yl)-3,3-dimethylbutanamide (370 mg, 0.91 mmol) obtained in Example 20 in methanol (5 mL) was added sodium borohydride (34 mg, 0.91 mmol) at room temperature and the mixture was stirred for 1 hour. The reaction solution was concentrated under reduced pressure and the residue was extracted with ethyl acetate. The organic layer was washed with water, dried over anhydrous sodium sulfate, and concentrated under reduced pressure. The obtained residue was recrystallized from ethyl acetate-hexane to obtain 290 mg (yield: 78%) of the title compound. Melting point: 274-275° C.

¹H-NMR (CDCl₃) δ: 1.12 (9H, s), 1.22 (6H, d, J=6.9 Hz), 1.86 (3H, s), 2.00 (1H, br s), 2.26 (5H, s), 2.86 (1H, septet, J=6.9 Hz), 4.43 (1H, dd, J=8.1, 4.8 Hz), 4.52 (1H, dd, J=9.3, 4.8 Hz), 4.64-4.93 (3H, m), 6.54 (1H, br s), 7.03 (2H, d, J=8.1 Hz), 7.11 (2H, d, J=8.1 Hz).

EXAMPLE 22

N-(7-(1-Hydroxyethyl)-3-(4-isopropylphenyl)-4,6-dimethyl-2,3-dihydro-1-benzofuran-5-yl)-3,3-dimethylbutanamide To methylmagnesium bromide (2.0 M THF solution, 5.0 mL, 10.0 mmol) was added N-(7-formyl-3-(4-isopropylphenyl)-4,6-dimethyl-2,3-dihydro-1-benzofuran-5-yl)-3,3-dimethylbutanamide (780 mg, 1.91 mmol) obtained in Example 20 at 0° C. and the reaction solution was stirred at the same temperature for 1 hour. The reaction solution was added to water and the product was extracted with ethyl acetate.

The organic layer was washed with water and saturated brine, dried over anhydrous sodium sulfate, and concentrated under reduced pressure. The obtained residue was recrystallized from hexane-ethyl acetate to obtain 590 mg (yield: 73%) of the title compound as a diastereomer mixture. Melting point: 156-157° C. (ethyl acetate-hexane).

¹H-NMR (CDCl₃) δ: 0.87-1.32 (15H, m), 1.50-1.62 (3H, m), 1.86 (3H, s), 2.17-2.25 (5H, s), 2.86 (1H, septet, J=6.9 Hz), 3.42-3.52 (1H, m), 4.47-4.52 (2H, m), 4.82-5.09 (2H, m), 6.50 (1H, br s), 7.00-7.05 (2H, m), 7.03-7.15 (2H, m).

EXAMPLE 23

N-(7-Ethyl-3-(4-isopropylphenyl)-4,6-dimethyl-2,3-dihydro-1-benzofuran-5-yl)-3,3-dimethylbutanamide To a mixture of N-(7-(1-hydroxyethyl)-3-(4-isopropylphenyl)-4,6-dimethyl-2,3-dihydro-1-benzofuran-5-yl)-3,3-dimethylbutanamide (200 mg, 0.47 mmol) obtained in Example 22 and trifluoroacetic acid (3 mL) was added under ice cooling triethylsilane (0.5 mL, 3.2 mmol) and the resulting mixture was stirred at room temperature for 30 minutes. After the reaction solution was concentrated under reduced pressure, to the residue was added an aqueous saturated sodium hydrogen carbonate solution and the aqueous layer was made alkaline, and the mixture was extracted with ethyl acetate. The organic layer was washed with water and saturated brine, dried over anhydrous sodium sulfate, and concentrated under reduced pressure. The obtained residue was purified by silica gel column chromatography (hexane:ethyl acetate=10:1) and recrystallized from hexane to obtain 100 mg (yield: 52%) of the title compound. Melting point: 135-136° C. (ethyl acetate-hexane).

¹H-NMR (CDCl₃) δ: 0.90-1.25 (18H, m), 1.84 (3H, s), 2.18 (3H, s), 2.24 (2H, s), 2.65 (2H, q, J=7.5 Hz), 2.85 (1H, septet, J=6.9 Hz), 4.40 (1H, dd, J=8.7, 4.8 Hz), 4.50 (1H, dd, J=9.0, 4.8 Hz), 4.81 (1H, t, J=9.0 Hz), 6.50 (1H, br s), 7.03 (2H, d, J=8.1 Hz), 7.11 (2H, d, J=8.1 Hz).

EXAMPLE 24

N-(3-(4-Isopropylphenyl)-4,6,7-trimethyl-2,3-dihydro-1-benzofuran-5-yl)-N,3,3-trimethylbutanamide To a solution of N-(3-(4-isopropylphenyl)-4,6,7-trimethyl-2,3-dihydro-1-benzofuran-5-yl)-3,3-dimethylbutanamide (200 mg, 0.51 mmol) synthesized in Example 1 in DMF (3 mL) was added sodium hydride (a 60% dispersion in liquid paraffin, 24 mg, 0.6 mmol) at 0° C. and the resulting mixture was stirred at room temperature for 30 minutes. To the reaction solution was added methyl iodide (78 mg, 0.55 mmol) and the resulting mixture was stirred at room temperature for 30 minutes. Water was added to the reaction solution and the product was extracted with diisopropyl ether. The extracts were washed with water, dried over magnesium sulfate, and then concentrated under reduced pressure. The obtained residue was purified by silica gel column chromatography (hexane ethyl acetate=4:1) to obtain 25 mg (yield: 12%) of the desired product having low polarity, of two rotational isomers of the title compound. Melting point: 122-123° C. (petroleum ether).

¹H-NMR (CDCl₃) δ: 0.99 (9H, s), 1.23 (6H, d, J=6.9 Hz), 1.75 (3H, s), 1.79 (2H, s), 2.06 (3H, s), 2.18 (3H, s), 2.87 (H, septet, J=6.9 Hz), 3.00 (3H, s), 4.44 (1H, dd, J=8.7, 4.8 Hz), 4.55 (1H, dd, J=9.0, 4.8 Hz), 4.87 (1H, t, J=9.0 Hz), 7.02 (2H, d, J=8.1 Hz), 7.13 (2H, d, J=8.1 Hz).

EXAMPLE 25

N-(3-(4-Isopropylphenyl)-4,6,7-trimethyl-2,3-dihydro-1-benzofuran-5-yl)-N,3,3-trimethylbutanamide By the silica gel column chromatography (hexane ethyl acetate=4:1) in Example 24, 28 mg (yield: 14%) of the title compound having high polarity of the two rotational isomers was obtained. Melting point: 80-82° C. (petroleum ether).

¹H-NMR (CDCl₃) δ: 0.91 (9H, s), 1.21 (6H, d, J=6.9 Hz), 1.72 (2H, s), 1.73 (3H, s), 2.07 (3H, s), 2.19 (3H, s), 2.86 (1H, septet, J=6.9 Hz), 3.06 (3H, s), 4.43 (1H, dd, J=8.7, 4.8 Hz), 4.55 (1H, dd, J=9.0, 4.8 Hz), 4.86 (1H, t, J=9.0 Hz), 6.95 (2H, d, J=8.1 Hz), 7.11 (2H, d, J=8.1 Hz).

EXAMPLE 26

N-(3-(4-Isopropylphenyl)-4,6-dimethyl-7-(1-pyrrolidinylmethyl)-2,3-dihydro-1-benzofuran-5-yl)-3,3-dimethylbutanamide To a solution of pyrrolidine (0.20 mL, 2.4 mmol) in methanol (5 mL) was added titanium tetraisopropoxide (0.36 mL, 1.20 mmol) and N-(7-formyl-3-(4-isopropylphenyl)-4,6-dimethyl-2,3-dihydro-1-benzofuran-5-yl)-3,3-dimethylbutanamide (250 mg; 0.61 mmol) obtained in Example 20 at 0° C. and the resulting mixture was stirred at room temperature for 14 hours. To the reaction solution was added sodium borohydride (23.2 mg, 0.61 mol) at room temperature and the resulting mixture was stirred for 1.5 hours. Water was added to the reaction solution and the product was concentrated under reduced pressure, and the residue was extracted with ethyl acetate. The obtained residue was purified by basic silica gel column chromatography (hexane:ethyl acetate=2:1) to obtain 140 mg (yield: 49%) of the title compound. Amorphous substance.

¹H-NMR (CDCl₃) δ: 1.09 (9H, s), 1.21 (6H, d, J=6.9 Hz), 1.62-1.87 (7H, m), 2.22 (2H, s), 2.26 (3H, s), 2.47-2.62 (4H, m), 2.85 (1H, septet, J=6.9 Hz), 3.58 (1H, d, J=12.0 Hz), 3.67 (1H, d, J=12.0 Hz), 4.38 (1H, dd, J=8.4, 4.5 Hz), 4.48 (1H, dd, J=9.0, 4.5 Hz), 4.78 (1H, t, J=9.0 Hz), 6.65 (1H, br s), 7.01 (2H, d, J=8.1 Hz), 7.10 (2H, d, J=8.1 Hz).

EXAMPLE 27

N-(7-((Dimethylamino)methyl)-3-(4-isopropylphenyl)-4,6-dimethyl-2,3-dihydro-1-benzofuran-5-yl)-3,3-dimethylbutanamide Using N-(7-formyl-3-(4-isopropylphenyl)-4,6-dimethyl-2,3-dihydro-1-benzofuran-5-yl)-3,3-dimethylbutanamide obtained in Example 20 and dimethylamine, the title compound was synthesized in the same manner as in Example 26. Yield: 37%. Amorphous substance.

$^1$H-NMR (CDCl$_3$) δ: 1.11 (9H, s), 1.21 (6H, d, J=6.9 Hz), 1.85 (3H, s), 2.20-2.32 (11H, m), 2.85 (1H, septet, J=6.9 Hz), 3.39 (H, d, J=12.3 Hz), 3.45 (1H, d, J=12.3 Hz), 4.40 (1H, dd, J=8.7, 4.8 Hz), 4.51 (1H, dd, J=9.0, 4.8 Hz), 4.80 (1H, t, J=8.7 Hz), 6.51 (1H, br s), 7.01 (2H, d, J=8.1 Hz), 7.10 (2H, d, J=8.1 Hz).

EXAMPLE 28

N-(7-(1-Hydroxyethyl)-3-(4-isopropylphenyl)-4,6-dimethyl-2,3-dihydro-1-benzofuran-5-yl)-3,3-dimethylbutanamide To methylmagnesium bromide (2.0 M THF solution, 5.0 mL, 10.0 mmol) was added N-(7-formyl-3-(4-isopropylphenyl)-4,6-dimethyl-2,3-dihydro-1-benzofuran-5-yl)-3,3-dimethylbutanamide (1.0 g, 1.91 mmol) obtained in Example 20 at 0° C. and the reaction solution was stirred at the same temperature for 1 hour. The reaction solution was poured into water and the product was extracted with ethyl acetate. The organic layer was washed with water and 1 N hydrochloric acid, dried over anhydrous sodium sulfate, and concentrated under reduced pressure. The obtained residue was purified by silica gel column chromatography (hexane:ethyl acetate=4:1) to obtain 192 mg (yield: 19%) of the title compound as a low polarity isomer. Melting point: 147-148° C. (ethyl acetate-hexane).

$^1$H-NMR (CDCl$_3$) δ: 1.12 (9H, s), 1.21 (6H, d, J=6.9 Hz), 1.51 (3H, d, J=6.6 Hz), 1.86 (3H, s), 2.17 (3H, s), 2.25 (2H, s), 2.86 (1H, septet, J=6.9 Hz), 3.51 (1H, d, J=10.5 Hz), 4.43-4.58 (2H, m), 4.82-5.11 (2H, m), 6.51 (1H, br s), 7.02 (2H, d, J=8.1 Hz), 7.11 (2H, d, J=8.1 Hz).

EXAMPLE 29

N-(7-(1-Hydroxyethyl)-3-(4-isopropylphenyl)-4,6-dimethyl-2,3-dihydro-1-benzofuran-5-yl)-3,3-dimethylbutanamide The residue treated in the same manner as described in the Example 28 was purified by silica gel column chromatography (hexane:ethyl acetate=4:1) to obtain 122 mg (yield: 12%) of the title compound as a high polarity isomer. Melting point: 169-170° C. (ethyl acetate-hexane).

$^1$H-NMR (CDCl$_3$) δ: 1.12 (9H, s), 1.22 (6H, d, J=6.9 Hz), 1.55 (3H, d, J=6.6 Hz), 1.85 (3H, s), 2.18 (3H, s), 2.25 (2H, s), 2.86 (1H, septet, J=6.9 Hz), 3.49 (1H, d, J=9.9 Hz), 4.43-4.58 (2H, m), 4.82-5.12 (2H, m), 6.53 (1H, br s), 7.03 (2H, d, J=8.1 Hz), 7.13 (2H, d, J=8.1 Hz).

EXAMPLE 30

N-(7-(1-Hydroxypropyl)-3-(4-isopropylphenyl)-4,6-dimethyl-2,3-dihydro-1-benzofuran-5-yl)-3,3-dimethylbutanamide To ethylmagnesium chloride (2.0 M THF solution, 5.0 mL, 10.0 mmol) was added N-(7-formyl-3-(4-isopropylphenyl)-4,6-dimethyl-2,3-dihydro-1-benzofuran-5-yl)-3,3-dimethylbutanamide (0.7 g, 1.72 mmol) obtained in Example 20 at 0° C. and the reaction solution was stirred at the same temperature for 1 hour. The reaction solution was added to water and the product was extracted with ethyl acetate. The organic layer was washed with water and 1 N hydrochloric acid, dried over anhydrous sodium sulfate, and concentrated under reduced pressure. The obtained residue was purified by silica gel column chromatography (hexane:ethyl acetate=4:1) to obtain 264 mg (yield: 35%) of the title compound as a low polarity isomer. Melting point: 145-146° C. (ethyl acetate-hexane).

$^1$H-NMR (CDCl$_3$) δ: 0.90-1.05 (3H, m), 1.11 (9H, s), 1.21 (6H, d, J=6.9 Hz), 1.69-1.95 (5H, m), 2.17 (3H, s), 2.25 (2H, s), 2.86 (1H, septet, J=6.9 Hz), 3.32 (1H, d, J=10.2 Hz), 4.41-4.57 (2H, m), 4.72-4.90 (2H, m), 6.51 (1H, br s), 7.01 (2H, d, J=8.1 Hz), 7.11 (2H, d, J=8.4 Hz).

EXAMPLE 31

N-(7-(1-Hydroxypropyl)-3-(4-isopropylphenyl)-4,6-dimethyl-2,3-dihydro-1-benzofuran-5-yl)-3,3-dimethylbutanamide The residue treated in the same manner as described in the Example 30 was purified by silica gel column chromatography (hexane:ethyl acetate=4:1) to obtain 160 mg (yield: 21%) of the title compound as a high polarity isomer. Melting point: 165-167° C. (ethyl acetate-hexane).

$^1$H-NMR (CDCl$_3$) δ: 0.87-1.09 (3H, m), 1.11 (9H, s), 1.22 (6H, d, J=6.9 Hz), 1.77-1.93 (5H, m), 2.17 (3H, s), 2.24 (2H, s), 2.86 (1H, septet, J=6.9 Hz), 3.36 (1H, d, J=10.2 Hz), 4.40-4.52 (2H, m), 4.72-4.90 (2H, m), 6.56 (1H, br s), 7.01 (2H, d, J=8.4 Hz), 7.12 (2H, d, J=8.4 Hz).

EXAMPLE 32

N-(7-Acetyl-3-(4-isopropylphenyl)-4,6-dimethyl-2,3-dihydro-1-benzofuran-5-yl)-3,3-dimethylbutanamide A mixture of N-(7-(1-hydroxyethyl)-3-(4-isopropylphenyl)-4,6-dimethyl-2,3-dihydro-1-benzofuran-5-yl)-3,3-dimethylbutanamide (580 mg, 1.37 mmol) obtained in Example 22 and manganese dioxide (1.43 g, 16.4 mmol) were stirred at 100° C. for two hours. Insoluble materials were filtered off, and the filtrate was concentrated under reduced pressure. The obtained residue was purified by silica gel column chromatography (hexane:ethyl acetate=4:1) to obtain 440 mg (yield: 76%) of the title compound. Melting point: 200-201° C. (ethyl acetate-hexane).

$^1$H-NMR (CDCl$_3$) δ: 1.12 (9H, s), 1.22 (6H, d, J=6.8 Hz), 1.89 (3H, s), 2.23 (3H, s), 2.26 (2H, s), 2.58 (3H, s), 2.87 (1H, septet, J=6.8 Hz), 4.41-4.58 (2H, m), 4.78-4.96 (1H, m), 6.47 (1H, br s), 7.03 (2H, d, J=8.2 Hz), 7.14 (2H, d, J=8.2 Hz).

EXAMPLE 33

N-(7-(1-Hydroxy-1-methylethyl)-3-(4-isopropylphenyl)-4,6-dimethyl-2,3-dihydro-1-benzofuran-5-yl)-3,3-dimethylbutanamide Using N-(7-acetyl-3-(4-isopropylphenyl)-4,6-dimethyl-2,3-dihydro-1-benzofuran-5-yl)-3,3-dimethylbutanamide obtained in Example 32, the title compound was synthesized in the same manner as in Example 22. Yield: 34%. Melting point: 133-134° C. (ethyl acetate-hexane).

$^1$H-NMR (CDCl$_3$) δ: 1.12 (9H, s), 1.21 (6H, d, J=6.8 Hz), 1.68 (3H, s), 1.70 (3H, s), 1.86 (3H, s), 2.26 (2H, s), 2.35 (3H, s), 2.86 (1H, septet, J=6.8 Hz), 4.37-4.55 (3H, m), 4.75-4.88 (1H, m), 6.47 (1H, br s), 7.03 (2H, d, J=8.2 Hz), 7.13 (2H, d, J=8.2 Hz).

EXAMPLE 34

N-(3-(4-Isopropylphenyl)-4,6-dimethyl-7-propyl-2,3-dihydro-1-benzofuran-5-yl)-3,3-dimethylbutanamide Using a diastereo mixture of N-(7-(1-hydroxypropyl)-3-(4-isopropylphenyl)-4,6-dimethyl-2,3-dihydro-1-benzofuran-5-yl)-3,3-dimethylbutanamide obtained in the synthesis in Examples 30 and 31, the title compound was synthesized in the same manner as in Example 23. Yield: 86%. Melting point: 145-148° C. (ethyl acetate-hexane).

$^1$H-NMR (CDCl$_3$) δ: 0.80-1.35 (18H, m), 1.45-1.65 (2H, m), 1.80 (3H, s), 2.17 (3H, s), 2.25 (2H, s), 2.57-2.68 (2H, m), 2.85 (1H, septet, J=6.8 Hz), 4.40 (1H, dd, J=8.4, 6.6 Hz), 4.50 (1H, dd, J=8.8, 6.6 Hz), 4.80 (1H, t, J=8.4 Hz), 6.49 (1H, br s), 7.04 (2H, d, J=8.4 Hz), 7.12 (2H, d, J=8.4 Hz).

EXAMPLE 35

N-(7-Bromo-3-(4-isopropylphenyl)-4,6-dimethyl-2,3-dihydro-1-benzofuran-5-yl)-3,3-dimethylbutanamide To a solution of N-(3-(4-isopropylphenyl)-4,6-dimethyl-2,3-dihydro-1-benzofuran-5-yl)-3,3-dimethylbutanamide (1.0 g, 2.63 mmol) obtained in Example 3 in acetonitrile (30 mL) was added N-bromosuccinimide (468 mg, 2.63 mmol) at 0° C. and the reaction mixture was stirred at room temperature for 2 hours. Water was added to the reaction solution, the organic layer was separated, and the aqueous layer was extracted with ethyl acetate. The combined organic layers were washed with water, dried over magnesium sulfate, filtered, and concentrated under reduced pressure. The solvent was distilled off under reduced pressure. The obtained residue was recrystallized from ethanol to obtain 1.10 g (yield: 91%) of the title compound. Melting point: 191-193° C.

$^1$H-NMR (CDCl$_3$) δ: 1.11 (9H, s), 1.22 (6H, d, J=6.9 Hz), 1.82 (3H, s), 2.24 (2H, s), 2.33 (3H, s), 2.86 (1H, septet, J=6.9 Hz), 4.51 (1H, dd, J=9.0, 4.8 Hz), 4.63 (1H, dd, J=9.0, 4.8 Hz), 4.93 (1H, t, J=9.3 Hz), 6.54 (1H, br s), 7.03 (2H, d, J=8.1 Hz), 7.12 (2H, d, J=8.1 Hz).

EXAMPLE 36

N-(3-(4-Isopropylphenyl)-7-methoxy-4,6-dimethyl-2,3-dihydro-1-benzofuran-5-yl)-3,3-dimethylbutanamide A mixture of N-(7-bromo-3-(4-isopropylphenyl)-4,6-dimethyl-2,3-dihydro-1-benzofuran-5-yl)-3,3-dimethylbutanamide (250 mg, 0.545 mmol) obtained in Example 35, copper (I) bromide (78 mg, 0.545 mmol), ethyl acetate (88 mg, 1.00 mmol), and 28% sodium methoxide-methanol solution (20 mL) was refluxed with heating for 6 hours. 1 N Hydrochloric acid was added to the reaction solution and the product was extracted with diisopropyl ether. The extracts were washed with water, dried over magnesium sulfate, filtered, and concentrated under reduced pressure. The obtained residue was purified by silica gel column chromatography (hexane:ethyl acetate=4:1) and recrystallized from hexane-ethyl acetate to obtain 130 mg (yield: 58%) of the title compound. Melting point: 191-193° C.

$^1$H-NMR (CDCl$_3$) δ: 1.11 (9H, s), 1.22 (6H, d, J=6.9 Hz), 1.83 (3H, s), 2.16 (3H, s), 2.25 (2H, s), 2.86 (1H, septet, J=6.9 Hz), 3.89 (3H, s), 4.44-4.55 (2H, m), 4.87 (1H, t, J=8.1 Hz), 6.47 (1H, br s), 7.05 (2H, d, J=8.1 Hz), 7.13 (2H, d, J=8.1 Hz).

EXAMPLE 37

(+)-N-((3R)-3-(4-Isopropylphenyl)-4,6-dimethyl-2,3-dihydro-1-benzofuran-5-yl)-3,3-dimethylbutanamide Using (+)-(3R)-3-(4-isopropylphenyl)-4,6-dimethyl-2,3-dihydro-1-benzofuran-5-amine obtained in Reference Example 141, the title compound was synthesized in the same manner as in Example 1. Yield: 93%. Melting point: 148-149° C. (ethyl acetate-hexane). [α]$_D^{20}$=+93.2° (c=0.54, chloroform).

$^1$H-NMR (CDCl$_3$) δ: 1.11 (9H, s), 1.22 (6H, d, J=6.9 Hz), 1.86 (3H, s), 2.22 (3H, s), 2.24 (2H, s), 2.86 (1H, septet, J=6.9 Hz), 4.41 (1H, dd, J=9.0, 4.8 Hz), 4.50 (1H, dd, J=9.0, 4.8 Hz), 4.83 (1H, t, J=9.0 Hz), 6.47 (1H, br s), 6.63 (1H, s), 7.04 (2H, d, J=8.1 Hz), 7.12 (2H, d, J=8.1 Hz).

EXAMPLE 38

(+)-N-((3R)-7-Acetyl-3-(4-isopropylphenyl)-4,6-dimethyl-2,3-dihydro-1-benzofuran-5-yl)-3,3-dimethylbutanamide To a solution of (+)-N-((3R)-3-(4-isopropylphenyl)-4,6-dimethyl-2,3-dihydro-1-benzofuran-5-yl)-3,3-dimethylbutanamide (933 mg, 2.46 mmol) obtained in Example 37 in dichloromethane (20 mL) was added aluminum chloride (721 mg, 5.40 mmol) at −70° C. under an argon atmosphere and the mixture was stirred for 20 minutes. To the reaction solution was added dropwise acetyl chloride (424 mg, 5.40 mmol) at the same temperature and the reaction mixture was gradually warmed to 10° C. The reaction solution was added to ice, the organic layer was separated and the aqueous layer was extracted with ethyl acetate. The combined organic layers were washed with water, an aqueous saturated sodium hydrogen carbonate solution and saturated brine, dried over sodium sulfate, filtered, and then concentrated under reduced pressure. The obtained residue was purified by silica gel column chromatography (hexane:ethyl acetate=2:1) to synthesize 873 mg (yield: 84%) of the title compound. Melting point: 176-177° C. (ethyl acetate-hexane). [α]$_D^{20}$=+6.2° (c=0.53, chloroform).

$^1$H-NMR (CDCl$_3$) δ: 1.11 (9H, s), 1.22 (6H, d, J=6.9 Hz), 1.88 (3H, s), 2.22 (3H, s), 2.25 (2H, s), 2.58 (3H, s), 2.86 (1H, septet, J=6.9 Hz), 4.46-4.55 (2H, m), 4.89 (1H, t, J=8.4 Hz), 6.53 (1H, br s), 7.03 (2H, d, J=8.1 Hz), 7.14 (2H, d, J=8.1 Hz).

EXAMPLE 39

(−)-N-((3R)-7-Formyl-3-(4-isopropylphenyl)-4,6-dimethyl-2,3-dihydro-1-benzofuran-5-yl)-3,3-dimethylbutanamide Using (+)-N-((3R)-3-(4-isopropylphenyl)-4,6-dimethyl-2,3-dihydro-1-benzofuran-5-yl)-3,3-dimethylbutanamide obtained in Example 37, the title compound was synthesized in the same manner as in Example 20. Yield: 83%. Melting point: 179-180° C. (ethyl acetate-hexane). $[\alpha]_D^{20}$=−25.8° (c=0.48, chloroform).
$^1$H-NMR (CDCl$_3$) δ: 1.12 (9H, s), 1.22 (6H, d, J=6.9 Hz), 1.92 (3H, s), 2.23 (2H, s), 2.52 (3H, s), 2.86 (1H, septet, J=6.9 Hz), 4.45-4.60 (2H, m), 4.97 (1H, t, J=10.8 Hz), 6.49 (1H, br s), 7.03 (2H, d, J=8.1 Hz), 7.14 (2H, d, J=8.1 Hz), 10.43 (1H, s)

EXAMPLE 40

(+)-N-((3R)-7-(1-Hydroxyethyl)-3-(4-isopropylphenyl)-4,6-dimethyl-2,3-dihydro-1-benzofuran-5-yl)-3,3-dimethylbutanamide A compound, which was produced according to the same manner as in Example 28 using (−)-N-((3R)-7-formyl-3-(4-isopropylphenyl)-4,6-dimethyl-2,3-dihydro-1-benzofuran-5-yl)-3,3-dimethylbutanamide obtained in Example 39, was purified by silica gel column chromatography (hexane ethyl acetate=4:1) to obtain a low polarity isomer of the title compound. Yield: 33%. Melting point: 188-189° C. (ethyl acetate-hexane). $[\alpha]_D^{20}$=+63.4° (c=0.49, chloroform).
$^1$H-NMR (CDCl$_3$) δ: 1.11 (9H, s), 1.22 (6H, d, J=6.9 Hz), 1.52 (3H, d, J=6.6 Hz), 1.85 (3H, s), 2.18 (3H, s), 2.25 (2H, s), 2.86 (1H, septet, J=6.9 Hz), 3.50 (1H, br d), 4.45-4.54 (2H, m), 4.85-4.94 (1H, m), 5.00-5.10 (1H, m), 6.50 (1H, br s), 7.02 (2H, d, J=8.1 Hz), 7.12 (2H, d, J=8.1 Hz).

EXAMPLE 41

(+)-N-((3R)-7-(1-Hydroxyethyl)-3-(4-isopropylphenyl)-4,6-dimethyl-2,3-dihydro-1-benzofuran-5-yl)-3,3-dimethylbutanamide A compound, which was produced according to the same manner as in Example 28 using (−)-N-((3R)-7-formyl-3-(4-isopropylphenyl)-4,6-dimethyl-2,3-dihydro-1-benzofuran-5-yl)-3,3-dimethylbutanamide obtained in Example 39, was purified by silica gel column chromatography (hexane:ethyl acetate=4:1) to obtain a high polarity isomer of the title compound. Yield: 49%. Melting point: 149-150° C. (ethyl acetate-hexane). $[\alpha]_D^{20}$=+15.2° (c=0.49, chloroform).
$^1$H-NMR (CDCl$_3$) δ: 1.12 (9H, s), 1.22 (6H, d, J=6.9 Hz), 1.55 (3H, d, J=6.6 Hz), 1.85 (3H, s), 2.19 (3H, s), 2.25 (2H, s), 2.86 (1H, septet, J=6.9 Hz), 3.47 (1H, br d), 4.40-4.55 (2H, m), 4.83-4.91 (1H, m), 5.01-5.11 (1H, m), 6.50 (1H, br s), 7.03 (2H, d, J=7.8 Hz), 7.13 (2H, d, J=7.8 Hz).

EXAMPLE 42

(+)-N-((3R)-7-Ethyl-3-(4-isopropylphenyl)-4,6-dimethyl-2,3-dihydro-1-benzofuran-5-yl)-3,3-dimethylbutanamide A solution of (+)-N-((3R)-7-(1-hydroxyethyl)-3-(4-isopropylphenyl)-4,6-dimethyl-2,3-dihydro-1-benzofuran-5-yl)-3,3-dimethylbutanamide (746 mg, 1.77 mmol) obtained in Examples 40 and 41, and 10% palladium on carbon (water content: 50%, 75 mg) in ethanol (8 mL) was refluxed with heating for 2 hours. The catalyst was removed and the reaction solution was concentrated under reduced pressure.
The obtained residue was recrystallized from THF-hexane to obtain 589 mg (yield: 96%) of the title compound. Melting point: 156-157° C. $[\alpha]_D^{20}$+50.7° (c 0.46, chloroform).
$^1$H-NMR (CDCl$_3$) δ: 1.12 (9H, s), 1.14 (3H, t, J=7.5 Hz), 1.22 (6H, d, J=6.9 Hz), 1.85 (3H, s), 2.18 (3H, s), 2.25 (2H, s), 2.66 (2H, q, J=7.5 Hz), 2.85 (1H, septet, J=6.9 Hz), 4.41 (1H, dd, J=9.0, 4.5 Hz), 4.51 (1H, dd, J=9.0, 4.5 Hz), 4.82 (1H, t, J=9.0 Hz), 6.47 (1H, br s), 7.04 (2H, d, J=7.8 Hz), 7.12 (2H, d, J=7.8 Hz).

EXAMPLE 43

(+)-N-((3R)-7-(1-Hydroxypropyl)-3-(4-isopropylphenyl)-4,6-dimethyl-2,3-dihydro-1-benzofuran-5-yl)-3,3-dimethylbutanamide A compound, which was produced according to the same manner as in Example 30 using (−)-N-((3R)-7-formyl-3-(4-isopropylphenyl)-4,6-dimethyl-2,3-dihydro-1-benzofuran-5-yl)-3,3-dimethylbutanamide obtained in Example 39, was purified by silica gel column chromatography (hexane:ethyl acetate=4:1) to obtain a low polarity isomer of the title compound. Yield: 25%. Melting point: 205-206° C. (ethyl acetate-hexane). $[\alpha]_D^{20}$=+54.80 (c=0.44, chloroform).
$^1$H-NMR (CDCl$_3$) δ: 0.99 (3H, t, J=7.5 Hz), 1.11 (9H, s), 1.21 (6H, d, J=6.9 Hz), 1.70-1.93 (5H, m), 2.17 (3H, s), 2.23 (2H, s), 2.86 (1H, septet, J=6.9 Hz), 3.31 (1H, br d), 4.42-4.52 (2H, m), 4.74-4.80 (1H, m), 4.85 (1H, t, J=8.1 Hz), 6.49 (1H, br s), 7.01 (2H, d, J=8.4 Hz), 7.11 (2H, d, J=8.4 Hz).

EXAMPLE 44

(+)-N-((3R)-7-(1-Hydroxypropyl)-3-(4-isopropylphenyl)-4,6-dimethyl-2,3-dihydro-1-benzofuran-5-yl)-3,3-dimethylbutanamide A compound, which was produced according to the same manner as in Example 30 using (−)-N-((3R)-7-formyl-3-(4-isopropylphenyl)-4,6-dimethyl-2,3-dihydro-1-benzofuran-5-yl)-3,3-dimethylbutanamide obtained in Example 39, was purified by silica gel column chromatography (hexane:ethyl acetate=4:1) to obtain a high polarity isomer of the title compound. Yield: 38%. Amorphous powder. $[\alpha]_D^{20}$=+16.1° (c=0.54, chloroform).
$^1$H-NMR (CDCl$_3$) δ: 1.00 (3H, t, J=7.5 Hz), 1.09 (9H, s), 1.24 (6H, d, J=6.9 Hz), 1.76-1.95 (5H, m), 2.15 (3H, s), 2.23 (2H, s); 2.85 (1H, septet, J=6.9 Hz), 3.41 (1H, br d), 4.41-4.49 (2H, m), 4.73-4.88 (2H, m), 6.85 (1H, br s), 7.02 (2H, d, J=8.1 Hz), 7.13 (2H, d, J=8.1 Hz).

EXAMPLE 45

(+)-N-((3R)-3-(4-Isopropylphenyl)-4,6-dimethyl-7-propyl-2,3-dihydro-1-benzofuran-5-yl)-3,3-dimethylbutanamide A solution of a diastereo mixture of (+)-N-((3R)-7-(1-hydroxypropyl)-3-(4-isopropylphenyl)-4,6-dimethyl-2,3-dihydro-1-benzofuran-5-yl)-3,3-dimethylbutanamide (620 mg, 1.42 mmol) obtained in Examples 43 and 44, and 10% palladium on carbon (water content: 50%, 62 mg) in acetic acid (3 mL) was reacted at 80° C. for 2 hours. The catalyst was removed, water was added to the reaction solution, and the product was extracted with ethyl acetate. The organic layer was washed with water, an aqueous saturated sodium hydrogen carbonate solution and saturated brine, dried over sodium sulfate, filtered, and then concentrated under reduced pressure. The obtained residue was recrystallized from ethyl acetate-hexane to obtain 423 mg (yield: 71%) of the title compound. Melting point: 184-185° C. $[\alpha]_D^{20}$=+41.6° (c=0.51, chloroform).

¹H-NMR (CDCl₃) δ: 0.98 (3H, t, J=7.5 Hz), 1.12 (9H, s), 1.22 (6H, d, J=6.9 Hz), 1.50-1.60 (2H, m), 1.85 (3H, s), 2.17 (3H, s), 2.25 (2H, s), 2.57-2.63 (2H, m), 2.85 (1H, septet, J=6.9 Hz), 4.40 (1H, dd, J=9.0, 4.5 Hz), 4.50 (1H, dd, J=9.0, 4.5 Hz), 4.80 (1H, t, J=9.0 Hz), 6.46 (1H, br s), 7.04 (2H, d, J=8.1 Hz), 7.12 (2H, d, J=8.1 Hz).

EXAMPLE 46

(+)-N-((3R)-7-(1-Hydroxy-1-methylethyl)-3-(4-isopropylphenyl)-4,6-dimethyl-2,3-dihydro-1-benzofuran-5-yl)-3,3-dimethylbutanamide Using (+)-N-((3R)-7-acetyl-3-(4-isopropylphenyl)-4,6-dimethyl-2,3-dihydro-1-benzofuran-5-yl)-3,3-dimethylbutanamide obtained in Example 38, the title compound was synthesized in the same manner as in Example 22. Yield: 82%. Melting point: 141-142° C. (ethyl acetate-hexane). $[\alpha]_D^{20}$+40.8° (c=0.46, chloroform).

¹H-NMR (CDCl₃) δ: 1.11 (9H, s), 1.22 (6H, d, J=6.9 Hz), 1.68 (3H, s), 1.70 (3H, s), 1.86 (3H, s), 2.25 (2H, s), 2.35 (3H, s), 2.86 (1H, septet, J=6.9 Hz), 4.37 (1H, s), 4.37-4.50 (2H, m), 4.75-4.87 (1H, m), 6.52 (1H, br s), 7.03 (2H, d, J=8.0 Hz), 7.13 (2H, d, J=8.0 Hz).

EXAMPLE 47

(+)-N-(tert-Butyl)-N'-((3R)-3-(4-isopropylphenyl)-4,6-dimethyl-2,3-dihydro-1-benzofuran-5-yl)urea To a solution of (+)-(3R)-3-(4-isopropylphenyl)-4,6-dimethyl-2,3-dihydro-1-benzofuran-5-amine (1.0 g, 3.55 mmol) obtained in Reference Example 141 in THF (10 mL) was added dropwise with ice-cooling 2,2,2-trichloroethyl chloroformate (0.49 mL, 3.55 mmol), was added triethylamine (0.52 mL, 3.73 mmol) and the reaction mixture was stirred for 30 minutes, and then the reaction solution was warmed to room temperature. Water was added to the reaction solution, and the product was extracted with ethyl acetate. The organic layer was washed with water, an aqueous saturated sodium hydrogen carbonate solution and saturated brine, dried over sodium sulfate, filtered, and then concentrated under reduced pressure. The solution of the obtained 2,2,2-trichloroethyl (3-(4-isopropylphenyl)-4,6-dimethyl-2,3-dihydro-1-benzofuran-5-yl)carbamate (1.60 g, 3.50 mmol) and tert-butylamine (779 mg, 10.65 mmol) in dimethylsulfoxide (20 mL) was stirred at 45° C. for 5 hours under an argon atmosphere. Water was added to the reaction solution, and the product was extracted with ethyl acetate. The organic layer was washed with water, an aqueous saturated sodium hydrogen carbonate solution and saturated brine, dried over sodium sulfate, filtered, and then concentrated under reduced pressure. The obtained residue was purified by silica gel column chromatography (hexane:ethyl acetate=2:1) to obtain 1.19 g (yield: 88%) of the title compound. Melting point: 205-206° C. (ethyl acetate-hexane). $[\alpha]_D^{20}$=+81.0° (c=0.51, chloroform).

¹H-NMR (CDCl₃) δ: 1.18-1.30 (15H, m), 1.89 (3H, s), 2.25 (3H, s), 2.86 (1H, septet, J=6.9 Hz), 4.00 (1H, br s), 4.45 (1H, dd, J=8.7, 4.8 Hz), 4.53 (1H, dd, J=8.7, 4.8 Hz), 4.88 (1H, t, J=8.7 Hz), 5.25 (1H, br s), 6.66 (1H, s), 7.00 (2H, d, J=8.1 Hz), 7.14 (2H, d, J=8.1 Hz).

EXAMPLE 48

(−)-N-(tert-Butyl)-N'-((3R)-7-formyl-3-(4-isopropylphenyl)-4,6-dimethyl-2,3-dihydro-1-benzofuran-5-yl)urea Using (+)-N-(tert-butyl)-N'-((3R)-3-(4-isopropylphenyl)-4,6-dimethyl-2,3-dihydro-1-benzofuran-5-yl)urea, the title compound was synthesized in the same manner as in Example 20. Yield: 78%. Melting point: 209-210° C. (ethyl acetate-hexane). $[\alpha]_D^{20}$=−31.2° (c=0.48, chloroform).

¹H-NMR (CDCl₃) δ: 1.10-1.40 (15H, m), 1.96 (3H, s), 2.57 (3H, s), 2.86 (1H, septet, J=6.9 Hz), 3.97 (1H, br s), 4.50-4.63 (2H, m), 4.95-5.05 (1H, m), 5.40 (1H, br s), 7.01 (2H, d, J=8.1 Hz), 7.15 (2H, d, J=8.1 Hz), 10.47 (1H, s).

EXAMPLE 49

(+)-N-(tert-Butyl)-N'-((3R)-7-(hydroxymethyl)-3-(4-isopropylphenyl)-4,6-dimethyl-2,3-dihydro-1-benzofuran-5-yl)urea Using (−)-N-(tert-butyl)-N'-((3R)-7-formyl-3-(4-isopropylphenyl)-4,6-dimethyl-2,3-dihydro-1-benzofuran-5-yl)urea obtained in Example 48, the title compound was synthesized in the same manner as in Example 21. Yield: 97%. Melting point: 187-188° C. (ethyl acetate-hexane). $[\alpha]_D^{20}$+34.0° (c=0.43, chloroform).

¹H-NMR (CDCl₃) δ: 1.12-1.28 (15H, m), 1.89 (3H, s), 2.05 (1H, br s), 2.31 (3H, s), 2.86 (1H, septet, J=6.9 Hz), 3.99 (1H, br s), 4.48 (1H, dd, J=9.0, 4.5 Hz), 4.56 (1H, dd, J=9.0, 4.5 Hz), 4.72-4.82 (2H, m), 4.88 (1H, t, J=9.0 Hz), 5.30 (1H, br s), 6.97 (2H, d, J=8.1 Hz), 7.13 (2H, d, J=8.1 Hz).

EXAMPLE 50

(+)-N-(tert-Butyl)-N'-((3R)-3-(4-isopropylphenyl)-4,6,7-trimethyl-2,3-dihydro-1-benzofuran-5-yl)urea Using (+)-N-(tert-butyl)-N'-((3R)-7-(hydroxymethyl)-3-(4-isopropylphenyl)-4,6-dimethyl-2,3-dihydro-1-benzofuran-5-yl)urea obtained in Example 49, the title compound was synthesized in the same manner as in Example 45. Yield: 57%. Melting point: 209-210° C. (ethyl acetate-hexane). $[\alpha]_D^{20}$=+53.2° (c=0.47, chloroform).

¹H-NMR (CDCl₃) δ: 1.10-1.38 (15H, m), 1.87 (3H, s), 2.19 (6H, s), 2.86 (1H, septet, J=6.9 Hz), 3.99 (1H, br s), 4.44 (1H, dd, J=9.0, 4.5 Hz), 4.54 (1H, dd, J=9.0, 4.5 Hz), 4.86 (1H, t, J=9.0 Hz), 5.29 (1H, br s), 6.99 (2H, d, J=8.1 Hz), 7.11 (2H, d, J=8.1 Hz).

EXAMPLE 51

(−)-N-((3R)-7-Bromo-3-(4-isopropylphenyl)-4,6-dimethyl-2,3-dihydro-1-benzofuran-5-yl)-3,3-dimethylbutanamide Using (+)-N-((3R)-3-(4-isopropylphenyl)-4,6-dimethyl-2,3-dihydro-1-benzofuran-5-yl)-3,3-dimethylbutanamide obtained in Example 37, the title compound was synthesized in the same manner as in Example 35. Yield: 90%. Melting point: 118-119° C. (ethyl acetate-hexane). $[\alpha]_D^{20}$=−13.0° (c=0.52, chloroform).

¹H-NMR (CDCl₃) δ: 1.11 (9H, s), 1.22 (6H, d, J=6.9 Hz), 1.82 (3H, s), 2.24 (2H, s), 2.32 (3H, s), 2.86 (1H, septet, J=6.9 Hz), 4.51 (1H, dd, J=9.0, 4.5 Hz), 4.62 (1H, dd, J=9.0, 4.5 Hz), 4.93 (1H, t, J=9.0 Hz), 6.56 (1H, br s), 7.03 (2H, d, J=8.1 Hz), 7.12 (2H, d, J=8.1 Hz).

EXAMPLE 52

(+)-N-((3R)-3-(4-Isopropylphenyl)-7-methoxy-4,6-dimethyl-2,3-dihydro-1-benzofuran-5-yl)-3,3-dimethylbutanamide Using (−)-N-((3R)-7-bromo-3-(4-isopropylphenyl)-4,6-dimethyl-2,3-dihydro-1-benzofuran-5-yl)-3,3-dimethylbutanamide obtained in Example 51, the title compound was synthesized in the same manner as in Example 36. Yield: 98%. Melting point: 150-151° C. (ethyl acetate-hexane). $[\alpha]_D^{20}$=+55.9° (c=0.50, chloroform).
$^1$H-NMR (CDCl$_3$) δ: 1.11 (9H, s), 1.22 (6H, d, J=6.9 Hz), 1.82 (3H, s), 2.15 (3H, s), 2.24 (2H, s), 2.86 (1H, septet, J=6.9 Hz), 3.88 (3H, s), 4.44-4.53 (2H, m), 4.86 (1H, t, J=8.1 Hz), 6.48 (1H, br s), 7.03 (2H, d, J=8.1 Hz), 7.12 (2H, d, J=8.1 Hz).

EXAMPLE 53

N-(3-(4-Isopropylphenyl)-4,6,7-trimethyl-2,3-dihydro-1-benzofuran-5-yl)methane sulfonamide To a solution of 3-(4-isopropylphenyl)-4,6,7-trimethyl-2,3-dihydro-1-benzofuran-5-amine (200 mg, 0.68 mmol) obtained in Reference Example 30 and triethylamine (0.09 mL, 0.68 mmol) in THF (4 mL) was added dropwise methanesulfonyl chloride (0.06 mL, 0.81 mmol) at 0° C. After the reaction solution was stirred at room temperature for 30 minutes, the reaction solution was added to water and the product was extracted with ethyl acetate. The combined organic layers were washed with saturated brine, dried over sodium sulfate, and concentrated under reduced pressure. The obtained residue was purified by basic silica gel column chromatography (ethyl acetate:hexane=3:2) to obtain 185 mg (yield: 73%) of the title compound. Melting point: 139-140° C. (ethyl acetate-hexane).
$^1$H-NMR (CDCl$_3$) δ: 1.22 (6H, d, J=6.9 Hz), 2.02 (3H, s), 2.18 (3H, s), 2.33 (3H, s), 2.86 (1H, septet, J=6.9 Hz), 2.99 (3H, s), 4.44 (1H, dd, J=4.5, 9.0 Hz), 4.53 (1H, dd, J=4.5, 9.0 Hz), 4.84 (1H, t, J=9.0 Hz), 5.66 (1H, br s), 7.02 (2H, d, J=8.1 Hz), 7.13 (2H, d, J=8.1 Hz).

EXAMPLE 54

N-(3-(4-Isopropylphenyl)-4,6,7-trimethyl-2,3-dihydro-1-benzofuran-5-yl)butane-1-sulfonamide To a solution of 3-(4-isopropylphenyl)-4,6,7-trimethyl-2,3-dihydro-1-benzofuran-5-amine (200 mg, 0.68 mmol) obtained in Reference Example 30 in pyridine (10 mL) was added dropwise 1-butanesulfonyl chloride (0.11 mL, 0.82 mmol) at 0° C., was added 4-dimethylaminopyridine (91 mg, 0.75 mmol) and the reaction mixture was stirred for 6 hours. Water was added to the reaction solution and the product was extracted with ethyl acetate. The combined organic layers were washed with 1 N hydrochloric acid and an aqueous saturated sodium hydrogen carbonate solution, dried over anhydrous sodium sulfate, and concentrated under reduced pressure. The obtained residue was purified by basic silica gel column chromatography (ethyl acetate:hexane=3:7) to obtain 174 mg (yield: 64%) of the title compound. Melting point: 96-97° C. (ethyl acetate-hexane).
$^1$H-NMR (CDCl$_3$) δ: 0.92 (3H, t, J=7.5 Hz), 1.22 (6H, d, J=6.9 Hz), 1.44 (2H, sixtet, J=7.5 Hz), 1.81-1.82 (2H, m), 2.01 (3H, s), 2.18 (3H, s), 2.32 (3H, s), 2.86 (1H, septet, J=6.9 Hz), 3.03-3.09 (2H, m), 4.43 (1H, dd, J=4.5, 9.0 Hz), 4.52 (1H, dd, J=4.5, 9.0 Hz), 4.84 (1H, t, J=9.0 Hz), 5.58 (1H, s), 7.02 (2H, d, J=8.1 Hz), 7.13 (2H, d, J=8.1 Hz).

EXAMPLE 55

4,4,4-Trifluoro-N-(3-(4-isopropylphenyl)-4,6,7-trimethyl-2,3-dihydro-1-benzofuran-5-yl)butane-1-sulfonamide Using 3-(4-isopropylphenyl)-4,6,7-trimethyl-2,3-dihydro-1-benzofuran-5-amine obtained in Reference Example 30 and 4,4,4-trifluoro-1-butanesulfonyl chloride, the title compound was synthesized in the same manner as in Example 53. Yield: 62%. Melting point: 149-150° C. (ethyl acetate-hexane).
$^1$H-NMR (CDCl$_3$) δ: 1.22 (6H, d, J=6.9 Hz), 2.00 (3H, s), 2.10-2.40 (10H, m), 2.86 (1H, septet, J=6.9 Hz), 3.14 (2H, t, J=7.3 Hz), 4.40-4.56 (2H, m), 4.84 (1H, t, J=8.9 Hz), 5.67 (1H, br s), 7.02 (2H, d, J=8.0 Hz), 7.14 (2H, d, J=8.0 Hz).

EXAMPLE 56

N-(3-(4-Isopropylphenyl)-4,6,7-trimethyl-2,3-dihydro-1-benzofuran-5-yl)ethanesulfonamide Using 3-(4-isopropylphenyl)-4,6,7-trimethyl-2,3-dihydro-1-benzofuran-5-amine obtained in Reference Example 30 and ethanesulfonyl chloride, the title compound was synthesized in the same manner as in Example 54. Yield: 56%. Melting point: 132-133° C. (ethanol).
$^1$H-NMR (CDCl$_3$) δ: 1.22 (6H, d, J=6.9 Hz), 1.42 (3H, t, J=7.5 Hz), 2.02 (3H, s), 2.18 (3H, s), 2.32 (3H, s), 2.87 (1H, septet, J=6.9 Hz), 3.11 (2H, q, J=7.5 Hz), 4.43 (1H, dd, J=8.7, 4.8 Hz), 4.52 (1H, dd, J=9.6, 5.1 Hz), 4.83 (1H, t, J=9.0 Hz), 5.53 (1H, br s), 7.02 (2H, d, J=8.1 Hz), 7.13 (2H, d, J=8.1 Hz).

EXAMPLE 57

N-(3-(4-Isopropylphenyl)-4,6,7-trimethyl-2,3-dihydro-1-benzofuran-5-yl)propane-1-sulfonamide Using 3-(4-isopropylphenyl)-4,6,7-trimethyl-2,3-dihydro-1-benzofuran-5-amine obtained in Reference Example 30 and 1-propanesulfonyl chloride, the title compound was synthesized in the same manner as in Example 54. Yield: 54%. Melting point: 133-134° C. (ethanol).
$^1$H-NMR (CDCl$_3$) δ: 1.04 (3H, t, J=7.2 Hz), 1.22 (6H, d, J=6.9 Hz), 1.81-2.05 (5H, m), 2.18 (3H, s), 2.32 (3H, s), 2.86 (1H, septet, J=6.9 Hz), 3.00-3.09 (2H, m), 4.40-4.58 (2H, m), 4.84 (1H, t, J=8.7 Hz), 5.55 (1H, br s), 7.02 (2H, d, J=7.5 Hz), 7.13 (2H, d, J=7.5 Hz).

EXAMPLE 58

(3-(4-Isopropylphenyl)-4,6-dimethyl-2,3-dihydro-1-benzofuran-5-yl)formamide

Using 3-(4-isopropylphenyl)-4,6-dimethyl-2,3-dihydro-1-benzofuran-5-amine obtained in Reference Example 32, the title compound was synthesized in the same manner as in Reference Example 73. Yield: 81%. Melting point: 193-196° C. (hexane-ethyl acetate).
$^1$H-NMR (CDCl$_3$) δ: 1.19-1.25 (6H, m), 1.87 (1.5H, s), 1.91 (1.5H, s), 2.22 (1.5H, s), 2.26 (1.5H, s), 2.79-2.93 (1H, m), 4.39-4.58 (2H, m), 4.79-4.90 (1H, m), 6.59-6.80 (2H, m), 6.98-7.04 (2H, m), 7.10-7.16 (2H, m), 7.94 (0.5H, d, J=12.6 Hz), 8.35 (0.5H, d, J=1.2 Hz).
$^1$H-NMR (CDCl$_3$)

EXAMPLE 59

(7-Bromo-3-(4-isopropylphenyl)-4,6-dimethyl-2,3-dihydro-1-benzofuran-5-yl)formamide Using (3-(4-isopropylphenyl)-4,6-dimethyl-2,3-dihydro-1-benzofuran-5-yl)formamide obtained in Example 58, the title compound was synthesized in the same manner as in Example 35. Yield: 91%. Melting point: 151-152° C. (hexane-ethyl acetate).

$^1$H-NMR (CDCl$_3$) δ: 1.18-1.30 (6H, m), 1.82-1.92 (3H, m), 2.32-2.44 (3H, m), 2.80-2.97 (1H, m), 4.45-4.65 (2H, m), 4.89-5.00 (1H, m), 6.80 (1H, br s), 7.00-7.17 (4H, m), 7.91 (0.4H, d, J=12.0 Hz), 8.35 (0.6H, d, J=1.5 Hz).

EXAMPLE 60

(7-Formyl-3-(4-isopropylphenyl)-4,6-dimethyl-2,3-dihydro-1-benzofuran-5-yl)formamide Using (3-(4-isopropylphenyl)-4,6-dimethyl-2,3-dihydro-1-benzofuran-5-yl)formamide obtained in Example 58, the title compound was synthesized in the same manner as in Example 20. Yield: 92%. Melting point: 123-124° C. (hexane-ethyl acetate).

$^1$H-NMR (CDCl$_3$) δ: 1.20-1.25 (6H, m), 1.94 (1.8H, s), 1.97 (1.2H, s), 2.53 (1.8H, s), 2.58 (1.2H, s), 2.80-2.95 (1H, m), 4.47-4.63 (2H, m), 4.93-5.04 (1H, m), 6.67 (1H, br s), 7.00-7.06 (2H, m), 7.12-7.18 (2H, m), 7.91 (0.4H, d, J=12.0 Hz), 8.39 (0.6H, d, J=1.2 Hz), 10.4 (0.6H, s), 10.5 (0.4H, s).

EXAMPLE 61

Ethyl 3-(5-((3,3-dimethylbutanoyl)amino)-3-(4-isopropylphenyl)-4,6-dimethyl-2,3-dihydro-1-benzofuran-7-yl)propanoate Using ethyl 3-(5-amino-3-(4-isopropylphenyl)-4,6-dimethyl-2,3-dihydro-1-benzofuran-7-yl)propanoate obtained in Reference Example 321, the title compound was synthesized in the same manner as in Example 1. Yield: 59%. Melting point: 150-151° C. (hexane-ethyl acetate).

$^1$H-NMR (CDCl$_3$) δ: 1.12 (9H, s), 1.22 (6H, d, J=6.9 Hz), 1.26 (3H, t, J=6.9 Hz), 1.84 (3H, s), 2.19 (3H, s), 2.25 (2H, s), 2.54 (2H, dd, J=9.0, 6.0 Hz), 2.85 (1H, septet, J=6.9 Hz), 2.96 (2H, dd, J=10.2, 7.2 Hz), 4.14 (2H, q, J=6.9 Hz), 4.40 (1H, dd, J=8.7, 4.8 Hz), 4.50 (1H, dd, J=9.3, 4.5 Hz), 4.81 (1H, t, J=9.3 Hz), 6.47 (1H, br s), 7.02 (2H, d, J=8.1 Hz), 7.11 (2H, d, J=8.1 Hz).

EXAMPLE 62

N-(7-(3-Hydroxypropyl)-3-(4-isopropylphenyl)-4,6-dimethyl-2,3-dihydro-1-benzofuran-5-yl)-3,3-dimethylbutanamide Using 3-(5-amino-3-(4-isopropylphenyl)-4,6-dimethyl-2,3-dihydro-1-benzofuran-7-yl)propan-1-ol obtained in Reference Example 322, the title compound was synthesized in the same manner as in Example 1. Yield: 36%. Oily matter.

$^1$H-NMR (CDCl$_3$) δ: 1.11 (9H, s), 1.21 (6H, d, J=6.9 Hz), 1.66-1.90 (5H, m), 2.18 (3H, s), 2.24 (2H, s), 2.56 (1H, br s), 2.77 (2H, t, J=6.9 Hz), 2.86 (1H, septet, J=6.9 Hz), 3.50-3.65 (2H, m), 4.43 (1H, dd, J=8.7, 4.5 Hz), 4.53 (1H, dd, J=8.7, 4.5 Hz), 4.81 (1H, t, J=8.7 Hz), 6.59 (1H, br s), 7.02 (2H, d, J=8.1 Hz), 7.12 (2H, d, J=8.1 Hz).

EXAMPLE 63

N-(4-Bromo-3-(4-isopropylphenyl)-6,7-dimethyl-2,3-dihydro-1-benzofuran-5-yl)-3,3-dimethylbutanamide Using (4-bromo-3-(4-isopropylphenyl)-6,7-dimethyl-2,3-dihydro-1-benzofuran-5-yl)amine obtained in Reference Example 323, the title compound was synthesized in the same manner as in Example 1. Yield: 51%. Melting point: 150-151° C. (hexane-ethyl acetate).

$^1$H-NMR (CDCl$_3$) δ: 1.13 (9H, s), 1.22 (6H, d, J=6.9 Hz), 2.17 (3H, s), 2.18 (3H, s), 2.26 (2H, s), 2.86 (1H, septet, J=6.9 Hz), 4.44-4.57 (2H, m), 4.83 (1H, t, J=7.5 Hz), 6.64 (1H, br s), 7.06 (2H, d, J=8.4 Hz), 7.12 (2H, d, J=8.4 Hz).

EXAMPLE 64

N-(3-(4-Isopropylphenyl)-4,7-dimethyl-2,3-dihydro-1-benzofuran-5-yl)-3,3-dimethylbutanamide Using 3-(4-isopropylphenyl)-4,7-dimethyl-2,3-dihydro-1-benzofuran-5-amine obtained in Reference Example 315, the title compound was synthesized in the same manner as in Example 1. Yield: 61%. Melting point: 135-136° C. (hexane-ethyl acetate).

$^1$H-NMR (CDCl$_3$) δ: 1.10 (9H, s), 1.22 (6H, d, J=6.9 Hz), 1.84 (3H, s), 2.19 (2H, s), 2.22 (3H, s), 2.86 (1H, septet, J=6.9 Hz), 4.42 (1H, dd, J=8.7, 4.8 Hz), 4.52 (1H, dd, J=9.0, 4.5 Hz), 4.83 (1H, t, J=9.0 Hz), 6.64 (1H, br s), 7.03 (2H, d, J=8.1 Hz), 7.12 (2H, d, J=8.1 Hz), 7.15 (1H, s)

EXAMPLE 65

N-(3-(4-Isopropylphenyl)-4,5,7-trimethyl-2,3-dihydro-1-benzofuran-6-yl)-3,3-dimethylbutanamide Using 3-(4-isopropylphenyl)-4,5,7-trimethyl-2,3-dihydro-1-benzofuran-6-amine obtained in Reference Example 316, the title compound was synthesized in the same manner as in Example 1. Yield: 58%. Melting point: 214-215° C. (hexane-ethyl acetate).

$^1$H-NMR (CDCl$_3$) δ: 1.16 (9H, s), 1.22 (6H, d, J=6.9 Hz), 1.90 (3H, s), 2.04 (3H, s), 2.14 (3H, s), 2.31 (2H, s), 2.87 (1H, septet, J=6.9 Hz), 4.40 (1H, dd, J=8.7, 4.5 Hz), 4.52 (1H, dd, J=9.0, 4.5 Hz), 4.81 (1H, t, J=9.0 Hz), 6.60 (1H, br s), 7.04 (2H, d, J=8.1 Hz), 7.13 (2H, d, J=8.1 Hz).

EXAMPLE 66

N-(3-(4-Isopropylphenyl)-4,5,6-trimethyl-2,3-dihydro-1-benzofuran-7-yl)-3,3-dimethylbutanamide Using 3-(4-isopropylphenyl)-4,5,6-trimethyl-2,3-dihydro-1-benzofuran-7-amine obtained in Reference Example 317, the title compound was synthesized in the same manner as in Example 1. Yield: 59%. Melting point: 190-191° C. (hexane-ethyl acetate).

$^1$H-NMR (CDCl$_3$) δ: 1.15 (9H, s), 1.22 (6H, d, J=6.9 Hz), 1.90 (3H, s), 2.09 (3H, s), 2.16 (3H, s), 2.29 (2H, s), 2.86 (1H, septet, J=6.9 Hz), 4.38 (1H, dd, J=8.7, 5.1 Hz), 4.55 (1H, dd, J=9.3, 4.5 Hz), 4.81 (1H, t, J=9.3 Hz), 6.71 (1H, br s), 7.04 (2H, d, J=8.4 Hz), 7.12 (2H, d, J=8.4 Hz).

EXAMPLE 67

4-(Benzyloxy)-N-(3-(4-isopropylphenyl)-4,6,7-trimethyl-2,3-dihydro-1-benzofuran-5-yl)butanamide Using 3-(4-isopropylphenyl)-4,6,7-trimethyl-2,3-dihydro-1-benzofuran-5-amine obtained in Reference Example 30 and 4-benzyloxybutyryl chloride, the title compound was synthesized in the same manner as in Example 1. Yield: 52%. Melting point: 85-86° C. (hexane-ethyl acetate).
$^1$H-NMR (CDCl$_3$) δ: 1.22 (6H, d, J=6.9 Hz), 1.78 (3H, s), 1.98-2.21 (8H, m), 2.50 (2H, t, J=6.9 Hz), 2.86 (1H, septet, J=6.9 Hz), 3.58 (2H, t, J=6.0 Hz), 4.37-4.56 (4H, m), 4.81 (1H, t, J=9.0 Hz), 6.80 (1H, br s), 7.03 (2H, d, J=8.1 Hz), 7.11 (2H, d, J=8.1 Hz), 7.18-7.37 (5H, m).

EXAMPLE 68

N-(3-(4-Isopropylphenyl)-4-methyl-2,3-dihydronaphtho[1,2-b]furan-5-yl)-3,3-dimethylbutanamide Using 3-(4-isopropylphenyl)-4-methyl-2,3-dihydronaphtho[1,2-b]furan-5-amine obtained in Reference Example 318, the title compound was synthesized in the same manner as in Example 1. Yield: 29%. Melting point: 183-184° C. (hexane-ethyl acetate).
$^1$H-NMR (CDCl$_3$) δ: 1.18 (9H, s), 1.22 (6H, d, J=6.9 Hz), 2.03 (3H, s), 2.37 (2H, s), 2.87 (1H, septet, J=6.9 Hz), 4.64 (1H, dd, J=8.7, 5.1 Hz), 4.72 (1H, dd, J=8.4, 4.5 Hz), 5.05 (1H, t, J=9.0 Hz), 6.86 (1H, br s), 7.06 (2H, d, J=8.1 Hz), 7.12 (2H, d, J=8.1 Hz), 7.37-7.52 (2H, m), 7.80 (1H, d, J=8.1 Hz), 8.00 (1H, d, J=8.1 Hz).

EXAMPLE 69

N-(3-(4-Isopropylphenyl)-4-methyl-2,3,6,7,8,9-hexahydronaphtho[1,2-b]furan-5-yl)-3,3-dimethylbutanamide Using 3-(4-isopropylphenyl)-4-methyl-2,3,6,7,8,9-hexahydronaphtho[1,2-b]furan-5-amine obtained in Reference Example 319, the title compound was synthesized in the same manner as in Example 1. Yield: 62%. Melting point: 183-184° C. (hexane-ethyl acetate).
$^1$H-NMR (CDCl$_3$) δ: 1.12 (9H, s), 1.22 (6H, d, J=6.9 Hz), 1.68-1.95 (7H, m), 2.24 (2H, s), 2.55-2.70 (4H, m), 2.86 (1H, septet, J=6.9 Hz), 4.43 (1H, dd, J=8.7, 5.1 Hz), 4.52 (1H, dd, J=9.0, 5.1 Hz), 4.84 (1H, t, J=9.0 Hz), 6.38 (1H, br s), 7.06 (2H, d, J=8.1 Hz), 7.12 (2H, d, J=8.1 Hz).

EXAMPLE 70

N-(3-(4-Isopropylphenyl)-4-methyl-3,6,7,8-tetrahydro-2H-indeno[4,5-b]furan-5-yl)-3,3-dimethylbutanamide Using 3-(4-isopropylphenyl)-4-methyl-3,6,7,8-tetrahydro-2H-indeno[4,5-b]furan-5-amine obtained in Reference Example 320, the title compound was synthesized in the same manner as in Example 1. Yield: 59%. Melting point: 201-202° C. (hexane-ethyl acetate).
$^1$H-NMR (CDCl$_3$) δ: 1.11 (9H, s), 1.22 (6H, d, J=6.9 Hz), 1.85 (3H, s), 2.04-2.28 (4H, m), 2.77-3.01 (5H, m), 4.41-4.57 (2H, m), 4.85 (1H, t, J=8.1 Hz), 6.52 (1H, br s), 7.05 (2H, d, J=8.1 Hz), 7.12 (2H, d, J=8.1 Hz).

EXAMPLE 71

N-((3S)-3-(4-Isopropylphenyl)-4,6-dimethyl-2,3-dihydro-1-benzofuran-5-yl)-3,3-dimethylbutanamide Using (S)-3-(4-isopropylphenyl)-4,6-dimethyl-2,3-dihydro-1-benzofuran-5-amine obtained in Reference Example 326, the title compound was synthesized in the same manner as in Example 1. Yield: 84%. Melting point: 147-148° C. (hexane-ethyl acetate). [α]$_D^{20}$=−93° (c=0.497, chloroform).
$^1$H-NMR (CDCl$_3$) δ: 1.11 (9H, s), 1.21 (6H, d, J=6.9 Hz), 1.85 (3H, s), 2.21 (3H, s), 2.23 (2H, s), 2.85 (1H, septet, J=6.9 Hz), 4.40 (1H, dd, J=8.4, 4.8 Hz), 4.49 (1H, dd, J=9.0, 4.8 Hz), 4.82 (1H, t, J=9.0 Hz), 6.49 (1H, br s), 6.62 (1H, s), 7.03 (2H, d, J=8.1 Hz), 7.11 (2H, d, J=8.1 Hz).

EXAMPLE 72

N-(3-(3-Methoxyphenyl)-4,6,7-trimethyl-2,3-dihydro-1-benzofuran-5-yl)-3,3-dimethylbutanamide Using 3-(3-methoxyphenyl)-4,6,7-trimethyl-2,3-dihydro-1-benzofuran-5-amine obtained in Reference Example 302, the title compound was synthesized in the same manner as in Example 1. Yield: 87%. Melting point: 169-170° C. (ethyl acetate-hexane).
$^1$H-NMR (CDCl$_3$) δ: 1.12 (9H, s), 1.85 (3H, s), 2.14 (3H, s), 2.17 (3H, s), 2.25 (2H, s), 3.76 (3H, s), 4.41 (1H, dd, J=4.8, 9.0 Hz), 4.53 (1H, dd, J=4.8, 9.0 Hz), 4.83 (1H, t, J=8.7 Hz), 6.50 (1H, br s), 6.68-6.76 (3H, m), 7.19 (1H, t, J=7.8 Hz).

EXAMPLE 73

N-(3-(3-(1,3-Dioxolan-2-yl)phenyl)-4,6,7-trimethyl-2,3-dihydro-1-benzofuran-5-yl)-3,3-dimethylbutanamide Using 3-(3-(1,3-dioxolan-2-yl)phenyl)-4,6,7-trimethyl-2,3-dihydro-1-benzofuran-5-amine obtained in Reference Example 301, the title compound was synthesized in the same manner as in Example 1. Yield: 91%. Melting point: 168-169° C. (ethyl acetate-hexane).
$^1$H-NMR (CDCl$_3$) δ: 1.12 (9H, s), 1.82 (3H, s), 2.14 (3H, s), 2.17 (3H, s), 2.25 (2H, s), 3.98-4.17 (4H, m), 4.32 (1H, dd, J=5.0, 8.8 Hz), 4.58 (1H, dd, J=5.0, 8.8 Hz), 4.84 (1H, t, J=8.8 Hz), 5.75 (1H, s), 6.49 (1H, br s), 7.08-7.12 (1H, m), 7.24-7.37 (3H, m).

EXAMPLE 74

N-(4-Isopropyl-2-methoxyphenyl)-4,6,7-trimethyl-2,3-dihydro-1-benzofuran-5-yl)-3,3-dimethylbutanamide Using 3-(4-isopropyl-2-methoxyphenyl)-4,6,7-trimethyl-2,3-dihydro-1-benzofuran-5-amine obtained in Reference Example 303, the title compound was synthesized in the same manner as in Example 1. Yield: 97%. Melting point: 195-196° C. (ethyl acetate-hexane).
$^1$H-NMR (CDCl$_3$) δ: 1.14 (9H, s), 1.18 (6H, d, J=6.9 Hz), 1.88 (3H, s), 2.16 (6H, s), 2.27 (2H, s), 2.85 (1H, septet, J=6.9 Hz), 3.86 (3H, s), 4.33 (1H, dd, J=3.3, 8.4 Hz), 4.82 (1H, t, J=8.4 Hz), 4.87 (1H, dd, J=3.3, 8.4 Hz), 6.54 (1H, br s), 6.66 (2H, s), 6.72 (1H, s).

EXAMPLE 75

3,3-Dimethyl-N-(4,6,7-trimethyl-3-phenyl-2,3-dihydro-1-benzofuran-5-yl)butanamide Using 4,6,7-trimethyl-3-phenyl-2,3-dihydro-1-benzofuran-5-amine obtained in Reference Example 306, the title compound was synthesized in the same manner as in Example 1. Yield: 50%. Melting point: 146-147° C. (ethyl acetate).

$^1$H-NMR (CDCl$_3$) δ: 1.12 (9H, s), 1.83 (3H, s), 2.15 (3H, s), 2.20 (3H, s), 2.25 (2H, s), 4.41 (1H, dd, J=4.8, 9.0 Hz), 4.56 (1H, dd, J=4.8, 9.0 Hz), 4.84 (1H, t, J=9.0 Hz), 6.50 (1H, br s), 7.06-7.18 (2H, m), 7.20-7.30 (3H, m).

EXAMPLE 76

3,3-Dimethyl-N-(4,6,7-trimethyl-3-(4-methylphenyl)-2,3-dihydro-1-benzofuran-5-yl)butanamide Using 4,6,7-trimethyl-3-(4-methylphenyl)-2,3-dihydro-1-benzofuran-5-amine obtained in Reference Example 307, the title compound was synthesized in the same manner as in Example 1. Yield: 80%. Melting point: 176-177° C. (ethyl acetate).

$^1$H-NMR (CDCl$_3$) δ: 1.11 (9H, s), 1.82 (3H, s), 2.13 (3H, s), 2.17 (3H, s), 2.23 (2H, s), 2.30 (3H, s), 4.38 (1H, dd, J=4.8, 9.0 Hz), 4.51 (1H, dd, J=4.8, 9.0 Hz), 4.82 (1H, t, J=9.0 Hz), 6.57 (1H, br s), 6.98 (2H, d, J=8.1 Hz), 7.07 (2H, d, J=8.1 Hz).

EXAMPLE 77

N-(3-(Biphenyl-4-yl)-4,6,7-trimethyl-2,3-dihydro-1-benzofuran-5-yl)-3,3-dimethylbutanamide Using 3-(biphenyl-4-yl)-4,6,7-trimethyl-2,3-dihydro-1-benzofuran-5-amine obtained in Reference Example 309, the title compound was synthesized in the same manner as in Example 1. Yield: 71%. Melting point: 218-219° C. (ethyl acetate).

$^1$H-NMR (CDCl$_3$) δ: 1.12 (9H, s), 1.88 (3H, s), 2.16 (3H, s), 2.19 (3H, s), 2.26 (2H, s), 4.45 (1H, dd, J=4.5, 9.0 Hz), 4.60 (1H, dd, J=4.5, 9.0 Hz), 4.87 (1H, t, J=9.0 Hz), 6.52 (1H, br s), 7.20 (2H, d, J=8.4 Hz), 7.32 (1H, t, J=8.4 Hz), 7.42 (2H, d, J=8.4 Hz), 7.50 (2H, d, J=8.4 Hz), 7.55 (2H, d, J=8.4 Hz).

EXAMPLE 78

3,3-Dimethyl-N-(4,6,7-trimethyl-3-(5-methylpyridin-2-yl)-2,3-dihydro-1-benzofuran-5-yl)butanamide Using 4,6,7-trimethyl-3-(5-methylpyridin-2-yl)-2,3-dihydro-1-benzofuran-5-amine obtained in Reference Example 308, the title compound was synthesized in the same manner as in Example 1. Yield: 78%. Melting point: 170-171° C. (ethyl acetate-hexane).

$^1$H-NMR (CDCl$_3$) δ: 1.12 (9H, s), 1.87 (3H, s), 2.05 (3H, s), 2.14 (3H, s), 2.17 (3H, s), 2.26 (2H, s), 4.55 (1H, dd, J=4.5, 9.0 Hz), 4.74 (1H, dd, J=4.5, 9.0 Hz), 4.88 (1H, t, J=9.0 Hz), 6.54 (1H, br s), 6.91 (1H, d, J=8.4 Hz), 7.38 (1H, dd, J=1.8, 8.4 Hz), 8.36 (1H, d, J=1.8 Hz).

EXAMPLE 79

3,3-Dimethyl-N-(3-(4-ethylphenyl)-4,6,7-trimethyl-2,3-dihydro-1-benzofuran-5-yl)butanamide Using 3-(4-ethylphenyl)-4,6,7-trimethyl-2,3-dihydro-1-benzofuran-5-amine obtained in Reference Example 314, the title compound was synthesized in the same manner as in Example 1. Yield: 87%. Melting point: 162-163° C. (THF-diisopropyl ether).

$^1$H-NMR (CDCl$_3$) δ: 1.12 (9H, s), 1.20 (3H, t, J=7.5 Hz), 1.84 (3H, s), 2.15 (3H, s), 2.17 (3H, s), 2.25 (2H, s), 2.60 (2H, q, J=7.5 Hz), 4.40 (1H, dd, J=4.8, 9.0 Hz), 4.53 (1H, dd, J=4.8, 9.0 Hz), 4.82 (1H, t, J=9.0 Hz), 6.50 (1H, br s), 7.04 (2H, d, J=8.4 Hz), 7.10 (2H, d, J=8.4 Hz)

EXAMPLE 80

N-(3-(4-Isobutylphenyl)-4,6,7-trimethyl-2,3-dihydro-1-benzofuran-5-yl)-3,3-dimethylbutanamide Using 3-(4-isobutylphenyl)-4,6,7-trimethyl-1-benzofuran-5-amine obtained in Reference Example 312, 3-(4-isobutylphenyl)-4,6,7-trimethyl-2,3-dihydro-1-benzofuran-5-amine was synthesized in the same manner as in Reference Example 144. Using this compound and tert-butylacetyl chloride, the title compound was synthesized in the same manner as in Example 1. Yield: 34%. Melting point: 153-154° C. (ethyl acetate-hexane).

$^1$H-NMR (CDCl$_3$) δ: 0.87 (6H, d, J=6.9 Hz), 1.12 (9H, s), 1.72-1.86 (4H, m), 2.14 (3H, s), 2.17 (3H, s), 2.25 (2H, s), 2.42 (2H, d, J=7.2 Hz), 4.40 (1H, dd, J=4.5, 9.0 Hz), 4.53 (1H, dd, J=4.5, 9.0 Hz), 4.83 (1H, t, J=9.0 Hz), 6.51 (1H, br s), 7.03 (4H, s).

EXAMPLE 81

N-(3-(4-Cyclohexylphenyl)-4,6,7-trimethyl-2,3-dihydro-1-benzofuran-5-yl)-3,3-dimethylbutanamide Using 3-(4-cyclohexylphenyl)-4,6,7-trimethyl-1-benzofuran-5-amine obtained in Reference Example 313, 3-(4-cyclohexylphenyl)-4,6,7-trimethyl-2,3-dihydro-1-benzofuran-5-amine was synthesized in the same manner as in Reference Example 144. Using this compound, the title compound was synthesized in the same manner as in Example 1. Yield: 43%. Melting point: 146-148° C. (ethyl acetate-hexane).

$^1$H-NMR (CDCl$_3$) δ: 1.12 (9H, s), 1.19-1.45 (4H, m), 1.70-1.95 (9H, m), 2.14 (3H, s), 2.17 (3H, s), 2.25 (2H, s), 2.45 (1H, br), 4.41 (1H, dd, J=4.8, 9.0 Hz), 4.52 (1H, dd, J=4.8, 9.0 Hz), 4.81 (1H, t, J=9.0 Hz), 6.51 (1H, br s), 7.04 (2H, d, J=8.1 Hz), 7.10 (2H, d, J=8.1 Hz).

EXAMPLE 82

N-(3-(4-(1,3-Dioxolan-2-yl)phenyl)-4,6,7-trimethyl-2,3-dihydro-1-benzofuran-5-yl)-3,3-dimethylbutanamide Using 3-(4-(1,3-dioxolan-2-yl)phenyl)-4,6,7-trimethyl-2,3-dihydro-1-benzofuran-5-amine obtained in Reference Example 310, the title compound was synthesized in the same manner as in Example 1. Yield: 96%. Melting point: 193-194° C. (ethyl acetate-hexane).

$^1$H-NMR (CDCl$_3$) δ: 1.12 (9H, s), 1.81 (3H, s), 2.14 (3H, s), 2.17 (3H, s), 2.25 (2H, s), 3.99-4.06 (2H, m), 4.07-4.14 (2H, m), 4.36 (1H, dd, J=4.5, 9.0 Hz), 4.57 (1H, dd, J=4.5, 9.0

Hz), 4.83 (1H, t, J=9.0 Hz), 5.76 (1H, s), 6.47 (1H, br s), 7.14 (2H, d, J=8.1 Hz), 7.38 (2H, d, J=8.1 Hz).

EXAMPLE 83

N-(3-(4-Isopropylphenyl)-4,6-dimethyl-7-vinyl-2,3-dihydro-1-benzofuran-5-yl)-3,3-dimethylbutanamide A solution of N-(7-(1-hydroxyethyl)-3-(4-isopropylphenyl)-4,6-dimethyl-2,3-dihydro-1-benzofuran-5-yl)-3,3-dimethylbutanamide (1.23 g, 3.02 mmol) obtained in Example 22 and p-toluenesulfonic acid monohydrate (20 mg) in toluene (20 mL) was refluxed with heating at 80° C. for 1 hour under an argon atmosphere. The reaction solution was washed with an aqueous saturated sodium hydrogen carbonate solution, dried over magnesium sulfate, and concentrated under reduced pressure. The obtained residue was purified by silica gel column chromatography (ethyl acetate:hexane=1:9) to obtain 1.09 g (yield: 89%) of the title compound. Melting point: 171-172° C. (hexane-ethyl acetate).
$^1$H-NMR (CDCl$_3$) δ: 1.12 (9H, s), 1.21 (6H, d, J=6.9 Hz), 1.86 (3H, s), 2.246 (3H, s), 2.85 (1H, septet, J=6.9 Hz), 4.42-4.58 (2H, m), 4.80-4.92 (1H, m), 5.49 (1H, dd, J=11.7, 2.1 Hz), 5.92 (1H, dd, J=17.7, 2.1 Hz), 6.51 (1H, br s), 6.76 (1H, dd, J=17.7, 11.7 Hz), 7.04 (2H, d, J=8.1 Hz), 7.11 (2H, d, J=8.1 Hz).

EXAMPLE 84

N-(7-(1,2-Dihydroxyethyl)-3-(4-isopropylphenyl)-4,6-dimethyl-2,3-dihydro-1-benzofuran-5-yl)-3,3-dimethylbutanamide To a solution of AD-mix β (4.62 g) in a mixed solvent of water (15 mL), tert-butanol (15 mL) and THF (15 mL) was added with ice-cooling N-(3-(4-isopropylphenyl)-4,6-dimethyl-7-vinyl-2,3-dihydro-1-benzofuran-5-yl)-3,3-dimethylbutanamide (670 mg, 1.65 mmol) obtained in Example 83 and the reaction mixture was stirred at 80° C. for 3 hours. To the reaction solution were added water and sodium sulfite and the resulting mixture was stirred at room temperature for 30 minutes. The product was extracted with ethyl acetate, and the organic layer was washed with water and saturated brine, dried over anhydrous sodium sulfate, and the solvent was distilled off under reduced pressure.

The obtained residue was purified by silica gel column chromatography (ethyl acetate:hexane=1:20) to obtain 558 mg (yield: 77%) of the title compound. Melting point: 159-161° C. (hexane-ethyl acetate).
$^1$H-NMR (CDCl$_3$) δ: 1.10 (9H, s), 1.22 (6H, d, J=6.9 Hz), 1.85 (3H, s), 2.10-2.24 (5H, m), 2.86 (1H, septet, J=6.9 Hz), 3.60-3.84 (2H, m), 4.40-4.57 (2H, m), 4.80-5.00 (2H, m), 6.70 (1H, br s), 7.01 (2H, d, J=8.1 Hz), 7.13 (2H, d, J=8.1 Hz), 2H unidentified.

EXAMPLE 85

N-(7-(2-Hydroxyethyl)-3-(4-isopropylphenyl)-4,6-dimethyl-2,3-dihydro-1-benzofuran-5-yl)-3,3-dimethylbutanamide A solution of N-(7-(1,2-dihydroxyethyl)-3-(4-isopropylphenyl)-4,6-dimethyl-2,3-dihydro-1-benzofuran-5-yl)-3,3-dimethylbutanamide (200 mg, 0.455 mmol) obtained in Example 84 and palladium hydroxide on carbon (20 mg) in ethanol (20 mL) was stirred at 60° C. for 3 hours under a hydrogen atmosphere. The catalyst was removed and the reaction solution was concentrated under reduced pressure. Water was added to the residue and the product was extracted with ethyl acetate. The organic layer was washed with water, dried over anhydrous sodium sulfate, and concentrated under reduced pressure. The obtained residue was purified by silica gel column chromatography (ethyl acetate:hexane=7:3) to obtain 40 mg (yield: 21%) of the title compound. Amorphous powder.
$^1$H-NMR (CDCl$_3$) δ: 1.11 (9H, s), 1.21 (6H, d, J=6.9 Hz), 1.85 (3H, s), 2.20 (3H, s), 2.25 (2H, s), 2.85 (1H, septet, J=6.9 Hz), 2.94 (2H, t, J=6.6 Hz), 3.80 (2H, t, J=6.6 Hz), 4.40 (1H, dd, J=8.4, 4.8 Hz), 4.52 (1H, dd, J=9.0, 5.1 Hz), 4.81 (1H, t, J=9.0 Hz), 6.53 (1H, br s), 7.02 (2H, d, J=8.1 Hz), 7.11 (2H, d, J=8.1 Hz), 1H unidentified.

EXAMPLE 86

N-(3-(4-Isopropylphenyl)-4,6-dimethyl-7-propionyl-2,3-dihydro-1-benzofuran-5-yl)-3,3-dimethylbutanamide Using a diastereo mixture of N-(7-(1-hydroxypropyl)-3-(4-isopropylphenyl)-4,6-dimethyl-2,3-dihydro-1-benzofuran-5-yl)-3,3-dimethylbutanamide obtained in the synthesis in Examples 30 and 31, the title compound was synthesized in the same manner as in Example 32. Yield: 18%. Melting point: 163-164° C. (hexane-ethyl acetate).
$^1$H-NMR (CDCl$_3$) δ: 1.11 (9H, s), 1.16 (3H, t, J=7.4 Hz), 1.22 (6H, d, J=7.0 Hz), 1.88 (3H, s), 2.17 (3H, s), 2.25 (2H, s), 2.78-3.01 (3H, m), 4.43-4.57 (2H, m), 4.87 (1H, t, J=8.0 Hz), 6.48 (1H, br s), 7.03 (2H, d, J=8.2 Hz), 7.14 (2H, d, J=8.2 Hz).

EXAMPLE 87

N-(6-Bromo-3-(4-isopropylphenyl)-4,7-dimethyl-2,3-dihydro-1-benzofuran-5-yl)-3,3-dimethylbutanamide Using N-(3-(4-isopropylphenyl)-4,7-dimethyl-2,3-dihydro-1-benzofuran-5-yl)-3,3-dimethylbutanamide obtained in Example 64, the title compound was synthesized in the same manner as in Reference Example 23. Yield: 32%. Melting point: 174-175° C. (hexane-ethyl acetate).
$^1$H-NMR (CDCl$_3$) δ: 1.13 (9H, s), 1.22 (6H, d, J=6.9 Hz), 1.89 (3H, s), 2.26 (2H, s), 2.31 (3H, s), 2.86 (1H, septet, J=6.9 Hz), 4.44 (1H, dd, J=8.7, 4.5 Hz), 4.52 (1H, dd, J=9.0, 4.8 Hz), 4.93 (1H, t, J=9.0 Hz), 6.68 (1H, br s), 7.03 (2H, d, J=8.1 Hz), 7.12 (2H, d, J=8.1 Hz).

EXAMPLE 88

N-(3-(4-Isopropylphenyl)-4-methoxy-6,7-dimethyl-2,3-dihydro-1-benzofuran-5-yl)-3,3-dimethylbutanamide Using N-(4-bromo-3-(4-isopropylphenyl)-6,7-dimethyl-2,3-dihydro-1-benzofuran-5-yl)-3,3-dimethylbutanamide obtained in Example 63, the title compound was synthesized in the same manner as in Example 36. Yield: 21%. Melting point: 161-162° C. (hexane-ethyl acetate).
$^1$H-NMR (CDCl$_3$) δ: 1.11 (9H, s), 1.21 (6H, d, J=6.9 Hz), 2.13 (3H, s), 2.15 (3H, s), 2.24 (2H, s), 2.86 (1H, septet, J=6.9 Hz), 3.44 (3H, s), 4.41 (1H, dd, J=8.4, 4.8 Hz), 4.71 (1H, dd, J=9.3, 4.8 Hz), 4.82 (1H, dd, J=9.3, 8.4 Hz), 6.66 (1H, br s), 7.08 (2H, d, J=8.1 Hz), 7.14 (2H, d, J=8.1 Hz).

EXAMPLE 89

N-(3-(4-Isopropylphenyl)-6-methoxy-4,7-dimethyl-2,3-dihydro-1-benzofuran-5-yl)-3,3-dimethylbutanamide Using N-(6-bromo-3-(4-isopropylphenyl)-4,7-dimethyl-2,3-dihydro-1-benzofuran-5-yl)-3,3-dimethylbutanamide obtained in Example 87, the title compound was synthesized in the same manner as in Example 36. Yield: 37%. Melting point: 162-163° C. (hexane-ethyl acetate).

$^1$H-NMR (CDCl$_3$) δ: 1.12 (9H, s), 1.22 (6H, d, J=6.9 Hz), 1.83 (3H, s), 2.17 (3H, s), 2.25 (2H, s), 2.86 (1H, septet, J=6.9 Hz), 3.69 (3H, s), 4.42 (1H, dd, J=8.7, 4.8 Hz), 4.51 (1H, dd, J=9.0, 5.1 Hz), 4.83 (1H, t, J=8.7 Hz), 6.67 (1H, br s), 7.04 (2H, d, J=8.1 Hz), 7.12 (2H, d, J=8.1 Hz).

EXAMPLE 90

N-(7-(1-Hydroxybutyl)-3-(4-isopropylphenyl)-4,6-dimethyl-2,3-dihydro-1-benzofuran-5-yl)-3,3-dimethylbutanamide To propylmagnesium chloride (2.0 M, THF solution 10.0 mL, 20.0 mmol) was added N-(7-formyl-3-(4-isopropylphenyl)-4,6-dimethyl-2,3-dihydro-1-benzofuran-5-yl)-3,3-dimethylbutanamide (2.2 g, 5.40 mmol) obtained in Example 20 at 0° C. and the reaction solution was stirred at the same temperature for 1 hour. The reaction solution was added to water and the product was extracted with ethyl acetate. The organic layer was washed with water and 1 N hydrochloric acid, dried over anhydrous sodium sulfate, and concentrated under reduced pressure. The obtained residue was purified by silica gel column chromatography (hexane:ethyl acetate=4:1) to obtain 627 mg (yield: 26%) of the title compound as a low polarity isomer. Melting point: 162-163° C. (hexane-ethyl acetate).

$^1$H-NMR (CDCl$_3$) δ: 0.87-1.05 (3H, m), 1.11 (9H, s), 1.22 (6H, d, J=7.0 Hz), 1.30-2.00 (7H, m), 2.15 (3H, s), 2.24 (2H, s), 2.86 (1H, septet, J=7.0 Hz), 3.30 (1H, d, J=10.2 Hz), 4.40-4.58 (2H, m), 4.78-4.92 (2H, m), 6.54 (1H, br s), 7.02 (2H, d, J=8.2 Hz), 7.12 (2H, d, J=8.2 Hz).

EXAMPLE 91

N-(7-(1-Hydroxybutyl)-3-(4-isopropylphenyl)-4,6-dimethyl-2,3-dihydro-1-benzofuran-5-yl)-3,3-dimethylbutanamide The residue treated in the same manner as described in the Example 90 was purified by silica gel column chromatography (hexane:ethyl acetate=4:1) to obtain 547 mg (yield: 22%) of the title compound as a high polarity isomer. Melting point: 150-151° C. (hexane-ethyl acetate).

$^1$H-NMR (CDCl$_3$) δ: 0.88-1.04 (3H, m), 1.12 (9H, s), 1.22 (6H, d, J=7.0 Hz), 1.30-2.00 (7H, m), 2.19 (3H, s), 2.25 (2H, s), 2.86 (1H, septet, J=7.0 Hz), 3.28 (1H, d, J=10.2 Hz), 4.40-4.55 (2H, m), 4.79-4.93 (2H, m), 6.47 (1H, br s), 7.02 (2H, d, J=8.2 Hz), 7.14 (2H, d, J=8.2 Hz).

EXAMPLE 92

N-(7-Butyl-3-(4-isopropylphenyl)-4,6-dimethyl-2,3-dihydro-1-benzofuran-5-yl)-3,3-dimethylbutanamide Using a diastereo mixture of N-(7-(1-hydroxybutyl)-3-(4-isopropylphenyl)-4,6-dimethyl-2,3-dihydro-1-benzofuran-5-yl)-3,3-dimethylbutanamide obtained in Examples 90 and 91, the title compound was synthesized in the same manner as in Example 23. Yield: 33%. Melting point: 149-151° C. (hexane-ethyl acetate).

$^1$H-NMR (CDCl$_3$) δ: 0.83-1.00 (3H, m), 1.11 (9H, s), 1.21 (6H, d, J=6.9 Hz), 1.34-1.58 (4H, m), 1.83 (3H, s), 2.16 (3H, s), 2.23 (2H, s), 2.62 (2H, t, J=7.5 Hz), 2.85 (1H, septet, J=6.9 Hz), 4.39 (1H, dd, J=8.4, 4.5 Hz), 4.49 (1H, dd, J=9.0, 4.5 Hz), 4.79 (1H, t, J=9.0 Hz), 6.52 (1H, br s), 7.03 (2H, d, J=8.1 Hz), 7.11 (2H, d, J=8.1 Hz).

EXAMPLE 93

4-Hydroxy-N-(3-(4-isopropylphenyl)-4,6,7-trimethyl-2,3-dihydro-1-benzofuran-5-yl)butanamide To a solution of 3-(4-isopropylphenyl)-4,6,7-trimethyl-2,3-dihydro-1-benzofuran-5-amine (300 mg, 1.02 mmol) obtained in Reference Example 30 in THF (20 mL) was added dropwise at 0° C. under an argon atmosphere n-butyllithium (1.6 M, hexane solution, 1.25 mL, 2.04 mmol) and the resulting mixture was stirred at the same temperature for 1 hour. To the reaction solution was added dropwise γ-butyrolactone (300 mg, 0.98 mmol) and the resulting mixture was stirred for 1 hour. Water was added to the reaction solution and the product was extracted with ethyl acetate. The organic layer was washed with water and saturated brine, dried over anhydrous sodium sulfate, and concentrated under reduced pressure. The obtained residue was purified by silica gel column chromatography (ethyl acetate:hexane=1:1) to obtain 174 mg (yield: 45%) of the title compound. Melting point: 156-157° C. (hexane-ethyl acetate).

$^1$H-NMR (CDCl$_3$) δ: 1.20-1.30 (6H, m), 1.80-2.20 (11H, m), 2.56 (2H, t, J=6.8 Hz), 2.70 (1H, br s), 2.86 (1H, septet, J=6.9 Hz), 3.55-3.78 (2H, m), 4.38-4.57 (2H, m), 4.78-4.90 (1H, m), 6.78 (1H, br s), 7.00-7.18 (4H, m).

EXAMPLE 94

N-(7-(Hydroxy(phenyl)methyl)-3-(4-isopropylphenyl)-4,6-dimethyl-2,3-dihydro-1-benzofuran-5-yl)-3,3-dimethylbutanamide A solution of bromobenzene (770 mg, 4.91 mmol) in THF (10 mL) was added under an argon atmosphere to a mixture of magnesium (119 mg, 4.91 mmol) and a catalytic amount of iodine, and the resulting mixture was stirred at room temperature for 20 minutes. To the reaction solution was added dropwise a solution of N-(7-formyl-3-(4-isopropylphenyl)-4,6-dimethyl-2,3-dihydro-1-benzofuran-5-yl)-3,3-dimethylbutanamide (400 mg, 0.98 mmol) obtained in Example 20 in THF (5 mL) and the resulting mixture was stirred at room temperature for 1 hour. The reaction solution was added to ice and the product was extracted with ethyl acetate. The organic layer was washed with 1 N hydrochloric acid and water, dried over anhydrous sodium sulfate, and concentrated under reduced pressure. The obtained residue was purified by silica gel column chromatography (ethyl acetate:hexane=1:2) to obtain 512 mg (yield: 99%) of the title compound. Yield: 99%. Oily matter.

¹H-NMR (CDCl₃) δ: 1.10 (9H, s), 1.22 (6H, d, J=6.9 Hz), 1.89 (3H, s), 2.15 (3H, s), 2.24 (2H, s), 2.78-2.91 (1H, m), 3.88-3.99 (1H, m), 4.37-4.55 (2H, m), 4.75-4.90 (1H, m), 6.03 (1H, d, J=9.3 Hz), 6.58-6.62 (1H, m), 6.98-7.45 (9H, m)

EXAMPLE 95

N-(7-(Hydroxy(4-isopropylphenyl)methyl)-3-(4-isopropylphenyl)-4,6-dimethyl-2,3-dihydro-1-benzofuran-5-yl)-3,3-dimethylbutanamide Using 4-isopropyl-1-bromobenzene, the title compound was synthesized in the same manner as in Example 94.
Yield: 70%. Amorphous powder.

¹H-NMR (CDCl₃) δ: 1.10 (9H, s), 1.18-1.31 (12H, m), 1.89 (3H, s), 2.13 (3H, s), 2.23 (2H, s), 2.79-2.95 (2H, m), 3.89-4.07 (1H, m), 4.39-4.48 (2H, m), 4.77-4.91 (1H, m), 5.98 (1H, d, J=8.4 Hz), 6.55 (1H, d, J=6.6 Hz), 6.98-7.22 (6H, m), 7.29 (2H, d, J=8.1 Hz).

EXAMPLE 96

N-(7-Benzyl-3-(4-isopropylphenyl)-4,6-dimethyl-2,3-dihydro-1-benzofuran-5-yl)-3,3-dimethylbutanamide A solution of N-(7-(hydroxy(phenyl)methyl)-3-(4-isopropylphenyl)-4,6-dimethyl-2,3-dihydro-1-benzofuran-5-yl)-3,3-dimethylbutanamide (512 mg, 1.05 mmol) obtained in Example 94 and 10% palladium on carbon (water content: 50%, 50 mg) in acetic acid (20 mL) was stirred at 80° C. for 1.5 hours under hydrogen atmosphere. The catalyst was removed and the reaction solution was concentrated under reduced pressure. Water was added to the residue and the product was extracted with ethyl acetate. The organic layer was washed with an aqueous saturated sodium hydrogen carbonate solution and water, dried over anhydrous sodium sulfate, and concentrated under reduced pressure. The obtained residue was recrystallized from hexane-ethyl acetate to obtain 330 mg (yield: 67%) of the title compound. Melting point: 153-154° C.

¹H-NMR (CDCl₃) δ: 1.10 (9H, s), 1.22 (6H, d, J=6.9 Hz), 1.88 (3H, s), 2.10 (3H, s), 2.23 (2H, s), 2.86 (1H, septet, J=6.9 Hz), 4.04 (2H, s), 4.43 (1H, dd, J=8.4, 4.2 Hz), 4.56 (1H, dd, J=9.0, 4.8 Hz), 4.83 (1H, t, J=9.0 Hz), 6.46 (1H, br s), 7.03-7.28 (9H, m).

EXAMPLE 97

N-(7-(4-Isopropylbenzyl)-3-(4-isopropylphenyl)-4,6-dimethyl-2,3-dihydro-1-benzofuran-5-yl)-3,3-dimethylbutanamide Using N-(7-(hydroxy(4-isopropylphenyl)methyl)-3-(4-isopropylphenyl)-4,6-dimethyl-2,3-dihydro-1-benzofuran-5-yl)-3,3-dimethylbutanamide obtained in Example 95, the title compound was synthesized in the same manner as in Example 96. Yield: 64%. Melting point: 157-158° C. (hexane-ethyl acetate).

¹H-NMR (CDCl₃) δ: 1.10 (9H, s), 1.21 (6H, d, J=6.9 Hz), 1.22 (6H, d, J=6.9 Hz), 1.87 (3H, s), 2.10 (3H, s), 2.22 (2H, s), 2.77-2.92 (2H, m), 3.99 (2H, s), 4.42 (1H, dd, J=9.0, 4.8 Hz), 4.55 (1H, dd, J=9.3, 4.8 Hz), 4.82 (1H, t, J=9.0 Hz), 6.45 (1H, br s), 7.00-7.17 (8H, m).

EXAMPLE 98

5-((3,3-Dimethylbutanoyl)amino)-3-(4-isopropylphenyl)-4,6-dimethyl-2,3-dihydro-1-benzofuran-7-carboxylic acid To a mixed solution of N-(7-formyl-3-(4-isopropylphenyl)-4,6-dimethyl-2,3-dihydro-1-benzofuran-5-yl)-3,3-dimethylbutanamide (500 mg, 1.23 mmol) obtained in Example 20, sodium dihydrogenphosphate (40 mg), and hydrogen peroxide (0.125 mL) in acetonitrile (5 mL)-water (2 mL) was added at room temperature a solution of sodium chlorite (190 mg, 1.69 mmol) in water (2 mL) and the resulting mixture was stirred at the same temperature for 2 hours. To the reaction solution was added an aqueous sodium hydrogensulfite solution, added 1 N hydrochloric acid to make the mixture acidic, and the mixture was extracted with ethyl acetate. The extracts were washed with water, dried over anhydrous sodium sulfate, and concentrated under reduced pressure. The obtained residue was crystallized from hexane-ethyl acetate to obtain 380 mg (yield: 73%) of the title compound. Melting point: 194-195° C.

¹H-NMR (CDCl₃) δ: 1.12 (9H, s), 1.22 (6H, d, J=6.9 Hz), 1.91 (3H, m), 2.28 (2H, s), 2.51 (3H, s), 2.86 (1H, septet, J=6.9 Hz), 4.47-4.65 (2H, m), 5.01 (1H, t, J=9.0 Hz), 6.59 (1H, br s), 7.02 (2H, d, J=8.1 Hz), 7.14 (2H, d, J=8.1 Hz), 1H unidentified.

EXAMPLE 99

N-(7-Cyano-3-(4-isopropylphenyl)-4,6-dimethyl-2,3-dihydro-1-benzofuran-5-yl)-3,3-dimethylbutanamide A solution of N-(7-bromo-3-(4-isopropylphenyl)-4,6-dimethyl-2,3-dihydro-1-benzofuran-5-yl)-3,3-dimethylbutanamide (0.5 g, 1.09 mmol) obtained in Example 35 and copper cyanide (300 mg 3.27 mmol) in dimethylsulfoxide (30 mL) was heated at 180° C. for 14 hours. To the reaction solution was added aqueous ammonia and the product was extracted with ethyl acetate. The extracts were washed with saturated brine, dried over anhydrous sodium sulfate, and the solvent was distilled off under reduced pressure. The obtained residue was purified by silica gel column chromatography (hexane: ethyl acetate 3:1) to obtain 360 mg (yield: 82%) of the title compound. Melting point: 135-136° C. (hexane-ethyl acetate).

¹H-NMR (CDCl₃) δ: 1.11 (9H, s), 1.22 (6H, d, J=6.9 Hz), 1.89 (3H, s), 2.25 (2H, s), 2.38 (3H, s), 2.87 (1H, septet, J=6.9 Hz), 4.50-4.65 (2H, m), 5.01 (1H, t, J=10.8 Hz), 6.58 (1H, br s), 7.02 (2H, d, J=8.1 Hz), 7.15 (2H, d, J=8.1 Hz).

EXAMPLE 100

N-((3S)-7-Acetyl-3-(4-isopropylphenyl)-4,6-dimethyl-2,3-dihydro-1-benzofuran-5-yl)-3,3-dimethylbutanamide Using N-((3S)-3-(4-isopropylphenyl)-4,6-dimethyl-2,3-dihydro-1-benzofuran-5-yl)-3,3-dimethylbutanamide obtained in Example 71, the title compound was synthesized in the same manner as in Example 38. Yield: 46%. Melting point: 177-178° C. (hexane-ethyl acetate). $[\alpha]_D^{20}$=−6.0° (c=0.510, chloroform).

¹H-NMR (CDCl₃) δ: 1.11 (9H, s), 1.22 (6H, d, J=6.9 Hz), 1.88 (3H, s), 2.22 (3H, s), 2.25 (2H, s), 2.58 (3H, s), 2.87 (1H, septet, J=6.9 Hz), 4.44-4.56 (2H, m), 4.89 (1H, t, J=8.1 Hz), 6.54 (1H, br s), 7.03 (2H, d, J=8.1 Hz), 7.14 (2H, d, J=8.1 Hz).

EXAMPLE 101

N-(3-(4-Isopropylphenyl)-4,6-dimethyl-7-phenyl-2, 3-dihydro-1-benzofuran-5-yl)-3,3-dimethylbutanamide A mixture of N-(7-bromo-3-(4-isopropylphenyl)-4,6-dimethyl-2,3-dihydro-1-benzofuran-5-yl)-3,3-dimethylbutanamide (300 mg, 0.654 mmol) obtained in Example 35, phenylboronic acid (88 mg, 0.720 mmol), and palladium (0) tetrakis (triphenylphosphine) (27 mg, 0.023 mmol) in an aqueous 2 M sodium carbonate solution (10 mL)-1,2-dimethoxyethane (5 mL) was refluxed with heating for 16 hours under a nitrogen atmosphere. The reaction solution was diluted with ethyl acetate. Insoluble materials were filtered off, and the filtrate was washed with saturated brine and dried over anhydrous sodium sulfate, and the solvent was distilled off under reduced pressure. The obtained residue was purified by silica gel column chromatography (ethyl acetate:hexane=1:4) to obtain 170 mg (yield: 57%) of the title compound. Melting point: 178-182° C. (hexane-ethyl acetate).

$^1$H-NMR (CDCl$_3$) δ: 1.11 (9H, s), 1.22 (6H, d, J=6.9 Hz), 1.92 (3H, s), 2.06 (3H, s), 2.26 (2H, s), 2.87 (1H, septet, J=6.9 Hz), 4.37 (1H, dd, J=9.0, 4.8 Hz), 4.56 (1H, dd, J=9.3, 5.1 Hz), 4.79 (1H, t, J=9.0 Hz), 6.59 (1H, br s), 7.09 (2H, d, J=8.1 Hz), 7.14 (2H, d, J=8.1 Hz), 7.30-7.50 (5H, m).

EXAMPLE 102

N-(3-(4-Isopropylphenyl)-7-(6-methoxypyridin-3-yl)-4,6-dimethyl-2,3-dihydro-1-benzofuran-5-yl)-3, 3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and (6-methoxypyridin-3-yl)boronic acid, the title compound was synthesized in the same manner as in Example 101. Yield: 48%. Melting point: 120-123° C. (hexane-ethyl acetate).

$^1$H-NMR (CDCl$_3$) δ: 1.12 (9H, s), 1.22 (6H, d, J=6.9 Hz), 1.92 (3H, s), 2.08 (3H, s), 2.26 (2H, s), 2.86 (1H, septet, J=6.9 Hz), 3.97 (3H, s), 4.38 (1H, dd, J=8.7, 4.8 Hz), 4.56 (1H, dd, J=9.3, 5.1 Hz), 4.79 (1H, t, J=9.3 Hz), 6.52 (1H, br s), 6.81 (1H, d, J=8.4 Hz), 7.09 (2H, d, J=8.4 Hz), 7.13 (2H, d, J=8.4 Hz), 7.57 (1H, dd, J=8.4, 2.4 Hz), 8.13 (1H, d, J=2.4 Hz).

EXAMPLE 103

N-(3-(4-Isopropylphenyl)-7-(4-methoxyphenyl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and (4-methoxyphenyl)boronic acid, the title compound was synthesized in the same manner as in Example 101. Yield: 40%. Melting point: 129-131° C. (hexane-ethyl acetate).

$^1$H-NMR (CDCl$_3$) δ: 1.12 (9H, s), 1.22 (6H, d, J=6.9 Hz), 1.92 (3H, s), 2.07 (3H, s), 2.26 (2H, s), 2.87 (1H, septet, J=6.9 Hz), 3.84 (3H, s), 4.38 (1H, dd, J=9.0, 4.8 Hz), 4.56 (1H, dd, J=9.3, 4.8 Hz), 4.79 (1H, t, J=9.0 Hz), 6.53 (1H, br s), 6.97 (2H, d, J=8.7 Hz), 7.09 (2H, d, J=8.4 Hz), 7.14 (2H, d, J=8.4 Hz), 7.27 (2H, d, J=8.7 Hz).

EXAMPLE 104

N-(7-(6-Fluoropyridin-3-yl)-3-(4-isopropylphenyl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and (6-fluoropyridin-3-yl)boronic acid, the title compound was synthesized in the same manner as in Example 101. Yield: 58%. Melting point: 135-137° C. (hexane-ethyl acetate).

$^1$H-NMR (CDCl$_3$) δ: 1.12 (9H, s), 1.23 (6H, d, J=6.9 Hz), 1.93 (3H, s), 2.07 (3H, s), 2.27 (2H, s), 2.87 (1H, septet, J=6.9 Hz), 4.38 (1H, dd, J=8.7, 4.8 Hz), 4.58 (1H, dd, J=9.0, 4.8 Hz), 4.81 (1H, t, J=9.0 Hz), 6.60 (1H, br s), 7.00 (1H, dd, J=8.4, 3.0 Hz), 7.08 (2H, d, J=8.1 Hz), 7.15 (2H, d, J=8.1 Hz), 7.79 (1H, dt, J=8.4, 2.1 Hz), 8.19 (1H, s).

EXAMPLE 105

N-(3-(4-Isopropylphenyl)-7-(3-methoxyphenyl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and (3-methoxyphenyl)boronic acid, the title compound was synthesized in the same manner as in Example 101. Yield: 64%. Melting point: 209-210° C. (hexane-ethyl acetate).

$^1$H-NMR (CDCl$_3$) δ: 1.12 (9H, s), 1.22 (6H, d, J=6.9 Hz), 1.92 (3H, s), 2.07 (3H, s), 2.27 (2H, s), 2.87 (1H, septet, J=6.9 Hz), 3.82 (3H, s), 4.38 (1H, dd, J=8.7, 4.8 Hz), 4.56 (1H, dd, J=9.0, 5.1 Hz), 4.80 (1H, t, J=9.0 Hz), 6.52 (1H, br s), 6.86-6.94 (3H, m), 7.10 (2H, d, J=8.1 Hz), 7.14 (2H, d, J=8.1 Hz), 7.35 (1H, dd, J=8.7, 7.8 Hz).

EXAMPLE 106

N-(3-(4-Isopropylphenyl)-4,7-dimethyl-6-phenyl-2, 3-dihydro-1-benzofuran-5-yl)-3,3-dimethylbutanamide Using N-(6-bromo-3-(4-isopropylphenyl)-4,7-dimethyl-2,3-dihydro-1-benzofuran-5-yl)-3,3-dimethylbutanamide obtained in Example 87 and phenylboronic acid, the title compound was synthesized in the same manner as in Example 101. Yield: 42%. Melting point: 212-213° C. (hexane-ethyl acetate).

$^1$H-NMR (CDCl$_3$) δ: 0.82 (9H, s), 1.23 (6H, d, J=6.9 Hz), 1.85-1.93 (8H, m), 2.88 (1H, septet, J=6.9 Hz), 4.48 (1H, dd, J=8.7, 4.8 Hz), 4.60 (1H, dd, J=9.0, 5.1 Hz), 4.89 (1H, t, J=9.0 Hz), 6.21 (1H, br s), 7.09-7.43 (9H, m).

EXAMPLE 107

N-(7-(3-(Acetylamino)phenyl)-3-(4-isopropylphenyl)-4,6-dimethyl-2,3-dihydro-1-benzofuran-5-yl)-3, 3-dimethylbutanamide A solution of N-(7-bromo-3-(4-isopropylphenyl)-4,6-dimethyl-2,3-dihydro-1-benzofuran-5-yl)-3,3-dimethylbutanamide (321 mg, 0.7 mmol) obtained in Example 35, (3-(acetylamino)phenyl)boronic acid (188 mg, 0.7 mmol), palladium (0) tetrakis(triphenylphosphine) (40.5 mg, 0.035 mmol), and an aqueous 2 N sodium carbonate solution (1.05 mL) in dimethoxyethane (2.1 mL)-ethanol (0.7 mL) was reacted with heating at 150° C. for 5 minutes in a microwave reactor. The reaction solution was cooled to room temperature, diluted with water, and extracted with ethyl acetate. The filtrate was washed with saturated brine and dried over sodium sulfate, and concentrated under reduced pressure. The obtained residue was purified by silica gel column chromatography (hexane:ethyl acetate=2:1) to obtain 308 mg (yield: 86%) of the title compound. Melting point: 247-248° C. (ethyl acetate-hexane).

$^1$H-NMR (CDCl$_3$) δ: 1.12 (9H, s), 1.22 (6H, d, J=6.9 Hz), 1.91 (3H, s), 2.05 (3H, s), 2.15 (3H, s), 2.26 (2H, s), 2.86 (1H, septet, J=6.9 Hz), 4.36 (1H, dd, J=4.9, 9.0 Hz), 4.54 (1H, dd, J=4.9, 9.0 Hz), 4.77 (1H, t, J=9.0 Hz), 6.54 (1H, s), 7.07-7.15 (5H, m), 7.26-7.39 (3H, m), 7.60 (1H, br).

EXAMPLE 108

N-(7-(3-Fluorophenyl)-3-(4-isopropylphenyl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and (3-fluorophenyl)boronic acid, the title compound was synthesized in the same manner as in Example 107. Yield: 67%. Melting point: 182-183° C. (ethyl acetate-hexane).

$^1$H-NMR (CDCl$_3$) δ: 1.12 (9H, s), 1.22 (6H, d, J=6.9 Hz), 1.92 (3H, s), 2.06 (3H, s), 2.26 (2H, s), 2.87 (1H, septet, J=6.9 Hz), 4.38 (1H, dd, J=4.9, 9.0 Hz), 4.56 (1H, dd, J=4.9, 9.0 Hz), 4.80 (1H, t, J=9.0 Hz), 6.51 (1H, s), 6.99-7.17 (7H, m), 7.34-7.42 (1H, m).

EXAMPLE 109

N-(7-(3-Nitrophenyl)-3-(4-isopropylphenyl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and (3-nitrophenyl)boronic acid, the title compound was obtained in the same manner as in Example 107. Yield: 59%. Melting point: 209-210° C. (ethyl acetate-hexane).

$^1$H-NMR (CDCl$_3$) δ: 1.13 (9H, s), 1.23 (6H, d, J=6.9 Hz), 1.94 (3H, s), 2.07 (3H, s), 2.27 (2H, s), 2.87 (1H, septet, J=6.9 Hz), 4.38 (1H, dd, J=4.9, 9.0 Hz), 4.57 (1H, dd, J=4.9, 9.0 Hz), 4.81 (1H, t, J=9.0 Hz), 6.52 (1H, s), 6.63-6.73 (3H, m), 7.07 (2H, d, J=8.2 Hz), 7.15 (2H, d, J=8.2 Hz), 7.59 (1H, t, J=7.7 Hz), 7.66-7.71 (1H, m), 8.17-8.23 (2H, m).

EXAMPLE 110

Methyl 3-(5-((3,3-dimethylbutanoyl)amino)-3-(4-isopropylphenyl)-4,6-dimethyl-2,3-dihydro-1-benzofuran-7-yl)benzoate Using N-(7-bromo-3-(4-isopropylphenyl)-4,6-dimethyl-2,3-dihydro-1-benzofuran-5-yl)-3,3-dimethylbutanamide obtained in Example 35 and (3-methoxycarbonyl)phenylboronic acid, the title compound was obtained in the same manner as in Example 107. Yield: 55%. Melting point: 206-208° C. (ethyl acetate-hexane).

$^1$H-NMR (CDCl$_3$) δ: 1.12 (9H, s), 1.22 (6H, d, J=6.9 Hz), 1.93 (3H, s), 2.05 (3H, s), 2.26 (2H, s), 2.87 (1H, septet, J=6.9 Hz), 3.91 (3H, s), 4.37 (1H, dd, J=4.9, 9.0 Hz), 4.57 (1H, dd, J=4.9, 9.0 Hz), 4.80 (1H, t, J=9.0 Hz), 6.57 (1H, s), 7.08 (2H, d, J=8.2 Hz), 7.13 (2H, d, J=8.2 Hz), 7.47-7.56 (2H, m), 7.98-8.03 (2H, m).

EXAMPLE 111

N-(7-(3-Acetylphenyl)-3-(4-isopropylphenyl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and (3-acetylphenyl)boronic acid, the title compound was obtained in the same manner as in Example 107. Yield: 79%. Melting point: 209-210° C. (ethyl acetate-hexane).

$^1$H-NMR (CDCl$_3$) δ: 1.12 (9H, s), 1.22 (6H, d, J=6.9 Hz), 1.93 (3H, s), 2.05 (3H, s), 2.27 (2H, s), 2.62 (3H, s), 2.87 (1H, septet, J=6.9 Hz), 4.37 (1H, dd, J=4.9, 9.0 Hz), 4.57 (1H, dd, J=4.9, 9.0 Hz), 4.80 (1H, t, J=9.0 Hz), 6.53 (1H, s), 7.08 (2H, d, J=8.2 Hz), 7.14 (2H, d, J=8.2 Hz), 7.50-7.56 (2H, m), 7.91-7.97 (2H, m).

EXAMPLE 112

Ethyl 3-(5-((3,3-dimethylbutanoyl)amino)-3-(4-isopropylphenyl)-4,6-dimethyl-2,3-dihydro-1-benzofuran-7-yl)benzoate Using N-(7-bromo-3-(4-isopropylphenyl)-4,6-dimethyl-2,3-dihydro-1-benzofuran-5-yl)-3,3-dimethylbutanamide obtained in Example 35 and 3-(ethoxycarbonyl)phenylboronic acid, the title compound was obtained in the same manner as in Example 107. Yield: 63%. Melting point: 175-177° C. (ethyl acetate-hexane).

$^1$H-NMR (CDCl$_3$) δ: 1.12 (9H, s), 1.22 (6H, d, J=6.9 Hz), 1.39 (3H, t, J=7.1 Hz), 1.93 (3H, s), 2.04 (3H, s), 2.27 (2H, s), 2.87 (1H, septet, J=6.9 Hz), 4.34-4.42 (3H, m), 4.57 (1H, dd, J=4.7, 9.3 Hz), 4.79 (1H, dd, J=8.8, 9.3 Hz), 6.52 (1H, s), 7.08 (2H, d, J=8.4 Hz), 7.14 (2H, d, J=8.4 Hz), 7.45-7.55 (2H, m), 8.00-8.05 (2H, m).

EXAMPLE 113

N-(7-(4-Methylphenyl)-3-(4-isopropylphenyl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and (4-methylphenyl)boronic acid, the title compound was obtained in the same manner as in Example 107. Yield: 68%. Melting point: 194-195° C. (ethyl acetate-hexane).

$^1$H-NMR (CDCl$_3$) δ: 1.12 (9H, s), 1.22 (6H, d, J=6.9 Hz), 1.92 (3H, s), 2.06 (3H, s), 2.26 (2H, s), 2.38 (3H, s), 2.86 (1H, septet, J=6.9 Hz), 4.36 (1H, dd, J=4.9, 8.8 Hz), 4.55 (1H, dd, J=4.9, 9.3 Hz), 4.81 (1H, dd, J=8.8, 9.3 Hz), 6.50 (1H, s), 7.07 (2H, d, J=8.3 Hz), 7.11 (2H, d, J=8.3 Hz), 7.22 (4H, s).

EXAMPLE 114

N-(3-(4-Isopropylphenyl)-7-(pyridin-3-yl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and pyridin-3-ylboronic acid, the title compound was obtained in the same manner as in Example 107. Yield: 32%. Melting point: 142-144° C. (ethyl acetate-hexane).

$^1$H-NMR (CDCl$_3$) δ: 1.12 (9H, s), 1.22 (6H, d, J=6.9 Hz), 1.93 (3H, s), 2.08 (3H, s), 2.27 (2H, s), 2.87 (1H, septet, J=6.9 Hz), 4.39 (1H, dd, J=5.0, 9.1 Hz), 4.58 (1H, dd, J=5.0, 9.1 Hz), 4.81 (1H, t, J=9.1 Hz), 6.56 (1H, s), 7.09 (2H, d, J=8.2 Hz), 7.15 (2H, d, J=8.2 Hz), 7.26-7.38 (1H, m), 7.67-7.72 (1H, m), 8.56-8.61 (2H, m).

EXAMPLE 115

N-(3-(4-Isopropylphenyl)-7-(pyridin-4-yl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and pyridin-4-ylboronic acid, the title compound was obtained in the same as in Example 107.

Yield: 72%. Melting point: 150-152° C. (ethyl acetate-hexane).

$^1$H-NMR (CDCl$_3$) δ: 1.12 (9H, s), 1.22 (6H, d, J=6.9 Hz), 1.93 (3H, s), 2.07 (3H, s), 2.27 (2H, s), 2.87 (1H, septet, J=6.9 Hz), 4.39 (1H, dd, J=4.9, 8.8 Hz), 4.57 (1H, dd, J=4.9, 9.3 Hz), 4.81 (1H, t, J=9.0 Hz), 6.53 (1H, s), 7.07 (2H, d, J=8.1 Hz), 7.14 (2H, d, J=8.1 Hz), 7.27 (2H, d, J=5.9 Hz), 8.65 (2H, d, J=5.9 Hz).

EXAMPLE 116

(5-((3,3-Dimethylbutanoyl)amino)-3-(4-isopropylphenyl)-4,6-dimethyl-2,3-dihydro-1-benzofuran-7-yl)boronic acid A solution of N-(7-bromo-3-(4-isopropylphenyl)-4,6-dimethyl-2,3-dihydro-1-benzofuran-5-yl)-3,3-dimethylbutanamide (1.38 g, 3 mmol) obtained in Example 35 in THF solution (20 mL) was cooled to −72° C. To the reaction solution was added n-butyllithium (1.6 M THF solution, 5.63 mL, 9 mmol) and the reaction mixture was stirred for 30 minutes, and thereto was further added triisopropyl boronate (2.42 mL, 10.5 mmol). The reaction solution was warmed to room temperature over a period of 1 hour, treated with 1 N hydrochloric acid, and extracted with ethyl acetate. The extracts were washed with saturated brine, dried over sodium sulfate, and concentrated under reduced pressure. The obtained residue was purified by silica gel column chromatography (ethyl acetate:methanol=9:1) to obtain 613 mg (yield: 48%) of the title compound. Melting point: 151-153° C. (ethyl acetate-hexane).

$^1$H-NMR (CDCl$_3$) δ: 1.12 (9H, s), 1.23 (6H, d, J=6.9 Hz), 1.90 (3H, s), 2.26 (2H, s), 2.49 (3H, s), 2.87 (1H, septet, J=6.9 Hz), 4.45-4.55 (2H, m), 4.87 (1H, t, J=9.0 Hz), 5.88 (2H, s), 6.49 (1H, s), 7.01 (2H, d, J=8.2 Hz), 7.11 (2H, d, J=8.2 Hz).

EXAMPLE 117

N-(3-(4-Isopropylphenyl)-7-(pyridin-2-yl)-4,6-dimethyl-2,3-dihydro-1-benzofuran-5-yl)-3,3-dimethylbutanamide Using (5-((3,3-dimethylbutanoyl)amino)-3-(4-isopropylphenyl)-4,6-dimethyl-2,3-dihydro-1-benzofuran-7-yl)boronic acid obtained in Example 116 and 2-bromopyridine, the title compound was obtained in the same manner as in Example 107.

Yield: 53%. Melting point: 198-200° C. (ethyl acetate-hexane).

$^1$H-NMR (CDCl$_3$) δ: 1.11 (9H, s), 1.22 (6H, d, J=6.9 Hz), 1.91 (3H, s), 2.04 (3H, s), 2.26 (2H, s), 2.87 (1H, septet, J=6.9 Hz), 4.37 (1H, dd, J=4.9, 9.0 Hz), 4.57 (1H, dd, J=4.9, 9.0 Hz), 4.83 (1H, t, J=9.0 Hz), 6.75 (1H, s), 7.05-7.13 (4H, m), 7.22-7.26 (1H, m), 7.43 (1H, d, J=7.7 Hz), 7.74 (1H, td, J=7.7, 0.8 Hz), 8.69-8.73 (1H, m).

EXAMPLE 118

N-(3-(4-Isopropylphenyl)-7-(5-methylpyridin-2-yl)-4,6-dimethyl-2,3-dihydro-1-benzofuran-5-yl)-3,3-dimethylbutanamide Using (5-((3,3-dimethylbutanoyl)amino)-3-(4-isopropylphenyl)-4,6-dimethyl-2,3-dihydro-1-benzofuran-7-yl)boronic acid obtained in Example 116 and 2-bromo-5-methylpyridine, the title compound was obtained in the same manner as in Example 107. Yield: 67%. Melting point: 228-229° C. (ethyl acetate-hexane).

$^1$H-NMR (CDCl$_3$) δ: 1.11 (9H, s), 1.21 (6H, d, J=6.9 Hz), 1.90 (3H, s), 2.01 (3H, s), 2.25 (2H, s), 2.37 (3H, s), 2.85 (1H, septet, J=6.9 Hz), 4.36 (1H, dd, J=4.9, 9.0 Hz), 4.57 (1H, dd, J=4.9, 9.0 Hz), 4.81 (1H, t, J=9.0 Hz), 6.90 (1H, s), 7.09 (2H, d, J=8.3 Hz), 7.11 (2H, d, J=8.3 Hz), 7.32 (1H, d, J=8.0 Hz), 7.53-7.58 (1H, m), 8.54 (1H, br s).

EXAMPLE 119

N-(7-(6-Aminopyridin-2-yl)-3-(4-isopropylphenyl)-4,6-dimethyl-2,3-dihydro-1-benzofuran-5-yl)-3,3-dimethylbutanamide Using (5-((3,3-dimethylbutanoyl)amino)-3-(4-isopropylphenyl)-4,6-dimethyl-2,3-dihydro-1-benzofuran-7-yl)boronic acid obtained in Example 116 and 2-amino-6-bromopyridine, the title compound was obtained in the same manner as in Example 107. Yield: 68%. Melting point: 237-239° C. (ethyl acetate-hexane).

$^1$H-NMR (CDCl$_3$) δ: 1.11 (9H, s), 1.23 (6H, d, J=6.9 Hz), 1.88 (3H, s), 2.10 (3H, s), 2.25 (2H, s), 2.86 (1H, septet, J=6.9 Hz), 4.36 (1H, dd, J=4.9, 9.0 Hz), 4.54 (2H, brs), 4.56 (1H, dd, J=4.9, 9.0 Hz), 4.83 (1H, t, J=9.0 Hz), 6.45 (1H, d, J=8.2 Hz), 6.47 (1H, s), 6.77 (1H, d, J=7.4 Hz), 7.08 (2H, d, J=8.6 Hz), 7.12 (2H, d, J=8.6 Hz), 7.50 (1H, dd, J=7.4, 8.2 Hz)

EXAMPLE 120

N-(7-(3-Dimethylaminophenyl)-3-(4-isopropylphenyl)-4,6-dimethyl-2,3-dihydro-1-benzofuran-5-yl)-3,3-dimethylbutanamide Using (5-((3,3-dimethylbutanoyl)amino)-3-(4-isopropylphenyl)-4,6-dimethyl-2,3-dihydro-1-benzofuran-7-yl)boronic acid obtained in Example 116 and 3-bromo-N,N-dimethylaniline, the title compound was obtained in the same manner as in Example 107. Yield: 77%. Melting point: 197-199° C. (ethyl acetate-hexane).

$^1$H-NMR (CDCl$_3$) δ: 1.12 (9H, s), 1.22 (6H, d, J=6.9 Hz), 1.91 (3H, s), 2.06 (3H, s), 2.26 (2H, s), 2.86 (1H, septet, J=6.9 Hz), 2.95 (6H, s), 4.34-4.39 (1H, m), 4.53-4.58 (1H, m), 4.77 (1H, t, J=9.1 Hz), 6.50 (1H, s), 6.63-6.77 (3H, m), 7.06-7.16 (4H, m), 7.27-7.33 (1H, m).

EXAMPLE 121

N-(7-(6-(Acetylamino)pyridin-2-yl)-3-(4-isopropylphenyl)-4,6-dimethyl-2,3-dihydro-1-benzofuran-5-yl)-3,3-dimethylbutanamide To a solution of N-(7-(6-aminopyridin-2-yl)-3-(4-isopropylphenyl)-4,6-dimethyl-2,3-dihydro-1-benzofuran-5-yl)-3,3-dimethylbutanamide (94.3 mg, 0.2 mmol) and triethylamine (0.042 mL, 0.3 mmol) in THF (1 mL) was added acetyl chloride (0.015 mL, 0.22 mmol) at 0° C. and the resulting mixture was stirred at room temperature for 1 hour. The reaction solution was diluted with saturated sodium bicarbonate solution and extracted with ethyl acetate. The extracts were washed with saturated brine, dried over sodium sulfate, and concentrated under reduced pressure. The obtained residue was purified by silica gel column chromatography (hexane:ethyl acetate=1:1) to obtain 51 mg (yield: 50%) of the title compound. Melting point: 205-208° C. (ethyl acetate-hexane).

$^1$H-NMR (CDCl$_3$) δ: 1.12 (9H, s), 1.22 (6H, d, J=6.9 Hz), 1.59 (3H, s), 1.90 (3H, s), 2.07 (3H, s), 2.26 (2H, s), 2.86 (1H, septet, J=6.9 Hz), 4.33-4.39 (1H, m), 4.57 (1H, dd, J=4.9, 9.3 Hz), 4.82 (1H, t, J=9.1 Hz), 6.49 (1H, s), 7.03-7.18 (5H, m), 7.76 (1H, t, J=7.9 Hz), 7.99 (1H, br), 8.14 (1H, d, J=7.9 Hz).

EXAMPLE 122

N-(7-(3-Aminophenyl)-3-(4-isopropylphenyl)-4,6-dimethyl-2,3-dihydro-1-benzofuran-5-yl)-3,3-dimethylbutanamide To a solution of N-(7-(3-nitrophenyl)-3-(4-isopropylphenyl)-4,6-dimethyl-2,3-dihydro-1-benzofuran-5-yl)-3,3-dimethylbutanamide (2.50 g, 5 mmol) obtained in Example 109 and ammonium formate (1.26 g, 20 mmol) in ethanol (50 mL) was added 10% palladium on carbon (water content: 50%, 0.25 g), and the resulting mixture was heated at 65° C. and stirred for 2 hours. The reaction solution was cooled to room temperature, the catalyst was filtered off, and the fitrate was concentrated under reduced pressure.

The residue was diluted with water and extracted with ethyl acetate. The extracts were washed with saturated brine, dried over sodium sulfate, and concentrated under reduced pressure. The obtained residue was purified by silica gel column chromatography (ethyl acetate) to obtain 2.15 g (yield: 92%) of the title compound. Melting point: 170-172° C. (ethyl acetate-hexane).

$^1$H-NMR (CDCl$_3$) δ: 1.12 (9H, s), 1.22 (6H, d, J=6.9 Hz), 1.91 (3H, s), 2.05 (3H, s), 2.26 (2H, s), 2.86 (1H, septet, J=6.9 Hz), 3.67 (2H, brs), 4.37 (1H, dd, J=4.9, 9.0 Hz), 4.54 (1H, dd, J=4.9, 9.0 Hz), 4.77 (1H, t, J=9.0 Hz), 6.51 (1H, s), 6.63-6.73 (3H, m), 7.05-7.15 (4H, m), 7.19 (1H, dd, J=5.0, 5.8 Hz).

EXAMPLE 123

N-(3-(4-Isopropylphenyl)-7-(3-propionylaminophenyl)-4,6-dimethyl-2,3-dihydro-1-benzofuran-5-yl)-3,3-dimethylbutanamide Using N-(7-(3-aminophenyl)-3-(4-isopropylphenyl)-4,6-dimethyl-2,3-dihydro-1-benzofuran-5-yl)-3,3-dimethylbutanamide obtained in Example 122 and propionyl chloride, the title compound was obtained in the same manner as in Example 121. Yield: 84%. Melting point: 237-239° C. (ethyl acetate-hexane).

$^1$H-NMR (CDCl$_3$) δ: 1.12 (9H, s), 1.20-1.26 (9H, m), 1.91 (3H, s), 2.05 (3H, s), 2.26 (2H, s), 2.37 (2H, q, J=7.4 Hz), 2.86 (1H, septet, J=6.9 Hz), 4.35 (1H, dd, J=4.9, 8.5 Hz), 4.54 (1H, dd, J=4.9, 9.2 Hz), 4.77 (1H, t, J=9.1 Hz), 6.50 (1H, s), 7.02-7.09 (3H, m), 7.13 (2H, d, J=8.0 Hz), 7.24 (1H, br), 7.30-7.40 (2H, m), 7.63 (1H, br).

EXAMPLE 124

N-(3-(4-Isopropylphenyl)-4,6-dimethyl-7-(pyrimidin-5-yl)-2,3-dihydro-1-benzofuran-5-yl)-3,3-dimethylbutanamide Using (5-((3,3-dimethylbutanoyl)amino)-3-(4-isopropylphenyl)-4,6-dimethyl-2,3-dihydro-1-benzofuran-7-yl)boronic acid obtained in Example 116 and 5-bromopyrimidine, the title compound was obtained in the same manner as in Example 107. Yield: 77%. Melting point: 167-169° C. (ethyl acetate-hexane).

$^1$H-NMR (CDCl$_3$) δ: 1.13 (9H, s), 1.22 (6H, d, J=6.9 Hz), 1.94 (3H, s), 2.12 (3H, s), 2.28 (2H, s), 2.87 (1H, septet, J=6.9 Hz), 4.40 (1H, dd, J=4.9, 9.0 Hz), 4.58 (1H, dd, J=4.9, 9.0 Hz), 4.83 (1H, t, J=9.0 Hz), 6.53 (1H, s), 7.07 (2H, d, J=8.4 Hz), 7.15 (2H, d, J=8.4 Hz), 8.76 (2H, s), 9.18 (1H, s).

EXAMPLE 125

N-(3-(4-Isopropylphenyl)-4,6-dimethyl-7-(1,3-thiazol-2-yl)-2,3-dihydro-1-benzofuran-5-yl)-3,3-dimethylbutanamide Using (5-((3,3-dimethylbutanoyl)amino)-3-(4-isopropylphenyl)-4,6-dimethyl-2,3-dihydro-1-benzofuran-7-yl)boronic acid obtained in Example 116 and 2-bromo-1,3-thiazole, the title compound was obtained in the same manner as in Example 107. Yield: 64%. Melting point: 164-166° C. (ethyl acetate-hexane).

$^1$H-NMR (CDCl$_3$) δ: 1.12 (9H, s), 1.22 (6H, d, J=6.9 Hz), 1.91 (3H, s), 2.25 (3H, s), 2.27 (2H, s), 2.86 (1H, septet, J=6.9 Hz), 4.46 (1H, dd, J=4.9, 9.0 Hz), 4.58 (1H, dd, J=4.9, 9.0 Hz), 4.90 (1H, t, J=9.0 Hz), 6.72 (1H, s), 7.07 (2H, d, J=8.4 Hz), 7.14 (2H, d, J=8.4 Hz), 7.47 (1H, d, J=3.2 Hz), 7.93 (1H, d, J=3.2 Hz).

EXAMPLE 126

N-(3-(4-Isopropylphenyl)-4,6-dimethyl-7-(3-thienyl)-2,3-dihydro-1-benzofuran-5-yl)-3,3-dimethylbutanamide Using (5-((3,3-dimethylbutanoyl)amino)-3-(4-isopropylphenyl)-4,6-dimethyl-2,3-dihydro-1-benzofuran-7-yl)boronic acid obtained in Example 116 and 3-bromothiophene, the title compound was obtained in the same manner as in Example 107. Yield: 49%. Melting point: 172-174° C. (ethyl acetate-hexane).
$^1$H-NMR (CDCl$_3$) δ: 1.12 (9H, s), 1.22 (6H, d, J=6.9 Hz), 1.91 (3H, s), 2.14 (3H, s), 2.27 (2H, s), 2.87 (1H, septet, J=6.9 Hz), 4.40 (1H, dd, J=4.9, 9.0 Hz), 4.55 (1H, dd, J=4.9, 9.0 Hz), 4.82 (1H, t, J=9.0 Hz), 6.51 (1H, s), 7.05-7.17 (5H, m), 7.26-7.43 (2H, m).

EXAMPLE 127

N-(7-(1H-Imidazol-4-yl)-3-(4-isopropylphenyl)-4,6-dimethyl-2,3-dihydro-1-benzofuran-5-yl)-3,3-dimethylbutanamide Using (5-((3,3-dimethylbutanoyl)amino)-3-(4-isopropylphenyl)-4,6-dimethyl-2,3-dihydro-1-benzofuran-7-yl)boronic acid obtained in Example 116 and 4-bromoimidazole, the title compound was obtained in the same manner as in Example 107. Yield: 48%. Melting point: 277-279° C. (ethyl acetate).
$^1$H-NMR (CDCl$_3$) δ: 1.11 (9H, s), 1.22 (6H, d, J=6.9 Hz), 1.91 (3H, s), 2.28 (2H, s), 2.34 (3H, brs), 2.86 (1H, septet, J=6.9 Hz), 4.40-4.58 (2H, m), 4.81-4.88 (1H, m), 6.50 (1H, s), 6.92 (1H, s), 7.06 (2H, d, J=8.3 Hz), 7.11 (2H, d, J=8.3 Hz), 7.21 (1H, br s), 7.68 (1H, s).

EXAMPLE 128

N-(7-(3-Furyl)-3-(4-isopropylphenyl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and 3-furylboronic acid, the title compound was obtained in the same manner as in Example 107. Yield: 51%. Melting point: 183-185° C. (ethyl acetate-hexane).
$^1$H-NMR (CDCl$_3$) δ: 1.12 (9H, s), 1.22 (6H, d, J=6.9 Hz), 1.90 (3H, s), 2.21 (3H, s), 2.26 (2H, s), 2.86 (1H, septet, J=6.9 Hz), 4.41 (1H, dd, J=8.5, 4.9 Hz), 4.55 (1H, dd, J=9.6, 4.9 Hz), 4.83 (1H, dd, J=8.5, 9.6 Hz), 6.50 (1H, s), 6.57 (1H, d, J=1.9 Hz), 7.06 (2H, d, J=8.3 Hz), 7.12 (2H, d, J=8.3 Hz), 7.48-7.50 (1H, m), 7.53-7.55 (1H, m).

EXAMPLE 129

N-(7-(1H-Pyrrol-2-yl)-3-(4-isopropylphenyl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and (1-(tert-butoxycarbonyl)-1H-pyrrol-2-yl) boronic acid, the title compound was obtained in the same manner as in Example 107. Yield: 19%. Melting point: 188-190° C. (ethyl acetate).
$^1$H-NMR (CDCl$_3$) δ: 1.13 (9H, s), 1.21 (6H, d, J=6.9 Hz), 1.90 (3H, s), 2.27 (2H, s), 2.39 (3H, s), 2.86 (1H, septet, J=6.9 Hz), 4.45-4.50 (1H, m), 4.53-4.59 (1H, m), 4.87 (1H, t, J=8.6 Hz), 6.30-6.34 (1H, m), 6.42 (1H, br), 6.53 (1H, s), 6.87 (1H, br), 7.05 (2H, d, J=8.0 Hz), 7.11 (2H, d, J=8.0 Hz), 9.32 (1H, br).

EXAMPLE 130

N-(3-(4-Isopropylphenyl)-4,6-dimethyl-7-(2-thienyl)-2,3-dihydro-1-benzofuran-5-yl)-3,3-dimethylbutanamide Using (5-((3,3-dimethylbutanoyl)amino)-3-(4-isopropylphenyl)-4,6-dimethyl-2,3-dihydro-1-benzofuran-7-yl) boronic acid obtained in Example 116 and 2-bromothiophene, the title compound was synthesized in the same manner as in Example 107. Yield: 58%. Melting point: 155-156° C. (hexane-ethyl acetate).
$^1$H-NMR (CDCl$_3$) δ: 1.12 (9H, s), 1.22 (6H, d, J=6.9 Hz), 1.91 (3H, s), 2.16 (3H, s), 2.26 (2H, s), 2.86 (1H, septet, J=6.9 Hz), 4.41 (1H, dd, J=8.7, 5.1 Hz), 4.57 (1H, dd, J=9.3, 5.1 Hz), 4.84 (1H, t, J=10.8 Hz), 6.50 (1H, br s), 7.00-7.16 (6H, m), 7.38 (1H, dd, J=5.1, 1.2 Hz).

EXAMPLE 131

N-(7-(5-Acetyl-2-thienyl)-3-(4-isopropylphenyl)-4,6-dimethyl-2,3-dihydro-1-benzofuran-5-yl)-3,3-dimethylbutanamide Using (5-((3,3-dimethylbutanoyl)amino)-3-(4-isopropylphenyl)-4,6-dimethyl-2,3-dihydro-1-benzofuran-7-yl)boronic acid obtained in Example 116 and 2-acetyl-5-bromothiophene, the title compound was synthesized in the same manner as in Example 107. Yield: 65%. Melting point: 157-158° C. (hexane-ethyl acetate).
$^1$H-NMR (CDCl$_3$) δ: 1.12 (9H, s), 1.22 (6H, d, J=6.9 Hz), 1.92 (3H, s), 2.19 (3H, s), 2.27 (2H, s), 2.57 (3H, s), 2.87 (1H, septet, J=6.9 Hz), 4.43 (1H, dd, J=8.1, 4.8 Hz), 4.58 (1H, dd, J=9.9, 4.5 Hz), 4.85 (1H, t, J=9.0 Hz), 6.54 (1H, br s), 7.05-7.21 (5H, m), 7.71 (1H, d, J=3.9 Hz).

EXAMPLE 132

N-(7-(5-Acetyl-3-thienyl)-3-(4-isopropylphenyl)-4,6-dimethyl-2,3-dihydro-1-benzofuran-5-yl)-3,3-dimethylbutanamide Using (5-((3,3-dimethylbutanoyl)amino)-3-(4-isopropylphenyl)-4,6-dimethyl-2,3-dihydro-1-benzofuran-7-yl)boronic acid obtained in Example 116 and 2-acetyl-4-bromothiophene, the title compound was synthesized in the same manner as in Example 107. Yield: 62%. Melting point: 133-134° C. (hexane-ethyl acetate).
$^1$H-NMR (CDCl$_3$) δ: 1.13 (9H, s), 1.23 (6H, d, J=6.9 Hz), 1.92 (3H, s), 2.15 (3H, s), 2.27 (2H, s), 2.58 (3H, s), 2.87 (1H, septet, J=6.9 Hz), 4.41 (1H, dd, J=8.7, 4.8 Hz), 4.58 (1H, dd, J=9.3, 5.1 Hz), 4.83 (1H, t, J=9.0 Hz), 6.56 (1H, br s), 7.08 (2H, d, J=8.1 Hz), 7.15 (2H, d, J=8.1 Hz), 7.58 (1H, d, J=1.2 Hz), 7.74 (1H, d, J=1.2 Hz).

EXAMPLE 133

N-(3-(4-Isopropylphenyl)-4,6-dimethyl-7-(4-methyl-1,3-thiazol-2-yl)-2,3-dihydro-1-benzofuran-5-yl)-3,3-dimethylbutanamide Using (5-((3,3-dimethylbutanoyl)amino)-3-(4-isopropylphenyl)-4,6-dimethyl-2,3-dihydro-1-benzofuran-7-yl)boronic acid obtained in Example 116 and 2-bromo-4-methyl-1,3-thiazole, the title compound was synthesized in the same manner as in Example 107. Yield: 62%. Melting point: 240-241° C. (hexane-ethyl acetate).

$^1$H-NMR (CDCl$_3$) δ: 1.11 (9H, s), 1.22 (6H, d, J=6.9 Hz), 1.90 (3H, s), 2.22 (3H, s), 2.26 (2H, s), 2.53 (3H, s), 2.86 (1H, septet, J=6.9 Hz), 4.44 (1H, dd, J=8.7, 5.4 Hz), 4.64 (1H, dd, J=9.3, 5.7 Hz), 4.90 (1H, t, J=9.0 Hz), 6.61 (1H, br s), 7.01 (1H, s), 7.07 (2H, d, J=8.1 Hz), 7.13 (2H, d, J=8.1 Hz).

EXAMPLE 134

(+)-N-((3R)-7-Hydroxy-3-(4-isopropylphenyl)-4,6-dimethyl-2,3-dihydro-1-benzofuran-5-yl)-3,3-dimethylbutanamide To a solution of (+)-N-((3R)-3-(4-isopropylphenyl)-7-methoxy-4,6-dimethyl-2,3-dihydro-1-benzofuran-5-yl)-3,3-dimethylbutanamide (500 mg, 1.22 mmol) obtained in Example 52 in dichloromethane (20 mL) was added dropwise at −78° C. under an argon atmosphere boron tribromide (1.0 M dichloromethane solution, 3.0 mL, 3.0 mmol). The reaction solution was warmed to room temperature, added to an aqueous saturated sodium hydrogen carbonate solution, and extracted with ethyl acetate. The combined organic layers were washed with saturated brine, dried over sodium sulfate, filtered, and then concentrated under reduced pressure.

The obtained residue was purified by silica gel column chromatography (ethyl acetate:hexane=1:2) to synthesize 378 mg (yield: 78%) of the title compound. Melting point: 202-203° C. (ethyl acetate-hexane).

$[\alpha]_D^{20}$=+79.00 (c=0.49, chloroform).

$^1$H-NMR (CDCl$_3$) δ: 1.12 (9H, s), 1.22 (6H, d, J=6.9 Hz), 1.80 (3H, s), 2.14 (3H, s), 2.24 (2H, s), 2.86 (1H, septet, J=6.9 Hz), 4.46 (1H, dd, J=4.5, 8.7 Hz), 4.55 (1H, dd, J=4.5, 8.7 Hz), 4.86 (1H, t, J=8.7 Hz), 4.89 (1H, br s), 6.49 (1H, br s), 7.03 (2H, d, J=8.1 Hz), 7.12 (2H, d, J=8.1 Hz).

EXAMPLE 135

N-(7-Hydroxy-3-(4-isopropylphenyl)-4,6-dimethyl-2,3-dihydro-1-benzofuran-5-yl)-3,3-dimethylbutanamide Using N-(3-(4-isopropylphenyl)-7-methoxy-4,6-dimethyl-2,3-dihydro-1-benzofuran-5-yl)-3,3-dimethylbutanamide obtained in Example 36, the title compound was synthesized in the same manner as in Example 134. Yield: 78%. Melting point: 181-182° C. (ethyl acetate-hexane).

$^1$H-NMR (CDCl$_3$) δ: 1.12 (9H, s), 1.22 (6H, d, J=6.9 Hz), 1.80 (3H, s), 2.14 (3H, s), 2.25 (2H, s), 2.86 (1H, septet, J=6.9 Hz), 4.46 (1H, dd, J=4.5, 8.7 Hz), 4.55 (1H, dd, J=4.5, 8.7 Hz), 4.84 (1H, t, J=8.7 Hz), 4.95 (1H, br s), 6.51 (1H, br s), 7.04 (2H, d, J=8.1 Hz), 7.13 (2H, d, J=8.1 Hz).

EXAMPLE 136

N-(7-Ethoxy-3-(4-isopropylphenyl)-4,6-dimethyl-2,3-dihydro-1-benzofuran-5-yl)-3,3-dimethylbutanamide A mixed solution of N-(7-hydroxy-3-(4-isopropylphenyl)-4,6-dimethyl-2,3-dihydro-1-benzofuran-5-yl)-3,3-dimethylbutanamide obtained in Example 135 (300 mg, 0.76 mmol), potassium carbonate (105 mg, 0.76 mmol) and diethyl sulfate (117 mg, 0.76 mmol) in acetone (15 mL) was refluxed with heating for 14 hours. Water was added to the reaction solution and the product was extracted with ethyl acetate. The combined organic layers were washed with saturated brine, dried over sodium sulfate, filtered, and then concentrated under reduced pressure. The obtained residue was purified by silica gel column chromatography (ethyl acetate:hexane=1:2) to synthesize 378 mg (yield: 78%) of the title compound. Melting point: 174-175° C. (hexane).

$^1$H-NMR (CDCl$_3$) δ: 1.12 (9H, s), 1.22 (6H, d, J=6.9 Hz), 1.37 (3H, t, J=7.2 Hz), 1.82 (3H, s), 2.16 (3H, s), 2.24 (2H, s), 2.86 (1H, septet, J=6.9 Hz), 4.07-4.20 (2H, m), 4.43-4.53 (2H, m), 4.85 (1H, t, J=8.1 Hz), 6.47 (1H, br s), 7.04 (2H, d, J=8.1 Hz), 7.13 (2H, d, J=8.1 Hz).

EXAMPLE 137 tert-Butyl (3-(4-isopropylphenyl)-4,6,7-trimethyl-2,3-dihydro-1-benzofuran-5-yl)carbamate Using 3-(4-isopropylphenyl)-4,6,7-trimethyl-2,3-dihydro-1-benzofuran-5-amine obtained in Reference Example 30, the title compound was synthesized in the same manner as in Reference Example 59. Yield: 53%. Melting point: 121-122° C. (ethyl acetate-hexane).

$^1$H-NMR (CDCl$_3$) δ: 1.22 (6H, d, J=6.9 Hz), 1.20-1.50 (9H, m), 1.87 (3H, s), 2.17 (6H, s), 2.86 (1H, septet, J=6.9 Hz), 4.40 (1H, dd, J=4.5, 8.7 Hz), 4.47-4.51 (1H, m), 4.80 (1H, t, J=8.7 Hz), 5.71 (1H, br s), 7.03 (2H, d, J=8.1 Hz), 7.11 (2H, d, J=8.1 Hz).

EXAMPLE 138

2,2,2-Trichloroethyl (3-(4-isopropylphenyl)-4,6,7-trimethyl-2,3-dihydro-1-benzofuran-5-yl)carbamate To a solution of 3-(4-isopropylphenyl)-4,6,7-trimethyl-2,3-dihydro-1-benzofuran-5-amine (1.48 g, 5 mmol) obtained in Reference Example 30 and triethylamine (0.22 mL, 1.61 mmol) in THF (15 mL) was added 2,2,2-trichloroethyl chloroformate (0.76 mL, 5.5 mmol) at 0° C. and the reaction mixture was stirred at room temperature for 1 hour. The reaction solution was diluted with water and extracted with ethyl acetate. The organic layer was washed with 1 N hydrochloric acid and an aqueous saturated sodium hydrogen carbonate solution, dried over sodium sulfate, and concentrated under reduced pressure. The obtained residue was purified by silica gel column chromatography (hexane:ethyl acetate=3:1) to obtain 2.19 g (yield: 93%) of the title compound. Melting point: 137-140° C. (ethyl acetate-hexane).

$^1$H-NMR (CDCl$_3$) δ: 1.21 (6H, d, J=6.9 Hz), 1.88 (3H, s), 2.10 (6H, s), 2.86 (1H, septet, J=6.9 Hz), 4.38-4.45 (1H, m), 4.50-4.56 (1H, m), 4.75-4.86 (3H, m), 6.15 (1H, s), 7.03 (2H, d, J=8.0 Hz), 7.11 (2H, d, J=8.0 Hz).

EXAMPLE 139

2,2,2-Trichloroethyl (7-ethyl-3-(4-isopropylphenyl)-4,6-dimethyl-2,3-dihydro-1-benzofuran-5-yl)carbamate Using 7-ethyl-3-(4-isopropylphenyl)-4,6-dimethyl-2,3-dihydro-1-benzofuran-5-amine obtained in Reference Example 328, the title compound was synthesized in the same manner as in Example 138. Yield: 82%. Oily matter.

$^1$H-NMR (CDCl$_3$) δ: 1.15 (3H, t, J=7.5 Hz), 1.22 (6H, d, J=6.9 Hz), 1.88 (3H, s), 2.22 (3H, s), 2.66 (2H, q, J=7.5 Hz), 2.86 (1H, septet, J=6.9 Hz), 4.42 (1H, dd, J=5.1, 8.7 Hz), 4.53 (1H, dd, J=4.8, 9.3 Hz), 4.75-4.90 (3H, m), 6.15 (1H, br s), 7.04 (2H, d, J=8.1 Hz), 7.13 (2H, d, J=8.1 Hz).

EXAMPLE 140

2,2,2-Trichloroethyl (3-(4-isopropylphenyl)-7-methoxy-4,6-dimethyl-2,3-dihydro-1-benzofuran-5-yl)carbamate Using 3-(4-isopropylphenyl)-7-methoxy-4,6-dimethyl-2,3-dihydro-1-benzofuran-5-amine obtained in Reference Example 327, the title compound was synthesized in the same manner as in Example 138. Yield: 68%. Oily matter.

$^1$H-NMR (CDCl$_3$) δ: 1.22 (6H, d, J=6.9 Hz), 1.86 (3H, s), 2.19 (3H, s), 2.86 (1H, septet, J=6.9 Hz), 3.90 (3H, s), 4.45-4.58 (2H, m), 4.77-4.92 (3H, m), 6.15 (1H, br s), 7.04 (2H, d, J=8.1 Hz), 7.14 (2H, d, J=8.1 Hz).

EXAMPLE 141

2,2,2-Trichloroethyl (7-(3-hydroxypropyl)-3-(4-isopropylphenyl)-4,6-dimethyl-2,3-dihydro-1-benzofuran-5-yl)carbamate Using 3-(5-amino-3-(4-isopropylphenyl)-4,6-dimethyl-2,3-dihydro-1-benzofuran-7-yl)propan-1-ol obtained in Reference Example 322, the title compound was synthesized in the same manner as in Example 138. Yield: 51%. Oily matter.

$^1$H-NMR (CDCl$_3$) δ: 1.22 (6H, d, J=6.9 Hz), 1.85-2.05 (5H, m), 2.21 (3H, s), 2.70-2.92 (3H, m), 4.27 (2H, t, J=6.6 Hz), 4.40 (1H, dd, J=5.1, 8.7 Hz), 4.52 (1H, dd, J=5.1, 9.1 Hz), 4.77-4.92 (3H, m), 6.15 (1H, br s), 7.02 (2H, d, J=8.1 Hz), 7.12 (2H, d, J=8.1 Hz), 1H unidentified.

EXAMPLE 142

2,2,2-Trichloroethyl (3-(4-isopropylphenyl)-4,6-dimethyl-7-phenyl-2,3-dihydro-1-benzofuran-5-yl)carbamate Using 3-(4-isopropylphenyl)-4,6-dimethyl-7-phenyl-2,3-dihydro-1-benzofuran-5-amine obtained in Reference Example 329, the title compound was synthesized in the same manner as in Example 138. Yield: 89%. Amorphous powder.

$^1$H-NMR (CDCl$_3$) δ: 1.22 (6H, d, J=6.9 Hz), 1.95 (3H, s), 2.10 (3H, s), 2.87 (1H, septet, J=6.9 Hz), 4.38 (1H, dd, J=5.1, 8.7 Hz), 4.56 (1H, dd, J=4.8, 9.3 Hz), 4.75-4.90 (3H, m), 6.20 (1H, br s), 7.08 (2H, d, J=8.1 Hz), 7.14 (2H, d, J=8.1 Hz), 7.24-7.50 (5H, m).

EXAMPLE 143

N-(3-(4-Isopropylphenyl)-4,6,7-trimethyl-2,3-dihydro-1-benzofuran-5-yl)pyrrolidin-1-carboxamide To a solution of 2,2,2-trichloroethyl (3-(4-isopropylphenyl)-4,6,7-trimethyl-2,3-dihydro-1-benzofuran-5-yl)carbamate (353 mg, 0.75 mmol) obtained in Example 138 and pyrrolidine (0.076 mL, 0.9 mmol) in dimethylsulfoxide (5 mL) was added diisopropylethylamine (0.13 mL, 0.75 mmol) at room temperature, and the resulting mixture was heated at 50° C. and reacted for 16 hours. The reaction solution was cooled to room temperature and poured into water, and the product was extracted with ethyl acetate. The organic layer was washed with an aqueous saturated sodium hydrogen carbonate solution, dried over sodium sulfate, and concentrated under reduced pressure. The obtained residue was purified by silica gel column chromatography (hexane:ethyl acetate=1:1) to obtain 130 mg (yield: 44%) of the title compound. Melting point: 186-188° C. (ethyl acetate-hexane).

$^1$H-NMR (CDCl$_3$) δ: 1.21 (6H, d, J=6.9 Hz), 1.87 (3H, s), 1.92-2.00 (4H, m), 2.17 (3H, s), 2.17 (3H, s), 2.85 (1H, septet, J=6.9 Hz), 3.43 (4H, br), 4.38-4.43 (1H, m), 4.48-4.53 (1H, m), 4.78-4.84 (1H, m), 5.43 (1H, s), 7.04 (2H, d, J=8.2 Hz), 7.10 (2H, d, J=8.2 Hz).

EXAMPLE 144

N,N-Diethyl-N'-(3-(4-isopropylphenyl)-4,6,7-trimethyl-2,3-dihydro-1-benzofuran-5-yl)urea Using 2,2,2-trichloroethyl (3-(4-isopropylphenyl)-4,6,7-trimethyl-2,3-dihydro-1-benzofuran-5-yl)carbamate obtained in Example 138 and diethylamine, the title compound was obtained in the same manner as in Example 143. Yield: 68%. Melting point: 79-81° C. (ethyl acetate-hexane).

$^1$H-NMR (CDCl$_3$) δ: 1.18-1.23 (12H, m), 1.86 (3H, s), 2.15 (3H, s), 2.17 (3H, s), 2.85 (1H, septet, J=7.0 Hz), 3.31-3.40 (4H, m), 4.38-4.43 (1H, m), 4.48-4.54 (1H, m), 4.80 (1H, t, J=8.8 Hz), 5.54 (1H, s), 7.04 (2H, d, J=8.1 Hz), 7.10 (2H, d, J=8.1 Hz).

EXAMPLE 145

N-(2-Hydroxyethyl)-N'-(3-(4-isopropylphenyl)-4,6,7-trimethyl-2,3-dihydro-1-benzofuran-5-yl)urea Using 2,2,2-trichloroethyl (3-(4-isopropylphenyl)-4,6,7-trimethyl-2,3-dihydro-1-benzofuran-5-yl)carbamate obtained in Example 138 and 2-hydroxyethylamine, the title compound was obtained in the same manner as in Example 143.

Yield: 89%. Melting point: 186-188° C. (ethyl acetate-hexane).

$^1$H-NMR (CDCl$_3$) δ: 1.22 (6H, d, J=6.9 Hz), 1.89 (3H, s), 2.19 (3H, s), 2.20 (3H, s), 2.85 (1H, septet, J=6.9 Hz), 3.23 (1H, br), 3.32 (2H, br), 3.64 (2H, br), 4.43-4.48 (1H, m), 4.50-4.56 (1H, m), 4.65 (1H, br), 4.85 (1H, t, J=8.8 Hz), 5.64 (1H, br), 7.03 (2H, d, J=8.1 Hz), 7.14 (2H, d, J=8.1 Hz).

EXAMPLE 146

N-(3-(4-Isopropylphenyl)-4,6,7-trimethyl-2,3-dihydro-1-benzofuran-5-yl)-N'-(2-methoxyethyl)urea Using 2,2,2-trichloroethyl (3-(4-isopropylphenyl)-4,6,7-trimethyl-2,3-dihydro-1-benzofuran-5-yl)carbamate obtained in Example 138 and 2-methoxyethylamine, the title compound was synthesized in the same manner as in Example 143. Yield: 58%. Melting point: 172-173° C. (hexane-ethyl acetate).

$^1$H-NMR (CDCl$_3$) δ: 1.22 (6H, d, J=6.9 Hz), 1.88 (3H, s), 2.18 (6H, s), 2.86 (1H, septet, J=6.9 Hz), 3.05-3.44 (7H, m), 4.40-4.63 (3H, m), 4.85 (1H, t, J=9.0 Hz), 5.53 (1H, br s), 7.03 (2H, d, J=8.1 Hz), 7.13 (2H, d, J=8.1 Hz).

EXAMPLE 147

N-(2-(Dimethylamino)ethyl)-N'-(3-(4-isopropylphenyl)-4,6,7-trimethyl-2,3-dihydro-1-benzofuran-5-yl)urea Using 2,2,2-trichloroethyl (3-(4-isopropylphenyl)-4,6,7-trimethyl-2,3-dihydro-1-benzofuran-5-yl)carbamate obtained in Example 138 and 2-(dimethylamino)ethylamine, the title compound was synthesized in the same manner as in Example 143. Yield: 54%. Melting point: 133-134° C. (hexane-ethyl acetate).

$^1$H-NMR (CDCl$_3$) δ: 1.22 (6H, d, J=6.9 Hz), 1.89 (3H, s), 2.10 (6H, br s), 2.19 (6H, s), 2.28 (2H, br s), 2.87 (1H, septet, J=6.9 Hz), 3.10-3.35 (2H, m), 4.44 (1H, dd, J=8.7, 4.8 Hz), 4.53 (1H, dd, J=9.0, 4.5 Hz), 4.69 (1H, br s), 4.85 (1H, t, J=9.0 Hz), 5.70 (1H, br s), 7.03 (2H, d, J=8.1 Hz), 7.13 (2H, d, J=8.1 Hz).

EXAMPLE 148

N-(7-Ethyl-3-(4-isopropylphenyl)-4,6-dimethyl-2,3-dihydro-1-benzofuran-5-yl)-N'-(2-hydroxyethyl)urea Using 2,2,2-trichloroethyl (7-ethyl-3-(4-isopropylphenyl)-4,6-dimethyl-2,3-dihydro-1-benzofuran-5-yl)carbamate obtained in Example 139 and 2-aminoethanol, the title compound was synthesized in the same manner as in Example 143. Yield: 57%. Melting point: 147-148° C. (hexane-ethyl acetate).

$^1$H-NMR (CDCl$_3$) δ: 1.15 (3H, t, J=7.5 Hz), 1.22 (6H, d, J=6.9 Hz), 1.89 (3H, s), 2.23 (3H, s), 2.25-2.75 (2H, m), 2.87 (1H, septet, J=6.9 Hz), 3.17-3.40 (3H, m), 3.44-3.70 (2H, m), 4.40-4.58 (2H, m), 4.68 (1H, br s), 4.85 (1H, t, J=8.4 Hz), 5.71 (1H, br s), 7.03 (2H, d, J=7.8 Hz), 7.14 (2H, d, J=7.8 Hz).

EXAMPLE 149

N-(2-Hydroxyethyl)-N'-(3-(4-isopropylphenyl)-7-methoxy-4,6-dimethyl-2,3-dihydro-1-benzofuran-5-yl)urea Using 2,2,2-trichloroethyl (3-(4-isopropylphenyl)-7-methoxy-4,6-dimethyl-2,3-dihydro-1-benzofuran-5-yl)carbamate obtained in Example 140 and 2-aminoethanol, the title compound was synthesized in the same manner as in Example 143. Yield: 59%. Melting point: 127-129° C. (hexane-ethyl acetate).

$^1$H-NMR (CDCl$_3$) δ: 1.22 (6H, d, J=6.9 Hz), 1.86 (3H, s), 2.19 (3H, s), 2.87 (1H, septet, J=6.9 Hz), 3.17-3.40 (3H, m), 3.44-3.72 (2H, m), 3.91 (3H, s), 4.40-4.90 (4H, m), 5.83 (1H, br s), 7.03 (2H, d, J=7.8 Hz), 7.14 (2H, d, J=7.8 Hz).

EXAMPLE 150

N-(2-Hydroxyethyl)-N'-(7-(3-hydroxypropyl)-3-(4-isopropylphenyl)-4,6-dimethyl-2,3-dihydro-1-benzofuran-5-yl)urea Using 2,2,2-trichloroethyl (7-(3-hydroxypropyl)-3-(4-isopropylphenyl)-4,6-dimethyl-2,3-dihydro-1-benzofuran-5-yl)carbamate obtained in Example 141 and 2-aminoethanol, the title compound was synthesized in the same manner as in Example 143. Yield: 53%. Melting point: 153-154° C. (hexane-ethyl acetate).

$^1$H-NMR (CDCl$_3$) δ: 1.22 (6H, d, J=6.9 Hz), 1.69-1.94 (5H, m), 2.07-2.40 (4H, m), 2.72-2.90 (3H, m), 3.00-3.40 (3H, m), 3.42-3.75 (4H, m), 4.41-4.70 (3H, m), 4.85 (1H, t, J=8.4 Hz), 5.63 (1H, br s), 7.00 (2H, d, J=7.8 Hz), 7.13 (2H, d, J=7.8 Hz).

EXAMPLE 151

N-(3-(4-Isopropylphenyl)-4,6,7-trimethyl-2,3-dihydro-1-benzofuran-5-yl)-N'-propylurea Using 2,2,2-trichloroethyl (3-(4-isopropylphenyl)-4,6,7-trimethyl-2,3-dihydro-1-benzofuran-5-yl)carbamate obtained in Example 138 and 1-propylamine, the title compound was synthesized in the same manner as in Example 143. Yield: 53%. Melting point: 177-178° C. (hexane-ethyl acetate).

$^1$H-NMR (CDCl$_3$) δ: 0.81 (3H, br s), 1.22 (6H, d, J=6.9 Hz), 1.41 (2H, br s), 1.87 (3H, s), 2.19 (6H, s), 2.86 (1H, septet, J=6.9 Hz), 3.14 (2H, br s), 4.18 (1H, br s), 4.45 (1H, dd, J=8.4, 4.8 Hz), 4.53 (1H, dd, J=9.3, 4.8 Hz), 4.85 (1H, t, J=9.0 Hz), 5.51 (1H, br s), 7.01 (2H, d, J=8.1 Hz), 7.12 (2H, d, J=7.8 Hz).

EXAMPLE 152

N-(2-Hydroxyethyl)-N'-(3-(4-isopropylphenyl)-4,6-dimethyl-7-phenyl-2,3-dihydro-1-benzofuran-5-yl)urea Using 2,2,2-trichloroethyl (3-(4-isopropylphenyl)-4,6-dimethyl-7-phenyl-2,3-dihydro-1-benzofuran-5-yl)carbamate obtained in Example 142 and 2-aminoethanol, the title compound was synthesized in the same manner as in Example 143. Yield: 59%. Melting point: 152-155° C. (hexane-ethyl acetate).

$^1$H-NMR (CDCl$_3$) δ: 1.22 (6H, d, J=6.9 Hz), 1.71 (2H, br s), 1.88 (3H, s), 2.19 (6H, s), 2.87 (1H, septet, J=6.9 Hz), 3.15-3.40 (3H, m), 3.42-3.67 (2H, m), 4.35-4.58 (3H, m), 4.85 (1H, t, J=8.7 Hz), 5.64 (1H, br s), 7.04 (2H, br s), 7.14 (2H, d, J=7.8 Hz).

EXAMPLE 153

N-(3-Hydroxypropyl)-N'-(3-(4-isopropylphenyl)-4,6-dimethyl-7-phenyl-2,3-dihydro-1-benzofuran-5-yl)urea Using 2,2,2-trichloroethyl (3-(4-isopropylphenyl)-4,6-dimethyl-7-phenyl-2,3-dihydro-1-benzofuran-5-yl)carbamate obtained in Example 142 and 3-amino-1-propanol, the title compound was synthesized in the same manner as in Example 143. Yield: 65%. Melting point: 145-146° C. (hexane-ethyl acetate).

$^1$H-NMR (CDCl$_3$) δ: 1.22 (6H, d, J=6.9 Hz), 1.40-1.60 (4H, m), 1.88 (3H, br s), 2.19 (6H, s), 2.87 (1H, septet, J=6.9 Hz), 3.00-3.70 (5H, m), 4.36 (1H, br s), 4.45 (1H, dd, J=8.4, 4.8 Hz), 4.52 (1H, dd, J=8.7, 4.8 Hz), 4.85 (1H, t, J=9.0 Hz), 5.50 (1H, br s), 7.02 (2H, d, J=8.1 Hz), 7.13 (2H, d, J=8.1 Hz).

EXAMPLE 154

N-(3-Hydroxypropyl)-N'-(3-(4-isopropylphenyl)-4,6,7-trimethyl-2,3-dihydro-1-benzofuran-5-yl)urea Using 2,2,2-trichloroethyl (3-(4-isopropylphenyl)-4,6,7-trimethyl-2,3-dihydro-1-benzofuran-5-yl)carbamate obtained in Example 138 and 3-amino-1-propanol, the title compound was synthesized in the same manner as in Example 143. Yield: 33%. Melting point: 185-186° C. (hexane-ethyl acetate).

$^1$H-NMR (CDCl$_3$) δ: 1.23 (6H, d, J=6.9 Hz), 1.97 (3H, s), 2.12 (3H, s), 2.88 (1H, septet, J=6.9 Hz), 3.24-3.78 (5H, m), 4.43 (1H, dd, J=9.0, 4.8 Hz), 4.57 (1H, dd, J=9.1, 4.5 Hz), 4.72-4.90 (2H, m), 5.66 (1H, br s), 7.09 (2H, d, J=8.1 Hz), 7.16 (2H, d, J=8.1 Hz), 7.28-7.50 (5H, m).

EXAMPLE 155

N-(4-Hydroxybutyl)-N'-(3-(4-isopropylphenyl)-4,6,7-trimethyl-2,3-dihydro-1-benzofuran-5-yl)urea Using 2,2,2-trichloroethyl 3-(4-isopropylphenyl)-4,6,7-trimethyl-2,3-dihydro-1-benzofuran-5-yl)carbamate obtained in Example 138 and 4-amino-1-butanol, the title compound was synthesized in the same manner as in Example 143. Yield: 28%. Melting point: 145-146° C. (ethanol-ethyl acetate).

$^1$H-NMR (CDCl$_3$) δ: 1.22 (6H, d, J=6.9 Hz), 1.40-1.60 (4H, m), 1.88 (3H, s), 2.19 (6H, s), 2.87 (1H, septet, J=6.9 Hz), 3.00-3.30 (2H, m), 3.40-3.71 (2H, m), 4.36 (1H, br s), 4.45 (1H, dd, J=8.4, 4.8 Hz), 4.52 (1H, dd, J=8.7, 4.8 Hz), 4.85 (1H, t, J=9.0 Hz), 5.50 (1H, br s), 7.02 (2H, d, J=7.8 Hz), 7.13 (2H, d, J=7.8 Hz), 1H unidentified.

EXAMPLE 156

N-(2-Hydroxy-1,1-dimethylethyl)-N'-(3-(4-isopropylphenyl)-4,6,7-trimethyl-2,3-dihydro-1-benzofuran-5-yl)urea Using 2,2,2-trichloroethyl (3-(4-isopropylphenyl)-4,6,7-trimethyl-2,3-dihydro-1-benzofuran-5-yl)carbamate obtained in Example 138 and 2-amino-2-methyl-1-propanol, the title compound was synthesized in the same manner as in Example 143. Yield: 39%. Melting point: 157-158° C. (hexane-ethyl acetate).

$^1$H-NMR (CDCl$_3$) δ: 1.00-1.30 (12H, m), 1.86 (3H, s), 2.18 (3H, s), 2.20 (3H, s), 2.86 (1H, septet, J=6.9 Hz), 3.42-3.60 (2H, m), 4.07-4.30 (1H, m), 4.45 (1H, dd, J=8.7, 4.8 Hz), 4.54 (1H, dd, J=9.0, 5.1 Hz), 4.87 (1H, t, J=9.0 Hz), 5.38-5.62 (2H, m), 6.94-7.05 (2H, m), 7.12 (2H, d, J=8.1 Hz)

EXAMPLE 157

N-(2-Hydroxy-1,1-dimethylethyl)-N'-(3-(4-isopropylphenyl)-4,6-dimethyl-7-phenyl-2,3-dihydro-1-benzofuran-5-yl)urea Using 2,2,2-trichloroethyl (3-(4-isopropylphenyl)-4,6-dimethyl-7-phenyl-2,3-dihydro-1-benzofuran-5-yl)carbamate obtained in Example 142 and 2-amino-2-methyl-1-propanol, the title compound was synthesized in the same manner as in Example 143. Yield: 49%. Melting point: 181-182° C. (hexane-ethyl acetate).

$^1$H-NMR (CDCl$_3$) δ: 1.00-1.37 (12H, m), 1.95 (3H, s), 2.11 (3H, s), 2.88 (1H, septet, J=6.9 Hz), 3.42-3.60 (2H, m), 4.10-4.47 (2H, m), 4.59 (1H, dd, J=9.3, 4.8 Hz), 4.85 (1H, t, J=9.0 Hz), 5.34 (1H, br s), 5.61 (1H, br s), 7.06 (2H, d, J=8.1 Hz), 7.16 (2H, d, J=8.1 Hz), 7.26-7.50 (5H, m).

EXAMPLE 158

N-(3-Hydroxy-2,2-dimethylpropyl)-N'-(3-(4-isopropylphenyl)-4,6,7-trimethyl-2,3-dihydro-1-benzofuran-5-yl)urea Using 2,2,2-trichloroethyl (3-(4-isopropylphenyl)-4,6,7-trimethyl-2,3-dihydro-1-benzofuran-5-yl)carbamate obtained in Example 138 and 3-amino-2,2-methyl-1-propanol, the title compound was synthesized in the same manner as in Example 143. Yield: 61%. Melting point: 117-118° C. (ethanol-hexane).

$^1$H-NMR (CDCl$_3$) δ: 0.48-0.80 (6H, m), 1.19 (6H, d, J=6.9 Hz), 1.89 (3H, s), 2.20 (6H, s), 2.57-3.35 (5H, m), 4.22-4.67 (4H, m), 4.88 (1H, t, J=9.0 Hz), 5.64 (1H, d, J=20.7 Hz), 7.02 (2H, d, J=6.6 Hz), 7.10-7.18 (2H, m).

EXAMPLE 159

N-(3-Hydroxy-2,2-dimethylpropyl)-N'-(3-(4-isopropylphenyl)-4,6-dimethyl-7-phenyl-2,3-dihydro-1-benzofuran-5-yl)urea Using 2,2,2-trichloroethyl (3-(4-isopropylphenyl)-4,6-dimethyl-7-phenyl-2,3-dihydro-1-benzofuran-5-yl)carbamate obtained in Example 142 and 3-amino-2,2-methyl-1-propanol, the title compound was synthesized in the same manner as in Example 143. Yield: 77%. Amorphous powder.

$^1$H-NMR (CDCl$_3$) δ: 0.48-0.85 (6H, m), 1.22 (6H, d, J=6.9 Hz), 1.97 (3H, s), 2.11 (3H, s), 2.57-3.35 (5H, m), 4.22-4.67 (4H, m), 4.84 (1H, t, J=9.0 Hz), 5.72 (1H, d, J=21.6 Hz), 7.07 (2H, d, J=8.1 Hz), 7.14 (2H, d, J=8.1 Hz), 7.27-7.45 (5H, m).

EXAMPLE 160

N-(2-Hydroxypropyl)-N'-(3-(4-isopropylphenyl)-4,6-dimethyl-7-phenyl-2,3-dihydro-1-benzofuran-5-yl)urea Using 2,2,2-trichloroethyl (3-(4-isopropylphenyl)-4,6-dimethyl-7-phenyl-2,3-dihydro-1-benzofuran-5-yl)carbamate obtained in Example 142 and 1-amino-2-propanol, the title compound was synthesized in the same manner as in Example 143. Yield: 58%. Melting point: 171-182° C. (ethanol-hexane).

$^1$H-NMR (CDCl$_3$) δ: 1.12 (3H, br s), 1.23 (6H, d, J=6.9 Hz), 1.97 (3H, s), 2.12 (3H, s), 2.60-3.50 (4H, m), 3.83 (1H, br s), 4.42 (1H, dd, J=9.0, 4.5 Hz), 4.56 (1H, dd, J=9.3, 4.8

Hz), 4.74 (1H, br s), 4.83 (1H, t, J=9.0 Hz), 5.65 (1H, br s), 7.07 (2H, d, J=6.6 Hz), 7.15 (2H, d, J=6.6 Hz), 7.27-7.48 (5H, m).

EXAMPLE 161

N-(3-(4-Isopropylphenyl)-4,6-dimethyl-2,3-dihydro-1-benzothien-5-yl)-3,3-dimethylbutanamide Using 3-(4-isopropylphenyl)-4,6-dimethyl-2,3-dihydro-1-benzothiophene-5-amine obtained in Reference Example 291, the title compound was synthesized in the same manner as in Example 1. Yield: 81%. Melting point: 151-152° C. (hexane-ethyl acetate).
$^1$H-NMR (CDCl$_3$) δ: 1.11 (9H, s), 1.21 (6H, d, J=6.9 Hz), 1.90 (3H, s), 2.21 (3H, s), 2.24 (2H, s), 2.85 (1H, septet, J=6.9 Hz), 3.14 (1H, dd, J=11.4, 1.8 Hz), 3.92 (1H, dd, J=11.4, 8.4 Hz), 4.64 (1H, d, J=7.8 Hz), 6.51 (1H, br s), 7.02 (2H, d, J=8.1 Hz), 7.03 (1H, s), 7.09 (2H, d, J=8.1 Hz).

EXAMPLE 162

N-(7-Bromo-3-(4-isopropylphenyl)-4,6-dimethyl-2,3-dihydro-1-benzothien-5-yl)-3,3-dimethylbutanamide Using N-(3-(4-isopropylphenyl)-4,6-dimethyl-2,3-dihydro-1-benzothien-5-yl)-3,3-dimethylbutanamide obtained in Example 161, the title compound was synthesized in the same manner as in Reference Example 259. Yield: 55%. Melting point: 207-208° C. (hexane-ethyl acetate).
$^1$H-NMR (CDCl$_3$) δ: 1.11 (9H, s), 1.21 (6H, d, J=6.9 Hz), 1.86 (3H, s), 2.24 (2H, s), 2.32 (3H, s), 2.85 (1H, septet, J=6.9 Hz), 3.13 (1H, dd, J=11.1, 2.1 Hz), 3.92 (1H, dd, J=11.1, 8.7 Hz), 4.83 (1H, d, J=8.1 Hz), 6.61 (1H, br s), 7.03 (2H, d, J=8.1 Hz), 7.10 (2H, d, J=8.1 Hz).

EXAMPLE 163

N-(7-Formyl-3-(4-isopropylphenyl)-4,6-dimethyl-2,3-dihydro-1-benzothien-5-yl)-3,3-dimethylbutanamide Using N-(3-(4-isopropylphenyl)-4,6-dimethyl-2,3-dihydro-1-benzothien-5-yl)-3,3-dimethylbutanamide obtained in Example 161, the title compound was synthesized in the same manner as in Example 20. Yield: 65%. Melting point: 134-140° C. (hexane-ethyl acetate).
$^1$H-NMR (CDCl$_3$) δ: 1.13 (9H, s), 1.20 (6H, d, J=6.9 Hz), 1.99 (3H, s), 2.29 (2H, s), 2.55 (3H, s), 2.84 (1H, septet, J=6.9 Hz), 3.16 (1H, dd, J=11.4, 1.8 Hz), 3.83 (1H, dd, J=11.4, 9.0 Hz), 4.64 (1H, d, J=9.0 Hz), 6.64 (1H, br s), 7.00 (2H, d, J=8.1 Hz), 7.09 (2H, d, J=8.1 Hz), 10.5 (1H, s).

EXAMPLE 164

N-(7-Ethyl-3-(4-isopropylphenyl)-4,6-dimethyl-2,3-dihydro-1-benzothien-5-yl)-3,3-dimethylbutanamide To methylmagnesium bromide (1.0 M, THF solution, 10 mL, 10 mmol) was added at 0° C. N-(7-formyl-3-(4-isopropylphenyl)-4,6-dimethyl-2,3-dihydro-1-benzothien-5-yl)-3,3-dimethylbutanamide (600 mg, 1.42 mmol) obtained in Example 163 and the reaction solution was stirred at room temperature for 1 hour. The reaction solution was added to water and the product was extracted with ethyl acetate. The organic layer was washed with 1 N hydrochloric acid and saturated brine, dried over anhydrous sodium sulfate, and concentrated under reduced pressure. To a mixture of the obtained residue in trifluoroacetic acid (3 mL) was added with ice-cooling triethylsilane (1.0 mL) and the resulting mixture was stirred at room temperature for 30 minutes. After the reaction solution was concentrated under reduced pressure, to the residue was added an aqueous saturated sodium hydrogen carbonate solution and the aqueous layer was made alkaline, and the mixture was extracted with ethyl acetate. The organic layer was washed with water and saturated brine, dried over anhydrous sodium sulfate, and concentrated under reduced pressure. The obtained residue was purified by silica gel column chromatography (ethyl acetate:hexane=1:4) to obtain 345 mg (yield: 57%) of the title compound. Melting point: 172-173° C. (hexane-ethyl acetate).
$^1$H-NMR (CDCl$_3$) δ: 1.12 (9H, s), 1.18 (3H, t, J=7.8 Hz), 1.21 (6H, d, J=6.9 Hz), 1.89 (3H, s), 2.20 (3H, s), 2.26 (2H, s), 2.66 (2H, q, J=7.8 Hz), 2.85 (1H, septet, J=6.9 Hz), 3.12 (1H, dd, J=11.4, 1.8 Hz), 3.87 (1H, dd, J=11.4, 8.7 Hz), 4.69 (1H, d, J=8.7 Hz), 6.51 (1H, br s), 7.03 (2H, d, J=8.1 Hz), 7.10 (2H, d, J=8.1 Hz).

EXAMPLE 165

N-(3-(4-Isopropylphenyl)-4,6-dimethyl-7-propyl-2,3-dihydro-1-benzothien-5-yl)-3,3-dimethylbutanamide Using N-(7-formyl-3-(4-isopropylphenyl)-4,6-dimethyl-2,3-dihydro-1-benzothien-5-yl)-3,3-dimethylbutanamide obtained in Example 163 and ethylmagnesium bromide, the title compound was synthesized in the same manner as in Example 164. Yield: 22%. Melting point: 159-160° C. (hexane-ethyl acetate).
$^1$H-NMR (CDCl$_3$) δ: 1.02 (3H, t, J=7.5 Hz), 1.12 (9H, s), 1.21 (6H, d, J=6.9 Hz), 1.50-1.70 (2H, m), 1.89 (3H, s), 2.18 (3H, s), 2.26 (2H, s), 2.61 (2H, t, J=6.9 Hz), 2.85 (1H, septet, J=6.9 Hz), 3.11 (1H, d, J=14.4 Hz), 3.86 (1H, dd, J=14.4, 8.4 Hz), 4.69 (1H, dd, J=8.4 Hz), 6.53 (1H, br s), 7.03 (2H, d, J=8.1 Hz), 7.10 (2H, d, J=8.1 Hz).

EXAMPLE 166

N-(7-Acetyl-3-(4-isopropylphenyl)-4,6-dimethyl-2,3-dihydro-1-benzothien-5-yl)-3,3-dimethylbutanamide Using N-(3-(4-isopropylphenyl)-4,6-dimethyl-2,3-dihydro-1-benzothien-5-yl)-3,3-dimethylbutanamide obtained in Example 161, the title compound was synthesized in the same manner as in Example 38. Yield: 69%. Melting point: 218-219° C. (hexane-ethyl acetate).
$^1$H-NMR (CDCl$_3$) δ: 1.12 (9H, s), 1.21 (6H, d, J=6.9 Hz), 1.94 (3H, s), 2.20 (3H, s), 2.27 (2H, s), 2.57 (3H, s), 2.85 (1H, septet, J=6.9 Hz), 3.15 (1H, dd, J=11.1, 1.8 Hz), 3.87 (1H, dd, J=11.1, 8.4 Hz), 4.66 (1H, d, J=8.4 Hz), 6.63 (1H, br s), 7.04 (2H, d, J=8.1 Hz), 7.11 (2H, d, J=8.1 Hz).

EXAMPLE 167

N-(7-Ethyl-3-(4-isopropylphenyl)-4,6-dimethyl-1-oxido-2,3-dihydro-1-benzothien-5-yl)-3,3-dimethylbutanamide To a mixture of N-(7-ethyl-3-(4-isopropylphenyl)-4,6-dimethyl-2,3-dihydro-1-benzothien-5-yl)-3,3-dimethylbutanamide (225 mg, 0.512 mmol) obtained in Example 164 and sodium hydrogen carbonate (65 mg, 1.01 mmol) in dichloromethane (10 mL) was added m-chloroperbenzoic acid (124 mg, 0.716 mmol) at 0° C. and the resulting mixture was stirred at room temperature for two hours. To reaction solution was added an aqueous sodium hydrogensulfite solution, the organic layer separated, and the aqueous layer was extracted with dichloromethane. The combined organic layers were washed with water and saturated brine, dried over anhydrous sodium sulfate, and concentrated under reduced pressure. The obtained residue was purified by silica gel column chromatography (hexane:ethyl acetate=3:1) to obtain 50 mg (yield: 22%) of the title compound. Melting point: 195-196° C. (diethyl ether-hexane).

$^1$H-NMR (CDCl$_3$) δ: 1.12 (9H, s), 1.18 (3H, t, J=7.8 Hz), 1.21 (6H, d, J=6.9 Hz), 1.72 (3H, s), 2.18 (3H, s), 2.26 (1H, d, J=13.2 Hz), 2.32 (1H, d, J=13.2 Hz), 2.87-2.98 (2H, m), 3.04-3.17 (1H, m), 3.26 (1H, dd, J=14.4, 7.2 Hz), 3.55 (1H, dd, J=13.8, 7.2 Hz), 5.10 (1H, d, J=6.6 Hz), 6.90 (2H, d, J=8.1 Hz), 7.12 (2H, d, J=8.1 Hz), 7.82 (1H, br s).

EXAMPLE 168

N-(7-Acetyl-3-(4-isopropylphenyl)-4,6-dimethyl-1-oxido-2,3-dihydro-1-benzothien-5-yl)-3,3-dimethylbutanamide To a mixture of N-(7-acetyl-3-(4-isopropylphenyl)-4,6-dimethyl-2,3-dihydro-1-benzothien-5-yl)-3,3-dimethylbutanamide (960 mg, 2.19 mmol) obtained in Example 166 and sodium hydrogen carbonate (276 mg, 3.29 mmol) in dichloromethane (20 mL) was added m-chloroperbenzoic acid (530 mg, 3.07 mmol) at 0° C. and the resulting mixture was stirred at room temperature for two hours. To reaction solution was added an aqueous sodium hydrogensulfite solution, the organic layer separated, and the aqueous layer was extracted with dichloromethane. The combined organic layers were washed with water and saturated brine, dried over anhydrous sodium sulfate, and concentrated under reduced pressure. The obtained residue was purified by silica gel column chromatography (ethyl acetate) to obtain 123 mg (yield: 12%) of the title compound as a low polarity isomer. Melting point: 214-216° C. (hexane-ethyl acetate).

$^1$H-NMR (CDCl$_3$) δ: 1.12 (9H, s), 1.20 (6H, d, J=6.9 Hz), 1.98 (3H, s), 2.20 (3H, s), 2.29 (2H, s), 2.71 (3H, s), 2.85 (1H, septet, J=6.9 Hz), 3.15 (1H, dd, J=14.4, 2.1 Hz), 3.70 (1H, dd, J=14.4, 8.7 Hz), 4.72 (1H, d, J=8.7. Hz), 6.81 (1H, br s), 7.12 (2H, d, J=8.1 Hz), 7.21 (2H, d, J=8.1 Hz).

EXAMPLE 169

N-(7-Acetyl-3-(4-isopropylphenyl)-4,6-dimethyl-1-oxido-2,3-dihydro-1-benzothien-5-yl)-3,3-dimethylbutanamide The residue treated in the same manner as described in the Example 168 was purified by silica gel column chromatography (ethyl acetate) to obtain 274 mg (yield: 28%) of the title compound as a high polarity isomer. Melting point: 214-215° C. (hexane-ethyl acetate).

$^1$H-NMR (CDCl$_3$) δ: 1.12 (9H, s), 1.22 (6H, d, J=6.9 Hz), 1.84 (3H, s), 2.20 (3H, s), 2.30 (2H, s), 2.65 (3H, s), 2.86 (1H, septet, J=6.9 Hz), 3.30-3.40 (1H, m), 3.56 (1H, dd, J=13.2, 7.5 Hz), 5.07 (1H, d, J=6.3 Hz), 6.90 (2H, d, J=8.1 Hz), 7.13 (2H, d, J=8.1 Hz), 7.56 (1H, br s).

EXAMPLE 170

N-(7-Bromo-3-(4-isopropylphenyl)-4,6-dimethyl-1,1-dioxido-2,3-dihydro-1-benzothien-5-yl)-3,3-dimethylbutanamide To a mixture of N-(3-(4-isopropylphenyl)-4,6-dimethyl-2,3-dihydro-1-benzothien-5-yl)-3,3-dimethylbutanamide (560 mg, 1.41 mmol) obtained in Example 161 and iron powder (5.2 mg, 0.094 mmol) in dichloromethane (10 mL) was added bromine (225 mg, 1.41 mmol) at 0° C. and the resulting mixture was stirred at the same temperature for 1 hour. Water was poured into the reaction mixture and the product was extracted with ethyl acetate. The extracts were washed with an aqueous sodium hydrogen carbonate solution and water, dried over magnesium sulfate, filtered, and concentrated under reduced pressure. To a mixture of the obtained residue and sodium hydrogen carbonate (150 mg, 1.79 mmol) in dichloromethane (5 mL) was added m-chloroperbenzoic acid (161 mg, 1.01 mmol) at 0° C. and the resulting mixture was stirred at room temperature for 1 hour. To the reaction solution was added an aqueous sodium hydrogensulfite solution, the organic layer was separated, and the aqueous layer was extracted with dichloromethane. The combined organic layers were washed with water and saturated brine, dried over anhydrous sodium sulfate, and concentrated under reduced pressure. The obtained residue was purified by silica gel column chromatography (hexane ethyl acetate=3:1) to obtain 393 mg (yield: 55%) of the title compound. Melting point: 211-213° C. (hexane-ethyl acetate).

$^1$H-NMR (CDCl$_3$) δ: 1.10 (9H, s), 1.20 (6H, d, J=6.9 Hz), 1.86 (3H, s), 2.28 (2H, s), 2.36 (3H, s), 2.85 (1H, septet, J=6.9 Hz), 3.47 (1H, dd, J=13.8, 2.4 Hz), 3.95 (1H, dd, J=13.8, 9.6 Hz), 4.65 (1H, d, J=9.6 Hz), 7.00 (2H, d, J=8.1 Hz), 7.07 (1H, br s), 7.12 (2H, d, J=8.1 Hz).

EXAMPLE 171

N-(7-Acetyl-3-(4-isopropylphenyl)-4,6-dimethyl-1,1-dioxido-2,3-dihydro-1-benzothien-5-yl)-3,3-dimethylbutanamide To a mixture of the diastereo mixture of N-(7-acetyl-3-(4-isopropylphenyl)-4,6-dimethyl-1-oxide-2,3-dihydro-1-benzothien-5-yl)-3,3-dimethylbutanamide (540 mg, 1.19 mmol) obtained in Examples 168 and 169, and sodium hydrogen carbonate (150 mg, 1.79 mmol) in dichloromethane (5 mL) was added m-chloroperbenzoic acid (287 mg, 1.67 mmol) at 0° C. and the resulting mixture was stirred at room temperature for 2 hours. To the reaction solution was added an aqueous sodium hydrogensulfite solution, the organic layer was separated, and the aqueous layer was extracted with dichloromethane. The combined organic layers were washed with water and saturated brine, dried over anhydrous sodium sulfate, and concentrated under reduced pressure. The obtained residue was purified by silica gel column chromatography (hexane:ethyl acetate=4:1) to obtain 320 mg (yield: 57%) of the title compound. Melting point: 184-186° C. (hexane-ethyl acetate).

$^1$H-NMR (CDCl$_3$) δ: 1.12 (9H, s), 1.21 (6H, d, J=6.9 Hz), 1.92 (3H, s), 2.07 (3H, s), 2.32 (2H, s), 2.68 (3H, s), 2.86 (1H, septet, J=6.9 Hz), 3.42 (1H, dd, J=14.4, 2.4 Hz), 3.86 (1H, dd, J=14.4, 9.3 Hz), 4.71 (1H, dd, J=9.3, 2.4 Hz), 7.00-7.21 (5H, m).

EXAMPLE 172

N-(7-Ethyl-3-(4-isopropylphenyl)-4,6-dimethyl-1,1-dioxido-2,3-dihydro-1-benzothien-5-yl)-3,3-dimethylbutanamide To a mixture of N-(7-ethyl-3-(4-isopropylphenyl)-4,6-dimethyl-2,3-dihydro-1-benzothien-5-yl)-3,3-dimethylbutanamide (225 mg, 0.512 mmol) obtained in Example 164 and sodium hydrogen carbonate (250 mg, 0.590 mmol) in dichloromethane (20 mL) was added m-chloroperbenzoic acid (283 mg, 1.65 mmol) at 0° C. and the resulting mixture was stirred at room temperature for 2 hours. To the reaction solution was added an aqueous sodium hydrogensulfite solution, the organic layer was separated, and the aqueous layer was extracted with dichloromethane. The combined organic layers were washed with water and saturated brine, dried over anhydrous sodium sulfate, and concentrated under reduced pressure. The obtained residue was purified by silica gel column chromatography (hexane:ethyl acetate=4:1) to obtain 74 mg (yield: 28%) of the title compound. Amorphous powder.

$^1$H-NMR (CDCl$_3$) δ: 1.11 (9H, s), 1.20 (6H, d, J=6.9 Hz), 1.29 (3H, t, J=7.2 Hz), 1.86 (3H, s), 2.25 (3H, s), 2.27 (2H, s), 2.84 (1H, septet, J=6.9 Hz), 3.07 (2H, q, J=7.8 Hz), 3.12 (1H, d, J=13.5 Hz), 3.87 (1H, dd, J=13.5, 9.6 Hz), 4.66 (1H, d, J=8.7 Hz), 6.86 (1H, br s), 7.01 (2H, d, J=8.1 Hz), 7.12 (2H, d, J=8.1 Hz).

EXAMPLE 173

N-(3-(3-Formylphenyl)-4,6,7-trimethyl-2,3-dihydro-1-benzofuran-5-yl)-3,3-dimethylbutanamide A mixed solution of N-(3-(3-(1,3-dioxolan-2-yl)phenyl)-4,6,7-trimethyl-2,3-dihydro-1-benzofuran-5-yl)-3,3-dimethylbutanamide (910 mg, 2.15 mmol) obtained in Example 73 and pyridinium p-toluenesulfonic acid (25 mg) in acetone (20 mL)-water (1.5 mL) was refluxed with heating for 30 minutes. The reaction solution was diluted with ethyl acetate, washed with an aqueous saturated sodium hydrogen carbonate solution, dried over anhydrous sodium sulfate, filtered, and then concentrated under reduced pressure to obtain 784 mg (yield: 96%) of the title compound. Melting point: 178-179° C. (ethyl acetate-hexane).

$^1$H-NMR (CDCl$_3$) δ: 1.11 (9H, s), 1.83 (3H, s), 2.16 (3H, s), 2.21 (3H, s), 2.25 (2H, s), 4.41 (1H, dd, J=4.5, 9.0 Hz), 4.64 (1H, dd, J=4.5, 9.0 Hz), 4.87 (1H, t, J=9.0 Hz), 6.52 (1H, br s), 7.39-7.48 (2H, m), 7.66 (1H, s), 7.72-7.76 (1H, m), 9.97 (1H, s).

EXAMPLE 174

N-(3-(4-Formylphenyl)-4,6,7-trimethyl-2,3-dihydro-1-benzofuran-5-yl)-3,3-dimethylbutanamide Using N-(3-(4-(1,3-dioxolan-2-yl)phenyl)-4,6,7-trimethyl-2,3-dihydro-1-benzofuran-5-yl)-3,3-dimethylbutanamide obtained in Example 82, the title compound was synthesized in the same manner as in Example 173. Yield: 95%. Melting point: 195-196° C. (ethyl acetate-hexane).

$^1$H-NMR (CDCl$_3$) δ: 1.12 (9H, s), 1.83 (3H, s), 2.16 (3H, s), 2.19 (3H, s), 2.25 (2H, s), 6.51 (1H, br s), 7.31 (2H, d, J=8.4 Hz), 7.80 (2H, d, J=8.4 Hz), 9.97 (1H, s).

EXAMPLE 175

N-(3-(4-(1-Hydroxyethyl)phenyl)-4,6,7-trimethyl-2,3-dihydro-1-benzofuran-5-yl)-3,3-dimethylbutanamide Using N-(3-(4-formylphenyl)-4,6,7-trimethyl-2,3-dihydro-1-benzofuran-5-yl)-3,3-dimethylbutanamide obtained in Example 174 and methylmagnesium bromide, the title compound was synthesized in the same manner as Example 22.

Yield: 93%. Melting point: 144-145° C. (ethyl acetate-hexane).

$^1$H-NMR (CDCl$_3$) δ: 1.12 (9H, s), 1.47 (3H, d, J=6.3 Hz), 1.78 (1H, br s), 1.83 (3H, s), 2.15 (3H, s), 2.17 (3H, s), 2.24 (2H, s), 4.39 (1H, dd, J=4.5, 9.0 Hz), 4.54 (1H, dd, J=4.5, 9.0 Hz), 4.79-4.90 (2H, m), 6.50 (1H, br s), 7.10 (2H, d, J=8.1 Hz), 7.27 (2H, d, J=8.1 Hz).

EXAMPLE 176

N-(3-(4-Acetylphenyl)-4,6,7-trimethyl-2,3-dihydro-1-benzofuran-5-yl)-3,3-dimethylbutanamide Using N-(3-(4-(1-hydroxyethyl)phenyl)-4,6,7-trimethyl-2,3-dihydro-1-benzofuran-5-yl)-3,3-dimethylbutanamide obtained in Example 175, the title compound was synthesized in the same manner as in Example 32. Yield: 65%. Melting point: 181-182° C. (THF-diisopropyl ether).

$^1$H-NMR (CDCl$_3$) δ: 1.12 (9H, s), 1.82 (3H, s), 2.16 (3H, s), 2.19 (3H, s), 2.25 (2H, s), 2.57 (3H, s), 4.40 (1H, dd, J=4.5, 9.0 Hz), 4.61 (1H, dd, J=4.5, 9.0 Hz), 4.86 (1H, t, J=9.0 Hz), 6.51 (1H, br s), 7.23 (2H, d, J=8.4 Hz), 7.87 (2H, d, J=8.4 Hz).

EXAMPLE 177

Ethyl (2E)-3-(3-(5-((3,3-dimethylbutanoyl)amino)-4,6,7-trimethyl-2,3-dihydro-1-benzofuran-3-yl)phenyl)acrylate To a solution of sodium hydride (a 60% dispersion in liquid paraffin, 79 mg, 1.98 mmol) in DMF (10 mL) was added dropwise at 0° C. under an argon atmosphere ethyl diethylphosphonoacetate (444 mg, 1.98 mmol) and the mixture was stirred for 30 minutes. To the reaction solution was added dropwise at 0° C. a solution of N-(3-(3-formylphenyl)-4,6,7-trimethyl-2,3-dihydro-1-benzofuran-5-yl)-3,3-dimethylbutanamide (684 mg, 1.80 mmol) obtained in Example 173 in DMF (5 mL) and the mixture was stirred for 30 minutes. The reaction solution was warmed to room temperature, was added to water and the product was extracted with ethyl acetate-THF. The organic layer was washed with water and saturated brine, dried over anhydrous sodium sulfate, filtered, and then concentrated under reduced pressure to obtain 750 mg (yield: 93%) of the title compound. Melting point: 199-200° C. (ethyl acetate-hexane).

$^1$H-NMR (CDCl$_3$) δ: 1.12 (9H, s), 1.33 (3H, t, J=7.5 Hz), 1.83 (3H, s), 2.16 (3H, s), 2.19 (3H, s), 2.25 (2H, s), 4.27 (2H, q, J=7.5 Hz), 4.39 (1H, dd, J=4.5, 9.0 Hz), 4.54 (1H, dd, J=4.5, 9.0 Hz), 4.84 (1H, t, J=9.0 Hz), 6.38 (1H, d, J=15.3

Hz), 6.50 (1H, br s), 7.14 (1H, d, J=7.5 Hz), 7.24-7.31 (2H, m), 7.37 (1H, d, J=7.5 Hz), 7.61 (1H, d, J=15.3 Hz).

EXAMPLE 178

Ethyl (2E)-3-(4-(5-((3,3-dimethylbutanoyl)amino)-4, 6,7-trimethyl-2,3-dihydro-1-benzofuran-3-yl)phenyl) acrylate Using N-(3-(4-formylphenyl)-4,6,7-trimethyl-2,3-dihydro-1-benzofuran-5-yl)-3,3-dimethylbutanamide obtained in Example 174, the title compound was synthesized in the same manner as in Example 177. Yield: 81%. Melting point: 176-177° C. (ethyl acetate).

$^1$H-NMR (CDCl$_3$) δ: 1.12 (9H, s), 1.33 (3H, t, J=6.9 Hz), 1.84 (3H, s), 2.15 (3H, s), 2.18 (3H, s), 2.25 (2H, s), 4.26 (2H, q, J=6.9 Hz), 4.40 (1H, dd, J=4.5, 9.0 Hz), 4.57 (1H, dd, J=4.5, 9.0 Hz), 4.84 (1H, t, J=9.0 Hz), 6.38 (1H, d, J=13.8 Hz), 6.51 (1H, br s), 7.15 (2H, d, J=8.1 Hz), 7.43 (2H, d, J=8.1 Hz), 7.64 (1H, d, J=13.8 Hz).

EXAMPLE 179

Ethyl (2E)-3-(4-(5-((3,3-dimethylbutanoyl)amino)-4, 6,7-trimethyl-2,3-dihydro-1-benzofuran-3-yl)phenyl) but-2-enoate Using N-(3-(4-acetylphenyl)-4,6,7-trimethyl-2,3-dihydro-1-benzofuran-5-yl)-3,3-dimethylbutanamide obtained in Example 176, the title compound was obtained in the same manner as in Example 177. Yield: 75%. Melting point: 179-180° C. (ethyl acetate-hexane).

$^1$H-NMR (CDCl$_3$) δ: 1.12 (9H, s), 1.31 (3H, t, J=7.2 Hz), 1.84 (3H, s), 2.15 (3H, s), 2.18 (3H, s), 2.25 (2H, s), 2.54 (3H, s), 4.20 (2H, q, J=7.2 Hz), 4.40 (1H, dd, J=4.5, 9.0 Hz), 4.56 (1H, dd, J=4.5, 9.0 Hz), 4.84 (1H, t, J=9.0 Hz), 6.09 (1H, s), 6.49 (1H, s), 7.12 (2H, d, J=8.4 Hz), 7.37 (2H, d, J=8.4 Hz).

EXAMPLE 180

Ethyl 3-(3-(5-((3,3-dimethylbutanoyl)amino)-4,6,7-trimethyl-2,3-dihydro-1-benzofuran-3-yl)phenyl) propanoate A mixed solution of ethyl (2E)-3-(3-(5-((3,3-dimethylbutanoyl)amino)-4,6,7-trimethyl-2,3-dihydro-1-benzofuran-3-yl)phenyl)acrylate (400 mg, 0.89 mmol) obtained in Example 177 and 10% palladium on carbon (water content: 50%, 40 mg) in ethanol (3 mL)-ethyl acetate (5 mL) was stirred at room temperature for 2 hours under a hydrogen atmosphere. The reaction solution was filtered through celite and the filtrate was concentrated under reduced pressure to obtain 326 mg (yield: 81%) of the title compound. Melting point: 136-138° C. (ethyl acetate-hexane).

$^1$H-NMR (CDCl$_3$) δ: 1.12 (9H, s), 1.22 (3H, t, J=7.2 Hz), 1.82 (3H, s), 2.15 (3H, s), 2.18 (3H, s), 2.25 (2H, s), 2.57 (2H, t, J=7.8 Hz), 2.89 (2H, t, J=7.8 Hz), 4.27 (2H, q, J=7.5 Hz), 4.39 (1H, dd, J=4.5, 9.0 Hz), 4.54 (1H, dd, J=4.5, 9.0 Hz), 4.84 (1H, t, J=9.0 Hz), 6.50 (1H, br s), 7.14 (1H, d, J=7.5 Hz), 7.24-7.31 (1H, t, J=7.5 Hz), 7.37 (1H, d, J=7.5 Hz), 7.61 (1H, d, J=15.3 Hz).

EXAMPLE 181

Ethyl 3-(4-(5-((3,3-dimethylbutanoyl)amino)-4,6,7-trimethyl-2,3-dihydro-1-benzofuran-3-yl)phenyl) propanoate Using ethyl (2E)-3-(4-(5-((3,3-dimethylbutanoyl)amino)-4,6,7-trimethyl-2,3-dihydro-1-benzofuran-3-yl)phenyl) acrylate obtained in Example 178, the title compound was synthesized in the same manner as in Example 180. Yield: 84%. Melting point: 103-105° C. (ethyl acetate-hexane).

$^1$H-NMR (CDCl$_3$) δ: 1.12 (9H, s), 1.22 (3H, t, J=6.9 Hz), 1.82 (3H, s), 2.14 (3H, s), 2.17 (3H, s), 2.25 (2H, s), 2.58 (2H, t, J=7.8 Hz), 2.90 (2H, t, J=7.8 Hz), 4.11 (2H, q, J=6.9 Hz), 4.38 (1H, dd, J=4.8, 9.0 Hz), 4.51 (1H, dd, J=4.8, 9.0 Hz), 4.81 (1H, t, J=9.0 Hz), 6.49 (1H, br s), 7.03 (2H, d, J=8.1 Hz), 7.09 (2H, d, J=8.1 Hz).

EXAMPLE 182

Ethyl 3-(4-(5-((3,3-dimethylbutanoyl)amino)-4,6,7-trimethyl-2,3-dihydro-1-benzofuran-3-yl)phenyl) butanoate Using ethyl (2E)-3-(4-(5-((3,3-dimethylbutanoyl)amino)-4,6,7-trimethyl-2,3-dihydro-1-benzofuran-3-yl)phenyl)but-2-enoate obtained in Example 179, the title compound was synthesized in the same manner as in Example 180. Yield: 76%. Melting point: 100-101° C. (ethyl acetate-hexane).

$^1$H-NMR (CDCl$_3$) δ: 1.12 (9H, s), 1.17 (3H, t, J=7.2 Hz), 1.26 (3H, d, J=6.6 Hz), 1.83 (3H, s), 2.15 (3H, s), 2.17 (3H, s), 2.25 (2H, s), 2.44-2.60 (2H, m), 3.18-3.30 (1H, m), 4.11 (2H, q, J=7.2 Hz), 4.39 (1H, dd, J=4.8, 9.0 Hz), 4.52 (1H, dd, J=4.8, 9.0 Hz), 4.81 (1H, t, J=9.0 Hz), 6.49 (1H, br s), 7.05 (2H, d, J=8.4 Hz), 7.11 (2H, d, J=8.4 Hz).

EXAMPLE 183

N-(3-(4-Acetyl-3-methoxyphenyl)-4,6,7-trimethyl-2, 3-dihydro-1-benzofuran-5-yl)-3,3-dimethylbutanamide To a solution of N-(3-(3-methoxyphenyl)-4,6,7-trimethyl-2,3-dihydro-1-benzofuran-5-yl)-3,3-dimethylbutanamide (1.0 g, 2.62 mmol) obtained in Example 72 in dichloromethane (20 mL) was added at −50° C. under an argon atmosphere aluminum chloride (769 mg, 5.77 mmol) and the resulting mixture was stirred for 10 minutes. To the reaction solution was added dropwise at the same temperature acetyl chloride (0.62 mL, 8.65 mmol and the resulting mixture was warmed to room temperature. The reaction solution was added to water and the product was extracted with ethyl acetate. The combined organic layers were washed with an aqueous saturated sodium hydrogen carbonate solution, dried over anhydrous sodium sulfate, and concentrated under reduced pressure to obtain 993 mg (yield: 89%) of the title compound. Melting point: 131-133° C. (ethyl acetate-hexane).

$^1$H-NMR (CDCl$_3$) δ: 1.12 (9H, s), 1.84 (3H, s), 2.15 (3H, s), 2.17 (3H, s), 2.26 (2H, s), 2.58 (3H, s), 3.84 (3H, s), 4.39 (1H, dd, J=4.8, 9.0 Hz), 4.58 (1H, dd, J=4.8, 9.0 Hz), 4.85 (1H, t, J=9.0 Hz), 6.54 (1H, br s), 6.72 (1H, s), 6.76 (1H, d, J=8.1 Hz), 7.65 (1H, d, J=8.1 Hz).

EXAMPLE 184

N-(3-(4-Isopropenyl-3-methoxyphenyl)-4,6,7-trimethyl-2,3-dihydro-1-benzofuran-5-yl)-3,3-dimethylbutanamide To a solution of potassium tert-butoxide (818 mg, 7.29 mmol) in toluene (45 mL) was added methyl triphenylphosphonium iodide (2.94 g, 7.29 mmol) and the resulting mixture was stirred at 120° C. for 1 hour under an argon atmosphere. To the reaction solution was added N-(3-(4-acetyl-3-methoxyphenyl)-4,6,7-trimethyl-2,3-dihydro-1-benzofuran-5-yl)-3,3-dimethylbutanamide (2.32 g, 5.48 mmol) obtained in Example 183 and the resulting mixture was stirred at 120° C. for 2 hours. Water was added to the reaction solution, the organic layer was separated, and the aqueous layer was extracted with ethyl acetate. The combined organic layers were dried over anhydrous sodium sulfate and concentrated under reduced pressure. The obtained residue was purified by silica gel column chromatography (ethyl acetate:hexane=2:3) to obtain 1.93 g (yield: 84%) of the title compound. Melting point: 186-187° C. (ethyl acetate-hexane).
$^1$H-NMR (CDCl$_3$) δ: 1.12 (9H, s), 1.87 (3H, s), 2.08 (3H, s), 2.15 (3H, s), 2.17 (3H, s), 2.26 (2H, s), 3.76 (3H, s), 4.42 (1H, dd, J=4.8, 9.0 Hz), 4.54 (1H, dd, J=4.8, 9.0 Hz), 4.83 (1H, t, J=9.0 Hz), 5.03 (1H, s), 5.11 (1H, s), 6.51 (1H, br s), 6.64-6.67 (2H, m), 7.60 (1H, d, J=7.5 Hz).

EXAMPLE 185

N-(3-(4-Isopropyl-3-methoxyphenyl)-4,6,7-trimethyl-2,3-dihydro-1-benzofuran-5-yl)-3,3-dimethylbutanamide A mixed solution of N-(3-(4-isopropenyl-3-methoxyphenyl)-4,6,7-trimethyl-2,3-dihydro-1-benzofuran-5-yl)-3,3-dimethylbutanamide (1.93 g, 4.58 mmol) obtained in Example 184 and 10% palladium on carbon (water content: 50%, 193 mg) in ethanol (10 mL) was stirred at room temperature for 2 hours under a hydrogen atmosphere. The catalyst was filtered and the filtrate was concentrated to give 1.80 g (yield: 93%) of the title compound. Melting point: 170-171° C. (ethyl acetate-hexane).
$^1$H-NMR (CDCl$_3$) δ: 1.12 (9H, s), 1.17 (6H, d, J=6.9 Hz), 1.86 (3H, s), 2.04 (3H, s), 2.14 (3H, s), 2.25 (2H, s), 3.24 (1H, septet, J=6.9 Hz), 3.75 (3H, s), 4.42 (1H, dd, J=5.1, 9.0 Hz), 4.52 (1H, dd, J=5.1, 9.0 Hz), 4.85 (1H, t, J=9.0 Hz), 6.50 (1H, br s), 6.61 (1H, s), 6.66 (1H, d, J=8.1 Hz) 7.60 (1H, d, J=8.1 Hz)

EXAMPLE 186

N-(3-(3-Hydroxy-4-isopropylphenyl)-4,6,7-trimethyl-2,3-dihydro-1-benzofuran-5-yl)-3,3-dimethylbutanamide To a solution of N-(3-(4-isopropyl-3-methoxyphenyl)-4,6,7-trimethyl-2,3-dihydro-1-benzofuran-5-yl)-3,3-dimethylbutanamide (500 mg, 1.18 mmol) obtained in Example 185 in dichloromethane (5 mL) was added dropwise at −70° C. under an argon atmosphere boron tribromide (1.0 M, dichloromethane solution, 2.36 mL, 2.36 mmol) and the resulting mixture was gradually warmed to room temperature.
Water was added to the reaction solution and the product was extracted with ethyl acetate. The combined organic layers were washed with an aqueous saturated sodium hydrogen carbonate solution, dried over anhydrous sodium sulfate, and concentrated under reduced pressure to obtain 465 mg (yield: 96%) of the title compound. Melting point: 220-221° C. (ethyl acetate-hexane).
$^1$H-NMR (CDCl$_3$) δ: 1.10 (9H, s), 1.17 (6H, d, J=6.9 Hz), 1.81 (3H, s), 2.09 (3H, s), 2.12 (3H, s), 2.24 (2H, s), 3.15 (1H, septet, J=6.9 Hz), 4.30-4.45 (2H, m), 4.74 (1H, t, J=9.0 Hz), 6.42 (1H, br s), 6.61 (1H, d, J=8.1 Hz), 6.87 (1H, br s), 7.03 (1H, d, J=8.1 Hz), 1H unidentified.

EXAMPLE 187

N-(2-Hydroxy-4-isopropylphenyl)-4,6,7-trimethyl-2,3-dihydro-1-benzofuran-5-yl)-3,3-dimethylbutanamide Using N-(4-isopropyl-2-methoxyphenyl)-4,6,7-trimethyl-2,3-dihydro-1-benzofuran-5-yl)-3,3-dimethylbutanamide obtained in Example 74, the title compound was synthesized in the same manner as in Example 186. Yield: 98%. Melting point: 265-266° C. (ethyl acetate-hexane).
$^1$H-NMR (CDCl$_3$) δ: 1.13 (9H, s), 1.18 (6H, d, J=6.9 Hz), 1.90 (3H, s), 2.15 (3H, s), 2.16 (3H, s), 2.27 (2H, s), 2.78 (1H, septet, J=6.9 Hz), 4.42 (1H, dd, J=9.9, 13.8 Hz), 4.75-4.85 (2H, m), 5.26 (1H, br), 6.53 (1H, br s), 6.62 (1H, s), 6.64 (1H, d, J=8.1 Hz), 6.76 (1H, d, J=8.1 Hz).

EXAMPLE 188

Ethyl (5-(5-((3,3-dimethylbutanoyl)amino)-4,6,7-trimethyl-2,3-dihydro-1-benzofuran-3-yl)-2-isopropylphenoxy)acetate A mixed solution of N-(3-(3-hydroxy-4-isopropylphenyl)-4,6,7-trimethyl-2,3-dihydro-1-benzofuran-5-yl)-3,3-dimethylbutanamide (500 mg, 1.22 mmol) obtained in Example 186, ethyl bromoacetate (245 mg, 1.47 mmol), potassium carbonate (253 mg, 1.83 mmol) and potassium iodide (10 mg) in acetone (10 mL) was heated for 16 hours under an argon atmosphere. Water was added to the reaction solution and the product was extracted with ethyl acetate.
The organic layer was washed with an aqueous saturated sodium hydrogen carbonate solution, dried over anhydrous sodium sulfate, and concentrated under reduced pressure to obtain 548 mg (yield: 91%) of the title compound. Melting point: 149-150° C. (ethyl acetate-hexane).
$^1$H-NMR (CDCl$_3$) δ: 1.12 (9H, s), 1.22 (6H, d, J=6.9 Hz), 1.26 (3H, t, J=7.2 Hz), 1.84 (3H, s), 2.14 (3H, s), 2.17 (3H, s), 2.25 (2H, s), 3.34 (1H, septet, J=6.9 Hz), 4.21 (2H, q, J=7.2 Hz), 4.38 (1H, dd, J=4.8, 9.0 Hz), 4.49 (1H, dd, J=4.8, 9.0 Hz), 4.55 (2H, s), 4.80 (1H, t, J=9.0 Hz), 6.47 (1H, s), 6.50 (1H, br s), 6.72 (1H, d, J=7.8 Hz), 7.10 (1H, d, J=7.8 Hz).

EXAMPLE 189

N-((3-(4-Isopropyl)-3-(2-oxopropoxy)phenyl)-4,6,7-trimethyl-2,3-dihydro-1-benzofuran-5-yl)-3,3-dimethylbutanamide Using N-(3-(3-hydroxy-4-isopropylphenyl)-4,6,7-trimethyl-2,3-dihydro-1-benzofuran-5-yl)-3,3-dimethylbutanamide obtained in Example 186 and chloroacetone, the title compound was obtained in the same manner as in Example 188. Yield: 82%. Melting point: 133-135° C. (ethyl acetate-hexane).
$^1$H-NMR (CDCl$_3$) δ: 1.13 (9H, s), 1.22 (6H, d, J=6.9 Hz), 1.85 (3H, s), 2.15 (3H, s), 2.17 (3H, s), 2.26 (2H, s), 2.28 (3H, s), 3.34 (1H, septet, J=6.9 Hz), 4.39 (1H, dd, J=4.5, 9.0 Hz), 4.44 (2H, s), 4.50 (1H, dd, J=4.5, 9.0 Hz), 4.81 (1H, t, J=8.4 Hz), 6.39 (1H, s), 6.52 (1H, s), 6.76 (1H, d, J=7.8 Hz), 7.14 (1H, d, J=7.8 Hz).

EXAMPLE 190

Ethyl(2-(5-((3,3-dimethylbutanoyl)amino)-4,6,7-trimethyl-2,3-dihydro-1-benzofuran-3-yl)-5-isopropylphenoxy)acetate Using N-(2-hydroxy-4-isopropylphenyl)-4,6,7-trimethyl-2,3-dihydro-1-benzofuran-5-yl)-3,3-dimethylbutanamide obtained in Example 187, the title compound was obtained in the same manner as in Example 188. Yield: 90%. Melting point: 183-184° C. (ethyl acetate-hexane).

$^1$H-NMR (CDCl$_3$) δ: 1.14 (9H, s), 1.19 (6H, d, J=6.9 Hz), 1.29 (3H, t, J=7.2 Hz), 1.90 (3H, s), 2.16 (6H, s), 2.27 (2H, s), 2.82 (1H, septet, J=6.9 Hz), 4.26 (2H, q, J=7.2 Hz), 4.38 (1H, dd, J=3.9, 9.0 Hz), 4.68 (2H, s), 4.83 (1H, t, J=9.0 Hz), 4.97 (1H, dd, J=3.9, 9.0 Hz), 6.53 (1H, br s), 6.58 (1H, s), 6.69 (2H, s).

EXAMPLE 191

N-((4-Isopropyl-3-(2-methoxyethoxy)phenyl)-4,6,7-trimethyl-2,3-dihydro-1-benzofuran-5-yl))-3,3-dimethylbutanamide A mixed solution of N-(3-(3-hydroxy-4-isopropylphenyl)-4,6,7-trimethyl-2,3-dihydro-1-benzofuran-5-yl)-3,3-dimethylbutanamide (200 mg, 0.49 mmol) obtained in Example 186, 2-bromoethyl methyl ether (0.069 mL, 0.49 mmol), potassium carbonate (135 mg, 0.98 mmol) and potassium iodide (10 mg) in acetonitrile (5 mL) was heated for 16 hours under an argon atmosphere. Water was added to the reaction solution and the product was extracted with ethyl acetate. The organic layer was washed with an aqueous saturated sodium hydrogen carbonate solution, dried over anhydrous sodium sulfate, and concentrated under reduced pressure. The obtained residue was purified by basic silica gel column chromatography (ethyl acetate hexane=2:3) to obtain 176 mg (yield: 77%) of the title compound. Melting point: 155-156° C. (ethyl acetate-hexane).

$^1$H-NMR (CDCl$_3$) δ: 1.12 (9H, s), 1.18 (6H, d, J=6.9 Hz), 1.85 (3H, s), 2.14 (3H, s), 2.17 (3H, s), 2.25 (2H, s), 3.28 (1H, septet, J=6.9 Hz), 3.44 (3H, s), 3.70-3.77 (2H, m), 4.02-4.06 (2H, m), 4.41 (1H, dd, J=4.8, 8.7 Hz), 4.51 (1H, dd, J=4.8, 8.7 Hz), 4.82 (1H, t, J=8.7 Hz), 6.49 (1H, br s), 6.60 (1H, s), 6.69 (1H, d, J=7.8 Hz), 7.08 (1H, d, J=7.8 Hz).

EXAMPLE 192

N-((4-Isopropyl-2-(2-methoxyethoxy)phenyl)-4,6,7-trimethyl-2,3-dihydro-1-benzofuran-5-yl))-3,3-dimethylbutanamide Using N-(2-hydroxy-4-isopropylphenyl)-4,6,7-trimethyl-2,3-dihydro-1-benzofuran-5-yl)-3,3-dimethylbutanamide obtained in Example 187, the title compound was synthesized in the same manner as in Example 191. Yield: 59%. Melting point: 119-120° C. (ethyl acetate-hexane).

$^1$H-NMR (CDCl$_3$) δ: 1.13 (9H, s), 1.20 (6H, d, J=6.9 Hz), 1.88 (3H, s), 2.15 (6H, s), 2.27 (2H, s), 2.83 (1H, septet, J=6.9 Hz), 3.45 (3H, s), 3.70-3.78 (2H, m), 4.14-4.18 (2H, m), 4.36 (1H, dd, J=4.2, 8.7 Hz), 4.83 (1H, t, J=8.7 Hz), 4.91 (1H, dd, J=4.2, 8.7 Hz), 6.55 (1H, br s), 6.65-6.75 (3H, m).

EXAMPLE 193

N-(3-(3-(2-Hydroxyethoxy)-4-isopropylphenyl)-4,6,7-trimethyl-2,3-dihydro-1-benzofuran-5-yl)-3,3-dimethylbutanamide To a solution of ethyl (5-(5-((3,3-dimethylbutanoyl)amino)-4,6,7-trimethyl-2,3-dihydro-1-benzofuran-3-yl)-2-isopropylphenoxy)acetate (200 mg, 0.49 mmol) obtained in Example 188 in THF (5 mL) was added with ice-cooling lithium borotetrahydride (43 mg, 2.00 mmol). The reaction solution was warmed to room temperature and stirred for 60 hours. The reaction solution was added to ice and water was added to the reaction solution, and the product was extracted with ethyl acetate. The combined organic layers were washed with saturated brine, dried over anhydrous sodium sulfate, and concentrated under reduced pressure to obtain 157 mg (yield: 71%) of the title compound. Melting point: 155-156° C. (ethyl acetate-hexane).

$^1$H-NMR (CDCl$_3$) δ: 1.12 (9H, s), 1.18 (6H, d, J=6.9 Hz), 1.86 (3H, s), 2.15 (3H, s), 2.17 (3H, s), 2.26 (2H, s), 3.25 (1H, septet, J=6.9 Hz), 3.80-3.93 (2H, m), 4.00-4.04 (2H, m), 4.40 (1H, dd, J=4.8, 9.0 Hz), 4.50-4.58 (1H, m), 4.82 (1H, t, J=9.0 Hz), 6.54 (1H, br s), 6.58 (1H, s), 6.73 (1H, d, J=8.1 Hz), 7.10 (1H, d, J=8.1 Hz), 1H unidentified.

EXAMPLE 194

N-(3-(3-(3-Hydroxypropyl)phenyl)-4,6,7-trimethyl-2,3-dihydro-1-benzofuran-5-yl)-3,3-dimethylbutanamide Using ethyl 3-(3-(5-((3,3-dimethylbutanoyl)amino)-4,6,7-trimethyl-2,3-dihydro-1-benzofuran-3-yl)phenyl)propanoate obtained in Example 180, the title compound was synthesized in the same manner as in Example 193. Yield: 95%. Amorphous powder.

$^1$H-NMR (CDCl$_3$) δ: 1.11 (9H, s), 1.79 (3H, s), 1.79-1.92 (2H, m), 2.15 (3H, s), 2.18 (3H, s), 2.25 (2H, s), 2.57-2.70 (2H, m), 3.53 (2H, br), 4.39 (1H, dd, J=5.1, 9.0 Hz), 4.57 (1H, dd, J=5.1, 9.0 Hz), 4.86 (1H, t, J=9.0 Hz), 6.56 (1H, br s), 6.91 (1H, br s), 6.99-7.05 (2H, m), 7.23 (1H, t, J=7.8 Hz), 1H unidentified.

EXAMPLE 195

N-(3-(4-(3-Hydroxypropyl)phenyl)-4,6,7-trimethyl-2,3-dihydro-1-benzofuran-5-yl)-3,3-dimethylbutanamide Using ethyl 3-(4-(5-((3,3-dimethylbutanoyl)amino)-4,6,7-trimethyl-2,3-dihydro-1-benzofuran-3-yl)phenyl)propanoate obtained in Example 181, the title compound was synthesized in the same manner as in Example 193. Yield: 77%. Melting point: 119-120° C. (ethyl acetate-hexane).

$^1$H-NMR (CDCl$_3$) δ: 1.11 (9H, s), 1.80-1.90 (5H, m), 2.14 (3H, s), 2.17 (3H, s), 2.24 (2H, s), 2.65 (2H, t, J=7.8 Hz), 3.64 (2H, t, J=7.8 Hz), 4.39 (1H, dd, J=4.8, 9.0 Hz), 4.52 (1H, dd, J=4.8, 9.0 Hz), 4.82 (1H, t, J=9.0 Hz), 6.56 (1H, br s), 7.04 (2H, d, J=8.1 Hz), 7.10 (2H, d, J=8.1 Hz), 1H unidentified.

EXAMPLE 196

N-(3-(4-(3-Hydroxy-1-methylpropyl)phenyl)-4,6,7-trimethyl-2,3-dihydro-1-benzofuran-5-yl)-3,3-dimethylbutanamide Using ethyl 3-(4-(5-((3,3-dimethylbutanoyl)amino)-4,6,7-trimethyl-2,3-dihydro-1-benzofuran-3-yl)phenyl)butanoate obtained in Example 182, the title compound was synthesized in the same manner as in Example 193. Yield: 85%. Melting point: 145-147° C. (ethyl acetate-hexane).

$^1$H-NMR (CDCl$_3$) δ: 1.12 (9H, s), 1.24 (3H, d, J=7.2 Hz), 1.76-1.90 (2H, m), 1.84 (3H, s), 2.15 (3H, s), 2.18 (3H, s), 2.25 (2H, s), 2.80-2.90 (1H, m), 3.54 (2H, br), 4.41 (1H, dd, J=4.8, 9.0 Hz), 4.52 (1H, dd, J=4.8, 9.0 Hz), 4.82 (1H, t, J=9.0 Hz), 6.49 (1H, br s), 7.05 (2H, d, J=8.1 Hz), 7.10 (2H, d, J=8.1 Hz), 1H unidentified.

EXAMPLE 197

N-((4-Isopropyl-2-(2-hydroxyethoxy)-4-isopropylphenyl)-4,6,7-trimethyl-2,3-dihydro-1-benzofuran-5-yl))-3,3-dimethylbutanamide Using ethyl 2-(5-((3,3-dimethylbutanoyl)amino)-4,6,7-trimethyl-2,3-dihydro-1-benzofuran-3-yl)-5-isopropylphenoxy)acetate obtained in Example 190, the title compound was synthesized in the same manner as in Example 193. Yield: 79%. Amorphous powder.

$^1$H-NMR (CDCl$_3$) δ: 1.12 (9H, s), 1.22 (6H, d, J=6.9 Hz), 1.87 (3H, s), 2.14 (3H, s), 2.18 (3H, s), 2.24 (2H, s), 2.85 (1H, septet, J=6.9 Hz), 3.70-3.78 (2H, m), 3.93-4.00 (2H, m), 4.54 (1H, dd, J=4.5, 8.1 Hz), 4.66 (1H, dd, J=4.5, 8.1 Hz), 4.80 (1H, t, J=8.1 Hz), 6.49 (1H, br s), 6.66 (1H, s), 6.74 (1H, d, J=7.8 Hz), 7.01 (1H, d, J=7.8 Hz), 1H unidentified.

EXAMPLE 198

3-(4-(5-((3,3-Dimethylbutanoyl)amino)-4,6,7-trimethyl-2,3-dihydro-1-benzofuran-3-yl)phenyl)butanoic acid Ethyl 3-(4-(5-((3,3-dimethylbutanoyl)amino)-4,6,7-trimethyl-2,3-dihydro-1-benzofuran-3-yl)phenyl)butanoate (150 mg, 0.32 mmol) obtained in Example 182, 1 N aqueous sodium hydroxide solution (2 mL) and THF (3 mL)-methanol (3 mL) were stirred at room temperature for 16 hours. To the reaction solution was added hydrochloric acid to make the solution acidic, and the aqueous layer was extracted with ethyl acetate. The combined organic layers were washed with saturated brine, dried over anhydrous sodium sulfate, and concentrated under reduced pressure to obtain 107 mg (yield: 74%) of the title compound. Melting point: 209-210° C. (ethyl acetate-hexane).

$^1$H-NMR (CDCl$_3$) δ: 1.11 (9H, s), 1.28 (3H, d, J=6.9 Hz), 1.81 (3H, s), 2.14 (3H, s), 2.17 (3H, s), 2.24 (2H, s), 2.48-2.62 (2H, m), 3.15-3.26 (1H, m), 4.38-4.42 (1H, m), 4.51 (1H, dd, J=4.2, 8.7 Hz), 4.81 (1H, t, J=8.7 Hz), 6.53 (1H, br s), 7.05 (2H, d, J=7.8 Hz), 7.10 (2H, d, J=7.8 Hz), 1H unidentified.

EXAMPLE 199

N-(3-(4-(1-Hydroxy-1-methylethyl)phenyl)-4,6,7-trimethyl-2,3-dihydro-1-benzofuran-5-yl)-3,3-dimethylbutanamide Using N-(3-(4-acetylphenyl)-4,6,7-trimethyl-2,3-dihydro-1-benzofuran-5-yl)-3,3-dimethylbutanamide obtained in Example 176 and methylmagnesium bromide, the title compound was synthesized in the same manner as in Example 22. Yield: 42%. Melting point: 132-134° C. (ethyl acetate-hexane).

$^1$H-NMR (CDCl$_3$) δ: 1.12 (9H, s), 1.55 (6H, s), 1.73 (1H, br s), 1.84 (3H, s), 2.15 (3H, s), 2.18 (3H, s), 2.25 (2H, s), 4.41 (1H, dd, J=4.8, 9.0 Hz), 4.54 (1H, dd, J=4.8, 9.0 Hz), 4.82 (1H, t, J=9.0 Hz), 6.53 (1H, br s), 7.10 (2H, d, J=8.1 Hz), 7.38 (2H, d, J=8.1 Hz).

EXAMPLE 200

4,4,4-Trifluoro-N-(3-(4-isopropylphenyl)-4,6,7-trimethyl-2,3-dihydro-1-benzofuran-5-yl)butanamide A mixed solution of 3-(4-isopropylphenyl)-4,6,7-trimethyl-2,3-dihydro-1-benzofuran-5-amine (200 mg, 0.68 mmol) obtained in Reference Example 30, 4,4,4-trifluorobutanoic acid (116 mg, 0.82 mmol), N-hydroxybenzotriazole (111 mg, 0.82 mmol), (3-(dimethylamino)propyl)ethylcarbodiimide hydrochloride (196 mg, 1.02 mmol), N,N-dimethylaminopyridine (25 mg, 0.2 mmol) in DMF (5 mL) was stirred at room temperature for 14 hours. Water was added to the reaction solution and the product was extracted with ethyl acetate. The organic layer was washed with water and saturated brine, dried over anhydrous sodium sulfate, and concentrated under reduced pressure.

The obtained residue was purified by basic silica gel column chromatography (ethyl acetate:hexane=3:7) to obtain 194 mg (yield: 68%) of the title compound. Melting point: 206-207° C. (THF-diisopropyl ether).

$^1$H-NMR (CDCl$_3$) δ: 1.22 (6H, d, J=6.9 Hz), 1.81 (3H, s), 1.96-2.35 (8H, m), 2.38-2.62 (2H, m), 2.86 (1H, septet, J=6.9 Hz), 4.42 (1H, dd, J=4.8, 9.0 Hz), 4.52 (1H, dd, J=4.8, 9.0 Hz), 4.86 (1H, t, J=9.0 Hz), 6.61 (1H, s), 7.00-7.05 (2H, m), 7.11-7.15 (2H, m).

EXAMPLE 201

N'-(3-(4-Isopropylphenyl)-4,6,7-trimethyl-2,3-dihydro-1-benzofuran-5-yl)-N$^2$,N$^2$-dimethylglycine amide Using 3-(4-isopropylphenyl)-4,6,7-trimethyl-2,3-dihydro-1-benzofuran-5-amine obtained in Reference Example 30 and N,N-dimethylglycine, the title compound was synthesized in the same manner as in Example 200. Yield: 40%. Melting point: 95-96° C. (ethyl acetate-hexane).

$^1$H-NMR (CDCl$_3$) δ: 1.22 (6H, d, J=6.9 Hz), 1.84 (3H, s), 2.13 (3H, s), 2.18 (3H, s), 2.40 (6H, s), 2.86 (1H, septet, J=6.9 Hz), 3.11 (2H, s), 4.42 (1H, dd, J=4.5, 9.0 Hz), 4.53 (1H, dd, J=4.5, 9.0 Hz), 4.83 (1H, t, J=9.0 Hz), 7.05 (2H, d, J=8.1 Hz), 7.12 (2H, d, J=8.1 Hz), 8.45 (1H, br s).

EXAMPLE 202

N-(3-(4-Isopropylphenyl)-4,6,7-trimethyl-2,3-dihydro-1-benzofuran-5-yl)-2,2-dimethylpropanamide Using 3-(4-isopropylphenyl)-4,6,7-trimethyl-2,3-dihydro-1-benzofuran-5-amine obtained in Reference Example 30 and pivaloyl chloride, the title compound was synthesized in the same manner as in Example 1. Yield: 76%. Melting point: 177-178° C. (ethyl acetate-hexane).
$^1$H-NMR (CDCl$_3$) δ: 1.21 (6H, d, J=6.9 Hz), 1.31 (9H, s), 1.80 (3H, s), 2.09 (3H, s), 2.17 (3H, s), 2.85 (1H, septet, J=6.9 Hz), 4.38-4.43 (1H, m), 4.48-4.54 (1H, m), 4.81 (1H, t, J=8.8 Hz), 6.75 (1H, br), 7.03 (2H, d, J=8.1 Hz), 7.10 (2H, d, J=8.1 Hz).

EXAMPLE 203

N-(7-Acetyl-3-(4-isopropylphenyl)-4,6-dimethyl-2,3-dihydro-1-benzofuran-5-yl)formamide Using N-(3-(4-isopropylphenyl)-4,6-dimethyl-2,3-dihydro-1-benzofuran-5-yl)formamide obtained in Example 58 and acetyl chloride, the title compound was obtained in the same manner as in Example 38. Yield: 48%. Melting point: 177-179° C. (ethyl acetate-hexane).
$^1$H-NMR (CDCl$_3$) δ: 1.24 (6H, m), 1.88 and 1.94 (3H), 2.25 and 2.28 (3H), 2.59 and 2.61 (3H), 2.81-2.85 (1H, m), 4.43-4.58 (2H, m), 4.88-4.98 (H, m), 6.63 and 6.66 (1H), 7.01-7.05 (2H, m), 7.13-7.18 (2H, m), 7.92 and 8.39 (1H).

EXAMPLE 204

N-(7-Acetyl-3-(4-isopropylphenyl)-4,6-dimethyl-2,3-dihydro-1-benzofuran-5-yl)-N'-(tert-butyl)urea 7-Acetyl-3-(4-isopropylphenyl)-4,6-dimethyl-2,3-dihydro-1-benzofuran-5-amine (711 mg, 2.2 mmol) obtained in Reference Example 344 was dissolved in N,N-dimethylacetamide (10 mL), to the reaction solution was added tert-butyl isocyanate (0.30 mL, 2.64 mmol) at room temperature, and then the mixture was heated at 60° C. The mixture was heated for 16 hours, to the mixture was further added tert-butyl isocyanate (0.30 mL, 2.64 mmol), and then the resulting mixture was stirred at 60° C. for 24 hours. The reaction solution was cooled to room temperature and poured into water, and the product was extracted with ethyl acetate. The extract was washed with saturated brine, dried over sodium sulfate, and then concentrated under reduced pressure. The obtained residue was purified by silica gel column chromatography (hexane:ethyl acetate=1:1) to obtain 70 mg (yield: 12%) of the title compound. Melting point: 207-208° C. (ethyl acetate-hexane).
$^1$H-NMR (CDCl$_3$) δ: 1.20-1.18 (15H, m), 1.92 (3H, s), 2.29 (3H, s), 2.61 (3H, s), 2.88 (1H, septet, J=7.0 Hz), 3.98 (1H, br), 4.50-4.59 (2H, m), 4.90-4.98 (1H, m), 5.28 (1H, br), 7.00 (2H, d, J=8.2 Hz), 7.15 (2H, d, J=8.2 Hz).

EXAMPLE 205

N-(Cyclohexyl)-N'-(3-(4-isopropylphenyl)-4,6,7-trimethyl-2,3-dihydro-1-benzofuran-5-yl)urea Using 2,2,2,-trichloroethyl (3-(4-isopropylphenyl)-4,6,7-trimethyl-2,3-dihydro-1-benzofuran-5-yl)carbamate obtained in Example 138 and cyclohexylamine, the title compound was obtained in the same manner as in Example 143. Yield: 92%. Melting point: 210-211° C. (ethyl acetate-hexane).
$^1$H-NMR (CDCl$_3$) δ: 0.78-1.17 (3H, m), 1.21 (6H, d, J=6.9 Hz), 1.21-1.38 (2H, m), 1.50-1.67 (3H, m), 1.78-1.88 (4H, m), 2.14-2.20 (7H, m), 2.86 (1H, septet, J=6.9 Hz), 3.61 (1H, br), 3.98 (1H, br), 4.42-4.47 (1H, m), 4.51-4.57 (1H, m), 4.86 (1H, t, J=9.0 Hz), 5.42 (1H, s), 6.99 (2H, d, J=8.2 Hz), 7.12 (2H, d, J=8.2 Hz).

EXAMPLE 206

2,2,2-Trichloroethyl (7-acetyl-3-(4-isopropylphenyl)-4,6-dimethyl-2,3-dihydro-1-benzofuran-5-yl)carbamate Using 7-acetyl-3-(4-isopropylphenyl)-4,6-dimethyl-2,3-dihydro-1-benzofuran-5-amine obtained in Reference Example 344 and 2,2,2-trichloroethyl chloroformate, the title compound was obtained in the same manner as in Example 138.
Yield: 91%. Melting point: 186-189° C. (ethyl acetate-hexane).
$^1$H-NMR (CDCl$_3$) δ: 1.22 (6H, d, J=6.9 Hz), 1.93 (3H, s), 2.28 (3H, s), 2.60 (3H, s), 2.87 (1H, septet, J=6.9 Hz), 4.47-4.59 (2H, m), 4.75-4.96 (3H, m), 6.16 (1H, s), 7.03 (2H, d, J=8.0 Hz), 7.15 (2H, d, J=8.0 Hz).

EXAMPLE 207

N-(7-Acetyl-3-(4-isopropylphenyl)-4,6-dimethyl-2,3-dihydro-1-benzofuran-5-yl)-N'-(3-hydroxypropyl)urea Using 2,2,2-trichloroethyl (7-acetyl-3-(4-isopropylphenyl)-4,6-dimethyl-2,3-dihydro-1-benzofuran-5-yl)carbamate obtained in Example 206 and 3-hydroxypropylamine, the title compound was obtained in the same as manner as in Example 143. Yield: 59%.
$^1$H-NMR (CDCl$_3$) δ: 1.23 (6H, d, J=6.9 Hz), 1.57 (2H, br), 1.93 (3H, s), 2.28 (3H, s), 2.61 (3H, s), 2.85 (1H, septet, J=6.9 Hz), 3.33 (2H, br), 3.58 (2H, br), 4.50-4.59 (3H, m), 4.92 (1H, t, J=10.3 Hz), 5.52 (1H, br), 7.02 (2H, d, J=8.1 Hz), 7.15 (2H, d, J=8.1 Hz).

EXAMPLE 208

N-(tert-Butyl)-N'-(3-(4-isopropylphenyl)-7-(1-hydroxyethyl)-4,6-dimethyl-2,3-dihydro-1-benzofuran-5-yl)urea To a solution of N-(7-acetyl-3-(4-isopropylphenyl)-4,6-dimethyl-2,3-dihydro-1-benzofuran-5-yl)-N'-(tert-butyl)urea (718 mg, 1.7 mmol) obtained in Example 204 in methanol (10 mL) was added sodium borohydride (64.3 mg, 1.7 mmol) at 0° C., and the resulting mixture was stirred for 3 hours. The reaction solution was diluted with water and the product was extracted with ethyl acetate. The extract was washed with saturated brine, dried over sodium sulfate, and then concentrated under reduced pressure. The obtained residue was purified by silica gel column chromatography (hexane:ethyl acetate=1:1) to obtain 115 mg (yield: 16%) of the title compound having high polarity of two isomers. Melting point: 212-214° C. (ethyl acetate-hexane).
$^1$H-NMR (CDCl$_3$) δ: 1.20-1.27 (15H, m), 1.52-1.58 (3H, m), 1.89 (3H, s), 2.23 (3H, s), 2.87 (1H, septet, J=7.0 Hz), 3.57 (1H, br), 4.03 (1H, br), 4.47-4.57 (2H, m), 4.88-4.97 (1H, m), 5.01-5.08 (1H, m), 5.26 (1H, br), 6.98 (2H, d, J=8.2 Hz), 7.13 (2H, d, J=8.2 Hz).

EXAMPLE 209

N-(tert-Butyl)-N'-(3-(4-isopropylphenyl)-7-ethyl-4,6-dimethyl-2,3-dihydro-1-benzofuran-5-yl)urea Using N-(tert-butyl)-N'-(3-(4-isopropylphenyl)-7-(1-hydroxyethyl)-4,6-dimethyl-2,3-dihydro-1-benzofuran-5-yl)urea obtained in Example 208, the title compound was obtained in the same manner as in Example 23. Yield: 53%. Melting point: 207-209° C. (ethyl acetate-hexane).

$^1$H-NMR (CDCl$_3$) δ: 1.12-1.30 (18H, m), 1.87 (3H, s), 2.22 (3H, s), 2.61-2.72 (2H, m), 2.86 (1H, septet, J=6.9 Hz), 4.00 (1H, br), 4.42-4.46 (1H, m), 4.50-4.56 (1H, m), 4.86 (1H, t, J=9.0 Hz), 5.28 (1H, br), 6.98 (2H, d, J=8.1 Hz), 7.11 (2H, d, J=8.1 Hz).

EXAMPLE 210

N-(7-Acetyl-3-(4-isopropylphenyl)-4,6-dimethyl-2,3-dihydro-1-benzofuran-5-yl)-N'-(2-hydroxyethyl)urea Using 2,2,2-trichloroethyl (7-acetyl-3-(4-isopropylphenyl)-4,6-dimethyl-2,3-dihydro-1-benzofuran-5-yl)carbamate obtained in Example 206 and 2-hydroxyethylamine, the title compound was obtained in the same manner as in Example 143. Yield: 66%.

$^1$H-NMR (CDCl$_3$) δ: 1.23 (6H, d, J=6.9 Hz), 1.94 (3H, s), 2.29 (3H, s), 2.60 (3H, s), 2.80-2.97 (2H, m), 3.32 (2H, br), 3.63 (2H, br), 4.49-4.57 (2H, m), 4.63 (1H, br), 4.92 (1H, t, J=10.1 Hz), 5.63 (1H, br), 7.01 (2H, d, J=8.1 Hz), 7.15 (2H, d, J=8.1 Hz).

EXAMPLE 211

N-(3-(4-Isopropylphenyl)-4,6-dimethyl-7-(3-(1-pyrrolidinyl)phenyl)-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and (3-(1-pyrrolidinyl)phenyl)boronic acid, the title compound was obtained in the same manner as in Example 107. Yield: 17%. Melting point: 206-207° C. (ethyl acetate-hexane).

$^1$H-NMR (CDCl$_3$) δ: 1.13 (9H, s), 1.24 (6H, d, J=6.9 Hz), 1.92 (3H, s), 1.95-2.04 (4H, m), 2.10 (3H, s), 2.26 (2H, d, J=1.4 Hz), 2.87 (1H, septet, J=6.9 Hz), 3.23-3.33 (4H, m), 4.36 (1H, dd, J=5.2, 8.7 Hz), 4.57 (1H, dd, J=5.2, 9.2 Hz), 4.79 (1H, dd, J=8.7, 9.2 Hz), 6.48-6.65 (4H, m), 7.11 (2H, d, J=8.7 Hz), 7.15 (2H, d, J=8.7 Hz), 7.27 (1H, t, J=7.7 Hz).

EXAMPLE 212

N-(7-(4-(Dimethylamino)phenyl)-3-(4-isopropylphenyl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and (4-(dimethylamino)phenyl)boronic acid, the title compound was obtained in the same manner as in Example 107. Yield: 17%. Melting point: 180-181° C. (ethyl acetate-hexane).

$^1$H-NMR (CDCl$_3$) δ: 1.13 (9H, s), 1.23 (6H, d, J=7.1 Hz), 1.92 (3H, s), 2.11 (3H, s), 2.27 (2H, d, J=1.4 Hz), 2.87 (1H, septet, J=7.0 Hz), 2.98 (6H, s), 4.38 (1H, dd, J=4.9, 8.5 Hz), 4.55 (1H, dd, J=4.9, 9.4 Hz), 4.79 (1H, dd, J=8.5, 9.4 Hz), 6.50 (1H, s), 6.80 (2H, d, J=7.7 Hz), 7.10 (2H, d, J=8.6 Hz), 7.14 (2H, d, J=8.6 Hz), 7.21 (2H, d, J=7.7 Hz).

EXAMPLE 213

N-(7-(6-(Dimethylamino)pyridin-3-yl)-3-(4-isopropylphenyl)-4,6-dimethyl-2,3-dihydro-1-benzofuran-5-yl)-3,3-dimethylbutanamide Using N-(7-bromo-3-(4-isopropylphenyl)-4,6-dimethyl-2,3-dihydro-1-benzofuran-5-yl)-3,3-dimethylbutanamide obtained in Example 35 and (6-(dimethylamino)pyridin-3-yl)boronic acid, the title compound was obtained in the same manner as in Example 107. Yield: 26%. Melting point: 217-220° C. (ethyl acetate-hexane).

$^1$H-NMR (CDCl$_3$) δ: 1.12 (9H, s), 1.23 (6H, d, J=6.9 Hz), 1.92 (3H, s), 2.12 (3H, s), 2.26 (2H, d, J=1.4 Hz), 2.86 (1H, septet, J=6.9 Hz), 3.12 (6H, s), 4.38 (1H, dd, J=4.9, 8.8 Hz), 4.56 (1H, dd, J=4.9, 9.4 Hz), 4.79 (1H, dd, J=8.8, 9.4 Hz), 6.53 (1H, s), 6.59 (1H, dd, J=0.8, 8.8 Hz), 7.09 (2H, d, J=8.4 Hz), 7.13 (2H, d, J=8.4 Hz), 7.47 (1H, dd, J=2.3, 8.8 Hz), 8.15 (1H, dd, J=0.8, 2.3 Hz).

EXAMPLE 214

N-(7-(4-Isopropylbenzyl)-3,4,6-trimethyl-2,3-dihydro-1-benzofuran-5-yl)-3,3-dimethylbutanamide Using 7-(4-isopropylbenzyl)-3,4,6-trimethyl-2,3-dihydro-1-benzofuran-5-amine obtained in Reference Example 292, the title compound was synthesized in the same manner as in Example 1. Yield: 66%. Melting point: 185-186° C. (ethyl acetate-hexane).

$^1$H-NMR (CDCl$_3$) δ: 1.13 (9H, s), 1.19 (6H, d, J=6.9 Hz), 1.27 (3H, d, J=6.9 Hz), 2.07 (3H, s), 2.27 (2H, s), 2.30 (3H, s), 2.80-2.90 (1H, septet, J=6.9 Hz), 3.40-3.55 (1H, m), 3.93 (2H, m), 4.20 (1H, dd, J=3.3, 8.7 Hz), 4.55 (1H, t, J=8.7 Hz), 6.51 (1H, br s), 7.07 (4H, s).

EXAMPLE 215

N-(3-Ethyl-7-(4-isopropylbenzyl)-4,6-dimethyl-2,3-dihydro-1-benzofuran-5-yl)-3,3-dimethylbutanamide Using 3-ethyl-7-(4-isopropylbenzyl)-4,6-dimethyl-2,3-dihydro-1-benzofuran-5-amine obtained in Reference Example 293, the title compound was synthesized in the same manner as in Example 1. Yield: 53%. Melting point: 156-157° C. (hexane).

$^1$H-NMR (CDCl$_3$) δ: 0.92 (3H, t, J=7.5 Hz), 1.13 (9H, s), 1.20 (6H, d, J=6.9 Hz), 1.50-1.61 (2H, m), 2.07 (3H, s), 2.16 (3H, s), 2.27 (2H, s), 2.83 (1H, septet, J=6.9 Hz), 3.24-3.33 (1H, m), 3.92 (2H, s), 4.37 (1H, dd, J=3.0, 9.0 Hz), 4.48 (1H, t, J=9.0 Hz), 6.50 (1H, br s), 7.06 (4H, s).

EXAMPLE 216

N-(7-(4-Isopropylbenzyl)-4,6-dimethyl-3-propyl-2,3-dihydro-1-benzofuran-5-yl)-3,3-dimethylbutanamide Using 7-(4-isopropylbenzyl)-4,6-dimethyl-3-propyl-2,3-dihydro-1-benzofuran-5-amine obtained in Reference Example 294, the title compound was synthesized in the same manner as in Example 1. Yield: 57%. Melting point: 144-145° C. (ethyl acetate-hexane).

¹H-NMR (CDCl₃) δ: 0.93 (3H, t, J=7.2 Hz), 1.13 (9H, s), 1.19 (6H, d, J=6.9 Hz), 1.30-1.43 (2H, m), 1.50-1.63 (2H, m), 2.06 (3H, s), 2.16 (3H, s), 2.26 (2H, s), 2.83 (1H, septet, J=6.9 Hz), 3.30-3.41 (1H, m), 3.92 (2H, s), 4.35 (1H, dd, J=3.3, 9.0 Hz), 4.46 (1H, t, J=8.7 Hz), 6.48 (1H, br s), 7.05 (4H, s).

EXAMPLE 217

N-(3-Isopropyl-7-(4-isopropylbenzyl)-4,6-dimethyl-2,3-dihydro-1-benzofuran-5-yl)-3,3-dimethylbutanamide Using 3-isopropyl-7-(4-isopropylbenzyl)-4,6-dimethyl-2,3-dihydro-1-benzofuran-5-amine obtained in Reference Example 295, the title compound was synthesized in the same manner as in Example 1. Yield: 88%. Amorphous powder.

¹H-NMR (CDCl₃) δ: 0.73 (3H, d, J=6.9 Hz), 0.99 (3H, d, J=6.9 Hz), 1.19 (6H, d, J=6.9 Hz), 2.06 (3H, s), 2.16 (3H, s), 2.26 (2H, s), 2.82 (1H, septet, J=6.9 Hz), 3.31-3.36 (1H, m), 3.85 (1H, d, J=15.6 Hz), 3.96 (1H, d, J=15.6 Hz), 4.35 (1H, t, J=9.0 Hz), 4.49 (1H, dd, J=2.7, 9.0 Hz), 6.48 (1H, br s), 7.04 (4H, s)

EXAMPLE 218

N-(7-(4-Isopropylbenzyl)-4,6-dimethyl-2,3-dihydro-1-benzofuran-5-yl)butanamide

Using 7-(4-isopropylbenzyl)-4,6-dimethyl-2,3-dihydro-1-benzofuran-5-amine obtained in Reference Example 298 and n-butanoyl chloride, the title compound was synthesized in the same manner as in Example 1. Yield: 81%. Melting point: 168-169° C. (ethyl acetate-hexane).

¹H-NMR (CDCl₃) δ: 1.03 (3H, t, J=7.5 Hz), 1.20 (6H, d, J=6.9 Hz), 1.72-1.89 (2H, m), 2.06 (3H, s), 2.10 (3H, s), 2.36 (2H, t, J=7.5 Hz), 2.84 (1H, septet, J=6.9 Hz), 3.15 (2H, t, J=8.7 Hz), 3.92 (2H, s), 4.55 (2H, t, J=8.7 Hz), 6.55 (1H, br s), 7.06 (4H, s).

EXAMPLE 219

N-(7-(4-Isopropylbenzyl)-4,6-dimethyl-2,3-dihydro-1-benzofuran-5-yl)propanamide

Using 7-(4-isopropylbenzyl)-4,6-dimethyl-2,3-dihydro-1-benzofuran-5-amine obtained in Reference Example 298 and n-propanoyl chloride, the title compound was synthesized in the same manner as in Example 1. Yield: 78%. Melting point: 177-178° C. (ethyl acetate-hexane).

¹H-NMR (CDCl₃) δ: 1.20 (6H, d, J=6.9 Hz), 1.29 (3H, t, J=7.5 Hz), 2.06 (3H, s), 2.10 (3H, s), 2.41 (2H, q, J=7.5 Hz), 2.78-2.88 (1H, septet, J=6.9 Hz), 3.15 (2H, t, J=8.7 Hz), 3.92 (2H, s), 4.56 (2H, t, J=8.7 Hz), 6.56 (1H, br s), 6.99-7.10 (4H, m).

EXAMPLE 220

N-(7-(1-(4-Isopropylphenyl)vinyl)-4,6-dimethyl-2,3-dihydro-1-benzofuran-5-yl)pentanamide Using 7-(4-isopropylbenzyl)-4,6-dimethyl-2,3-dihydro-1-benzofuran-5-amine obtained in Reference Example 298 and n-pentanoyl chloride, the title compound was synthesized in the same manner as in Example 1. Yield: 82%. Melting point: 172-173° C. (ethyl acetate-hexane).

¹H-NMR (CDCl₃) δ: 0.96 (3H, t, J=7.5 Hz), 1.20 (6H, d, J=6.9 Hz), 1.33-1.53 (2H, m), 1.69-1.79 (2H, m), 2.06 (3H, s), 2.10 (3H, s), 2.39 (2H, t, J=7.5 Hz), 2.78-2.88 (1H, septet, J=6.9 Hz), 3.18 (2H, t, J=8.4 Hz), 3.92 (2H, s), 4.56 (2H, t, J=8.4 Hz), 6.54 (1H, br s), 7.01-7.13 (4H, m).

EXAMPLE 221 tert-Butyl (4,6-dimethyl-2,3-dihydro-1-benzofuran-5-yl)carbamate

Using 4,6-dimethyl-2,3-dihydro-1-benzofuran-5-amine obtained in Reference Example 297, the title compound was synthesized in the same manner as in Reference Example 59. Yield: 96%. Melting point: 121-122° C. (ethyl acetate-hexane).

¹H-NMR (CDCl₃) δ: 1.50 (9H, br), 2.14 (3H, s), 2.20 (3H, s), 3.09 (2H, t, J=8.7 Hz), 4.54 (2H, t, J=8.7 Hz), 5.73 (1H, br s), 6.50 (1H, s).

EXAMPLE 222 tert-Butyl (7-bromo-4,6-dimethyl-2,3-dihydro-1-benzofuran-5-yl)carbamate

Using tert-butyl (4,6-dimethyl-2,3-dihydro-1-benzofuran-5-yl)carbamate obtained in Example 221, the title compound was synthesized in the same manner as in Reference Example 66. Yield: 93%. Melting point: 176-177° C. (methanol).

¹H-NMR (CDCl₃) δ: 1.50 (9H, br), 2.13 (3H, s), 2.32 (3H, s), 3.23 (2H, t, J=8.4 Hz), 4.66 (2H, t, J=8.4 Hz), 5.83 (1H, br s).

EXAMPLE 223 tert-Butyl (7-(1-hydroxy-1-(4-isopropylphenyl)ethyl)-4,6-dimethyl-2,3-dihydro-1-benzofuran-5-yl)carbamate To a mixed solution of tert-butyl (7-bromo-4,6-dimethyl-2,3-dihydro-1-benzofuran-5-yl)carbamate obtained in Example 222 (500 mg, 1.46 mmol) and cerous chloride (360 mg, 3.21 mmol) in THF (8 mL) was added dropwise at −78° C. under an argon atmosphere n-butyllithium (1.6 M hexane solution, 2.0 mL, 3.21 mmol). The mixture was stirred at the same temperature for 30 minutes, and then to the reaction solution was added dropwise a solution of 4-isopropylacetophenone (261 mg, 1.61 mmol) in THF (4 mL) and the resulting mixture was stirred for 30 minutes and elevated to room temperature. Water was added to the reaction solution and the product was extracted with ethyl acetate. The combined organic layers were washed with saturated brine, dried over anhydrous sodium sulfate, filtered, and then concentrated under reduced pressure.

The residue was purified by silica gel column chromatography (ethyl acetate:hexane=2:3) to obtain 118 mg (yield: 19%) the title compound. Melting point: 185-186° C. (ethyl acetate-hexane).

¹H-NMR (CDCl₃) δ: 1.22 (6H, d, J=6.9 Hz), 1.46 (9H, br), 1.56 (3H, br s), 1.97 (3H, s), 2.15 (3H, s), 2.87 (1H, septet, J=6.9 Hz), 3.12 (2H, t, J=8.7 Hz), 4.58 (2H, t, J=8.7 Hz), 4.81 (1H, br s), 5.66 (1H, br s), 7.11 (2H, d, J=8.1 Hz), 7.28 (2H, d, J=8.1 Hz).

EXAMPLE 224

N-(7-(1-(4-Isopropylphenyl)ethyl)-4,6-dimethyl-2,3-dihydro-1-benzofuran-5-yl)butanamide To a mixed solution of tert-butyl 7-(1-hydroxy-1-(4-isopropylphenyl)ethyl)-4,6-dimethyl-2,3-dihydro-1-benzofuran-5-yl)carbamate (120 mg, 0.28 mmol) obtained in Example 223 in trifluoroacetic acid (1.5 mL) was added dropwise triethylsilane (66 mg, 0.56 mmol), and the mixture was stirred at room temperature for 1 hour. Water was added to the reaction solution and the product was extracted with ethyl acetate. The organic layer was washed with an aqueous saturated sodium hydrogen carbonate solution, dried over anhydrous sodium sulfate, filtered, and then concentrated under reduced pressure to obtain N-(7-(1-(4-isopropylphenyl)ethyl)-4,6-dimethyl-2,3-dihydro-1-benzofuran-5-yl)amine. To a solution of the compound and triethylamine (0.047 mL, 0.34 mmol) in THF (3 mL) was added dropwise with ice-cooling n-butanoyl chloride (0.034 mL, 0.34 mmol). Water was added to the reaction solution and the product was extracted with ethyl acetate. The combined organic layers was washed with saturated brine, dried over anhydrous sodium sulfate, filtered, and then concentrated under reduced pressure to obtain 62 mg (yield: 58%) of the title compound. Melting point: 152-153° C. (ethyl acetate-hexane).

$^1$H-NMR (CDCl$_3$) δ: 1.03 (3H, t, J=7.5 Hz), 1.21 (6H, d, J=6.9 Hz), 1.66 (3H, d, J=7.5 Hz), 1.71-1.89 (2H, m), 2.04 (3H, s), 2.09 (3H, s), 2.36 (2H, t, J=7.5 Hz), 2.84 (1H, septet, J=6.9 Hz), 3.09 (2H, t, J=8.7 Hz), 4.43-4.60 (3H, m), 6.52 (1H, br s), 7.07 (2H, d, J=8.1 Hz), 7.16 (2H, d, J=8.1 Hz).

EXAMPLE 225

N-(7-(1-(4-Isopropylphenyl)ethyl)-4,6-dimethyl-2,3-dihydro-1-benzofuran-5-yl)-3,3-dimethylbutanamide Using tert-butyl (7-(1-hydroxy-1-(4-isopropylphenyl)ethyl)-4,6-dimethyl-2,3-dihydro-1-benzofuran-5-yl)carbamate obtained in Example 223 and tert-butylacetyl chloride, the title compound was synthesized in the same manner as in Example 224. Yield: 61%. Melting point: 189-190° C. (ethyl acetate-hexane).

$^1$H-NMR (CDCl$_3$) δ: 1.13 (9H, s), 1.21 (6H, d, J=6.9 Hz), 1.66 (3H, d, J=7.2 Hz), 2.05 (3H, s), 2.11 (3H, s), 2.26 (2H, s), 2.84 (1H, septet, J=6.9 Hz), 3.09 (2H, t, J=8.7 Hz), 4.40-4.55 (3H, m), 6.47 (1H, br s), 7.07 (2H, d, J=8.1 Hz), 7.16 (2H, d, J=8.1 Hz).

EXAMPLE 226

N-(7-(1-(4-Isopropylphenyl)vinyl)-4,6-dimethyl-2,3-dihydro-1-benzofuran-5-yl)-3,3-dimethylbutanamide Using (7-(1-(4-isopropylphenyl)vinyl)-4,6-dimethyl-2,3-dihydro-1-benzofuran-5-yl)amine obtained in Reference Example 334, the title compound was synthesized in the same manner as in Example 1. Yield: 51%. Melting point: 188-189° C. (ethyl acetate-hexane).

$^1$H-NMR (CDCl$_3$) δ: 1.14 (9H, s), 1.22 (6H, d, J=6.9 Hz), 1.99 (3H, s), 2.18 (3H, s), 2.28 (2H, s), 2.86 (1H, septet, J=6.9 Hz), 3.15 (2H, t, J=8.7 Hz), 4.51 (2H, t, J=8.7 Hz), 5.14 (1H, s), 5.92 (1H, s), 6.53 (1H, br s), 7.10 (2H, d, J=8.4 Hz), 7.24 (2H, d, J=8.1 Hz).

EXAMPLE 227

N-(tert-Butyl)-N'-(7-(4-isopropylbenzyl)-4,6-dimethyl-2,3-dihydro-1-benzofuran-5-yl)urea Using 7-(4-isopropylbenzyl)-4,6-dimethyl-2,3-dihydro-1-benzofuran-5-amine obtained in Reference Example 298 and tert-butylamine, the title compound was synthesized in the same manner as in Example 47. Yield: 83%. Melting point: 197-198° C. (ethyl acetate-hexane).

$^1$H-NMR (CDCl$_3$) δ: 1.20 (6H, d, J=6.9 Hz), 1.24 (9H, s), 2.11 (3H, s), 2.16 (3H, s), 2.78-2.88 (1H, septet, J=6.9 Hz), 3.17 (2H, t, J=8.4 Hz), 3.94 (2H, s), 4.04 (1H, br s), 4.60 (2H, t, J=8.4 Hz), 5.30 (1H, br s), 7.02 (2H, d, J=8.1 Hz), 7.07 (2H, d, J=8.1 Hz).

EXAMPLE 228

N-(2-Hydroxyethyl)-N'-(7-(4-isopropylbenzyl)-4,6-dimethyl-2,3-dihydro-1-benzofuran-5-yl)urea Using 7-(4-isopropylbenzyl)-4,6-dimethyl-2,3-dihydro-1-benzofuran-5-amine obtained in Reference Example 298 and 2-hydroxyethylamine, the title compound was synthesized in the same manner as in Example 47. Yield: 80%. Melting point: 176-177° C. (ethyl acetate-hexane).

$^1$H-NMR (CDCl$_3$) δ: 1.20 (6H, d, J=6.9 Hz), 2.14 (3H, s), 2.17 (3H, s), 2.78-2.88 (1H, septet, J=6.9 Hz), 3.06 (1H, t, J=4.5 Hz), 3.16 (2H, t, J=8.4 Hz), 3.28-3.34 (2H, m), 3.60-3.66 (2H, m), 3.94 (2H, br s), 4.60 (2H, t, J=8.4 Hz), 4.65 (1H, br s), 5.64 (1H, s), 7.07 (4H, s).

EXAMPLE 229

N-(7-(4-Isopropylbenzyl)-4,6-dimethyl-2,3-dihydro-1-benzofuran-5-yl)-3,3-dimethylbutanamide To a solution of N-benzyl-N-(3-bromo-4-chloroethoxy-5-(4-isopropylbenzyl)-2,6-dimethylphenyl)-3,3-dimethylbutanamide (486 mg, 0.81 mmol) obtained in Reference Example 338 in THF (8 mL) was added dropwise at −50° C. under an argon atmosphere n-butyllithium (1.6 M hexane solution, 0.56 mL, 0.89 mmol), and the mixture was stirred for 30 minutes. The reaction solution was warmed to room temperature, water was added to the reaction solution, and the product was extracted with ethyl acetate. The combined organic layers were washed with saturated brine, dried over anhydrous sodium sulfate, filtered, and then concentrated under reduced pressure. The residue was purified by silica gel column chromatography (ethyl acetate:hexane=1:4) to obtain 186 mg (yield: 47%) of N-benzyl-N-(7-(4-isopropylbenzyl)-4,6-dimethyl-2,3-dihydro-1-benzofuran-5-yl)-3,3-dimethylbutanamide. A mixed solution of the compound (186 mg, 0.38 mmol) and 10% palladium on carbon (water content: 50%, 19 mg) in acetic acid (2 mL) was stirred at 85° C. for 14 hours under a hydrogen atmosphere. The reaction solution was filtered through celite, and water was added to filtrate and the product was extracted with ethyl acetate. The combined organic layers were washed with an aqueous saturated sodium hydrogen carbonate solution, dried over anhydrous sodium sulfate, filtered, and then concentrated under reduced pressure to obtain 60 mg (yield: 40%) of the title compound. Melting point: 201-202° C. (ethyl acetate-hexane). $^1$H-NMR (CDCl$_3$) δ: 1.14 (9H, s), 1.20 (6H, d, J=6.9 Hz), 2.08 (3H, s), 2.13 (3H, s), 2.27 (2H, s), 2.83 (1H, septet, J=6.9 Hz), 3.15 (2H, t, J=5.7 Hz), 3.92 (2H, s), 4.56 (2H, t, J=5.7 Hz), 6.51 (1H, br s), 7.07 (4H, s).

EXAMPLE 230

N-(3-Hydroxymethyl-7-(4-isopropylbenzyl)-4,6-dimethylphenyl-2,3-dihydro-1-benzofuran-5-yl)-3,3-dimethylbutanamide To a solution of N-(4-(allyloxy)-3-bromo-5-(4-isopropylbenzyl)-2,6-dimethylphenyl)-3,3-dimethylbutanamide (674 mg, 1.39 mmol) obtained in Reference Example 340 in dichloromethane (7 mL) was added with ice-cooling m-chloroperbenzoic acid (239 mg, 1.39 mmol) and the mixture was stirred for 30 minutes. The reaction solution was added to an aqueous saturated sodium hydrogen carbonate solution and the product was extracted with ethyl acetate. The combined organic layers were washed with a 10% aqueous sodium sulfite solution, dried over anhydrous sodium sulfate, filtered, and then concentrated under reduced pressure to obtain N-(3-bromo-5-(4-isopropylbenzyl)-2,6-dimethylphenyl-4-(oxiran-2-ylmethoxy)-3,3-dimethylbutanamide. To a solution of the compound in THF (5 mL) was added dropwise at −78° C. under an argon atmosphere n-butyllithium (1.6 M hexane solution, 0.83 mL, 1.33 mmol), and the mixture was stirred for 30 minutes. The reaction solution was warmed to room temperature and added to water, and the product was extracted with ethyl acetate. The organic layer was dried over anhydrous sodium sulfate, filtered, and then concentrated under reduced pressure. The obtained residue was purified by silica gel column chromatography (ethyl acetate:hexane=1:4) to obtain 162 mg (yield: 28%) of the title compound. Melting point: 136-137° C. (THF-hexane).

$^1$H-NMR (CDCl$_3$) δ: 1.07 (9H, s), 1.19 (6H, d, J=6.9 Hz), 2.07 (3H, s), 2.17 (3H, s), 2.26 (2H, s), 2.82 (1H, septet, J=6.9 Hz), 3.50-3.76 (3H, m), 3.92 (2H, s), 4.48 (1H, t, J=9.0 Hz), 4.61 (1H, dd, J=2.4, 9.0 Hz), 6.52 (1H, br s), 7.05 (4H, s), 1H unidentified.

EXAMPLE 231

N-(4,6-Dimethyl-3-phenyl-2,3-dihydro-1-benzofuran-5-yl)-3,3-dimethylbutanamide Using 4,6-dimethyl-3-phenyl-2,3-dihydro-1-benzofuran-5-amine obtained in Reference Example 358, the title compound was synthesized in the same manner as in Example 1. Yield: 97%. Melting point: 158-159° C. (ethyl acetate-hexane).

$^1$H-NMR (CDCl$_3$) δ: 1.11 (9H, s), 1.85 (3H, s), 2.22 (3H, s), 2.24 (2H, s), 4.41 (1H, dd, J=8.7, 4.8 Hz), 4.53 (1H, dd, J=9.3, 4.8 Hz), 4.85 (1H, t, J=9.3 Hz), 6.45 (1H, br s), 6.63 (1H, s), 7.09-7.30 (5H, m).

EXAMPLE 232

N-(7-Formyl-4,6-dim ethyl-3-phenyl-2,3-dihydro-1-benzofuran-5-yl)-3,3-dimethylbutanamide Using N-(4,6-dimethyl-3-phenyl-2,3-dihydro-1-benzofuran-5-yl)-3,3-dimethylbutanamide obtained in Example 231, the title compound was synthesized in the same manner as in Example 20. Yield: 74%. Oily matter.

$^1$H-NMR (CDCl$_3$) δ: 1.12 (9H, s), 1.91 (3H, s), 2.27 (2H, s), 2.53 (3H, s), 4.53-4.62 (2H, m), 5.00 (1H, dd, J=10.2 Hz), 6.45 (1H, br s), 7.13 (2H, d, J=7.8 Hz), 7.20-7.35 (3H, m), 10.5 (1H, s).

EXAMPLE 233

N-(7-(4-Isopropylbenzyl)-4,6-dimethyl-3-phenyl-2,3-dihydro-1-benzofuran-5-yl)-3,3-dimethylbutanamide To a mixture of magnesium (119 mg, 4.91 mmol) and a catalytic amount of iodine was added dropwise under an argon atmosphere a solution of 4-isopropyl-1-bromobenzene (978 mg, 4.91 mmol) in THF (10 mL) and the mixture was stirred at room temperature for 20 minutes. To the reaction solution was added dropwise a solution of N-(7-formyl-4,6-dimethyl-3-phenyl-2,3-dihydro-1-benzofuran-5-yl)-3,3-dimethylbutanamide (200 mg, 0.547 mmol) obtained in Example 232 in THF (5 mL) and the mixture was stirred at room temperature for 1 hour. The reaction solution was added to ice and the product was extracted with ethyl acetate. The organic layer was washed with 1 N hydrochloric acid and water, dried over anhydrous sodium sulfate, and then concentrated under reduced pressure. The obtained residue was purified by silica gel column chromatography (ethyl acetate:hexane=1:2) to obtain N-(7-(hydroxy(4-isopropylphenyl)methyl)-4,6-dimethyl-3-phenyl-2,3-dihydro-1-benzofuran-5-yl)-3,3-dimethylbutanamide. To a mixture of the compound and trifluoroacetic acid (5 mL) was added with ice-cooling triethylsilane (0.161 mL, 1.01 mmol), and the mixture was stirred at room temperature for 30 minutes. After the reaction solution was concentrated under reduced pressure, to the residue was added an aqueous saturated sodium bicarbonate solution and the aqueous layer was made alkaline, and the mixture was extracted with ethyl acetate.

The organic layer was washed with water and saturated brine, dried over anhydrous sodium sulfate, and concentrated under reduced pressure. The obtained residue was purified by silica gel column chromatography (hexane:ethyl acetate=4:1) and crystallized from hexane to obtain 70 mg (yield: 28%) of the title compound. Melting point: 137-141° C. (ethyl acetate-hexane).

$^1$H-NMR (CDCl$_3$) δ: 1.10 (9H, s), 1.21 (6H, d, J=6.9 Hz), 1.85 (3H, s), 2.11 (3H, s), 2.23 (2H, s), 2.85 (1H, septet, J=6.9 Hz), 4.00 (2H, s), 4.42 (1H, dd, J=8.7, 4.8 Hz), 4.58 (1H, dd, J=13.8, 4.8 Hz), 4.85 (1H, d, J=6.6 Hz), 6.45 (1H, br s), 7.05-7.35 (9H, m).

EXAMPLE 234

N-(3-Hydroxy-2,2,4,6,7-pentamethyl-2,3-dihydro-1-benzofuran-5-yl)-3,3-dimethylbutanamide To a solution of 3,3-dimethyl-N-(2,2,4,6,7-pentamethyl-3-oxo-2,3-dihydro-1-benzofuran-5-yl)butanamide (1.0 g, 3.15 mmol) obtained in Reference Example 63 in methanol (100 mL) was added sodium borohydride (238 mg, 6.30 mmol) at room temperature, and the mixture was stirred for 1 hour. The reaction solution was concentrated under reduced pressure, and the residue was extracted with ethyl acetate. The organic layer was washed with water, dried over anhydrous sodium sulfate, and then concentrated under reduced pressure. The obtained residue was crystallized from ethyl acetate to obtain 950 mg (yield: 94%) of the title compound. Melting point: 204-206° C.

¹H-NMR (CDCl₃) δ: 1.15 (9H, s), 1.29 (3H, s), 1.49 (3H, s), 2.09 (3H, s), 2.11 (3H, s), 2.23 (3H, s), 2.30 (2H, s), 4.70 (1H, d, J=9.2 Hz), 6.61 (1H, br s), 1H unidentified.

EXAMPLE 235

N-(3-Hydroxy-2,2,6,7-tetramethyl-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65, the title compound was synthesized in the same manner as in Example 234. Yield: 92%. Melting point: 184-185° C. (THF-hexane).

¹H-NMR (CDCl₃) δ: 1.13 (9H, s), 1.32 (3H, s), 1.48 (3H, s), 1.81 (1H, brs), 2.13 (6H, s), 2.25 (2H, s), 4.73 (1H, brs), 6.79 (1H, brs), 7.34 (1H, s).

EXAMPLE 236 tert-Butyl (7-bromo-3-hydroxy-2,2,4,6-tetramethyl-2,3-dihydro-1-benzofuran-5-yl)carbamate Using tert-butyl (7-bromo-2,2,4,6-tetramethyl-3-oxo-2,3-dihydro-1-benzofuran-5-yl)carbamate obtained in Reference Example 66, the title compound was synthesized in the same manner as in Example 234. Yield: 98%. Melting point: 187-188° C. (ethyl acetate-hexane).

¹H-NMR (CDCl₃) δ: 1.28-1.71 (15H, m), 1.70 (1H, brs), 2.26 (3H, s), 2.34 (3H, s), 4.80 (1H, d, J=9.0 Hz), 5.84 (1H, brs).

EXAMPLE 237 tert-Butyl (2,2,4,6-tetramethyl-2,3-dihydro-1-benzofuran-5-yl)carbamate

A mixture of N-benzyl-2,2,4,6-tetramethyl-2,3-dihydro-1-benzofuran-5-amine (4.1 g, 14.6 mmol) obtained in Reference Example 98, 10% palladium on carbon (water content: 50%, 400 mg) and ammonium formate (1.84 g, 29.2 mmol) in methanol (70 mL) was refluxed with heating for 2 hours. The catalyst was filtered off, and the filtrate was distilled off under reduced pressure. Water and ethyl acetate were added to the residue. The organic layer was separated and the aqueous layer was extracted with ethyl acetate. The combined organic layers were washed with water and dried over anhydrous sodium sulfate. The solvent was distilled off under reduced pressure, and the obtained residue was crystallized from ethyl acetate-hexane to obtain 2.60 g of 2,2,4,6-tetramethyl-2,3-dihydro-1-benzofuran-5-ylamine. A solution of the compound (2.60 g, 13.5 mmol) and di-tert-butyl dicarbonate (6.20 mL, 27.0 mmol) in THF (50 mL) was refluxed with heating for 16 hours. Water was added to the reaction solution. The organic layer was separated and the aqueous layer was extracted with ethyl acetate. The combined organic layers were washed with water and dried over anhydrous sodium sulfate, and the solvent was distilled off under reduced pressure. The obtained residue was crystallized from hexane-ethyl acetate to obtain 2.57 g (yield: 60%) of the title compound. Melting point: 121-123° C.

¹H-NMR (CDCl₃) δ: 1.45 (6H, s), 1.50 (9H, s), 2.11 (3H, s), 2.19 (3H, s), 2.90 (2H, s), 5.72 (1H, br s), 6.44 (1H, s).

EXAMPLE 238 tert-Butyl (7-bromo-2,2,4,6-tetramethyl-2,3-dihydro-1-benzofuran-5-yl)carbamate

Using (2,2,4,6-tetramethyl-2,3-dihydro-1-benzofuran-5-yl)carbamic acid obtained in Example 237, the title compound was synthesized in the same manner as in Reference Example 18. Yield: 54%. Melting point: 115-117° C.

¹H-NMR (CDCl₃) δ: 1.38-1.59 (15H, m), 2.08 (3H, s), 2.31 (3H, s), 3.01 (2H, s), 5.81 (1H, br s).

EXAMPLE 239

N-(3-Hydroxy-2,2,6,7-tetramethyl-3-(3-methylphenyl)-2,3-dihydro-1-benzofuran-5-yl)-3,3-dimethylbutanamide To a solution of 3,3-dimethyl-N-(2,2,6,7-tetramethyl-3-oxo-2,3-dihydro-1-benzofuran-5-yl)butanamide (303 mg, 1 mmol) obtained in Reference Example 65 in THF (10 mL) was added dropwise at 0° C. under an argon atmosphere a solution of 3-tolylmagnesium bromide (1.0 M, 10 mL, 10 mmol) in THF, and the mixture was warmed to room temperature. The mixture was stirred for 1 hour, and the reaction solution was added to ice and the product was extracted with ethyl acetate. The organic layer was washed with water and saturated brine, dried over anhydrous sodium sulfate, and then concentrated under reduced pressure. The obtained residue was recrystallized from ethyl acetate-hexane to obtain 265 mg (yield: 67%) of the title compound. Melting point: 113-114° C.

¹H-NMR (CDCl₃) δ: 0.86 (3H, s), 1.10 (9H, s), 1.59 (3H, s), 2.18-2.22 (8H, m), 2.36 (3H, s), 2.40 (1H, brs), 6.80 (1H, brs), 7.10-7.20 (2H, m), 7.22-7.26 (2H, m), 7.35 (1H, s).

EXAMPLE 240

N-(3-Hydroxy-2,2,6,7-tetramethyl-3-(2-phenylethyl)-2,3-dihydro-1-benzofuran-5-yl)-3,3-dimethylbutanamide A solution of 2-chloroethylbenzene (648 mg, 4.6 mmol) in THF (5 mL) was added dropwise under an argon atmosphere to a mixture of magnesium (112 mg, 4.6 mmol) and a catalytic amount of iodine, and the mixture was stirred for 30 minutes. To the reaction solution was added dropwise a solution of 3,3-dimethyl-N-(2,2,6,7-tetramethyl-3-oxo-2,3-dihydro-1-benzofuran-5-yl)butanamide (300 mg, 0.98 mmol) obtained in Reference Example 65 in THF (3 mL), and the mixture was stirred at room temperature for 1 hour. The reaction solution was added to ice and the product was extracted with ethyl acetate. The extract was washed with water and saturated brine, dried over anhydrous sodium sulfate, and concentrated under reduced pressure. The obtained residue was purified by silica gel column chromatography (ethyl acetate:hexane=2:3) and recrystallized from ethyl acetate-hexane to obtain 201 mg (yield: 51%) of the title compound. Melting point: 99-100° C.

¹H-NMR (CDCl₃) δ: 1.12 (9H, s), 1.37 (3H, s), 1.54 (3H, s), 1.99-2.30 (1H, m), 2.80 (1H, dt, J=12.9, 4.8 Hz), 2.97 (1H, dt, J=12.9, 4.8 Hz), 6.77 (1H, brs), 7.15-7.31 (6H, m).

EXAMPLE 241

N-(3-Hydroxy-2,2,6,7-tetramethyl-3-(2-(trifluoromethoxy)phenyl-2,3-dihydro-1-benzofuran-5-yl)-3,3-dimethylbutanamide To a solution of 1-bromo-2-(trifluoromethoxy)benzene (827 mg, 3.43 mmol) in THF (8 mL) was added dropwise at −78° C. under an argon atmosphere n-butyllithium (1.59 M hexane solution, 1.85 mL, 2.94 mmol), and the mixture was stirred for 30 minutes. To the reaction solution was added dropwise at −78° C. a solution of 3,3-dimethyl-N-(2,2,6,7-tetramethyl-3-oxo-2,3-dihydro-1-benzofuran-5-yl)butanamide (300 mg, 0.98 mmol) obtained in Reference Example 65 in THF (3 mL), and the mixture was stirred for 30 minutes. The reaction solution was warmed to room temperature and stirred for 1 hour, and water was added to the reaction solution and the product was extracted with ethyl acetate.

The organic layer was washed with water and saturated brine, dried over anhydrous sodium sulfate, and concentrated under reduced pressure. The obtained residue was purified by silica gel column chromatography (ethyl acetate:hexane=2:3), and then recrystallized from ethyl acetate-hexane to obtain 267 mg (yield: 59%) of the title compound. Melting point: 160-161° C.

$^1$H-NMR (CDCl$_3$) δ: 0.97 (3H, s), 1.11 (9H, s), 1.62 (3H, s), 2.18 (6H, s), 2.22 (2H, s), 3.00 (1H, brs), 6.79 (1H, brs), 7.15-7.36 (5H, m).

EXAMPLE 242

N-(3-Hydroxy-2,2,6,7-tetramethyl-3-(2-methylphenyl)-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and 2-tolylmagnesium bromide, the title compound was synthesized in the same manner as in Example 239.

Yield: 43%. Melting point: 111-112° C. (ethyl acetate-hexane).

$^1$H-NMR (CDCl$_3$) δ: 0.95 (3H, s), 1.10 (9H, s), 1.68 (3H, s), 2.17-2.26 (9H, m), 2.64 (3H, s), 6.82 (1H, brs), 6.90-7.26 (5H, m).

EXAMPLE 243

N-(3-Hydroxy-2,2,6,7-tetramethyl-3-phenyl-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and phenyllithium, the title compound was synthesized in the same manner as in Example 241. Yield: 58%. Melting point: 109-111° C. (ethyl acetate-hexane).

$^1$H-NMR (CDCl$_3$) δ: 0.85 (3H, s), 1.10 (9H, s), 1.62 (3H, s), 2.18-2.22 (8H, m), 2.37 (1H, brs), 6.79 (1H, brs), 7.12 (1H, s), 7.27-7.38 (3H, m), 7.47-7.50 (2H, m).

EXAMPLE 244

N-(3-Hydroxy-2,2,6,7-tetramethyl-3-(2-naphthyl)-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and 2-bromonaphthalene, the title compound was synthesized in the same manner as in Example 240. Yield: 65%. Melting point: 142-144° C. (ethyl acetate-hexane).

$^1$H-NMR (CDCl$_3$) δ: 0.89 (3H, s), 1.09 (9H, s), 1.65 (3H, s), 2.20-2.24 (8H, m), 2.46 (1H, brs), 6.82 (1H, brs), 7.16 (1H, s), 7.46-7.51 (2H, m), 7.60 (1H, d, J=8.8 Hz), 7.80-7.86 (3H, m), 7.99 (1H, s).

EXAMPLE 245

N-(3-Hydroxy-3-(3-isopropylphenyl)-2,2,6,7-tetramethyl-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and 1-bromo-3-isopropylbenzene, the title compound was synthesized in the same manner as in Example 240. Yield: 76%. Melting point: 136-137° C. (ethyl acetate-hexane).

$^1$H-NMR (CDCl$_3$) δ: 0.84 (3H, s), 1.10 (9H, s), 1.22 (6H, d, J=6.9 Hz), 1.60 (3H, s), 2.14-2.22 (9H, m), 2.90 (1H, septet, J=6.9 Hz), 6.77 (1H, brs), 7.14-7.18 (2H, m), 7.23-7.28 (2H, m), 7.39 (1H, s).

EXAMPLE 246

N-(3-Hydroxy-3-(2-methoxyphenyl)-2,2,6,7-tetramethyl-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and 2-methoxyphenylmagnesium bromide, the title compound was synthesized as in Example 239. Yield: 58%. Melting point: 168-169° C. (ethyl acetate-hexane).

$^1$H-NMR (CDCl$_3$) δ: 0.92 (3H, s), 1.10 (9H, s), 1.66 (3H, s), 2.15-2.21 (8H, m), 3.94 (3H, s), 5.17 (1H, brs), 6.82 (1H, brs), 6.89-6.97 (2H, m), 7.09 (1H, s), 7.12 (1H, d, J=8.1 Hz), 7.28 (1H, d, J=8.1 Hz).

EXAMPLE 247

N-(3-Hydroxy-3-(4-isopropylphenyl)-2,2,6,7-tetramethyl-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and 1-bromo-4-isopropylbenzene, the title compound was synthesized in the same manner as in Example 240. Yield: 42%. Melting point: 119-121° C. (ethyl acetate-hexane).

$^1$H-NMR (CDCl$_3$) δ: 0.84 (3H, s), 1.11 (9H, s), 1.26 (6H, d, J=6.9 Hz), 1.60 (3H, s), 2.18-2.22 (8H, m), 2.29 (1H, s), 2.86 (1H, septet, J=6.9 Hz), 6.80 (1H, br s), 7.15 (1H, s), 7.21 (2H, d, J=8.0 Hz), 7.41 (2H, d, J=8.0 Hz).

EXAMPLE 248

N-(3-Hydroxy-2,2,6,7-tetramethyl-3-(2-thienyl)-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and 2-bromothiophene, the title compound of oily matter was obtained in the same manner as in Example 240. Yield: 86%.

$^1$H-NMR (CDCl$_3$) δ: 0.95 (3H, s), 1.12 (9H, s), 1.64 (3H, s), 2.18 (3H, s), 2.19 (3H, s), 2.23 (2H, s), 2.63 (1H, brs), 6.81 (1H, brs), 6.94-7.01 (2H, m), 7.29-7.32 (2H, m).

EXAMPLE 249

N-(3-Benzyl-3-hydroxy-2,2,6,7-tetramethyl-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and benzylmagnesium chloride, the title compound was synthesized in the same manner as in Reference Example 239. Yield: 88%. Melting point: 212-213° C. (ethyl acetate-hexane).

$^1$H-NMR (CDCl$_3$) δ: 1.08 (9H, s), 1.31 (3H, s), 1.43 (3H, s), 1.75 (1H, s), 2.09-2.17 (8H, m), 3.02 (1H, d, J=13.6 Hz), 3.16 (1H, d, J=13.6 Hz), 6.56 (1H, s), 6.66 (1H, brs), 7.20-7.38 (5H, m).

EXAMPLE 250

N-(3-Hydroxy-3-(4-isopropylbenzyl)-2,2,6,7-tetramethyl-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and 4-isopropylbenzyl chloride, the title compound was synthesized in the same manner as in Example 240. Yield: 94%. Melting point: 177-178° C. (ethyl acetate-hexane).

$^1$H-NMR (CDCl$_3$) δ: 1.10 (9H, s), 1.25 (6H, d, J=6.9 Hz), 1.33 (3H, s), 1.43 (3H, s), 2.04 (1H, s), 2.11 (3H, s), 2.14 (3H, s), 2.19 (2H, m), 2.90 (1H, septet, J=6.9 Hz), 3.00 (1H, d, J=13.6 Hz), 3.13 (1H, d, J=13.6 Hz), 6.66 (2H, brs), 7.15 (2H, d, J=8.0 Hz), 7.24 (2H, d, J=8.0 Hz).

EXAMPLE 251

N-(3-Butyl-3-hydroxy-2,2,6,7-tetramethyl-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and n-butyllithium, the title compound was synthesized in the same manner as in Example 241. Yield: 78%. Melting point: 161-162° C. (ethyl acetate-hexane).

$^1$H-NMR (CDCl$_3$) δ: 0.91 (3H, t, J=7.2 Hz), 1.13 (9H, s), 1.30-1.43 (6H, m), 1.49 (3H, s), 1.60-1.79 (3H, m), 1.90-1.99 (1H, m), 2.13 (6H, s), 2.24 (2H, s), 6.77 (1H, brs), 7.23 (1H, s).

EXAMPLE 252

N-(3-(2-Furyl)-3-hydroxy-2,2,6,7-tetramethyl-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and furan, the title compound was synthesized in the same manner as in Example 241. Yield: 88%. Melting point: 108-110° C. (ethyl acetate-hexane).

$^1$H-NMR (CDCl$_3$) δ: 0.96 (3H, s), 1.13 (9H, s), 1.59 (3H, s), 2.17 (3H, s), 2.18 (3H, s), 2.24 (2H, s), 2.59 (1H, brs), 6.35-6.37 (2H, m), 6.79 (1H, brs), 7.37 (1H, s), 7.43 (1H, s).

EXAMPLE 253

N-(3-(2,4-Dimethoxyphenyl)-3-hydroxy-2,2,6,7-tetramethyl-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and 1-bromo-2,4-dimethoxybenzene, the title compound was synthesized in the same manner as in Example 240. Yield: 62%. Melting point: 150-151° C. (ethyl acetate-hexane).

$^1$H-NMR (CDCl$_3$) δ: 0.91 (3H, s), 1.10 (9H, s), 1.65 (3H, s), 2.12-2.20 (8H, m), 3.79 (3H, s), 3.91 (3H, s), 5.03 (1H, brs), 6.43 (1H, dd, J=8.4, 2.4 Hz), 6.52 (1H, d, J=2.4 Hz), 6.92 (1H, brs), 7.05-7.08 (2H, m).

EXAMPLE 254

N-(3-(4-Bromophenyl)-3-hydroxy-2,2,6,7-tetramethyl-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and 1,4-dibromobenzene, the title compound was synthesized in the same manner as in Example 241. Yield: 93%. Melting point: 118-119° C. (ethyl acetate-hexane).

$^1$H-NMR (CDCl$_3$) δ: 0.86 (3H, s), 1.10 (9H, s), 1.56 (3H, s), 2.17-2.22 (8H, m), 2.44 (1H, brs), 6.80 (1H, brs), 7.10 (1H, s), 7.36 (2H, d, J=8.4 Hz), 7.48 (2H, d, J=8.4 Hz).

EXAMPLE 255

N-(3-Hydroxy-3-(4-methoxyphenyl)-2,2,6,7-tetramethyl-2,3-dihydro-1-benzofuran-5-yl)-3,3-dimethylbutanamide Using 3,3-dimethyl-N-(2,2,6,7-tetramethyl-3-oxo-2,3-dihydro-1-benzofuran-5-yl)butanamide obtained in Reference Example 65 and 1-bromo-4-methoxybenzene, the title compound was synthesized in the same manner as in Example 240. Yield: 72%. Melting point: 110-111° C. (ethyl acetate-hexane).

$^1$H-NMR (CDCl$_3$) δ: 0.84 (3H, s), 1.11 (9H, s), 1.58 (3H, s), 2.18-2.24 (9H, m), 3.81 (3H, s), 6.78 (1H, brs), 6.88 (2H, d, J=9.0 Hz), 7.12 (1H, s), 7.40 (2H, d, J=9.0 Hz).

EXAMPLE 256

N-(3-Cyclohexyl-3-hydroxy-2,2,4,6,7-pentamethyl-2,3-dihydro-1-benzofuran-5-yl)-3,3-dimethylbutanamide Using 3,3-dimethyl-N-(2,2,4,6,7-pentamethyl-3-oxo-2,3-dihydro-1-benzofuran-5-yl)butanamide obtained in Reference Example 63 and cyclohexylmagnesium bromide, the title compound was synthesized in the same manner as in Example 239. Yield: 66%. Melting point: 170-171° C. (ethyl acetate-hexane).

$^1$H-NMR (CDCl$_3$) δ: 0.60-2.10 (30H, m), 2.12 (3H, s), 2.20-2.40 (5H, m), 6.55 (1H, br s).

EXAMPLE 257

N-(3-Hydroxy-2,2,4,6,7-pentamethyl-3-(2-pyridyl)-2,3-dihydro-1-benzofuran-5-yl)-3,3-dimethylbutanamide Using 3,3-dimethyl-N-(2,2,4,6,7-pentamethyl-3-oxo-2,3-dihydro-1-benzofuran-5-yl)butanamide obtained in Reference Example 63 and 2-bromopyridine, the title compound was synthesized in the same manner as in Example 241. Yield: 45%. Melting point: 205-207° C.

$^1$H-NMR (CDCl$_3$) δ: 0.89 (3H, s), 1.12 (9H, s), 1.53 (3H, s), 1.64 (3H, s), 2.13 (3H, s), 2.14 (3H, s), 2.25 (2H, s), 6.01 (1H, br s), 6.85 (1H, br s), 7.06 (1H, d, J=6.0 Hz), 7.18-7.24 (1H, m), 7.60 (1H, dt, J=7.8, 1.8 Hz), 8.56 (1H, dd, J=7.8, 4.8 Hz).

EXAMPLE 258

N-(3-Hydroxy-3-(4-methoxyphenyl)-2,2,4,6,7-pentamethyl-2,3-dihydro-1-benzofuran-5-yl)-3,3-dimethylbutanamide Using 3,3-dimethyl-N-(2,2,4,6,7-pentamethyl-3-oxo-2,3-dihydro-1-benzofuran-5-yl)butanamide obtained in Reference Example 63 and 4-bromoanisole, the title compound was synthesized in the same manner as in Example 241. Yield: 47%. Melting point: 98-99° C. (ethyl acetate-hexane).

$^1$H-NMR (CDCl$_3$) δ: 0.86 (3H, s), 1.13 (9H, s), 1.51 (3H, s), 1.85 (3H, s), 2.15 (3H, s), 2.16 (3H, s), 2.27 (2H, s), 3.79 (3H, s), 6.59 (H, br), 6.83 (3H, br), 7.38 (1H, br).

EXAMPLE 259

N-(3-Hydroxy-3-(3-methoxyphenyl)-2,2,4,6,7-pentamethyl-2,3-dihydro-1-benzofuran-5-yl)-3,3-dimethylbutanamide Using 3,3-dimethyl-N-(2,2,4,6,7-pentamethyl-3-oxo-2,3-dihydro-1-benzofuran-5-yl)butanamide obtained in Reference Example 63 and 3-bromoanisole, the title compound was synthesized in the same manner as in Example 241. Yield: 46%. Melting point: 154-155° C. (ethyl acetate-hexane).

$^1$H-NMR (CDCl$_3$) δ: 0.89 (3H, s), 1.13 (9H, s), 1.52 (3H, s), 1.87 (3H, s), 2.16 (3H, s), 2.17 (3H, s), 2.27 (2H, s), 3.80 (3H, brs), 6.45 (1H, br), 6.53 (1H, s), 6.75-6.84 (1H, m), 7.20 (2H, br).

EXAMPLE 260

N-(3-Hydroxy-3-(4-isopropylphenyl)-2,2,4,5,6-pentamethyl-2,3-dihydro-1-benzofuran-7-yl)-3,3-dimethylbutanamide Using 3,3-dimethyl-N-(2,2,4,5,6-pentamethyl-3-oxo-2,3-dihydro-1-benzofuran-7-yl)butanamide obtained in Reference Example 64 and 1-bromo-4-isopropylbenzene, the title compound was synthesized in the same manner as in Example 240. Yield: 71%. Melting point: 178-179° C. (ethyl acetate-hexane).

$^1$H-NMR (CDCl$_3$) δ: 0.82 (3H, s), 1.14 (9H, s), 1.24 (6H, d, J=6.9 Hz), 1.49 (3H, s), 1.91 (3H, s), 2.12 (3H, s), 2.19 (3H, s), 2.29 (2H, s), 2.35 (1H, s), 2.89 (1H, septet, J=6.9 Hz), 6.40-7.80 (5H, m).

EXAMPLE 261 tert-Butyl (3-hydroxy-2,2,4,6,7-pentamethyl-3-(4-methylphenyl)-2,3-dihydro-1-benzofuran-5-yl)carbamate Using tert-butyl (2,2,4,6,7-pentamethyl-3-oxo-2,3-dihydro-1-benzofuran-5-yl)carbamate obtained in Reference Example 62 and 1-bromo-4-methylbenzene, the title compound was synthesized in the same manner as in Example 241.

Yield: 64%. Amorphous powder.

$^1$H-NMR (CDCl$_3$) δ: 0.85 (3H, s), 1.20-1.60 (9H, m), 1.50 (3H, s), 1.88 (3H, s), 2.15 (3H, s), 2.19 (3H, s), 2.34 (3H, s), 5.77 (1H, br s), 6.40-8.20 (4H, m), 1H unidentified.

EXAMPLE 262 tert-Butyl (3-hydroxy-3-(4-isopropylphenyl)-2,2,4,6,7-pentamethyl-2,3-dihydro-1-benzofuran-5-yl)carbamate Using tert-butyl (2,2,4,6,7-pentamethyl-3-oxo-2,3-dihydro-1-benzofuran-5-yl)carbamate obtained in Reference Example 62 and 1-iodo-4-isopropylbenzene, the title compound was synthesized in the same manner as in Example 241. Yield: 34%. Melting point: 155-157° C. (hexane).

$^1$H-NMR (CDCl$_3$) δ: 0.85 (3H, s), 1.24 (6H, d, J=7.0 Hz), 1.20-1.64 (9H, m), 1.52 (3H, s), 1.89 (3H, s), 2.08 (1H, s), 2.16 (3H, s), 2.20 (3H, s), 2.74-3.06 (1H, m), 5.75 (1H, br s), 6.40-8.20 (4H, m).

EXAMPLE 263 tert-Butyl (3-hydroxy-2,2,4,6,7-pentamethyl-3-(2-naphthyl)-2,3-dihydro-1-benzofuran-5-yl)carbamate Using tert-butyl (2,2,4,6,7-pentamethyl-3-oxo-2,3-dihydro-1-benzofuran-5-yl)carbamate obtained in Reference Example 62 and 2-bromonaphthalene, the title compound was synthesized in the same manner as in Example 241. Yield: 50%. Amorphous powder.

$^1$H-NMR (CDCl$_3$) δ: 0.90 (3H, br s), 1.20-1.70 (9H, m), 1.57 (3H, s), 1.86 (3H, br s), 2.19 (3H, s), 2.22 (3H, s), 2.29 (1H, s), 5.77 (1H, br s), 6.60-8.60 (7H, m).

EXAMPLE 264

N-(3-(3-Formylphenyl)-3-hydroxy-2,2,6,7-tetramethyl-2,3-dihydro-1-benzofuran-5-yl)-3,3-dimethylbutanamide To a solution of 2-(3-bromophenyl)-1,3-dioxolane (1.65 mL, 10.9 mmol) in THF (20 mL) was added dropwise at −78° C. under an argon atmosphere n-butyllithium (1.59 M hexane solution, 6.4 mL, 10.2 mmol), and the resulting mixture was stirred for 30 minutes. To the reaction solution was added dropwise at −78° C. a solution of 3,3-dimethyl-N-(2,2,6,7-tetramethyl-3-oxo-2,3-dihydro-1-benzofuran-5-yl)butanamide (1.0 g, 3.30 mmol) obtained in Reference Example 65 in THF (10 mL), and the resulting mixture was stirred for 30 minutes. The reaction solution was warmed to room temperature and stirred for 1 hour, and water was added to the reaction solution and the product was extracted with ethyl acetate. The organic layer was washed with water and saturated brine, dried over anhydrous sodium sulfate, and concentrated under reduced pressure. The obtained residue was purified by silica gel column chromatography (ethyl acetate:hexane=2:3) to obtain 1.38 g (yield: 92%) of N-(3-(3-(1,3-dioxolan-2-yl)phenyl)-3-hydroxy-2,2,6,7-tetramethyl-2,3-dihydro-1-benzofuran-5-yl)-3,3-dimethylbutanamide as an amorphous powder. To a mixed solution of the obtained N-(3-(3-(1,3-dioxolan-2-yl)phenyl)-3-hydroxy-2,2,6,7-tetramethyl-2,3-dihydro-1-benzofuran-5-yl)-3,3-dimethylbutanamide (300 mg, 0.66 mmol) in acetone (4 mL)-water (0.3 mL) was added pyridinium p-toluenesulfonate (5 mg, 0.03 mmol), and the mixture was stirred for 30 minutes. The reaction solution was cooled to room temperature, and water was added to the reaction solution and the product was extracted with ethyl acetate. The organic layer was washed with water and saturated brine, dried over anhydrous sodium sulfate, and concentrated under reduced pressure. The obtained residue was recrystallized from THF-diisopropyl ether to obtain 194 mg (yield: 72%) of the title compound. Melting point: 189-190° C.

$^1$H-NMR (CDCl$_3$) δ: 0.86 (3H, s), 1.09 (9H, s), 1.59 (3H, s), 2.18-2.22 (8H, m), 2.66 (1H, s), 6.86 (1H, br s), 7.11 (1H, s), 7.52 (1H, t, J=7.5 Hz), 7.76 (1H, d, J=7.5 Hz), 7.84 (1H, d, J=7.5 Hz), 7.99 (1H, s), 10.01 (1H, s).

EXAMPLE 265

N-(3-Hydroxy-3-(3-(hydroxymethyl)phenyl)-2,2,6,7-tetramethyl-2,3-dihydro-1-benzofuran-5-yl)-3,3-dimethylbutanamide Using N-(3-(3-formylphenyl)-3-hydroxy-2,2,6,7-tetramethyl-2,3-dihydro-1-benzofuran-5-yl)-3,3-dimethylbutanamide obtained in Example 264, the title compound was obtained in the same manner as in Example 21.

Yield: 86%. Melting point: 169-171° C. (THF-diisopropyl ether).

$^1$H-NMR (CDCl$_3$) δ: 0.85 (3H, s), 1.09 (9H, s), 1.60 (3H, s), 1.65 (1H, brs), 2.17-2.20 (8H, m), 2.41 (1H, br s), 4.60 (2H, s), 6.85 (1H, br s), 7.10 (1H, s), 7.25-7.42 (3H, m), 7.49 (1H, s).

EXAMPLE 266

N-(3-Hydroxy-3-(3-(1-hydroxyethyl)phenyl)-2,2,6,7-tetramethyl-2,3-dihydro-1-benzofuran-5-yl)-3,3-dimethylbutanamide Using N-(3-(3-formylphenyl)-3-hydroxy-2,2,6,7-tetramethyl-2,3-dihydro-1-benzofuran-5-yl)-3,3-dimethylbutanamide obtained in Reference Example 264 and methylmagnesium bromide, the title compound was synthesized in the same manner as in Example 22. Yield: 43%. Melting point: 206-207° C. (THF-diisopropyl ether).

$^1$H-NMR (CDCl$_3$) δ: 0.85 (3H, s), 1.09 (9H, s), 1.46-1.49 (3H, m), 1.60 (3H, s), 2.17-2.21 (9H, m), 2.27 (1H, brs), 4.88 (1H, br s), 6.80 (1H, s), 7.14 (1H, s), 7.30-7.45 (3H, m), 7.52 (1H, s).

EXAMPLE 267

N-(3-Hydroxy-2,2,4,6,7-pentamethyl-3-(4-methylphenyl)-2,3-dihydro-1-benzofuran-5-yl)-3,3-dimethylbutanamide Using 5-amino-2,2,4,6,7-pentamethyl-3-(4-methylphenyl)-2,3-dihydro-1-benzofuran-3-ol obtained in Reference Example 80, the title compound was synthesized in the same manner as in Reference Example 63. Yield: 59%. Melting point: 146-148° C. (ethyl acetate-hexane).

$^1$H-NMR (CDCl$_3$) δ: 0.86 (3H, s), 1.12 (9H, s), 1.51 (3H, s), 1.71 (1H, s), 1.85 (3H, s), 2.16 (6H, s), 2.27 (2H, s), 2.33 (3H, s), 6.60 (1H, br s), 6.82-7.80 (4H, m).

EXAMPLE 268

N-(3-Hydroxy-2,2,4,6,7-pentamethyl-3-(2-naphthyl)-2,3-dihydro-1-benzofuran-5-yl)-3,3-dimethylbutanamide Using 5-amino-2,2,4,6,7-pentamethyl-3-(2-naphthyl)-2,3-dihydro-1-benzofuran-3-ol obtained in Reference Example 81, the title compound was synthesized in the same manner as in Reference Example 63. Yield: 82%. Amorphous powder.

$^1$H-NMR (CDCl$_3$) δ: 0.90 (3H, br. s), 1.11 (9H, s), 1.58 (3H, s), 1.83 (3H, br. s), 2.19 (6H, s), 2.26 (2H, s), 2.38 (1H, br. s), 6.40-8.60 (7H, m), 6.60 (1H, br s).

EXAMPLE 269

N-(3-Hydroxy-2,2,4,6,7-pentamethyl-3-(2-naphthyl)-2,3-dihydro-1-benzofuran-5-yl)-3-methylbutanamide Using 5-amino-2,2,4,6,7-pentamethyl-3-(2-naphthyl)-2,3-dihydro-1-benzofuran-3-ol obtained in Reference Example 81 and 3-methylbutyryl chloride, the title compound was synthesized in the same manner as in Reference Example 63.

Yield: 32%. Melting point: 108-110° C. (ethyl acetate-hexane).

$^1$H-NMR (CDCl$_3$) δ: 0.80-1.10 (9H, m), 1.50-1.95 (7H, m), 2.05-2.80 (9H, m), 6.65 (1H, br s), 7.00-8.32 (7H, m).

EXAMPLE 270

N-(tert-Butyl)-N'-(3-hydroxy-2,2,4,6,7-pentamethyl-3-(2-naphthyl)-2,3-dihydro-1-benzofuran-5-yl)urea Using 5-amino-2,2,4,6,7-pentamethyl-3-(2-naphthyl)-2,3-dihydro-1-benzofuran-3-ol obtained in Reference Example 81, the title compound was synthesized in the same manner as in Example 14. Yield: 74%. Melting point: 212-214° C. (ethyl acetate-hexane).
$^1$H-NMR (CDCl$_3$) δ: 0.92 (3H, br s), 1.27 (9H, s), 1.60 (3H, s), 1.88 (3H, br s), 2.21 (3H, s), 2.23 (3H, s), 2.44 (1H, br s), 4.12 (1H, br s), 5.33 (1H, br. s), 6.60-8.60 (7H, m).

EXAMPLE 271

3,3-Dimethyl-N-(2,2,6,7-tetramethyl-3-(2-methylphenyl)-2,3-dihydro-1-benzofuran-5-yl)butanamide To a solution of N-(3-hydroxy-2,2,6,7-tetramethyl-3-(2-methylphenyl)-2,3-dihydro-1-benzofuran-5-yl)-3,3-dimethylbutanamide (120 mg, 0.3 mmol) obtained in Example 242 in trifluoroacetic acid (2 mL) was added triethylsilane (71 mg, 0.6 mmol) under ice-cooling, and the mixture was stirred at room temperature for 1 hour. The reaction solution was added to water and the product was extracted with ethyl acetate. The organic layer was washed with an aqueous 1 N sodium hydroxide solution, water and saturated brine, dried over anhydrous sodium sulfate, and concentrated under reduced pressure. The residue was purified by silica gel column chromatography (ethyl acetate:hexane=1:2) and recrystallized from ethyl acetate-hexane to obtain 93 mg (yield: 79%) of the title compound. Melting point: 161-162° C.
$^1$H-NMR (CDCl$_3$) δ: 1.00 (3H, s), 1.09 (9H, s), 1.56 (3H, s), 2.15-2.19 (8H, m), 2.39 (3H, s), 4.57 (1H, s), 6.60-6.75 (2H, m), 6.91 (1H, s), 7.00-7.18 (3H, m).

EXAMPLE 272

3,3-Dimethyl-N-(2,2,6,7-tetramethyl-3-(3-methylphenyl)-2,3-dihydro-1-benzofuran-5-yl)butanamide Using N-(3-hydroxy-2,2,6,7-tetramethyl-3-(3-methylphenyl)-2,3-dihydro-1-benzofuran-5-yl)-3,3-dimethylbutanamide obtained in Example 239, the title compound was synthesized in the same manner as in Example 271. Yield: 87%. Melting point: 156-157° C. (ethyl acetate-hexane).
$^1$H-NMR (CDCl$_3$) δ: 0.96 (3H, s), 1.09 (9H, s), 1.55 (3H, s), 2.15-2.19 (8H, m), 2.31 (3H, s), 4.27 (1H, s), 6.70 (1H, br s), 6.85-6.92 (3H, m), 7.04 (1H, d, J=8.4 Hz), 7.16 (1H, t, J=8.4 Hz).

EXAMPLE 273

N-(3-(3-Isopropylphenyl)-2,2,6,7-tetramethyl-2,3-dihydro-1-benzofuran-5-yl)-3,3-dimethylbutanamide Using N-(3-hydroxy-3-(3-isopropylphenyl)-2,2,6,7-tetramethyl-2,3-dihydro-1-benzofuran-5-yl)-3,3-dimethylbutanamide obtained in Example 245, the title compound was synthesized in the same manner as in Example 271. Yield: 65%. Melting point: 162-163° C. (ethyl acetate-hexane).
$^1$H-NMR (CDCl$_3$) δ: 0.93 (3H, s), 1.09 (9H, s), 1.22 (6H, d, J=6.9 Hz), 1.57 (3H, s), 2.15-2.20 (8H, m), 2.86 (1H, septet, J=6.9 Hz), 4.32 (1H, s), 6.72 (1H, br s), 6.90-7.09 (3H, m), 7.08-7.25 (2H, m).

EXAMPLE 274

N-(2,2,6,7-Tetramethyl-3-phenyl-2,3-dihydro-1-benzofuran-5-yl)-3,3-dimethylbutanamide Using N-(3-hydroxy-2,2,6,7-tetramethyl-3-phenyl-2,3-dihydro-1-benzofuran-5-yl)-3,3-dimethylbutanamide obtained in Example 243, the title compound was synthesized in the same manner as in Example 271. Yield: 82%. Melting point: 182-183° C. (ethyl acetate-hexane).
$^1$H-NMR (CDCl$_3$) δ: 0.95 (3H, s), 1.09 (9H, s), 1.57 (3H, s), 2.15-2.20 (8H, m), 4.32 (1H, s), 6.72 (1H, br s), 6.95 (1H, s), 7.06-7.11 (2H, m), 7.23-7.31 (3H, m).

EXAMPLE 275

N-(2,2,6,7-Tetramethyl-3-(2-naphthyl)-2,3-dihydro-1-benzofuran-5-yl)-3,3-dimethylbutanamide Using N-(3-hydroxy-2,2,6,7-tetramethyl-3-(2-naphthyl)-2,3-dihydro-1-benzofuran-5-yl)-3,3-dimethylbutanamide obtained in Example 244, the title compound of an oily matter was obtained in the same manner as in Example 271. Yield: 84%.
$^1$H-NMR (CDCl$_3$) δ: 0.99 (3H, s), 1.06 (9H, s), 1.60 (3H, s), 2.16-2.22 (8H, m), 4.47 (1H, s), 6.77 (1H, brs), 6.93 (1H, s), 7.18 (1H, dd, J=8.6, 1.6 Hz), 7.42-7.49 (2H, m), 7.58 (1H, br s), 7.73-7.82 (3H, m).

EXAMPLE 276

N-(3-(2-Methoxyphenyl)-2,2,6,7-tetramethyl-2,3-dihydro-1-benzofuran-5-yl)-3,3-dimethylbutanamide Using N-(3-hydroxy-3-(2-methoxyphenyl)-2,2,6,7-tetramethyl-2,3-dihydro-1-benzofuran-5-yl)-3,3-dimethylbutanamide obtained in Example 246, the title compound was synthesized in the same manner as in Example 271. Yield: 82%. Melting point: 169-170° C. (ethyl acetate-hexane).
$^1$H-NMR (CDCl$_3$) δ: 0.97 (3H, s), 1.10 (9H, s), 1.57 (3H, s), 2.15-2.19 (8H, m), 3.85 (3H, s), 4.82 (1H, s), 6.72 (1H, br s), 6.75-6.91 (4H, m), 7.15-7.26 (1H, m).

EXAMPLE 277

N-(3-Benzyl-2,2,6,7-tetramethyl-2,3-dihydro-1-benzofuran-5-yl)-3,3-dimethylbutanamide Using N-(3-benzyl-3-hydroxy-2,2,6,7-tetramethyl-2,3-dihydro-1-benzofuran-5-yl)-3,3-dimethylbutanamide obtained in Example 249, the title compound was synthesized in the same manner as in Example 271. Yield: 56%. Melting point: 186-187° C. (ethyl acetate-hexane).
$^1$H-NMR (CDCl$_3$) δ: 1.08 (9H, s), 1.33 (3H, s), 1.37 (3H, s), 2.09 (3H, s), 2.12 (3H, s), 2.17 (2H, s), 2.89 (2H, d, J=7.8 Hz), 3.42 (1H, t, J=7.8 Hz), 6.49 (1H, s), 6.62 (1H, br s), 7.17-7.33 (5H, m).

EXAMPLE 278

N-(3-(4-Isopropylbenzyl)-2,2,6,7-tetramethyl-2,3-dihydro-1-benzofuran-5-yl)-3,3-dimethylbutanamide Using N-(3-hydroxy-3-(4-isopropylbenzyl)-2,2,6,7-tetramethyl-2,3-dihydro-1-benzofuran-5-yl)-3,3-dimethylbutanamide obtained in Example 250, the title compound was synthesized in the same manner as in Example 271. Yield: 63%. Melting point: 130-132° C. (ethyl acetate-hexane).
$^1$H-NMR (CDCl$_3$) δ: 1.10 (9H, s), 1.25 (6H, d, J=6.9 Hz), 1.33 (3H, s), 1.43 (3H, s), 2.04 (1H, s), 2.11 (3H, s), 2.14 (3H, s), 2.19 (2H, m), 2.86 (1H, septet, J=6.9 Hz), 3.00 (1H, d, J=13.6 Hz), 3.13 (1H, d, J=13.6 Hz), 6.66 (2H, br s), 7.15 (2H, d, J=8.0 Hz), 7.24 (2H, d, J=8.0 Hz).

EXAMPLE 279

N-(2,2,6,7-Tetramethyl-3-(2-thienyl)-2,3-dihydro-1-benzofuran-5-yl)-3,3-dimethylbutanamide Using N-(3-hydroxy-2,2,6,7-tetramethyl-3-(2-thienyl)-2,3-dihydro-1-benzofuran-5-yl)-3,3-dimethylbutanamide obtained in Example 248, the title compound was synthesized in the same manner as in Example 271. Yield: 65%. Melting point: 137-138° C. (ethyl acetate-hexane).
$^1$H-NMR (CDCl$_3$) δ: 1.05 (3H, s), 1.10 (9H, s), 1.58 (3H, s), 2.15-2.21 (8H, m), 4.61 (1H, s), 6.77 (1H, br s), 6.85 (1H, d, J=3.4 Hz), 6.97 (1H, dd, J=4.8, 3.4 Hz), 7.10 (1H, s), 7.19 (1H, d, J=4.8 Hz).

EXAMPLE 280

N-(2,2,6,7-Tetramethyl-3-(2-(trifluoromethoxy)phenyl)-2,3-dihydro-1-benzofuran-5-yl)-3,3-dimethylbutanamide Using N-(3-hydroxy-2,2,6,7-tetramethyl-3-(2-(trifluoromethoxy)phenyl-2,3-dihydro-1-benzofuran-5-yl)-3,3-dimethylbutanamide obtained in Example 241, the title compound was synthesized in the same manner as in Example 271. Yield: 47%. Melting point: 155-156° C. (ethyl acetate-hexane).
$^1$H-NMR (CDCl$_3$) δ: 0.97 (3H, s), 1.11 (9H, s), 1.62 (3H, s), 2.18 (6H, s), 2.22 (2H, s), 3.00 (1H, br s), 6.79 (1H, br s), 7.15-7.36 (5H, m).

EXAMPLE 281

N-(3-Butyl-2,2,6,7-tetramethyl-2,3-dihydro-1-benzofuran-5-yl)-3,3-dimethylbutanamide Using N-(3-butyl-3-hydroxy-2,2,6,7-tetramethyl-2,3-dihydro-1-benzofuran-5-yl)-3,3-dimethylbutanamide obtained in Example 251, the title compound was synthesized in the same manner as in Example 271. Yield: 77%. Melting point: 129-130° C. (ethyl acetate-hexane).
$^1$H-NMR (CDCl$_3$) δ: 0.91 (3H, t, J=7.2 Hz), 1.13 (9H, s), 1.30-1.43 (6H, m), 1.49 (3H, s), 1.60-1.79 (3H, m), 1.90-1.99 (1H, m), 2.13 (6H, s), 2.24 (2H, s), 6.77 (1H, br s), 7.23 (1H, s).

EXAMPLE 282

N-(3-(2-Furyl)-2,2,6,7-tetramethyl-2,3-dihydro-1-benzofuran-5-yl)-3,3-dimethylbutanamide Using N-(3-(2-furyl)-3-hydroxy-2,2,6,7-tetramethyl-2,3-dihydro-1-benzofuran-5-yl)-3,3-dimethylbutanamide obtained in Example 252, the title compound was synthesized in the same manner as in Example 271. Yield: 67%. Melting point: 126-127° C. (ethyl acetate-hexane).
$^1$H-NMR (CDCl$_3$) δ: 1.06 (3H, s), 1.12 (9H, s), 1.59 (3H, s), 2.12-2.22 (8H, m), 4.44 (1H, s), 6.10 (1H, d, J=3.2 Hz), 6.30-6.33 (1H, m), 6.74 (1H, br s), 7.10 (1H, s), 7.35-7.36 (1H, m).

EXAMPLE 283

N-(2,2,6,7-Tetramethyl-3-(2-phenylethyl)-2,3-dihydro-1-benzofuran-5-yl)-3,3-dimethylbutanamide Using N-(3-hydroxy-2,2,6,7-tetramethyl-3-(2-phenylethyl)-2,3-dihydro-1-benzofuran-5-yl)-3,3-dimethylbutanamide obtained in Example 240, the title compound was synthesized in the same manner as in Example 271. Yield: 92%. Melting point: 158-159° C. (ethyl acetate-hexane).
$^1$H-NMR (CDCl$_3$) δ: 1.13 (9H, s), 1.37 (3H, s), 1.45 (3H, s), 1.86-1.96 (2H, m), 2.12 (6H, s), 2.33 (2H, s), 2.65-2.83 (2H, m), 3.03 (1H, t, J=7.8 Hz), 6.73 (1H, br s), 7.17-7.31 (6H, m).

EXAMPLE 284

N-(3-(4-Bromophenyl)-2,2,6,7-tetramethyl-2,3-dihydro-1-benzofuran-5-yl)-3,3-dimethylbutanamide Using N-(3-(4-bromophenyl)-3-hydroxy-2,2,6,7-tetramethyl-2,3-dihydro-1-benzofuran-5-yl)-3,3-dimethylbutanamide obtained in Example 254, the title compound was synthesized in the same manner as in Example 271. Yield: 88%. Melting point: 171-172° C. (ethyl acetate-hexane).
$^1$H-NMR (CDCl$_3$) δ: 0.95 (3H, s), 1.10 (9H, s), 1.54 (3H, s), 2.15 (3H, s), 2.18 (3H, s), 2.20 (2H, s), 4.28 (1H, s), 6.72 (1H, br s), 6.94-6.98 (3H, m), 7.41 (2H, d, J=8.4 Hz).

EXAMPLE 285

N-(3-(4-Methoxyphenyl)-2,2,6,7-tetramethyl-2,3-dihydro-1-benzofuran-5-yl)-3,3-dimethylbutanamide Using N-(3-hydroxy-3-(4-methoxyphenyl)-2,2,6,7-tetramethyl-2,3-dihydro-1-benzofuran-5-yl)-3,3-dimethylbutanamide obtained in Example 255, the title compound was synthesized in the same manner as in Example 271. Yield: 82%. Melting point: 169-170° C. (ethyl acetate-hexane).
$^1$H-NMR (CDCl$_3$) δ: 0.95 (3H, s), 1.10 (9H, s), 1.54 (3H, s), 2.14-2.20 (8H, m), 3.79 (3H, s), 4.27 (1H, s), 6.71 (1H, br s), 6.82 (2H, d, J=8.7 Hz), 6.93 (1H, s), 7.01 (2H, d, J=8.7 Hz).

EXAMPLE 286

N-(3-(2,4-(Dimethoxyphenyl)-2,2,6,7-tetramethyl-2,3-dihydro-1-benzofuran-5-yl)-3,3-dimethylbutanamide Using N-(3-(2,4-(dimethoxyphenyl)-3-hydroxy-2,2,6,7-tetramethyl-2,3-dihydro-1-benzofuran-5-yl)-3,3-dimethylbutanamide obtained in Example 253, the title compound was synthesized in the same manner as in Example 271. Yield: 82%. Melting point: 146-147° C. (ethyl acetate-hexane).
$^1$H-NMR (CDCl$_3$) δ: 0.97 (3H, s), 1.09 (9H, s), 1.55 (3H, s), 2.14-2.19 (8H, m), 3.78 (3H, s), 3.82 (3H, s), 4.73 (1H, s), 6.35 (1H, dd, J=8.4, 2.4 Hz), 6.45 (1H, d, J=2.4 Hz), 6.66 (1H, d, J=8.4 Hz), 6.76 (1H, br s), 6.90 (1H, s).

EXAMPLE 287

N-(3-Cyclohexyl-2,2,4,6,7-pentamethyl-2,3-dihydro-1-benzofuran-5-yl)-3,3-dimethylbutanamide Using N-(3-cyclohexyl-3-hydroxy-2,2,4,6,7-pentamethyl-2,3-dihydro-1-benzofuran-5-yl)-3,3-dimethylbutanamide obtained in Example 256, the title compound was synthesized in the same manner as in Example 271. Yield: 48%. Melting point: 198-199° C. (ethyl acetate-hexane).

$^1$H-NMR (CDCl$_3$) δ: 0.50-2.20 (35H, m), 2.24-2.35 (2H, m), 2.67 (1H, d, J=2.7 Hz), 6.55 (1H, br s).

EXAMPLE 288

3,3-Dimethyl-N-(2,2,4,6,7-pentamethyl-3-(2-pyridyl)-2,3-dihydro-1-benzofuran-5-yl)butanamide Using N-(3-hydroxy-2,2,4,6,7-pentamethyl-3-(2-pyridyl)-2,3-dihydro-1-benzofuran-5-yl)-3,3-dimethylbutanamide obtained in Example 257, the title compound was synthesized in the same manner as in Example 271. Yield: 52%. Melting point: 210-212° C.

$^1$H-NMR (CDCl$_3$) δ: 1.04 (3H, s), 1.12 (9H, s), 1.55 (3H, s), 1.79 (3H, s), 2.17 (6H, s), 2.26 (2H, s), 4.41 (1H, s), 6.52 (1H, br s), 6.78 (1H, d, J=7.6 Hz), 7.12 (1H, dd, J=7.6, 4.4 Hz), 7.54-7.61 (1H, m), 8.53 (1H, d, J=4.4 Hz).

EXAMPLE 289

N-(3-(4-Methoxyphenyl)-2,2,4,6,7-pentamethyl-2,3-dihydro-1-benzofuran-5-yl)-3,3-dimethylbutanamide Using N-(3-hydroxy-3-(4-methoxyphenyl)-2,2,4,6,7-pentamethyl-2,3-dihydro-1-benzofuran-5-yl)-3,3-dimethylbutanamide obtained in Example 258, the title compound was synthesized in the same manner as in Example 271. Yield: 40%. Melting point: 175-176° C. (ethyl acetate-hexane).

$^1$H-NMR (CDCl$_3$) δ: 1.00 (3H, s), 1.12 (9H, s), 1.48 (3H, s), 1.77 (3H, s), 2.15 (6H, s), 2.24 (2H, s), 3.76 (3H, s), 4.08 (1H, s), 6.48 (1H, s), 6.76 (1H, br d, J=5.4 Hz), 6.83 (2H, br).

EXAMPLE 290

N-(3-(3-Methoxyphenyl)-2,2,4,6,7-pentamethyl-2,3-dihydro-1-benzofuran-5-yl)-3,3-dimethylbutanamide Using N-(3-hydroxy-3-(3-methoxyphenyl)-2,2,4,6,7-pentamethyl-2,3-dihydro-1-benzofuran-5-yl)-3,3-dimethylbutanamide obtained in Example 259, the title compound was synthesized in the same manner as in Example 271. Yield: 77%. Melting point: 166-167° C. (ethyl acetate-hexane).

$^1$H-NMR (CDCl$_3$) δ: 1.04 (3H, s), 1.12 (9H, s), 1.49 (3H, s), 1.79 (3H, s), 2.15 (6H, s), 2.25 (2H, s), 3.76 (3H, s), 4.09 (1H, s), 6.25 (1H, br), 6.47 (1H, s), 6.60-6.85 (2H, m), 7.08 (1H, br).

EXAMPLE 291

N-(3-(4-Isopropylphenyl)-2,2,4,5,6-pentamethyl-2,3-dihydro-1-benzofuran-7-yl)-3,3-dimethylbutanamide Using N-(3-hydroxy-3-(4-isopropylphenyl)-2,2,4,5,6-pentamethyl-2,3-dihydro-1-benzofuran-7-yl)-3,3-dimethylbutanamide obtained in Example 260, the title compound was synthesized in the same manner as in Example 271. Yield: 53%. Melting point: 152-153° C. (ethyl acetate-hexane).

$^1$H-NMR (CDCl$_3$) δ: 0.97 (3H, s), 1.14 (9H, s), 1.21 (6H, d, J=6.9 Hz), 1.46 (3H, s), 1.83 (3H, s), 2.08 (3H, s), 2.17 (3H, s), 2.29 (2H, s), 2.85 (1H, septet, J=6.9 Hz), 4.11 (1H, s), 6.40-7.15 (5H, m).

EXAMPLE 292

N-(3-(4-Formylphenyl)-2,2,6,7-tetramethyl-2,3-dihydro-1-benzofuran-5-yl)-3,3-dimethylbutanamide To a solution of N-(3-(4-bromophenyl)-2,2,6,7-tetramethyl-2,3-dihydro-1-benzofuran-5-yl)-3,3-dimethylbutanamide (500 mg, 1.13 mmol) obtained in Example 284 in THF (10 mL) was added dropwise at −78° C. under an argon atmosphere n-butyllithium (1.59 M hexane solution, 1.56 mL, 2.48 mmol), and the mixture was stirred for 30 minutes. DMF (90 mg, 1.24 mmol) was added to the reaction solution at the same temperature, and the mixture was stirred for 30 minutes, warmed to room temperature, and stirred for 1 hour. Water was added to the reaction solution and the product was extracted with ethyl acetate. The organic layer was washed with water and saturated brine, dried over anhydrous sodium sulfate, and concentrated under reduced pressure. The residue was purified by silica gel column chromatography (ethyl acetate:hexane=2:3) and recrystallized from ethyl acetate-hexane to obtain 204 mg (yield: 46%) of the title compound. Melting point: 169-170° C.

$^1$H-NMR (CDCl$_3$) δ: 0.97 (3H, s), 1.09 (9H, s), 1.58 (3H, s), 2.04-2.20 (8H, m), 4.38 (1H, s), 6.74 (1H, br s), 6.99 (1H, s), 7.25 (2H, d, J=8.4 Hz), 7.81 (2H, dd, J=8.4 Hz), 9.99 (1H, s).

EXAMPLE 293

N-(3-(4-Acetylphenyl)-2,2,6,7-tetramethyl-2,3-dihydro-1-benzofuran-5-yl)-3,3-dimethylbutanamide Using N-(3-(4-bromophenyl)-2,2,6,7-tetramethyl-2,3-dihydro-1-benzofuran-5-yl)-3,3-dimethylbutanamide obtained in Example 284 and N,N-dimethylacetamide, the title compound was synthesized in the same manner as in Example 292. Yield: 20%. Melting point: 195-196° C. (ethyl acetate-hexane).

$^1$H-NMR (CDCl$_3$) δ: 0.96 (3H, s), 1.09 (9H, s), 1.57 (3H, s), 2.16-2.19 (8H, m), 2.59 (3H, s), 4.36 (1H, s), 6.73 (1H, br s), 6.97 (1H, s), 7.18 (2H, d, J=8.0 Hz), 7.88 (2H, d, J=8.0 Hz).

EXAMPLE 294

N-(3-(4-(Hydroxymethyl)phenyl)-2,2,6,7-tetramethyl-2,3-dihydro-1-benzofuran-5-yl)-3,3-dimethylbutanamide Using N-(3-(4-formylphenyl)-2,2,6,7-tetramethyl-2,3-dihydro-1-benzofuran-5-yl)-3,3-dimethylbutanamide obtained in Example 292, the title compound was synthesized in the same manner as in Example 21. Yield: 80%. Melting point: 162-163° C. (THF-diisopropyl ether).

$^1$H-NMR (CDCl$_3$) δ: 0.95 (3H, s), 1.09 (9H, s), 1.56 (3H, s), 1.65 (1H, t, J=6.0 Hz), 2.15-2.19 (8H, m), 4.32 (1H, s), 4.67 (2H, d, J=6.0 Hz), 6.72 (1H, br s), 6.94 (1H, s), 7.09 (2H, d, J=8.0 Hz), 7.29 (2H, d, J=8.0 Hz).

EXAMPLE 295

N-(3-(4-(1-Hydroxyethyl)phenyl)-2,2,6,7-tetramethyl-2,3-dihydro-1-benzofuran-5-yl)-3,3-dimethylbutanamide Using N-(3-(4-acetylphenyl)-2,2,6,7-tetramethyl-2,3-dihydro-1-benzofuran-5-yl)-3,3-dimethylbutanamide obtained in Example 293, the title compound of an oily matter was synthesized in the same manner as in Example 21. Yield: 65%.

$^1$H-NMR (CDCl$_3$) δ: 0.95 (3H, s), 1.09 (9H, s), 1.48 (3H, d, J=6.4 Hz), 1.55 (3H, s), 1.66 (1H, brs), 2.14-2.19 (8H, m), 4.30 (1H, s), 4.87 (1H, q, J=6.4 Hz), 6.79 (1H, br s), 6.93 (1H, s), 7.07 (2H, d, J=8.0 Hz), 7.29 (2H, d, J=8.0 Hz).

EXAMPLE 296

N-(3-(2-Isopropylphenyl)-2,2,6,7-tetramethyl-2,3-dihydro-1-benzofuran-5-yl)-3,3-dimethylbutanamide A solution of 1-bromo-2-isopropylbenzene (1.20 g, 6.03 mmol) in THF (5 mL) was added dropwise under an argon atmosphere to a mixture of magnesium (147 mg, 6.03 mmol) and a catalytic amount of iodine, and the mixture was stirred at 70° C. for 30 minutes. To the reaction solution was added dropwise a solution of 3,3-dimethyl-N-(2,2,6,7-tetramethyl-3-oxo-2,3-dihydro-1-benzofuran-5-yl)butanamide (350 mg, 1.15 mmol) obtained in Reference Example 65 in THF (3 mL), and the mixture was refluxed with heating for 12 hours. The reaction solution was added to ice and the product was extracted with ethyl acetate. The organic layer was washed with water and saturated brine, dried over anhydrous sodium sulfate, and concentrated under reduced pressure. The obtained residue was purified by silica gel column chromatography (ethyl acetate:hexane=1:2) to obtain 79 mg (yield: 16%) of N-(3-hydroxy-3-(3-isopropylphenyl)-2,2,6,7-tetramethyl-2,3-dihydro-1-benzofuran-5-yl)-3,3-dimethylbutanamide. To a solution of the compound (79 mg, 0.19 mmol) in trifluoroacetic acid (1 mL) was added with ice-cooling triethylsilane (44 mg, 0.38 mmol), and the mixture was stirred at room temperature for 1 hour. The reaction solution was added to water and the product was extracted with ethyl acetate. The organic layer was washed with an aqueous 1 N sodium hydroxide solution, water and saturated brine, dried over anhydrous sodium sulfate, and concentrated under reduced pressure.

The residue was purified by silica gel column chromatography (ethyl acetate:hexane=1:2) to obtain 39 mg (yield: 51%) of the title compound. Yield: 51%. Melting point: 188-189° C. (ethyl acetate-hexane).

$^1$H-NMR (CDCl$_3$) δ: 1.01 (3H, s), 1.09 (9H, s), 1.27 (3H, d, J=7.0 Hz), 1.32 (3H, d, J=7.0 Hz), 1.57 (3H, s), 2.15-2.20 (8H, m), 3.15-3.30 (1H, m), 4.67 (1H, s), 6.67 (1H, d, J=7.8 Hz), 6.69 (1H, br s), 6.88 (1H, s), 7.02 (1H, t, J=7.8 Hz), 7.17 (1H, t, J=7.8 Hz), 7.29 (1H, d, J=7.8 Hz).

EXAMPLE 297

3,3-Dimethyl-N-(2,2,4,6,7-pentamethyl-3-piperidin-1-yl-2,3-dihydro-1-benzofuran-5-yl)butanamide To a solution of N-(3-hydroxy-2,2,4,6,7-pentamethyl-2,3-dihydro-1-benzofuran-5-yl)-3,3-dimethylbutanamide (450 mg, 1.41 mmol) obtained in Example 234 in dichloromethane (3 mL) was added triethylamine (0.79 mL, 5.64 mmol), and then added dropwise with ice-cooling methanesulfonyl chloride (0.22 mL, 2.82 mmol). The reaction solution was stirred for 30 minutes, and to the reaction solution was added piperidine (0.70 mL, 7.05 mmol), and the mixture was stirred at room temperature for 16 hours. Water was added to the reaction solution and the product was extracted with ethyl acetate. The organic layer was washed with water and saturated brine, dried over anhydrous sodium sulfate, and concentrated under reduced pressure. The obtained residue was purified by silica gel column chromatography (hexane ethyl acetate=20:1) to obtain 270 mg (yield: 50%) of the title compound. Melting point: 229-230° C. (ethyl acetate-hexane).

$^1$H-NMR (CDCl$_3$) δ: 1.10-1.82 (22H, m), 2.08 (3H, s), 2.12 (3H, s), 2.18 (3H, s), 2.22-2.43 (3H, m), 2.78 (1H, br s), 2.95 (1H, br s), 3.68 (1H, s), 6.56 (1H, s)

EXAMPLE 298

3,3-Dimethyl-N-(2,2,4,6,7-pentamethyl-3-pyrrolidin-1-yl-2,3-dihydro-1-benzofuran-5-yl)butanamide Using N-(3-hydroxy-2,2,4,6,7-pentamethyl-2,3-dihydro-1-benzofuran-5-yl)-3,3-dimethylbutanamide obtained in Example 234 and pyrrolidine, the title compound was synthesized in the same manner as in Example 297. Yield: 36%. Melting point: 197-198° C. (ethyl acetate-hexane). $^1$H-NMR (CDCl$_3$) δ: 1.16 (9H, s), 1.23 (3H, s), 1.49 (3H, s), 1.58-1.72 (4H, m), 2.09 (3H, s), 2.13 (6H, s), 2.30 (2H, s), 2.48-2.80 (4H, m), 4.02 (1H, s), 6.55 (1H, br s).

EXAMPLE 299

N-(3-Anilino-2,2,6,7-tetramethyl-2,3-dihydro-1-benzofuran-5-yl)-3,3-dimethylbutanamide Using N-(3-hydroxy-2,2,6,7-tetramethyl-2,3-dihydro-1-benzofuran-5-yl)-3,3-dimethylbutanamide obtained in Example 235 and aniline, the title compound was synthesized in the same manner as in Example 297. Yield: 79%. Melting point: 151-152° C. (ethyl acetate-hexane).

$^1$H-NMR (CDCl$_3$) δ: 1.11 (9H, s), 1.37 (3H, s), 1.53 (3H, s), 2.14 (6H, s), 2.22 (2H, s), 3.93 (1H, d, J=8.7 Hz), 4.81 (1H, d, J=8.7 Hz), 6.60 (2H, d, J=7.8 Hz), 6.67-6.75 (2H, m), 7.17 (3H, t, J=7.8 Hz).

EXAMPLE 300

N-(3-((2-Methoxyphenyl)amino)-2,2,6,7-tetramethyl-2,3-dihydro-1-benzofuran-5-yl)-3,3-dimethylbutanamide Using N-(3-hydroxy-2,2,6,7-tetramethyl-2,3-dihydro-1-benzofuran-5-yl)-3,3-dimethylbutanamide obtained in Example 235 and (2-methoxyphenyl)amine, the title compound was synthesized in the same manner as in Example 297. Yield: 75%. Melting point: 184-185° C. (ethyl acetate-hexane).

$^1$H-NMR (CDCl$_3$) δ: 1.11 (9H, s), 1.34 (3H, s), 1.53 (3H, s), 2.14 (6H, s), 2.22 (2H, s), 3.78 (3H, s), 4.53 (1H, d, J=8.1 Hz), 4.86 (1H, d, J=8.1 Hz), 6.63-6.68 (2H, m), 6.75-6.77 (2H, m), 6.86 (1H, t, J=9.0 Hz), 7.16 (1H, s).

EXAMPLE 301

N-(3-((2-(Trifluoromethoxy)phenyl)amino)-2,2,6,7-tetramethyl-2,3-dihydro-1-benzofuran-5-yl)-3,3-dimethylbutanamide Using N-(3-hydroxy-2,2,6,7-tetramethyl-2,3-dihydro-1-benzofuran-5-yl)-3,3-dimethylbutanamide obtained in Example 235 and (2-(trifluoromethoxy)phenyl)amine, the title compound was synthesized in the same manner as in Example 297. Yield: 73%. Melting point: 196-197° C. (ethyl acetate-hexane).

$^1$H-NMR (CDCl$_3$) δ: 1.11 (9H, s), 1.35 (3H, s), 1.54 (3H, s), 2.15 (6H, s), 2.23 (2H, s), 4.32 (1H, d, J=9.0 Hz), 4.85 (1H, d, J=9.0 Hz), 6.67 (1H, t, J=6.9 Hz), 6.70-6.80 (2H, m), 7.12-7.17 (3H, m).

EXAMPLE 302 tert-Butyl (7-bromo-2,2,4,6-tetramethyl-3-(pyrrolidin-1-yl)-2,3-dihydro-1-benzofuran-5-yl)carbamate Using tert-butyl (7-bromo-3-hydroxy-2,2,4,6-tetramethyl-2,3-dihydro-1-benzofuran-5-yl)carbamate obtained in Example 236 and pyrrolidine, the title compound was synthesized in the same manner as in Example 297.
Yield: 43%. Melting point: 128-130° C. (ethyl acetate-hexane).
$^1$H-NMR (CDCl$_3$) δ: 1.28-1.57 (15H, m), 1.60-1.70 (4H, m), 2.14 (3H, s), 2.33 (3H, s), 2.40-2.67 (2H, m) 2.70-2.80 (2H, m), 4.13 (1H, s), 5.82 (1H, br s).

EXAMPLE 303 tert-Butyl (7-bromo-3-(dimethylamino)-2,2,4,6-tetramethyl-2,3-dihydro-1-benzofuran-5-yl)carbamate Using tert-butyl (7-bromo-3-hydroxy-2,2,4,6-tetramethyl-2,3-dihydro-1-benzofuran-5-yl)carbamate obtained in Example 236 and dimethylamine, the title compound was synthesized in the same manner as in Example 297. Yield: 89%. Melting point: 111-112° C. (ethyl acetate-hexane).
$^1$H-NMR (CDCl$_3$) δ: 1.27 (3H, s), 1.36-1.60 (12H, m), 2.04-2.60 (12H, m), 3.86 (1H, s), 5.84 (1H, b rs).

EXAMPLE 304 tert-Butyl (3-(4-isopropylphenyl)-2,2,4,6,7-pentamethyl-2,3-dihydro-1-benzofuran-5-yl)carbamate Using 3-(4-isopropylphenyl)-2,2,4,6,7-pentamethyl-2,3-dihydro-1-benzofuran-5-amine obtained in Reference Example 120, the title compound was synthesized in the same manner as in Reference Example 59. Yield: 24%. Melting point: 119-120° C. (ethyl acetate-hexane).
$^1$H-NMR (CDCl$_3$) δ: 1.00 (3H, s), 1.21 (6H, d, J=6.6 Hz), 1.25-1.58 (12H, m), 1.81 (3H, s), 2.16 (3H, s), 2.17 (3H, s), 2.85 (1H, septet, J=6.9 Hz), 4.08 (1H, s), 5.72 (1H, s), 6.64-7.10 (4H, m).

EXAMPLE 305 tert-Butyl (2,2,4,6,7-pentamethyl-3-(4-methylphenyl)-2,3-dihydro-1-benzofuran-5-yl)carbamate Using 2,2,4,6,7-pentamethyl-3-(4-methylphenyl)-2,3-dihydro-1-benzofuran-5-amine obtained in Reference Example 122, the title compound was synthesized in the same manner as in Reference Example 59. Yield: 18%. Melting point: 124-125° C. (hexane).
$^1$H-NMR (CDCl$_3$) δ: 1.01 (3H, s), 1.20-1.64 (9H, m), 1.48 (3H, s), 1.80 (3H, s), 2.16 (3H, s), 2.17 (3H, s), 2.30 (3H, s), 4.08 (1H, s), 5.71 (1H, br s), 6.20-7.60 (4H, m).

EXAMPLE 306

N-(7-(4-Isopropylbenzyl)-2,2,4,6-tetramethyl-2,3-dihydro-1-benzofuran-5-yl)-3,3-dimethylbutanamide To a solution of tert-butyl (7-bromo-2,2,4,6-tetramethyl-2,3-dihydro-1-benzofuran-5-yl)carbamate (1.77 g, 4.78 mmol) obtained in Example 238 in THF (20 mL) was added dropwise at −78° C. under argon atmosphere n-butyllithium (1.60 M hexane solution, 6.25 mL, 10.0 mmol), and the mixture was stirred for 30 minutes. To the reaction solution was added dropwise at −78° C. a solution of 4-isopropylbenzaldehyde (815 mg, 5.50 mmol) in THF (5 mL). The reaction solution was warmed to room temperature and stirred for 1 hour. Water was added to the reaction solution and the product was extracted with ethyl acetate. The organic layer was washed with water and saturated brine, dried over anhydrous sodium sulfate, and concentrated under reduced pressure. The obtained residue was purified by silica gel column chromatography (ethyl acetate:hexane=1:4) to obtain 1.20 g (yield: 59%) of tert-butyl (7-(hydroxy(4-isopropylphenyl)methyl)-2,2,4,6-tetramethyl-2,3-dihydro-1-benzofuran-5-yl)carbamate. To a mixture of the compound (1.00 g, 2.27 mmol) in trifluoroacetic acid (5 mL) was added with ice-cooling triethylsilane (1.0 mL, 6.4 mmol), and the mixture was stirred at room temperature for 1 hour. After the reaction solution was concentrated under reduced pressure, to the residue was added an aqueous saturated sodium hydrogen carbonate solution and the aqueous layer was made alkaline, and the mixture was extracted with ethyl acetate. The organic layer was washed with water and saturated brine, dried over anhydrous sodium sulfate, and concentrated under reduced pressure to obtain a crude product of 7-(4-isopropylbenzyl)-2,2,4,6-tetramethyl-2,3-dihydro-1-benzofuran-5-amine. To a solution of the compound (330 mg, about 1.02 mmol) and tert-butylacetyl chloride (0.16 mL, 1.12 mmol) in dichloromethane (30 mL) was added triethylamine (0.16 mL, 1.12 mmol) at room temperature, and the mixture was stirred at room temperature for 1 hour. Water was added to the reaction solution, the organic layer was separated, and the aqueous layer was extracted with dichloromethane. The combined organic layers were washed with 1 N hydrochloric acid and an aqueous saturated sodium hydrogen carbonate solution, dried over magnesium sulfate, filtered, and then concentrated under reduced pressure. The obtained residue was purified by silica gel column chromatography (hexane:ethyl acetate=4:1) to obtain 273 mg (yield: 17%) of the title compound. Melting point: 170-171° C. (ethyl acetate-hexane).
$^1$H-NMR (CDCl$_3$) δ: 1.13 (9H, s), 1.19 (6H, d, J=7.2 Hz), 1.46 (6H, s), 2.05 (3H, s), 2.08 (3H, s), 2.25 (2H, s), 2.82 (1H, septet, J=7.2 Hz), 2.96 (2H, s), 3.89 (2H, s), 6.46 (1H, br s), 7.04 (2H, d, J=8.1 Hz), 7.09 (2H, d, J=8.1 Hz).

EXAMPLE 307

N-(7-(4-Isopropylbenzyl)-2,2,4,6-tetramethyl-3-(pyrrolidin-1-yl)-2,3-dihydro-1-benzofuran-5-yl)-3,3-dimethylbutanamide Using tert-butyl (7-bromo-2,2,4,6-tetramethyl-3-(pyrrolidin-1-yl)-2,3-dihydro-1-benzofuran-5-yl)carbamate obtained in Example 302, the title compound was synthesized in the same manner as in Example 306. Yield: 61%. Melting point: 179-180° C. (ethyl acetate-hexane).
$^1$H-NMR (CDCl$_3$) δ: 1.13 (9H, s), 1.18 (3H, s), 1.21 (3H, s), 1.25 (3H, s), 1.49 (3H, s), 1.62-1.72 (4H, m), 2.05 (3H, s), 2.14 (3H, s), 2.25 (2H, dd, J=17.1, 13.2 Hz), 2.59 (2H, br), 2.70-2.90 (3H, m), 3.80-3.95 (2H, br), 4.05 (1H, s), 6.48 (1H, s), 7.00-7.10 (4H, m).

EXAMPLE 308

N-(3-(Dimethylamino)-7-(4-isopropylbenzyl)-2,2,4,6-tetramethyl-2,3-dihydro-1-benzofuran-5-yl)-3,3-dimethylbutanamide Using tert-butyl (7-bromo-3-(dimethylamino)-2,2,4,6-tetramethyl-2,3-dihydro-1-benzofuran-5-yl)carbamate obtained in Example 303, the title compound was synthesized in the same manner as in Example 306. Yield: 33%. Melting point: 138-139° C. (ethyl acetate-hexane).

$^1$H-NMR (CDCl$_3$) δ: 1.13 (9H, s), 1.18 (3H, s), 1.21 (3H, s), 1.24 (3H, s), 1.51 (3H, s), 2.03-2.06 (14H, m), 2.70-2.88 (1H, m), 3.78 (1H, s), 3.90 (2H, br s), 6.49 (1H, s), 6.98-7.05 (4H, m).

EXAMPLE 309

N-(2,2,6,7-Tetramethyl-3-(4-methylphenyl)-2,3-dihydro-1-benzofuran-5-yl)-3,3-dimethylbutanamide Using 2,2,6,7-tetramethyl-3-(4-methylphenyl)-2,3-dihydro-1-benzofuran-5-amine obtained in Reference Example 139, the title compound (yield: 88%) was obtained in the same manner as in Reference Example 63. Amorphous powder.

$^1$H-NMR (CDCl$_3$) δ: 0.95 (3H, s), 1.08 (9H, s), 1.54 (3H, s), 2.14 (3H, s), 2.17 (5H, s), 2.32 (3H, s), 4.28 (1H, s), 6.75 (1H, brs), 6.90 (1H, s), 6.96 (2H, d, J=7.9 Hz), 7.08 (2H, d, J=7.9 Hz).

EXAMPLE 310

N-(2,2,4,6,7-Pentamethyl-3-(4-methylphenyl)-2,3-dihydro-1-benzofuran-5-yl)butanamide Using 2,2,4,6,7-pentamethyl-3-(4-methylphenyl)-2,3-dihydro-1-benzofuran-5-amine obtained in Reference Example 122 and butyryl chloride, the title compound was synthesized in the same manner as in Reference Example 63.

Yield: 50%. Melting point: 138-139° C. (ethyl acetate-hexane).

$^1$H-NMR (CDCl$_3$) δ: 0.74-2.41 (25H, m), 4.10 (1H, s), 6.54 (1H, br s), 7.03 (4H, br s).

EXAMPLE 311

N-(2,2,4,6,7-Pentamethyl-3-(4-methylphenyl)-2,3-dihydro-1-benzofuran-5-yl)pentanamide Using 2,2,4,6,7-pentamethyl-3-(4-methylphenyl)-2,3-dihydro-1-benzofuran-5-amine obtained in Reference Example 122 and pentanoyl chloride, the title compound was synthesized in the same manner as in Reference Example 63.

Yield: 62%. Melting point: 156-157° C. (ethyl acetate-hexane).

$^1$H-NMR (CDCl$_3$) δ: 0.78-2.43 (27H, m), 4.10 (1H, s), 6.55 (1H, br s), 7.04 (4H, br s).

EXAMPLE 312

N-(2,2,4,6,7-Pentamethyl-3-(4-methylphenyl)-2,3-dihydro-1-benzofuran-5-yl)hexanamide Using 2,2,4,6,7-pentamethyl-3-(4-methylphenyl)-2,3-dihydro-1-benzofuran-5-amine obtained in Reference Example 122 and hexanoyl chloride, the title compound was synthesized in the same manner as in Reference Example 63.

Yield: 52%. Melting point: 96-97° C. (ethyl acetate-hexane).

$^1$H-NMR (CDCl$_3$) δ: 0.77-2.41 (29H, m), 4.10 (1H, s), 6.55 (1H, br s), 7.03 (4H, br s).

EXAMPLE 313

N-(3-(4-Fluorophenyl)-2,2,4,6,7-pentamethyl-2,3-dihydro-1-benzofuran-5-yl)-3,3-dimethylbutanamide Using 3-(4-fluorophenyl)-2,2,4,6,7-pentamethyl-2,3-dihydro-1-benzofuran-5-amine obtained in Reference Example 123, the title compound was synthesized in the same manner as in Reference Example 63. Yield: 60%. Melting point: 194-195° C. (ethyl acetate-hexane).

$^1$H-NMR (CDCl$_3$) δ: 1.00 (3H, s), 1.12 (9H, s), 1.49 (3H, s), 1.77 (3H, s), 2.15 (6H, s), 2.25 (2H, s), 4.11 (1H, s), 6.40-7.20 (5H, m).

EXAMPLE 314

3,3-Dimethyl-N-(2,2,4,6,7-pentamethyl-3-phenyl-2,3-dihydro-1-benzofuran-5-yl)butanamide Using 2,2,4,6,7-pentamethyl-3-phenyl-2,3-dihydro-1-benzofuran-5-amine obtained in Reference Example 121, the title compound was synthesized in the same manner as in Reference Example 63. Yield: 55%. Melting point: 214-215° C. (ethyl acetate-hexane).

$^1$H-NMR (CDCl$_3$) δ: 0.92-1.20 (12H, m), 1.50 (3H, s), 1.77 (3H, s), 2.16 (6H, s), 2.25 (2H, s), 4.13 (1H, s), 6.40-7.38 (6H, m).

EXAMPLE 315

N-(3-(4-Bromophenyl)-2,2,4,6,7-pentamethyl-2,3-dihydro-1-benzofuran-5-yl)-3,3-dimethylbutanamide Using 3-(4-bromophenyl)-2,2,4,6,7-pentamethyl-2,3-dihydro-1-benzofuran-5-amine obtained in Reference Example 124, the title compound was synthesized in the same manner as in Reference Example 63. Yield: 65%. Melting point: 201-202° C. (ethyl acetate-hexane).

$^1$H-NMR (CDCl$_3$) δ: 0.92-1.18 (12H, m), 1.49 (3H, s), 1.76 (3H, s), 2.15 (6H, s), 2.25 (2H, s), 4.09 (1H, s), 6.51-7.44 (5H, m).

EXAMPLE 316

N-(3-(4-tert-Butylphenyl)-2,2,4,6,7-pentamethyl-2,3-dihydro-1-benzofuran-5-yl)-3,3-dimethylbutanamide To a solution of 3-(4-tert-butylphenyl)-2,2,4,6,7-pentamethyl-2,3-dihydro-1-benzofuran-5-amine hydrochloride obtained in Reference Example 76 (400 mg, 1.16 mmol) and tert-butylacetyl chloride (0.17 mL, 1.22 mmol) in dichloromethane (10 mL) was added triethylamine (0.35 mL, 2.50 mmol) at room temperature, and the mixture was stirred at room temperature for 1 hour. Water was added to the reaction solution, the organic layer was separated, and the aqueous layer was extracted with dichloromethane. The combined organic layers were washed with 1 N hydrochloric acid and an aqueous saturated sodium hydrogen carbonate solution, dried over magnesium sulfate, filtered, and then concentrated under reduced pressure. The obtained residue was purified by silica gel column chromatography (hexane:ethyl acetate=8:1) to obtain 110 mg (yield: 41%) of the title compound. Amorphous substance.

¹H-NMR (CDCl₃) δ: 0.99 (3H, s), 1.06 (9H, s), 1.12 (9H, s), 1.49 (3H, s), 1.78 (3H, s), 2.16 (6H, s), 2.25 (2H, s), 4.10 (1H, s), 6.50 (1H, br s), 6.70-7.24 (4H, m).

EXAMPLE 317

N-(3-(4-Isopropylphenyl)-2,2,6,7-tetramethyl-2,3-dihydro-1-benzofuran-5-yl)-3,3-dimethylbutanamide Using 3-(4-isopropylphenyl)-2,2,6,7-tetramethyl-2,3-dihydro-1-benzofuran-5-amine hydrochloride obtained in Reference Example 74, the title compound was synthesized in the same manner as in Example 316. Yield: 38%. Melting point: 172-173° C. (ethyl acetate-hexane).

¹H-NMR (CDCl₃) δ: 0.94 (3H, s), 1.06 (9H, s), 1.23 (6H, d, J=6.9 Hz), 1.55 (3H, s), 2.15 (3H, s), 2.18 (3H, s), 2.19 (2H, s), 2.87 (1H, septet, J=6.6 Hz), 4.29 (1H, s), 6.71 (1H, br s), 6.94 (1H, s), 7.00 (2H, d, J=7.8 Hz), 7.13 (2H, d, J=7.8 Hz).

EXAMPLE 318

N-(3-(4-Isopropylphenyl)-2,2,4,7-tetramethyl-2,3-dihydro-1-benzofuran-5-yl)-3,3-dimethylbutanamide Using 3-(4-isopropylphenyl)-2,2,4,7-tetramethyl-2,3-dihydro-1-benzofuran-5-amine hydrochloride obtained in Reference Example 75, the title compound was synthesized in the same manner as in Example 316. Yield: 23%. Melting point: 118-119° C. (ethyl acetate-hexane).

¹H-NMR (CDCl₃) δ: 1.01 (3H, s), 1.10 (9H, s), 1.21 (6H, d, J=6.9 Hz), 1.48 (3H, s), 1.78 (3H, s), 2.19 (2H, s), 2.21 (3H, s), 2.85 (1H, septet, J=6.9 Hz), 4.08 (1H, s), 6.52-7.24 (6H, m)

EXAMPLE 319

N-(3-(4-Isopropylphenyl)-2,2,4,6-tetramethyl-2,3-dihydro-1-benzofuran-5-yl)-3,3-dimethylbutanamide Using 3-(4-isopropylphenyl)-2,2,4,6-tetramethyl-2,3-dihydro-1-benzofuran-5-amine obtained in Reference Example 78, the title compound was synthesized in the same manner as in Reference Example 63. Yield: 52%. Amorphous substance.

¹H-NMR (CDCl₃) δ: 1.00 (3H, s), 1.11 (9H, s), 1.21 (6H, d, J=6.9 Hz), 1.49 (3H, s), 1.79 (3H, s), 2.21 (3H, s), 2.23 (2H, s), 2.84 (1H, septet, J=6.9 Hz), 4.08 (1H, s), 6.53 (1H, br s), 6.56 (1H, s), 6.70-7.10 (4H, m).

EXAMPLE 320

N-(3-(4-Isopropylphenyl)-2,2-dimethyl-2,3-dihydro-1-benzofuran-5-yl)-3,3-dimethylbutanamide Using 3-(4-isopropylphenyl)-2,2-dimethyl-2,3-dihydro-1-benzofuran-5-amine obtained in Reference Example 86, the title compound was synthesized in the same manner as in Reference Example 63. Yield: 52%. Melting point: 126-127° C. (ethyl acetate-hexane).

¹H-NMR (CDCl₃) δ: 0.96 (3H, s), 1.07 (9H, s), 1.24 (6H, d, J=6.6 Hz), 1.56 (3H, s), 2.12 (2H, s), 2.88 (1H, septet, J=6.6 Hz), 4.29 (1H, s), 6.75 (1H, d, J=8.1 Hz), 6.91 (1H, br s), 6.99 (2H, d, J=8.1 Hz), 7.14 (2H, d, J=8.1 Hz), 7.16-7.25 (2H, m).

EXAMPLE 321

N-(3-(4-Isopropylphenyl)-2,2-dimethyl-2,3-dihydro-1-benzofuran-5-yl)butanamide

Using 3-(4-isopropylphenyl)-2,2-dimethyl-2,3-dihydro-1-benzofuran-5-amine obtained in Reference Example 86 and butyryl chloride, the title compound was synthesized in the same manner as in Reference Example 63. Yield: 27%. Amorphous substance.

¹H-NMR (CDCl₃) δ: 0.97 (3H, s), 0.98 (3H, t, J=7.2 Hz), 1.24 (6H, d, J=6.9 Hz), 1.56 (3H, s), 1.60-1.80 (2H, m), 2.26 (2H, t, J=7.5 Hz), 2.88 (1H, septet, J=6.9 Hz), 4.29 (1H, s), 6.75 (1H, d, J=9.3 Hz), 6.90-7.05 (3H, m), 7.13 (2H, d, J=8.1 Hz), 7.17-7.22 (2H, m).

EXAMPLE 322

N-(3-(4-Isopropylphenyl)-2,2,4,6,7-pentamethyl-2,3-dihydro-1-benzofuran-5-yl)butanamide Using 3-(4-isopropylphenyl)-2,2,4,6,7-pentamethyl-2,3-dihydro-1-benzofuran-5-amine obtained in Reference Example 120 and butyryl chloride, the title compound was synthesized in the same manner as in Reference Example 63. Yield: 59%. Melting point: 120-122° C. (ethyl acetate-hexane).

¹H-NMR (CDCl₃) δ: 0.78-1.10 (6H, m), 1.21 (6H, d, J=6.9 Hz), 1.60-1.90 (8H, m), 2.10-2.40 (8H, m), 2.84 (1H, septet, J=6.9 Hz), 4.10 (1H, s), 6.50-7.20 (5H, m).

EXAMPLE 323

N-(3-(4-Isopropylphenyl)-2,2,4,6,7-pentamethyl-2,3-dihydro-1-benzofuran-5-yl)pentanamide Using 3-(4-isopropylphenyl)-2,2,4,6,7-pentamethyl-2,3-dihydro-1-benzofuran-5-amine obtained in Reference Example 120 and pentanoyl chloride, the title compound was synthesized in the same manner as in Reference Example 63. Yield: 44%. Melting point: 106-107° C. (ethyl acetate-hexane).

¹H-NMR (CDCl₃) δ: 0.70-1.90 (22H, m), 2.05-2.41 (8H, m), 2.84 (1H, septet, J=6.6 Hz), 4.10 (1H, s), 6.42-7.18 (5H, m).

EXAMPLE 324

N-(3-(4-Isopropylphenyl)-2,2,4,6,7-pentamethyl-2,3-dihydro-1-benzofuran-5-yl)-3,3-dimethylbutanamide Using 3-(4-isopropylphenyl)-2,2,4,6,7-pentamethyl-2,3-dihydro-1-benzofuran-5-amine obtained in Reference Example 120, the title compound was synthesized in the same manner as in Reference Example 63. Yield: 41%. Amorphous substance.

¹H-NMR (CDCl₃) δ: 0.90-1.20 (12H, m), 1.21 (6H, d, J=7.2 Hz), 1.48 (3H, s), 1.78 (3H, s), 2.15-2.27 (8H, m), 2.84 (1H, septet, J=7.2 Hz), 4.09 (1H, s), 6.40-7.10 (5H, m).

EXAMPLE 325

N-(3-(4-Isopropylphenyl)-2,2,4,5,7-pentamethyl-2,3-dihydro-1-benzofuran-6-yl)-3,3-dimethylbutanamide Using 3-(4-isopropylphenyl)-2,2,4,5,7-pentamethyl-2,3-dihydro-1-benzofuran-6-amine obtained in Reference Example 77, the title compound was synthesized in the same manner as in Reference Example 63. Yield: 50%. Melting point: 128-129° C. (ethyl acetate-hexane).

$^1$H-NMR (CDCl$_3$) δ: 1.02 (3H, s), 1.17 (9H, s), 1.21 (6H, d, J=6.9 Hz), 1.48 (3H, s), 1.83 (3H, s), 2.04 (3H, s), 2.12 (3H, s), 2.31 (2H, s), 2.84 (1H, septet, J=7.2 Hz), 4.10 (1H, s), 6.50-7.18 (5H, m).

EXAMPLE 326

N-(3-Benzyl-2,2,4,5,7-pentamethyl-2,3-dihydro-1-benzofuran-6-yl)-3,3-dimethylbutanamide Using 3-benzyl-2,2,4,5,7-pentamethyl-2,3-dihydro-1-benzofuran-6-amine obtained in Reference Example 79, the title compound was synthesized in the same manner as in Reference Example 63. Yield: 38%. Melting point: 209-210° C. (ethyl acetate-hexane).

$^1$H-NMR (CDCl$_3$) δ: 1.15 (9H, s), 1.26 (3H, s), 1.40 (3H, s), 1.80 (3H, s), 2.01 (3H, s), 2.07 (3H, s), 2.29 (2H, s), 2.75 (1H, dd, J=14.7, 6.0 Hz), 2.89 (1H, dd, J=14.7, 8.4 Hz), 3.29 (1H, dd, J=8.4, 6.0 Hz), 6.60 (1H, br s), 7.10-7.30 (5H, m).

EXAMPLE 327

N-(3-(4-Isopropylphenyl)-2,2,5-trimethyl-2,3-dihydro-1-benzofuran-7-yl)-3,3-dimethylbutanamide Using 3-(4-isopropylphenyl)-2,2,5-trimethyl-2,3-dihydro-1-benzofuran-7-amine obtained in Reference Example 96, the title compound was synthesized in the same manner as in Reference Example 63. Yield: 51%. Melting point: 64-68° C. (hexane).

$^1$H-NMR (CDCl$_3$) δ: 0.95 (3H, s), 1.12 (9H, s), 1.24 (6H, d, J=6.9 Hz), 1.57 (3H, s), 2.25 (3H, s), 2.27 (2H, s), 2.89 (1H, septet, J=6.9 Hz), 4.30 (1H, s), 6.59 (1H, s), 6.99 (2H, d, J=8.1 Hz), 7.14 (2H, d, J=8.1 Hz), 7.17 (1H, br s), 7.98 (1H, s).

EXAMPLE 328

N-(3-(4-Isopropylphenyl)-5-methoxy-2,2,4,6-tetramethyl-2,3-dihydro-1-benzofuran-7-yl)-3,3-dimethylbutanamide Using 3-(4-isopropylphenyl)-5-methoxy-2,2,4,6-tetramethyl-2,3-dihydro-1-benzofuran-7-amine obtained in Reference Example 97, the title compound was synthesized in the same manner as in Reference Example 63. Yield: 67%. Melting point: 140-141° C. (ethyl acetate-hexane).

$^1$H-NMR (CDCl$_3$) δ: 0.96 (3H, s), 1.14 (9H, s), 1.22 (6H, d, J=6.9 Hz), 1.47 (3H, s), 1.83 (3H, s), 2.20 (3H, s), 2.28 (2H, s), 2.85 (1H, septet, J=6.9 Hz), 3.64 (3H, s), 4.10 (1H, s), 6.40-7.18 (5H, m).

EXAMPLE 329

N-(3-(4-Isopropylphenyl)-2,2-dimethyl-2,3-dihydro-1-benzofuran-5-yl)-N,3,3-trimethylbutanamide To a solution of N-(3-(4-isopropylphenyl)-2,2-dimethyl-2,3-dihydro-1-benzofuran-5-yl)-3,3-dimethylbutanamide (110 mg, 290 mmol) obtained in Example 320 in DMF (3 mL) was added sodium hydride (a 60% dispersion in liquid paraffin, 12.8 mg, 319 mmol) at 0° C. and the mixture was stirred at room temperature for 30 minutes. Methyl iodide (8.0 g, 319 mmol) was added to the reaction solution and the mixture was stirred at room temperature for 30 minutes. Water was added to the reaction solution and the product was extracted with diisopropyl ether. The combined extracts were washed with water, dried over magnesium sulfate, and concentrated under reduced pressure. The obtained residue was purified by silica gel column chromatography (hexane:ethyl acetate=4:1) to obtain 47 mg (yield: 41%) of the title compound. Melting point: 78-79° C. (ethyl acetate-hexane).

$^1$H-NMR (CDCl$_3$) δ: 0.93 (9H, s), 1.00 (3H, s), 1.24 (6H, d, J=7.0 Hz), 1.62 (3H, s), 1.94-2.10 (2H, m), 2.90 (1H, septet, J=7.0 Hz), 3.19 (3H, s), 4.36 (1H, s), 6.77-6.92 (3H, m), 6.98 (2H, d, J=8.0 Hz), 7.16 (2H, d, J=8.0 Hz).

EXAMPLE 330

N-(3-(4-Isopropylphenyl)-2,2,4,6,7-pentamethyl-2,3-dihydro-1-benzofuran-5-yl)-3-(4-morpholinyl)propionamide hydrochloride To a solution of 3-(4-isopropylphenyl)-2,2,4,6,7-pentamethyl-2,3-dihydro-1-benzofuran-5-amine (350 mg, 1.08 mmol) obtained in Reference Example 120 and 3-chloropropionyl chloride (0.39 mL, 3.72 mmol) in dichloromethane (15 mL) was added triethylamine (0.18 mL, 1.30 mmol) at room temperature and the mixture was stirred at room temperature for 1 hour. Water was added to the reaction solution, the organic layer was separated, and the aqueous layer was extracted with dichloromethane. The combined organic layers were washed with 1 N hydrochloric acid and an aqueous saturated sodium hydrogen carbonate solution, dried over magnesium sulfate, filtered, and then concentrated under reduced pressure to obtain a crude product of N-(3-(4-isopropylphenyl)-2,2,4,6,7-pentamethyl-2,3-dihydro-1-benzofuran-5-yl)-3-chloropropionamide. A mixture of the compound, morpholine and potassium carbonate in ethanol was refluxed with heating for 16 hours. The mixture was poured into water and the product was extracted with ethyl acetate. The organic layer was washed with water, dried over magnesium sulfate, filtered, and then concentrated under reduced pressure. The obtained residue was purified by basic silica gel column chromatography (hexane:ethyl acetate=10:1) to obtain a free base of the title compound. The compound was crystallized from 4 N hydrochloric acid-ethyl acetate to obtain 230 mg (yield: 42%) of the title compound. Melting point: 158-161° C. (methanol-diethyl ether).

$^1$H-NMR (DMSO-d$_6$) δ: 0.94 (3H, s), 1.17 (6H, d, J=6.9 Hz), 1.43 (3H, s), 1.66 (3H, s), 2.02 (3H, s), 2.09 (3H, s), 2.77-2.98 (3H, m), 3.08-3.18 (2H, m), 3.25-3.47 (4H, m), 3.80 (2H, t, J=12.0 Hz), 3.94 (2H, d, J=11.4 Hz), 4.18 (1H, s), 4.42 (1H, br s), 6.60-7.20 (4H, m), 9.35 (1H, s).

EXAMPLE 331 tert-Butyl (2,4,6-trimethyl-2,3-dihydro-1-benzofuran-5-yl)carbamate

Using 2,4,6-trimethyl-2,3-dihydro-1-benzofuran-5-amine obtained in Reference Example 304, the title compound was synthesized in the same manner as in Reference Example 59. The yield was quantitative. Oily matter.

¹H-NMR (CDCl₃) δ: 1.43 (3H, d, J=6.3 Hz), 1.45 (9H, s), 2.12 (3H, s), 2.19 (3H, s), 2.69 (1H, dd, J=7.5, 15.0 Hz), 3.21 (1H, dd, J=8.7, 15.0 Hz), 4.80-4.97 (1H, m), 5.72 (1H, br s), 6.46 (1H, s).

EXAMPLE 332 tert-Butyl (7-bromo-2,4,6-trimethyl-2,3-dihydro-1-benzofuran-5-yl)carbamate

Using tert-butyl (2,4,6-trimethyl-2,3-dihydro-1-benzofuran-5-yl)carbamate obtained in Example 331, the title compound was synthesized in the same manner as in Reference Example 66. Yield: 75%. Melting point: 115-116° C. (ethyl acetate-hexane).
¹H-NMR (CDCl₃) δ: 1.35-1.58 (12H, m), 2.10 (3H, s), 2.31 (3H, s), 2.82 (1H, dd, J=7.5, 15.0 Hz), 3.34 (1H, dd, J=8.7, 15.0 Hz), 4.96-5.08 (1H, m), 5.83 (1H, br s).

EXAMPLE 333 tert-Butyl (7-(hydroxy(4-isopropylphenyl)methyl)-2,4,6-trimethyl-2,3-dihydro-1-benzofuran-5-yl)carbamate Using tert-butyl (7-bromo-2,4,6-trimethyl-2,3-dihydro-1-benzofuran-5-yl)carbamate obtained in Example 332, the title compound was synthesized in the same manner as in Reference Example 82. Yield: 71%. Melting point: 141-142° C. (ethyl acetate-hexane).
¹H-NMR (CDCl₃) δ: 1.21 (6H, d, J=6.9 Hz), 1.38 (3H, d, J=6.0 Hz), 1.49 (9H, s), 2.14 (6H, s), 2.71 (1H, dd, J=7.5, 15.0 Hz), 2.80-2.90 (1H, septet, J=6.9 Hz), 3.24 (1H, dd, J=8.7, 15.0 Hz), 4.07 (1H, br d, J=9.9 Hz), 4.93-5.08 (1H, m), 5.75 (1H, br s), 5.90 (1H, d, J=9.9 Hz), 7.13 (2H, d, J=8.1 Hz), 7.27 (2H, d, J=8.1 Hz).

EXAMPLE 334

N-(7-(4-Isopropylbenzyl)-2,4,6-trimethyl-2,3-dihydro-1-benzofuran-5-yl)-3,3-dimethylbutanamide Using tert-butyl (7-(hydroxy(4-isopropylphenyl)methyl)-2,4,6-trimethyl-2,3-dihydro-1-benzofuran-5-yl)carbamate obtained in Example 333, the title compound was synthesized in the same manner as in Example 224. Yield: 32%. Melting point: 179-180° C. (ethyl acetate-hexane).
¹H-NMR (CDCl₃) δ: 1.13 (9H, s), 1.20 (6H, d, J=6.9 Hz), 1.44 (3H, d, J=6.0 Hz), 2.06 (3H, s), 2.10 (3H, s), 2.26 (2H, s), 2.71-2.90 (2H, m), 3.27 (1H, dd, J=8.7, 15.0 Hz), 3.91 (2H, s), 4.80-4.97 (1H, m), 6.49 (1H, br s), 7.07 (4H, s).

EXAMPLE 335

N-(2-(Hydroxymethyl)-7-(4-isopropylbenzyl)-2,4,6-trimethyl-2,3-dihydro-1-benzofuran-5-yl)-3,3-dimethylbutanamide To a solution of N-(4-hydroxy-3-(4-isopropylbenzyl)-2,6-dimethyl-5-(2-methylprop-2-en-1-yl)phenyl)-3,3-dimethylbutanamide (300 mg, 0.71 mmol) obtained in Reference Example 341 in dichloromethane (2 mL) were added with ice-cooling an aqueous saturated sodium hydrogen carbonate solution (1 mL) and m-chloroperbenzoic acid (302 mg, 1.75 mmol). The reaction solution was stirred at room temperature for 1 hour. Water was added to the reaction solution and the product was extracted with ethyl acetate. The combined organic layers were washed with a 10% aqueous sodium sulfite solution and saturated aqueous sodium bicarbonate solution, dried over anhydrous sodium sulfate, filtered, and then concentrated under reduced pressure.

The residue was purified by silica gel column chromatography (ethyl acetate:hexane=3:2) to obtain 61 mg (yield: 20%) of the title compound. Melting point: 186-187° C. (ethyl acetate-hexane).
¹H-NMR (CDCl₃) δ: 1.13 (9H, s), 1.20 (6H, d, J=6.9 Hz), 1.42 (3H, s), 2.09 (6H, s), 2.27 (2H, s), 2.76-2.90 (2H, m), 3.14 (1H, d, J=15.0 Hz), 3.56 (2H, m), 3.87 (1H, d, J=15.6 Hz), 3.93 (1H, d, J=15.6 Hz), 6.49 (1H, br s), 7.06 (2H, d, J=8.1 Hz), 7.09 (2H, d, J=8.1 Hz), 1H unidentified.

EXAMPLE 336

N-(2-(Iodomethyl)-7-(4-isopropylbenzyl)-2,4,6-trimethyl-2,3-dihydro-1-benzofuran-5-yl)-3,3-dimethylbutanamide A solution of N-(4-hydroxy-3-(4-isopropylbenzyl)-2,6-dimethyl-5-(2-methylprop-2-en-1-yl)phenyl)-3,3-dimethylbutanamide (300 mg, 0.71 mmol) obtained in Reference Example 341, benzyltrimethylammonium iododichloride (272 mg, 0.78 mmol) and calcium carbonate (92 mg, 0.92 mmol) in THF (5 mL)-methanol (5 mL) was stirred at room temperature for 12 hours. Water and an aqueous saturated sodium hydrogen carbonate solution were added to the reaction solution and the product was extracted with ethyl acetate. The organic layer was washed with a 10% aqueous sodium sulfite solution and saturated aqueous sodium bicarbonate solution, dried over anhydrous sodium sulfate, filtered, and then concentrated under reduced pressure to obtain 380 mg (yield: 98%) of the title compound. Oily matter.
¹H-NMR (CDCl₃) δ: 1.04 (9H, s), 1.19 (6H, d, J=6.9 Hz), 1.65 (3H, s), 2.03 (3H, s), 2.06 (3H, s), 2.21 (2H, s), 2.84 (1H, septet, J=6.9 Hz), 2.98 (1H, d, J=15.6 Hz), 3.26 (1H, d, J=15.6 Hz), 3.41 (2H, s), 3.87 (2H, s), 6.68 (1H, br s), 7.05 (2H, d, J=8.1 Hz), 7.10 (2H, d, J=8.1 Hz).

EXAMPLE 337

N-(7-(4-Isopropylbenzyl)-2,4,6-trimethyl-2-(pyrrolidin-1-ylmethyl)-2,3-dihydro-1-benzofuran-5-yl)-3,3-dimethylbutanamide A mixture of N-(2-(iodomethyl)-7-(4-isopropylbenzyl)-2,4,6-trimethyl-2,3-dihydro-1-benzofuran-5-yl)-3,3-dimethylbutanamide (102 mg, 0.19 mmol) obtained in Example 336 and pyrrolidine (1.5 mL) was reacted using a microwave reactor (110° C., hold time 20 min, 250 W). Water was added to the reaction solution and the product was extracted with ethyl acetate. The combined organic layers were washed with water and saturated brine, dried over anhydrous sodium sulfate, filtered, and then concentrated under reduced pressure to obtain 86 mg (yield: 95%) of the title compound. Melting point: 143-144° C. (THF-hexane).
¹H-NMR (CDCl₃) δ: 1.13 (9H, s), 1.19 (6H, d, J=6.9 Hz), 1.43 (3H, s), 1.50-1.75 (4H, m), 2.07 (3H, s), 2.09 (3H, s), 2.26 (2H, s), 2.42-2.63 (4H, m), 2.69 (2H, s), 2.73-2.90 (2H, m), 3.23 (1H, d, J=15.0 Hz), 3.84 (1H, d, J=15.3 Hz), 3.92 (1H, d, J=15.3 Hz), 6.47 (1H, br s), 7.03 (2H, d, J=8.1 Hz), 7.07 (2H, d, J=8.1 Hz).

EXAMPLE 338

3,3-Dimethyl-N-(3-hydroxy-2,2,4,6-tetramethyl-2,3-dihydro-1-benzofuran-5-yl)butanamide Using 3,3-dimethyl-N-(2,2,4,6-tetramethyl-3-oxo-2,3-dihydro-1-benzofuran-5-yl)butanamide obtained in Reference Example 342, the title compound was synthesized in the same manner as in Example 234. Yield: 82%. Melting point: 217-218° C. (THF-hexane).

$^1$H-NMR (CDCl$_3$) δ: 1.15 (9H, s), 1.30 (3H, s), 1.49 (3H, s), 1.78 (1H, d, J=9.0 Hz), 2.19 (3H, s), 2.25 (3H, s), 2.28 (2H, s), 4.69 (1H, d, J=9.0 Hz), 6.51 (1H, s), 6.57 (1H, br s).

EXAMPLE 339

3,3-Dimethyl-N-(2,2,4,6-tetramethyl-2,3-dihydro-1-benzofuran-5-yl)butanamide

To a mixed solution of 3,3-dimethyl-N-(3-hydroxy-2,2,4,6-tetramethyl-2,3-dihydro-1-benzofuran-5-yl)butanamide (2.0 g, 6.55 mmol) obtained in Example 338 in trifluoroacetic acid (3 mL) was added dropwise with ice-cooling triethylsilane (2.09 g, 13.10 mmol). The reaction solution was warmed to room temperature and stirred for 30 minutes. Water was added to the reaction solution and the product was extracted with ethyl acetate. The combined organic layers were washed with an aqueous 1 N sodium hydroxide solution and an aqueous saturated sodium hydrogen carbonate solution, dried over anhydrous sodium sulfate, filtered, and then concentrated under reduced pressure to obtain 1.75 g (yield: 92%) of the title compound. Melting point: 181-182° C. (THF-hexane).

$^1$H-NMR (CDCl$_3$) δ: 1.14 (9H, s), 1.46 (6H, s), 2.08 (3H, s), 2.17 (3H, s), 2.27 (2H, s), 2.91 (2H, s), 6.45 (1H, s), 6.48 (1H, br s).

EXAMPLE 340

N-(7-Formyl-2,2,4,6-tetramethyl-2,3-dihydro-1-benzofuran-5-yl)-3,3-dimethylbutanamide Using 3,3-dimethyl-N-(2,2,4,6-tetramethyl-2,3-dihydro-1-benzofuran-5-yl)butanamide obtained in Example 339, the title compound was synthesized in the same manner as in Example 20. Yield: 85%. Melting point: 180-181° C. (THF-hexane).

$^1$H-NMR (CDCl$_3$) δ: 1.14 (9H, s), 1.52 (6H, s), 2.13 (3H, s), 2.20 (2H, s), 2.47 (3H, s), 2.92 (2H, s), 6.54 (1H, br s), 10.33 (1H, s).

EXAMPLE 341

N-(7-(Hydroxy(4-isopropylphenyl)methyl)-2,2,4,6-tetramethyl-2,3-dihydro-1-benzofuran-5-yl)-3,3-dimethylbutanamide To a mixture of magnesium (198 mg, 8.13 mmol) and a catalytic amount of iodine was added dropwise under argon atmosphere a solution of 1-bromo-4-isopropylbenzene (1.62 g, 8.13 mmol) in THF (5 mL) under argon atmosphere at room temperature, and the reaction solution was heated until the color of iodine disappeared. To the reaction solution was added dropwise at room temperature a solution of N-(7-formyl-2,2,4,6-tetramethyl-2,3-dihydro-2,3-dihydro-1-benzofuran-5-yl)-3,3-dimethylbutanamide obtained in Example 340 (860 mg, 2.71 mmol) in THF (5 mL) and the mixture was stirred for 1 hour. Water was added to the reaction solution and the product was extracted with ethyl acetate.

The combined organic layers were washed with saturated brine, dried over anhydrous sodium sulfate, filtered, and then concentrated under reduced pressure to synthesize 1.15 g (yield: 97%) of the title compound. Amorphous powder.

$^1$H-NMR (CDCl$_3$) δ: 1.13 (9H, s), 1.21 (6H, d, J=6.9 Hz), 1.42 (3H, s), 1.49 (3H, s), 2.07 (3H, s), 2.10 (3H, s), 2.27 (2H, s), 2.85 (1H, septet, J=6.9 Hz), 2.92 (2H, s), 4.17 (1H, d, J=10.2 Hz), 5.86 (1H, d, J=10.2 Hz), 6.59 (1H, br s), 7.11 (2H, d, J=8.1 Hz), 7.25 (2H, d, J=8.1 Hz).

EXAMPLE 342

N-(7-(4-Isopropylbenzoyl)-2,2,4,6-tetramethyl-2,3-dihydro-1-benzofuran-5-yl)-3,3-dimethylbutanamide To a solution of N-(7-(hydroxy(4-isopropylphenyl)methyl)-2,2,4,6-tetramethyl-2,3-dihydro-1-benzofuran-5-yl)-3,3-dimethylbutanamide (209 mg, 0.48 mmol) obtained in Example 341 in dichloromethane (7 mL) was added manganese dioxide (415 mg, 4.8 mmol) and the mixture was stirred at room temperature for 8 hours. The reaction solution was filtered and the filtrate was concentrated. The obtained residue was purified by silica gel column chromatography (ethyl acetate:hexane=2:3) to obtain 156 mg (yield: 75%) of the title compound. Melting point: 194-195° C. (ethyl acetate-hexane).

$^1$H-NMR (CDCl$_3$) δ: 1.15 (9H, s), 1.26 (6H, d, J=7.0 Hz), 1.35 (6H, s), 2.00 (3H, s), 2.14 (3H, s), 2.30 (2H, s), 2.84-3.05 (3H, m), 6.62 (1H, br s), 7.25 (2H, d, J=8.0 Hz), 7.80 (2H, d, J=8.0 Hz).

EXAMPLE 343

N-(7-Bromo-2,2,4,6-tetramethyl-2,3-dihydro-1-benzofuran-5-yl)-3,3-dimethylbutanamide Using 3,3-dimethyl-N-(2,2,4,6-tetramethyl-2,3-dihydro-1-benzofuran-5-yl)butanamide obtained in Example 339, the title compound was synthesized in the same manner as in Reference Example 66. Yield: 85%. Melting point: 205-206° C. (methanol).

$^1$H-NMR (CDCl$_3$) δ: 1.15 (9H, s), 1.51 (6H, s), 2.05 (3H, s), 2.28 (2H, s), 2.28 (3H, s), 3.02 (2H, s), 6.58 (1H, br s).

EXAMPLE 344

N-(7-(4-Isopropylphenoxy)-2,2,4,6-tetramethyl-2,3-dihydro-1-benzofuran-5-yl)-3,3-dimethylbutanamide A mixed solution of N-(7-bromo-2,2,4,6-tetramethyl-2,3-dihydro-1-benzofuran-5-yl)-3,3-dimethylbutanamide (500 mg, 1.36 mmol) obtained in Example 343, 4-isopropylphenol (556 mg, 4.08 mmol) and potassium carbonate (188 mg, 1.36 mmol) in pyridine (16 mL) was stirred at 140° C. under argon atmosphere for 1 hour. Copper iodide (259 mg, 1.36 mmol) was added to the reaction solution and the mixture was stirred at 140° C. for 60 hours. Water was added to the reaction solution and the product was extracted with ethyl acetate. The combined organic layers were washed with 1 N hydrochloric acid and an aqueous saturated sodium hydrogen carbonate solution, dried over anhydrous sodium sulfate, filtered, and then concentrated under reduced pressure. The obtained residue was purified by silica gel column chromatography (ethyl acetate:hexane=1:4) and Gilson HPLC to obtain 230 mg (yield: 40%) of the title compound. Melting point: 148-149° C. (ethyl acetate-hexane).

$^1$H-NMR (CDCl$_3$) δ: 1.14 (9H, s), 1.20 (6H, d, J=6.9 Hz), 1.42 (6H, s), 2.00 (3H, s), 2.11 (3H, s), 2.27 (2H, s), 2.84 (1H, septet, J=6.9 Hz), 2.97 (2H, s), 6.56 (1H, br s), 6.77 (2H, d, J=8.7 Hz), 7.06 (2H, d, J=8.7 Hz).

EXAMPLE 345

3,3-Dimethyl-N-(2,2,4,6-tetramethyl-7-(4-methylphenoxy)-2,3-dihydro-1-benzofuran-5-yl)butanamide Using N-(7-bromo-2,2,4,6-tetramethyl-2,3-dihydro-1-benzofuran-5-yl)-3,3-dimethylbutanamide obtained in Example 343 and 4-methylphenol, the title compound was synthesized in the same manner as in Example 344. Yield: 19%. Melting point: 182-184° C. (hexane).

$^1$H-NMR (CDCl$_3$) δ: 1.12 (9H, s), 1.35 (3H, s), 1.48 (3H, s), 1.98 (3H, br s), 2.08 (3H, s), 2.25 (2H, s), 2.86-2.97 (2H, m), 5.28 (1H, br s), 6.14 (1H, d, J=3.84 Hz), 6.66 (1H, br s), 7.11-7.17 (2H, m), 7.54-7.59 (1H, m), 8.51 (1H, d, J=5.0 Hz).

EXAMPLE 346

N-(3-Hydroxy-7-(4-isopropylbenzyl)-2,2,4,6-tetramethyl-2,3-dihydro-1-benzofuran-5-yl)-3,3-dimethylbutanamide Using N-(7-(4-isopropylbenzyl)-2,2,4,6-tetramethyl-3-oxo-2,3-dihydro-1-benzofuran-5-yl)-3,3-dimethylbutanamide obtained in Reference Example 330, the title compound was synthesized in the same manner as in Example 234. Yield: 81%. Melting point: 244-245° C. (THF-hexane).

$^1$H-NMR (CDCl$_3$) δ: 1.13 (9H, s), 1.20 (6H, d, J=6.9 Hz), 1.33 (3H, s), 1.51 (3H, s), 2.09 (3H, s), 2.26 (5H, m), 2.84 (1H, septet, J=6.9 Hz), 3.91 (2H, d, J=15.0 Hz), 4.76 (1H, d, J=8.7 Hz), 6.53 (1H, br s), 7.07 (4H, s), 1H unidentified.

EXAMPLE 347

N-(3-Hydroxy-7-(4-isopropylbenzyl)-2,2,3,4,6-pentamethyl-2,3-dihydro-1-benzofuran-5-yl)-3,3-dimethylbutanamide Using N-(7-(4-isopropylbenzyl)-2,2,4,6-tetramethyl-3-oxo-2,3-dihydro-1-benzofuran-5-yl)-3,3-dimethylbutanamide obtained in Reference Example 330 and methylmagnesium bromide, the title compound was synthesized in the same manner as in Example 239. Yield: 92%. Melting point: 170-171° C. (ethyl acetate-hexane).

$^1$H-NMR (CDCl$_3$) δ: 1.13 (9H, s), 1.20 (6H, d, J=6.9 Hz), 1.33 (3H, s), 1.41 (3H, s), 1.44 (3H, s), 2.08 (3H, s), 2.27 (2H, s), 2.32 (3H, s), 2.83 (1H, septet, J=6.9 Hz), 3.91 (2H, br), 6.49 (1H, br s), 7.06 (4H, s), 1H unidentified.

EXAMPLE 348

N-(3-(4-Isopropylphenyl)-4,6,7-trimethyl-3H-spiro(1-benzofuran-2,1'-cyclopentan)-5-yl)-3,3-dimethylbutanamide Using 3-(4-isopropylphenyl)-4,6,7-trimethyl-3H-spiro(1-benzofuran-2,1'-cyclopentane)-5-amine obtained in Reference Example 325, the title compound was synthesized in the same manner as in Example 1. Yield: 57%. Melting point: 209-210° C. (hexane-ethyl acetate).

$^1$H-NMR (CDCl$_3$) δ: 1.06-1.38 (16H, m), 1.50-1.92 (9H, m), 1.99-2.08 (1H, m), 2.14 (3H, s), 2.15 (3H, s), 2.24 (2H, s), 2.84 (1H, septet, J=6.9 Hz), 4.16 (1H, s), 6.48 (1H, br s), 6.88 (2H, d, J=8.1 Hz), 7.05 (2H, d, J=8.1 Hz).

EXAMPLE 349

N-((cis)-3-(4-Isopropylphenyl)-2,6,7-trimethyl-2,3-dihydro-1-benzofuran-5-yl)-3,3-dimethylbutanamide Using (cis)-3-(4-isopropylphenyl)-2,6,7-trimethyl-2,3-dihydro-1-benzofuran-5-amine hydrochloride obtained in Reference Example 351 and tert-butylacetyl chloride, the title compound was synthesized in the same manner as in Example 316. Yield: 83%. Melting point: 94-95° C. (hexane).

$^1$H-NMR (CDCl$_3$) δ: 1.03 (3H, d, J=7.0 Hz), 1.09 (9H, s), 1.22 (6H, d, J=7.0 Hz), 2.15 (3H, s), 2.19 (2H, s), 2.21 (3H, s), 2.86 (1H, septet, J=7.0 Hz), 4.31 (1H, d, J=8.0 Hz), 4.96-5.05 (1H, m), 6.72 (1H, s), 6.89 (2H, d, J=8.0 Hz), 7.00 (1H, s), 7.11 (2H, d, J=8.0 Hz).

EXAMPLE 350

(cis)-3-(4-Isopropylphenyl)-2,4,6,7-tetramethyl-2,3-dihydro-1-benzofuran-5-amine Using (cis)-3-(4-isopropylphenyl)-2,4,6,7-tetramethyl-2,3-dihydro-1-benzofuran obtained in Reference Example 352, (cis)-5-bromo-3-(4-isopropylphenyl)-2,4,6,7-tetramethyl-2,3-dihydro-1-benzofuran was synthesized in the same manner as in Reference Example 23. Using the compound, (cis)-N-benzyl-3-(4-isopropylphenyl)-2,4,6,7-tetramethyl-2,3-dihydro-1-benzofuran-5-amine was synthesized in the same manner as in Reference Example 24. Using the compound, the title compound was synthesized in the same manner as in Reference Example 30. Yield: 83%. Melting point: 91-92° C. (hexane).

$^1$H-NMR (200 MHz, CDCl$_3$) δ: 1.06 (3H, d, J=7.0 Hz), 1.21 (6H, d, J=7.0 Hz), 1.84 (3H, s), 2.12 (3H, s), 2.21 (3H, s), 2.85 (1H, septet, J=7.0 Hz), 3.25 (2H, br s), 4.29 (1H, d, J=8.0 Hz), 4.83-4.96 (1H, m), 6.83 (2H, d, J=8.0 Hz), 7.07 (2H, d, J=8.0 Hz).

EXAMPLE 351

N-((trans)-3-(4-Isopropylphenyl)-2,4,6,7-tetramethyl-2,3-dihydro-1-benzofuran-5-yl)-3,3-dimethylbutanamide Using 3-(4-isopropylphenyl)-2,4,6,7-tetramethyl-1-benzofuran obtained in Reference Example 347, a mixture of cis isomer and trans isomer (3:2) of 3-(4-isopropylphenyl)-2,4,6,7-tetramethyl-2,3-dihydro-1-benzofuran was synthesized in the same manner as in Reference Example 199. Using the mixture as it is as the compound, a mixture of cis isomer and trans isomer of 5-bromo-3-(4-isopropylphenyl)-2,4,6,7-tetramethyl-2,3-dihydro-1-benzofuran was obtained in the same manner as in Reference Example 23. Using the compound, a mixture of cis isomer and trans isomer of N-benzyl-(3-(4-isopropylphenyl)-2,4,6,7-tetramethyl-2,3-dihydro-1-benzofuran-5-yl)amine was obtained in the same manner as in Reference Example 24. Using the compound, (3-(4-isopropylphenyl)-2,4,6,7-tetramethyl-2,3-dihydro-1-benzofuran-5-yl)amine was synthesized in the same manner as in Reference Example 30. Using the compound and tert-butylacetyl chloride, a mixture of cis isomer and trans isomer of N-(3-(4-isopropylphenyl)-2,4,6,7-tetramethyl-2,3-dihydro-1-benzofuran-5-yl)-3,3-dimethylbutanamide was obtained in the same manner as in Example 1. The compound was purified by silica gel column chromatography (ethyl acetate:hexane=1:4) to synthesize the title compound. Yield: 18%. Melting point: 143-144° C. (hexane)

$^1$H-NMR (CDCl$_3$) δ: 1.12 (9H, s), 1.22 (6H, d, J=7.0 Hz), 1.46 (3H, d, J=6.0 Hz), 1.76 (3H, s), 2.14 (3H, s), 2.17 (3H, s), 2.24 (2H, s), 2.86 (1H, septet, J=7.0 Hz), 4.08 (1H, d, J=6.0 Hz), 4.58-4.67 (1H, m), 6.48 (1H, s), 7.05 (2H, d, J=8.0 Hz), 7.13 (2H, d, J=8.0 Hz).

EXAMPLE 352

N-(7-(Hydroxy(pyridin-2-yl)methyl)-2,2,4,6-tetramethyl-2,3-dihydro-1-benzofuran-5-yl)-3,3-dimethylbutanamide To a solution of 2-bromopyridine (553 mg, 3.5 mmol) in diethyl ether (3.0 mL) was added dropwise at −70° C. under argon atmosphere n-butyllithium (1.6 M, hexane solution, 2.13 mL, 3.4 mmol) and the mixture was stirred for 30 minutes. To the reaction solution was added dropwise at −70° C. a solution of N-(7-formyl-2,2,4,6-tetramethyl-2,3-dihydro-1-benzofuran-5-yl)-3,3-dimethylbutanamide (317 mg, 1.0 mmol) obtained in Example 340 in THF (4.0 mL) and the mixture was stirred for 30 minutes, and then warmed to room temperature. Water was added to the reaction solution and the product was extracted with ethyl acetate. The organic layer was washed with saturated brine, dried over anhydrous sodium sulfate, and then concentrated under reduced pressure. The residue was purified by basic silica gel column chromatography (ethyl acetate:hexane=1:10), and then by silica gel column chromatography (ethyl acetate:hexane=1:1) to obtain 270 mg (yield: 68%) of the title compound. Melting point: 176-177° C. (ethyl acetate-hexane).

$^1$H-NMR (CDCl$_3$) δ: 1.12 (9H, s), 1.35 (3H, s), 1.48 (3H, s), 1.98 (3H, br s), 2.08 (3H, s), 2.25 (2H, s), 2.86-2.97 (2H, m), 5.28 (1H, br s), 6.14 (1H, d, J=3.84 Hz), 6.66 (1H, br s), 7.11-7.17 (2H, m), 7.54-7.59 (1H, m), 8.51 (1H, d, J=5.0 Hz).

EXAMPLE 353

N-(7-(1-Hydroxy-2-(4-isopropylphenyl)ethyl)-2,2,4,6-tetramethyl-2,3-dihydro-1-benzofuran-5-yl)-3,3-dimethylbutanamide Using N-(7-formyl-2,2,4,6-tetramethyl-2,3-dihydro-2,3-dihydro-1-benzofuran-5-yl)-3,3-dimethylbutanamide obtained in Example 340 and 4-isopropylbenzyl chloride, the title compound was synthesized in the same manner as in Example 341. Yield: 92%. Amorphous substance.

$^1$H-NMR (CDCl$_3$) δ: 1.12 and 1.17 (9H, s x 2), 1.20-1.25 (6H, m), 1.45 and 1.48 (6H, s x 2), 1.88 (3H, s), 2.05 and 2.07 (3H, s x 2), 2.24 and 2.25 (2H, s x 2), 2.79-3.11 (5H, m), 3.76 (1H, br d, J=16.0 Hz), 4.87-5.00 (1H, m), 6.69 (1H, br s), 7.03-7.13 (4H, m).

EXAMPLE 354

N-(7-(2-(4-Isopropylphenyl)ethyl))-2,2,4,6-tetramethyl-2,3-dihydro-1-benzofuran-5-yl)-3,3-dimethylbutanamide Using N-(7-(1-hydroxy-2-(4-isopropylphenyl)ethyl)-2,2,4,6-tetramethyl-2,3-dihydro-1-benzofuran-5-yl)-3,3-dimethylbutanamide obtained in Example 353, the title compound was synthesized in the same manner as in Example 271. Yield: 64%. Melting point: 144-145° C. (hexane-ethyl acetate).

$^1$H-NMR (CDCl$_3$) δ: 1.15 (9H, s), 1.23 (3H, s), 1.25 (3H, s), 1.43 (6H, s), 2.07 (3H, s), 2.13 (3H, s), 2.29 (2H, s), 2.69-2.88 (5H, m), 2.92 (2H, br s), 6.51 (1H, br s), 7.15 (4H, s).

EXAMPLE 355

N-(7-(1-Hydroxy(phenyl)methyl)-2,2,4,6-tetramethyl-2,3-dihydro-1-benzofuran-5-yl)-3,3-dimethylbutanamide Using N-(7-formyl-2,2,4,6-tetramethyl-2,3-dihydro-1-benzofuran-5-yl)-3,3-dimethyl-butanamide obtained in Example 340 and phenylmagnesium bromide, the title compound was synthesized in the same manner as in Example 239. The yield was quantitative. Amorphous substance.

$^1$H-NMR (CDCl$_3$) δ: 1.13 (9H, s), 1.38 (3H, s), 1.49 (3H, s), 2.07 (3H, s), 2.10 (3H, s), 2.27 (2H, s), 2.92 (2H, s), 4.24 (1H, br d, J=10.0 Hz), 5.91 (1H, d, J=10.0 Hz), 6.68 (1H, br s), 7.20-7.36 (5H, m).

EXAMPLE 356

N-((7-Benzyl)-2,2,4,6-tetramethyl-2,3-dihydro-1-benzofuran-5-yl)-3,3-dimethylbutanamide Using N-(7-(1-hydroxy(phenyl)methyl)-2,2,4,6-tetramethyl-2,3-dihydro-1-benzofuran-5-yl)-3,3-dimethylbutanamide obtained in Example 355, the title compound was synthesized in the same manner as in Example 271. Yield: 74%. Melting point: 129-130° C. (ethyl acetate-hexane).

$^1$H-NMR (CDCl$_3$) δ: 1.12 (9H, s), 1.46 (6H, s), 2.04 (3H, s), 2.08 (3H, s), 2.25 (2H, s), 2.96 (2H, br s), 3.93 (2H, br s), 6.49 (1H, br s), 7.10-7.20 (5H, m).

EXAMPLE 357

3,3-Dimethyl-N-(2,2,4,6-tetramethyl-7-(2-methylbenzyl)-2,3-dihydro-1-benzofuran-5-yl)butanamide Using N-(7-formyl-2,2,4,6-tetramethyl-2,3-dihydro-1-benzofuran-5-yl)-3,3-dimethyl-butanamide obtained in Example 340 and 2-methylphenylmagnesium bromide, N-(7-(hydroxy(2-methylphenyl)methyl)-2,2,4,6-tetramethyl-2,3-dihydro-1-benzofuran-5-yl)-3,3-dimethylbutanamide was synthesized in the same manner as in Example 239. Using the compound, the title compound was synthesized in the same manner as in Example 271. Yield: 24%. Melting point: 175-176° C. (ethyl acetate-hexane).

$^1$H-NMR (CDCl$_3$) δ: 1.13 (9H, s), 1.41 (6H, s), 1.94 (3H, s), 2.12 (3H, s), 2.27 (2H, s), 2.38 (3H, s), 2.96 (2H, br s), 3.85 (2H, br s), 6.54 (1H, br s), 6.76 (1H, d, J=7.0 Hz), 6.98-7.14 (3H, m)

EXAMPLE 358

N-((3R)-7-(2-Furyl)-3-(4-isopropylphenyl)-4,6-dimethyl-2,3-dihydro-1-benzofuran-5-yl)-3,3-dimethylbutanamide Using (−)-N-((3R)-7-bromo-3-(4-isopropylphenyl)-4,6-dimethyl-2,3-dihydro-1-benzofuran-5-yl)-3,3-dimethylbutanamide obtained in Example 51 and 2-furyl(diphenyl)methanol, the title compound was obtained in the same manner as in Example 107. Yield: 6%. Melting point: 214-217° C. (ethyl acetate-hexane).

$^1$H-NMR (CDCl$_3$) δ: 1.12 (9H, s), 1.22 (6H, d, J=6.9 Hz), 1.89 (3H, s), 2.27 (5H, s), 2.86 (1H, septet, J=6.9 Hz), 4.46 (1H, dd, J=4.9, 8.6 Hz), 4.56 (1H, dd, J=4.9, 9.1 Hz), 4.87 (1H, dd, J=8.6, 9.1 Hz), 6.51 (1H, dd, J=1.6, 3.3 Hz), 6.53 (1H, s), 6.58 (1H, d, J=3.3 Hz), 7.07 (2H, d, J=8.2 Hz), 7.13 (2H, d, J=8.2 Hz), 7.53 (1H, d, J=1.6 Hz).

EXAMPLE 359

N-((3R)-7-Benzoyl-3-(4-isopropylphenyl)-4,6-dimethyl-2,3-dihydro-1-benzofuran-5-yl)-3,3-dimethylbutanamide Using (+)-N-((3R)-3-(4-isopropylphenyl)-4,6-dimethyl-2,3-dihydro-1-benzofuran-5-yl)-3,3-dimethylbutanamide obtained in Example 37 and benzoyl chloride, the title compound was obtained in the same manner as in Example 38.

Yield: 74%. Melting point: 205-206° C. (ethyl acetate-hexane).

$^1$H-NMR (CDCl$_3$) δ: 1.11 (9H, s), 1.23 (6H, d, J=6.9 Hz), 1.93 (3H, s), 2.07 (3H, s), 2.27 (2H, s), 2.87 (1H, septet, J=6.9 Hz), 4.34 (1H, dd, J=4.9, 8.6 Hz), 4.54 (1H, dd, J=4.9, 9.1 Hz), 4.77 (1H, dd, J=8.6, 9.1 Hz), 6.59 (1H, s), 7.06 (2H, d, J=7.9 Hz), 7.14 (2H, d, J=7.9 Hz), 7.46 (2H, dd, J=7.4, 7.7 Hz), 7.57 (1H, t, J=7.4 Hz), 7.92 (2H, d, J=7.7 Hz).

The structures of the compounds of Examples are shown in the following tables 1 to 7.

TABLE 1

| Example | X | R$^2$ | R$^3$ | R$^4$ | R$^{7a}$ | R$^{7b}$ | R$^{7c}$ | R$^{7d}$ | comment |
|---|---|---|---|---|---|---|---|---|---|
| 1 | O | H | 4-iPrPh | H | Me | t-BuCH$_2$CONH | Me | Me | |
| 2 | O | H | 4-iPrPh | H | H | t-BuCH$_2$CONH | Me | Me | |
| 3 | O | H | 4-iPrPh | H | Me | t-BuCH$_2$CONH | Me | H | |
| 4 | O | H | 4-iPrPh | H | H | t-BuCH$_2$CONH | H | H | |
| 5 | O | H | 4-iPrPh | Me | Me | t-BuCH$_2$CONH | Me | Me | |
| 6 | O | H | 4-iPrPh | Me | H | t-BuCH$_2$CONH | Me | Me | |
| 7 | O | H | 4-iPrPh | H | Me | t-BuCH$_2$CONH | Me | Me | (R)-(+) form |
| 8 | O | H | 4-iPrPh | H | Me | t-BuCH$_2$CONH | Me | Me | (S)-(−) form |
| 9 | O | H | 4-iPrPh | H | Me | CH$_3$CH$_2$CONH | Me | Me | |
| 10 | O | H | 4-iPrPh | H | Me | CH$_3$(CH$_2$)$_2$CONH | Me | Me | |
| 11 | O | H | 4-iPrPh | H | Me | CH$_3$(CH$_2$)$_3$CONH | Me | Me | |
| 12 | O | H | 4-iPrPh | H | Me | 4-MeOPhCH$_2$CONH | Me | Me | |
| 13 | O | H | 4-iPrPh | H | Me | 4-MeOPh(CH$_2$)$_2$CONH | Me | Me | |
| 14 | O | H | 4-iPrPh | H | Me | t-BuNHCONH | Me | Me | |
| 15 | O | H | 4-iPrPh | H | Me | EtOC(O)CONH | Me | Me | |
| 16 | O | H | 4-iPrPh | H | Me | t-BuC(O)CONH | Me | Me | |
| 17 | O | H | 4-iPrPh | H | Me | EtC(O)CONH | Me | Me | |
| 18 | O | H | 4-iPrPh | H | Me | EtCH(OH)CONH | Me | Me | |
| 19 | O | H | 4-iPrPh | H | Me | t-BuCH(OH)CONH | Me | Me | |
| 20 | O | H | 4-iPrPh | H | Me | t-BuCH$_2$CONH | Me | CHO | |
| 21 | O | H | 4-iPrPh | H | Me | t-BuCH$_2$CONH | Me | CH$_2$OH | |
| 22 | O | H | 4-iPrPh | H | Me | t-BuCH$_2$CONH | Me | MeCH(OH) | |
| 23 | O | H | 4-iPrPh | H | Me | t-BuCH$_2$CONH | Me | Et | |
| 24 | O | H | 4-iPrPh | H | Me | t-BuCH$_2$CON(Me) | Me | Me | less polar |
| 25 | O | H | 4-iPrPh | H | Me | t-BuCH$_2$CON(Me) | Me | Me | more polar |
| 26 | O | H | 4-iPrPh | H | Me | t-BuCH$_2$CONH | Me | CH$_2$pyrrolidine | |
| 27 | O | H | 4-iPrPh | H | Me | t-BuCH$_2$CONH | Me | CH$_2$NMe$_2$ | |
| 28 | O | H | 4-iPrPh | H | Me | t-BuCH$_2$CONH | Me | MeCH(OH) | less polar |
| 29 | O | H | 4-iPrPh | H | Me | t-BuCH$_2$CONH | Me | MeCH(OH) | more polar |
| 30 | O | H | 4-iPrPh | H | Me | t-BuCH$_2$CONH | Me | EtCH(OH) | less polar |
| 31 | O | H | 4-iPrPh | H | Me | t-BuCH$_2$CONH | Me | EtCH(OH) | more polar |
| 32 | O | H | 4-iPrPh | H | Me | t-BuCH$_2$CONH | Me | Ac | |
| 33 | O | H | 4-iPrPh | H | Me | t-BuCH$_2$CONH | Me | Me$_2$C(OH) | |
| 34 | O | H | 4-iPrPh | H | Me | t-BuCH$_2$CONH | Me | n-Pr | |
| 35 | O | H | 4-iPrPh | H | Me | t-BuCH$_2$CONH | Me | Br | |
| 36 | O | H | 4-iPrPh | H | Me | t-BuCH$_2$CONH | Me | MeO | |

TABLE 1-continued

| Example | X | R² | R³ | R⁴ | R⁷ᵃ | R⁷ᵇ | R⁷ᶜ | R⁷ᵈ | comment |
|---|---|---|---|---|---|---|---|---|---|
| 37 | O | H | 4-iPrPh | H | Me | t-BuCH₂CONH | Me | H | (R)-(+) form |
| 38 | O | H | 4-iPiPh | H | Me | t-BuCH₂CONH | Me | Ac | (R)-(+) form |
| 39 | O | H | 4-iPrPh | H | Me | t-BuCH₂CONH | Me | CHO | (R)-(−) form |
| 40 | O | H | 4-iPrPh | H | Me | t-BuCH₂CONH | Me | MeCH(OH) | less polar (R)-(+) form |
| 41 | O | H | 4-iPrPh | H | Me | t-BuCH₂CONH | Me | MeCH(OH) | more polar (R)-(+) form |
| 42 | O | H | 4-iPrPh | H | Me | t-BuCH₂CONH | Me | Et | (R)-(+) form |
| 43 | O | H | 4-iPrPh | H | Me | t-BuCH₂CONH | Me | EtCH(OH) | less polar (R)-(+) form |
| 44 | O | H | 4-iPrPh | H | Me | t-BuCH₂CONH | Me | EtCH(OH) | more polar (R)-(+) form |
| 45 | O | H | 4-iPrPh | H | Me | t-BuCH₂CONH | Me | n-Pr | (R)-(+) form |
| 46 | O | H | 4-iPrPh | H | Me | t-BuCH₂CONH | Me | Me₂C(OH) | (R)-(+) form |
| 47 | O | H | 4-iPrPh | H | Me | t-BuNHCONH | Me | H | (R)-(+) form |
| 48 | O | H | 4-iPrPh | H | Me | t-BuNHCONH | Me | CHO | (R)-(−) form |
| 49 | O | H | 4-iPrPh | H | Me | t-BuNHCONH | Me | CH₂OH | (R)-(+) form |
| 50 | O | H | 4-iPrPh | H | Me | t-BuNHCONH | Me | Me | (R)-(+) form |
| 51 | O | H | 4-iPrPh | H | Me | t-BuCH₂CONH | Me | Br | (R)-(−) form |
| 52 | O | H | 4-iPrPh | H | Me | t-BuCH₂CONH | Me | MeO | (R)-(+) form |

TABLE 2

| Example | X | R¹ | R² | R³ | R⁴ | R⁷ᵃ | R⁷ᵇ | R⁷ᶜ | R⁷ᵈ | comment |
|---|---|---|---|---|---|---|---|---|---|---|
| 53 | O | H | H | 4-iPr-Ph | H | Me | MeSO₂NH | Me | Me | |
| 54 | O | H | H | 4-iPr-Ph | H | Me | nBuSO₂NH | Me | Me | |
| 55 | O | H | H | 4-iPr-Ph | H | Me | CF₃(CH₂)₃SO₂NH | Me | Me | |
| 56 | O | H | H | 4-iPr-Ph | H | Me | EtSO₂NH | Me | Me | |
| 57 | O | H | H | 4-iPr-Ph | H | Me | nPrSO₂NH | Me | Me | |
| 58 | O | H | H | 4-iPr-Ph | H | Me | OHCNH | Me | H | |
| 59 | O | H | H | 4-iPr-Ph | H | Me | OHCNH | Me | Br | |
| 60 | O | H | H | 4-iPr-Ph | H | Me | OHCNH | Me | CHO | |
| 61 | O | H | H | 4-iPr-Ph | H | Me | t-BuCH₂CONH | Me | (CH₂)₂CO₂Et | |
| 62 | O | H | H | 4-iPr-Ph | H | Me | t-BuCH₂CONH | Me | (CH₂)₃OH | |
| 63 | O | H | H | 4-iPr-Ph | H | Me | t-BuCH₂CONH | Me | Me | |
| 64 | O | H | H | 4-iPr-Ph | H | Me | t-BuCH₂CONH | H | Me | |
| 65 | O | H | H | 4-iPr-Ph | H | Me | Me | t-BuCH₂CONH | Me | |
| 66 | O | H | H | 4-iPr-Ph | H | Me | Me | Me | t-BuCH₂CONH | |
| 67 | O | H | H | 4-iPr-Ph | H | Me | BzO(CH₂)₃CONH | Me | Me | |
| 68 | O | H | H | 4-iPr-Ph | H | Me | t-BuCH₂CONH | CH=CH—CH=CH | | |
| 69 | O | H | H | 4-iPr-Ph | H | Me | t-BuCH₂CONH | (CH₂)₄ | | |
| 70 | O | H | H | 4-iPr-Ph | H | Me | t-BuCH₂CONH | (CH₂)₃ | | |
| 71 | O | H | H | 4-iPr-Ph | H | Me | t-BuCH₂CONH | Me | H | |
| 72 | O | H | H | 3-MeO-Ph | H | Me | t-BuCH₂CONH | Me | Me | s-form |
| 73 | O | H | H | 3-(1,3-dioxolan-2-yl)-Ph | H | Me | t-BuCH₂CONH | Me | Me | |
| 74 | O | H | H | 4-iPr-2-MeO-Ph | H | Me | t-BuCH₂CONH | Me | Me | |
| 75 | O | H | H | Ph | H | Me | t-BuCH₂CONH | Me | Me | |
| 76 | O | H | H | 4-Me-Ph | H | Me | t-BuCH₂CONH | Me | Me | |
| 77 | O | H | H | biphenyl | H | Me | t-BuCH₂CONH | Me | Me | |
| 78 | O | H | H | 5-Me-2-Py | H | Me | t-BuCH₂CONH | Me | Me | |
| 79 | O | H | H | 4-Et-Ph | H | Me | t-BuCH₂CONH | Me | Me | |
| 80 | O | H | H | 4-iBu-Ph | H | Me | t-BuCH₂CONH | Me | Me | |

TABLE 2-continued

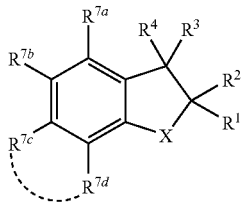

| Example | X | $R^1$ | $R^2$ | $R^3$ | $R^4$ | $R^{7a}$ | $R^{7b}$ | $R^{7c}$ | $R^{7d}$ | comment |
|---|---|---|---|---|---|---|---|---|---|---|
| 81 | O | H | H | 4-cHex-Ph | H | Me | t-BuCH$_2$CONH | Me | Me | |
| 82 | O | H | H | 4-(1,3-dioxolan-2-yl)-Ph | H | Me | t-BuCH$_2$CONH | Me | Me | |
| 83 | O | H | H | 4-iPr-Ph | H | Me | t-BuCH$_2$CONH | Me | CH=CH$_2$ | |
| 84 | O | H | H | 4-iPr-Ph | H | Me | t-BuCH$_2$CONH | Me | CH(OH)CH$_2$OH | |
| 85 | O | H | H | 4-iPr-Ph | H | Me | t-BuCH$_2$CONH | Me | (CH$_2$)$_2$OH | |
| 86 | O | H | H | 4-iPr-Ph | H | Me | t-BuCH$_2$CONH | Me | EtCO | |
| 87 | O | H | H | 4-iPr-Ph | H | Me | t-BuCH$_2$CONH | Br | Me | |
| 88 | O | H | H | 4-iPr-Ph | H | OMe | t-BuCH$_2$CONH | Me | Me | |
| 89 | O | H | H | 4-iPr-Ph | H | Me | t-BuCH$_2$CONH | OMe | Me | |
| 90 | O | H | H | 4-iPr-Ph | H | Me | t-BuCH$_2$CONH | Me | CH(OH)(CH$_2$)$_2$CH$_3$ | |
| 91 | O | H | H | 4-iPr-Ph | H | Me | t-BuCH$_2$CONH | Me | CH(OH)(CH$_2$)$_2$CH$_3$ | |
| 92 | O | H | H | 4-iPr-Ph | H | Me | t-BuCH$_2$CONH | Me | nBu | less polar |
| 93 | O | H | H | 4-iPr-Ph | H | Me | HO(CH$_2$)$_3$CONH | Me | Me | more polar |
| 94 | O | H | H | 4-iPr-Ph | H | Me | t-BuCH$_2$CONH | Me | CH(OH)Ph | |
| 95 | O | H | H | 4-iPr-Ph | H | Me | t-BuCH$_2$CONH | Me | CH(OH)(4-iPr-Ph) | |
| 96 | O | H | H | 4-iPr-Ph | H | Me | t-BuCH$_2$CONH | Me | CH$_2$Ph | |
| 97 | O | H | H | 4-iPr-Ph | H | Me | t-BuCH$_2$CONH | Me | CH$_2$(4-iPr-Ph) | |
| 98 | O | H | H | 4-iPr-Ph | H | Me | t-BuCH$_2$CONH | Me. | COOH | |
| 99 | O | H | H | 4-iPr-Ph | H | Me | t-BuCH$_2$CONH | Me | CN | |
| 100 | O | H | H | 4-iPr-Ph | H | Me | t-BuCH$_2$CONH | Me | Ac | |
| 101 | O | H | H | 4-iPr-Ph | H | Me | t-BuCH$_2$CONH | Me | Ph | |
| 102 | O | H | H | 4-iPr-Ph | H | Me | t-BuCH$_2$CONH | Me | 6-MeO-3-Py | s-form |
| 103 | O | H | H | 4-iPr-Ph | H | Me | t-BuCH$_2$CONH | Me | 4-MeO-Ph | |
| 104 | O | H | H | 4-iPr-Ph | H | Me | t-BuCH$_2$CONH | Me | 6-F-3-Py | |

TABLE 3

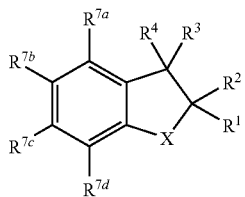

| Example | X | $R^1$ | $R^2$ | $R^3$ | $R^4$ | $R^{7a}$ | $R^{7b}$ | $R^{7c}$ | $R^{7d}$ | comment |
|---|---|---|---|---|---|---|---|---|---|---|
| 105 | O | H | H | 4-iPr-Ph | H | Me | t-BuCH$_2$CONH | Me | 3-MeO-Ph | |
| 106 | O | H | H | 4-iPr-Ph | H | Me | t-BuCH$_2$CONH | Ph | Me | |
| 107 | O | H | H | 4-iPr-Ph | H | Me | t-BuCH$_2$CONH | Me | 3-(AcNH)-Ph | |
| 108 | O | H | H | 4-iPr-Ph | H | Me | t-BuCH$_2$CONH | Me | 3-F-Ph | |
| 109 | O | H | H | 4-iPr-Ph | H | Me | t-BuCH$_2$CONH | Me | 3-NO$_2$-Ph | |
| 110 | O | H | H | 4-iPr-Ph | H | Me | t-BuCH$_2$CONH | Me | 3-(CO$_2$Me)-Ph | |
| 111 | O | H | H | 4-iPr-Ph | H | Me | t-BuCH$_2$CONH | Me | 3-AcPh | |
| 112 | O | H | H | 4-iPr-Ph | H | Me | t-BuCH$_2$CONH | Me | 3-(CO$_3$Et)-Ph | |
| 113 | O | H | H | 4-iPr-Ph | H | Me | t-BuCH$_2$CONH | Me | 4-Me-Ph | (R)-(+) form |
| 114 | O | H | H | 4-iPr-Ph | H | Me | t-BuCH$_2$CONH | Me | 3-Py | |
| 115 | O | H | H | 4-iPr-Ph | H | Me | t-BuCH$_2$CONH | Me | 4-Py | |
| 116 | O | H | H | 4-iPr-Ph | H | Me | t-BuCH$_2$CONH | Me | B(OH)$_2$ | |
| 117 | O | H | H | 4-iPr-Ph | H | Me | t-BuCH$_2$CONH | Me | 2-Py | |
| 118 | O | H | H | 4-iPr-Ph | H | Me | t-BuCH$_2$CONH | Me | 5-Me-2-Py | |
| 119 | O | H | H | 4-iPr-Ph | H | Me | t-BuCH$_2$CONH | Me | 6-NH$_2$-2-Py | |
| 120 | O | H | H | 4-iPr-Ph | H | Me | t-BuCH$_2$CONH | Me | 3-(Me$_2$N)-Ph | |
| 121 | O | H | H | 4-iPr-Ph | H | Me | t-BuCH$_2$CONH | Me | 6-(AcNH)-2-Py | |
| 122 | O | H | H | 4-iPr-Ph | H | Me | t-BuCH$_2$CONH | Me | 3-NH$_2$-Ph | |
| 123 | O | H | H | 4-iPr-Ph | H | Me | t-BuCH$_2$CONH | Me | 3-(EtCONH)-Ph | |
| 124 | O | H | H | 4-iPr-Ph | H | Me | t-BuCH$_2$CONH | Me | 5-pyrimidinyl | |
| 125 | O | H | H | 4-iPr-Ph | H | Me | t-BuCH$_2$CONH | Me | 2-thiazoiyl | |
| 126 | O | H | H | 4-iPr-Ph | H | Me | t-BuCH$_2$CONH | Me | 3-thienyl | |
| 127 | O | H | H | 4-iPr-Ph | H | Me | t-BuCH$_2$CONH | Me | 4-imidazolyl | |
| 128 | O | H | H | 4-iPr-Ph | H | Me | t-BuCH$_2$CONH | Me | 3-furyl | |

TABLE 3-continued

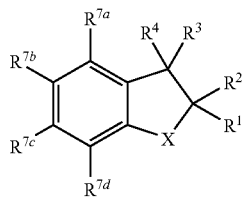

| Example | X | R¹ | R² | R³ | R⁴ | R⁷ᵃ | R⁷ᵇ | R⁷ᶜ | R⁷ᵈ | comment |
|---|---|---|---|---|---|---|---|---|---|---|
| 129 | O | H | H | 4-iPr-Ph | H | Me | t-BuCH₂CONH | Me | 2-pyrrolyl | |
| 130 | O | H | H | 4-iPr-Ph | H | Me | t-BuCH₂CONH | Me | 2-thienyl | |
| 131 | O | H | H | 4-iPr-Ph | H | Me | t-BuCH₂CONH | Me | 5-Ac-2-thienyl | |
| 132 | O | H | H | 4-iPr-Ph | H | Me | t-BuCH₂CONH | Me | 5-Ac-3-thienyl | |
| 133 | O | H | H | 4-iPr-Ph | H | Me | t-BuCH₂CONH | Me | 4-Me-2-thiazolyl | |
| 134 | O | H | H | 4-iPr-Ph | H | Me | t-BuCH₂CONH | Me | OH | |
| 135 | O | H | H | 4-iPr-Ph | H | Me | t-BuCH₂CONH | Me | OH | |
| 136 | O | H | H | 4-iPr-Ph | H | Me | t-BuCH₂CONH | Me | EtO | |
| 137 | O | H | H | 4-iPr-Ph | H | Me | t-BuOCONH | Me | Me | |
| 138 | O | H | H | 4-iPr-Ph | H | Me | Cl₃CCH₂OCONH | Me | Me | |
| 139 | O | H | H | 4-iPr-Ph | H | Me | Cl₃CCH₂OCONH | Me | Et | |
| 140 | O | H | H | 4-iPr-Ph | H | Me | Cl₃CCH₂OCONH | Me | OMe | |
| 141 | O | H | H | 4-iPr-Ph | H | Me | Cl₃CCH₂OCONH | Me | (CH₂)₃OH | |
| 142 | O | H | H | 4-iPr-Ph | H | Me | Cl₃CCH₂OCONH | Me | Ph | |
| 143 | O | H | H | 4-iPr-Ph | H | Me | C₄H₈NCONH | Me | Me | less polor |
| 144 | O | H | H | 4-iPr-Ph | H | Me | Et₂NCONH | Me | Me | more polor |
| 145 | O | H | H | 4-iPr-Ph | H | Me | HO(CH₂)₃NHCONH | Me | Me | |
| 146 | O | H | H | 4-iPr-Ph | H | Me | MeO(CH₂)₃NHCONH | Me | Me | |
| 147 | O | H | H | 4-iPr-Ph | H | Me | Me₂N(CH₂)₂NHCONH | Me | Me | |
| 148 | O | H | H | 4-iPr-Ph | H | Me | HO(CH₂)₃NHCONH | Me | Me | |
| 149 | O | H | H | 4-iPr-Ph | H | Me | HO(CH₂)₃NHCONH | Me | OMe | |
| 150 | O | H | H | 4-iPr-Ph | H | Me | HO(CH₂)₃NHCONH | Me | (CH₂)₃OH | |
| 151 | O | H | H | 4-iPr-Ph | H | Me | nPrNHCONH | Me | Me | |
| 152 | O | H | H | 4-iPr-Ph | H | Me | HO(CH₂)₃NHCONH | Me | Ph | |
| 153 | O | H | H | 4-iPr-Ph | H | Me | HO(CH₂)₃NHCONH | Me | Ph | |
| 154 | O | H | H | 4-iPr-Ph | H | Me | HO(CH₂)₃NHCONH | Me | Me | |
| 155 | O | H | H | 4-iPr-Ph | H | Me | HO(CH₂)₃NHCONH | Me | Me | |
| 156 | O | H | H | 4-iPr-Ph | H | Me | HOCH₂C(Me)₃NHCONH | Me | Me | |

TABLE 4

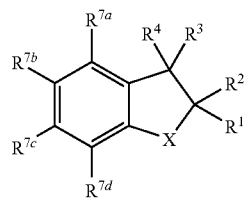

| Example | X | R¹ | R² | R³ | R⁴ | R⁷ᵃ | R⁷ᵇ | R⁷ᶜ | R⁷ᵈ | Note |
|---|---|---|---|---|---|---|---|---|---|---|
| 157 | O | H | H | 4-iPr-Ph | H | Me | HOCH₂C(Me)₂NHCONH | Me | Ph | |
| 158 | O | H | H | 4-iPr-Ph | H | Me | HOCH₂C(Me)₂CH₂NHCONH | Me | Me | |
| 159 | O | H | H | 4-iPr-Ph | H | Me | HOCH₂C(Me)₂CH₂NHCONH | Me | Ph | |
| 160 | O | H | H | 4-iPr-Ph | H | Me | HOCH(Me)CH₂NHCONH | Me | Ph | |
| 161 | S | H | H | 4-iPr-Ph | H | Me | t-BuCH₂CONH | Me | H | |
| 162 | S | H | H | 4-iPr-Ph | H | Me | t-BuCH₂CONH | Me | Br | |
| 163 | S | H | H | 4-iPr-Ph | H | Me | t-BuCH₂CONH | Me | CHO | |
| 164 | S | H | H | 4-iPr-Ph | H | Me | t-BuCH₂CONH | Me | Et | |
| 165 | S | H | H | 4-iPr-Ph | H | Me | t-BuCH₂CONH | Me | nPr | |
| 166 | S | H | H | 4-iPr-Ph | H | Me | t-BuCH₂CONH | Me | Ac | |
| 167 | S(O) | H | H | 4-iPr-Ph | H | Me | t-BuCH₂CONH | Me | Et | |
| 168 | S(O) | H | H | 4-iPr-Ph | H | Me | t-BuCH₂CONH | Me | Ac | |
| 169 | S(O) | H | H | 4-iPr-Ph | H | Me | t-BuCH₂CONH | Me | Ac | |
| 170 | SO2 | H | H | 4-iPr-Ph | H | Me | t-BuCH₂CONH | Me | Br | |
| 171 | SO2 | H | H | 4-iPr-Ph | H | Me | t-BuCH₂CONH | Me | Ac | |
| 172 | SO2 | H | H | 4-iPr-Ph | H | Me | t-BuCH₂CONH | Me | Et | |
| 173 | O | H | H | 4-iPr-Ph | H | Me | t-BuCH₂CONH | Me | Me | |
| 174 | O | H | H | 4-iPr-Ph | H | Me | t-BuCH₂CONH | Me | Me | |
| 175 | O | H | H | 4-MeCH(OH)-Ph | H | Me | t-BuCH₂CONH | Me | Me | |
| 176 | O | H | H | 4-AcPh | H | Me | t-BuCH₂CONH | Me | Me | |
| 177 | O | H | H | 3-EtOC(=O)CH=CHPh | H | Me | t-BuCH₂CONH | Me | Me | |

TABLE 4-continued

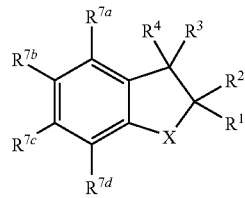

| Example | X | R¹ | R² | R³ | R⁴ | R⁷ᵃ | R⁷ᵇ | R⁷ᶜ | R⁷ᵈ | Note |
|---|---|---|---|---|---|---|---|---|---|---|
| 178 | O | H | H | 4-EtOC(=O)CH=CHPh | H | Me | t-BuCH₂CONH | Me | Me | |
| 179 | O | H | H | 4-EtOC(=O)CH=C(Me)Ph | H | Me | t-BuCH₂CONH | Me | Me | |
| 180 | O | H | H | 3-EtOC(=O)(CH₂)₂Ph | H | Me | t-BuCH₂CONH | Me | Me | |
| 181 | O | H | H | 3-EtOC(=O)(CH₂)₂Ph | H | Me | t-BuCH₂CONH | Me | Me | |
| 182 | O | H | H | 4-EtOC(=O)CH₃CH(Me)Ph | H | Me | t-BuCH₂CONH | Me | Me | |
| 183 | O | H | H | 4-Ac-3-MeOPh | H | Me | t-BuCH₂CONH | Me | Me | |
| 184 | O | H | H | 4-(H₂C=C(Me))-3-MeOPh | H | Me | t-BuCH₂CONH | Me | Me | |
| 185 | O | H | H | 4-iPr-3-MeOPh | H | Me | t-BuCH₂CONH | Me | Me | |
| 186 | O | H | H | 4-iPr-3-(HO)Ph | H | Me | t-BuCH₂CONH | Me | Me | |
| 187 | O | H | H | 4-iPr-2-(HO)Ph | H | Me | t-BuCH₂CONH | Me | Me | |
| 188 | O | H | H | 4-iPr-3-(EtOC(O)CH₂O)Ph | H | Me | t-BuCH₂CONH | Me | Me | |
| 189 | O | H | H | 4-iPr-2-(MeC(O)CH₂O)Ph | H | Me | t-BuCH₂CONH | Me | Me | |
| 190 | O | H | H | 4-iPr-2-(EtOC(O)CH₂O)Ph | H | Me | t-BuCH₂CONH | Me | Me | |
| 191 | O | H | H | 4-iPr-3-(MeO(CH₂)₂O)Ph | H | Me | t-BuCH₂CONH | Me | Me | |
| 192 | O | H | H | 4-iPr-2-(MeO(CH₂)₂O)Ph | H | Me | t-BuCH₂CONH | Me | Me | |
| 193 | O | H | H | 4-iPr-3-(HO(CH₂)₂O)Ph | H | Me | t-BuCH₂CONH | Me | Me | |
| 194 | O | H | H | 3-HO(CH₂)₃Ph | H | Me | t-BuCH₂CONH | Me | Me | |
| 195 | O | H | H | 4-HO(CH₂)₃Ph | H | Me | t-BuCH₂CONH | Me | Me | |
| 196 | O | H | H | 4-HO(CH₂)₂CH(Me)Ph | H | Me | t-BuCH₂CONH | Me | Me | |
| 197 | O | H | H | 4-iPr-2-(HO(CH₂)₂O)Ph | H | Me | t-BuCH₂CONH | Me | Me | |
| 198 | O | H | H | 4-HOC(=O)CH₂CH(Me)Ph | H | Me | t-BuCH₂CONH | Me | Me | |
| 199 | O | H | H | 4-Me₂C(OH)Ph | H | Me | t-BuCH₂CONH | Me | Me | |
| 200 | O | H | H | 4-iPr-Ph | H | Me | CF₃(CH₂)₂CONH | Me | Me | |
| 201 | O | H | N | 4-iPr-Ph | H | Me | Me₂NCH₂CONH | Me | Me | |
| 202 | O | H | H | 4-iPr-Ph | H | Me | t-BuCONH | Me | Me | |
| 203 | O | H | H | 4-iPr-Ph | H | Me | NHCHO | Me | Ac | |
| 204 | O | H | H | 4-iPr-Ph | H | Me | t-BuNHCONH | Me | Me | |
| 205 | O | H | H | 4-iPr-Ph | H | Me | (c-Hex)NHCONH | Me | Me | |
| 206 | O | H | H | 4-iPr-Ph | H | Me | Cl₃CCH₂OCONH | Me | Ac | |
| 207 | O | H | H | 4-iPr-Ph | H | Me | HO(CH₂)₃NHCONH | Me | Ac | |
| 208 | O | H | H | 4-iPr-Ph | H | Me | t-BuNHCONH | Me | CH(OH)Me | |

TABLE 5

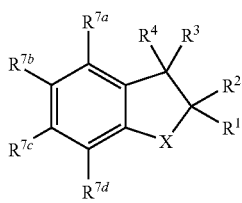

| Example | X | R¹ | R² | R³ | R⁴ | R⁷ᵃ | R⁷ᵇ | R⁷ᶜ | R⁷ᵈ | Note |
|---|---|---|---|---|---|---|---|---|---|---|
| 209 | O | H | H | 4-iPr-Ph | H | Me | t-BuNHCONH | Me | Me | |
| 210 | O | H | H | 4-iPr-Ph | H | Me | HO(CH₂)₂NHCONH | Me | Ac | |
| 211 | O | H | H | 4-iPr-Ph | H | Me | t-BuCH₂CONH | Me | 3-(1-pyrrolidinyl)Ph | |
| 212 | O | H | H | 4-iPr-Ph | H | Me | t-BuCH₂CONH | Me | (4-Me₂N)Ph | |
| 213 | O | H | H | 4-iPr-Ph | H | Me | t-BuCH₂CONH | Me | 6-Me₂N-3-Py | |
| 214 | O | H | H | Me | H | Me | t-BuCH₂CONH | Me | 4-iPr-Bz | |
| 215 | O | H | H | Et | H | Me | t-BuCH₂CONH | Me | 4-iPr-Bz | |
| 216 | O | H | H | n-Pr | H | Me | t-BuCH₂CONH | Me | 4-iPr-Bz | |
| 217 | O | H | H | i-Pr | H | Me | t-BuCH₂CONH | Me | 4-iPr-Bz | |
| 218 | O | H | H | H | H | Me | n-PrCONH | Me | 4-iPr-Bz | |
| 219 | O | H | H | H | H | Me | EtCONH | Me | 4-iPr-Bz | |
| 220 | O | H | H | H | H | Me | n-BuCONH | Me | 4-iPr-Bz | |
| 221 | O | H | H | H | H | Me | t-BuOCONH | Me | H | |
| 222 | O | H | H | H | H | Me | t-BuOCONH | Me | Br | |
| 223 | O | H | H | H | H | Me | t-BuOCONH | Me | C(OH)(Me)(4-iPr-Ph) | |
| 224 | O | H | H | H | H | Me | n-PrCONH | Me | CH(Me)(4-iPr-Ph) | |
| 225 | O | H | H | H | H | Me | t-BuCH₂CONH | Me | CH(Me)(4-iPr-Ph) | |
| 226 | O | H | H | H | H | Me | t-BuCH₂CONH | Me | C(=CH₂)(4-iPr-Ph) | |

TABLE 5-continued

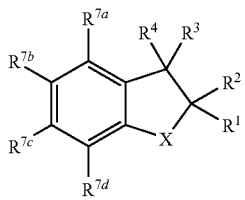

| Example | X | R¹ | R² | R³ | R⁴ | R⁷ᵃ | R⁷ᵇ | R⁷ᶜ | R⁷ᵈ | Note |
|---|---|---|---|---|---|---|---|---|---|---|
| 227 | O | H | H | H | H | Me | t-BuNHCONH | Me | 4-iPr-Bz | |
| 228 | O | H | H | H | H | Me | HO(CH₂)₂NHCONH | Me | 4-iPr-Bz | |
| 229 | O | H | H | H | H | Me | t-BuCH₂CONH | Me | 4-iPr-Bz | |
| 230 | O | H | H | CH₂OH | H | Me | t-BuCH₂CONH | Me | 4-iPr-Bz | |
| 231 | O | H | H | Ph | H | Me | t-BuCH₂CONH | Me | H | |
| 232 | O | H | H | Ph | H | Me | t-BuCH₂CONH | Me | CHO | |
| 233 | O | H | H | Ph | H | Me | t-BuCH₂CONH | Me | 4-iPr-Bz | |
| 234 | O | Me | Me | OH | H | Me | t-BuCH₂CONH | Me | Me | |
| 235 | O | Me | Me | OH | H | H | t-BuCH₂CONH | Me | Me | |
| 236 | O | Me | Me | OH | H | Me | t-BuOCONH | Me | Br | |
| 237 | O | Me | Me | H | H | Me | t-BuOCONH | Me | H | |
| 238 | O | Me | Me | H | H | Me | t-BuOCONH | Me | Br | |
| 239 | O | Me | Me | 3-Me-Ph | OH | H | t-BuCH₂CONH | Me | Me | |
| 240 | O | Me | Me | (CH₂)₂Ph | OH | H | t-BuCH₂CONH | Me | Me | |
| 241 | O | Me | Me | 2-CF₃O-Ph | OH | H | t-BuCH₂CONH | Me | Me | |
| 242 | O | Me | Me | 2-Me-Ph | OH | H | t-BuCH₂CONH | Me | Me | |
| 243 | O | Me | Me | Ph | OH | H | t-BuCH₂CONH | Me | Me | |
| 244 | O | Me | Me | 2-naph | OH | H | t-BuCH₂CONH | Me | Me | |
| 245 | O | Me | Me | 3-iPr-Ph | OH | H | t-BuCH₂CONH | Me | Me | |
| 246 | O | Me | Me | 2-MeO-Ph | OH | H | t-BuCH₂CONH | Me | Me | |
| 247 | O | Me | Me | 4-iPr-Ph | OH | H | i-BuCH₂CONH | Me | Me | |
| 248 | O | Me | Me | 2-thienyl | OH | H | t-BuCH₂CONH | Me | Me | |
| 249 | O | Me | Me | Bz | OH | H | t-BuCH₂CONH | Me | Me | |
| 250 | O | Me | Me | 4-iPr-Bz | OH | H | t-BuCH₂CONH | Me | Me | |
| 251 | O | Me | Me | n-Bu | OH | H | t-BuCH₂CONH | Me | Me | |
| 252 | O | Me | Me | 2-furyl | OH | H | t-BuCH₂CONH | Me | Me | |
| 253 | O | Me | Me | 2,4-MeO-Ph | OH | H | t-BuCH₂CONH | Me | Me | |
| 254 | O | Me | Me | 4-Br-Ph | OH | H | t-BuCH₂CONH | Me | Me | |
| 255 | O | Me | Me | 4-MeO-Ph | OH | H | t-BuCH₂CONH | Me | Me | |
| 256 | O | Me | Me | c-Hex | OH | Me | t-BuCH₂CONH | Me | Me | |
| 257 | O | Me | Me | 2-Py | OH | Me | t-BuCH₂CONH | Me | Me | |
| 258 | O | Me | Me | 4-MeO-Ph | OH | Me | t-BuCH₂CONH | Me | Me | |
| 259 | O | Me | Me | 3-MeO-Ph | OH | Me | t-BuCH₂CONH | Me | Me | |
| 260 | O | Me | Me | 4-iPr-Ph | OH | Me | Me | Me | t-BuCH₂CONH | |

TABLE 6

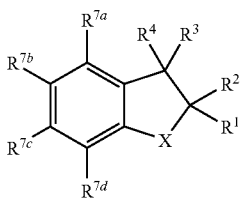

| Example | X | R¹ | R² | R³ | R⁴ | R⁷ᵃ | R⁷ᵇ | R⁷ᶜ | R⁷ᵈ | Note |
|---|---|---|---|---|---|---|---|---|---|---|
| 261 | O | Me | Me | 4-Me-Ph | OH | Me | t-BuOCONH | Me | Me | |
| 262 | O | Me | Me | 4-iPr-Ph | OH | Me | t-BuOCONH | Me | Me | |
| 263 | O | Me | Me | 2-naph | OH | Me | t-BuOCONH | Me | Me | |
| 264 | O | Me | Me | 3-CHO-Ph | OH | H | t-BuCH₂CONH | Me | Me | |
| 265 | O | Me | Me | 3-(CH₂OH)-Ph | OH | H | t-BuCH₂CONH | Me | Me | |
| 266 | O | Me | Me | 3-(CH(Me)OH)-Ph | OH | H | t-BuCH₂CONH | Me | Me | |
| 267 | O | Me | Me | 4-Me-Ph | OH | Me | t-BuCH₂CONH | Me | Me | |
| 268 | O | Me | Me | 2-naph | OH | Me | t-BuCH₂CONH | Me | H | |
| 269 | O | Me | Me | 2-naph | OH | Me | i-BuCH₂CONH | Me | Me | |
| 270 | O | Me | Me | 2-naph | OH | Me | t-BuNHCONH | Me | Me | |
| 271 | O | Me | Me | 2-Me-Ph | H | H | t-BuCH₂CONH | Me | Me | |
| 272 | O | Me | Me | 3-Me-Ph | H | H | t-BuCH₂CONH | Me | Me | |
| 273 | O | Me | Me | 3-iPr-Ph | H | H | t-BuCH₂CONH | Me | Me | |
| 274 | O | Me | Me | Ph | H | H | t-BuCH₂CONH | Me | Me | |
| 275 | O | Me | Me | 2-naph | H | H | t-BuCH₂CONH | Me | Me | |

TABLE 6-continued

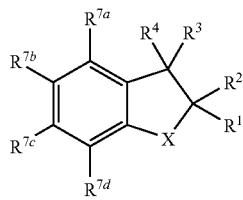

| Example | X | R$^1$ | R$^2$ | R$^3$ | R$^4$ | R$^{7a}$ | R$^{7b}$ | R$^{7c}$ | R$^{7d}$ | Note |
|---|---|---|---|---|---|---|---|---|---|---|
| 276 | O | Me | Me | 2-MeO-Ph | H | H | t-BuCH$_2$CONH | Me | Me | |
| 277 | O | Me | Me | Bz | H | H | t-BuCH$_2$CONH | Me | Me | |
| 278 | O | Me | Me | 4-iPr-Bz | H | H | t-BuCH$_2$CONH | Me | Me | |
| 279 | O | Me | Me | 2-thienyl | H | H | t-BuCH$_2$CONH | Me | Me | |
| 280 | O | Me | Me | 2-CF$_3$O-Ph | H | H | t-BuCH$_2$CONH | Me | Me | |
| 281 | O | Me | Me | n-Bu | H | H | t-BuCH$_2$CONH | Me | Me | |
| 282 | O | Me | Me | 2-furyl | H | H | t-BuCH$_2$CONH | Me | Me | |
| 283 | O | Me | Me | (CH$_2$)$_2$Ph | H | H | t-BuCH$_2$CONH | Me | Me | |
| 284 | O | Me | Me | 4-Br-Ph | H | H | t-BuCH$_2$CONH | Me | Me | |
| 285 | O | Me | Me | 4-MeO-Ph | H | H | t-BuCH$_2$CONH | Me | Me | |
| 286 | O | Me | Me | 2,4-MeO-Ph | H | H | t-BuCH$_2$CONH | Me | Me | |
| 287 | O | Me | Me | c-Hex | H | Me | t-BuCH$_2$CONH | Me | Me | |
| 288 | O | Me | Me | 2-Py | H | Me | t-BuCH$_2$CONH | Me | Me | |
| 289 | O | Me | Me | 4-MeO-Ph | H | Me | t-BuCH$_2$CONH | Me | Me | |
| 290 | O | Me | Me | 3-MeO-Ph | H | Me | t-BuCH$_2$CONH | Me | Me | |
| 291 | O | Me | Me | 4-iPr-Ph | H | Me | Me | Me | t-BuCH$_2$CONH | |
| 292 | O | Me | Me | 4-CHO-Ph | H | H | t-BuCH$_2$CONH | Me | Me | |
| 293 | O | Me | Me | 4-Ac-Ph | H | H | t-BuCH$_2$CONH | Me | Me | |
| 294 | O | Me | Me | 3-(CH$_2$OH)-Ph | H | H | t-BuCH$_2$CONH | Me | Me | |
| 295 | O | Me | Me | 3-(CH(Me)OH)-Ph | H | H | t-BuCH$_2$CONH | Me | Me | |
| 296 | O | Me | Me | 2-iPr-Ph | H | H | t-BuCH$_2$CONH | Me | Me | |
| 297 | O | Me | Me | 1-piperidyl | H | Me | t-BuCH$_2$CONH | Me | Me | |
| 298 | O | Me | Me | 1-pyrrolidinyl | H | H | t-BuCH$_2$CONH | Me | Me | |
| 299 | O | Me | Me | NHPh | H | H | t-BuCH$_2$CONH | Me | Me | |
| 300 | O | Me | Me | NH-(2-MeO-Ph) | H | H | t-BuCH$_2$CONH | Me | Me | |
| 301 | O | Me | Me | NH-(2-CF$_3$O-Ph) | H | H | t-BuCH$_2$CONH | Me | Me | |
| 302 | O | Me | Me | 1-pyrrolidinyl | H | Me | t-BuOCONH | Me | Br | |
| 303 | O | Me | Me | Me$_2$N | H | Me | t-BuOCONH | Me | Br | |
| 304 | O | Me | Me | 4-iPr-Ph | H | Me | t-BuOCONH | Me | Me | |
| 305 | O | Me | Me | 4-Me-Ph | H | Me | t-BuOCONH | Me | Me | |
| 306 | O | Me | Me | H | H | Me | t-BuCH$_2$CONH | Me | 4-iPr-Bz | |
| 307 | O | Me | Me | 1-pyrrolidinyl | H | Me | t-BuCH$_2$CONH | Me | 4-iPr-Bz | |
| 308 | O | Me | Me | Me$_2$N | H | Me | t-BuCH$_2$CONH | Me | 4-iPr-Bz | |
| 309 | O | Me | Me | 4-Me-Ph | H | H | t-BuCH$_2$CONH | Me | Me | |
| 310 | O | Me | Me | 4-Me-Ph | H | Me | n-PrCONH | Me | Me | |
| 311 | O | Me | Me | 4-Me-Ph | H | Me | n-BuCONH | Me | Me | |
| 312 | O | Me | Me | 4-Me-Ph | H | Me | n-PenCONH | Me | Me | |

TABLE 7

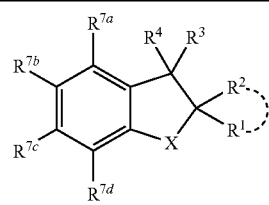

| Example | X | R$^1$ | R$^2$ | R$^3$ | R$^4$ | R$^{7a}$ | R$^{7b}$ | R$^{7c}$ | R$^{7d}$ | Note |
|---|---|---|---|---|---|---|---|---|---|---|
| 313 | O | Me | Me | 4-F-Ph | H | Me | t-BuCH$_2$CONH | Me | Me | |
| 314 | O | Me | Me | Ph | H | Me | t-BuCH$_2$CONH | Me | Me | |
| 315 | O | Me | Me | 4-Bt-Ph | H | Me | t-BuCH$_2$CONH | Me | Me | |
| 316 | O | Me | Me | 4-t-Bu-Ph | H | Me | t-BuCH$_2$CONH | Me | Me | |
| 317 | O | Me | Me | 4-iPr-Ph | H | H | t-BuCH$_2$CONH | Me | Me | |
| 318 | O | Me | Me | 4-iPr-Ph | H | Me | t-BuCH$_2$CONH | H | Me | |
| 319 | O | Me | Me | 4-iPr-Ph | H | Me | t-BuCH$_2$CONH | Me | H | |
| 320 | O | Me | Me | 4-iPr-Ph | H | H | t-BuCH$_2$CONH | H | H | |
| 321 | O | Me | Me | 4-iPr-Ph | H | H | n-PrCONH | H | H | |
| 322 | O | Me | Me | 4-iPr-Ph | H | Me | n-PrCONH | Me | Me | |
| 323 | O | Me | Me | 4-iPr-Ph | H | Me | n-BuCONH | Me | Me | |
| 324 | O | Me | Me | 4-iPr-Ph | H | Me | t-BuCH$_2$CONH | Me | Me | |

TABLE 7-continued

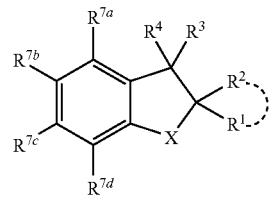

| Example | X | R$^1$ | R$^2$ | R$^3$ | R$^4$ | R$^{7a}$ | R$^{7b}$ | R$^{7c}$ | R$^{7d}$ | Note |
|---|---|---|---|---|---|---|---|---|---|---|
| 325 | O | Me | Me | 4-iPr-Ph | H | Me | Me | t-BuCH$_2$CONH | Me | |
| 326 | O | Me | Me | Bz | H | Me | Me | t-BuCH$_2$CONH | H | |
| 327 | O | Me | Me | 4-iPr-Ph | H | H | Me | H | t-BuCH$_2$CONH | |
| 328 | O | Me | Me | 4-iPr-Ph | H | Me | MeO | Me | t-BuCH$_2$CONH | |
| 329 | O | Me | Me | 4-iPr-Ph | H | H | t-BuCH$_2$CON(Me) | H | H | |
| 330 | O | Me | Me | 4-iPr-Ph | H | Me | (4-morpholinyl)(CH$_2$)$_2$CONH | Me | Me | |
| 331 | O | Me | H | H | H | Me | t-BuOCONH | Me | H | |
| 332 | O | Me | H | H | H | Me | t-BuOCONH | Me | Br | |
| 333 | O | Me | H | H | H | Me | t-BuOCONH | Me | 4-iPr-Ph-CH(OH) | |
| 334 | O | Me | H | H | H | Me | t-BuCH$_2$CONH | Me | 4-iPr-Bz | |
| 335 | O | Me | CH$_2$OH | H | H | Me | t-BuCH$_2$CONH | Me | 4-iPr-Bz | |
| 336 | O | Me | CH$_2$I | H | H | Me | t-BuCH$_2$CONH | Me | 4-iPr-Bz | |
| 337 | O | Me | CH$_2$(1-pyrrolidynyl) | H | H | Me | t-BuCH$_2$CONH | Me | 4-iPr-Bz | |
| 338 | O | Me | Me | OH | H | Me | t-BuCH$_2$CONH | Me | H | |
| 339 | O | Me | Me | H | H | Me | t-BuCH$_2$CONH | Me | H | |
| 340 | O | Me | Me | H | H | Me | t-BuCH$_2$CONH | Me | CHO | |
| 341 | O | Me | Me | H | H | Me | t-BuCH$_2$CONH | Me | 4-iPr-Ph-CH(OH) | |
| 342 | O | Me | Me | H | H | Me | t-BuCH$_2$CONH | Me | 4-iPr-Ph-CO | |
| 343 | O | Me | Me | H | H | Me | t-BuCH$_2$CONH | Me | Br | |
| 344 | O | Me | Me | H | H | Me | t-BuCH$_2$CONH | Me | 4-iPr-Ph-O | |
| 345 | O | Me | Me | H | H | Me | t-BuCH$_2$CONH | Me | 4-Me-Ph-O | |
| 346 | O | Me | Me | OH | H | Me | t-BuCH$_2$CONH | Me | 4-iPr-Bz | |
| 347 | O | Me | Me | OH | Me | Me | t-BuCH$_2$CONH | Me | 4-iPr-Bz | |
| 348 | O | | (CH$_2$)$_4$ | 4-iPr-Ph | H | Me | t-BuCH$_2$CONH | Me | Me | |
| 349 | O | Me | H | 4-iPr-Ph | H | H | t-BuCH$_2$CONH | Me | Me | cis-form |
| 350 | O | Me | H | 4-iPr-Ph | H | Me | t-BuCH$_2$CONH | Me | Me | cis-form |
| 351 | O | Me | H | 4-iPr-Ph | H | Me | t-BuCH$_2$CONH | Me | Me | trans-form |
| 352 | O | Me | Me | H | H | Me | t-BuCH$_2$CONH | Me | (2-Py)CH(OH) | |
| 353 | O | Me | Me | H | H | Me | t-BuCH$_2$CONH | Me | 4-iPr-Ph-CH$_2$CH(OH) | |
| 354 | O | Me | Me | H | H | Me | t-BuCH$_2$CONH | Me | 4-iPr-Ph-(CH$_2$)$_2$ | |
| 355 | O | Me | Me | H | H | Me | t-BuCH$_2$CONH | Me | PHCH(OH) | |
| 356 | O | Me | Me | H | H | Me | t-BuCH$_2$CONH | Me | Bz | |
| 357 | O | Me | Me | H | H | Me | t-BuCH$_2$CONH | Me | 2-Me-Bz | |
| 358 | O | Me | Me | H | H | Me | t-BuCH$_2$CONH | Me | 2-furyl | R-form |
| 359 | O | Me | Me | H | H | Me | t-BuCH$_2$CONH | Me | benzoyl | R-form |

FORMULATION EXAMPLE 1

The compound obtained in Example 1 was dissolved in a 30% (w/v) polyethylene glycol 400-containing saline to prepare a 0.01% solution of the compound. This solution was filtered through a bacterial filter and dispensed into vials by 10 mL, to provide an injectable solution for intravenous administration which contained 1 mg of the compound in each vial.

FORMULATION EXAMPLE 2

The compound obtained in Example 1 was dissolved in a 5% cyclodextrin-containing saline to prepare a 0.1% solution of the compound. This solution was filtered through a bacterial filter and dispensed into vials by 10 mL, to provide an injectable solution for intravenous administration which contained 10 mg of the compound in each vial.

FORMULATION EXAMPLE 3

| | |
|---|---|
| (1) The compound obtained in Example 1 | 50 mg |
| (2) Lactose | 34 mg |
| (3) Corn Starch | 10.6 mg |
| (4) Corn Starch (paste) | 5 mg |
| (5) Magnesium stearate | 0.4 mg |
| (6) Calcium carboxylmethylcellulose | 20 mg |
| Total | 120 mg |

According to a conventional method, the above-mentioned (1) to (6) are mixed and compressed by a tableting machine to produce tablets.

EXPERIMENTAL EXAMPLE 1

[$^3$H]-CP55,940 Binding Assay with a Cell Membrane Fraction Expressing Human CB1 and CB2 Receptor

[$^3$H]-CP55940 binding inhibition assay was conducted by incubating a CHO cell membrane fraction expressing human CB1 receptor and the test compound and 500 pM [$^3$H]-CP55940 in reaction buffer (50 mM Tris-HCl (pH7.4), 5 mM MgCl$_2$, 2.5 mM EDTA and 0.5% BSA (fatty acid free)) at room temperature for 60 minutes. The reaction solution was filtered through GF/C filter, washed with 30011 of washing buffer (50 mM Tris-HCl (pH7.4), 0.05% BSA (fatty acid free)) four times, and the radioactivity of the filter was measured with a Top Count scintillation counter (Packard). As results, the test compound has inhibited binding of [$^3$H]-CP55940 to the membrane fraction dose-dependently.

The inhibitory activity of the test compound to [$^3$H]-CP55940 binding was calculated by percent on the basis that radioactivity is 100% when only 500 pM [$^3$H]-CP55940 was added, and 0% when 500 pM [$^3$H]-CP55940 and 100 nM CP55940 were added at the same time. Further, IC$_{50}$ value of the test compound was calculated by analyzing concentrations and percents of the test compound with PRISM 3.0 (Graphpad Software, Inc.).

The same assay was also conducted for a CHO cell membrane fraction expressing human CB2 receptor, and the inhibitory activity to [$^3$H]-CP55940 binding was calculated.

The results are shown in Table 8.

TABLE 8

| Compound No. | CB1 IC$_{50}$ value (nM) | CB2 IC$_{50}$ value (nM) |
|---|---|---|
| Reference Example 153 | 110 | 560 |
| Reference Example 212 | 69 | <10 |
| Reference Example 230 | 55 | 55 |
| Reference Example 233 | 38 | 47 |
| Reference Example 234 | 40 | 31 |
| Example 1 | 20 | <10 |
| Example 7 | <10 | <10 |
| Example 9 | 79 | 11 |
| Example 14 | 20 | <10 |
| Example 22 | 11 | <10 |
| Example 23 | <10 | <10 |
| Example 28 | <10 | <10 |
| Example 29 | <10 | <10 |
| Example 31 | <10 | <10 |
| Example 32 | <10 | <10 |
| Example 33 | 14 | <10 |
| Example 34 | <10 | <10 |
| Example 35 | <10 | <10 |
| Example 36 | <10 | <10 |

EXPERIMENTAL EXAMPLE 2

Body Temperature-lowering Action on Mouse

CB1 receptor agonistic activity of the compound of the present invention in vivo was evaluated by investigating the effect on the body temperature of mouse after the drug was administered to the mouse. In this experiment, Jcl: ICR male mice (5 weeks old) were used. After measuring the rectal temperature with a thermometer (Physitemp BAT-12) that was connected to a probe for measuring body temperature, the compound dissolved in 2.2% EtOH and 5% G2-β-cyclodextrin (solvent) was administered intraperitoneally. Solvent only was administered to the control group. 30 minutes after administration, rectal temperature was measured again. The experiment was conducted for 4 subjects per a group.

The test result was estimated as effective if the compound of the present invention lowered the body temperature substantially by 1° C. or more when compared with the control group 30 minutes after administration of 1 mg/kg, i.p.

The results are shown in Table 9.

TABLE 9

| Compound No. | Test Results |
|---|---|
| Example 1 | Effective |
| Example 7 | Effective |
| Example 14 | Effective |
| Example 22 | Effective |
| Example 23 | Effective |
| Example 28 | Effective |
| Example 29 | Effective |
| Example 31 | Effective |
| Example 32 | Effective |
| Example 33 | Effective |
| Example 34 | Effective |
| Example 35 | Effective |
| Example 36 | Effective |

As shown in Table 9, the compound of the present invention exerted unusually body temperature-lowering action based on CB1 receptor agonistic activity at the low doses.

EXPERIMENTAL EXAMPLE 3

Effects of Reducing Cerebral Infarction in Experimental Model of Cerebral Infarction In this experiment, Jcl: SD male rats (8 weeks old) were used. A canula for infusion was inserted into the left common carotid vein under halothane anesthesia.

Silicon-coated embolus was inserted into the left common carotid artery, to obstruct the middle cerebral artery (MCAO). 120 minutes after the obstruction, light anesthesia was conducted again with halothane, and reperfusion was done with the embolus removed. During MCAO, the rats were observed for neural symptoms. The rats expressing typical neural symptoms were used in the experiment. The drug was dissolved in 2.2% EtOH and 5% G2-β-cyclodextrin (solvent). The test compound was administered intraperitoneally at three times as much as the minimum dose which was recognized to have body temperature lowering action immediately after the reperfusion, and further administered after 2, 4 and 6 hours at the same dose. As used herein, the test compound was selected from the compounds which had excellent activities in Experimental Example 1 and Experimental Example 2. The same amount of the solvent was administered to the control group. 2 days after treating MCAO, the rats were decapitated, the brain was extracted and 6 frontal slices of 2 mm thickness was constructed under ice-cooling. Each slice was dyed with a 1% TTC solution at 37° C. for 15 minutes, and photographed with a digital camera. White-part area of each slice was measured by image analyzing software (Photoshop (trademark)), and the volume of the infarction was calculated by multiplying the area by the thickness of the slice. As a result, 30% or more of infarction volume was recognized to be substantially reduced at the dose of 0.5 mg/kg.

As shown above, Compound (I), etc. have excellent modulating action on cannabinoid receptor function.

Further, Compound (I), etc. have protective action on cerebral infarction, and, therefore, have medical actions such as treating cerebrovascular disorders. Further, Compound (I), etc. are considered to have very low toxicity and be well transferred into the brain.

INDUSTRIAL APPLICABILITY

As described above, an excellent cannabinoid receptor modulator which is useful as a drug is provided according to the present invention.

The invention claimed is:
1. (+)-N-((3R)-7-(1-hydroxyethyl)-3-(4-isopropylphenyl)-4,6-dimethyl-2,3-dihydro-1-benzofuran-5-yl)-3,3-dimethylbutanamide or a salt thereof.
2. (+)-N-((3R)-7-(1-hydroxyethyl)-3-(4-isopropylphenyl)-4,6-dimethyl-2,3-dihydro-1-benzofuran-5-yl)-3,3-dimethylbutanamide.

* * * * *

UNITED STATES PATENT AND TRADEMARK OFFICE
CERTIFICATE OF CORRECTION

PATENT NO. : 7,507,841 B2  Page 1 of 1
APPLICATION NO. : 11/822941
DATED : March 24, 2009
INVENTOR(S) : Shigenori Ohkawa et al.

It is certified that error appears in the above-identified patent and that said Letters Patent is hereby corrected as shown below:

Title page,
Delete "(62) Division of application No. 10/561,483, filed on December 20, 2005," and please insert --(62) Division of application No. 10/561,483, filed on December 20, 2005, which is the National Stage of International Application No. PCT/JP2004/009355, filed on June 25, 2004.--

Signed and Sealed this

Thirtieth Day of June, 2009

JOHN DOLL
*Acting Director of the United States Patent and Trademark Office*